United States Patent
Tang et al.

(10) Patent No.: US 9,839,642 B2
(45) Date of Patent: Dec. 12, 2017

(54) BETA-TETRAZOLYL-PROPIONIC ACIDS AS METALLO-BETA-LACTAMASE INHIBITORS

(71) Applicant: Merck Sharp & Dohme Corp., Rahway, NJ (US)

(72) Inventors: Haifeng Tang, Metuchen, NJ (US); Shu-Wei Yang, Edison, NJ (US); Mihir Mandal, Westfield, NJ (US); Jing Su, Scotch Plains, NJ (US); Guoqing Li, Belle Mead, NJ (US); Weidong Pan, Hillsborough, NJ (US); Haiqun Tang, Belle Mead, NJ (US); Reynalda DeJesus, East Brunswick, NJ (US); Jianping Pan, Monmouth Junction, NJ (US); William Hagmann, Westfield, NJ (US); Fa-Xiang Ding, Staten Island, NY (US); Li Xiao, Cranbury, NJ (US); Alexander Pasternak, Princeton, NJ (US); Yuhua Huang, Westfield, NJ (US); Shuzhi Dong, Plainsboro, NJ (US); Dexi Yang, Livingston, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/309,533

(22) PCT Filed: May 4, 2015

(86) PCT No.: PCT/US2015/028989
§ 371 (c)(1),
(2) Date: Nov. 8, 2016

(87) PCT Pub. No.: WO2015/171474
PCT Pub. Date: Nov. 12, 2015

(65) Prior Publication Data
US 2017/0173035 A1  Jun. 22, 2017

Related U.S. Application Data

(60) Provisional application No. 61/991,167, filed on May 9, 2014.

(51) Int. Cl.
| | | |
|---|---|---|
| A61K 31/407 | (2006.01) |
| A61K 31/41 | (2006.01) |
| A61K 31/427 | (2006.01) |
| A61K 31/43 | (2006.01) |
| A61K 31/44 | (2006.01) |
| A61K 31/496 | (2006.01) |
| A61K 31/546 | (2006.01) |

(52) U.S. Cl.
CPC .......... *A61K 31/546* (2013.01); *A61K 31/407* (2013.01); *A61K 31/41* (2013.01); *A61K 31/427* (2013.01); *A61K 31/43* (2013.01); *A61K 31/44* (2013.01); *A61K 31/496* (2013.01); *A61K 2121/00* (2013.01)

(58) Field of Classification Search
None
See application file for complete search history.

(56) References Cited

U.S. PATENT DOCUMENTS

| | | | |
|---|---|---|---|
| 4,746,353 A | 5/1988 | Levitt |
| 4,786,311 A | 11/1988 | Levitt |
| 4,838,925 A | 6/1989 | Tseng |
| 5,510,343 A | 4/1996 | Charnas et al. |
| 5,698,577 A | 12/1997 | Hubschwerlen et al. |
| 6,472,406 B1 | 10/2002 | Besterman et al. |
| 2003/0199541 A1 | 10/2003 | Lampilas et al. |
| 2004/0082568 A1 | 4/2004 | Yang |
| 2004/0157826 A1 | 8/2004 | Lampilas et al. |

FOREIGN PATENT DOCUMENTS

| | | |
|---|---|---|
| CN | 1095549 | 11/1994 |
| CN | 103130686 | 6/2013 |
| CN | 103191091 | 7/2013 |
| EP | 204513 | 12/1986 |
| EP | 244166 | 11/1987 |
| WO | 2008039420 | 4/2008 |

OTHER PUBLICATIONS

Ito et al. in Cancer Science 94(1), 3-8 (2003).*
Coulton et al., "6 Beta-Lactamases: Targets for Drug Design", Progress in Medicinal Chemistry, vol. 31, pp. 297-349 (1994).
Dudley, "Bacterial Resistance Mechanisms to Beta-Lactam Antibiotics: Assessment of Management Strategies", Pharmacotherapy, vol. 15, pp. 9S-14S (1995).
English language abstract for CN1095549.
International Search Report of PCT/US20151028989, dated Jul. 24, 2015.
Livermore et al., "Potentiation of beta-lactams against *Pseudomonas aeruginosa* strains by Ro 48-1256, a bridged monobactam inhibitor of AmpC beta-lactamases", J. Antimicrob. Chemoth., vol. 40, pp. 335-343 (1997).
Poole, "Resistance to beta-lactam antibiotics", Cell. Mol. Life Sci., vol. 61, pp. 2200-2223 (2004).

(Continued)

*Primary Examiner* — Alicia L Otton
(74) *Attorney, Agent, or Firm* — Alysia A. Finnegan; Gloria Fuentes

(57) ABSTRACT

The present invention relates to compounds of formula I that are metallo-β-lactamase inhibitors, the synthesis of such compounds, and the use of such compounds for use with β-lactam antibiotics for overcoming resistance.

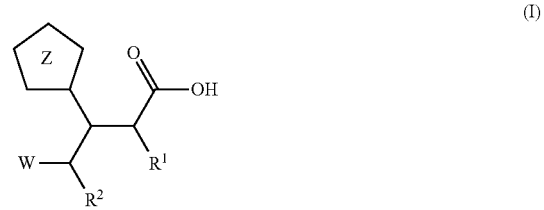

(I)

19 Claims, No Drawings

(56) References Cited

OTHER PUBLICATIONS

PubChem—CID11381943. Create Date: Oct. 26, 2006, p. 3.
PubChem CID22243674. Create Date: Dec. 5, 2007, p. 3.
Written Opinion of PCT/US2015/028989, dated Jul. 24, 2015.
Yang et al, "Diastereoselective alkylations of beta-tetrazolyl propionic acids", Tetrahedron Letters, vol. 45, pp. 111-112, vol. 45 (2013).
Shen et al., "Inhibitor Discovery of Full-Length New Delhi Metallo-Beta-Lactamase-1 (NDM-1)", PLOS One, e62955, pp. 1-7, vol. 8, Issue 5 (May 2013).
English Language Abstract for CN103130686.
English Language Abstract for CN103191091.
Fast et al., "Metallo-β-lactamase: Inhibitors and reporter substrates", Biochimica et Biophysica Acta 1834, pp. 1648-1659 (2013).

* cited by examiner

BETA-TETRAZOLYL-PROPIONIC ACIDS AS METALLO-BETA-LACTAMASE INHIBITORS

CROSS-REFERENCE TO RELATED APPLICATIONS

This application is a §371 National Phase Application of International Application No. PCT/US2015/028989, filed May 4, 2015, which claims the benefit of U.S. application Ser. No. 61/991,167, filed May 9, 2014, now expired.

FIELD OF THE INVENTION

This invention relates to novel metallo-β-lactamase inhibitors and their use for reducing bacterial antibiotic resistance. More particularly, the invention relates to β-tetrazolyl-propionic acids as metallo-β-lactamase inhibitors and methods of use thereof for overcoming beta-lactam antibiotic resistance.

BACKGROUND OF THE INVENTION

Bacterial antibiotic resistance has become one of the most serious threats to modern health care. Infections caused by resistant bacteria frequently result in longer hospital stays, higher mortality and increased cost of treatment. See, e.g., Cohen, *Science* 1992, 257:1051-1055. The spread of antibiotic resistance has been referred to as a pandemic and that a solution to the growing public health threat will require an interdisciplinary approach. See, e.g., Anderson, *Nat. Med.* 1999, 5: 147-149. See also Bush et al., *Nat. Rev. Microbiol.* 2011, 9: 894-896; Levy and Marshall, *Nat. Med.* 2004, 10: S122-S129; Livermore, *Clin. Infect. Dis.* 2003, 36: S11-S23; and Roberts et al., *Clin. Infect. Dis.* 2009, 49: 1175-1184.

The present crisis has prompted various efforts to elucidate the mechanisms responsible for bacterial resistance. The widespread use of penicillins and cephalosporins has resulted in the emergence of β-lactamases, a family of bacterial enzymes that catalyze the hydrolysis of the β-lactam ring common to numerous presently used antibiotics. See, Coulton et al., *Prog. Med. Chem.* 1994, 31: 297-349. This family of bacterial β-lactamases is further divided into four sub-families: A, C, and D which have a serine at the active site that catalyzes the hydrolysis of β-lactam antibiotics and a B family β-lactamases which are zinc metalloenzymes. Resistance mediated by β-lactamases is a critical aspect at the core of the development of bacterial antibiotic resistance. See, Dudley, *Pharmacotherapy* 1995, 15: 9S-14S. Clavulanic acid, which is a metabolite of *Streptomyces clavuligerus*, and two semi-synthetic inhibitors, sulbactam and tazobactam, are currently available semi-synthetic or natural product β-lactamase inhibitors. Synthetic β-lactamase inhibitors have also been described. See, U.S. Pat. Nos. 5,698,577; 5,510,343; 6,472,406; Hubschwerlen et al., *J. Med. Chem.* 1998, 41: 3961; and Livermore et al., *J. Med. Chem.* 1997, 40:335-343. Poole, *Cell. Mol. Life Sci.* 2004, 61: 2200-2223 provides a review of the resistance of bacterial pathogens to β-lactam antibiotics and approaches for overcoming resistance. For a review of inhibitors of metallo β-lactamases, see Fast and Sutton, *Biochim. Biophys. Acta—Proteins and Proteomics* 2013, 1834(8):1648-1659.

U.S. Patent Application Publication No. US 2003/0199541 A1 discloses certain azabicyclic compounds including certain 7-oxo-6-diazabicyclic[3.2.1]octane-2-carboxamides and their use as anti-bacterial agents. U.S. Patent Application Publication No. US 2004/0157826 A1 discloses heterobicyclic compounds including certain diazepine carboxamide and diazepine carboxylate derivatives and their use as anti-bacterials and β-lactamase inhibitors. International Patent Application Publication No. WO 2008/039420 A2 discloses 7-oxo-2,6-diazabicyclo[3.2.0]heptane-6-sulfooxy-2-carboxamides and their use as β-lactamase inhibitors.

Zheng et al., in PLOS One 2013, 8(5), e62955, discloses substituted 2,5-bis-tetrazolylmethyl-thiophenes and their use as β-lactamase inhibitors. Chinese Patent Application Publication No. CN103130686 A discloses N,N'-diarylureas and their use as inhibitors of metallo β-lactamases. Chinese Patent Application Publication No. CN103191091 A discloses substituted arylsulfonamides and their use as inhibitors of metallo β-lactamases.

U.S. Pat. Nos. 4,786,311; 4,746,353; 4,838,925; European Patent Application Publication Nos. EP204513A2, EP244166A2, and Chinese Patent Application Publication No. CN1095549A disclose substituted 2-(1H-tetrazol-5-yl)benzenesulfonamides and their use as herbicides.

Substituted β-tetrazolyl-propionamides and their use as agents for the treatment of Alzheimer's disease have been described. See Yang et al., *Tet. Lett.* 2004, 45: 111-112 and U.S. Patent Application Publication No. US 2004/0082568 A1.

SUMMARY OF THE INVENTION

The present invention is directed to certain substituted 1H-tetrazol-5-yl carboxylic acid compounds which are metallo-β-lactamase inhibitors. The compounds and their pharmaceutically acceptable salts, are useful, for example, in combination with β-lactam antibiotics for the treatment of bacterial infections, particularly antibiotic-resistant bacterial infections where the bacterial resistance is due to metallo-β-lactamase. More particularly, the present invention includes compounds of Formula I:

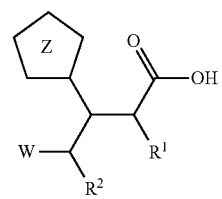

(I)

or a pharmaceutically acceptable salt thereof,
wherein Z is tetrazoyl which is attached in formula I by a carbon-carbon bond;
$R^1$ is selected from the group consisting of
1) hydrogen,
2) $C_{1-8}$alkyl,
3) $C_{2-8}$alkenyl,
4) $C_{2-8}$alkynyl,
5) —$C_{0-8}$alkyl-$C_{3-7}$cycloalkyl,
6) —$C_{0-8}$alkyl-$C_{3-7}$cycloheteroalkyl,
7) aryl,
8) heteroaryl,
9) —$C_{1-8}$alkyl-aryl, and
10) —$C_{1-8}$alkyl-heteroaryl,
wherein the $R^1$ $C_{1-8}$alkyl, $C_{2-8}$alkenyl, $C_{2-8}$alkynyl, —$C_{0-8}$alkyl-$C_{3-7}$cycloalkyl, or —$C_{0-8}$alkyl-$C_{3-7}$cycloheteroalkyl, is optionally substituted with one to three $R^a$ substituents, each $R^1$ $C_{1-8}$alkyl of —$C_{1-8}$alkyl-aryl or —$C_{1-8}$alkyl-heteroaryl is optionally substituted with one to three $R^a$ substituents, and each $R^1$ aryl and heteroaryl (including in —$C_{1-8}$alkyl-aryl and —$C_{1-8}$alkyl-heteroaryl) is optionally substituted with one to three $R^b$ substituents;

$R^2$ is selected from the group consisting of
1) hydrogen,
2) $C_{1-4}$alkyl,
3) $C_{1-4}$alkoxy,
4) $C_{3-7}$cycloalkyl, and
5) —$C_{1-2}$alkyl-$C_{3-7}$cycloalkyl,
wherein the $R^2$ $C_{1-4}$alkyl, $C_{1-4}$alkoxy, $C_{3-7}$cycloalkyl or —$C_{1-2}$alkyl-$C_{3-7}$cycloalkyl is optionally substituted with one to three fluoro substituents;

W is selected from the group consisting of
1) $C_{1-8}$alkyl,
2) $C_{2-8}$alkenyl,
3) $C_{2-8}$alkynyl,
4) —$C_{0-8}$alkyl-$C_{3-7}$cycloalkyl,
5) —$C_{0-8}$alkyl-$C_{3-7}$cycloheteroalkyl,
6) aryl,
7) —$C_{1-4}$alkyl-aryl,
8) —$C_{0-4}$alkyl-O—$C_{0-4}$alkyl-aryl,
9) —$C_{0-4}$alkyl-S—$C_{0-4}$alkyl-aryl,
10) —$C_{0-4}$alkyl-$NR^g$—$C_{0-4}$alkyl-aryl,
11) heteroaryl, and
12) —$C_{1-4}$alkyl-heteroaryl,
wherein the W $C_{1-8}$alkyl, $C_{2-8}$alkenyl, $C_{2-8}$alkynyl, —$C_{0-8}$alkyl-$C_{3-7}$cycloalkyl, or —$C_{0-8}$alkyl-$C_{3-7}$cycloheteroalkyl, is optionally substituted with one to three $R^a$ substituents, each W $C_{1-4}$alkyl of —$C_{1-4}$alkyl-aryl or —$C_{1-4}$alkyl-heteroaryl (and any alkyl present in W—$C_{0-4}$alkyl-O—$C_{0-4}$alkyl-aryl, —$C_{0-4}$alkyl-S—$C_{0-4}$alkyl-aryl, or —$C_{0-4}$alkyl-$NR^g$—$C_{0-4}$alkyl-aryl) is optionally substituted with one to three $R^a$ substituents, and each W aryl and heteroaryl (including in —$C_{1-4}$alkyl-aryl, —$C_{1-4}$alkyl-heteroaryl, —$C_{0-4}$alkyl-O—$C_{0-4}$alkyl-aryl, —$C_{0-4}$alkyl-S—$C_{0-4}$alkyl-aryl, and —$C_{0-4}$alkyl-$NR^g$—$C_{0-4}$alkyl-aryl) is optionally substituted with one to three $R^b$ substituents;

each $R^a$ is independently selected from the group consisting of:
1) -halogen,
2) —$OR^e$,
3) —$S(O)_m R^e$,
4) —$S(O)_m NR^c R^d$,
5) —$C(O)R^e$,
6) —$OC(O)R^e$,
7) —$C(O)OR^e$,
8) —CN,
9) —$C(NH_2)$=NOH
10) —$C(O)NR^c R^d$,
11) —$NR^c R^d$,
12) —$NHC_{1-4}$alkyl-$C(O)R^e$,
13) —$NHC_{1-4}$alkyl-$C(O)OR^e$,
14) —$NHC_{1-4}$alkyl-$NR^c R^d$,
15) —$NHC_{1-4}$alkyl-$C(O)NR^c R^d$,
16) —$NHC_{1-4}$alkyl-$S(O)_m R^e$,
17) —$NHC_{1-4}$alkyl-$S(O)_m NR^c R^d$,
18) —$CF_3$,
19) —$OCF_3$,
20) —$OCHF_2$,
21) —$C_{3-6}$cycloalkyl,
22) —O—$C_{3-6}$cycloalkyl,
23) —$C_{4-6}$cycloheteroalkyl, and
24) —O—$C_{4-6}$cycloheteroalkyl, wherein each $R^a$ $C_{3-6}$cycloalkyl, and $C_{4-6}$cycloheteroalkyl is optionally substituted with one to three $R^h$ substituents and each $R^a$ $C_{1-4}$alkyl is optionally substituted with one to three halo substitutents;

each $R^b$ is independently selected from the group consisting of:
1) $C_{1-8}$alkyl,
2) $C_{2-8}$alkenyl,
3) $C_{2-8}$alkynyl,
4) halogen,
5) —$OR^e$,
6) —$S(O)_m R^e$,
7) —$S(O)_m NR^c R^d$,
8) —$C(O)R^e$,
9) —$OC(O)R^e$,
10) —$C(O)OR^e$,
11) —CN,
12) —$C(NH_2)$=NOH,
13) —$C(O)NR^c R^d$,
14) —$NR^c R^d$,
15) —$NHC_{1-4}$alkyl-$C(O)R^e$,
16) —$NHC_{1-4}$alkyl-$C(O)OR^e$,
17) —$NHC_{1-4}$alkyl-$NR^c R^d$,
18) —$NHC_{1-4}$alkyl-$C(O)NR^c R^d$,
19) —$NHC_{1-4}$alkyl-$S(O)_m R^e$,
20) —$NHC_{1-4}$alkyl-$S(O)_m NR^c R^d$,
21) —$NHC$(=$NH$)$NH_2$,
22) —$CF_3$,
23) —$OCF_3$,
24) —$OCHF_2$,
25) $C_{3-6}$cycloalkyl,
26) $C_{3-6}$cycloalkenyl,
27) —O—$C_{3-6}$cycloalkyl,
28) —$C_{1-6}$alkyl-$C_{3-6}$cycloalkyl,
29) —O—$C_{1-6}$alkyl-$C_{3-6}$cycloalkyl,
30) —$C_{4-10}$cycloheteroalkyl,
31) —$C_{4-10}$cycloheteroalkenyl,
32) —O—$C_{4-10}$cycloheteroalkyl,
33) —$C_{1-6}$alkyl-$C_{4-10}$cycloheteroalkyl,
34) —$C_{1-6}$alkyl-O—$C_{0-6}$alkyl-$C_{4-10}$cycloheteroalkyl,
35) aryl,
36) heteroaryl,
37) —O-aryl,
38) —O-heteroaryl,
39) —$C_{1-6}$alkyl-aryl,
40) —$C_{1-6}$alkyl-heteroaryl,
41) —O—$C_{1-6}$alkyl-aryl, and
42) —O—$C_{1-6}$alkyl-heteroaryl,
wherein each $R^b$ $C_{1-6}$alkyl, $C_{1-8}$alkyl, $C_{2-8}$alkenyl, $C_{2-8}$alkynyl, $C_{3-6}$cycloalkyl, $C_{3-6}$cycloalkyl, $C_{4-10}$cycloheteroalkenyl, and $C_{4-10}$cycloheteroalkyl is optionally substituted with one to four $R^h$ substituents, each $R^b$ $C_{1-4}$alkyl is optionally substituted with one to three halo substituents, and each $R^b$ aryl and heteroaryl is optionally substituted with one to three $R^i$ substituents; each $R^c$ and $R^d$ are each independently selected from the group consisting of:
1) hydrogen,
2) $C_{1-8}$alkyl,
3) —$S(O)_m$—$C_{1-4}$alkyl,
4) $C_{2-8}$alkenyl,
5) $C_{3-6}$cycloalkyl,
6) —$C_{1-6}$alkyl-$C_{3-6}$cycloalkyl,
7) $C_{4-10}$cycloheteroalkyl,
8) —$C_{1-6}$alkyl-$C_{4-10}$cycloheteroalkyl,
9) aryl,
10) heteroaryl, 11) —C$_{1-6}$alkyl-aryl, and
12) —C$_{1-6}$alkyl-heteroaryl,
wherein each R$^c$ and R$^d$ is optionally substituted with one to three R$^f$ substituents, or
R$^c$ and R$^d$ together with the atom(s) to which they are attached form a cycloheteroalkyl ring of 4 to 7 members containing 0 to 2 additional heteroatoms independently selected from oxygen, sulfur and —NR$^g$;
each R$^e$ is independently selected from the group consisting of:
1) hydrogen,
2) C$_{1-8}$alkyl,
3) C$_{2-8}$alkenyl,
4) C$_{3-6}$cycloalkyl,
5) —C$_{1-6}$alkyl-C$_{3-6}$cycloalkyl,
6) C$_{4-6}$cycloheteroalkyl,
7) —C$_{1-6}$alkyl-C$_{4-6}$cycloheteroalkyl,
8) aryl,
9) heteroaryl,
10) —C$_{1-6}$alkyl-aryl, and
11) —C$_{1-6}$alkyl-heteroaryl,
wherein each R$^e$ is optionally substituted with one to three R$^h$ substituents;
each R$^f$ is independently selected from the group consisting of:
1) halogen,
2) C$_{1-6}$alkyl,
3) —OH,
4) —OC$_{1-4}$alkyl,
5) —NH$_2$,
6) —NHC$_{1-3}$alkyl,
7) —N(CH$_3$)$_2$,
8) —S(O)$_m$C$_{1-4}$ alkyl,
9) —CN,
10) —CF$_3$,
11) —OCHF$_2$, and
12) —OCF$_3$,
wherein each R$^f$C$_{1-6}$alkyl is optionally substituted with one to three substituents independently selected from —OH, —NH$_2$, halogen, cyano, and —S(O)$_2$CH$_3$;
each R$^g$ is independently selected from the group consisting of:
1) hydrogen,
2) —C(O)R$^e$,
3) —SO$_2$R$^e$, and
4) C$_{1-6}$alkyl,
wherein R$^g$ C$_{1-6}$alkyl is optionally substituted with one to five fluoros;
each R$^h$ is independently selected from the group consisting of:
1) halogen,
2) C$_{1-6}$alkyl,
3) —C(O)NR$^c$R$^d$,
4) —OH,
5) oxo,
6) —NR$^c$R$^d$,
7) —N$^+$(CH$_3$)$_3$,
8) —OC$_{1-4}$alkyl,
9) —S(O)$_m$—C$_{1-4}$alkyl,
10) —CN,
11) —CH(=NH),
12) —C(=NH)NH$_2$,
13) —CF$_3$,
14) —OCHF$_2$,
15) —OCF$_3$,
16) aryl, and
17) heteroaryl, wherein each R$^h$ C$_{1-6}$alkyl is optionally substituted with one to three substituents independently selected from —OH, halogen, cyano, —NR$^c$R$^d$, and —S(O)$_2$CH$_3$;
each R$^i$ is independently selected from the group consisting of:
1) C$_{1-6}$alkyl,
2) halogen,
3) —OR$^e$,
4) oxo,
5) —S(O)$_m$—R$^e$,
6) —S(O)$_m$NR$^c$R$^d$,
7) —C(O)R$^e$,
8) —OC(O)R$^e$,
9) —C(O)OR$^e$,
10) —CN,
11) —C(O)NR$^c$R$^d$,
12) —NR$^c$R$^d$,
13) —NHC$_{0-4}$alkyl-C(O)R$^e$,
14) —NHC$_{1-4}$alkyl-C(O)OR$^e$,
15) —NHC$_{1-4}$alkyl-NR$^c$R$^d$,
16) —NHC$_{1-4}$alkyl-C(O)NR$^c$R$^d$,
17) —NHC$_{1-4}$alkyl-S(O)$_m$R$^e$,
18) —NHC$_{1-4}$alkyl-S(O)$_m$NR$^c$R$^d$,
19) —CF$_3$,
20) —OCF$_3$,
21) —OCHF$_2$,
22) C$_{3-6}$cycloalkyl,
23) —O—C$_{3-6}$cycloalkyl,
24) —C$_{1-2}$alkyl-C$_{3-6}$cycloalkyl,
25) —O—C$_{1-2}$alkyl-C$_{3-6}$cycloalkyl,
26) C$_{4-6}$cycloheteroalkyl,
27) —O—C$_{4-6}$cycloheteroalkyl,
28) —C$_{1-2}$alkyl-C$_{3-6}$cycloheteroalkyl,
29) —O—C$_{1-2}$alkyl-C$_{3-6}$cycloheteroalkyl,
30) aryl,
31) heteroaryl,
32) —C$_{1-6}$alkyl-aryl,
33) —C$_{1-6}$alkyl-heteroaryl,
34) —CH(=NH),
35) —C(=NH)NH$_2$,
36) —C(=O)NHCH$_3$,
37) —C(=O)NHSO$_2$CH$_3$, and
38) oxo;
wherein each R$^i$ C$_{1-6}$alkyl is optionally substituted with one to three substituents independently selected from: —OH, —OC$_{1-3}$alkyl, halogen, —NH$_2$, —N(CH$_3$)$_2$, cyano, and —S(O)$_2$C$_{1-6}$alkyl; and each R$^i$ C$_{4-6}$cycloheteroalkyl is optionally substituted with 1 or 2 substituents selected from —CH$_3$, —OH and oxo;
each m is independently selected from: 0, 1 or 2; and
each n is independently selected from: 0, 1, 2, 3 or 4.

In one aspect, the tetrazolyl is 1H-tetrazolyl. In another aspect, the tetrazolyl is 2H-tetrazolyl. In one aspect, at least one of R$_1$, R$_2$ or W contains a cyclic ring (e.g., an aryl, heteroaryl, cycloalkyl, heterocycloalkyl, including as part of a larger substituent, e.g., —C$_{1-4}$alkyl-aryl, or any of the substituents described herein).

As illustrated by the Examples provided below, compounds of Formula I inhibit one or more metallo-β-lactamases. Thus, compounds of Formula I can synergize the antibacterial effects of β-lactam antibiotics (e.g., imipenem, ceftazidime and piperacillin) against microorganisms normally resistant to β-lactam antibiotics as a result of the presence of the metallo-β-lactamases. Accordingly, in certain embodiments, the present invention includes combinations of a compound of Formula I with a β-lactam antibiotic suitable for use against metallo-β-lactamase producing bacteria such as *Pseudomonas* spp. and *Klebsiella* spp. The invention also includes compositions comprising a compound of Formula I or its pharmaceutically acceptable salt, and a pharmaceutically acceptable carrier. The invention further includes methods for treating bacterial infections and inhibiting bacterial growth by use of a compound of Formula I or its salt or a combination or composition containing the compound or its salt.

Embodiments, sub-embodiments, aspects and features of the present invention are either further described in or will be apparent from the ensuing description, examples and appended claims.

DETAILED DESCRIPTION OF THE INVENTION

As noted above, the present invention includes compounds of Formula I, wherein the compounds are metallo-β-lactamase inhibitors suitable for use in combination with β-lactam antibiotics, optionally with class A, C, and D β-lactamase inhibitors for the treatment of bacterial infections.

In a first embodiment of the invention, the compound is a compound of formula Ia or Ib, or a pharmaceutically acceptable salt thereof,

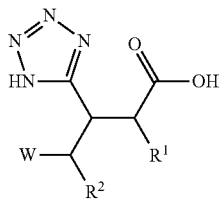
(Ia)

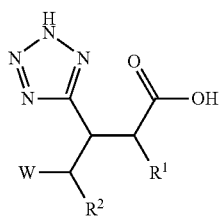
(Ib)

wherein:

$R^1$ is:
  a) —$C_{2-8}$ alkyl,
  b) —$C_{1-4}$ alkyl substituted with 1, 2, or 3 halo substituents or 1 substituent selected from —$C_{3-6}$cycloalkyl, —CN, —C(=O)$NH_2$, —OH, —$C_1$-$C_3$alkoxy, phenyl, and HetY,
  c) —$C_{2-6}$alkenyl,
  d) —$C_{3-6}$cycloalkyl, or
  e) HetY, $R^2$ is hydrogen, $C_{1-4}$alkyl, or $C_{1-4}$alkoxy;

HetY is a 4- to 6-membered saturated monocyclic ring with 1 heteroatom ring atom selected from N and O;

W is AryA; HetA; —$(CH_2)_{1-2}$-AryA; —CH($CH_3$)-phenyl; or cyclohexyl substituted with —COOH or —$NH_2$;

AryA is an aromatic ring system selected from:
  a) 5- to 6-membered monocyclic aromatic ring with 0, 1, 2 or 3 heteroatom ring atoms independently selected from N and S, optionally substituted with 1 or 2 substituents R; or
  b) 9- to 11-membered bicyclic aromatic ring system with 1, 2 or 3 heteroatom ring atoms selected from N, O, and S, optionally substituted with 1 substituent R' selected from Br, $C_{1-6}$alkyl, —$NH_2$, and —$NHCH_2CH_2OH$;

HetA is a 6-membered saturated monocyclic ring with 1 N ring atom, optionally substituted with 1 substituent selected from —C(=O)$CH_3$;

each R is independently
  halo;
  —$CF_3$;
  $C_{1-6}$alkyl optionally substituted with —$NR^xR^y$ or 1 or 2 —OH;
  $C_{3-6}$ cycloalkenyl optionally substituted with —$NR^xR^y$;
  —$(CH_2)_{0-1}NHR^z$;
  —CN;
  —C($NH_2$)=NOH;
  —C(=O)$NR^xR^y$;
  —C(=O)$NHR^z$;
  —C(=O)OH;
  —$NR^xR^y$;
  —$N^+(CH_3)_3$;
  —$NHCH_2CH_2CH(CF_3)NH_2$;
  —$NHCH_2C(=O)N(CH_3)_2$;
  —$NHCH_2CH_2SO_2NH_2$;
  —NHC(=NH)$NH_2$;
  —OH;
  $OR^z$;
  —$OCH_2CH(NH_2)CH_2OH$;
  —$SCH_3$;
  —$SO_2R^w$;
  AryB;
  —$NH(CH_2)_{0-2}$-AryB;
  —O-AryB;
  —$(CH_2)_{0-2}$-HetB;
  —$CH_2O(CH_2)_{0-2}$-HetB;
  —C(=O)—HetB;
  —$NH(CH_2)_{0-2}$-HetB;
  —O-HetB;

AryB is
  a) a 5- to 6-membered monocyclic aromatic ring with 0, 1, or 2 heteroatom ring atoms independently selected from N and S, optionally substituted with 1, 2 or 3 substituents independently selected from
    F;
    —$CH_3$;
    —$CH_2NH_2$;
    —$CH_2N(CH_3)_2$;
    —$CH_2CH_2NH_2$;
    —$CH_2C(CH_3)_2NH_2$;
    —$CH_2OH$;
    —$C(CH_3)_2OH$;
    —C(=O)$NR^xR^y$;
    —$NR^xR^y$;
    —NHC(=O)$CH_3$;
    —$NHSO_2CH_3$;
    —N($CH_3$)$SO_2CH_3$;
    —OH;
    —$OCH_3$;
    —$SO_2CH_3$;
    —$SO_2NH_2$;
    —$(CH_2)_{0-1}$-AryC;
    —$C_{0-2}$alkyl-HetC;
    O-HetC; or
  b) triazolyl;
  c) tetrazolyl;
  d) 1,3-dimethylpyrimidine-2,4(1H,3H)-dione; or e) a 9- to -10 membered bicyclic aromatic ring with 0, 1, 2 or 3 heteroatom ring atoms independently selected from N or O, optionally substituted with Br, —CH$_3$, —CN, —NH$_2$, or oxo;

HetB is
  a) a 4- to 6-membered saturated or monosaturated monocyclic ring with 1 or 2 heteroatom ring atoms independently selected from N and O, optionally substituted with 1, 2, 3, or 4 substituents independently selected from halo; —CF$_3$; C$_{1-6}$alkyl, C$_{1-6}$aminoalkyl; C$_{1-6}$hydroxyalkyl; —CH(=NH); —C(=NH)NH$_2$; —C(=O)CH$_3$; —C(=O)NHCH$_3$; —C(=O)NHSO$_2$CH$_3$; —NH$_2$; —NHSO$_2$CH$_3$, —OH; oxo; —SO$_2$CH$_3$; AryC; or HetC; or
  b) a 8- to 10-membered bicyclic saturated ring system with 1, 2 or 3 ring atoms independently selected from N or O, optionally substituted with 1 or 2 substituents independently selected from —CH$_3$ and oxo; wherein the rings in the bicyclic ring system are fused or spirocyclic;

AryC is phenyl, pyridinyl, or tetrazolyl;

HetC is a 4- to 6-membered saturated monocyclic ring with 1 or 2 heteroatom ring atoms independently selected from N and O, optionally substituted with 1 or 2 substituents selected from —CH$_3$, —OH and oxo;

each R$^x$ and R$^y$ is independently hydrogen or C$_{1-6}$alkyl;

each R$^z$ is independently —(CH$_2$)$_{0-1}$—C$_{3-6}$cycloalkyl optionally substituted with —NH$_2$; C$_{1-6}$aminoalkyl; or C$_{1-6}$hydroxyalkyl; and R$^w$ is selected from C$_{1-10}$alkyl and C$_{3-7}$cycloalkyl; and the other groups are as provided in the general formula I above.

In a second embodiment of the invention, the compound has the formula

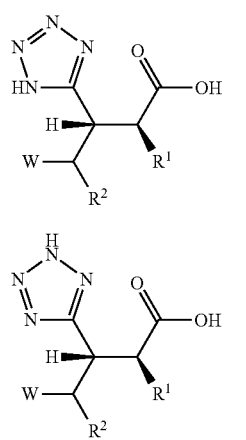

(Ic)

(Id)

or a pharmaceutically acceptable salt thereof, and the groups are as provided in the general formula I above or as in the first embodiment.

In a third embodiment of the invention, the compound is a compound of formula Ia or Ib, or a pharmaceutically acceptable salt thereof, wherein R$^1$ is —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)CH$_2$CH$_3$, —C(CH$_3$)$_3$, —CH$_2$CH$_2$CH$_2$CH$_3$, —CH(CH$_3$)CH$_2$CH$_2$CH$_3$, —CH$_2$CH$_2$CH$_2$CH(CH$_3$)$_2$, —CH$_2$CH$_2$CH$_2$CH$_2$CH(CH$_3$)$_2$, —CH$_2$CH$_2$F, —CH$_2$CHF$_2$, —CH$_2$CF$_3$, —CH$_2$CH$_2$CH$_2$CF$_3$, —CH$_2$-cyclopropyl, —CH$_2$-cyclopentyl, —CH$_2$CH$_2$-cyclohexyl, —CH$_2$CH$_2$CH$_2$CH$_2$CN, —CH$_2$CH$_2$CH$_2$CH$_2$C(=O)NH$_2$, —CH$_2$CH$_2$CH$_2$CH$_2$OH, —CH$_2$CH$_2$CH$_2$OCH$_3$, —CH$_2$-phenyl, —CH$_2$CH$_2$CH$_2$CH$_2$-phenyl, CH$_2$—CH(CH$_3$)-phenyl, —CH$_2$CH$_2$CH$_2$-piperidinyl, —CH$_2$-oxetanyl, —CH$_2$CH=CH$_2$, —CH$_2$CH$_2$CH=C(CH$_3$)$_2$, cyclopentyl, tetrahydrofuranyl, or tetrahydropyranyl; and the other groups are as provided in the first or second embodiment.

In a fourth embodiment of the invention, the compounds is a compound of formula Ia, Ib, Ic or Id, or a pharmaceutically acceptable salt thereof, wherein W is

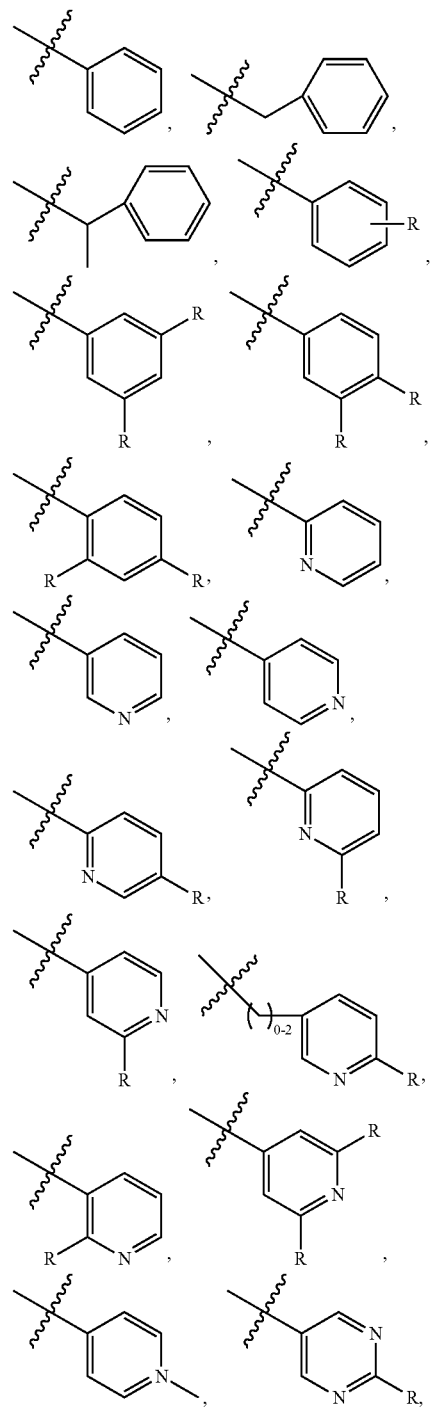

-continued

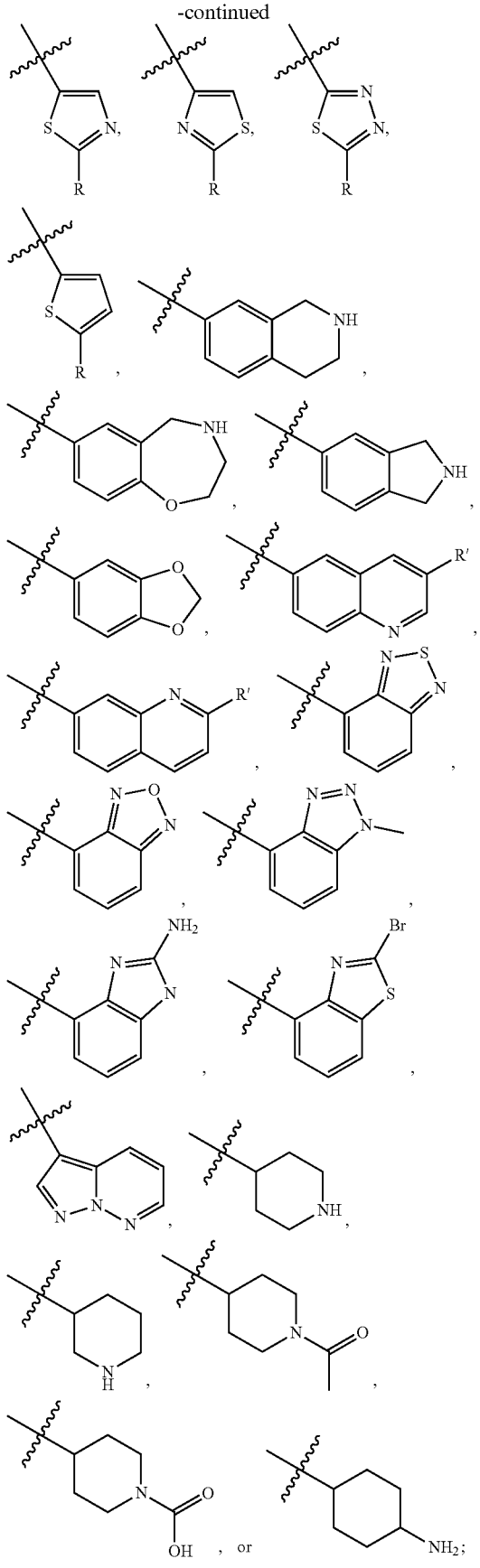

and the other groups are as provided in the first or second embodiment.

In a fourth embodiment of the invention, the compound is a compound of formula I, or a pharmaceutically acceptable salt thereof, wherein W is

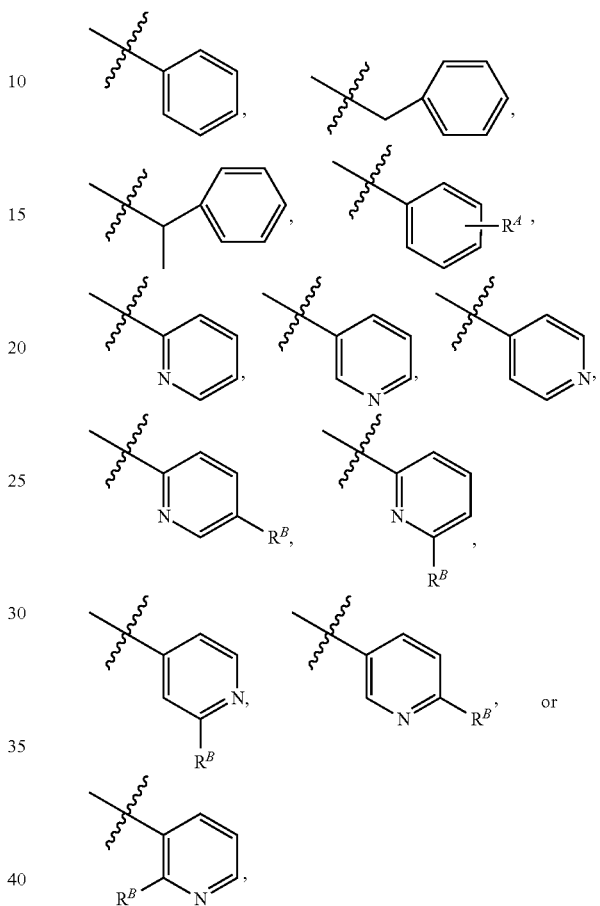

wherein
$R^A$ and $R^B$ are independently Br; F; Cl; —CF$_3$; —CH$_3$; —CH$_2$NH$_2$; —CH$_2$CH$_2$NH$_2$; —CN; —CH$_2$OH; —CONH$_2$; —CONCH$_3$; —CON(CH$_3$)$_2$; —CONH-cyclopropyl; —CONHCH$_2$-cyclopropyl; —CONHCH$_2$CH$_2$NH$_2$; —CONHCH$_2$CH$_2$OH; —COOH; —NH$_2$; —NHCH$_3$; —NHCH$_2$CH$_2$OH; —NHC(=NH)NH$_2$; —OH; —OCH$_2$CH$_2$NH$_2$; —NH-cyclopentyl-NH$_2$; —SO$_2$CH$_3$; —SO$_2$-cyclopropyl; AryB; HetB; —CO-piperazinyl; —CH$_2$-tetrahydropyranyl; —CH$_2$-piperidinyl optionally substituted with —NH$_2$; —NH-pyrrolidinyl; —NHCH$_2$-piperidinyl substituted with —OH; —NH-tetrahydroisoquinolinyl; —O-phenyl substituted with —CONH$_2$, —CH$_2$OH, —CH$_2$NH$_2$, —CH$_2$C(CH$_3$)$_2$NH$_2$, —CH(CH$_3$)NH$_2$, —CH$_2$CH$_2$NH$_2$, piperidinyl, pyrrolidinyl, or piperazinyl; —O-tetrahydroisoquinolinyl; —O-tetrahydroquinolinyl; or —O-pyridinyl optionally substituted with piperazinyl;
AryB is
1) phenyl substituted with —CH$_2$NH$_2$, —CH$_2$N(CH$_3$)$_2$, —CH$_2$OH, —CONH$_2$, —CONHCH$_3$, —NHSO$_2$CH$_3$, —SO$_2$CH$_3$, —SO$_2$NH$_2$, AryC, HetC, —CH$_2$—HetC, or tetrazolyl;
2) pyridinyl optionally substituted with —C(CH$_3$)$_2$OH, —NH$_2$, —N(CH$_3$)$_2$, —NH$_2$ or F;

3) piperazinyl optionally substituted with —CH$_3$, —CH$_2$-piperidinyl, —O-piperidinyl, or morpholinyl;
4) pyrimidinyl substituted with —NH$_2$, —N(CH$_3$)$_2$, —NHCH$_2$CH$_2$OH, —NHCOCH$_3$, —NCH$_3$SO$_2$CH$_3$, or HetC;
5) pyrazinyl substituted with two —CH$_3$,
6) pyrazolyl optionally substituted with 1 or 3 substitutents selected from —CH$_3$, phenyl, and —CH$_2$-pyridinyl;
7) dimethylpyrimidinedione;
8) tetrazolyl;
9) thiazolyl substituted with —CH$_2$OH;
10) 1,2,3,4-tetrahydroquinoline;
11) imidazopyridinone;
12) indazolyl;
13) isoindolinone;
14) isoindolinyl;
15) isoquinolinyl optionally substituted with —CN;
16) methylbenzotriazolyl;
17) benzooxazinone;
18) triazolopyridinyl; or
19) 1,2,3,4-tetrahydronaphthalen-2-amine;

HetB is
1) azetidinyl substituted with —NH$_2$; —CH$_2$NH$_2$; —CH$_2$CH$_2$NH$_2$; —C(CH$_3$)$_2$NH$_2$; —CH$_2$CH$_2$OH; —SO$_2$CH$_3$; morpholinyl; piperazinyl; (CH$_2$OH)$_2$; —CH$_2$NH$_2$ and —CH$_3$; or —OH and —CF$_3$;
2) pyrrolidinyl optionally substituted with —CH$_2$NH$_2$, —CH$_2$OH, —CONHCH$_3$, —NH$_2$, —OH, or AryC;
3) piperidinyl optionally substituted with —CH$_3$, —CH$_2$NH$_2$, —C(CH$_3$)$_2$NH$_2$, —CH$_2$OH, —CONHCH$_3$, —CH$_2$NHSO$_2$CH$_3$, —NH$_2$, —OH, —C(=NH)NH; —C(=NH$_2$)NH$_2$, or CH=NH;
4) piperazinyl substituted with —CH$_3$, —CH$_2$OH, —CH$_2$CH$_2$OH, —COCH$_3$, =O, or AryC,
5) morpholinyl;
6) dihydropyrrolyl;
7) tetrahydropyridinyl optionally substituted with —CH$_3$; or
8) octahydropyrrolo[1,2-a]pyrazine;
9) diazaspirononanyl;
10) diazaspirooctanyl;
11) 2,6-diazaspiro[3.4]octan-7-one; or
12) 7-methyl-5-oxa-2,7-diazaspiro[3.4]octan-6-one;

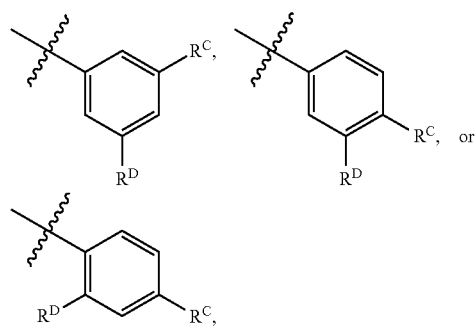

wherein
R$^C$ is F; Br; —CF$_3$; —CH$_2$NH$_2$; pyrrolidinyl; 2,5-dihydro-1H-pyrrole; pyridinyl substituted with —NH$_2$; or piperazinyl;
R$^D$ is F, Br, —CH$_3$, or —CF$_3$;

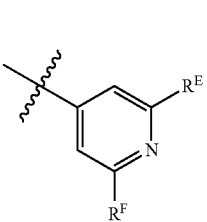

wherein
R$^E$ is Cl, —NH$_2$ or —NHCH$_2$CH$_2$OH;
R$^E$ is Cl;

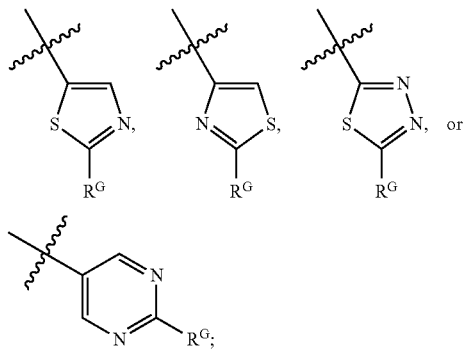

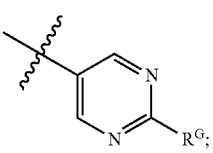

wherein R$^G$ is —NH$_2$, —N(CH$_3$)$_2$, —NHCH$_2$CH$_2$OH, —SCH$_3$, —SO$_2$CH$_3$, morpholinyl, pyrrolidinyl, piperidinyl, piperazinyl, 2,5-dihydro-1H-pyrrole, or —O-piperidinyl; or

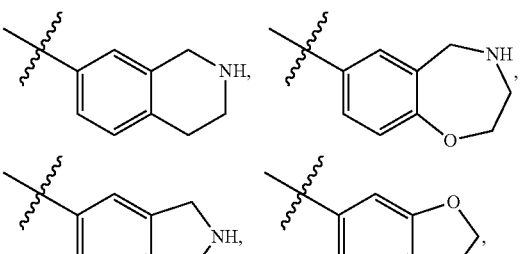

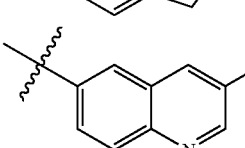

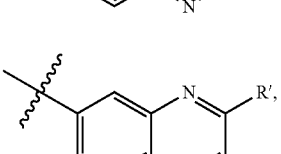

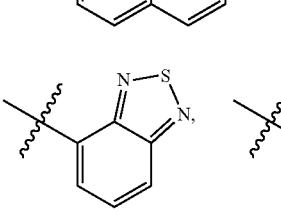

-continued

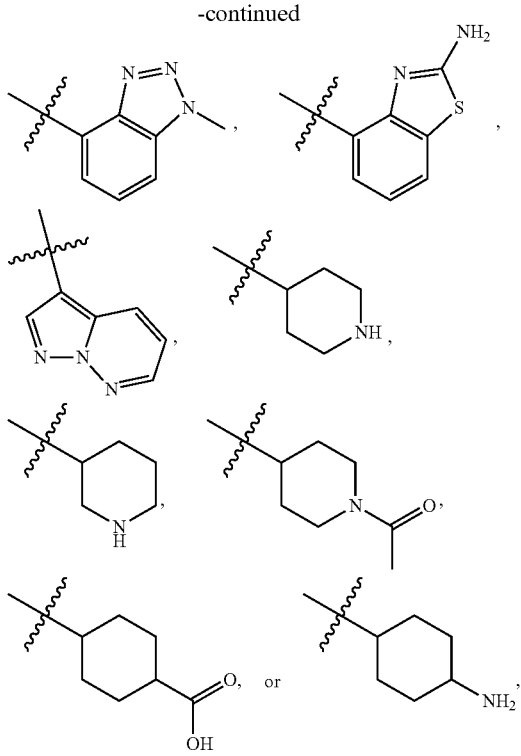

and the other groups are as provided in the general formula I above, or as in any of the first through third embodiments.

In one aspect of this embodiment, $R^A$ is Br; F; Cl; —$CF_3$; —$CH_3$; —$CH_2NH_2$; —$CH_2CH_2NH_2$; —CN; —$CH_2OH$; —$CONH_2$; —$CONCH_3$; —$CON(CH_3)_2$; —CONH-cyclopropyl; —$CONHCH_2$-cyclopropyl; —$CONHCH_2CH_2NH_2$; —$CONHCH_2CH_2OH$; —COOH; —$NH_2$; —$SO_2CH_3$; AryB; HetB; —CO-piperazinyl; —$CH_2$-tetrahydropyranyl; or —$CH_2$-piperidinyl optionally substituted with —$NH_2$;

AryB is
1) phenyl substituted with —$CH_2NH_2$, —$CH_2N(CH_3)_2$, —$CH_2OH$, —$CONH_2$, —$CONHCH_3$, —$NHSO_2CH_3$, —$SO_2CH_3$, —$SO_2NH_2$, HetC, —$CH_2$—HetC, or tetrazolyl;
2) pyridinyl optionally substituted with —$C(CH_3)_2OH$, —$NH_2$, —$N(CH_3)_2$, —$NH_2$ or F;
3) piperazinyl optionally substituted with —$CH_3$, —$CH_2$-piperidinyl, —O-piperidinyl, or morpholinyl;
4) pyrimidinyl substituted with —$NHCH_2CH_2OH$, —$NCH_3SO_2CH_3$, or HetC;
5) pyrazinyl substituted with two —$CH_3$;
6) pyrazolyl optionally substituted with 1 to 3 substitutents selected from —$CH_3$, phenyl, and —$CH_2$-pyridinyl;
7) dimethylpyrimidinedione;
8) tetrazolyl;
9) thiazolyl substituted with —$CH_2OH$;
10) 1,2,3,4-tetrahydroquinoline;
11) imidazopyridinone;
12) isoindolinone;
13) isoindolinyl;
14) isoquinolinyl;
15) methylbenzotriazolyl;
16) triazolopyridinyl; or
17) 1,2,3,4-tetrahydronaphthalen-2-amine;

HetB is
1) pyrrolidinyl optionally substituted with —$NH_2$;
2) piperidinyl optionally substituted with —$CH_3$, —$NH_2$, —OH, —CH=NH, or —C(=NH)NH;
3) piperazinyl substituted with —$CH_3$, —$CH_2OH$, —$CH_2CH_2OH$, —$COCH_3$, =O, or AryC;
4) morpholinyl;
5) dihydropyrrolyl;
6) tetrahydropyridinyl optionally substituted with —$CH_3$; or
7) octahydropyrrolo[1,2-a]pyrazine.

In another aspect of this embodiment, $R^B$ is Br; Cl; —$CH_3$; —CN; —$CONH_2$; —COOH; —$NH_2$; —$NHCH_3$; —$NHCH_2CH_2OH$; —OH; —NH-cyclopentyl-$NH_2$; —$SO_2$-cyclopropyl; AryB; HetB; —NH-tetrahydroisoquinolinyl; —O-phenyl substituted with —$CH_2NH_2$; —NH-pyrrolidinyl; —$NHCH_2$-piperidinyl substituted with —OH; —O-phenyl substituted with —$CONH_2$, —$CH_2OH$, —$CH_2NH_2$, —$CH_2C(CH_3)_2NH_2$, —$CH(CH_3)NH_2$, —$CH_2CH_2NH_2$, piperidinyl, pyrrolidinyl, or piperazinyl; —O-tetrahydroisoquinolinyl; —O-tetrahydroquinolinyl; or —O-pyridinyl optionally substituted with piperazinyl;

AryB is
1) —$NHCH_2CH_2OH$;
2) —$OCH_2CH_2NH_2$;
3) phenyl substituted with —$CH_2OH$, —$CH_2NH_2$, —$SO_2NH_2$, AryC, HetC;
4) pyridinyl substituted with —$NH_2$;
5) pyrimidinyl substituted with —$NH_2$, —$N(CH_3)_2$, or —$NHCOCH_3$;
6) pyrazolyl substituted with three —$CH_3$;
7) isoindolinyl;
8) indazolyl;
9) isoquinolinyl substituted with —CN; or
10) benzooxazinone;

HetB is
1) azetidinyl substituted with —$NH_2$; —$CH_2NH_2$; —$CH_2CH_2NH_2$; —$C(CH_3)_2NH_2$; —$CH_2CH_2OH$; —$SO_2CH_3$; morpholinyl; piperazinyl; $(CH_2OH)_2$; —$CH_2NH_2$ and —$CH_3$; or —OH and —$CF_3$;
2) tetrahydropyridinyl;
3) pyrrolidinyl optionally substituted with —$CH_2NH_2$, —$CH_2OH$, —$CONHCH_3$, —$NH_2$, —OH, or AryC;
4) piperidinyl optionally substituted with —$CH_2NH_2$, —$C(CH_3)_2NH_2$, —$CH_2OH$, —$CONHCH_3$, —$CH_2NHSO_2CH_3$, —C(=$NH_2$)$NH_2$, or —CH=NH;
5) piperazinyl optionally substituted with —$CH_3$;
6) dihydropyrrolyl;
7) diazaspirononanyl;
8) diazaspirooctanyl;
9) 2,6-diazaspiro[3.4]octan-7-one; or
10) 7-methyl-5-oxa-2,7-diazaspiro[3.4]octan-6-one.

In a fifth embodiment of the invention, the compound is a compound of formula Ia, Ib, Ic, or Id, or a pharmaceutically acceptable salt thereof, wherein
$R^1$ is selected from the group consisting of:
a) —$C_{2-4}$ alkyl,
b) ethyl substituted with 3 halo substituents, or
c) —$C_{3-6}$cycloalkyl,
$R^2$ is hydrogen;
W is AryA; —$CH_2$-phenyl; or —$CH(CH_3)$-phenyl;
AryA is an aromatic ring system selected from:
a) 5- to 6-membered monocyclic aromatic ring with 0, 1, or 2 heteroatom ring atoms independently selected from N and S, optionally substituted with 1 or 2 substituents R; or b) 9- to 10-membered bicyclic aromatic ring system with 1, 2 or 3 heteroatom ring atoms selected from N and S, substituted with 1 substituent selected from $C_{1-6}$alkyl and —$NH_2$;

each R is independently fluoro $NHR^z$, —$NR^xR^y$—NHC(=NH)$NH_2$; —$OR^z$, AryB, —O-AryB, or —$(CH_2)_{0-1}$-HetB;

AryB is a 5- to 6-membered monocyclic aromatic ring with 0, 1, or 2 N ring atoms, optionally substituted with 1 substituent selected from —$CH_2NH_2$, —$CH_2OH$, —C(=O)$NR^xR^y$, —$NR^xR^y$, —$NHSO_2CH_3$, and HetC;

HetB is a) a 5- to 6-membered saturated or monosaturated monocyclic ring with 1 or 2 N ring atoms, optionally substituted with 1 substituent selected from $C_{1-6}$hydroxyalkyl, —CH(=NH), —C(=NH)$NH_2$, and —OH; or
b) a 9-membered saturated spirocyclic ring system with 2 N ring atoms;

HetC is a 6-membered saturated monocyclic ring with 1 N ring atom;

each $R^x$ and $R^y$ is independently hydrogen or methyl; and each $R^z$ is independently $C_{1-6}$aminoalkyl or $C_{1-6}$hydroxyalkyl; and the other groups are as provided in any of the first through fourth embodiments.

In a sixth embodiment of the invention, the compound is a compound of formula Ia, Ib, Ic, or Id, or a pharmaceutically acceptable salt thereof, wherein AryA is a monocyclic ring selected from thiazolyl, phenyl, and pyridinyl, wherein the monocyclic ring optionally substituted with 1 or 2 R substituents; or
a bicyclic ring selected from quinolinyl, benzo[d]thiazolyl, and 1H-benzo[d][1,2,3]triazole, wherein the bicyclic is optionally substituted with one substituent selected from $C_1$-$C_6$alkyl and —$NH_2$;

AryB is a monocyclic ring selected from pyrazolyl, phenyl or pyridyl, wherein the monocyclic is optionally substituted with one substituent selected from —$CH_2NH_2$, —$CH_2OH$, —C(=O)$NR^xR^y$, —$NR^xR^y$, —$NHSO_2CH_3$, and HetC; and HetB is a monocyclic ring selected from pyrrolidinyl, dihydropyrrolyl, piperidinyl, or piperazinyl, wherein the monocyclic is optionally substituted with 1 substituent selected from $C_1$-$C_6$hydroxyalkyl, —CH(=NH), —C(=NH)$NH_2$, and —OH; or diazaspirononanyl; and the other groups are as provided in the general formula I above, or as in any of the first through fifth embodiments.

In a seventh embodiment of the invention, the compound is a compound of formula I, Ia, Ib, Ic, or Id, or a pharmaceutically acceptable salt thereof, wherein W is
1) phenyl optionally substituted with
a) phenyl substituted with —$CONH_2$, —$NHSO_2CH_3$, or piperidinyl,
b) pyridinyl substituted with —$NH_2$,
c) pyrrolidinyl,
d) pyrrolidinyl and fluoro,
e) piperidinyl substituted with —CH=NH,
f) piperidinyl substituted with —CH(=NH)$NH_2$,
g) piperizinyl and fluoro,
h) dihydropyrrolyl,
i) pyrazolyl, or
j) —$CH_2$-piperazinyl;
2) —$CH_2$-phenyl;
3) —CH($CH_3$)-phenyl;
4) pyridinyl optionally substituted with
a) —$NH_2$,
b) —$NHCH_3$,
c) —$NHCH_2CH_2NH_2$,
d) —$NHCH_2CH_2OH$,
e) —NHC(=NH)$NH_2$,
f) pyrrolidinyl optionally substituted with —OH,
g) piperidinyl optionally substituted with —$CH_2OH$,
h) phenyl substituted with —$CH_2NH_2$ or —$CH_2OH$,
i) —O-phenyl substituted with —$CH_2NH_2$,
j) pyridinyl substituted with —$NH_2$, or
k) diazaspirononanyl,
5) thiazolyl substituted with —$NH_2$,
6) quinolinyl substituted with —$NH_2$,
7) benzo[d]thiazolyl substituted with —$NH_2$, or
8) 1H-benzo[d][1,2,3]triazole] substituted with —$CH_3$;
and the other groups are as provided in the general formula I above, or as in any of the first through sixth embodiments.

In another embodiment of the invention, the compound of the invention is selected from the exemplary species depicted in EXAMPLES 1-456 shown below, and pharmaceutically acceptable salts thereof.

In another embodiment of the invention, the compound of the invention is selected from the exemplary species depicted in EXAMPLES 4, 8, 55, 60, 61, 62, 63, 72, 78, 79, 80, 88, 96, 100, 101, 109, 111, 112, 113, 114, 115, 116, 121, 122, 123, 129, 130, 131, 134, 146, 148, 152, 155, 176, 177, 265, 266, 274, 296, 297, 308, 313, 314, 341, 349, 351, 395, 402, 420, 422, 427, 428, 431, shown below, and pharmaceutically acceptable salts thereof.

Reference to different embodiments with respect to Formula I compounds, specifically includes different embodiments of Formula I such as Formula Ia, Ib, Ic, and Id, sub-embodiments of Formula Ia, Ib, Ic, and Id, other embodiments provided herein, and individual compounds described herein. In certain embodiments, Formulas Ia, Ib, Ic, and Id can encompass each of the specific definitions for substituents in Formula I.

Other embodiments of the present invention include the following:

(a) A pharmaceutical composition comprising an effective amount of a compound of Formula I, as defined above, or a pharmaceutically acceptable salt thereof, and a pharmaceutically acceptable carrier.

(b) The pharmaceutical composition of (a), further comprising an effective amount of a β-lactam antibiotic.

(c) The pharmaceutical composition of (b), wherein the β-lactam antibiotic is selected from the group consisting of imipenem, ertapenem, meropenem, doripenem, biapenem, panipenem, ticarcillin, ampicillin, amoxicillin, carbenicillin, piperacillin, azlocillin, mezlocillin, ticarcillin, cefoperazone, cefotaxime, ceftriaxone, and ceftazidime.

(d) The pharmaceutical composition of (b), wherein the β-lactam antibiotic is imipenem.

(e) The pharmaceutical composition of (b), wherein the β-lactam antibiotic is ceftazidime.

(f) The pharmaceutical composition of (b), wherein the β-lactam antibiotic is piperacillin.

(g) The pharmaceutical composition of (a), further comprising effective amounts of a β-lactam antibiotic and a renal dehydropeptidase (DHP) inhibitor.

(h) The pharmaceutical composition of (g), wherein the β-lactam antibiotic is imipenem, and the DHP inhibitor is cilastatin or a pharmaceutically acceptable salt thereof.

(i) A combination of effective amounts of a compound of Formula I as defined above, or a pharmaceutically acceptable salt thereof, and a β-lactam antibiotic.

(j) The combination of (i), wherein the β-lactam antibiotic is selected from the group consisting of imipenem, ertapenem, meropenem, doripenem, biapenem, panipenem, ticarcillin, ampicillin, amoxicillin, carbenicillin, piperacillin, azlocillin, mezlocillin, ticarcillin, cefoperazone, cefotaxime, ceftriaxone, and ceftazidime.

(k) The combination of (i), wherein the β-lactam antibiotic is imipenem.

(l) The combination of (i), wherein the β-lactam antibiotic is ceftazidime.

(m) The combination of (i), wherein the β-lactam antibiotic is piperacillin.

(n) A combination of effective amounts of a compound of Formula I as defined above, or a pharmaceutically acceptable salt thereof, a β-lactam antibiotic and a DHP inhibitor.

(o) The combination of (n), wherein the β-lactam antibiotic is imipenem, and the DHP inhibitor is cilastatin or a pharmaceutically acceptable salt thereof.

(p) A method for inhibiting beta-lactamase and/or treating a bacterial infection which comprises administering to a subject in need of such treatment an effective amount of a compound of Formula I or a pharmaceutically acceptable salt thereof, optionally in combination with an effective amount of a β-lactam antibiotic.

(q) A method for inhibiting beta-lactamase and/or treating a bacterial infection which comprises administering to a subject in need of such treatment an effective amount of a compound of Formula I, or a pharmaceutically acceptable salt thereof, in combination with effective amounts of a β-lactam antibiotic and a DHP inhibitor.

(r) A method for treating a bacterial infection which comprises administering to a subject in need of such treatment a therapeutically effective amount of the composition of (a), (b), (c), (d), (e), (f), (g) and (h).

(s) A method for treating a bacterial infection which comprises administering to a subject in need of such treatment a therapeutically effective amount of the combination (i), (j), (k), (l), (m), (n) and (o).

(t) The method of treating a bacterial infection as set forth in (p), (q), (r), or (s), wherein the bacterial infection is due to *Pseudomonas* spp., *Klebsiella* spp., *Enterobacter* spp., *Escherichia* spp., *Morganella* spp., *Citrobacter* spp., *Serratia* spp. or *Acintetobacter* spp.

The present invention also includes a compound of Formula I, or a pharmaceutically acceptable salt thereof, (i) for use in, (ii) for use as a medicament for, or (iii) for use in the preparation (or manufacture) of a medicament for, medicine or inhibiting beta-lactamase activity or treating bacterial infection. In these uses, the compounds of the present invention can optionally be employed in combination with one or more β-lactam antibiotics and/or one or more DHP inhibitors.

Additional embodiments of the invention include the pharmaceutical compositions, combinations and methods set forth in (a)-(t) above and the uses set forth in the preceding paragraph, wherein the compound of the present invention employed therein is a compound of one of the embodiments, sub-embodiments, classes or sub-classes described above. The compound may optionally be used in the form of a pharmaceutically acceptable salt in these embodiments.

In the embodiments of the compounds and salts provided above, it is to be understood that each embodiment may be combined with one or more other embodiments, to the extent that such a combination provides a stable compound or salt and is consistent with the description of the embodiments. It is further to be understood that the embodiments of compositions and methods provided as (a) through (t) above are understood to include all embodiments of the compounds and/or salts, including such embodiments as result from combinations of embodiments.

Additional embodiments of the present invention include each of the pharmaceutical compositions, combinations, methods and uses set forth in the preceding paragraphs, wherein the compound of the present invention or its salt employed therein is substantially pure. With respect to a pharmaceutical composition comprising a compound of Formula I or its salt and a pharmaceutically acceptable carrier and optionally one or more excipients, it is understood that the term "substantially pure" is in reference to a compound of Formula I or its salt per se; i.e., the purity of the active ingredient in the composition.

The term "metallo-β-lactamase inhibitor" refers to a compound which is capable of inhibiting metallo-β-lactamase activity. As used herein, inhibiting metallo-β-lactamase activity means inhibiting the activity of a class B metallo-β-lactamase. For antimicrobial applications inhibition at a 50% inhibitory concentration is preferably achieved at or below about 100 micrograms/mL, or at or below about 50 micrograms/mL, or at or below about 25 micrograms/mL. The terms "class A", "class B", "class C", and "class D" β-lactamases are understood by those skilled in the art and are described in S. G. Waley, β-lactamase: mechanisms of action, in The Chemistry of β-Lactams, M. I. Page, Ed.; Chapman and Hall, London, (1992) 198-228.

The term "metallo-β-lactamase" denotes a metalloprotein capable of inactivating a β-lactam antibiotic. The β-lactamase can be an enzyme which catalyzes the hydrolysis of the β-lactam ring of a β-lactam antibiotic. The metallo-β-lactamase can be, for example, a zinc metallo-β-lactamase. β-Lactamases of interest include those disclosed in, e.g., S. G. Waley, β-lactamase: mechanisms of action, in The Chemistry of β-Lactams, M. I. Page, Ed.; Chapman and Hall, London, (1992) 198-228. β-Lactamases of particular interest herein include a metallo-β-lactamases of *Escherichia coli* (such as New Delhi Metallo-b-lactamase, NDM), *Serratia marcescens* (such as IMP), and *Klebsiella* spp. (such as Verona integron-encoded metallo-β-lactamase, VIM).). Additional metallo-β-lactamases of interest herein include SPM-, GIM-, SIM-, KHM-, AIM-, DIM-, SMB-, TMB-, and FIM-type enzymes.

The term "antibiotic" refers to a compound or composition which decreases the viability of a microorganism, or which inhibits the growth or proliferation of a microorganism. The phrase "inhibits the growth or proliferation" means increasing the generation time (i.e., the time required for the bacterial cell to divide or for the population to double) by at least about 2-fold. Preferred antibiotics are those which can increase the generation time by at least about 10-fold or more (e.g., at least about 100-fold or even indefinitely, as in total cell death). As used in this disclosure, an antibiotic is further intended to include an antimicrobial, bacteriostatic, or bactericidal agent. Examples of antibiotics suitable for use with respect to the present invention include penicillins, cephalosporins and carbapenems.

The term "β-lactam antibiotic" refers to a compound with antibiotic properties that contains a β-lactam functionality. Non-limiting examples of β-lactam antibiotics useful with respect to the invention include penicillins, cephalosporins, penems, carbapenems, and monobactams.

The term "about", when modifying the quantity (e.g., kg, L, or equivalents) of a substance or composition, or the value of a physical property, or the value of a parameter characterizing a process step (e.g., the temperature at which a process step is conducted), or the like refers to variation in the numerical quantity that can occur, for example, through typical measuring, handling and sampling procedures involved in the preparation, characterization and/or use of the substance or composition; through inadvertent error in these procedures; through differences in the manufacture, source, or purity of the ingredients employed to make or use the compositions or carry out the procedures; and the like. In certain embodiments, "about" can mean a variation of ±0.1, 0.2, 0.3, 0.4, 0.5, 1.0, 2.0, 3.0, 4.0, or 5.0 of the appropriate unit. In certain embodiments, "about" can mean a variation of ±1%, 2%, 3%, 4%, 5%, 10%, or 20%.

Another embodiment of the present invention is a compound of Formula I, or a pharmaceutically acceptable salt thereof, as originally defined or as defined in any of the foregoing embodiments, sub-embodiments, aspects, classes or sub-classes, wherein the compound or its salt is in a substantially pure form. As used herein "substantially pure" means suitably at least about 60 wt. %, typically at least about 70 wt. %, preferably at least about 80 wt. %, more preferably at least about 90 wt. % (e.g., from about 90 wt. % to about 99 wt. %), even more preferably at least about 95 wt. % (e.g., from about 95 wt. % to about 99 wt. %, or from about 98 wt. % to 100 wt. %), and most preferably at least about 99 wt. % (e.g., 100 wt. %) of a product containing a compound of Formula I or its salt (e.g., the product isolated from a reaction mixture affording the compound or salt) consists of the compound or salt. The level of purity of the compounds and salts can be determined using a standard method of analysis such as thin layer chromatography, gel electrophoresis, high performance liquid chromatography, and/or mass spectrometry. If more than one method of analysis is employed and the methods provide experimentally significant differences in the level of purity determined, then the method providing the highest level of purity governs. A compound or salt of 100% purity is one which is free of detectable impurities as determined by a standard method of analysis.

Recitation or depiction of a specific compound in the claims (i.e., a species) without a specific stereoconfiguration designation, or with such a designation for less than all chiral centers, is intended to encompass the racemate, racemic mixtures, each individual enantiomer, a diastereoisomeric mixture and each individual diastereomer of the compound where such forms are possible due to the presence of one or more asymmetric centers.

With respect to a compound of the invention which has one or more asymmetric centers and can occur as mixtures of stereoisomers, a substantially pure compound can be either a substantially pure mixture of the stereoisomers or a substantially pure individual diastereomer or enantiomer. All isomeric forms of these compounds, whether individually or in mixtures, are within the scope of the present invention.

Definitions:

"Alkyl" means saturated carbon chains which may be linear or branched or combinations thereof, unless the carbon chain is defined otherwise. Other groups having the prefix "alk", such as alkoxy and alkanoyl, also may be linear or branched, or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon-carbon double bond, and which may be linear or branched, or combinations thereof, unless otherwise defined. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched, or combinations thereof, unless otherwise defined. Examples of alkynyl include ethynyl, propargyl, 3-methyl-1-pentynyl, 2-heptynyl and the like.

"Aromatic ring system" means monocyclic, bicyclic or tricyclic aromatic ring or ring system containing 5-14 ring atoms, wherein at least one of the rings is aromatic. The term may be used to describe a carbocyclic ring fused to an aryl group. For example, a 5-7-membered cycloalkyl can be fused through two adjacent ring atoms to a 5-6-membered heteroaryl containing 1, 2, or 3 heteroatom ring atoms selected from N, O, and S. In another example, a heteromonocyclic ring is fused through two ring atoms to a phenyl or 5-6-membered heteroaryl containing 1, 2, or 3 heteroatoms selected from N, O, and S.

"Aryl" means a monocyclic, bicyclic or tricyclic carbocyclic aromatic ring or ring system containing 6-14 carbon atoms, wherein at least one of the rings is aromatic. Examples of aryl include phenyl and naphthyl. In one embodiment of the present invention, aryl is phenyl.

"Cycloalkyl" means a saturated monocyclic, bicyclic or bridged carbocyclic ring, having a specified number of carbon atoms. Examples of cycloalkyl include cyclopropyl, cyclobutyl, cyclopentyl, cyclohexyl, cycloheptyl, indanyl, and the like. In one embodiment of the present invention, cycloalkyl is selected from: cyclopropane, cyclobutane, cyclopentane, and cyclohexane.

"Cycloalkenyl" means a nonaromatic monocyclic or bicyclic carbocyclic ring containing at least one double bond. Examples of cycloalkenyl include cyclopropenyl, cyclobutenyl, cyclopentenyl, cyclohexenyl, cycloheptenyl, cyclooxtenyl and the like.

"Cycloheteroalkyl" means a saturated or partly unsaturated non-aromatic monocyclic, bicyclic or bridged carbocyclic ring or ring system containing at least one ring heteroatom selected from N, NH, S (including SO and $SO_2$) and O. When a cycloheteroalkyl contains two rings, the rings may be fused or spirocyclic. The cycloheteroalkyl ring may be substituted on the ring carbons and/or the ring nitrogen(s). Examples of cycloheteroalkyl include tetrahydrofuran, piperazine, piperidine, morpholine, oxetane, tetrahydropyran, indolinyl, isoindolinyl, azabicyclooctane, hexose, pentose, isosorbide and isomannide, dianhydromannitol, 1, 4:3, 6-dianhydromannitol, 1, 4:3, 6-dianhydro[D]mannitol, hexahydrofuro[3,2-b]furan, and 2,3,3a,5,6,6a-hexahydrofuro[3,2-b]furan. In one embodiment of the present invention, cycloheteroalkyl is selected from: oxetane, tetrahydropyran, azetidine, tetrahydrothiopyran and pyrrolidine. In another embodiment of the present invention cycloheteroalkyl is selected from: piperidine, piperazine, azetidine, pyrrolidine, morpholine and spiro(indene-1,4-piperidine).

"Cycloheteroalkenyl" means a nonaromatic monocyclic, bicyclic or bridged carbocyclic ring or ring system containing at least one double bond and containing at least one heteroatom selected from N, NH, S and O.

"Heteroaryl" means monocyclic, bicyclic or tricyclic ring or ring system containing 5-14 carbon atoms and containing at least one ring heteroatom selected from N, NH, S (including SO and $SO_2$) and O, wherein at least one of the heteroatom containing rings is aromatic. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzisoxazolyl, benzoxazolyl, benzothiazolyl, benzimidazolyl, benzopyrazolyl, benzofuranyl, benzothiophenyl (including S-oxide and dioxide), benzotriazolyl, furo(2,3-b)pyridyl, quinolyl, indolyl, isoquinolyl, quinazolinyl, dibenzofuranyl, and the like. In one embodiment of the present invention, heteroaryl is selected from: pyridine, pyrimidine, thiazole, benzimidazole, benzthiazole, benzoxazole, and benzisoxazole. In another embodiment of the present invention, heteroaryl is pyridine.

"Halogen" includes fluorine, chlorine, bromine and iodine.

"Oxo" means an oxygen atom connected to another atom by a double bond and is can be represented "=O".

When any variable (e.g., $R^1$, $R^a$, etc.) occurs more than one time in any constituent or in formula I, its definition on each occurrence is independent of its definition at every other occurrence. Also, combinations of substituents and/or variables are permissible only if such combinations result in stable compounds. A squiggly line across a bond in a substituent variable represents the point of attachment.

Under standard nomenclature used throughout this disclosure, the terminal portion of the designated side chain is described last, preceded by the adjacent functionality toward the point of attachment.

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

When a group, e.g., $C_{1-8}$alkyl, is indicated as being substituted, such substitutions can also be occur where such group is part of a larger substituent, e.g., —$C_{1-8}$alkyl-$C_{3-7}$cycloalkyl and —$C_{1-8}$alkyl-aryl.

In the compounds of formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of formula I. For example, different isotopic forms of hydrogen (H) include protium ($^1$H) and deuterium ($^2$H or D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within formula I can be prepared without undue experimentation by conventional techniques well known to those skilled in the art or by processes analogous to those described in the EXAMPLES herein using appropriate isotopically-enriched reagents and/or intermediates.

Unless expressly stated to the contrary in a particular context, any of the various cyclic rings and ring systems described herein may be attached to the rest of the compound at any ring atom (i.e., any carbon atom or any heteroatom) provided that a stable compound results.

Unless expressly stated to the contrary, all ranges cited herein are inclusive. For example, a heteroaromatic ring described as containing from "1 to 4 heteroatoms" means the ring can contain 1, 2, 3 or 4 heteroatoms. It is also to be understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, 3 heteroatoms, and 4 heteroatoms. Similarly, $C_{1-6}$ when used with a chain, for example an alkyl chain, means that the chain can contain 1, 2, 3, 4, 5 or 6 carbon atoms. It also includes all ranges contained therein including $C_{1-5}$, $C_{1-4}$, $C_{1-3}$, $C_{1-2}$, $C_{2-6}$, $C_{3-6}$, $C_{4-6}$, $C_{5-6}$, and all other possible combinations.

A "stable" compound is a compound which can be prepared and isolated and whose structure and properties remain or can be caused to remain essentially unchanged for a period of time sufficient to allow use of the compound for the purposes described herein (e.g., therapeutic administration to a subject). The compounds of the present invention are limited to stable compounds embraced by Formula I.

The term "compound" refers to the free compound and, to the extent they are stable, any hydrate or solvate thereof. A hydrate is the compound complexed with water, and a solvate is the compound complexed with an organic solvent.

As indicated above, the compounds of the present invention can be employed in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). A suitable pharmaceutically acceptable salt is a salt formed by treating the compound of the invention (e.g., a compound of Formula I) with one molar equivalent of a mild base (e.g., sodium carbonate, sodium bicarbonate, potassium bicarbonate, or sodium acetate). In this case, M is a cation, such as $Na^+$ in the event of treatment with a sodium base.

The compound of the invention can also be employed in the form of a prodrug. In certain aspects of this embodiment, the hydrogen in —COOH in formula I can be replaced with any the following groups: $C_{1-6}$alkyl, $C_{3-6}$cycloalkyl, —$C_{1-6}$alkyl-$C_{3-6}$cycloalkyl, $C_{3-7}$cycloheteroalkyl, —$C_{1-6}$alkyl-$C_{3-7}$cycloheteroalkyl, aryl, —$C_{1-10}$alkyl-aryl, heteroaryl, and —$C_{1-10}$alkyl-heteroaryl. In certain aspects of this embodiment, the $C_{1-6}$alkyl, $C_{3-6}$cycloalkyl, or $C_{3-7}$cycloheteroalkyl can be substituted. In other aspects of this embodiment, each aryl and heteroaryl can be substituted.

As set forth above, the present invention includes pharmaceutical compositions comprising a compound of Formula I of the present invention, optionally one or more other active components (e.g., a β-lactam antibiotic), and a pharmaceutically acceptable carrier. The characteristics of the carrier will depend on the route of administration. By "pharmaceutically acceptable" is meant that the ingredients of the pharmaceutical composition must be compatible with each other, do not interfere with the effectiveness of the active ingredient(s), and are not deleterious (e.g., toxic) to the recipient thereof. Thus, compositions according to the invention may, in addition to the inhibitor, contain diluents, fillers, salts, buffers, stabilizers, solubilizers, and other materials well known in the art.

Also as set forth above, the present invention includes a method for treating a bacterial infection which comprises administering to a subject in need of such treatment a therapeutically effective amount of a compound of Formula I, or a pharmaceutically acceptable salt thereof, optionally in combination with a β-lactam antibiotic and/or a DHP inhibitor. The term "subject" (or, alternatively, "patient") as used herein refers to an animal, preferably a mammal, most preferably a human, who has been the object of treatment, observation or experiment. The term "administration" and variants thereof (e.g., "administering" a compound) in reference to a compound of Formula I mean providing the compound, or a pharmaceutically acceptable salt thereof, to the individual in need of treatment. When a compound or a salt thereof is provided in combination with one or more other active agents (e.g., a carbapenem antibiotic or a DHP inhibitor or both), "administration" and its variants are each understood to include provision of the compound or its salt and the other agents at the same time or at different times. When the agents of a combination are administered at the same time, they can be administered together in a single composition or they can be administered separately. It is understood that a "combination" of active agents can be a single composition containing all of the active agents or multiple compositions each containing one or more of the active agents. In the case of two active agents a combination can be either a single composition comprising both agents or two separate compositions each comprising one of the agents; in the case of three active agents a combination can be either a single composition comprising all three agents, three separate compositions each comprising one of the agents, or two compositions one of which comprises two of the agents and the other comprises the third agent; and so forth.

The compositions and combinations of the present invention are suitably administered in effective amounts. The term "effective amount" as used herein with respect to β-lactamase means the amount of active compound sufficient to inhibit β-lactamase activity. In one embodiment, the effective amount is a "therapeutically effective amount" meaning the amount of active compound that can overcome bacterial drug resistance and which, when used in combination with a β-lactam antibiotic, is sufficient to inhibit bacterial replication and/or result in bacterial killing. When the active compound (i.e., active ingredient) is administered as the salt, references to the amount of active ingredient are to the free acid or free base form of the compound.

The administration of a composition of the present invention is suitably parenteral, oral, sublingual, transdermal, topical, intranasal, intratracheal, intraocular, or intrarectal, wherein the composition is suitably formulated for administration by the selected route using formulation methods well known in the art, including, for example, the methods for preparing and administering formulations described in chapters 39, 41, 42, 44 and 45 in Remington—The Science and Practice of Pharmacy, 21$^{st}$ edition, 2006. In one embodiment, compounds of the invention are administered intravenously in a hospital setting. In another embodiment, administration is oral in the form of a tablet or capsule or the like. The dosage of the β-lactamase inhibitors and of their pharmaceutically acceptable salts may vary within wide limits and should naturally be adjusted, in each particular case, to the individual conditions and to the pathogenic agent to be controlled. In general, for a use in the treatment of bacterial infections, the daily dose may be between 0.005 mg/kg to 100 mg/kg, 0.01 mg/kg to 10 mg/kg, 0.05 mg/kg to 5 mg/kg, 0.05 mg/kg to 1 mg/kg. Moreover, the ratio of the β-lactamase inhibitor or of the pharmaceutically acceptable salt thereof to the β-lactam antibiotic may also vary within wide limits and should be adjusted, in each particular case, to the individual conditions, in general, a ratio ranging from about 1:1000 to about 100:1 is recommended. In one embodiment, the ratio is 1:1000, 1:500, 1:250, 1:100, 1:50, 1:25, 1:10, 1:5, 1:1, 5:1, 10:1, 25:1, 50:1 or 100:1.

Intravenous administration of a compound of the invention can be conducted by reconstituting a powdered form of the compound with an acceptable solvent. Suitable solvents include, for example, saline solutions (e.g., 0.9% Sodium Chloride Injection) and sterile water (e.g., Sterile Water for Injection, Bacteriostatic Water for Injection with methylparaben and propylparaben, or Bacteriostatic Water for Injection with 0.9% benzyl alcohol). The powdered form of the compound can be obtained by gamma-irradiation of the compound or by lyophilization of a solution of the compound, after which the powder can be stored (e.g., in a sealed vial) at or below room temperature until it is reconstituted. The concentration of the compound in the reconstituted IV solution can be, for example, in a range of from about 0.1 mg/mL to about 20 mg/mL.

The present invention also includes a method for inhibiting β-lactamase activity which comprises administering to a bacterial cell culture, or to a bacterially infected cell culture, tissue, or organism, an inhibition effective amount of a compound of Formula I. Additional embodiments of the invention include the inhibiting method just described, wherein the compound of the present invention employed therein is a compound of one of the embodiments, sub-embodiments or classes described above. The compound may optionally be used in the form of a pharmaceutically acceptable salt in these embodiments. The method can involve administration of a compound of Formula I, in combination with a β-lactam antibiotic to an experimental cell culture in vitro to prevent the growth of β-lactam resistant bacteria. The method can alternatively involve administration of a compound of Formula I, in combination with a β-lactam antibiotic, to an animal, including a human, to prevent the growth of β-lactam resistant bacteria in vivo.

Compounds of the invention can be employed for the treatment, prophylaxis or inhibition of bacterial growth or infections due to bacteria that are resistant to β-lactam antibiotics. In an embodiment, the bacteria can be metallo-β-lactamase positive strains that are highly resistant to β-lactam antibiotics. The terms "slightly resistant" and "highly resistant" are well-understood by those of ordinary skill in the art (see, e.g., Payne et al., *Antimicrobial Agents and Chemotherapy* 38:767-772 (1994); Hanaki et al., *Antimicrobial Agents and Chemotherapy* 30:11.20-11.26 (1995)). For the purposes of this invention, bacterial strains which are highly resistant to imipenem are those against which the MIC of imipenem is >16 μg/mL, and bacterial strains which are slightly resistant to imipenem are those against which the MIC of imipenem is >4 μg/mL.

Compounds of the invention can be used in combination with antibiotic agents for the treatment of infections caused by Class B-β-lactamase producing strains, in addition to those infections which are subsumed within the antibacterial spectrum of the antibiotic agent. Examples of class B-metallo-β-lactamase producing bacteria are *Pseudomonas aeruginosa, Pseudomonas putida, Enterobacter cloacae, Klebsiella pneumoniae, Klebsiella oxytoca, Escherichia coli, Serratia marcescens, Enterobacter aerogenes, Enterobacter asburiae, Citrobacter freundii, Proteus mirabilis, Morganella morganii, Providencia rettgeri*, and *Acinetobacter baumannii*.

It is generally advantageous to use a compound of Formula I in admixture or conjunction with a carbapenem, penicillin, cephalosporin, or other β-lactam antibiotic, or a prodrug thereof. It is advantageous to use a compound of Formula I in combination with one or more β-lactam antibiotics because of the class B β-lactamase inhibitory properties of the compounds. It is also advantageous to use a compound of Formula I in combination with one or more Class A, C, and D β-lactamase inhibitors to further limit β-lactam susceptibility. As already noted, the compound of Formula I and the β-lactam antibiotic can be administered separately (at the same time or as different times) or in the form of a single composition containing both active ingredients.

Carbapenems, penicillins, cephalosporins and other β-lactam antibiotics suitable for use in the present invention include both those known to show instability to or to be otherwise susceptible to class B-β-lactamases.

When the compounds of Formula I are combined with a carbapenem antibiotic, a dehydropeptidase (DHP) inhibitor can also be combined. Many carbapenems are susceptible to attack by a renal enzyme known as DHP. This attack or degradation may reduce the efficacy of the carbapenem antibacterial agent. Inhibitors of DHP and their use with carbapenems are disclosed in, e.g., U.S. Pat. Nos. 4,539,208; 4,616,038; 4,880,793; and 5,071,843. A preferred DHP inhibitor is 7-(L-2-amino-2-carboxyethylthio)-2-(2,2-dimethylcyclopropanecarboxamide)-2-heptenoic acid or a pharmaceutically acceptable salt thereof.

Carbapenems suitable for co-administration with compounds of the present invention include imipenem, meropenem, biapenem, (4R, 5S, 6S)-3-[3S, 5S)-5-(3-carboxyphenyl-carbamoyl)pyrrolidin-3-ylthio]-6-(1R)-1-hydroxyethyl]-4-methyl-7-oxo-1-azabicyclo[3.2.0]hept-2-ene-2-carboxylic acid, (1S, 5R, 6S)-2-(4-(2-(((carbamoylmethyl)-1,4-diazoniabicyclo[2.2.2]oct-1-yl)-ethyl(1,8-naphthosultam)methyl)-6-[1(R)-hydroxyethyl]-1-methylcarbapen-2-em-3-carboxylate chloride, BMS181139 ([4R-[4α,5β,6β(R*)]]-4-[2-[(aminoiminomethyl)amino]ethyl]-3-[(2-cyanoethyl)thio]-6-(1-hydroxyethyl)-7-oxo-1-azabicyclo[3.2.0]hept-2-ene-2-carboxylic acid), BO2727 ([4R-3[3S*,5S*(R*)], 4α,5β,6β(R*)]]-6-(1-hydroxyethyl)-3-[[5-[1-hydroxy-3-(methylamino)propyl]-3-pyrrolidinyl]thio]-4-methyl-7-oxo-1-azabicyclo[3.2.0]hept-2-ene-2-carboxylic acid monohydrochloride), E1010 ((1R, 5S, 6S)-6-[1(R)-hydroxymethyl]-2-[2(S)-[1(R)-hydroxy-1-[pyrrolidin-3(R)-yl]methyl]pyrrolidin-4(S)-ylsulfanyl]-1-methyl-1-carba-2-penem-3-carboxylic acid hydrochloride) and S4661 ((1R,5S,6S)-2-[(3S,5S)-5-(sulfamoylaminomethyl) pyrrolidin-3-yl]thio-6-[(1R)-1-hydroxyethyl]-1-methylcarbapen-2-em-3-carboxylic acid), (1 S,5R,6S)-1-methyl-2-{7-[4-(aminocarbonylmethyl)-1,4-diazoniabicyclo(2.2.2)octan-1yl]-methyl-fluoren-9-on-3-yl}-6-(1R-hydroxyethyl)-carbapen-2-em-3 carboxylate chloride.

Penicillins suitable for co-administration with compounds of the present invention include benzylpenicillin, phenoxymethylpenicillin, carbenicillin, azidocillin, propicillin, ampicillin, amoxicillin, epicillin, ticarcillin, cyclacillin, pirbenicillin, azlocillin, mezlocillin, sulbenicillin, piperacillin, and other known penicillins. The penicillins may be used in the form of pro-drugs thereof; for example as in vivo hydrolysable esters, for example the acetoxymethyl, pivaloyloxymethyl, α-ethoxycarbonyloxy-ethyl and phthalidyl esters of ampicillin, benzylpenicillin and amoxicillin; as aldehyde or ketone adducts of penicillins containing a 6-α-aminoacetamido side chain (for example hetacillin, metampicillin and analogous derivatives of amoxicillin); and as esters of carbenicillin and ticarcillin, for example the phenyl and indanyl α-esters.

Cephalosporins suitable for co-administration with compound of the present invention include cefatrizine, cepha-loridine, cephalothin, cefazolin, cephalexin, cephacetrile, cephapirin, cephamandole nafate, cephradine, 4-hydroxycephalexin, cephaloglycin, cefoperazone, cefsulodin, ceftazidime, cefuroxime, cefmetazole, cefotaxime, ceftriaxone, and other known cephalosporins, all of which may be used in the form of pro-drugs thereof.

β-Lactam antibiotics other than penicillins and cephalosporins that may be co-administered with compounds of the present invention include aztreonam, latamoxef (Moxalactam-trade mark), and other known β-lactam antibiotics such as carbapenems like imipenem, meropenem or (4R, 5S, 6S)-3-[(3S,5S)-5-(3-carboxyphenylcarbamoyl)pyrrolidin-3-ylthio]-6-(1R)-1-hydroxyethyl]-4-methyl-7-oxo-1-azabicyclo[3.2.0]hept-2-ene-2-carboxylic acid, all of which may be used in the form of pro-drugs thereof.

In one embodiment, the antibiotic co-administered with a compound of the present invention is selected from the group consisting of imipenem, ertapenem, meropenem and (4R, 5S, 6S)-3-[(3S,5S)-5-(3-carboxyphenylcarbamoyl)pyrrolidin-3-ylthio]-6-(1R)-1-hydroxyethyl]-4-methyl-7-oxo-1-azabicyclo[3.2.0]hept-2-ene-2-carboxylic acid.

In another embodiment, the antibiotic co-administered with a compound of the present invention is selected from the group of penicillins consisting of ampicillin, amoxicillin, carbenicillin, piperacillin, azlocillin, mezlocillin, and ticarcillin. Such penicillins can optionally be used in the form of their pharmaceutically acceptable salts, for example their sodium salts. Ampicillin or amoxicillin can alternatively be employed in the form of fine particles of the zwitterionic form (generally as ampicillin trihydrate or amoxicillin trihydrate) for use in an injectable or infusable suspension. In an aspect of this embodiment, the penicillin co-administered with a compound of the present invention is amoxicillin, optionally in the form of its sodium salt or the trihydrate.

In another embodiment, the antibiotic co-administered with a compound of the present invention is selected from the group of cephalosporins consisting of cefotaxime, ceftriaxone and ceftazidime, which are optionally used in the form of their pharmaceutically acceptable salts, for example their sodium salts.

When co-administered with a β-lactam antibiotic, the combination of the compound of the invention and the antibiotic can provide a synergistic effect. The terms "synergistic effect" and "synergy" indicate that the effect produced when two or more drugs are co-administered is greater than would be predicted based on the effect produced when the compounds are administered individually. While not wishing to be bound by theory, it is believed that the compounds of the present invention are β-lactamase inhibitors that act to prevent degradation of β-lactam antibiotics, thereby enhancing their efficacy and producing a synergistic effect.

Abbreviations employed herein include the following: acac=acetylacetonate; AcOH=acetic acid; Ad2nBuP=n-butyldiadamantylphosphine; ACN=acetonitrile; AIBN=2,2-azobisisobutyronitrile; BLI=β-lactamase inhibitor; Bn=benzyl; BOC (or Boc)=t-butyloxycarbonyl; BOC-ON=2-(tert-butoxycarbonyloxyamino)-2-phenyl acetonitrile; BOC-OSN=N-tert-butoxycarbonyloxy)succinimide; BOP=benzotriazol-1-yloxy)tris(dimethylamino)phosphonium hexafluorophosphate; BSA=bovine serum albumin; CBZ (or Cbz)=carbobenzoxy (alternatively, benzyloxycarbonyl); CH$_3$CN=acetonitrile; COD=cyclooctadieneyl; DBU=1,8-diazabicyclo[5.4.0]undec-7-ene; DCC=dicyclohexyl carbodiimide; DCE=1,2-dichloroethane; DCM=dichloromethane; DEAD=diethyl azodicarboxylate; DIBAL-H=diisobutylaluminum hydride; DIEA=diethylamine; DIPA=diisopropylamine; DIPEA=diisopropylethylamine (or Hunig's base);

DMA=dimethylacetamide; DMAC=N,N-dimethylacetamide; DMAP=4-dimethylaminopyridine or N,N-dimethylaminopyridine; DME=1,2-dimethoxyethane; DMF=N,N-dimethylformamide; DMSO=dimethyl sulfoxide; EDC=1-ethyl-3-(3-dimethylaminopropyl) carbodiimide; DSC=differential scanning calorimetry; Et=ethyl; Et$_3$N=triethylamine; EtOAc=ethyl acetate; EtOH=ethanol; hex=hexane; HATU=1-[Bis(dimethylamino)methylene]-1H-1,2,3-triazolo[4,5-b]pyridinium 3-oxide hexafluorophosphate; HMDS=hexamethyldisilazide; HMPA=hexamethylphosphoramide; HOBT=1-hydroxy benzotriazole; HOPO=2-hydroxypyridine-N-oxide; HPLC=high-performance liquid chromatography; IPA=isopropyl alcohol; IPAc=isopropyl acetate; i-Pr=isopropyl; LAH=lithium aluminum hydride; LC/MS=liquid chromatography/mass spectrometry; LDA=lithium diisopropylamide; LHMDS=lithium hexamethyldisilazide; m-CPBA=m-chloroperoxybenzoic acid; Me=methyl; MeCN=acetonitrile; MeOH=methanol; MHBII=Mueller Hinton Broth type II; MIC=minimum inhibitory concentration; MPLC=medium pressure liquid chromatography; MSA=methanesulfonic acid; MTBE=methyl tert-butyl ether; n-BuLi=n-butyllithium; NaHMDS=sodium hexamethyldisilazide; NBS=N-Bromosuccinimide; NMO=N-Methylmorpholine N-oxide; NMP=N-methyl pyrrolidinone; MS=mass spectrometry; MW=molecular weight; PdCl$_2$(dppf)=[1,2'-bis(diphenylphosphino)ferrocene] dichloropalladium(II); PE=petroleum ether; PG=protective group; Ph=phenyl; RB=round bottom; RT=room temperature; SEM=2-(trimethylsilyl)ethoxymethyl; SFC=supercritical fluid chromatography; SM=starting material; tBu=tert butyl; t-BuOH=tert-butanol; TEA=triethylamine; TFA=trifluoroacetic acid; TFAA=trifluoroacetic anhydride; TFE=2,2,2-trifluoroethanol; THF=tetrahydrofuran; TLC=thin layer chromatography; TMS=trimethylsilyl; TSB=trypticase soy broth; TsOH=p-toluenesulfonic acid; UPLC=ultrapressure liquid chromatography; XRPD=X-ray powder diffraction.

The compounds disclosed herein can be prepared according to the following reaction schemes and EXAMPLES, or modifications thereof, using readily available starting materials, reagents and conventional synthesis procedures. In these reactions, it is also possible to make use of variations which are themselves known to those of ordinary skill in this art, but are not mentioned in greater detail. Furthermore, other methods for preparing compounds disclosed herein will be readily apparent to the person of ordinary skill in the art in light of the following reaction schemes and EXAMPLES. Unless otherwise indicated, all variables are as defined above.

Biological Assays

Enzyme Activity: Determination of IC$_{50}$

The Class B enzyme activities were measured in the presence of a compound of the EXAMPLES as a test inhibitor in a fluorescence assay against a commercially available substrate consisting of a cephalosporin core linking 7-hydroxycoumarin to fluorescein (CCF2-FA; Life Technologies, Grand Island, N.Y.). The enzyme (NDM-1, IMP-1 or VIM-1) and the substrate were diluted in 100 mM KH$_2$PO$_4$ buffer (pH 7) containing 0.005% Tween-20 and 10 μM ZnSO$_4$. In the assay, the final concentration of enzyme was 1 pM, 2 pM and 30 pM for NDM-1, IMP-1 and VIM-1, respectively, and the final concentration of CCF2-FA was 1.25 μM. The test inhibitor was dissolved in DMSO and diluted 1:50 in the assay, resulting in a final concentration range of 20 μM to 0.00063 μM. In a 384-well microplate, the test inhibitor was incubated with the metallo-β-lactamase enzyme and the substrate for 2 hours at 25° C. Fluorescence at 460 nm following excitation at 405 nm was measured. The IC$_{50}$ value was determined from semi-logarithmic plots of enzyme inhibition versus inhibitor concentration, with a curve generated using a 4-parameter fit.

Representative compounds of the present invention exhibit inhibition of Class B β-lactamases in this assay. For example, the compounds of EXAMPLES 1-456 were tested in this assay and were found to have the IC$_{50}$ values shown in Table 1.

Antibiotic Potentiation Activity: Determination of Synergistic Concentration

The concentrations of metallo-β-lactamase inhibitors required to restore the susceptibility of various strains of bacteria to inactive concentrations of antibiotics were determined in an assay that assessed bacterial growth by measuring the optical density at 600 nm (OD$_{600}$). The bacterial strains tested included the clinical strains *Escherichia coli* expressing NDM-1 (CLB30005, CLB30016), *Serratia marcescens* expressing IMP-1 (CL5741), and *Klebsiella pneumoniae* expressing VIM-1 (IHMA599644). Inhibitor activity was measured in the presence and absence of imipenem or ceftazidime in a 384-well microplate.

The clinical strains CLB30016, CL5741, and IHMA599644 were grown on trypticase soy agar containing 5% sheep's blood. The clinical strain CLB30005 was grown on Mueller Hinton broth agar containing 8 μg/ml imipenem. The bacteria on agar plates were incubated overnight at 35° C. with ambient humidity (achieved from an open pan of water inside the incubator). The following day, individual colonies from each clinical strain were picked and resuspended in 5 ml saline to attain an OD$_{600}$ of 0.14, 0.11, 0.15 and 0.13, for CLB30005, CLB30016, CL5741 and IHMA599644, respectively. These were further diluted 1:100 into 1.1×CAMHB and used to inoculate the test wells as described below.

Imipenem in 10 mM 3-(N-morpholino)propanesulfonic acid (MOPS, pH 7) was stored in single use aliquots at −80° C. Test inhibitors were dissolved in DMSO and diluted 1:50 in the assay, resulting in a final concentration range of 200 μM to 0.195 μM. On the day of the assay, 4 μl of antibiotic was added to 45 μl of bacteria followed by 1 μl of test compound and mixed by pipetting and with an orbital shaker. The concentration of antibiotic used in the assay was 1 μg/ml or 4 μg/ml. Microplates were covered and incubated at 35° C. for 22 hours to 24 hours. At the end of the incubation, absorbance was determined using a spectrophotometer. The synergistic concentration of MBLI was determined by identifying the lowest concentration of test compound in the presence of a given concentration of antibiotic that was required to inhibit 95% of the growth of the bacteria. The results for EXAMPLES 1-456 are reported in Table 1, expressed as the concentration of compound that potentiated the action of antibiotic (imipenem) affecting 95% inhibition of bacterial growth (MITC95).

Representative compounds of the present invention display a synergistic effect. For example, representative compounds of EXAMPLES 1-456 were determined to restore susceptibility to imipenem at concentrations of 200 μM or less.

TABLE 1

Inhibition of metallo-β-lactamases (IMP-1, NDM-1, VIM-1) and antibiotic potentiation vs. MBL-expressing bacteria by EXAMPLES 1-456.

| Ex. No. | NDM1 IC50 (nM) | IMP1 IC50 (nM) | VIM1 IC50 (nM) | NDM1 EC30005 MITC95 (μM) | NDM1 EC30016 MITC95 (μM) | IMP1 SM5741 MITC95 (μM) | VIM1 KP599644 MITC95 (μM) |
|---|---|---|---|---|---|---|---|
| 1 | 870 | 280 | >20000 | 75 | | 138 | >200 |
| 2 | 5400 | 68 | 8200 | >200 | | 100 | >200 |
| 3 | 350 | 550 | 640 | 200 | | 112.5 | >200 |
| 4 | 49 | 380 | 14 | 9.4 | | >200 | 50 |
| 5 | 230 | 1500 | 61 | 62.5 | | >200 | 200 |
| 6 | 240 | 730 | 130 | 75 | | 106.3 | >200 |
| 7 | 19 | 52 | 3.3 | 18.8 | | 62.5 | 37.5 |
| 8 | 81 | 1800 | 21 | 9.4 | | 125 | 62.5 |
| 9 | 97 | 850 | 63 | 31 | | 25 | 200 |
| 10 | 47 | 48 | 29 | 50 | | 7.0 | 150 |
| 11 | 57 | 230 | 34 | 25 | | 27 | >200 |
| 12 | 99 | 1046 | 84.73 | 12.5 | | 200 | 200 |
| 13 | 127.8 | 460 | 16 | 12.5 | | 150 | 50 |
| 14 | 150 | 1600 | 37 | 15.6 | | 200 | 100 |
| 15 | 380 | 4800 | 120 | 15.6 | | >200 | 200 |
| 16 | 12 | 120 | 0.75 | | 9.4 | 4.7 | 9.4 |
| 17 | 16 | 110 | 3.7 | 18.8 | | 37.5 | 37.5 |
| 18 | 26 | 30 | 36 | 18.8 | | 37.5 | 200 |
| 19 | 31 | 62 | 24 | 9.4 | | 50 | 50 |
| 20 | 26 | 390 | 22 | 4.7 | | 128 | 69 |
| 21 | 190 | 2700 | 15 | 75 | | >200 | >200 |
| 22 | 280 | 2600 | 14 | 31 | | 200 | 50 |
| 23 | 20 | 88 | 1.4 | | 6.3 | 3.1 | 31 |
| 24 | 18 | 230 | 0.60 | | 9.4 | 4.7 | 12.5 |
| 25 | 32 | 87 | 2.6 | | 4.7 | 3.1 | 12.5 |
| 26 | 9.9 | 570 | 2.4 | | 3.1 | 12.5 | 18.8 |
| 27 | 16 | 62 | 7.7 | 15.6 | | 13 | 37.5 |
| 28 | 310 | 1800 | 190 | 200 | | >200 | >200 |
| 29 | 530 | 2300 | 210 | 25 | | >200 | 200 |
| 30 | 4700 | 220 | 240 | >200 | | 50 | >200 |
| 31 | 740 | 410 | 590 | >200 | | >200 | >200 |
| 32 | 720 | 5000 | 240 | 75 | | >200 | 200 |
| 33 | 390 | 2100 | 110 | 75 | | 50 | >200 |
| 34 | 200 | 1500 | 40 | 25 | | 200 | 200 |
| 35 | 1400 | 3100 | 210 | 100 | | >200 | >200 |
| 36 | 30 | 2000 | 21 | 60 | | 108 | 100 |
| 37 | 27 | 120 | 10 | 200 | | 106 | >200 |
| 38 | 12 | 49 | 5.5 | 100 | | 31 | >200 |
| 39 | 86 | 210 | 11 | 75 | | >200 | 100 |
| 40 | 160 | 2500 | 4.3 | 8.3 | | 100 | 25 |
| 41 | 60 | 590 | 0.87 | | 18.8 | 37.5 | 18.8 |
| 42 | 74 | 190 | 1.4 | | 18.8 | 12.5 | 37.5 |
| 43 | 22 | 1600 | 3.2 | | 4.7 | 50 | 31 |
| 44 | 21 | 640 | 5.5 | | 150 | 18.8 | 200 |
| 45 | 93 | 850 | 3.3 | 4.2 | | 37.5 | 25 |
| 46 | 70 | 1600 | 5.9 | | 9.4 | 37.5 | 12.5 |
| 47 | 120 | 7200 | 73 | | 9.4 | 200 | 37.5 |
| 48 | 43 | 130 | 2.2 | | 6.2 | 4.7 | 50 |
| 49 | 69 | 720 | 7.6 | 6.2 | | 37.5 | 50 |
| 50 | 47 | 100 | 6.6 | | 25 | 6.2 | 50 |
| 51 | 180 | 540 | 25 | 75 | | 25 | 150 |
| 52 | 87 | 680 | 10 | | 18.8 | 18.8 | 25 |
| 53 | 37 | 89 | 5.8 | | 18.8 | 4.7 | 75 |
| 54 | 1600 | 13000 | 40 | | 18.8 | 75 | 12.5 |
| 55 | 120 | 810 | 19 | | 6.2 | 18.8 | 25 |
| 56 | 520 | 1700 | 10 | | 9.4 | 47 | 18.8 |
| 57 | 650 | 2800 | 170 | 200 | | 150 | >200 |
| 58 | <0.64 | 1.4 | 5.1 | 18.8 | | 12.9 | 200 |
| 59 | 9.0 | 55 | 10 | 12.5 | | 56.2 | 150 |
| 60 | 56 | 760 | 1.9 | | 3.1 | 9.4 | 4.7 |
| 61 | 32 | 150 | 1.9 | | 2.3 | 3.9 | 6.2 |
| 62 | 6.5 | 66 | 6.9 | | 9.4 | 6.2 | 18.8 |
| 63 | 4.5 | 25 | 1.1 | | 6.2 | 2.0 | 18.8 |
| 64 | 300 | 12000 | 8.4 | | 6.2 | 50 | 12.5 |
| 65 | 760 | >20000 | 72 | | 3.1 | 200 | 12.5 |
| 66 | 370 | 6400 | 18 | | 4.7 | 75 | 12.5 |
| 67 | 890 | 12000 | 25 | | 12.5 | 50 | 25 |
| 68 | 24 | 1100 | 0.79 | | 4.7 | 12.5 | 6.2 |
| 69 | 25 | 770 | 1.3 | | 3.1 | 6.2 | 6.2 |
| 70 | 180 | >20000 | 240 | | 12.5 | >200 | 50 |
| 71 | 570 | 20000 | 120 | | 12.5 | >200 | 25 |
| 72 | 5.6 | 19 | 3.8 | | 6.2 | 0.39 | 12.5 |

TABLE 1-continued

Inhibition of metallo-β-lactamases (IMP-1, NDM-1, VIM-1) and antibiotic potentiation vs. MBL-expressing bacteria by EXAMPLES 1-456.

| Ex. No. | NDM1 IC50 (nM) | IMP1 IC50 (nM) | VIM1 IC50 (nM) | NDM1 EC30005 MITC95 (μM) | NDM1 EC30016 MITC95 (μM) | IMP1 SM5741 MITC95 (μM) | VIM1 KP599644 MITC95 (μM) |
|---|---|---|---|---|---|---|---|
| 73 | 4.4 | 40 | 7.1 | | 18.8 | 1.2 | 37.5 |
| 74 | 34 | 110 | 18 | | 3.1 | 1.6 | 12.5 |
| 75 | 25 | 36 | 4.3 | | 3.1 | 0.78 | 9.4 |
| 76 | 120 | 2600 | 18 | | 9.4 | 37.5 | 18.8 |
| 77 | 6.1 | 99 | 5.7 | | 6.2 | 4.7 | 50 |
| 78 | 23 | 460 | 4.5 | | 3.1 | 6.2 | 6.2 |
| 79 | 24 | 190 | 2.3 | | 3.1 | 4.7 | 6.2 |
| 80 | 17 | 73 | 2.2 | | 6.2 | 1.6 | 9.4 |
| 81 | 46 | 65 | 4.4 | | 2.3 | 2.3 | 6.2 |
| 82 | 240 | 4600 | 5.7 | 6.2 | | 200 | 25 |
| 83 | 880 | >20000 | 71 | 8.3 | | >200 | 100 |
| 84 | 1200 | >20000 | 47 | | 18.8 | >200 | 50 |
| 85 | 250 | 6500 | 6.2 | | 0.78 | 100 | 18.8 |
| 86 | 130 | 3300 | 11 | | 50 | 125 | 100 |
| 87 | 300 | 6600 | 2.3 | | 12.5 | >200 | 25 |
| 88 | 180 | 2000 | 5.6 | | 0.78 | 37.5 | 6.2 |
| 89 | 18000 | >20000 | 2100 | | 18.8 | >200 | 37.5 |
| 90 | 200 | 14000 | 310 | | 62 | >200 | 200 |
| 91 | 32 | 2200 | 7.9 | | 7.8 | 50 | 12.5 |
| 92 | 110 | 5500 | 28 | | 9.4 | 100 | 25 |
| 93 | 580 | >20000 | 90 | | 6.2 | >200 | 25 |
| 94 | 4500 | >20000 | 2900 | | 50 | >200 | 200 |
| 95 | 160 | 2500 | 6.5 | 3.1 | | 50 | 12.5 |
| 96 | 280 | 3100 | 9.0 | | 6.2 | 37 | 18.8 |
| 97 | 1.2 | 380 | 5.9 | | 100 | 31 | 200 |
| 98 | 120 | 3200 | 110 | | 18.8 | 150 | 200 |
| 99 | 600 | 3900 | 350 | | 31 | 75 | 100 |
| 100 | 280 | 2900 | 4.9 | | 6.2 | 25 | 12.5 |
| 101 | 130 | 2000 | 13 | | 1.6 | 18.8 | 18.8 |
| 102 | 40 | 72 | 5.3 | | 12.5 | 2.3 | 37 |
| 103 | 150 | 960 | 3.4 | | 6.2 | 18.8 | 18.8 |
| 104 | 180 | 7000 | 14 | | 3.1 | 37 | 18.8 |
| 105 | 170 | 14000 | 20 | | 3.1 | 50 | 12.5 |
| 106 | 610 | >20000 | 98 | | 1.6 | 200 | 18.8 |
| 107 | 380 | 5900 | 30 | | 9.4 | 50 | 12.5 |
| 108 | 2800 | >20000 | 750 | | 12.5 | >200 | 37 |
| 109 | 17 | 450 | 1.2 | | 3.1 | 12.5 | 4.7 |
| 110 | 24 | 1400 | 4.4 | | 4.7 | 18.8 | 6.2 |
| 111 | 230 | 7700 | 77 | | 0.49 | 44 | 5.5 |
| 112 | 110 | 570 | 4.9 | | 0.54 | 11 | 5.5 |
| 113 | 130 | 2100 | 79 | | 0.78 | 18.8 | 9.4 |
| 114 | 180 | 3700 | 6.2 | | 0.39 | 18.8 | 2.3 |
| 115 | 170 | 1500 | 6.5 | | 0.78 | 25 | 9.4 |
| 116 | 140 | 290 | 4.4 | | 3.1 | 9.4 | 18.8 |
| 117 | 1300 | >20000 | 370 | | 1.6 | >200 | 18.8 |
| 118 | 1100 | >20000 | 10 | | 2.3 | 200 | 6.2 |
| 119 | 12 | 52 | 1.0 | | 9.4 | 3.1 | 25 |
| 120 | 1200 | 20000 | 8.5 | | 25 | >200 | 37 |
| 121 | 120 | 6000 | 35 | | 0.21 | 37 | 5.5 |
| 122 | 39 | 620 | 1.4 | | 0.39 | 12.5 | 6.2 |
| 123 | 1100 | >20000 | 590 | | 3.1 | >200 | 50 |
| 124 | 540 | 15000 | 59 | | 4.7 | 100 | 50 |
| 125 | 170 | 12000 | 240 | | 0.39 | 75 | 12.5 |
| 126 | 63 | 530 | 34 | | 6.2 | 25 | 50 |
| 127 | 320 | 10000 | 280 | | 12.5 | 200 | 200 |
| 128 | 150 | 16000 | 51 | | 9.4 | >200 | 50 |
| 129 | 77 | 830 | 5.6 | | 0.39 | 9.4 | 9.4 |
| 130 | 900 | 8400 | 8.3 | | 4.7 | 50 | 18.8 |
| 131 | 12 | 200 | 1.9 | | 0.78 | 6.2 | 9.4 |
| 132 | 160 | 1500 | 31 | | 9.4 | 38 | 25 |
| 133 | 12 | 79 | 1.6 | | 25 | 6.2 | 75 |
| 134 | 88 | 230 | 6.6 | | 0.78 | 4.7 | 18.8 |
| 135 | 490 | 1600 | 6.1 | | 6.2 | 25 | 25 |
| 136 | 340 | 6800 | 150 | | 1.2 | 100 | 18.8 |
| 137 | 110 | 300 | 3.5 | | 6.2 | 12.5 | 37 |
| 138 | 490 | >20000 | 670 | | 3.1 | >200 | 75 |
| 139 | 56 | 1900 | 34 | | 0.39 | 38 | 12.5 |
| 140 | 320 | >20000 | 8.7 | | 1.6 | 75 | 12.5 |
| 141 | 3600 | >20000 | 800 | | 12.5 | >200 | 150 |
| 142 | 340 | 5000 | 130 | | 3.1 | 50 | 25 |
| 143 | 53 | 1700 | 2.6 | 12.5 | | >200 | 100 |
| 144 | 16 | 370 | 15 | | 7.8 | 62 | 200 |

TABLE 1-continued

Inhibition of metallo-β-lactamases (IMP-1, NDM-1, VIM-1) and antibiotic potentiation vs. MBL-expressing bacteria by EXAMPLES 1-456.

| Ex. No. | NDM1 IC50 (nM) | IMP1 IC50 (nM) | VIM1 IC50 (nM) | NDM1 EC30005 MITC95 (μM) | NDM1 EC30016 MITC95 (μM) | IMP1 SM5741 MITC95 (μM) | VIM1 KP599644 MITC95 (μM) |
|---|---|---|---|---|---|---|---|
| 145 | 700 | 12000 | 18 | 6.2 | | 200 | 75 |
| 146 | 36 | 100 | 1.6 | | 6.2 | 5.5 | 15.6 |
| 147 | 110 | 4500 | 0.85 | | 3.1 | 100 | 6.2 |
| 148 | 25 | 400 | 0.94 | | 25 | 12.5 | 25 |
| 149 | 170 | 1600 | 98 | | 0.39 | 38 | 18.8 |
| 150 | 480 | >20000 | 300 | | 1.6 | >200 | 25 |
| 151 | 300 | 7900 | 120 | | 0.39 | 100 | 12.5 |
| 152 | 62 | 5300 | 29 | | 0.39 | 38 | 6.2 |
| 153 | 58 | 510 | 2.1 | | 9.4 | 25 | 25 |
| 154 | 430 | 13000 | 140 | | 0.78 | 100 | 25 |
| 155 | 12 | 290 | 7.3 | | 16 | 18.8 | 18.8 |
| 156 | 150 | 5400 | 1.5 | | 31 | >200 | 25 |
| 157 | 730 | 12000 | 8.5 | | 18.8 | >200 | 25 |
| 158 | 14 | 61 | 25 | 62 | | 12.5 | 100 |
| 159 | 400 | 3700 | 23 | | 12.5 | 75 | 50 |
| 160 | 50 | 1600 | 5.7 | | 38 | 50 | 75 |
| 161 | 30 | 1100 | 3.3 | | 18.8 | 18.8 | 50 |
| 162 | 22 | 560 | 3.7 | | 75 | 12.5 | 125 |
| 163 | 25 | 600 | 3.8 | | 38 | 16 | 125 |
| 164 | 530 | 13000 | 3.9 | | 9.4 | 50 | 18.8 |
| 165 | 1500 | >20000 | 68 | | 3.1 | 150 | 25 |
| 166 | 500 | 9300 | 170 | | 9.4 | 100 | 38 |
| 167 | 200 | 5700 | 140 | | 9.4 | >200 | 100 |
| 168 | 100 | 3000 | 53 | | 25 | 200 | >200 |
| 169 | 88 | 1600 | 38 | | 18.8 | 100 | 200 |
| 170 | 250 | 3600 | 22 | | 1.6 | 50 | 12.5 |
| 171 | 47 | 740 | 56 | | 75 | 62 | 200 |
| 172 | 52 | 800 | 49 | | 12.5 | 38 | 50 |
| 173 | 27 | 500 | 110 | | 25 | 31 | >200 |
| 174 | 240 | 2700 | 110 | | 9.4 | 50 | 25 |
| 175 | 19 | 840 | 12 | | 18.8 | 75 | 50 |
| 176 | 25 | 150 | 5.7 | | 16 | 6.2 | 25 |
| 177 | 40 | 140 | 5.1 | | 12.5 | 4.7 | 38 |
| 178 | 43 | 390 | 2.4 | | 9.4 | 12.5 | 25 |
| 179 | 66 | 1300 | 24 | | 12.5 | 38 | 50 |
| 180 | 17 | 130 | 1.7 | | 25 | 3.1 | 50 |
| 181 | 1000 | 4400 | 17 | | 38 | 100 | 75 |
| 182 | 1000 | 16000 | 330 | | 150 | >200 | >200 |
| 183 | 660 | 200 | 700 | >200 | | >200 | >200 |
| 184 | 900 | 200 | 300 | >200 | | 100 | >200 |
| 185 | 880 | 11 | 740 | >200 | | 100 | >200 |
| 186 | 750 | 140 | 60 | 200 | | 12.5 | >200 |
| 187 | 980 | 180 | 140 | >200 | | 103 | >200 |
| 188 | 640 | 140 | 180 | >200 | | 53 | >200 |
| 189 | 13 | 29 | 4.3 | 2.3 | | 7.8 | 100 |
| 190 | 110 | 610 | 5.4 | 9.4 | | 38 | 75 |
| 191 | 260 | 1100 | 8.3 | 25 | | 62 | 62 |
| 192 | 29 | 45 | 29 | 7.8 | | 9.4 | 200 |
| 193 | 58 | 45 | 18 | 4.7 | | 6.2 | 50 |
| 194 | 170 | 640 | 6.7 | 27 | | 75 | 50 |
| 195 | 85 | 110 | 11 | 4.7 | | 28 | 38 |
| 196 | 9.5 | 45 | 4.1 | 7.8 | | 14 | 125 |
| 197 | 4.9 | 28 | 0.89 | 4.7 | | 14 | 18.8 |
| 198 | 14 | 75 | 1.2 | 6.2 | | 6.2 | 18.8 |
| 199 | 48 | 110 | 7.4 | 4.7 | 9.4 | 17 | 31 |
| 200 | 8.1 | 34 | 1.5 | 4.7 | | 9.4 | 18.8 |
| 201 | 9.0 | 29 | 2.1 | 7.8 | | 12.5 | 62 |
| 202 | 5.9 | 22 | 2.3 | 9.4 | | 4.7 | 50 |
| 203 | 14 | 60 | 4.3 | 9.4 | | 9.4 | 200 |
| 204 | 3.4 | 26 | 2.1 | 3.9 | | 4.7 | 100 |
| 205 | 500 | 63 | 360 | 50 | | 7.8 | >200 |
| 206 | 82 | 130 | 7.2 | 18.8 | | 18.8 | 50 |
| 207 | 64 | 100 | 8.0 | 16 | | 16 | 150 |
| 208 | 61 | 100 | 16 | 25 | | 18.8 | 200 |
| 209 | 84 | 110 | 14 | 2.3 | 6.2 | 4.3 | 12.5 |
| 210 | 100 | 130 | 8.2 | 6.2 | | 12.5 | 18.8 |
| 211 | 12 | 20 | 3.4 | 3.1 | | 2.3 | 25 |
| 212 | 31 | 91 | 15 | 18.8 | | 18.8 | 150 |
| 213 | 28 | 120 | 17 | 9.4 | | 18.8 | 75 |
| 214 | 24 | 10 | 180 | 7.8 | | 2.0 | >200 |
| 215 | 170 | 1100 | 29 | | 12.5 | 18.8 | 50 |
| 216 | 140 | 490 | 110 | | 31 | 18.8 | 150 |

TABLE 1-continued

Inhibition of metallo-β-lactamases (IMP-1, NDM-1, VIM-1) and antibiotic potentiation vs. MBL-expressing bacteria by EXAMPLES 1-456.

| Ex. No. | NDM1 IC50 (nM) | IMP1 IC50 (nM) | VIM1 IC50 (nM) | NDM1 EC30005 MITC95 (μM) | NDM1 EC30016 MITC95 (μM) | IMP1 SM5741 MITC95 (μM) | VIM1 KP599644 MITC95 (μM) |
|---|---|---|---|---|---|---|---|
| 217 | 500 | 2400 | 38 | | 12.5 | 50 | 50 |
| 218 | 40 | 460 | 21 | | 31 | 25 | 50 |
| 219 | 210 | 1000 | 93 | | 25 | 25 | 100 |
| 220 | 360 | 1600 | 75 | | 25 | 50 | 50 |
| 221 | 84 | 220 | 27 | | 31 | 16 | 100 |
| 222 | 710 | 1700 | 9.1 | | 18.8 | 25 | 25 |
| 223 | 500 | 1300 | 71 | | 38 | 25 | 75 |
| 224 | 1000 | 1100 | 82 | | 25 | 18.8 | 50 |
| 225 | 110 | 280 | 66 | | 25 | 12.5 | 50 |
| 226 | 20 | 39 | 66 | | 38 | 3.1 | >200 |
| 227 | 54 | 380 | 51 | | 16 | 12.5 | 75 |
| 228 | 33 | 220 | 15 | | 75 | 16 | 200 |
| 229 | 370 | 1200 | 25 | | 12.5 | 25 | 25 |
| 230 | 300 | 1100 | 25 | | 31 | 25 | 25 |
| 231 | 160 | 450 | 69 | | 18.8 | 18.8 | 50 |
| 232 | 180 | 420 | 90 | | 12.5 | 12.5 | 50 |
| 233 | 18 | 52 | 4.0 | 18.8 | | 16 | 75 |
| 234 | 17 | 56 | 2.9 | 25 | | 7.0 | 50 |
| 235 | 8.3 | 5.8 | 7.6 | 100 | | 0.78 | >200 |
| 236 | 99 | 71 | 4.4 | 12.5 | | 7.8 | 50 |
| 237 | 88 | 88 | 4.0 | 9.4 | | 4.7 | 38 |
| 238 | 6.5 | 49 | 1.7 | 50 | | 6.2 | 200 |
| 239 | 20 | 190 | 1.7 | 38 | | 38 | 75 |
| 240 | 100 | 75 | 6.5 | 25 | | 7.8 | 125 |
| 241 | 13 | 58 | 0.64 | 75 | | 9.4 | 38 |
| 242 | 9.3 | 70 | 1.6 | 38 | | 12.5 | 100 |
| 243 | 400 | 500 | 3.8 | 18.8 | | 25 | 25 |
| 244 | 66 | 250 | 4.8 | 9.4 | | 25 | 38 |
| 245 | 57 | 85 | 3.7 | 9.4 | | 6.2 | 25 |
| 246 | 1.1 | 9.7 | 2.2 | 38 | | 6.2 | 100 |
| 247 | 13 | 92 | 0.64 | 31 | | 16 | 100 |
| 248 | 700 | 4700 | 230 | 100 | | >200 | >200 |
| 249 | 8.4 | 46 | 1.9 | 100 | | >200 | 100 |
| 250 | 9.6 | 82 | 7.5 | 25 | | 200 | >200 |
| 251 | 330 | 1300 | 430 | 8.3 | | 38 | 75 |
| 252 | 180 | 800 | 89 | 15 | | 150 | 50 |
| 253 | 34 | 97 | 9.1 | 12.5 | | 38 | 50 |
| 254 | 37 | 180 | 9.0 | 5.2 | | 31 | 25 |
| 255 | 44 | 190 | 12 | 10.4 | | 18.8 | 50 |
| 256 | 27 | 45 | 16 | 10.4 | | 6.2 | 150 |
| 257 | 13 | 33 | 14 | 7.3 | | 6.2 | 200 |
| 258 | 91 | 35 | 100 | | 11 | 2.3 | 100 |
| 259 | 37 | 930 | 4.2 | | 9.4 | 12.5 | 12.5 |
| 260 | 75 | 870 | 3.7 | | 6.2 | 12.5 | 18.8 |
| 261 | 110 | 910 | 3.8 | | 9.4 | 12.5 | 12.5 |
| 262 | 70 | 1300 | 3.1 | | 6.2 | 18.8 | 12.5 |
| 263 | 57 | 430 | 2.4 | | 9.4 | 12.5 | 9.4 |
| 264 | 370 | 7100 | 16 | | 2.3 | 100 | 18.8 |
| 265 | 130 | 1800 | 24 | | 18.8 | 50 | 75 |
| 266 | 190 | 1000 | 20 | | 12.5 | 38 | 25 |
| 267 | 14 | 280 | 0.86 | | 9.4 | 9.4 | 18.8 |
| 268 | 6.4 | 2700 | 3.2 | | 7.8 | 75 | 12.5 |
| 269 | 36 | 1500 | 0.76 | | 18.8 | 38 | 38 |
| 270 | 810 | 6800 | 8.2 | | 9.4 | 150 | 9.4 |
| 271 | 84 | 650 | 1.1 | | 6.2 | 50 | 12.5 |
| 272 | 12 | 600 | 0.35 | | 4.7 | 38 | 9.4 |
| 273 | 260 | 2200 | 1.9 | | 12.5 | 150 | 9.4 |
| 274 | 56 | 690 | 1.3 | | 9.4 | 50 | 25 |
| 275 | 39 | 520 | 41 | | 9.4 | 25 | 38 |
| 276 | 1100 | 5400 | 8.4 | | 12.5 | 100 | 25 |
| 277 | 10 | 130 | 13 | | 25 | 12.5 | 75 |
| 278 | 10 | 200 | 120 | | 12.5 | 6.2 | 50 |
| 279 | 1000 | 9500 | 100 | | 150 | >200 | >200 |
| 280 | 140 | 880 | 2.7 | | 18.8 | 25 | 25 |
| 281 | 770 | 5300 | 86 | | 100 | 200 | 200 |
| 282 | 98 | 730 | 19 | | 18.8 | 50 | 50 |
| 283 | 50 | 850 | 17 | | 100 | 38 | 200 |
| 284 | 13000 | >20000 | 340 | | 25 | >200 | 38 |
| 285 | 190 | 14000 | 3.3 | | 25 | >200 | 25 |
| 286 | 4600 | >20000 | 37 | | 25 | >200 | 18.8 |
| 287 | 100 | 9200 | 5.0 | | 25 | 75 | 50 |
| 288 | 520 | >20000 | 4.1 | | 12.5 | 150 | 12.5 |

TABLE 1-continued

Inhibition of metallo-β-lactamases (IMP-1, NDM-1, VIM-1) and antibiotic potentiation vs. MBL-expressing bacteria by EXAMPLES 1-456.

| Ex. No. | NDM1 IC50 (nM) | IMP1 IC50 (nM) | VIM1 IC50 (nM) | NDM1 EC30005 MITC95 (μM) | NDM1 EC30016 MITC95 (μM) | IMP1 SM5741 MITC95 (μM) | VIM1 KP599644 MITC95 (μM) |
|---|---|---|---|---|---|---|---|
| 289 | 3100 | >20000 | 6.8 | | 25 | >200 | 38 |
| 290 | 110 | 14000 | 2.1 | | 18.8 | 150 | 38 |
| 291 | 650 | 6500 | 120 | | 3.1 | 50 | 38 |
| 292 | 2600 | 16000 | 78 | | 38 | 150 | 50 |
| 293 | 2400 | 16000 | 22 | | 25 | 100 | 50 |
| 294 | 170 | 690 | 76 | | 12.5 | 9.4 | 25 |
| 295 | 440 | 1100 | 1600 | | 12.5 | 12.5 | 25 |
| 296 | 32 | 180 | 21 | | 4.7 | 6.2 | 12.5 |
| 297 | 26 | 200 | 25 | | 4.7 | 6.2 | 18.8 |
| 298 | 110 | 2700 | 10 | | 1.6 | 25 | 12.5 |
| 299 | 220 | 4400 | 22 | | 1.6 | 50 | 25 |
| 300 | 550 | 2100 | 140 | | 50 | 25 | 100 |
| 301 | 43 | 68 | 31 | | 12.5 | 2.3 | 100 |
| 302 | 980 | 3100 | 18 | | 38 | 50 | 50 |
| 303 | 14 | 96 | 3.9 | | 18.8 | 4.7 | 200 |
| 304 | 170 | 1300 | 7.8 | | 4.7 | 38 | 18.8 |
| 305 | 120 | 250 | 12 | | 2.3 | 6.2 | 25 |
| 306 | 670 | 2700 | 13 | | 3.1 | 25 | 12.5 |
| 307 | 120 | 390 | 24 | | 4.7 | 6.2 | 25 |
| 308 | 120 | 370 | 32 | | 3.1 | 9.4 | 25 |
| 309 | 62 | 150 | 24 | | 6.2 | 6.2 | 75 |
| 310 | 430 | 1800 | 4.6 | | 4.7 | 25 | 12.5 |
| 311 | 87 | 150 | 26 | | 6.2 | 9.4 | 100 |
| 312 | 42 | 250 | 48 | | 9.4 | 31 | 150 |
| 313 | 75 | 360 | 3.8 | | 1.6 | 12.5 | 12.5 |
| 314 | 49 | 190 | 16 | | 6.2 | 12.5 | 75 |
| 315 | 67 | 61 | 6.0 | | 3.1 | 6.2 | 38 |
| 316 | 450 | 1200 | 22 | | 1.6 | 12.5 | 12.5 |
| 317 | 350 | 1600 | 14 | | 1.6 | 12.5 | 18.8 |
| 318 | 370 | 2000 | 11 | | 1.6 | 18.8 | 12.5 |
| 319 | 350 | 1000 | 13 | | 12.5 | 18.8 | 25 |
| 320 | 83 | 320 | 15 | | 1.6 | 12.5 | 50 |
| 321 | 440 | 1600 | 5.1 | | 3.1 | 18.8 | 18.8 |
| 322 | 340 | 550 | 11 | | 18.8 | 25 | 50 |
| 323 | 120 | 930 | 17 | | 1.6 | 6.2 | 18.8 |
| 324 | 4400 | 12000 | 330 | | >200 | >200 | >200 |
| 325 | 1100 | 4400 | 36 | | 12.5 | 75 | 75 |
| 326 | 6400 | >20000 | 29 | | 50 | >200 | 6.2 |
| 327 | 470 | 2600 | 17 | | 9.4 | 38 | 38 |
| 328 | 260 | 1100 | 12 | | 9.4 | 50 | 50 |
| 329 | 170 | 450 | 49 | | 12.5 | 25 | >200 |
| 330 | 100 | 400 | 22 | | 16 | 25 | 100 |
| 331 | 130 | 340 | 49 | | 9.4 | 18.8 | 100 |
| 332 | 160 | 540 | 24 | | 4.7 | 12.5 | 50 |
| 333 | 58 | 170 | 8.2 | | 1.6 | 12.5 | 38 |
| 334 | 280 | 1100 | 53 | | 6.2 | 25 | 50 |
| 335 | 59 | 56 | 4.9 | | 6.2 | 3.1 | 75 |
| 336 | 180 | 1200 | 20 | | 3.1 | 25 | 25 |
| 337 | 62 | 300 | 10 | | 9.4 | 18.8 | 75 |
| 338 | 110 | 200 | 38 | | 31 | 9.4 | 150 |
| 339 | 3.6 | 160 | 1.4 | | 18.8 | 6.2 | 38 |
| 340 | 46 | 180 | 3.5 | | 38 | 4.7 | 50 |
| 341 | 6.6 | 110 | 0.99 | | 18.8 | 2.3 | 18.8 |
| 342 | 4.7 | 170 | 1.1 | | 6.2 | 3.1 | 12.5 |
| 343 | 11 | 22 | 2.4 | | 25 | 0.39 | 18.8 |
| 344 | 14 | 28 | 1.7 | | 38 | 0.59 | 50 |
| 345 | 39 | 270 | 1.7 | | 25 | 6.2 | 18.8 |
| 346 | 21 | 320 | 2.2 | | 75 | 6.2 | 38 |
| 347 | 160 | 1600 | 6.5 | | 50 | 25 | 25 |
| 348 | 22 | 540 | 2.2 | | 18.8 | 6.2 | 18.8 |
| 349 | 11 | 140 | 1.3 | | 9.4 | 3.9 | 12.5 |
| 350 | 26 | 380 | 3.0 | | 25 | 6.2 | 25 |
| 351 | 0.78 | 24 | 1.6 | | 7.8 | 0.59 | 25 |
| 352 | 1.7 | 7.8 | 1.7 | | 18.8 | 0.39 | 50 |
| 353 | 13 | 160 | 2.3 | | 38 | 6.2 | 100 |
| 354 | 13 | 310 | 1.4 | | 9.4 | 4.7 | 9.4 |
| 355 | 21 | 550 | 2.8 | | 12.5 | 9.4 | 18.8 |
| 356 | 6.2 | 170 | 1.5 | | 25 | 4.7 | 18.8 |
| 357 | 170 | 2100 | 63 | | 150 | 38 | 150 |
| 358 | 47 | 1000 | 6.2 | | 38 | 12.5 | 62 |
| 359 | 60 | 750 | 2.5 | | 9.4 | 12.5 | 6.2 |
| 360 | 47 | 510 | 13 | | 25 | 18.8 | 150 |

TABLE 1-continued

Inhibition of metallo-β-lactamases (IMP-1, NDM-1, VIM-1) and antibiotic potentiation vs. MBL-expressing bacteria by EXAMPLES 1-456.

| Ex. No. | NDM1 IC50 (nM) | IMP1 IC50 (nM) | VIM1 IC50 (nM) | NDM1 EC30005 MITC95 (μM) | NDM1 EC30016 MITC95 (μM) | IMP1 SM5741 MITC95 (μM) | VIM1 KP599644 MITC95 (μM) |
|---|---|---|---|---|---|---|---|
| 361 | 390 | 8700 | 29 | 38 | 150 | 25 | |
| 362 | 640 | 11000 | 10 | 25 | 150 | 18.8 | |
| 363 | 150 | 810 | 20 | 100 | 25 | 100 | |
| 364 | 110 | 1600 | 2.4 | 9.4 | 38 | 12.5 | |
| 365 | 82 | 1500 | 20 | 38 | 38 | 50 | |
| 366 | 870 | 8600 | 13 | 50 | 150 | 25 | |
| 367 | 1400 | >20000 | 260 | >200 | >200 | >200 | |
| 368 | 46 | 740 | 9.7 | 25 | 37.5 | 50 | |
| 369 | 150 | 2300 | 3.2 | 12.5 | 50 | 12.5 | |
| 370 | 870 | 9000 | 6.3 | 44 | 175 | 41 | |
| 371 | 93 | 290 | 94 | 12.5 | 12.5 | 75 | |
| 372 | 570 | 1600 | 190 | 38 | 75 | >200 | |
| 373 | 4300 | 16000 | 2200 | >200 | >200 | >200 | |
| 374 | 12 | 90 | 3.0 | 9.4 | 9.4 | 62 | |
| 375 | 730 | 3200 | 570 | >200 | 200 | >200 | |
| 376 | 77 | 660 | 4.6 | 25 | 25 | 50 | |
| 377 | 22 | 37 | 24 | 12.5 | 4.7 | 200 | |
| 378 | 37 | 80 | 7.8 | 18.8 | 6.2 | 50 | |
| 379 | 32 | 370 | 7.1 | 9.4 | 16 | 100 | |
| 380 | 12 | 64 | 2.4 | 4.7 | 4.7 | 50 | |
| 381 | 24 | 86 | 4.1 | 9.4 | 4.7 | 75 | |
| 382 | 140 | 170 | 34 | 12.5 | 12.5 | 75 | |
| 383 | 34 | 150 | 56 | 25 | 12.5 | 150 | |
| 384 | 39 | 130 | 7.8 | 12.5 | 6.2 | 75 | |
| 385 | 810 | 4900 | 190 | >200 | >200 | >200 | |
| 386 | 120 | 180 | 100 | 25 | 12.5 | >200 | |
| 387 | 880 | 2400 | 920 | >200 | >200 | >200 | |
| 388 | 130 | 340 | 18 | 25 | 18.8 | 38 | |
| 389 | 16 | 58 | 4.4 | 25 | 6.2 | 100 | |
| 390 | 35 | 240 | 5.3 | 1.6 | 12.5 | 25 | |
| 391 | 44 | 640 | 52 | 25 | 25 | 100 | |
| 392 | 49 | 270 | 18 | 6.2 | 25 | 75 | |
| 393 | 3.2 | 1000 | 4.5 | 4.7 | 25 | 75 | |
| 394 | 2.2 | 450 | 3.9 | 4.7 | 25 | 38 | |
| 395 | 0.10 | 120 | 0.48 | 6.2 | 6.25 | 16 | |
| 396 | 9.2 | 2800 | 18 | 9.4 | 75 | 50 | |
| 397 | 13 | 5000 | 16 | 6.2 | 200 | 75 | |
| 398 | 1.6 | 1100 | 10 | 3.1 | 75 | 25 | |
| 399 | 1.4 | 430 | 1.6 | 6.2 | 25 | 25 | |
| 400 | 340 | 750 | 42 | 12.5 | 25 | 50 | |
| 401 | 3.9 | 1900 | 13 | 9.4 | 50 | 50 | |
| 402 | 9.5E−02 | 230 | 1.5 | 3.1 | 12.5 | 25 | |
| 403 | 2.4 | 550 | 3.3 | 9.4 | 18.8 | 50 | |
| 404 | 227.8 | 622.3 | 21.89 | 18.75 | 75 | 75 | |
| 405 | 2826 | 14770 | 39.64 | 12.5 | 200 | 12.5 | |
| 406 | 427.7 | 815.4 | 14.93 | 6.25 | 37.5 | 6.25 | |
| 407 | 34.38 | 922.8 | 2.223 | 18.75 | 75 | 50 | |
| 408 | 249.5 | 3446 | 6.495 | 7.813 | 75 | 25 | |
| 409 | 809.9 | 19810 | 14.04 | 12.5 | 200 | 25 | |
| 410 | 417.5 | 6035 | 6.229 | 7.813 | 75 | 25 | |
| 411 | 179.3 | 2771 | 2.958 | 4.688 | 50 | 12.5 | |
| 412 | 71.4 | 275.5 | 4.491 | 9.375 | 9.375 | 12.5 | |
| 413 | 146 | 1095 | 4.602 | 6.25 | 25 | 12.5 | |
| 414 | 68.98 | 214.3 | 1.52 | 4.688 | 9.375 | 12.5 | |
| 415 | 121.1 | 390.2 | 4.323 | 9.375 | 12.5 | 18.75 | |
| 416 | 280.2 | 1137 | 20.76 | 25 | 25 | 25 | |
| 417 | 1284 | 11090 | 45.14 | 4.688 | 200 | 9.375 | |
| 418 | 404.7 | 1991 | 30.81 | 18.75 | 37.5 | 25 | |
| 419 | 869 | 5917 | 5.508 | 6.25 | 50 | 12.5 | |
| 420 | 72.44 | 51.7 | 19.15 | 0.3906 | 1.563 | 2.344 | |
| 421 | 156.8 | 156 | 24.88 | 25 | 100 | 25 | |
| 422 | 228 | 104.4 | 4.013 | 12.5 | 25 | 6.25 | |
| 423 | 1.222 | 2.771 | 0.9894 | 12.5 | 25 | 50 | |
| 424 | 2.677 | 9.294 | 10.76 | 12.5 | 25 | 200 | |
| 425 | 104.9 | 281.6 | 3.631 | 12.5 | 25 | 12.5 | |
| 426 | 141.9 | 27.93 | 49.49 | 12.5 | 2.344 | 150 | |
| 427 | 119.3 | 342.1 | 17.92 | 1.563 | 3.125 | 9.375 | |
| 428 | 45.35 | 18.82 | 37.16 | 0.7813 | 1.563 | 12.5 | |
| 429 | 781.5 | 615 | 23.78 | 12.5 | 18.75 | 25 | |

TABLE 1-continued
Inhibition of metallo-β-lactamases (IMP-1, NDM-1, VIM-1) and antibiotic potentiation vs. MBL-expressing bacteria by EXAMPLES 1-456.
| Ex. No. | NDM1 IC50 (nM) | IMP1 IC50 (nM) | VIM1 IC50 (nM) | NDM1 EC30005 MITC95 (μM) | NDM1 EC30016 MITC95 (μM) | IMP1 SM5741 MITC95 (μM) | VIM1 KP599644 MITC95 (μM) |
|---|---|---|---|---|---|---|---|
| 430 | 619.8 | 543.5 | 52.62 |  | 12.5 | 25 | 25 |
| 431 | 71.7 | 32.4 | 16.64 |  | 6.25 | 2.344 | 12.5 |
| 432 | 141.2 | 1009 | 5.584 |  | 9.375 | 12.5 | 12.5 |
| 433 | 86.95 | 2000 | 10.13 |  | 12.5 | 100 | 12.5 |
| 434 | 67.87 | 2000 | 16.6 |  | 12.5 | 100 | 25 |
| 435 | 431.8 | 7743 | 13.58 |  | 0.7813 | 50 | 2.344 |
| 436 | 1051 | 8291 | 53.96 |  | 2.344 | 100 | 25 |
| 437 | 533 | 11400 | 1.73 |  | 4.688 | 150 | 6.25 |
| 438 | 13.43 | 4.845 | 1.574 |  | 25 | 1.172 | 75 |
| 439 | 225 | 483.3 | 4.32 |  | 31.25 | 37.5 | 37.5 |
| 440 | 37.51 | 124.2 | 1.616 |  | 6.25 | 6.25 | 12.5 |
| 441 | 112.6 | 214 | 19.7 |  | 25 | 18.75 | 50 |
| 442 | 74.69 | 110.2 | 8.732 |  | 12.5 | 6.25 | 25 |
| 443 | 298.4 | 1058 | 4.286 |  | 12.5 | 37.5 | 25 |
| 444 | 82.87 | 215.6 | 76.52 |  | 9.375 | 12.5 | 25 |
| 445 | 281.4 | 693 | 1.984 |  | 9.375 | 25 | 12.5 |
| 446 | 169.6 | 379.5 | 6.936 |  | 12.5 | 18.75 | 25 |
| 447 | 104.1 | 162.8 | 6.348 |  | 9.375 | 6.25 | 25 |
| 448 | 92.47 | 7794 | 48.59 |  | 12.5 | 200 | 37.5 |
| 449 | 72.86 | 8858 | 87.19 |  | 9.375 | 200 | 25 |
| 450 | 88.93 | 137.9 | 2.178 |  | 7.813 | 6.25 | 18.75 |
| 451 | 30.75 | 27.21 | 10.11 |  | 9.375 | 3.125 | 25 |
| 452 | 93.14 | 222.5 | 0.937 |  | 9.375 | 9.375 | 12.5 |
| 453 | 64.53 | 100.8 | 2.252 |  | 6.25 | 3.125 | 12.5 |
| 454 | 29.51 | 24.74 | 3.523 |  | 4.688 | 1.563 | 25 |
| 455 | 23.37 | 23.88 | 3.381 |  | 4.688 | 3.125 | 18.75 |
| 456 | 4.349 | 7.093 | 0.6366 |  | 18.75 | 0.7813 | 37.5 |
Intermediate 1
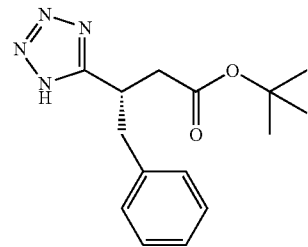 [SMILES: CC(C)(C)OC(=O)C[C@H](Cc1ccccc1)c1nnn[nH]1]
(S)-tert-butyl 4-phenyl-3-(1H-tetrazol-5-yl)butanoate
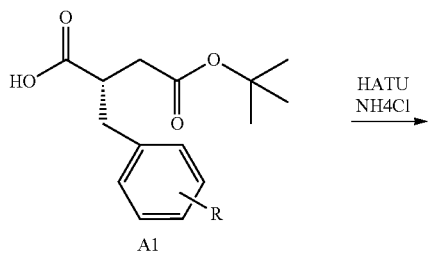
A1
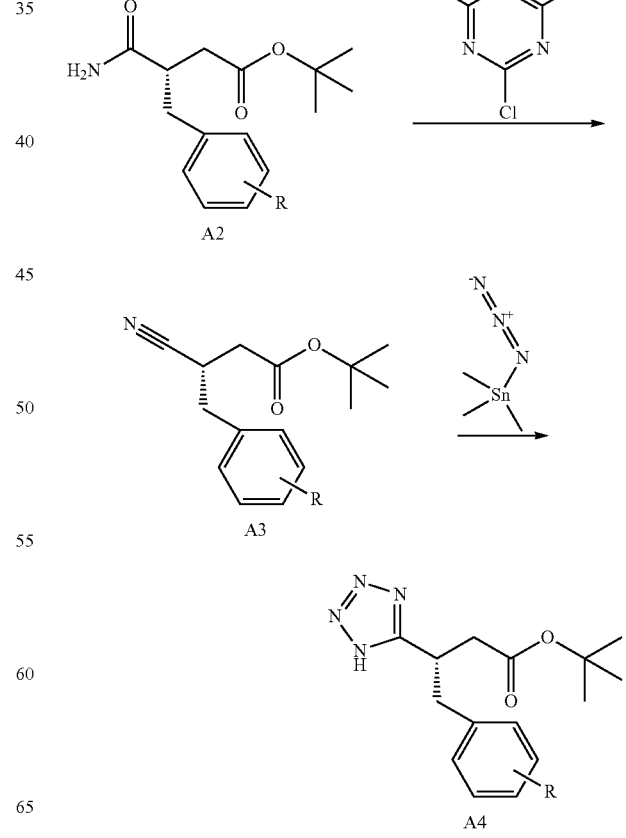

Step A: (S)-tert-butyl 4-amino-3-benzyl-4-oxobutanoate (S)-2-benzyl-4-(tert-butoxy)-4-oxobutanoic acid and its bromo derivatives were prepared according to the literature methods (Liu, Jian-Chao, et al. Synthetic Communications, 2004, 34 (14), 2633-2640). A mixture of (S)-2-benzyl-4-(tert-butoxy)-4-oxobutanoic acid (520 mg, 2.0 mmol), HATU (1130 mg, 3.0 mmol), ammonium chloride (640 mg, 12 mmol), and Hunig's Base (3.5 ml, 20 mmol) in DMF (10 ml) was stirred at RT overnight. The reaction mixture was partitioned with EtOAc and sat. aq. NaHCO$_3$, washed with brine (3×), dried over Na$_2$SO$_4$, and evaporated to get the crude product. The crude was used in Step B.

Step B: (S)-tert-butyl 3-cyano-4-phenylbutanoate

The crude containing (S)-tert-butyl 4-amino-3-benzyl-4-oxobutanoate (~440 mg, 1.7 mmol) from Step A was dissolved in DMF and cooled to 0° C. Cyanuric chloride (2200 mg, 12 mmol) was added to the reaction mixture at 0° C. The ice bath was removed and the mixture was stirred at RT and for two days. The mixture was cooled in ice bath to which was added sat'd NaHCO$_3$ until bubbling ceased. The mixture was extracted with EtOAc (3×). The combined EtOAc layer was washed with water (2×), brine, dried (Na$_2$SO$_4$), filtered, and concentrated to obtain the crude.

Step C: (S)-tert-butyl 4-phenyl-3-(1H-tetrazol-5-yl)butanoate

A solution of the crude containing (S)-tert-butyl 3-cyano-4-phenylbutanoate (334 mg, 1.36 mmol) from Step B, azidotrimethyltin (IV) (510 mg, 2.5 mmol) in toluene (10 ml) was heated at 110° C. for two days. The reaction mixture was concentrated under vacuum after quenching with MeOH. The crude was purified using silica gel Flash Chromatography, eluted with EtOAc-hexane, 0-50% to obtain pure product, (S)-tert-butyl 4-phenyl-3-(1H-tetrazol-5-yl)butanoate. LC-MS: m/z 289.17 (calc. 289.16)

The following INTERMEDIATES were prepared according to the methods for INTERMEDIATE 1

| INT. NO. | Structure | Name | Calc'd (M + H)$^+$ | HPLC m/z (M + H)$^+$ |
|---|---|---|---|---|
| 1 | 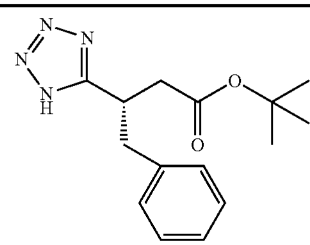 | (S)-tert-butyl 4-phenyl-3-(1H-tetrazol-5-yl)butanoate | 289.16 | 289.17 |
| 2 | 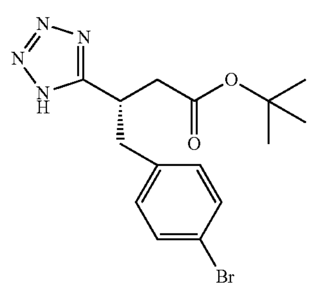 [SMILES: CC(C)(C)OC(=O)C[C@H](Cc1ccc(Br)cc1)c1nnn[nH]1] | (S)-tert-butyl 4-(4-bromophenyl)-3-(1H-tetrazol-5-yl)butanoate | 367.08 | 367.04 |
| 3 | 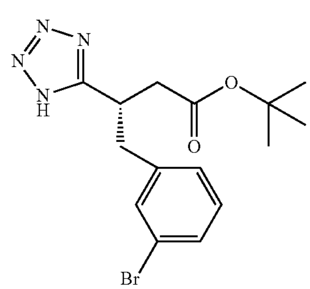 [SMILES: CC(C)(C)OC(=O)C[C@H](Cc1cccc(Br)c1)c1nnn[nH]1] | (S)-tert-butyl 4-(3-bromophenyl)-3-(1H-tetrazol-5-yl)butanoate | 367.08 | 367.04 |
| 4 | 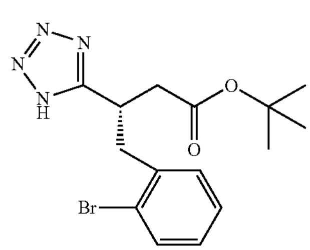 [SMILES: CC(C)(C)OC(=O)C[C@H](Cc1ccccc1Br)c1nnn[nH]1] | (S)-tert-butyl 4-(2-bromophenyl)-3-(1H-tetrazol-5-yl)butanoate | 367.08 | 369.10 |

-continued

| INT. NO. | Structure | Name | Calc'd (M + H)+ | HPLC m/z (M + H)+ |
|---|---|---|---|---|
| 5 | 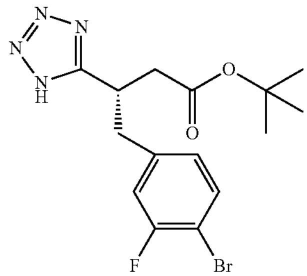 [SMILES: CC(C)(C)OC(=O)C[C@H](Cc1ccc(Br)c(F)c1)c1nnn[nH]1] | (S)-tert-butyl 4-(4-bromo-3-fluorophenyl)-3-(1H-tetrazol-5-yl)butanoate | 385.07 | 385.00 |
| 6 | 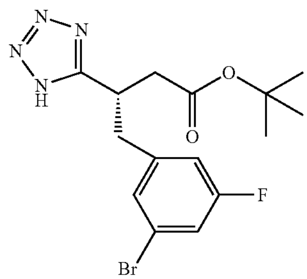 [SMILES: CC(C)(C)OC(=O)C[C@H](Cc1cc(F)cc(Br)c1)c1nnn[nH]1] | (S)-tert-butyl 4-(3-bromo-5-fluorophenyl)-3-(1H-tetrazol-5-yl)butanoate | 387.07 | 386.98 |

Intermediates 7 and 8

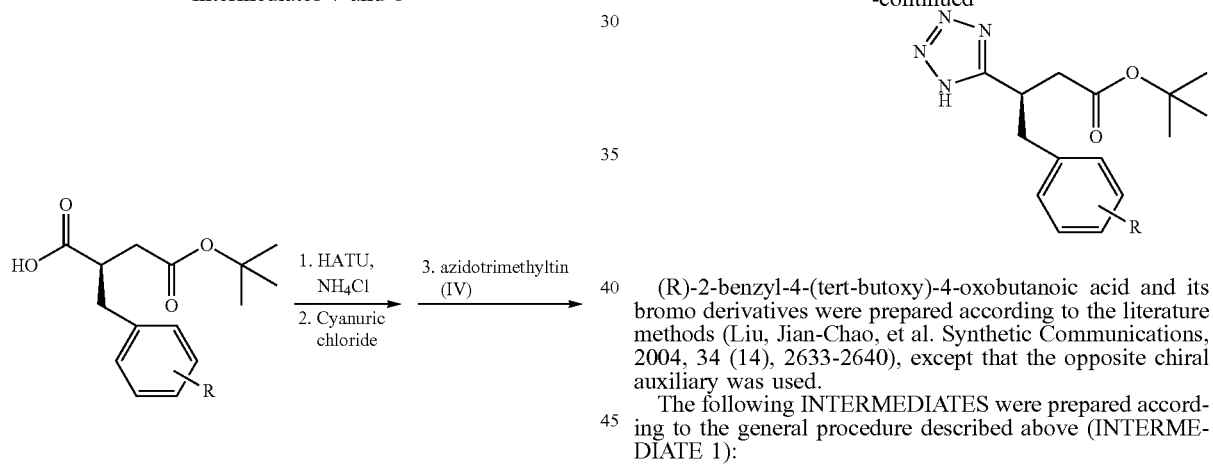

(R)-2-benzyl-4-(tert-butoxy)-4-oxobutanoic acid and its bromo derivatives were prepared according to the literature methods (Liu, Jian-Chao, et al. Synthetic Communications, 2004, 34 (14), 2633-2640), except that the opposite chiral auxiliary was used.

The following INTERMEDIATES were prepared according to the general procedure described above (INTERMEDIATE 1):

| INT. NO. | Structure | Name | Calculated (M + H)+ | HPLC-MS m/z (M + H)+ |
|---|---|---|---|---|
| 7 | 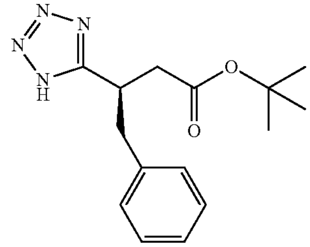 [SMILES: CC(C)(C)OC(=O)C[C@@H](Cc1ccccc1)c1nnn[nH]1] | (R)-tert-butyl 4-phenyl-3-(1H-tetrazol-5-yl)butanoate | 289.16 | 289.14 |

| INT. NO. | Structure | Name | Calculated (M + H)+ | HPLC-MS m/z (M + H)+ |
|---|---|---|---|---|
| 8 | 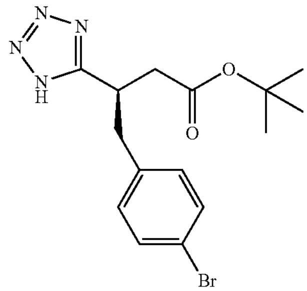 [SMILES: CC(C)(C)OC(=O)C[C@@H](Cc1ccc(Br)cc1)c1nnn[nH]1] | (R)-tert-butyl 4-(4-bromophenyl)-3-(1H-tetrazol-5-yl)butanoate | 367.08 | 367.12 |

Intermediate 9

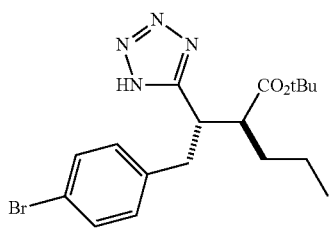

(S)-tert-butyl 2-((S)-2-(4-bromophenyl)-1-(1H-tetrazol-5-yl)ethyl)pentanoate

To a solution of (S)-tert-butyl 4-(4-bromophenyl)-3-(1H-tetrazol-5-yl)butanoate (2.1 g, 5.7 mmol) in THF (30 ml) at −78° C., lithium diisopropylamide in THF (7.2 ml, 14 mmol) was added dropwise and then stirred at −78° C. for 1 hour. 1-Iodopropane (2.0 g, 12 mmol) was added dropwise and the reaction mixture was stirred at −78° C. for 2 hrs, then slowly warmed to RT overnight. LCMS indicated all of SM was gone, quenched with 20 ml of saturated NH$_4$Cl, extracted with EtOAc (60 ml×4). The extracts were combined, washed with brine and dried over with MgSO$_4$/Na$_2$SO$_4$. The combined extracts were filtered and evaporated to give the crude oil, which was purified by MPLC with a 120 G silica gel column to furnish a light yellow solid. LC-MS: m/z (M+H)+ 411.29

The following INTERMEDIATES were prepared following the same procedure of INT-9:

| INT. NO. | Structure | Name | Calculated (M + H)+ | HPLC-MS m/z (M + H)+ |
|---|---|---|---|---|
| 10 | 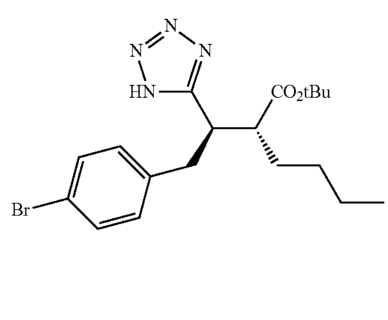 [SMILES: CCCC[C@@H](C(=O)OC(C)(C)C)[C@@H](Cc1ccc(Br)cc1)c1nnn[nH]1] | (R)-tert-butyl 2-((R)-2-(4-bromophenyl)-1-(1H-tetrazol-5-yl)ethyl)hexanoate | 423.14 | 423.31 |
| 11 | 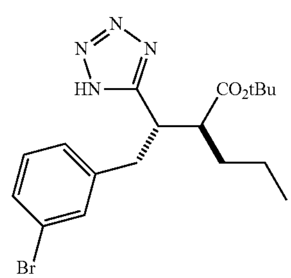 [SMILES: CCC[C@H](C(=O)OC(C)(C)C)[C@H](Cc1cccc(Br)c1)c1nnn[nH]1] | (S)-tert-butyl 2-((S)-2-(3-bromophenyl)-1-(1H-tetrazol-5-yl)ethyl)pentanoate | 411.12 | 411.17 |

-continued

| INT. NO. | Structure | Name | Calculated (M + H)+ | HPLC-MS m/z (M + H)+ |
|---|---|---|---|---|
| 12 | 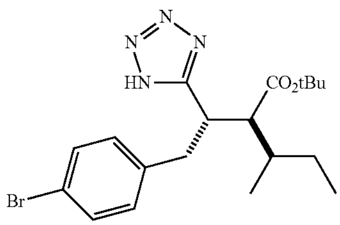 [SMILES: CCC(C)[C@H](C(=O)OC(C)(C)C)[C@H](Cc1ccc(Br)cc1)c1nnn[nH]1] | (2S,3R)-tert-butyl 2-((S)-2-(4-bromophenyl)-1-(1H-tetrazol-5-yl)ethyl)-3-methylpentanoate | 425.14 | 425.19 |
| 13 | 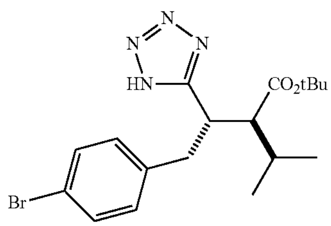 [SMILES: CC(C)[C@H](C(=O)OC(C)(C)C)[C@H](Cc1ccc(Br)cc1)c1nnn[nH]1] | (2S,3S)-tert-butyl 4-(4-bromophenyl)-2-isopropyl-3-(1H-tetrazol-5-yl)butanoate | 411.12 | 411.19 |
| 14 | 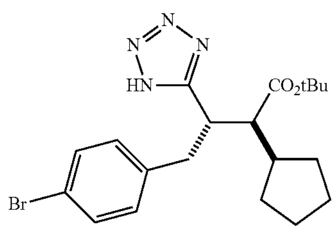 [SMILES: CC(C)(C)OC(=O)[C@@H](C1CCCC1)[C@H](Cc1ccc(Br)cc1)c1nnn[nH]1] | (2S,3S)-tert-butyl 4-(4-bromophenyl)-2-cyclopentyl-3-(2H-tetrazol-5-yl)butanoate | 437.14 | 437.17 |

Intermediate 15

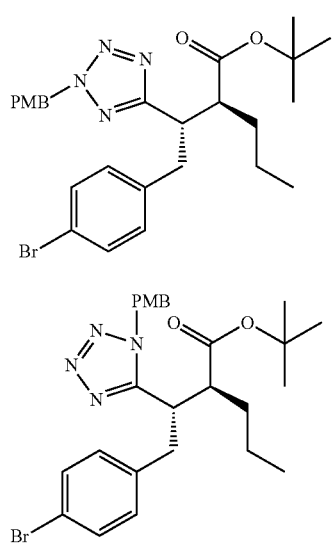

Mixture of (S)-tert-butyl 2-((S)-2-(4-bromophenyl)-1-(1-(4-methoxybenzyl)-1H-tetrazol-5-yl)ethyl)pentanoate (S)-tert-butyl 2-((S)-2-(4-bromophenyl)-1-(2-(4-methoxybenzyl)-2H-tetrazol-5-yl)ethyl)pentanoate Potassium carbonate (1.27 g, 9.2 mmol) was added to a stirred mixture of (S)-tert-butyl 2-((S)-2-(4-bromophenyl)-1-(1H-tetrazol-5-yl)ethyl)-4-methylpentanoate (1.3 g, 3.1 mmol), tetrabutyl ammonium chloride hydrate (0.27 g, 0.92 mmol), and 1-(chloromethyl)-4-methoxybenzene (1.045 ml, 7.68 mmol) in $CHCl_3$ (3.0 ml) and water (3.0 ml) at room temperature and the mixture was stirred at 35° C. for overnight. The reaction was cooled to RT, organic layers were separated and the inorganic layer was extracted with DCM for 3 times (10 mL×3). The combined organic layers were dried over $MgSO_4$, concentrated down to give the crude material, which was purified by column chromatography with 40 g silica gel, and eluted with EtOAc/Hexane (0-35%) to give the product. LC-MS: m/z (M+H)+ 529.33

The following INTERMEDIATES were prepared following the same procedure of INT-15:

| INT. NO. | Structure | Name | Calculated (M + H)+ | HPLC-MS (M + H)+ m/z |
|---|---|---|---|---|
| 16 | | (S)-tert-butyl 2-((S)-2-(4-bromo-3-fluorophenyl)-1-(1-(4-methoxybenzyl)-1H-tetrazol-5-yl)ethyl)-4-methylpentanoate And (S)-tert-butyl 2-((S)-2-(4-bromo-3-fluorophenyl)-1-(2-(4-methoxybenzyl)-2H-tetrazol-5-yl)ethyl)-4-methylpentanoate | 563.19 | 563.11 |
| 17 | | (S)-tert-butyl 2-((S)-2-(3-bromo-5-fluorophenyl)-1-(1-(4-methoxybenzyl)-1H-tetrazol-5-yl)ethyl)-4-methylpentanoate And (S)-tert-butyl 2-((S)-2-(3-bromo-5-fluorophenyl)-1-(2-(4-methoxybenzyl)-2H-tetrazol-5-yl)ethyl)-4-methylpentanoate | 563.19 | 563.04 |

Intermediate 18

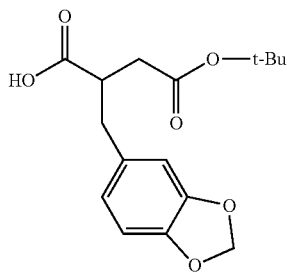 [SMILES: CC(C)(C)OC(=O)CC(Cc1ccc2c(c1)OCO2)C(=O)O]

2-(benzo[d][1,3]dioxol-5-ylmethyl)-4-(tert-butoxy)-4-oxobutanoic acid

Step A: (E)-4-(benzo[d][1,3]dioxol-5-yl)-3-(methoxycarbonyl)but-3-enoic acid

A solution of benzo[d][1,3]dioxole-5-carbaldehyde (1.5 g, 10 mmol), and dimethyl succinate (1.9 g, 13 mmol) in anhydrous t-BuOH (5.0 ml) was added dropwise within 15 min to a refluxing mixture of potassium tert-butoxide (280 mg, 2.5 mmol) in t-BuOH (10 ml). The reaction mixture was refluxed overnight. After cooling to RT, to the solution was added water/1N HCl (15 mL) and EtOAc for partitioning. Then, the reaction mixture was extracted three times with EtOAc (15 ml), the combined organic layers were dried over with $Na_2SO_4$/$MgSO_4$, filtered, and evaporated to dryness to give a yellow crude solid which was purified by chromatography on silica gel and eluted with Hexane-EtOAc (0-100%), to provide the desired product. LC-MS m/z $[M+Na]^+$ 287.06

Step B: (E)-4-tert-butyl 1-methyl 2-(benzo[d][1,3]dioxol-5-ylmethylene)succinate (Z)-4-(benzo[d][1,3]dioxol-5-yl)-3-(methoxycarbonyl)but-3-enoic acid (6.6 g, 25 mmol) was dissolved in Toluene (100 ml) at 80° C., then N,N-dimethylformamide di-tert-butyl acetal (18 ml, 75 mmol) was added dropwise for 10 mins, and the solution was heated at 70° C. for overnight. The reaction was cooled to RT, washed with 40 ml of water, 40 ml×2 of saturated $NaHCO_3$, and brine; dried over with $MgSO_4$, filtered to give the crude which was purified by chromatography on silica gel and eluted with Hexane-EtOAc (0-30%). LC-MS m/z $[M+Na]^+$ 343.45.

Step C: 4-tert-butyl 1-methyl 2-(benzo[d][1,3]dioxol-5-ylmethyl)succinate

To a solution of (Z)-4-tert-butyl 1-methyl 2-(benzo[d][1,3]dioxol-5-ylmethylene)succinate (300 mg, 0.94 mmol) in MeOH (8.0 ml) under $N_2$, palladium hydroxide on carbon (66 mg, 0.094 mmol) was added and then the reaction mixture was stirred at RT under $H_2$ at 1 atm. After 1 hr, LCMS showed that all of the SM was gone. The reaction mixture was filtered with HPLC filtration and dried on rotovap to give the crude. The crude was used as is in the following step Step D: 2-(benzo[d][1,3]dioxol-5-ylmethyl)-4-(tert-butoxy)-4-oxobutanoic acid To a stirred solution of 4-tert-butyl 1-methyl 2-(benzo[d][1,3]dioxol-5-ylmethyl)succinate (560 mg, 1.7 mmol) in MeOH (20 ml) and Water (10 ml) at RT, lithium hydroxide hydrate (210 mg, 5.0 mmol) was added and the reaction mixture was stirred at RT overnight. LCMS showed all of SM was gone and most of the solvent was evaporated. To the residue was added DCM and water, and the mixture was acidified with 2N HCl to pH<2 and extracted with DCM three times. The combined organic layers were dried over with Na2SO4, filtered and dried in vacuum to give the crude. The crude was used as is. LC-MS m/z $[M+Na]^+$ 331.26

Intermediate 19

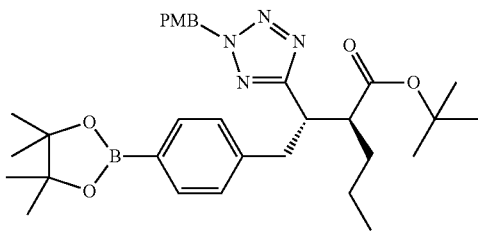

(S)-tert-butyl 2-((S)-1-(2-(4-methoxybenzyl)-2H-tetrazol-5-yl)-2-(4-(4,4,5,5-tetramethyl-1,3,2-dioxaborolan-2-yl)phenyl)ethyl)pentanoate A round bottle flask was charged with (S)-tert-butyl 2-((S)-2-(4-bromophenyl)-1-(1-(4-methoxybenzyl)-1H-tetrazol-5-yl)ethyl)pentanoate (414 mg, 0.78 mmol), bis(pinacolato)diboron (300 mg, 1.2 mmol), 1,1'-bis(diphenylphosphino)ferrocene-palladium(II)dichloride dichloromethane complex (32 mg, 0.039 mmol), potassium acetate (150 mg, 1.6 mmol) and then purged with $N_2$. DMA (2.5 ml) was added and the reaction heated to 85° C. overnight, cooled to RT and filtered through syringe filter. The filtrate was added to sat. aqueous sodium bicarbonate, diluted with EtOAc/water and extracted 3 times with EtOAc. The combined extractions were washed with brine, dried over $MgSO_4$, filtered, and concentrated to produce a crude brown oil. The crude oil was purified via 0-30% EtOAc/Hexane ISCO, 24 g silica gel, to furnish a white sticky solid. LC-MS m/z $[M+H]^+$ 577.43

Intermediate 20

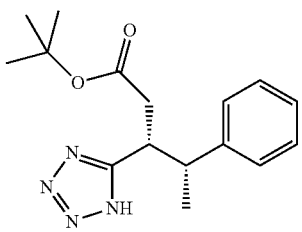 [SMILES: C[C@@H](c1ccccc1)[C@@H](CC(=O)OC(C)(C)C)c1nnn[nH]1]

(3R,4R)-tert-butyl 4-phenyl-3-(1H-tetrazol-5-yl)pentanoate

Step A: (S)-triethyl 2-phenylpropane-1,1,1-tricarboxylate

To a solution of (R)-1-phenylethanol (20 g, 0.16 mol) and $HC(CO_2Et)_3$ (76 g, 0.33 mol) in toluene (800 mL) at room temperature was added PMe₃ (25 g, 0.327 mol) in one portion. The resulting solution was cooled to −53° C. DEAD (57 g, 0.327 mol) was added dropwise keeping the internal temperature at −53° C. The reaction was stirred at −53° C. for 30 minutes and warmed to room temperature for 4 hours. TLC (PE/EtOAc 5:1) showed the SM was consumed completely. The solvent was removed under reduced pressure. The residue was dissolved in MTBE (500 mL), washed with aqueous NaOH (3.3 N, 200 mL×2) and aqueous HCl (200 mL). The organic phase was washed with brine, dried over Na₂SO₄ and concentrated to give an oil. The crude product was purified by silica gel column chromatography (PE/EtOAc 50:1) to give (S)-triethyl 2-phenylpropane-1,1,1-tricarboxylate as a colorless oil. ¹H-NMR (DMSO, 400 MHz) δ 7.35 (m, 5H), 4.12 (m, 6H), 3.74 (m, 1H), 1.39 (d, J=7.2 Hz, 3H), 1.12 (t, J=7.2 Hz, 9H).

Step B: (R)-3-phenylbutanoic acid

To a solution of (S)-triethyl 2-phenylpropane-1,1,1-tricarboxylate (54.3 g, 0.162 mol) in MeOH (480 mL) was added aqueous NaOH (291 mL, 0.96 mol, 3.3 N). The resulting solution was stirred at reflux for 6 hours. HPLC showed there was no starting material remaining. The reaction solution was concentrated to give crude (S)-2-phenylpropane-1,1,1-tricarboxylic acid, which was immediately used for the next step. Crude (S)-2-phenylpropane-1,1,1-tricarboxylic acid was immediately dissolved in AcOH (970 mL). The resulting solution was stirred at reflux for 16 hours. HPLC showed there was no starting material remaining. AcOH was removed in vacuo. The residue was dissolved in water (1 L), extracted with EtOAc (500 mL×3), dried over Na₂SO₄, and concentrated to give (R)-3-phenylbutanoic acid as an oil. ¹H-NMR (DMSO, 400 MHz) δ 7.30 (m, 5H), 3.18 (m, 1H), 2.50 (m, 2H), 1.22 (d, J=7.2 Hz, 3H).

Step C: (R)-4-benzyl-3-((R)-3-phenylbutanoyl)oxazolidin-2-one

To a solution of (R)-3-phenylbutanoic (25.6 g, 0.156 mol) in anhydrous THF (580 mL) was added Et₃N (21.7 mL) under N₂. The mixture was cooled to −70° C. and t-BuCOCl (19.7 g, 0.163 mol) was added dropwise. The resulting suspension was stirred at −70° C. for 10 minutes and continued to be stirred at 0° C. for 1 hour. Then the resulting mixture was cooled to −70° C. Meanwhile, in a different flask, to a solution of (R)-4-benzyloxazolidin-2-one (27.6 g, 0.156 mol) in THF (580 mL) was added n-BuLi (62.3 mL, 0.156 mol) dropwise below −70° C. The lithiated chiral auxiliary was transferred via a cannula into the reaction flask containing the preformed mixed anhydride at −70° C. The mixture was stirred at 0° C. for 1 hour and allowed to warm to room temperature for 16 hours. TLC (CH₂Cl₂/MeOH 20:1) showed the starting material was consumed. The reaction was quenched with saturated aqueous solution of NH₄Cl. THF was removed and extracted with CH₂Cl₂ (500 mL×3). The organic phase was dried over Na₂SO₄ and concentrated under vacuum. The crude product was purified by recrystallization to give (R)-4-benzyl-3-((R)-3-phenylbutanoyl)oxazolidin-2-one as a white solid. ¹H-NMR (DMSO, 400 MHz) δ 7.31 (m, 10H), 4.58 (m, 1H), 4.27 (m, 1H), 4.16 (m, 1H), 3.14 (1, 1H), 3.13 (m, 2H), 2.95 (m, 1H), 2.90 (m, 1H), 1.28 (d, J=6.8 Hz, 3H).

Step D: (3R,4R)-tert-butyl 3-((R)-4-benzyl-2-oxooxazolidine-3-carbonyl)-4-phenylpentanoate To a solution of (R)-4-benzyl-3-((R)-3-phenylbutanoyl)oxazolidin-2-one (35 g, 0.11 mol) in anhydrous THF (750 mL) was added NaN(TMS)₂ (119 mL, 0.119 mol) dropwise at −70° C. under N₂. After 1.5 hours, a solution of BrCH₂CO₂tBu (27.4 g, 0.141 mol) in dried THF (120 mL) was added dropwise below −70° C. The reaction mixture was maintained at −70° C. for 1 hour and was then allowed to warm to −60° C. during 3 hours. TLC (PE/EtOAc 5:1) showed the SM was consumed. The mixture was allowed to warm to −20° C. and quenched with saturated aqueous NH₄Cl. THF was removed under reduced pressure. The aqueous phase was extracted with EtOAc (500 mL×3). The organic phase was dried over Na₂SO₄ and concentrated under vacuum. The crude product was purified by silica gel column chromatography (PE/EtOAc 40:1) to give (3R,4R)-tert-butyl 3-((R)-4-benzyl-2-oxooxazolidine-3-carbonyl)-4-phenylpentanoate as a colorless oil. ¹H-NMR (DMSO, 400 MHz) δ 7.31 (m, 10H), 4.38 (m, 1H), 4.30 (m, 1H), 4.07 (m, 1H), 4.04 (m, 1H), 3.15 (m, 1H), 2.91 (m, 3H), 2.26 (m, 1H), 1.34 (s, 9H), 1.21 (d, J=6.8 Hz, 3H).

Step E: (R)-4-(tert-butoxy)-4-oxo-2-((R)-1-phenylethyl)butanoic acid

To a solution of 3-((R)-4-benzyl-2-oxooxazolidine-3-carbonyl)-4-phenylpentanoate (19 g, 43.4 mmol) in THF and H₂O (700 mL) was added H₂O₂ (18.2 mL, 178 mmol) dropwise at 0° C. After the addition, 1.0 M aqueous solution of LiOH (86.8 mL, 86.8 mmol) was added dropwise at 0° C. The reaction was then stirred at room temperature for 16 hours. TLC (PE/EtOAc 5:1) showed most of the starting material was consumed. The reaction was quenched with 1.5 M aqueous solution of Na₂SO₃ (131 mL) and was given a pH=8~9 by addition of saturated aqueous solution of NaHCO₃. THF was removed in vacuo. The residue was dissolved in water (200 mL) and extracted with MTBE (200 mL×6). The aqueous phase was acidized to pH=3~4 by addition of 1 N HCl and extracted with EtOAc (200 mL×3). The organic phase was washed with brine (200 mL), dried over Na₂SO₄ and concentrated under vacuum. The crude product was purified by SFC to give the acid as a white solid. ¹H-NMR (DMSO, 400 MHz) δ 7.33 (m, 5H), 3.34 (m, 1H), 3.12 (m, 1H), 2.65 (m, 1H), 2.20 (m, 1H), 1.37 (s, 9H), 1.33 (d, J=7.2 Hz, 3H).

Step F: (3R,4R)-tert-butyl 4-phenyl-3-(1H-tetrazol-5-yl)pentanoate

To a solution of (R)-4-(tert-butoxy)-4-oxo-2-((R)-1-phenylethyl)butanoic acid (2.0 g, 7.19 mmol) in Dichloromethane (20 ml) was added 2-(3H-[1,2,3]triazolo[4,5-b]pyridin-3-yl)-1,1,3,3-tetramethylisouronium hexafluorophosphate (V) (3.28 g, 8.62 mmol), ammonia hydrochloride (1.153 g, 21.56 mmol) and DIEA (1.255 ml, 7.19 mmol), and the resulting mixture were stirred at RT for 12 hr. The reaction mixture was evaporated to dryness and purified using 0 to 100% ethyl acetate in hexanes to provide (3R,4R)-tert-butyl 3-carbamoyl-4-phenylpentanoate.

Step G: (3R,4R)-tert-butyl 3-cyano-4-phenylpentanoate

To a solution of (3R,4R)-tert-butyl 3-carbamoyl-4-phenylpentanoate (2.44 g, 8.8 mmol) in DCM (20 ml) were added Pyridine (2.135 ml, 26.4 mmol) followed by TFAA (1.864 ml, 13.20 mmol) at 0° C. The reaction mixture was slowly warmed to room temperature and stirred for 2 hrs. The reaction mixture was diluted with ethyl acetate, transferred to a separatory funnel, washed with saturated NaHCO₃, then with brine. The organic layer was dried with MgSO₄, evaporated and purified using 0 to 100% ethyl acetate to provide (3R,4R)-tert-butyl 3-cyano-4-phenylpentanoate.

Step H: (3R,4R)-tert-butyl 4-phenyl-3-(1H-tetrazol-5-yl)pentanoate

To a solution of (3R,4R)-tert-butyl 3-cyano-4-phenylpentanoate (2.6 g, 10.03 mmol) in Toluene (20 ml) was added azidotrimethylstannane (4.13 g, 20.05 mmol) and heated at 110° C. for 48 hr. The reaction mixture was evaporated to dryness and purified using 0 to 100% ethyl acetate hexanes to provide (3R,4R)-tert-butyl 4-phenyl-3-(1H-tetrazol-5-yl)pentanoate. LC-MS [M+H]⁺: 303.34

Intermediate 21

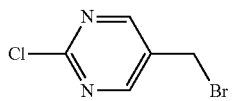

5-(bromomethyl)-2-chloropyrimidine

CBr₄ (2.68 g, 8.07 mmol) in 5 mL of DCM was added to a stirred, cooled (to 0° C.) mixture of (2-chloropyrimidin-5-yl)methanol (1.19 g, 8.23 mmol) and triphenylphosphine (2.116 g, 8.07 mmol) in 35 mL of DCM and the mixture was stirred at 0° C. for 10 min. Then, the reaction mixture was removed from the ice bath and stirred at RT for 30 min. TLC showed the reaction was near completion. The reaction mixture was concentrated to ½ volume, filtered and concentrated down. The residue was purified by silica gel column chromatography, eluting with EtOAc/isohexane (0-30%) to give the desired product. LC-MS [M+H]⁺: 208.93

Intermediate 22

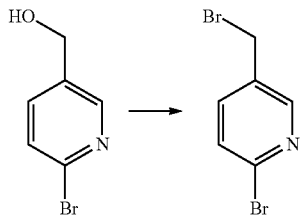 [SMILES: OCc1ccc(Br)nc1 ; BrCc1ccc(Br)nc1]

2-bromo-5-(bromomethyl)pyridine

To a solution of (6-bromopyridin-3-yl)methanol (5.0 g, 27 mmol) in DCM (50 ml) was added triphenylphosphine (6.3 g, 24 mmol), at 0° C. To this reaction mixture was added a solution of carbon tetrabromide (7.1 g, 21 mmol) in 15 ml DCM. The resulting mixture was stirred for 5 minutes, then evaporated, and purified using 0 to 10% ethyl acetate in hexanes to provide 2-bromo-5-(bromomethyl)pyridine. LC-MS [M+H]⁺: 251.89

Intermediate 23

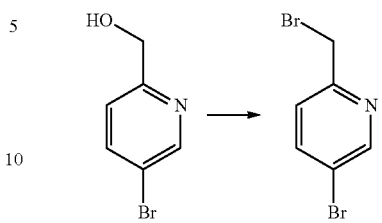

5-bromo-2-(bromomethyl)pyridine

To a solution of (5-bromopyridin-2-yl)methanol (1.5 g, 8.0 mmol) in DCM (10 ml) was added triphenylphosphine (1.9 g, 7.2 mmol), then was added a solution of carbon tetrabromide (2.1 g, 6.4 mmol) in 5 mL THF. The resulting mixture was stirred for 5 min, then evaporated to dryness, and purified using 0 to 10% ethyl acetate in hexanes. LC-MS [M+H]⁺: 251.74

Intermediate 24

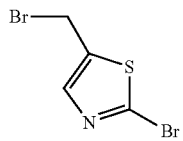

2-Bromo-5-(bromomethyl)thiazole

To a solution of (2-bromothiazol-5-yl)methanol (900 mg, 4.6 mmol) and triphenylphosphine (1300 mg, 5.1 mmol) in DCM (20 ml) was added a DCM solution of CBr₄ (1500 mg, 4.6 mmol) at 0° C. The reaction was allowed to warm to RT after 30 minutes. LC showed good reaction after 1 hour. About 20 mL of hexanes was added to the reaction, and the white precipitate was filtered off. The filtration was adsorbed onto silica gel, and purified by MPLC with a 40 G ISCO column, eluting with hexanes and EtOAc. LC-MS [M+H]⁺: 256.0

Intermediate 25

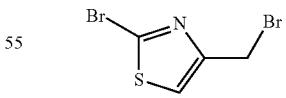

2-Bromo-4-(bromomethyl)thiazole

To a solution of (2-bromothiazol-4-yl)methanol (1.9 g, 9.8 mmol) and triphenylphosphine (2.6 g, 9.8 mmol) in DCM (20 ml) was added a DCM solution of CBr₄ (3.2 g, 9.8 mmol) at 0° C. The reaction was allowed to warm to RT after 30 minutes. LC showed good reaction after 1 hour. About 20 mL of hexanes was added to the reaction, and the white precipitate was filtered off. The filtration was adsorbed onto silica gel, and purified by MPLC with a 40 G ISCO column, eluting with hexanes and EtOAc. LC-MS [M+H]+: 258.2

Intermediate 26

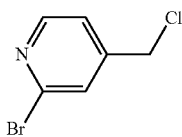

2-Bromo-4-(chloromethyl)pyridine

In a 100 ml RB flask, (2-bromopyridin-4-yl)methanol (4.8 g, 26 mmol) was dissolved in DCM (50 ml) and cooled to 0° C. then TEA (4.6 ml, 33 mmol) was added, followed by Mesyl-Cl (2.4 ml, 31 mmol). The mixture was stirred for 0.5 hour. The reaction was poured into a brine solution and the DCM was separated, dried over Na₂SO₄, filtered and concentrated. The residue was dissolved in Acetonitrile (50 ml) and lithium chloride (2.2 g, 51 mmol) was added. The reaction was stirred at RT over the weekend. The reaction was diluted with DCM (30 ml) and filtered. The filtrate was concentrated and the residue was purified by MPLC ISCO Combi-flash on ISCO Redi-Sep 120 g column, eluting with 0-50% EtOAc/hexane to give the product. LC-MS [M+H]+: 206.0

Intermediate 27

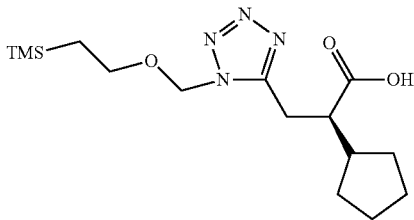 [SMILES: C[Si](C)(C)CCOCn1nnnc1C[C@@H](C(=O)O)C1CCCC1]

(R)-2-cyclopentyl-3-(1-((2-(trimethylsilyl)ethoxy) methyl)-1H-tetrazol-5-yl)propanoic acid Step A: (R)-4-benzyl-3-(2-cyclopentylacetyl)oxazolidin-2-one A solution of (R)-4-benzyloxazolidin-2-one (21.6 g, 122 mmol) in THF (300 ml) was cooled to −78° C., then nBuLi was added dropwise. The mixture was stirred for 15 minutes, then the 2-cyclopentylacetyl chloride in 10 mL THF was added dropwise. The mixture was stirred for 30 minutes at −78° C., then the cold bath was removed and the mixture stirred for an additional hour while warming to RT. Then 20 mL sat. NH₄Cl(aq) was added, and THF was removed in vacuo. 20 mL H₂O was added, and the aqueous layer extracted with 2×100 mL Et₂O. The combined organic extracts were washed with 50 mL 0.5 N NaOH (aq) and 50 mL brine, then dried (Na₂SO₄; CH₂Cl₂ added) and concentrated in vacuo to provided (R)-4-benzyl-3-(2-cyclopentylacetyl)oxazolidin-2-one.

Step B: (R)-4-((R)-4-benzyl-2-oxooxazolidin-3-yl)-3-cyclopentyl-4-oxobutanenitrile To a solution of (R)-4-benzyl-3-(2-cyclopentylacetyl)oxazolidin-2-one (10 g, 34.8 mmol) in THF (100 ml) was added sodium bis(trimethylsilyl)amide (41.8 ml, 41.8 mmol) at −78° C. The resulting solution was stirred at −78° C. for 1 hr. Then, to the reaction was added a solution of 2-bromoacetonitrile (7.3 ml, 104 mmol) in 15 ml THF. The resulting solution was slowly warmed to RT. Then, to the reaction, was added a solution of saturated ammonia hydrochloride (9.3 g, 170 mmol). The reaction mixture was partially evaporated, then extracted with ethyl acetate. The organic layer was dried, concentrated and purified using 0 to 100% ethyl acetate in hexanes to provide (R)-4-((R)-4-benzyl-2-oxooxazolidin-3-yl)-3-cyclopentyl-4-oxobutanenitrile.

Step C: (R)-4-benzyl-3-((R)-2-cyclopentyl-3-(1H-tetrazol-5-yl)propanoyl)oxazolidin-2-one To a solution of (R)-4-((R)-4-benzyl-2-oxooxazolidin-3-yl)-3-cyclopentyl-4-oxobutanenitrile (8.5 g, 26 mmol) in Toluene (50 ml) was added azidotrimethylsilane (10.4 ml, 78 mmol) and dibutyltin oxide (1.9 g, 7.8 mmol), and the resulting solution was heated at 110° C. for 12 hr. The reaction mixture was evaporated to dryness and purified using 0 to 100% ethyl acetate in hexanes to provide (R)-4-benzyl-3-((R)-2-cyclopentyl-3-(1H-tetrazol-5-yl)propanoyl)oxazolidin-2-one.

Step D: (R)-4-benzyl-3-((R)-2-cyclopentyl-3-(1-((2-(trimethylsilyl)ethoxy)methyl)-1H-tetrazol-5-yl) propanoyl)oxazolidin-2-one To a solution of (R)-4-benzyl-3-((R)-2-cyclopentyl-3-(1H-tetrazol-5-yl)propanoyl)oxazolidin-2-one (9.6 g, 26 mmol) in acetonitrile (50 ml) was added N-ethyl-N-isopropylpropan-2-amine (9.1 ml, 52 mmol), and the resulting mixture was stirred at 0° C. for 10 min. Then, to the reaction was added (2-(chloromethoxy)ethyl)trimethylsilane (5.5 ml, 31 mmol), and the reaction mixture was slowly warmed to RT. The reaction mixture was diluted with ethyl acetate, transferred to a separatory funnel, washed with saturated NaHCO₃, then with brine. The organic layer was dried with MgSO₄, evaporated and purified using 0 to 100% ethyl acetate in hexanes to separate (R)-4-benzyl-3-((R)-2-cyclopentyl-3-(1-((2-(trimethylsilyl)ethoxy)methyl)-1H-tetrazol-5-yl)propanoyl)oxazolidin-2-one from its regio-isomer.

Step E: (R)-2-cyclopentyl-3-(1-((2-(trimethylsilyl) ethoxy)methyl)-1H-tetrazol-5-yl)propanoic acid To a solution of (R)-4-benzyl-3-((R)-2-cyclopentyl-3-(2-((2-(trimethylsilyl)ethoxy)methyl)-2H-tetrazol-5-yl)propanoyl)oxazolidin-2-one (4.0 g, 8.0 mmol) in tetrahydrofuran (40 ml) was added H₂O₂ (2.8 ml, 32 mmol) at 0° C. Then a solution of LiOH (0.38 g, 16 mmol) in 8 mL water was added. The resulting mixture was stirred at 0° C., and then slowly warmed to RT and stirred for 2 hr. Then, to the reaction was added a solution of sodium sulfite (8.1 g, 64 mmol) and sodium bicarbonate (5.4 g, 64 mmol) at 0° C. The resulting mixture was stirred for 10 min, then partially concentrated, and extracted with ethyl acetate. The organic layer was evaporated, then was dissolved in ether and repeatedly extracted with 1 N NaOH. The aq. layer was acidified using 7 N HCl to pH 2, then extracted with ethyl acetate. The ethyl acetate layer was dried, evaporated to provide pure product (R)-2-cyclopentyl-3-(1-((2-(trimethylsilyl)ethoxy)methyl)-1H-tetrazol-5-yl)propanoic acid. LC-MS m/z [M+H]+: 341.24

Intermediate 28

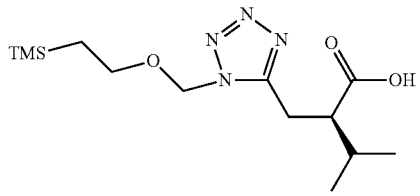 [SMILES: CC(C)[C@@H](Cc1nnnn1COCC[Si](C)(C)C)C(=O)O]

(R)-3-Methyl-2-((1-((2-(trimethylsilyl)ethoxy)methyl)-1H-tetrazol-5-yl)methyl)butanoic acid The INTERMEDIATE was prepared following the same procedure as 1-27. LC-MS m/z [M+H]+: 315.21

Intermediate 29

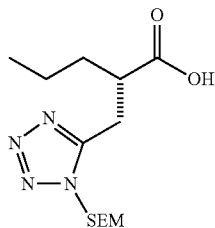 [SMILES: CCC[C@@H](Cc1nnnn1COCC[Si](C)(C)C)C(=O)O]

(S)-2-((1-((2-(trimethylsilyl)ethoxy)methyl)-1H-tetrazol-5-yl)methyl)pentanoic acid Step A: (4R,5S)-4-methyl-3-pentanoyl-5-phenyloxazolidin-2-one To a solution of (4R,5S)-4-methyl-5-phenyloxazolidin-2-one (5.0 g, 28 mmol) in THF (200 ml) was added N-butyllithium (13.5 ml, 34 mmol) at −78° C. The colorless solution turned orange toward the end of base addition. The mixture was kept at −78° C. for 20 minutes before valeryl chloride (4.5 ml, 37 mmol) was dropped in. LC after 15 minutes showed a clean reaction. The reaction was allowed to warm to RT, quenched with NH4Cl, extracted with EtOAc, and separated. The solution was dried over sodium sulfate, filtered and concentrated. The residue was loaded onto a 80 G silica gel column and purified by MPLC with hexane and EtOAc. LC-MS [M+H]+: 262.1.

Step B: (S)-3-((4R,5S)-4-methyl-2-oxo-5-phenyloxazolidine-3-carbonyl)hexanenitrile To a solution of (4R,5S)-4-methyl-3-pentanoyl-5-phenyloxazolidin-2-one (3.3 g, 12.6 mmol) in THF (50 ml) was added LHMDS (16.4 ml, 16.4 mmol) at −78° C. The mixture was allowed to stir for 30 minutes before 2-bromoacetonitrile (7.6 g, 63 mmol) was added. The reaction was allowed to stir overnight, warming up naturally. LC showed good reaction. The reaction was quenched with NH4Cl, washed with brine, separated and dried over sodium sulfate. The solution was filtered, and concentrated to give a sticky oil. The oil was dissolved in DCM and loaded onto a 80 G ISCO column, and purified by MPLC with hexanes and EtOAc. The product eluted at about 40% EtOAc. LC-MS [M+H]+: 301.2.

Step C: (4R,5S)-3-((S)-2-((1H-tetrazol-5-yl)methyl)pentanoyl)-4-methyl-5-phenyloxazolidin-2-one The reaction mixture was allowed to stir at 100° C. for 24 hours. LC showed a good reaction. White solids formed during the reaction. The solids were collected by filtration and washed twice with hexane and EtOAc (1:1). The white solids were collected as the desired product. LC-MS [M+H]+: 344.2.

Step D: (4R,5S)-4-methyl-5-phenyl-3-((S)-2-((1-((2-(trimethylsilyl)ethoxy)methyl)-1H-tetrazol-5-yl)methyl)pentanoyl)oxazolidin-2-one To a solution of (4R,5S)-3-((S)-2-((1H-tetrazol-5-yl)methyl)pentanoyl)-4-methyl-5-phenyloxazolidin-2-one (3.7 g, 10.8 mmol) in acetonitrile (25 ml) was added Hunig's Base (2.82 ml, 16.2 mmol) and SEM-Cl (2.1 ml, 12 mmol) at RT. The reaction was allowed to stir for 15 minutes. LC at that point showed the reaction was almost done, with two product peaks. The reaction was allowed to stand for another 10 minutes, and then diluted with EtOAc (50 mL), washed with aq. NH4Cl (10 mL) and brine, separated and dried over sodium sulfate. The solution was filtered and concentrated, and the residue was injected onto a 120 G ISCO column, and separated by MPLC with hexanes and EtOAc. The product peaks eluted at about 30% EtOAc. The desired regio-isomer was the second product peak coming off the column. LC-MS [M+H]+: 374.4.

Step E: (S)-2-((1-((2-(trimethylsilyl)ethoxy)methyl)-1H-tetrazol-5-yl)methyl)pentanoic acid A solution of (4R,5S)-4-methyl-5-phenyl-3-((S)-2-((1-((2-(trimethylsilyl)ethoxy)methyl)-1H-tetrazol-5-yl)methyl)pentanoyl)oxazolidin-2-one in THF (65 ml) was cooled to 0° C. Hydrogen peroxide (10.5 ml, 120 mmol) cooled in ice bath and a solution of lithium hydroxide (0.57 g, 23.7 mmol) dissolved in 8 mL of water which was also cooled in ice bath were added to the reaction mixture and stirred for 2 hours. A solution of sodium bisulfate (3.33 g, 32.0 mmol) and sodium sulfite (6.0 g, 47 mmol) dissolved in 20 mL of water was added and stirred at room temperature for 15 minutes. The organic was separated and the aqueous (acidic) was extracted repeatedly with ether, 3 times. After combining all the organic layer, it was washed with brine, dried over Na2SO4, filtered and concentrated. The residue was taken up with ether (40 mL) and extracted with 1N NaOH (3×). The aqueous NaOH layer was acidified with 1N HCl to pH~1 and extracted with EtOAc (4×), dried over Na2SO4, filtered and concentrated. The crude was taken on as is for next step. LC-MS [M+H]+: 329.1

Intermediate 30

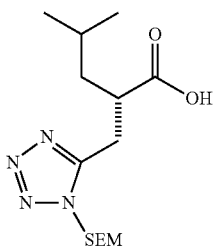 [SMILES: CC(C)C[C@@H](Cc1nnnn1COCC[Si](C)(C)C)C(=O)O]

(S)-4-methyl-2-((1-((2-(trimethylsilyl)ethoxy)
methyl)-1H-tetrazol-5-yl)methyl)pentanoic acid Step A: (4R,5S)-4-methyl-3-(4-methylpentanoyl)-5-phenyloxazolidin-2-one To a solution of (4R,5S)-4-methyl-5-phenyloxazolidin-2-one (6.6 g, 37 mmol) in THF (100 ml) under N$_2$ at −78° C. was added N-butyllithium (28 ml, 45 mmol). The solution was allowed to stir for 15 min before 4-methylvaleroyl chloride (5.1 ml, 37 mmol) was added. After 30 minutes of stirring, the crude UPLC showed a desire peak with 276 m/z. The reaction was quenched with water, and extracted with EtOAc (3×). The organic layer was washed with brine, separated, and dried over sodium sulfate. The reaction was used without further purification. LC-MS [M+H]$^+$: 276.2.

Step B: (S)-5-methyl-3-((4R,5S)-4-methyl-2-oxo-5-phenyloxazolidine-3-carbonyl)hexanenitrile To a solution of (4R,5S)-4-methyl-3-(4-methylpentanoyl)-5-phenyloxazolidin-2-one (7.2 g, 26 mmol) in THF (100 ml) was added lithium bis(trimethylsilyl)amide (LHMDS) (34 ml, 34 mmol) at −78° C. under N$_2$. The reaction was allowed to stir for 30 minutes before bromoacetonitrile (5.2 ml, 78 mmol) was added in. The mixture was allowed to stir overnight. The crude UPLC indicated a desired peak with 315 m/z. The reaction was quenched with aq. NH$_4$Cl, extracted with EtOAc (3×), washed with brine, separated and dried over Na$_2$SO$_4$. The crude solution was filtered and concentrated. The crude was purified by ISCO column with Solvent A: A1 hexane, Solvent B: B1 ethyl acetate. LC-MS [M+H]$^+$: 315.3.

Step C: (4R,5S)-3-((S)-2-((1H-tetrazol-5-yl)methyl)-4-methylpentanoyl)-4-methyl-5-phenyloxazolidin-2-one A solution of (S)-5-methyl-3-((4R,5S)-4-methyl-2-oxo-5-phenyloxazolidine-3-carbonyl)hexanenitrile (7.4 g, 24 mmol), dibutyltin oxide (1.8 g, 7.1 mmol) and azidotrimethylsilane (9.4 ml, 71 mmol) in toluene (100 ml) was heated at 110° C. for 16 hr. The crude UPLC indicated complete consumption of SM and the desired peak at 358 m/z. The reaction mixture was concentrated under reduced pressure and purified by ISCO chromatography, 80 G silica gel, with Solvent A: A1 hexane, Solvent B: B1 ethyl acetate. LC-MS [M+H]$^+$: 358.3.

Step D: (4R,5S)-4-methyl-3-((S)-4-methyl-2-((1-((2-(trimethylsilyl)ethoxy)methyl)-1H-tetrazol-5-yl)methyl)pentanoyl)-5-phenyloxazolidin-2-one To a solution of (4R,5S)-3-((S)-2-((1H-tetrazol-5-yl)methyl)-4-methylpentanoyl)-4-methyl-5-phenyloxazolidin-2-one (7.2 g, 20 mmol) in Acetonitrile (100 ml) was added N,N-diisopropylethylamine (7.1 ml, 40 mmol). The mixture was stirred for 10 minutes then 2-(trimethylsilyl)ethoxymethyl chloride (4.3 ml, 24 mmol) was added. The reaction was slowly warmed to room temperature and stirred for 1 hour. The mixture was concentrated and EtOAC and brine were added. The organic was extracted with EtOAC, 3×, dried over Na$_2$SO$_4$, filtered and concentrated. The crude was purified by ISCO chromatography, RediSep Column: Silica 120 g, Solvent A: A1 hexane, Solvent B: B1 ethyl acetate to give both regioisomer compounds. The desired regio-isomer came out as the second peak. LC-MS [M+H]$^+$: 488.4.

Step E: (S)-4-methyl-2-((1-((2-(trimethylsilyl)ethoxy)methyl)-1H-tetrazol-5-yl)methyl)pentanoic acid A solution of (4R,5S)-4-methyl-3-((S)-4-methyl-2-((2-((2-(trimethylsilyl)ethoxy)methyl)-2H-tetrazol-5-yl)methyl)pentanoyl)-5-phenyloxazolidin-2-one (regioisomer 2, cream white solid) (5.8 g, 11.8 mmol) in THF (65 ml) was cooled to 0° C. hydrogen peroxide (10.5 ml, 120 mmol) cooled in ice bath and a solution of lithium hydroxide (0.57 g, 24 mmol) dissolved in 8 mL of water which was also cooled in ice bath were both added to the reaction mixture and stirred for 2 hours. A solution of sodium bisulfite (3.3 g, 32 mmol) and sodium sulfite (6.0 g, 47 mmol) dissolved in 20 mL of water was added and stirred at room temperature for 15 minutes. The organic was separated and the aqueous (acidic) was extracted repeatedly with ether (3×). After combining all the organic layer, it was washed with brine, dried over Na$_2$SO$_4$, filtered and concentrated. The residue was taken up with ether (40 mL) and extracted with 1N NaOH (3×). The aqueous NaOH layer was acidified with 1N HCl to pH~1 and extracted with EtOAc (4×), dried over Na$_2$SO$_4$, filtered and concentrated. The crude was taken on as is for next step. LC-MS [M+H]$^+$: 329.1.

Intermediate 31

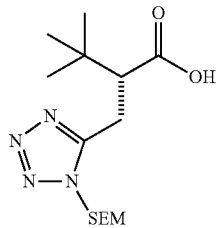 [SMILES: CC(C)(C)[C@@H](Cc1nnnn1COCC[Si](C)(C)C)C(=O)O]

(R)-3,3-dimethyl-2-((1-((2-(trimethylsilyl)ethoxy)methyl)-1H-tetrazol-5-yl)methyl)butanoic acid Step A: (R)-4-benzyl-3-(3,3-dimethylbutanoyl)oxazolidin-2-one A solution of the (R)-4-benzyloxazolidin-2-one (10 g, 56 mmol) in THF (250 ml) was cooled to −78° C., then butyllithium (21 ml, 58 mmol) was added dropwise. The mixture was stirred for 30 minutes, then 3,3-dimethylbutanoyl chloride (8.0 ml, 56 mmol) was added dropwise. The mixture was stirred for 120 minutes at −78° C., and the cold bath was removed and the mixture stirred for an additional 1 hour while warming to room temperature. The reaction was quenched by adding 100 mL sat. NH₄Cl(aq) at 0° C., followed by 20 mL H₂O, and extracted with EtOAc. The reaction mixture was washed with 0.5 M NaOH and brine, then dried over (MgSO₄) and concentrated to dryness to give 14.97 g of (R)-4-benzyl-3-(3,3-dimethylbutanoyl)oxazolidin-2-one. LC-MS [M+H]⁺: 276.09

Step B: (R)-3-((R)-4-benzyl-2-oxooxazolidine-3-carbonyl)-4,4-dimethylpentanenitrile To a solution of diisopropylamine (8.5 ml, 60 mmol) in 30 mL of THF was added butyllithium (24 ml, 60 mmol) at −10 to 0° C. The mixture was stirred at 0 to 5° C. for 30 minutes, and then added dropwise into (R)-4-benzyl-3-(3,3-dimethylbutanoyl)oxazolidin-2-one (15 g, 54 mmol) in 200 mL of THF at −78° C. After 40 minutes, 2-bromoacetonitrile (12 ml, 160 mmol) was added dropwise at −78° C. and stirred at −78° C. for 1 hour and then gradually warmed up to room temperature and stirred for 24 hrs. The reaction mixture was added to an aqueous solution NH₄Cl and extracted with EtOAc. The organic layer was washed with 1N HCl and brine, dried over MgSO₄, filtered and concentrated down. The residue was purified by column chromatography on silica gel, eluting with EtOAc/Hexane (0~30%) to give (R)-3-((R)-4-benzyl-2-oxooxazolidine-3-carbonyl)-4,4-dimethylpentanenitrile. LC-MS [M+H]⁺: 315.19

Step C: (R)-3-((R)-2-((1H-tetrazol-5-yl)methyl)-3,3-dimethylbutanoyl)-4-benzyloxazolidin-2-one Azidotrimethylsilane (11 ml, 85 mmol) was added to a stirred, room temperature mixture of (R)-3-((R)-4-benzyl-2-oxooxazolidine-3-carbonyl)-4,4-dimethylpentanenitrile (8.9 g, 28 mmol) and dibutylstannanone (2.1 g, 8.5 mmol) in toluene and the mixture was stirred at 110° C. overnight. After cooling, the mixture was concentrated down. The residue was purified by column chromatography on silica gel column, eluting with EtOAc/Hexane (5~100%) to give (R)-3-((R)-2-((1H-tetrazol-5-yl)methyl)-3,3-dimethylbutanoyl)-4-benzyloxazolidin-2-one. LC-MS [M+H]⁺: 358.13

Step D: (R)-4-benzyl-3-((R)-3,3-dimethyl-2-((1-((2-(trimethylsilyl)ethoxy)methyl)-1H-tetrazol-5-yl)methyl)butanoyl)oxazolidin-2-one To a solution of (R)-3-((R)-2-((1H-tetrazol-5-yl)methyl)-3,3-dimethylbutanoyl)-4-benzyloxazolidin-2-one (8.6 g, 24 mmol) in acetonitrile (100 mL) at 0° C. was added N-ethyl-N-isopropylpropan-2-amine (8.4 ml, 48 mmol). The mixture was stirred for 10 minutes, then (2-(chloromethoxy)ethyl)trimethylsilane (5.1 ml, 29 mmol) was added. The reaction was slowly warmed to room temperature and stirred for 1 hour. The mixture was concentrated and EtOAc and water were added. The mixture was extracted with EtOAc. Organic layer was washed with brine, dried over MgSO₄, filtered and concentrated. The residue was purified by column chromatography on silica gel column, eluting with EtOAc/Hexane (0~30%) to give (R)-4-benzyl-3-((R)-3,3-dimethyl-2-((1-((2-(trimethylsilyl)ethoxy)methyl)-1H-tetrazol-5-yl)methyl)butanoyl)oxazolidin-2-one. LC-MS [M+H]⁺: 488.19

Step E: (R)—S-ethyl 3,3-dimethyl-2-((1-((2-(trimethylsilyl)ethoxy)methyl)-1H-tetrazol-5-yl)methyl)butanethioate To a solution of ethanethiol (4.0 ml, 53 mmol) in THF (10 mL) was added butyllithium (16 ml, 39 mmol) at −78° C. The resulting mixture was slowly warmed to 0° C., and stirred for 15 min. Then it was added to a precooled (−78° C.) solution of (R)-4-benzyl-3-((R)-3,3-dimethyl-2-((1-((2-(trimethylsilyl)ethoxy)methyl)-1H-tetrazol-5-yl)methyl)butanoyl)oxazolidin-2-one (7.6 g, 16 mmol) and the resulting mixture was stirred at 0° C. for 18 hours. The reaction mixture was diluted with 1 N NaOH and extracted with ether. The crude product was purified using 0 to 100% ethyl acetate in hexanes to give (R)—S-ethyl 3,3-dimethyl-2-((1-((2-(trimethylsilyl)ethoxy)methyl)-1H-tetrazol-5-yl)methyl)butanethioate. LC-MS [M+H]⁺: 373.16

Step F: (R)-3,3-dimethyl-2-((1-((2-(trimethylsilyl)ethoxy)methyl)-1H-tetrazol-5-yl)methyl)butanoic acid Hydrogen peroxide (3.8 ml, 44 mmol) was added slowly in three portions in 10 min into (R)—S-ethyl 3,3-dimethyl-2-((1-((2-(trimethylsilyl)ethoxy)methyl)-1H-tetrazol-5-yl)methyl)butanethioate (4.7 g, 13 mmol) and lithium hydroxide (1.1 g, 44 mmol) in water/EtOH at 50-55° C. The mixture was stirred at 55° C. for 1 hr. After cooling, the reaction mixture was acidified to pH~3 by 1N HCl. The reaction mixture was extracted with EtOAc, washed with sat. Na₂S₂O₃ and brine. The organic layer was dried over MgSO₄, filtered and concentrated to dryness to give crude (R)-3,3-dimethyl-2-((1-((2-(trimethylsilyl)ethoxy)methyl)-1H-tetrazol-5-yl)methyl)butanoic acid. LC-MS [M+H]⁺: 329.20

Intermediate 32

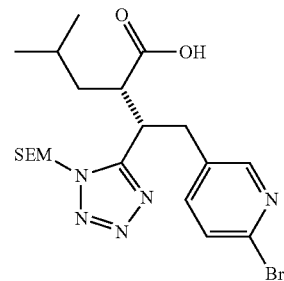 [SMILES: CC(C)CC(C(=O)O)[C@H](Cc1ccc(Br)nc1)c1nnnn1COCC[Si](C)(C)C]

(S)-2-((S)-2-(6-bromopyridin-3-yl)-1-(1-((2-(trimethylsilyl)ethoxy)methyl)-1H-tetrazol-5-yl)ethyl)-4-methylpentanoic acid To a solution of (S)-4-methyl-2-((1-((2-(trimethylsilyl)ethoxy)methyl)-1H-tetrazol-5-yl)methyl)pentanoic acid (2950 mg, 9.0 mmol) in THF (25 ml) was added LDA (32.1 ml, 22.5 mmol freshly prepared from DIPA and n-BuLi). The solution turned light yellow half-way through the base addition, and then bright yellow. The mixture was allowed to stir at −78° C. for 30 minutes before 2-bromo-5-(chloromethyl)pyridine (2410 mg, 11.7 mmol) was added. The yellow color turned slightly red. The reaction was allowed to age for 5 hours at −78° C. LC showed most of the conversion occurred when the electrophile was added. The reaction went to about 70% conversion slowly over time. The reaction was quenched with aq. NH₄Cl, extracted with EtOAc, separated and dried over sodium sulfate. The solution was filtered and concentrated. The residue was dissolved in water and ACN, and loaded onto a 130 G C-18 column for purification. The fraction containing the desired product was collected, and evaporated under reduced pressure to afford a light yellow solid. LC-MS [M+H]$^+$: 500.2.

Intermediate 33

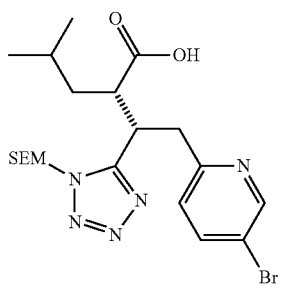 [SMILES: CC(C)CC(C(=O)O)[C@H](Cc1ccc(Br)cn1)c1nnnn1COCC[Si](C)(C)C]

(S)-2-((S)-2-(5-bromopyridin-2-yl)-1-(1-((2-(trimethylsilyl)ethoxy)methyl)-1H-tetrazol-5-yl)ethyl)-4-methylpentanoic acid To a solution of (S)-4-methyl-2-((2-((2-(trimethylsilyl)ethoxy)methyl)-2H-tetrazol-5-yl)methyl)pentanoic acid (800 mg, 2.44 mmol) in THF (30 ml) was added LDA (8.7 ml, 6.1 mmol). The solution turned bright yellow half way through the base addition. The mixture was allowed to stir at −78° C. for 45 minutes before 5-bromo-2-(chloromethyl)pyridine (600 mg, 2.90 mmol) was added. The reaction turned red right away. The reaction was allowed to age for 4 hours at −78° C. LC showed most of the conversion occurred when the electrophile was added. The reaction went to about 50% conversion slowly over time. The reaction was quenched with aq. NH$_4$Cl, extracted with EtOAc, separated and dried over sodium sulfate. The solution was filtered and concentrated. The residue was dissolved in water and ACN, and loaded onto a 130 G reverse phase MPLC column, and flashed with ACN and water (with 0.05% TFA). The product came out at about 70% ACN. The product peak was collected and concentrated under reduced pressure. Light yellow solids precipitated during the process. The solids were collected, and LC suggested that it was pure. LC-MS [M+H]$^+$: 500.2.

Intermediate 34

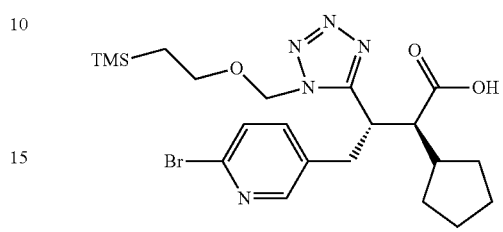

(2S,3S)-4-(6-bromopyridin-3-yl)-2-cyclopentyl-3-(1-((2-(trimethylsilyl)ethoxy)methyl)-1H-tetrazol-5-yl)butanoic acid To a solution of diisopropylamine (0.50 ml, 3.5 mmol) in Tetrahydrofuran (5 ml) was added nBuLi (1.3 ml, 3.5 mmol) at −5° C. Then the resulting solution was slowly warmed to RT, then cooled to −78° C. To the solution was added a solution of (R)-2-cyclopentyl-3-(1-((2-(trimethylsilyl)ethoxy)methyl)-1H-tetrazol-5-yl)propanoic acid (500 mg, 1.5 mmol) in 1 ml THF. The resulting mixture was stirred for 1 hr, then was added a solution of 2-bromo-5-(bromomethyl)pyridine (480 mg, 1.9 mmol) in 1 mL THF. The reaction mixture was slowly warmed to RT over 12 hr. The reaction mixture was diluted with saturated ammonium chloride, and then extracted with ethyl acetate. The crude product was purified using 0 to 100% ethyl acetate in hexanes to provide (2S,3S)-4-(6-bromopyridin-3-yl)-2-cyclopentyl-3-(1-((2-(trimethylsilyl)ethoxy)methyl)-1H-tetrazol-5-yl)butanoic acid. LC-MS m/z [M+H]$^+$ 510.19

The following INTERMEDIATES were prepared following the same procedure of INTERMEDIATE 34:

| INT. NO. | Structure | Name | LC-MS Calculated (M + H)$^+$ | LC-MS m/e (M + H)$^+$ |
|---|---|---|---|---|
| 35 | 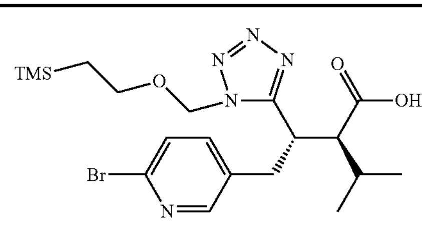 | (2S,3S)-4-(6-bromopyridin-3-yl)-2-isopropyl-3-(1-((2-(trimethylsilyl)ethoxy)methyl)-1H-tetrazol-5-yl)butanoic acid | 486.14 | 486.15 |
| 36 | 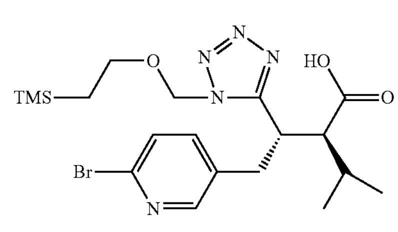 [SMILES: CC(C)[C@H](C(=O)O)[C@H](Cc1ccc(Br)nc1)c1nnnn1COCC[Si](C)(C)C] | (2S,3S)-4-(5-bromopyridin-2-yl)-2-isopropyl-3-(1-((2-(trimethylsilyl)ethoxy)methyl)-1H-tetrazol-5-yl)butanoic acid | 486.14 | 486.16 |

-continued

| INT. NO. | Structure | Name | Calculated (M + H)⁺ | LC-MS m/e (M + H)⁺ |
|---|---|---|---|---|
| 37 | 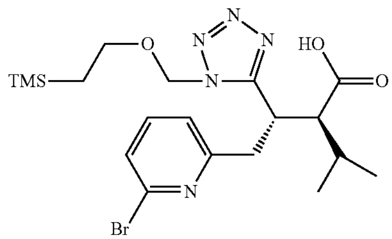 [SMILES: CC(C)[C@H](C(=O)O)[C@H](Cc1cccc(Br)n1)c1nnnn1COCC[Si](C)(C)C] | (2S,3S)-4-(6-bromopyridin-2-yl)-2-isopropyl-3-(1-((2-(trimethylsilyl)ethoxy)methyl)-1H-tetrazol-5-yl)butanoic acid | 486.14 | 486.07 |
| 38 | 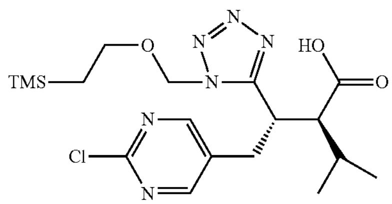 [SMILES: CC(C)[C@H](C(=O)O)[C@H](Cc1cnc(Cl)nc1)c1nnnn1COCC[Si](C)(C)C] | (2S,3S)-4-(2-chloropyrimidin-5-yl)-2-isopropyl-3-(1-((2-(trimethylsilyl)ethoxy)methyl)-1H-tetrazol-5-yl)butanoic acid OH | 441.18 | 441.14 |
| 39 | 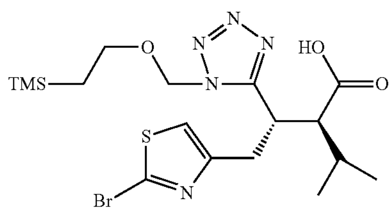 [SMILES: CC(C)[C@H](C(=O)O)[C@H](Cc1csc(Br)n1)c1nnnn1COCC[Si](C)(C)C] | (2S,3S)-4-(2-bromothiazol-4-yl)-2-isopropyl-3-(1-((2-(trimethylsilyl)ethoxy)methyl)-1H-tetrazol-5-yl)butanoic acid | 490.10 | 490.02 |
| 40 | 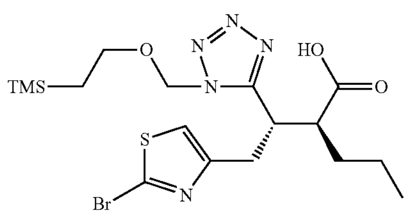 [SMILES: CCC[C@H](C(=O)O)[C@H](Cc1csc(Br)n1)c1nnnn1COCC[Si](C)(C)C] | (S)-2-((S)-2-(2-bromothiazol-4-yl)-1-(1-((2-(trimethylsilyl)ethoxy)methyl)-1H-tetrazol-5-yl)ethyl)pentanoic acid | 490.10 | 490.11 |
| 41 | 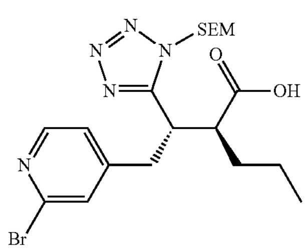 [SMILES: CCC[C@H](C(=O)O)[C@H](Cc1ccnc(Br)c1)c1nnnn1COCC[Si](C)(C)C] | (S)-2-((S)-2-(2-bromopyridin-4-yl)-1-(1-((2-(trimethylsilyl)ethoxy)methyl)-1H-tetrazol-5-yl)ethyl)pentanoic acid | 484.14 | 484.12 |
| 42 | 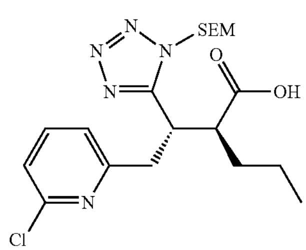 [SMILES: CCC[C@H](C(=O)O)[C@H](Cc1cccc(Cl)n1)c1nnnn1COCC[Si](C)(C)C] | (S)-2-((S)-2-(6-chloropyridin-2-yl)-1-(1-((2-(trimethylsilyl)ethoxy)methyl)-1H-tetrazol-5-yl)ethyl)pentanoic acid | 440.19 | 440.22 |

| INT. NO. | Structure | Name | Calculated (M + H)+ | LC-MS m/e (M + H)+ |
|---|---|---|---|---|
| 43 | 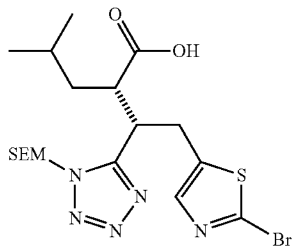 [SMILES: CC(C)CC(C(=O)O)[C@H](Cc1cnc(Br)s1)c1nnnn1COCC[Si](C)(C)C] | (S)-2-((S)-2-(2-bromothiazol-5-yl)-1-(1-((2-(trimethylsilyl)ethoxy)methyl)-1H-tetrazol-5-yl)ethyl)-4-methylpentanoic acid | 506.11 | 506.03 |
| 44 | 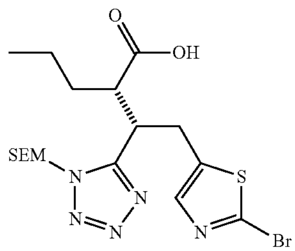 [SMILES: CCCC(C(=O)O)[C@H](Cc1cnc(Br)s1)c1nnnn1COCC[Si](C)(C)C] | (S)-2-((S)-2-(2-bromothiazol-5-yl)-1-(1-((2-(trimethylsilyl)ethoxy)methyl)-1H-tetrazol-5-yl)ethyl)pentanoic acid | 492.09 | 491.99 |

Intermediate 45

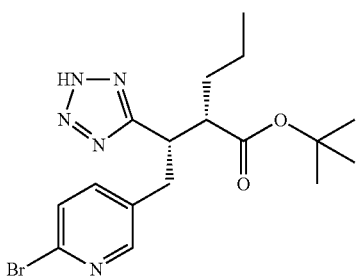

(S)-tert-butyl 2-((S)-2-(6-bromopyridin-3-yl)-1-(1H-tetrazol-5-yl)ethyl)pentanoate Step A: (4R,5S)-3-(3-(6-bromopyridin-3-yl)propanoyl)-4-methyl-5-phenyloxazolidin-2-one To a solution of 3-(6-bromopyridin-3-yl)propanoic acid (5000 mg, 22 mmol) in THF (100 ml) was added Hunig's Base (4.93 ml, 28.3 mmol) and pivaloyl chloride (2600 mg, 22 mmol) at −78° C. The mixture was allowed to stir overnight, warming up to RT naturally.

In a second flask, to a solution of (4R,5S)-4-methyl-5-phenyloxazolidin-2-one (4.22 g, 23.8 mmol) in THF (100 ml) was added N-butyllithium (10.39 ml, 26.0 mmol) at −78° C.

The mixture was allowed to stir for 30 minutes before (4R,5S)-3-(3-(6-bromopyridin-3-yl)propanoyl)-4-methyl-5-phenyloxazolidin-2-one (prepared as described above) was transferred into the reaction via cannulation.

The reaction was allowed to stir for 16 hours, warming up to RT naturally. LC showed excellent reaction. The reaction was quenched by adding aq. NH4Cl (50 mL), extracted with EtOAc (250 mL), and separated. The solution was dried over sodium sulfate, filtered and concentrated to about 50 mL. At that point, solids formed in the flask. The flask was heated to dissolve all the solids. The hot solution was allowed to cool down slowly, allowing for crystallization. Once the solution reached RT, about 50 mL hexane was added to force crystallization. The off-white solids were collected by filtration to provide the pure product. LC-MS [M+H]+: 391.1.

Step B: (S)-tert-butyl 3-((6-bromopyridin-3-yl)methyl)-4-((4R,5S)-4-methyl-2-oxo-5-phenyloxazolidin-3-yl)-4-oxobutanoate In a 50 ml RB flask equipped with a stirrer, (4R,5S)-3-(3-(6-bromopyridin-3-yl)propanoyl)-4-methyl-5-phenyloxazolidin-2-one (200 mg, 0.514 mmol) was dissolved in THF (15 ml) under $N_2$ then cooled to −60° C. and then sodium bis(trimethylsilyl)amide (0.617 ml, 0.617 mmol, 1 M) was added. The reaction mixture was stirred for 30 mins and tert-butyl 2-bromoacetate (0.091 ml, 0.617 mmol) was added and the reaction mixture continued to be stirred at −50°-40° C. for 2 hrs. The reaction was quenched at −50° C. with saturated NH4Cl solution (10 ml) and the two layers were separated. The aqueous layer was extracted with ether (2×15 ml), then washed with brine, dried (Na2SO4), filtered and concentrated. The residue was purified by MPLC ISCO Combi-flash with 0-50% EtOAc/hexane. LC-MS [M+H]: 503.2.

$^1$H-NMR (500 MHz, CDCl3) δ ppm: 8.23 (1 H, d, J=2.50 Hz), 7.59 (1 H, dd, J=8.18, 2.54 Hz), 7.45-7.36 (4 H, m), 7.30 (2H, dd, J=8.25, 1.35 Hz), 5.56 (1 H, d, J=7.34 Hz), 4.72 (1 H, m, J=6.85 Hz), 4.41 (1 H, dddd, J=10.01, 8.55, 6.28, 4.53 Hz), 3.04-2.97 (1 H, m), 2.79 (1 H, dd, J=16.82, 10.01 Hz), 2.64 (1 H, dd, J=13.50, 8.60 Hz), 2.32 (1 H, dd, J=16.82, 4.58 Hz), 1.38 (7 H, s),0.89 (3 H, d, J=6.59 Hz).

Step C: (S)-tert-butyl 4-amino-3-((6-bromopyridin-3-yl)methyl)-4-oxobutanoate

In a 50 mL RB flask, (S)-2-((6-bromopyridin-3-yl)methyl)-4-(tert-butoxy)-4-oxobutanoic acid (3200 mg, 9.2 mmol) was dissolved in DCM (50 ml), cooled to 0° C. and, to the reaction was added HATU (4200 mg, 11.1 mmol). DIPEA (13 ml, 74 mmol) and ammonium chloride (2500 mg, 46 mmol). The reaction mixture was stirred at 0° C. for 5 hr. TLC showed mostly product. The mixture was poured into water and extracted with more DCM 1×10 ml. DCM layer was washed with brine 1×, dried over $Na_2SO_4$, filtered and concentrated. The residue was purified by MPLC ISCO Combi-flash on ISCO Redi-Sep 40 g column, eluting with 5% $CH_2Cl_2$/MeOH. LC-MS $[M+H]^+$: 344.8.

Step D: (S)-tert-butyl 4-(6-bromopyridin-3-yl)-3-cyanobutanoate

In a 100-ml RB flask, (S)-tert-butyl 4-amino-3-((6-bromopyridin-3-yl)methyl)-4-oxobutanoate (34000 mg, 9.8 mmol) was dissolved in DCM (100 ml), cooled to 0° C. and, to the reaction was added pyridine (1.6 ml, 20 mmol) and TFAA (1.7 ml, 12 mmol). The reaction mixture was stirred at 0° C. then warmed up to RT followed by stirring for 3 hrs. LC-MS showed only product peak.

The reaction was poured into water and extracted with more DCM. The DCM layer was washed with brine, dried over $Na_2SO_4$, filtered and concentrated. The residue was purified by MPLC ISCO Combi-flash on a 120 g Redi-sep column, eluting with 0-50% EtOAc/hexane to give a colorless oil. LC-MS $[M+H]^+$: 328.2.

Step E: (S)-tert-butyl 4-(6-bromopyridin-3-yl)-3-(1H-tetrazol-5-yl)butanoate

In a 25 ml MW tube was added (S)-tert-butyl 4-(6-bromopyridin-3-yl)-3-cyanobutanoate (1.13 g, 3.5 mmol), azidotrimethylstannane (2.9 g, 14 mmol) and toluene (11 ml). The tube was sealed then heated to 120° C. for 24 hrs. The reaction was cooled then concentrated. The residue was purified by MPLC ISCO Combi-flash on ISCO Redi-Sep 40 g column, eluting with $CH_2Cl_2$/MeOH (10%) to afford a colorless solid. LC-MS $[M+H]^+$: 368.0.

Step F: (S)-tert-butyl 2-((S)-2-(6-bromopyridin-3-yl)-1-(1H-tetrazol-5-yl)ethyl)pentanoate In a 50-ml RB flask, (S)-tert-butyl 4-(6-bromopyridin-3-yl)-3-(1H-tetrazol-5-yl)butanoate (52 mg, 0.14 mmol) and HMPA (0.024 ml, 0.14 mmol) were dissolved in THF (2 ml), and added LDA at −78° C., formed by addition of BuLi in hexane (0.22 ml, 0.35 mmol) to diisopropylamine (0.050 ml, 0.35 mmol) in THF (5 ml) at −70° C. The reaction was stirred at −70° C. for 1 hr then 1-iodopropane (0.034 ml, 0.35 mmol) was added and the reaction warmed up to RT. The reaction was quenched with sat'd $NH_4Cl$ solution and extracted with EtOAc 2 times, dried over $Na_2SO_4$, filtered and concentrated to give the desired product. LC-MS $[M+H]^+$: 412.2.

Intermediate 46

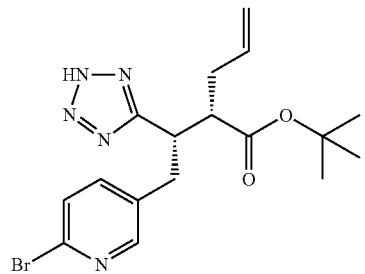 [SMILES: C=CC[C@H](C(=O)OC(C)(C)C)[C@H](Cc1ccc(Br)nc1)c1nn[nH]n1]

(S)-tert-butyl 2-((S)-2-(6-bromopyridin-3-yl)-1-(2H-tetrazol-5-yl)ethyl)pent-4-enoate The LDA solution was freshly prepared from DIPA and 2.5 M n-BuLi in THF. To a solution of (R)-tert-butyl 2-((2H-tetrazol-5-yl)methyl)-3-(6-bromopyridin-3-yl)propanoate (600 mg, 1.63 mmol) in THF (12 ml) was added LDA (4.1 ml, 4.1 mmol). The solution turned yellow and then brown at the end of the addition. The solution then turned orange in a few minutes. The mixture was kept at −78° C. for 30 minutes before allyl bromide (490 mg, 0.41 mmol) was added into the reaction. The mixture was kept at −78° C. for 4 hours. LC suggested slow progression of the reaction. The reaction was quenched with aq. $NH_4Cl$ after 4 hours. The organic layer was extracted with EtOAc, separated, dried over sodium sulfate, filtered and concentrated. The residue was adsorbed onto silica gel, and purified by MPLC with DCM and MeOH. LC-MS $[M+H]^+$: 410.2.

Intermediate 47

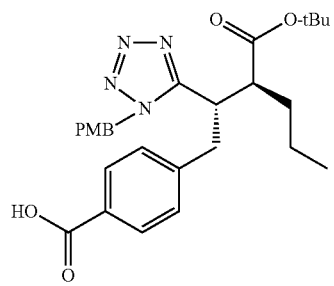

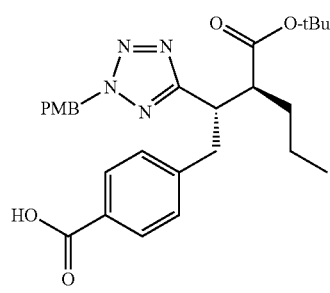

4-((2S,3S)-3-(tert-butoxycarbonyl)-2-(1-(4-methoxy-benzyl)-1H-tetrazol-5-yl)hexyl)benzoic acid compound and 4-((2S,3S)-3-(tert-butoxycarbonyl)-2-(2-(4-methoxybenzyl)-2H-tetrazol-5-yl)hexyl)benzoic acid The reaction mixture of (S)-tert-butyl 2-((S)-2-(4-bromophenyl)-1-(1-(4-methoxybenzyl)-1H-tetrazol-5-yl)ethyl)pentanoate (1200 mg, 2.3 mmol), sodium acetate (570 mg, 7.0 mmol) and PdCl$_2$(dppf)-CH$_2$Cl$_2$ adduct (190 mg, 0.23 mmol) in DMF (20 mL) and water (2.0 mL) was stirred with 100 psi of CO at 100° C. overnight. The reaction was cooled to RT, filtered with celite, and evaporated to dryness. To the residue was added EtOAc, and filtered. To the EtOAc layer was added silica gel, and volatiles were removed under reduced pressure. The product mixture was isolated by MPLC. LC-MS [M+H]$^+$:

Intermediate 48

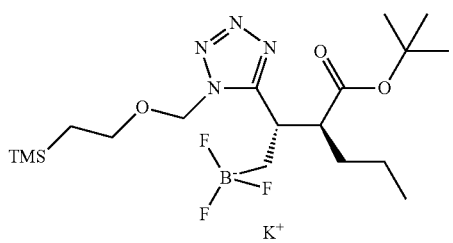 [SMILES: CCC[C@H](C(=O)OC(C)(C)C)[C@H](C[B-](F)(F)F)c1nnnn1COCC[Si](C)(C)C ; [K+]]

Potassium ((2S,3S)-3-(tert-butoxycarbonyl)-2-(1-((2-(trimethylsilyl)ethoxy)methyl)-1H-tetrazol-5-yl)hexyl)trifluoroborate Step A. (S)-2-((S)-2-(4,4,5,5-tetramethyl-1,3,2-dioxaborolan-2-yl)-1-(((2(trimethylsilyl)ethoxy)methyl)-1H-tetrazol-5-yl)ethyl)pentanoic acid (S)-2-((1-((2-(trimethylsilyl)ethoxy)methyl)-1H-tetrazol-5-yl)methyl)pentanoic acid (1100 mg, 3.3 mmol) was dissolved in THF (15 ml) then cooled to −78° C. and to the reaction mixture was added LDA (10 ml, 0.64 M, 6.4 mmol). The reaction was stirred for 45 mins, and then to the reaction mixture was added 2-(iodomethyl)-4,4,5,5-tetramethyl-1,3,2-dioxaborolane (1100 mg, 4.0 mmol). The mixture was stirred at −78° C. for 5 hrs, and then quenched with saturated NH$_4$Cl solution. The reaction was extracted with EtOAC (2×), dried (Na$_2$SO$_4$), and then filtered and concentrated to give (S)-2-((S)-2-(4,4,5,5-tetramethyl-1,3,2-dioxaborolan-2-yl)-1-(1-((2-(trimethylsilyl)ethoxy) methyl)-1H-tetrazol-5-yl)ethyl)pentanoic acid.

Step B. (S)-tert-butyl 2-((S)-2-(4,4,5,5-tetramethyl-1,3,2-dioxaborolan-2-yl)-1-(1-((2(trimethylsilyl)ethoxy) methyl)-1H-tetrazol-5-yl)ethyl)pentanoate In a 200 ml RB flask, (S)-2-((S)-2-(4,4,5,5-tetramethyl-1,3,2-dioxaborolan-2-yl)-1-(1-((2-(trimethylsilyl)ethoxy)methyl)-1H-tetrazol-5-yl)ethyl)pentanoic acid (1.4 g, 3.0 mmol) was dissolved in toluene (25 ml), heated to 60° C., and then added N,N-dimethylformamide di-tert-butyl acetal (2.2 ml, 9.0 mmol) and continued heating for 16 hours. The reaction was concentrated and the residue was purified by MPLC with 0-100% EtOAc/Hexane to yield (5)-tert-butyl 2-((S)-2-(4,4,5,5-tetramethyl-1,3,2-dioxaborolan-2-yl)-1-(1-((2(trimethylsilyl)ethoxy) methyl)-1H-tetrazol-5-yl)ethyl)pentanoate. LC-MS [M+1]: 511.2

Step C. Potassium ((2S,3S)-3-(tert-butoxycarbonyl)-2-(1-((2-(trimethylsilyl)ethoxy)methyl)-1H-tetrazol-5-yl)hexyl)trifluoroborate (S)-tert-butyl 2-((S)-2-(4,4,5,5-tetramethyl-1,3,2-dioxaborolan-2-yl)-1-(1-((2-(trimethylsilyl)ethoxy)methyl)-1H-tetrazol-5-yl)ethyl)pentanoate (380 mg, 0.74 mmol) was dissolved in MeOH (2 mL), and then to the mixture was added potassium hydrogen fluoride (190 mg, 2.4 mmol) in water (0.54 mL). The mixture was stirred at RT for 1 hr. The solvent was removed in vacuo and acetone was added and stirred for 15 min at RT. The suspension was filtered, and the filtrate was evaporated to dryness to obtain potassium ((2S,3S)-3-(tert-butoxycarbonyl)-2-(1-((2-(trimethylsilyl)ethoxy) methyl)-1H-tetrazol-5-yl)hexyl)trifluoroborate. The crude was used directly without purification.

EXAMPLES 1-2

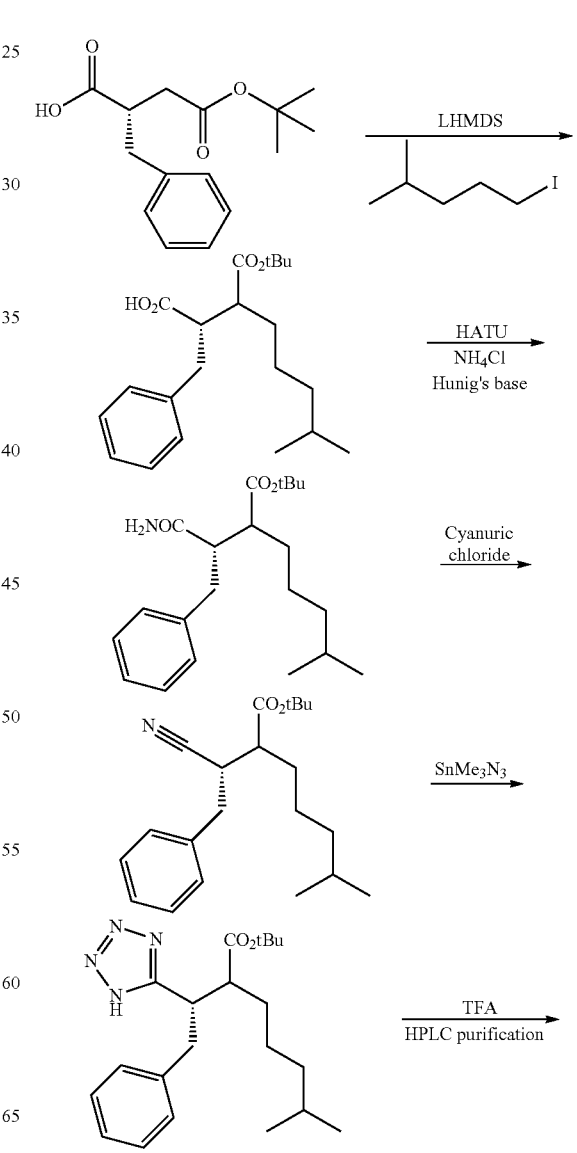

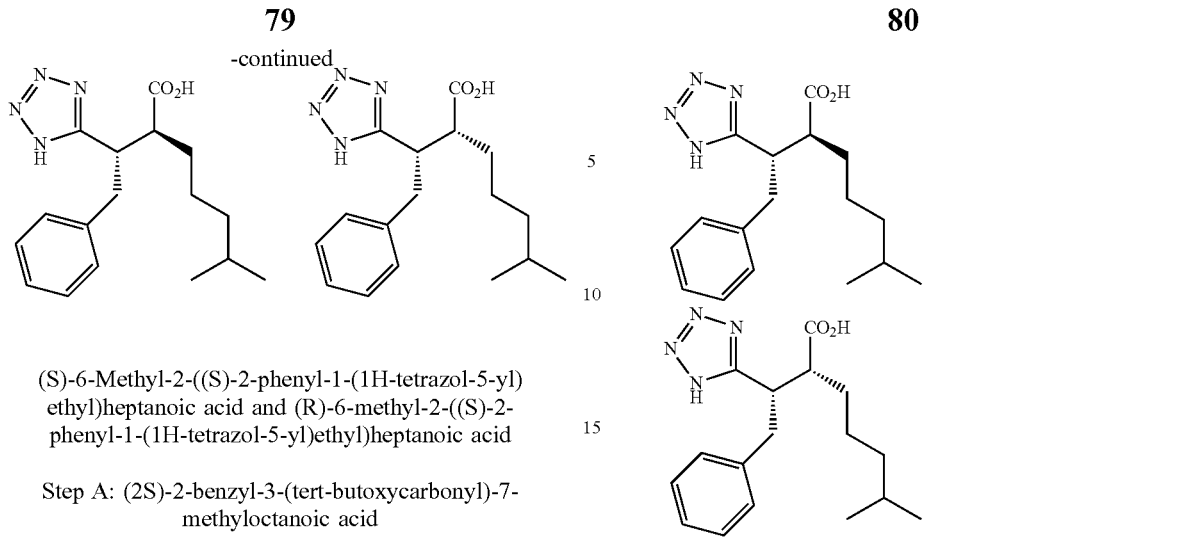

(S)-6-Methyl-2-((S)-2-phenyl-1-(1H-tetrazol-5-yl)ethyl)heptanoic acid and (R)-6-methyl-2-((S)-2-phenyl-1-(1H-tetrazol-5-yl)ethyl)heptanoic acid Step A: (2S)-2-benzyl-3-(tert-butoxycarbonyl)-7-methyloctanoic acid Intermediate (S)-2-benzyl-4-(tert-butoxy)-4-oxobutanoic acid was prepared according to the literature methods (Synthetic communications, 2004, 2633-2640). To a stirred solutions of (S)-2-benzyl-4-(tert-butoxy)-4-oxobutanoic acid (164 mg, 0.620 mmol) in THF (1.5 ml) at −78° C., was added slowly LHMDS (1.6 ml, 1.6 mmol). The solution was stirred at −78° C. for 1 hour, and then 1-iodo-4-methylpentane (250 mg, 1.2 mmol) was added slowly, stirred at −78° C. for 1 hour, and then warmed to 0° C. and stirred for 3 hrs, and then at RT for 3 hrs. The solution was quenched with sat. $NH_4Cl$ at 0° C., extracted with EtOAc, dried over $Na_2SO_4$, and evaporated to dryness to give the crude product. The crude was used in Step B.

Step B: tert-butyl 2-((S)-1-amino-1-oxo-3-phenyl-propan-2-yl)-6-methylheptanoate A mixture of the crude from Step A, (2S,3S)-2-benzyl-3-(tert-butoxycarbonyl)-7-methyloctanoic acid, (~0.62 mmol), HATU (350 mg, 0.92 mmol), ammonium chloride (198 mg, 3.7 mmol), and Hunig's Base (0.86 ml, 4.94 mmol) in DMF (4 ml) was stirred at RT overnight. The reaction mixture was partitioned with EtOAc and Bicarbonate, dried over $Na_2SO_4$, and evaporated to dry to obtain the crude material. The crude was used in Step C.

Step C: tert-butyl 2-((S)-1-cyano-2-phenylethyl)-6-methylheptanoate

The crude (~0.62 mmol) from Step B was dissolved in DMF and cooled to 0° C. Cyanuric chloride (1100 mg, 6.2 mmol) was added to the mixture at 0° C., and then the mixture was stirred at RT for 5 hours. The mixture was cooled in ice bath and saturated aq. $NaHCO_3$ was added until bubbling ceased. The mixture was extracted with EtOAc (3×), and the organic layer was washed with water (2×), brine, dried over $Na_2SO_4$, and concentrated to obtain the crude material.

Step D: tert-butyl 6-methyl-2-((S)-2-phenyl-1-(1H-tetrazol-5-yl)ethyl)heptanoate A solution of (S)-tert-butyl 2-((S)-1-cyano-2-phenylethyl)-6-methylheptanoate (88 mg, 0.27 mmol) from Step C, azidotrimethylstannane (137 mg, 0.67 mmol) in toluene (3 ml) was heated at 110° C. for two days. After cooling, the solution was used directly for the next reaction.

Step E: (S)-6-methyl-2-((S)-2-phenyl-1-(1H-tetrazol-5-yl)ethyl)heptanoic acid & (R)-6-methyl-2-((S)-2-phenyl-1-(1H-tetrazol-5-yl)ethyl)heptanoic acid A solution of (S)-tert-butyl 6-methyl-2-((S)-2-phenyl-1-(1H-tetrazol-5-yl)ethyl)heptanoate (99 mg, 0.266 mmol) from Step D, TFA (9 ml, 117 mmol) in DCM (3 mL) and toluene (3 ml) was stirred at RT overnight. The mixture was evaporated to dryness to obtain the crude for HPLC purification. (Reverse phase HPLC: on a 30×100 mm, Gemini C18 column, 10 μm particle size, linear gradient, 10-100% acetonitrile/$H_2O$, buffering with 0.05% TFA at flow rate 25 mL/min over 11.0 min). Two products were obtained:
(S)-6-methyl-2-((S)-2-phenyl-1-(1H-tetrazol-5-yl)ethyl)heptanoic acid. LC-MS: m/z 317.2 (calc. 317.19);
(R)-6-methyl-2-((S)-2-phenyl-1-(1H-tetrazol-5-yl)ethyl)heptanoic acid. LC-MS: m/z 317.2 (calc. 317.19)

EXAMPLE 3

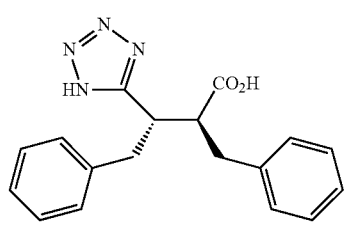 [SMILES: O=C(O)[C@@H](Cc1ccccc1)[C@H](Cc1ccccc1)c1nnn[nH]1]

(2S,3S)-2-benzyl-4-phenyl-3-(1H-tetrazol-5-yl)butanoic acid

Step A: (2S,3S)-tert-butyl 2-benzyl-4-phenyl-3-(1H-tetrazol-5-yl)butanoate

To a stirred solution of (S)-tert-butyl 4-phenyl-3-(1H-tetrazol-5-yl)butanoate (75 mg, 0.26 mmol) in THF (1 ml) at −78° C., was added slowly LDA (0.32 ml, 0.65 mmol). The solution was stirred at −78° C. for 0.7 hour, then benzyl bromide (0.124 ml, 1.04 mmol) was added slowly, stirred at −78° C., and then slowly warmed to RT and stirred overnight. The solution was quenched with saturated NH₄Cl at RT, extracted with EtOAc, dried over Na₂SO₄, filtered and evaporated to dryness. The crude was used directly in Step B.

Step B: (2S,3S)-2-benzyl-4-phenyl-3-(1H-tetrazol-5-yl)butanoic acid

The crude containing (2S,3S)-tert-butyl 2-benzyl-4-phenyl-3-(1H-tetrazol-5-yl)butanoate (98 mg, 0.26 mmol) from Step A was dissolved in dichloromethane (1.7 ml), thioanisole (0.61 ml, 5.2 mmol) followed by TFA (1.3 ml, 17 mmol). The reaction was stirred at RT overnight. The mixture was washed with hexane (2×) to remove thioanisole. The residue was evaporated to dry. The residue was purified by preparative Reverse HPLC on a 19×100 mm, Waters Sunfire C18 column, 5 μm particle size, acetonitrile/H₂O buffering with 0.16% TFA with flow rate 25 mL/min, to obtain (2S,3S)-2-benzyl-4-phenyl-3-(1H-tetrazol-5-yl)butanoic acid: LC-MS m/z 323.15 (M+H⁺, calc. 323.14)

EXAMPLES 4-26

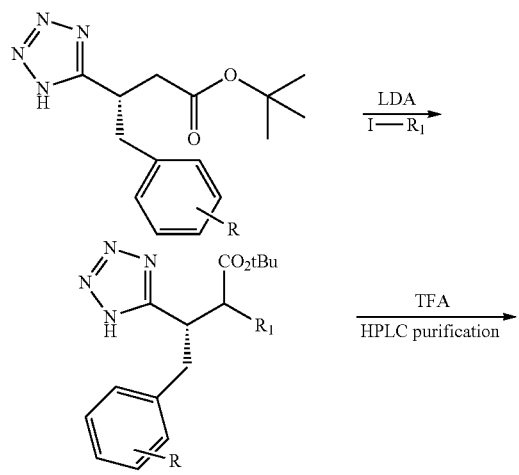

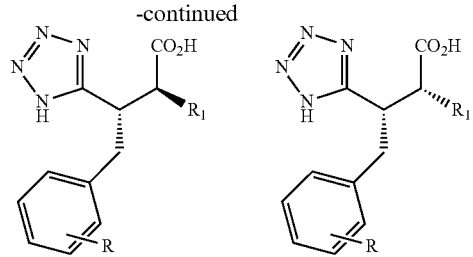

Step A: (S)-tert-butyl 2-((S)-2-phenyl-1-(1H-tetrazol-5-yl)ethyl)pentanoate

To a stirred solution of (S)-tert-butyl 4-phenyl-3-(1H-tetrazol-5-yl)butanoate (84 mg, 0.29 mmol) in THF (1 ml) at −78° C., was added slowly LDA (0.37 ml, 0.73 mmol). The solution was stirred at −78° C. for 0.5 hour, then 1-iodopropane (0.15 ml, 1.46 mmol) was added slowly, stirred at −78° C. for 30 mins, and then slowly warmed to RT and stirred overnight. The solution was quenched with sat. NH₄Cl at RT, extracted with EtOAc, dried over Na₂SO₄, filtered and evaporated to dryness. The crude was purified by silica gel column chromatography, eluted with EtOAc-hexane (0-100%) to yield the product.

Step B: (R)-2-((S)-2-phenyl-1-(1H-tetrazol-5-yl)ethyl)pentanoic acid and (S)-2-((S)-2-phenyl-1-(1H-tetrazol-5-yl)ethyl)pentanoic acid To a stirred solution of tert-butyl 2-((S)-2-phenyl-1-(1H-tetrazol-5-yl)ethyl)pentanoate (44 mg, 0.13 mmol) in toluene (1.2 ml) was added TFA (1.8 ml, 23 mmol). The solution was stirred at RT for 5 hrs under lightly capped condition. The mixture was evaporated to dryness. The crude was purified by HPLC.

prep HPLC: Gemini column, 30×100 mm, AcN—H₂O (0.05% TFA, 10-100% in 12 min) to obtain the two products: (S)-2-((S)-2-phenyl-1-(1H-tetrazol-5-yl)ethyl)pentanoic acid; (R)-2-((S)-2-phenyl-1-(1H-tetrazol-5-yl)ethyl)pentanoic acid and (S)-2-((S)-1-(1-(tert-butyl)-1H-tetrazol-5-yl)-2-phenylethyl)pentanoic acid.

The following EXAMPLES 4-26 were prepared according to the general procedure mentioned above:

| Ex. No. | Structure | Name | Calc'd MW (M + H+) | LC/MS m/e (M + H+) |
|---|---|---|---|---|
| 4 | 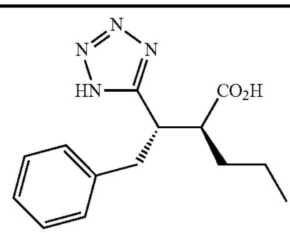 | (S)-2-((S)-2-phenyl-1-(1H-tetrazol-5-yl)ethyl)pentanoic acid | 275.15 | 275.1 |
| 5 | 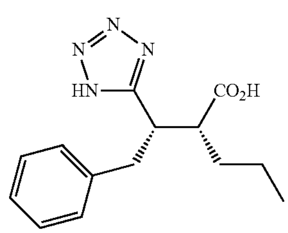 [SMILES: CCC[C@@H](C(=O)O)[C@H](Cc1ccccc1)c1nnn[nH]1] | (R)-2-((S)-2-phenyl-1-(1H-tetrazol-5-yl)ethyl)pentanoic acid | 275.15 | 275.1 |

-continued

| Ex. No. | Structure | Name | Calc'd MW (M + H+) | LC/MS m/e (M + H+) |
|---|---|---|---|---|
| 6 | 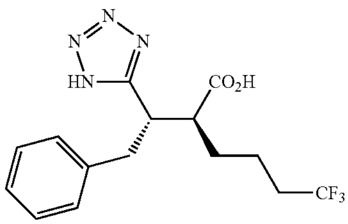 [SMILES: O=C(O)[C@@H](CCCC(F)(F)F)[C@H](Cc1ccccc1)c1nnn[nH]1] | (S)-6,6,6-trifluoro-2-((S)-2-phenyl-1-(1H-tetrazol-5-yl)ethyl)hexanoic acid | 342.14 | 342.24 |
| 7 | 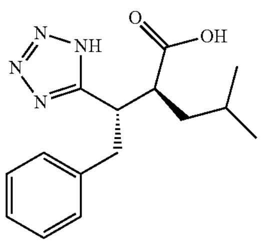 [SMILES: CC(C)C[C@H](C(=O)O)[C@H](Cc1ccccc1)c1nnn[nH]1] | (2S)-4-methyl-2-[(2S)-2-phenyl-1-(1H-tetrazol-5-yl)ethyl]pentanoic acid | 289.17 | 289.16 |
| 8 | 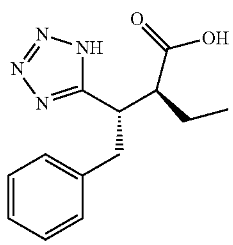 [SMILES: CC[C@H](C(=O)O)[C@H](Cc1ccccc1)c1nnn[nH]1] | (2S,3S)-2-ethyl-4-phenyl-3-(1H-tetrazol-5-yl)butanoic acid | 261.14 | 261.16 |
| 9 | 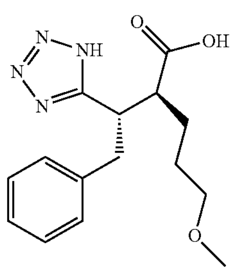 [SMILES: COCCC[C@H](C(=O)O)[C@H](Cc1ccccc1)c1nnn[nH]1] | (2S)-5-methoxy-2-[(1S)-2-phenyl-1-(1H-tetrazol-5-yl)ethyl]pentanoic acid | 305.16 | 305.16 |
| 10 | 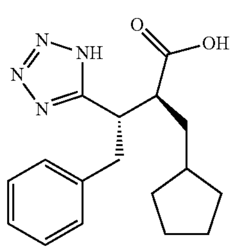 [SMILES: O=C(O)[C@@H](CC1CCCC1)[C@H](Cc1ccccc1)c1nnn[nH]1] | (2S,3S)-2-(cyclopentylmethyl)-4-phenyl-3-(1H-tetrazol-5-yl)butanoic acid | 315.18 | 315.20 |
| 11 | 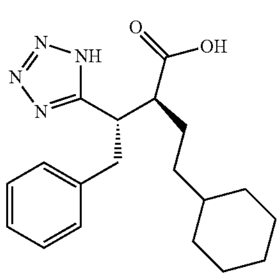 [SMILES: O=C(O)[C@@H](CCC1CCCCC1)[C@H](Cc1ccccc1)c1nnn[nH]1] | (2S,3S)-2-(2-cyclohexylethyl)-4-phenyl-3-(1H-tetrazol-5-yl)butanoic acid | 343.21 | 343.26 |

-continued

| Ex. No. | Structure | Name | Calc'd MW (M + H+) | LC/MS m/e (M + H+) |
|---|---|---|---|---|
| 12 | 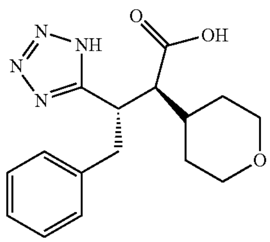 [SMILES: O=C(O)[C@@H](C1CCOCC1)[C@H](Cc1ccccc1)c1nnn[nH]1] | (2S,3S)-4-phenyl-2-(tetrahydro-2H-pyran-4-yl)-3-(1H-tetrazol-5-yl)butanoic acid | 317.16 | 317.17 |
| 13 | 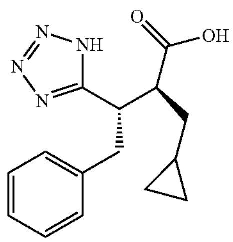 [SMILES: O=C(O)[C@@H](CC1CC1)[C@H](Cc1ccccc1)c1nnn[nH]1] | (2S,3S)-2-(cyclopropylmethyl)-4-phenyl-3-(1H-tetrazol-5-yl)butanoic acid | 287.15 | 287.18 |
| 14 | 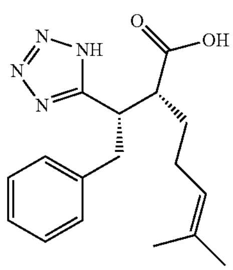 [SMILES: CC(C)=CCC[C@@H](C(=O)O)[C@H](Cc1ccccc1)c1nnn[nH]1] | (2R)-6-methyl-2-[(1S)-2-phenyl-1-(1H-tetrazol-5-yl)ethyl]hept-5-enoic acid | 315.18 | 315.25 |
| 15 | 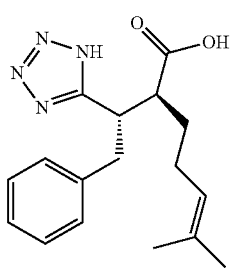 [SMILES: CC(C)=CCC[C@H](C(=O)O)[C@H](Cc1ccccc1)c1nnn[nH]1] | (2R)-6-methyl-2-[(1S)-2-phenyl-1-(1H-tetrazol-5-yl)ethyl]hept-5-enoic acid | 315.18 | 315.26 |
| 16 | 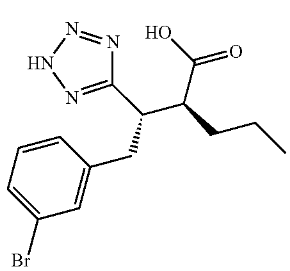 [SMILES: CCC[C@H](C(=O)O)[C@H](Cc1cccc(Br)c1)c1nn[nH]n1] | (S)-2-((S)-2-(3-bromophenyl)-1-(2H-tetrazol-5-yl)ethyl)pentanoic acid | 353.22 | 353.10 |

-continued

| Ex. No. | Structure | Name | Calc'd MW (M + H+) | LC/MS m/e (M + H+) |
|---|---|---|---|---|
| 17 | 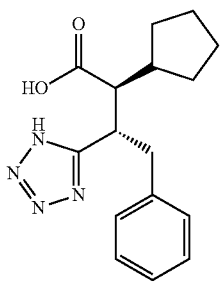 [SMILES: O=C(O)[C@@H](C1CCCC1)[C@H](Cc1ccccc1)c1nnn[nH]1] | (2S,3S)-2-cyclopentyl-4-phenyl-3-(1H-tetrazol-5-yl)butanoic acid | 301.4 | 301.2 |
| 18 | 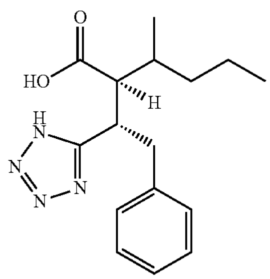 [SMILES: CCCC(C)[C@H](C(=O)O)[C@H](Cc1ccccc1)c1nnn[nH]1] | (2S)-3-methyl-2-((S)-2-phenyl-1-(1H-tetrazol-5-yl)ethyl)hexanoic acid | 303.4 | 303.2 |
| 19 | 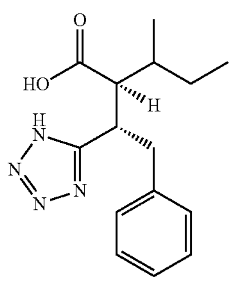 [SMILES: CCC(C)[C@H](C(=O)O)[C@H](Cc1ccccc1)c1nnn[nH]1] | (2S)-3-methyl-2-((S)-2-phenyl-1-(1H-tetrazol-5-yl)ethyl)pentanoic acid | 289.4 | 289.2 |
| 20 | 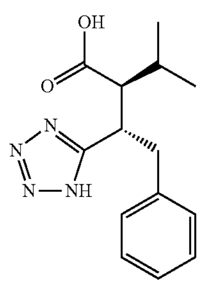 [SMILES: CC(C)[C@H](C(=O)O)[C@H](Cc1ccccc1)c1nnn[nH]1] | (2S,3S)-2-isopropyl-4-phenyl-3-(1H-tetrazol-5-yl)butanoic acid | 275.3 | 275.2 |
| 21 | 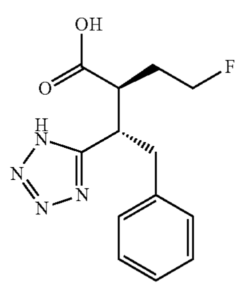 [SMILES: O=C(O)[C@@H](CCF)[C@H](Cc1ccccc1)c1nnn[nH]1] | (2S,3S)-2-(2-fluoroethyl)-4-phenyl-3-(1H-tetrazol-5-yl)butanoic acid | 279.3 | 279.2 |

-continued

| Ex. No. | Structure | Name | Calc'd MW (M + H+) | LC/MS m/e (M + H+) |
|---|---|---|---|---|
| 22 | 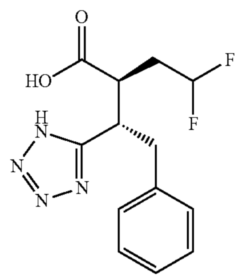 [SMILES: O=C(O)[C@@H](CC(F)F)[C@H](Cc1ccccc1)c1nnn[nH]1] | (2S,3S)-2-(2,2-difluoroethyl)-4-phenyl-3-(1H-tetrazol-5-yl)butanoic acid | 297.3 | 297.2 |
| 23 | 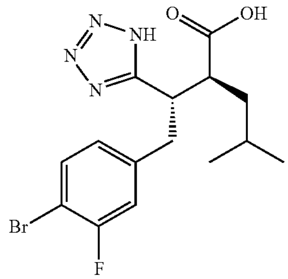 [SMILES: CC(C)C[C@H](C(=O)O)[C@H](Cc1ccc(Br)c(F)c1)c1nnn[nH]1] | (2S)-2-[(1S)-2-(4-bromo-3-fluorophenyl)-1-(1H-tetrazol-5-yl)ethyl]-4-methylpentanoic acid | 385.07 | 387.14 385.19 |
| 24 | 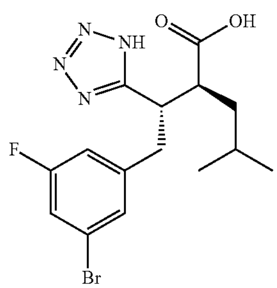 [SMILES: CC(C)C[C@H](C(=O)O)[C@H](Cc1cc(F)cc(Br)c1)c1nnn[nH]1] | (2S)-2-[(1S)-2-(3-bromo-5-fluorophenyl)-1-(1H-tetrazol-5-yl)ethyl]-4-methylpentanoic acid | 385.07 | 387.15 385.17 |
| 25 | 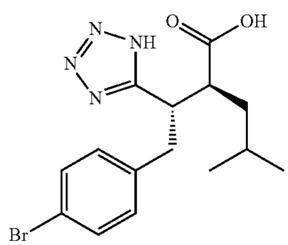 [SMILES: CC(C)C[C@H](C(=O)O)[C@H](Cc1ccc(Br)cc1)c1nnn[nH]1] | (2S)-2-[(1S)-2-(4-bromophenyl)-1-(1H-tetrazol-5-yl)ethyl]-4-methylpentanoic acid | 367.08 | 367.04 |
| 26 | 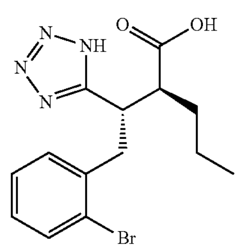 [SMILES: CCC[C@H](C(=O)O)[C@H](Cc1ccccc1Br)c1nnn[nH]1] | (2S)-2-[(1S)-2-(2-bromophenyl)-1-(1H-tetrazol-5-yl)ethyl]pentanoic acid | 353.06 | 352.98 |

EXAMPLE 27

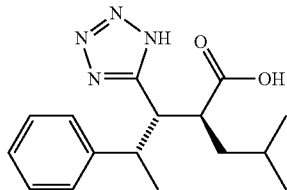 [SMILES: CC(C)C[C@H](C(=O)O)C(c1nnn[nH]1)[C@H](C)c1ccccc1]

(2S,3S,4S)-2-isobutyl-4-phenyl-3-(1H-tetrazol-5-yl)
pentanoic acid

Step A: (2S,3S,4S)-tert-butyl 2-isobutyl-4-phenyl-3-(1H-tetrazol-5-yl)pentanoate To a solution of diisopropylamine (0.10 ml, 0.73 mmol) in 1.5 mL of THF was added n-BuLi (0.29 ml, 0.73 mmol) at 0° C. The mixture was stirred at 0~5° C. for 30 min. After the mixture was cooled to −78° C., (3R,4R)-tert-butyl 4-phenyl-3-(1H-tetrazol-5-yl)pentanoate (100 mg, 0.33 mmol) in 1 mL of THF was added dropwise and stirred at −78° C. for 1 hour. 1-iodo-2-methylpropane (0.038 ml, 0.33 mmol) was added dropwise at −78° C. and stirred at −78° C. for 1 hour and then gradually warmed up to RT and stirred for 72 hrs. The reaction mixture was added to an aqueous solution of NH$_4$Cl and extracted with EtOAc. The organic layer was washed with brine, dried over MgSO$_4$, filtered and concentrated down to give the crude product. LC-MS m/z (M+H)$^+$ 359.3

Step B: (2S,3S,4S)-2-isobutyl-4-phenyl-3-(1H-tetrazol-5-yl)pentanoic acid

TFA (1 mL, 13 mmol) was added to a stirred, room temperature mixture of (2S,3S,4S)-tert-butyl 2-isobutyl-4-phenyl-3-(1H-tetrazol-5-yl)pentanoate (68 mg, 0.15 mmol), thioanisole (0.10 ml, 0.84 mmol) in a flask and the mixture was stirred at room temperature for 3 hours. LC-MS showed the reaction was near completion. The reaction mixture was concentrated down. The residue was treated with hexane. The residue oil was dissolved in CH$_3$CN/water. The residue was purified by preparative HPLC [HPLC], eluting with Acetonitrile/Water+0.1% TFA (10~70%~10%), to give the product. LC-MS m/z (M+H)$^+$ 359.3

The following 2 compounds were prepared following the above procedure of EXAMPLE 27:

| Ex. No. | Structure | IUPAC Name | Calc'd Mass [M + H]+ | LC/MS m/e [M +H]+ |
|---|---|---|---|---|
| 28 | ![structure] | (2S,3S,4R)-2-(2-fluoroethyl)-4-phenyl-3-(1H-tetrazol-5-yl)pentanoic acid | 293.3 | 293.2 |
| 29 | ![structure] | (2S,3S,4R)-2-ethyl-4-phenyl-3-(1H-tetrazol-5-yl)pentanoic acid | 275.3 | 275.2 |

EXAMPLE 30

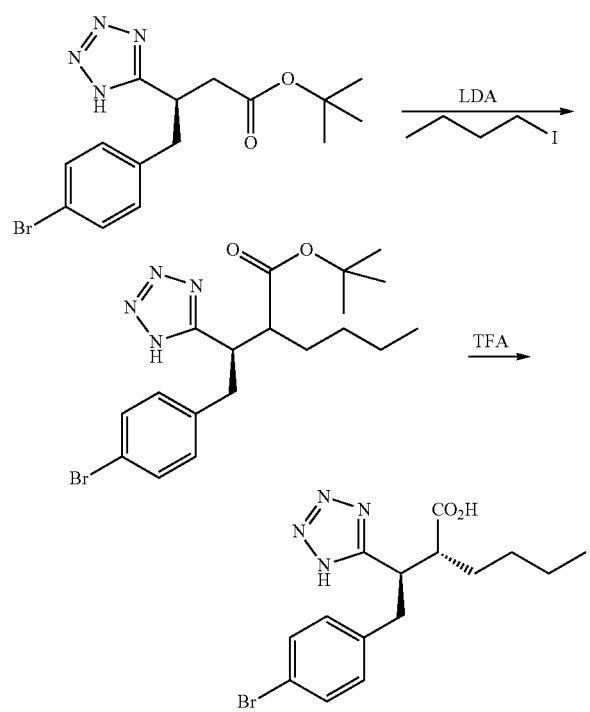

(R)-2-((R)-2-(4-bromophenyl)-1-(1H-tetrazol-5-yl)ethyl)hexanoic acid

Step A: tert-butyl 2-((R)-2-(4-bromophenyl)-1-(1H-tetrazol-5-yl)ethyl)hexanoate

To a stirred solution of (R)-tert-butyl 4-(4-bromophenyl)-3-(1H-tetrazol-5-yl)butanoate (420 mg, 1.4 mmol) in THF (4 ml) at −78° C., was slowly added LDA (1.8 ml, 3.6 mmol). The solution was stirred at −78° C. for 0.5 hr, then 1-iodobutane (0.82 ml, 7.2 mmol) was added slowly, stirred at −78° C. for 30 mins, and then slowly warmed to RT and stirred overnight. The solution was quenched with sat. NH$_4$Cl at RT, extracted with EtOAc, dried over Na$_2$SO$_4$, filtered and evaporated to dryness. The crude was used directly in the next step.

Step B: (R)-2-((R)-2-(4-bromophenyl)-1-(1H-tetrazol-5-yl)ethyl)hexanoic acid

The crude containing tert-butyl 2-((R)-2-(4-bromophenyl)-1-(1H-tetrazol-5-yl)ethyl)hexanoate (400 mg, 1.2 mmol) was dissolved in DCM (5.8 ml) and thioanisole (2.75 ml, 23 mmol), followed by addition of TFA (1 mL, 13 mmol). The reaction was stirred at RT overnight. The solvent was removed in vacuo, and the mixture was washed with hexane (2×) to remove thioanisole. The residue was evaporated to dryness. The residue was purified by preparative HPLC Reverse phase with C18 Prep Column, 100 Å, 10 μm, 30 mm×100 mm (multiple injections), eluted with 5-100% acetonitrile/Water, with 0.05% TFA in 22 min to deliver (R)-2-((R)-2-(4-bromophenyl)-1-(1H-tetrazol-5-yl)ethyl)hexanoic acid. LC-MS m/z (M+H)+ 367.2

EXAMPLE 31

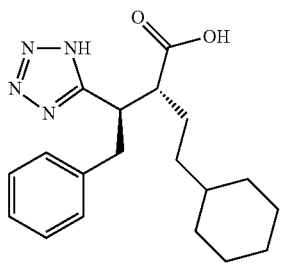 [SMILES: O=C(O)[C@H](CCC1CCCCC1)[C@@H](Cc1ccccc1)c1nnn[nH]1]

(2R,3R)-2-(2-cyclohexylethyl)-4-phenyl-3-(1H-tetrazol-5-yl)butanoic acid

Compound 31 was prepared following the same procedure as EXAMPLE 30 from (R)-tert-butyl 4-phenyl-3-(1H-tetrazol-5-yl)butanoate. LC-MS m/z (M+H)+ 343.2

EXAMPLE 32

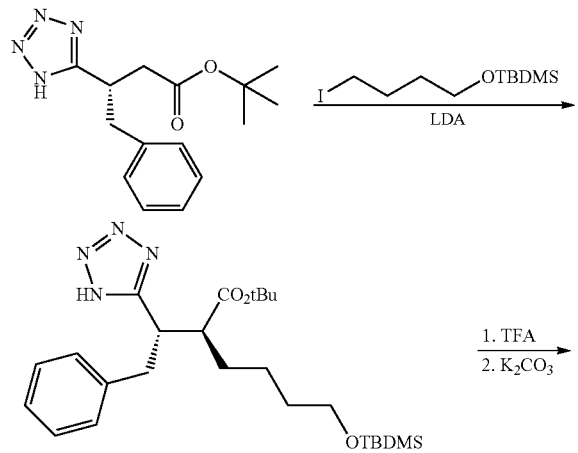

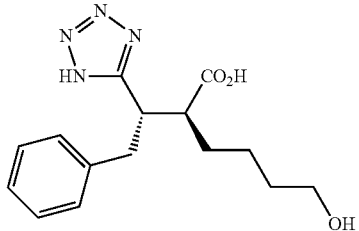

Step A: (S)-tert-butyl 6-((tert-butyldimethylsilyl)oxy)-2-((S)-2-phenyl-1-(1H-tetrazol-5-yl)ethyl)hexanoate To a stirred solution of (S)-tert-butyl 4-phenyl-3-(1H-tetrazol-5-yl)butanoate (30 mg, 0.104 mmol) in THF (0.3 ml) at −78° C., was added slowly LDA (0.13 ml, 0.26 mmol). The solution was stirred at −78° C. for 0.5 hr, then tert-butyl(4-iodobutoxy)dimethylsilane (62 mg, 0.20 mmol) was added slowly. The mixture was stirred at −78° C. for 30 mins, warmed to RT, and then stirred at RT for 3 days. The solution was quenched with sat. NH4Cl at RT, extracted with EtOAc, dried over Na2SO4, filtered and evaporated to dryness. The crude was purified by Flash Si gel CC, EtOAc-hexane (0-100%) to yield the product for Step B.

Step B: (S)-6-hydroxy-2-((S)-2-phenyl-1-(1H-tetrazol-5-yl)ethyl)hexanoic acid

To a stirred solution of (S)-tert-butyl 6-((tert-butyldimethylsilyl)oxy)-2-((S)-2-phenyl-1-(1H-tetrazol-5-yl)ethyl)hexanoate (8.5 mg, 0.018 mmol) in toluene (0.4 ml) was added TFA (0.6 ml, 7.8 mmol). The solution was stirred at RT overnight under lightly capped condition. The mixture was evaporated to dryness. The crude was purified by HPLC (prep HPLC: C18 column, 30×100 mm, AcN—H2O (0.05% TFA, 10-100% in 12 min). Dried fractions containing TFA ester product were treated with MeOH—H2O (4:1) and K2CO3 (6 mg) for 1 hr, evaporated, acidified with 2N HCl, extracted with EtOAc to get the product, (S)-6-hydroxy-2-((S)-2-phenyl-1-(1H-tetrazol-5-yl)ethyl)hexanoic acid. LC-MS m/z 305.09 (calc. m/z 305.15).

EXAMPLE 33

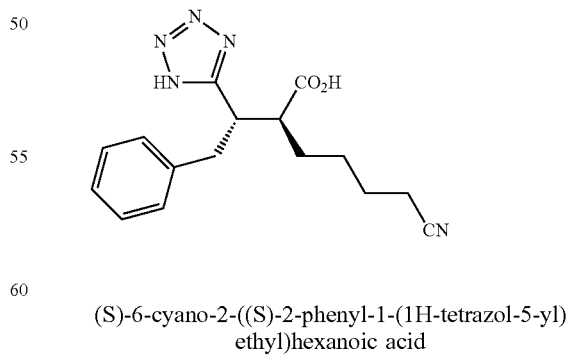

(S)-6-cyano-2-((S)-2-phenyl-1-(1H-tetrazol-5-yl)ethyl)hexanoic acid

Step A: 5-iodopentanenitrile

To a solution of 5-bromopentanenitrile (500 mg, 3.1 mmol) in acetone (15 ml), sodium iodide (920 mg, 6.2 mmol) was added and the reaction mixture was stirred at RT over the weekend. The mixture was filtered and concentrated. The residue was partitioned between brine and ether. Ether layer was dried over MgSO₄, and evaporated to dry to get the product.

Step B: (S)-tert-butyl 6-cyano-2-((S)-2-phenyl-1-(1H-tetrazol-5-yl)ethyl)hexanoate To a stirred solution of (S)-tert-butyl 4-phenyl-3-(1H-tetrazol-5-yl)butanoate (150 mg, 0.52 mmol) in THF at −78° C., was added slowly lithium diisopropylamide (0.65 ml, 1.3 mmol). The solution was stirred at −78° C. for 0.7 hr, then 5-iodopentanenitrile (435 mg, 2.1 mmol) was added slowly, stirred at −78° C., and then slowly warmed to RT and stirred overnight. The solution was quenched with sat. NH₄Cl at RT, extracted with EtOAc, dried over Na₂SO₄, filtered, and evaporated to dryness. One third of the crude was used directly in Step C.

Step C: (S)-6-cyano-2-((S)-2-phenyl-1-(1H-tetrazol-5-yl)ethyl)hexanoic acid

The crude containing (S)-tert-butyl 6-cyano-2-((S)-2-phenyl-1-(1H-tetrazol-5-yl)ethyl)hexanoate (100 mg, 0.27 mmol) was dissolved in DCM (1.4 ml) and thioanisole (0.64 ml, 5.4 mmol), followed by addition of TFA (1.4 ml, 18 mmol). The reaction was stirred at RT overnight. The mixture was evaporated in vacuo and washed with hexane (3×) to remove thioanisole. The residue was evaporated to dryness. The residue was purified using preparative Reverse HPLC on a 19×100 mm, Waters Sunfire C18 column, 5 μm particle size, acetonitrile/H₂O buffering with 0.16% TFA at flow rate 50 mL/min to obtain 20 mg product. (S)-6-cyano-2-((S)-2-phenyl-1-(1H-tetrazol-5-yl)ethyl)hexanoic acid. LC-MS m/z 314.16 (calc. m/z 314.16)

EXAMPLES 34-35

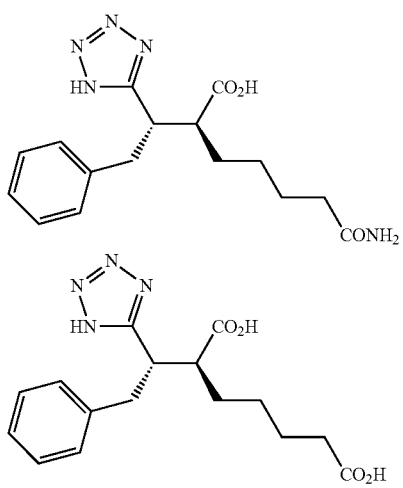

(S)-2-((S)-2-phenyl-1-(1H-tetrazol-5-yl)ethyl)heptanedioic acid and (S)-7-amino-7-oxo-2-((S)-2-phenyl-1-(1H-tetrazol-5-yl)ethyl)heptanoic acid (S)-6-cyano-2-((S)-2-phenyl-1-(1H-tetrazol-5-yl)ethyl)hexanoic acid (13 mg, 0.042 mmol) was dissolved in ethanol (0.5 ml), and to the mixture was added KOH (9.5 mg, 0.17 mmol) and hydrogen peroxide (0.074 ml, 0.85 mmol). The mixture was heated to 70° C. for 1 day. The mixture was partitioned between ethyl acetate and NH₄Cl. The aqueous solution was further acidified by 1 N HCl and extracted with EtOAc (2×). The combined organic was dried over sodium sulfate, filtered and evaporated. The crude was purified on C18 HPLC: product 1, (S)-7-amino-7-oxo-2-((S)-2-phenyl-1-(1H-tetrazol-5-yl)ethyl)heptanoic acid, LC-MS m/z 332.3 (calc. m/z 332.17); product 2, (S)-2-((S)-2-phenyl-1-(1H-tetrazol-5-yl)ethyl)heptanedioic acid, LC-MS m/z 333.3 (calc. m/z 333.16).

EXAMPLE 36

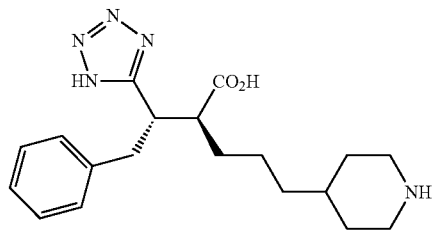 [SMILES: O=C(O)[C@@H](CCCC1CCNCC1)[C@H](Cc1ccccc1)c1nnn[nH]1]

(S)-2-((S)-2-phenyl-1-(1H-tetrazol-5-yl)ethyl)-5-(piperidin-4-yl)pentanoic acid

Step A: tert-butyl 4-(3-iodopropyl)piperidine-1-carboxylate

To a mixture of imidazole (180 mg, 2.7 mmol) and triphenylphosphine (700 mg, 2.7 mmol) in acetonitrile (2.5 ml) and ether (7.5 ml) was added iodine (680 mg, 2.7 mmol) at 0° C., and then stirred at room temperature for 15 minutes. t-butyl 4-(3-hydroxypropyl)piperidine-1-carboxylate (500 mg, 2.1 mmol) in the same solvent system (2 mL) was added dropwise at 0° C. The solution was stirred at RT overnight. The mixture was evaporated, and DCM (20 mL) was added. The suspension was filtered and evaporated to get the crude. The crude was purified by column chromatography on silica gel (40 g, ISCO Flash Chromatography), eluting with 0-100% EtOAc/hexane to give a colorless oil, used in the next step.

Step B: tert-butyl 4-((4S,5S)-4-(tert-butoxycarbonyl)-6-phenyl-5-(1H-tetrazol-5-yl)hexyl)piperidine-1-carboxylate To a stirred solution of (S)-tert-butyl 4-phenyl-3-(1H-tetrazol-5-yl)butanoate (100 mg, 0.35 mmol), in THF (1 ml) at −78° C., was added slowly LDA (0.40 ml, 0.80 mmol).

The solution was stirred at −78° C. for 0.7 hr, then tert-butyl 4-(3-iodopropyl)piperidine-1-carboxylate (340 mg, 0.96 mmol) was added slowly, stirred at −78° C., and then slowly warmed to RT and stirred overnight. The solution was quenched with sat. NH$_4$Cl at RT, extracted with EtOAc, dried over Na$_2$SO$_4$, filtered and evaporated to dryness. The crude was used directly in Step C.

Step C: (S)-2-((S)-2-phenyl-1-(1H-tetrazol-5-yl)ethyl)-5-(piperidin-4-yl)pentanoic acid The crude containing tert-butyl 4-((4S,5S)-4-(tert-butoxycarbonyl)-6-phenyl-5-(1H-tetrazol-5-yl)hexyl)piperidine-1-carboxylate (180 mg, 0.35 mmol) from Step B was dissolved in DCM (1.7 ml) and thioanisole (0.82 ml, 6.9 mmol), followed by addition of TFA (1.7 ml, 23 mmol). The reaction was stirred at RT overnight. The mixture was evaporated and then washed with hexane (2×) and hexane-ether (1:1) to remove thioanisole. The residue was evaporated to dryness. The residue was purified by preparative reverse HPLC on a 19×100 mm, Luna C18 column, 5 μm particle size, acetonitrile/H$_2$O buffering with 0.05% TFA at flow rate 20 mL/min, to afford TFA salt of (S)-2-((S)-2-phenyl-1-(1H-tetrazol-5-yl)ethyl)-5-(piperidin-4-yl)pentanoic acid, LC-MS: m/z 358.4 (calc. m/z 358.23)

EXAMPLES 37-39

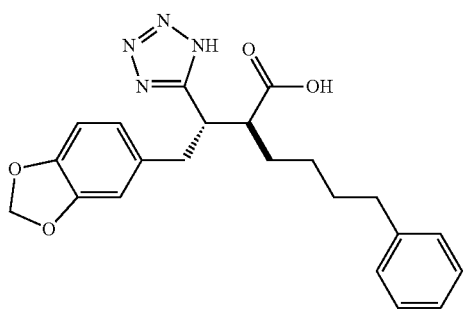 [SMILES: O=C(O)[C@@H](CCCCc1ccccc1)[C@H](Cc1ccc2c(c1)OCO2)c1nnn[nH]1]

(S)-2-((S)-2-(benzo[d][1,3]dioxol-5-yl)-1-(1H-tetrazol-5-yl)ethyl)-6-phenylhexanoic acid Step A: (2S,3S)-2-(benzo[d][1,3]dioxol-5-ylmethyl)-3-(tert-butoxycarbonyl)-7-phenylheptanoic acid To a stirred solution of 2-(benzo[d][1,3]dioxol-5-ylmethyl)-4-(tert-butoxy)-4-oxobutanoic acid (150 mg, 0.49 mmol) in THF (2.5 ml) at −78° C., was added slowly LHMDS 1 M in toluene (1.22 ml, 1.22 mmol). The solution was stirred at −78° C. for 1 hr, then (4-iodobutyl)benzene (240 mg, 0.92 mmol) was added slowly, stirred at −78° C. for 60 mins, and then slowly warmed to RT overnight. The solution was quenched with sat. NH$_4$Cl at 0° C., extracted with EtOAc. The aqueous Layer was acidified to acidic with 2N HCl, then extracted with EtOAc 2 times. The combined organic layers were dried with MgSO$_4$, filtered and rotovap to dry to give a light yellow oil, which was purified by chromatography on silica gel, eluted with Hexane-EtOAc (0-30%), provided the desired compound. LC-MS m/z [M+Na]$^+$ 463.30

Step B: (S)-tert-butyl 2-((S)-1-amino-3-(benzo[d][1,3]dioxol-5-yl)-1-oxopropan-2-yl)-6-phenylhexanoate A mixture of (2S,3S)-2-(benzo[d][1,3]dioxol-5-ylmethyl)-3-(tert-butoxycarbonyl)-9-methyldecanoic acid (68 mg, 0.16 mmol), HATU (123 mg, 0.32 mmol), ammonium chloride (35 mg, 0.65 mmol), and DIPEA (0.17 ml, 0.97 mmol) in DMF (3.0 ml) was stirred overnight. The reaction mixture was worked up with EtOAc/sodium bicarbonate, dried over Na$_2$SO$_4$ to get the crude and used directly in the next step.

Step C: (S)-tert-butyl 2-((S)-2-(benzo[d][1,3]dioxol-5-yl)-1-cyanoethyl)-6-phenylhexanoate (S)-tert-butyl 2-((S)-1-amino-3-(benzo[d][1,3]dioxol-5-yl)-1-oxopropan-2-yl)-8-methylnonanoate (110 mg, 0.26 mmol) was dissolved in DMF (3.0 ml) and cooled to 0° C. To the reaction was added 2,4,6-trichloro-1,3,5-triazine (480 mg, 2.6 mmol), then removed from the cooling bath and allowed to warm to RT overnight. The reaction mixture was cooled in an ice bath and sat'd NaHCO$_3$ was added until bubbling ceased. The reaction mixture was extracted with EtOAc (3×). The combined extracts were washed with brine (2×), dried with Na$_2$SO$_4$, filtered, and concentrated to a pale yellow liquid. Chromatographed, silica gel, 12 g, gradient 0-50% EtOAc/Hexane, gave a colorless oil of desired compound. LC-MS m/z [M+H]$^+$ 402.30

Step D: (S)-tert-butyl 2-((S)-2-(benzo[d][1,3]dioxol-5-yl)-1-(2H-tetrazol-5-yl)ethyl)-6-phenylhexanoate The reaction mixture of (S)-tert-butyl 2-((S)-2-(benzo[d][1,3]dioxol-5-yl)-1-cyanoethyl)-8-methylnonanoate (23 mg, 0.057 mmol) and azidotrimethylstannane (15 mg, 0.072 mmol) in toluene (2.0 ml) was heated at 110° C. overnight. LCMS showed that most of SM remained. Additional azidotrimethylstannane (15 mg, 0.072 mmol) was added and heated at 110° C. overnight. The solvent was removed on rotovap and to the residue was added DMSO (1.5 ml), and then filtered for HPLC purification to furnish the desired product as a colorless oil. LC-MS m/z [M+H]$^+$ 445.68

Step E: (S)-2-((S)-2-(benzo[d][1,3]dioxol-5-yl)-1-(1H-tetrazol-5-yl)ethyl)-6-phenylhexanoic acid The reaction mixture of (S)-tert-butyl 2-((S)-2-(benzo[d][1,3]dioxol-5-yl)-1-(2H-tetrazol-5-yl)ethyl)-8-methylnonanoate (15 mg, 0.034 mmol), 2,2,2-trifluoroacetic acid (190 mg, 1.7 mmol) in DCM (200 μL) was stirred at RT and monitored by LCMS. After the reaction was complete, the solvent was removed and to the residue was added 1.5 ml of DMSO, then filtered for HPLC purification to afford the desired product. LC-MS m/z [M+H]$^+$ 409.21

| EX. NO. | Structure | Name | Calc'd mass [M + H]+ | MS found |
|---|---|---|---|---|
| 37 | 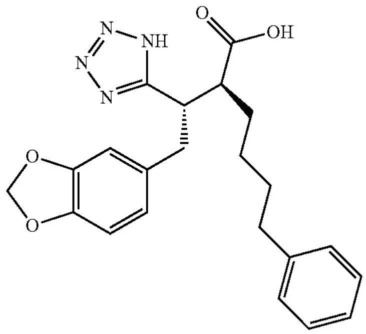 [SMILES: O=C(O)[C@@H](CCCCc1ccccc1)[C@H](Cc1ccc2c(c1)OCO2)c1nnn[nH]1] | (2S)-2-[(1S)-2-(1,3-benzodioxol-5-yl)-1-(2H-tetrazol-5-yl)ethyl]-6-phenylhexanoic acid | 409.19 | 409.21 |
| 38 | 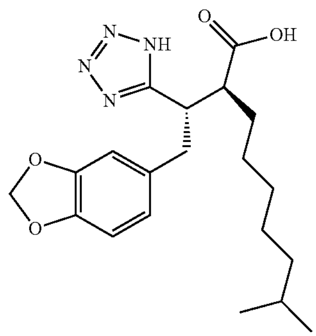 [SMILES: CC(C)CCCCC[C@H](C(=O)O)[C@H](Cc1ccc2c(c1)OCO2)c1nnn[nH]1] | (2S)-2-[(1S)-2-(1,3-benzodioxol-5-yl)-1-(2H-tetrazol-5-yl)ethyl]-8-methylnonanoic acid | 389.22 | 389.24 |
| 39 | 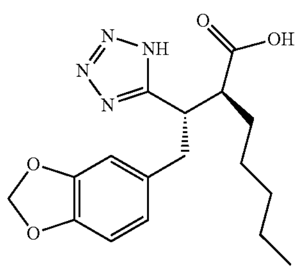 [SMILES: CCCCC[C@H](C(=O)O)[C@H](Cc1ccc2c(c1)OCO2)c1nnn[nH]1] | (2S)-2-[(1S)-2-(1,3-benzodioxol-5-yl)-1-(1H-tetrazol-5-yl)ethyl]heptanoic acid | 347.17 | 347.18 |

EXAMPLE 40

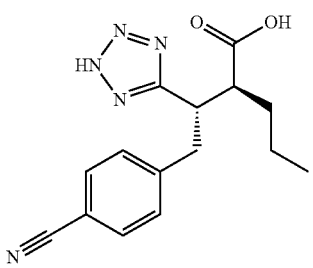 [SMILES: CCC[C@H](C(=O)O)[C@H](Cc1ccc(C#N)cc1)c1nn[nH]n1]

(S)-2-((S)-2-(4-cyanophenyl)-1-(2H-tetrazol-5-yl)ethyl)pentanoic acid

Step A: (S)-tert-butyl 2-((S)-2-(4-cyanophenyl)-1-(2-(4-methoxybenzyl)-2H-tetrazol-5-yl)ethyl)pentanoate Catalyst Prep: X-PHOS (18 mg, 0.038 mmol) and Palladium acetate (4.2 mg, 0.019 mmol) were added to a septum-topped vial, followed by DMA (2.0 ml) and then Sulfuric acid, 98% (1.0 µl, 0.019 mmol). This was then sealed and sparged with $N_2$ for 5 minutes, then heated at 80° C. for 30 minutes to give a homogeneous brown solution.

Reaction Set-Up: In a second septum-topped vial, Zinc Cyanide (26.6 mg, 0.227 mmol), Zinc dust (1.235 mg, 0.019 mmol) and (S)-tert-butyl 2-((S)-2-(4-bromophenyl)-1-(2-(4-methoxybenzyl)-2H-tetrazol-5-yl)ethyl)pentanoate were added, followed by DMA (2000 µl). This was then sealed and sparged with $N_2$ for 5 minutes, then the catalyst solution was transferred via syringe to the reaction. This was then heated at 120° C. overnight.

Work-Up: The mixture was cooled, diluted with ethyl acetate (30 mL), washed with saturated $NaHCO_3$, $H_2O$, $NH_4Cl$, $H_2O$ and Brine, dried ($MgSO_4$), filtered and the solvent was evaporated under reduced pressure.

Purification: The residue was purified by preparative ISCO eluting with EtOAc/Hexanes, to give a colorless oil. LC-MS m/z [M+H]+ 476.37

Step B: (S)-2-((S)-2-(4-cyanophenyl)-1-(2H-tetrazol-5-yl)ethyl)pentanoic acid

To a solution of (S)-tert-butyl 2-((S)-2-(4-cyanophenyl)-1-(2-(4-methoxybenzyl)-2H-tetrazol-5-yl)ethyl)pentanoate (70 mg, 0.15 mmol) in thioanisole (500 μl, 4.2 mmol) at 0° C., TFA (500 μl, 6.5 mmol) was added and stirred at RT for 1 hour, then stirred at 50° C. and checked by LCMS. LCMS showed all of SM was gone. The reaction mixture was rotovap concentrated and to the residue was added 10 ml of Hexane, titurated and to the residue oil was then added DMSO (3.0 ml), and then filtered for purification under HPLC conditions. LC-MS m/z [M+H]⁺ 300.15

The following compounds were prepared according to the procedure of EXAMPLE 40.

(S)-2-((S)-2-(4-(1H-tetrazol-5-yl)phenyl)-1-(2H-tetrazol-5-yl)ethyl)pentanoic acid Step A: (S)-tert-butyl 2-((S)-2-(4-cyanophenyl)-1-(2-(4-methoxybenzyl)-2H-tetrazol-5-yl)ethyl)pentanoate The intermediate was prepared according to the cyanation procedure described in EXAMPLE 42. LC-MS m/z [M+H]⁺ 476.34

| EX. NO. | Structure | IUPAC Name | Calc'd Mass [M + H]⁺ | LC/MS m/e [M + H]⁺ |
|---|---|---|---|---|
| 41 | 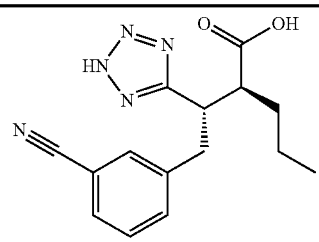 | (2S)-2-[(1S)-2-(3-cyanophenyl)-1-(1H-tetrazol-5-yl)ethyl]pentanoic acid | 300.15 | 300.17 |
| 42 | 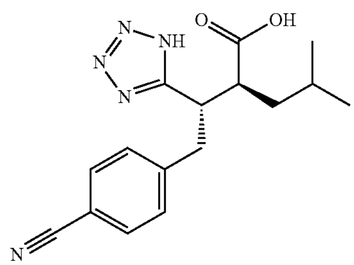 [SMILES: CC(C)C[C@H](C(=O)O)[C@H](Cc1ccc(C#N)cc1)c1nnn[nH]1] | (2S)-2-[(1S)-2-(4-cyanophenyl)-1-1H-tetrazol-5-yl)ethyl]-4-methylpentanoic acid | 314.16 | 313.98 |
| 43 | 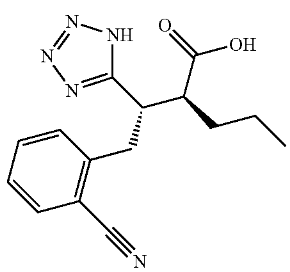 [SMILES: CCC[C@H](C(=O)O)[C@H](Cc1ccccc1C#N)c1nnn[nH]1] | (2S)-2-[(1S)-2-(2-cyanophenyl)-1-(1H-tetrazol-5-yl)ethyl]pentanoic acid | 300.15 | 300.02 |

EXAMPLE 44

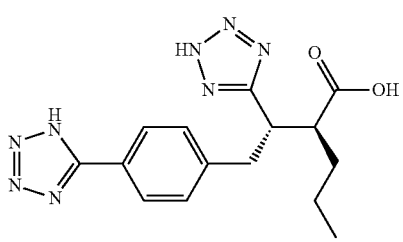 [SMILES: CCC[C@H](C(=O)O)[C@H](Cc1ccc(-c2nnn[nH]2)cc1)c1nn[nH]n1]

Step B: (S)-tert-butyl 2-((S)-2-(4-(1H-tetrazol-5-yl)phenyl)-1-(2-(4-methoxybenzyl)-2H-tetrazol-5-yl)ethyl)pentanoate A solution of (S)-tert-butyl 2-((S)-2-(4-cyanophenyl)-1-(2-(4-methoxybenzyl)-2H-tetrazol-5-yl)ethyl)pentanoate (84 mg, 0.18 mmol), dibutyltin oxide (13 mg, 0.053 mmol) and azidotrimethylsilane (0.070 ml, 0.53 mmol) in Toluene (1.5 ml) was heated at 110° C. for 16 hours. The reaction mixture was concentrated under reduced pressure and purified by ISCO chromatography, normal phase, with hexane and ethyl acetate. LC-MS m/z [M+H]⁺ 519.30

Step C: (S)-2-((S)-2-(4-(1H-tetrazol-5-yl)phenyl)-1-(2H-tetrazol-5-yl)ethyl)pentanoic acid To a solution of (S)-tert-butyl 2-((S)-2-(4-(1H-tetrazol-5-yl)phenyl)-1-(2-(4-methoxybenzyl)-2H-tetrazol-5-yl)ethyl)pentanoate (15 mg, 0.029 mmol) in DCM (300 μl) was added thioanisole (300 μl, 2.5 mmol), and TFA (300 μl, 2.7 mmol). The mixture was stirred at 50° C. overnight. The volatiles were removed under reduced pressure, and the residue was dissolved in DMSO and purified by reverse-phase HPLC. LC-MS m/z [M+H]⁺ 343.24

EXAMPLE 45

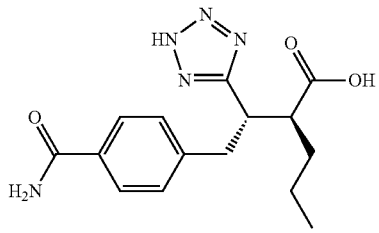 [SMILES: CCC[C@H](C(=O)O)[C@H](Cc1ccc(C(N)=O)cc1)c1nn[nH]n1]

(S)-2-((S)-2-(4-carbamoylphenyl)-1-(2H-tetrazol-5-yl)ethyl)pentanoic acid (S)-tert-butyl 2-((S)-2-(4-cyanophenyl)-1-(2-(4-methoxybenzyl)-2H-tetrazol-5-yl)ethyl)pentanoate (85 mg, 0.18 mmol) was dissolved in DMSO (3.0 ml) cooled to 0° C., and then to the reaction was added $K_2CO_3$ (25 mg, 0.18 mmol) and hydrogen peroxide (0.078 ml, 0.89 mmol). The reaction mixture was then warmed up to RT, and stirred for about 1 hour. LC-MS has product M+1=493. Work up: poured into water and extracted with EtOAc 2 times, washed with brine, dried over with $MgSO_4$, filtered and evaporated to dryness, to give the crude which was used as is.

To a solution of above intermediate in thioanisole (500 µL) at 0° C. was added TFA (500 µL). The mixture was allowed to stir for 1 hour at RT, and then at 50° C. for 1 hour. LC-MS indicated complete reaction. The volatiles were removed under reduced pressure, and the residue was dissolved in DMSO and the products separated by HPLC. LC-MS m/z [M+H]⁺ 318.19

The following compounds were prepared according to the procedure of EXAMPLE 45.

| Ex. No. | Structure | IUPAC Name | Calc'd Mass [M + H]+ | LC/MS m/e [M + H]+ |
|---|---|---|---|---|
| 46 | 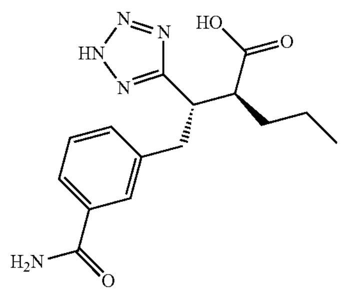 [SMILES: CCC[C@H](C(=O)O)[C@H](Cc1cccc(C(N)=O)c1)c1nn[nH]n1] | (2S)-2-[(1S)-2-(3-carbamoylphenyl)-1-(2H-tetrazol-5-yl)ethyl]pentanoic acid | 318.16 | 318.27 |
| 47 | 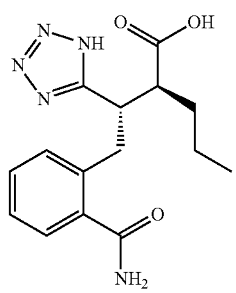 [SMILES: CCC[C@H](C(=O)O)[C@H](Cc1ccccc1C(N)=O)c1nnn[nH]1] | (2S)-2-[(1S)-2-(2-carbamoylphenyl)-1-(1H-tetrazol-5-yl)ethyl]pentanoic acid | 318.16 | 318.14 |
| 48 | 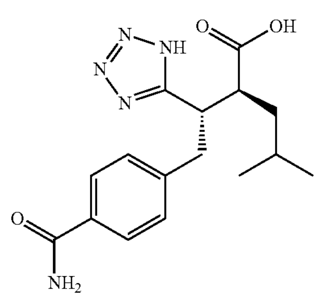 [SMILES: CC(C)C[C@H](C(=O)O)[C@H](Cc1ccc(C(N)=O)cc1)c1nnn[nH]1] | (2S)-2-[(1S)-2-(4-carbamoylphenyl)-1-(1H-tetrazol-5-yl)ethyl]-4-methylpentanoic acid | 332.17 | 332.19 |

EXAMPLE 49

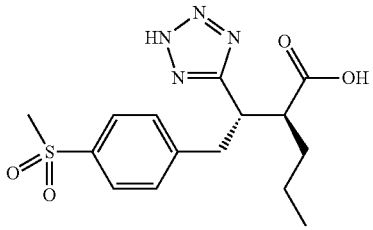 [SMILES: CCC[C@H](C(=O)O)[C@H](Cc1ccc(S(C)(=O)=O)cc1)c1nn[nH]n1]

(S)-2-((S)-2-(4-(methylsulfonyl)phenyl)-1-(2H-tetrazol-5-yl)ethyl)pentanoic acid To a microwave tube was added (S)-tert-butyl 2-((S)-1-(1-(4-methoxybenzyl)-1H-tetrazol-5-yl)-2-(4-(4,4,5,5-tetramethyl-1,3,2-dioxaborolan-2-yl)phenyl)ethyl)pentanoate (84 mg, 0.15 mmol) in DMSO (1 ml). To the mixture was added Copper(II) acetate monohydrate (3.1 μl, 0.029 mmol) 1-benzylimidazole (9.2 mg, 0.058 mmol), sodium methanesulfinate (22 mg, 0.22 mmol), potassium carbonate (20 mg, 0.15 mmol) and 4 Å molecular sieves (0.5 g). The reaction mixture was stirred at 60° C. overnight and then filtered on a Celite pad and eluted with EtOAc. The filtrate was diluted with EtOAc and aqueous ammonium chloride and the aqueous layer was extracted with EtOAc. The combined organic layer was washed with brine, dried over $Na_2SO_4$, filtered and concentrated to give the crude material.

To a solution of the crude product above (77 mg, 0.15 mmol) in DCM (500 μL), TFA (0.3 ml, 3.9 mmol) was added and stirred at RT for 2 hrs. All SM was gone at that point. The reaction was evaporated to dryness, then anisole (0.064 ml, 0.58 mmol) and TFA (0.3 ml, 3.9 mmol) were added and stirred at 50° C. overnight. The reaction mixture was cooled to RT, rotovap concentrated and the residue was washed with 8 ml×3 of Hexane, triturated and then to the residue oil was added DMSO (3.0 ml), and filtered for HPLC purification. LC-MS m/z [M+H]$^+$ 353.20

EXAMPLES 50 and 51

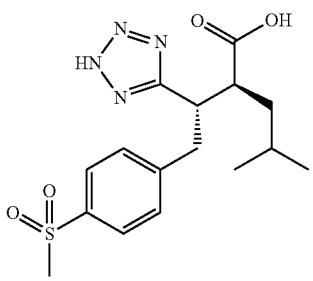

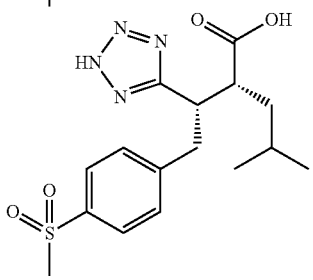

(S)-4-methyl-2-((S)-2-(4-(methylsulfonyl)phenyl)-1-(2H-tetrazol-5-yl)ethyl)pentanoic acid and CAN-4-methyl-2-((S)-2-(4-(methylsulfonyl)phenyl)-1-(2H-tetrazol-5-yl)ethyl)pentanoic acid The compounds were prepared following the same procedure as EXAMPLE 49. 50: LC-MS m/z [M+H]$^+$ 367.13, 51: LC-MS m/z [M+H]$^+$ 367.17

EXAMPLE 52

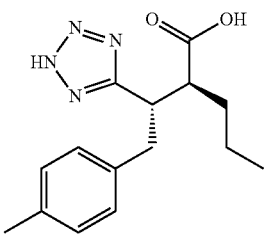 [SMILES: CCC[C@H](C(=O)O)[C@H](Cc1ccc(C)cc1)c1nn[nH]n1]

(S)-2-((S)-1-(2H-tetrazol-5-yl)-2-(p-tolyl)ethyl)pentanoic acid

In a 2 dram vial, (S)-tert-butyl 2-((S)-1-(1-(4-methoxybenzyl)-1H-tetrazol-5-yl)-2-(4-(4,4,5,5-tetramethyl-1,3,2-dioxaborolan-2-yl)phenyl)ethyl)pentanoate (90 mg, 0.16 mmol), potassium carbonate (250 μl, 0.50 mmol), toluene (2000 μl) and ethanol (250 μL) were stirred at RT and purged with $N_2$ for 5 mins, then iodomethane (15 μl, 0.240 mmol) and tetrakis(triphenylphosphine) palladium(0) (80 mg, 0.069 mmol) were added and stirred at 80° C. overnight. The reaction was cooled to RT, 30 ml of EtOAc was added, and the reaction washed with saturated $NH_4Cl$, $H_2O$ and brine, dried over $MgSO_4$, filtered and rotovap down. The crude material was purified by ISCO 24 g silica gel, EtOAc-Hexanes, to give a yellow solid. The solid was next dissolved in DCM, and TFA (0.57 ml, 7.4 mmol) was added and stirred at RT for 1 hr. LC-MS showed all of SM was gone and MW=408. The reaction was evaporated to dryness, then anisole (0.064 ml, 0.58 mmol) and TFA (0.3 ml, 3.89 mmol) were added and stirred at 50° C. overnight. The reaction was cooled to RT, rotovap concentrated and the residue was washed with 8 ml×3 of Hexane, triturated and to the residue oil was then added DMSO (1.5 ml), filtered for HPLC to afford the desired product. LC-MS m/z [M+H]$^+$ 289.19

EXAMPLE 53

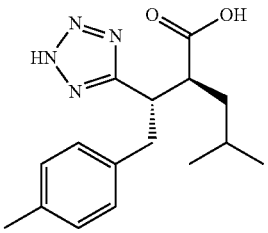 [SMILES: Cc1ccc(C[C@H](c2nn[nH]n2)[C@H](CC(C)C)C(=O)O)cc1]

(S)-2-((S)-1-(2H-tetrazol-5-yl)-2-(p-tolyl)ethyl)-4-methylpentanoic acid

The compound was prepared following the same procedure as EXAMPLE 52. LC-MS m/z [M+H]+ 303.16

EXAMPLE 54

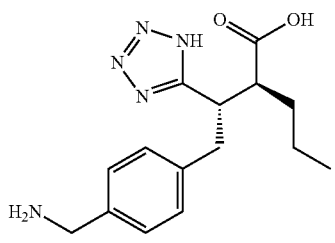 [SMILES: CCC[C@H](C(=O)O)[C@H](Cc1ccc(CN)cc1)c1nnn[nH]1]

(S)-2-((S)-2-(4-(aminomethyl)phenyl)-1-(1H-tetrazol-5-yl)ethyl)pentanoic acid

Step A: (S)-tert-butyl 2-((S)-2-(4-(((tert-butoxycarbonyl)amino)methyl)phenyl)-1-(1-(4-methoxybenzyl)-1H-tetrazol-5-yl)ethyl)pentanoate A mixture of (S)-tert-butyl 2-((S)-2-(4-bromophenyl)-1-(1-(4-methoxybenzyl)-1H-tetrazol-5-yl)ethyl)pentanoate (110 mg, 0.20 mmol), potassium N-Boc-aminomethyltrifluoroborate (48 mg, 0.20 mmol), cesium carbonate (200 mg, 0.61 mmol), and Ad2nBuP biphenyl precatalyst (14 mg, 0.020 mmol) in toluene (1.2 mL) and water (0.12 mL) was heated to 100° C. for 16 hours. The mixture was cooled, diluted with EtOAc, washed with H₂O, brine, dried over MgSO₄, filtered and the solvent was evaporated under reduced pressure to give the crude material, which was used directly in the next step. LC-MS m/z [M+H]+ 580.42

Step B: (S)-2-((S)-2-(4-(aminomethyl)phenyl)-1-(1H-tetrazol-5-yl)ethyl)pentanoic acid To a solution of (S)-tert-butyl 2-((S)-2-(4-(((tert-butoxycarbonyl)amino)methyl)phenyl)-1-(1-(4-methoxybenzyl)-1H-tetrazol-5-yl)ethyl)pentanoate (65 mg, 0.11 mmol) in DCM (1 mL) was added TFA (500 µl, 6.5 mmol). The mixture was allowed to stir at RT for 2 hours. The reaction was concentrated, and the residue was dissolved in DMSO, and purified by reverse-phase HPLC. LC-MS m/z [M+H]+ 304.23

EXAMPLE 55

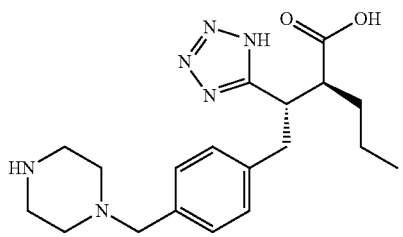 [SMILES: CCC[C@H](C(=O)O)[C@H](Cc1ccc(CN2CCNCC2)cc1)c1nnn[nH]1]

(S)-2-((S)-2-(4-(piperazin-1-ylmethyl)phenyl)-1-(1H-tetrazol-5-yl)ethyl)pentanoic acid The compound was prepared following the same procedure as EXAMPLE 54. LC-MS m/z [M+H]+ 373.34

EXAMPLE 56

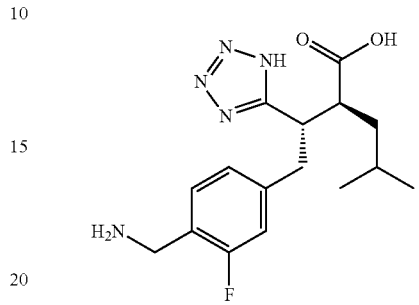

(S)-2-((S)-2-(4-(aminomethyl)-3-fluorophenyl)-1-(1H-tetrazol-5-yl)ethyl)-4-methylpentanoic acid The compound was prepared following the same procedure as EXAMPLE 54. LC-MS m/z [M+H]+ 336.18

EXAMPLE 57

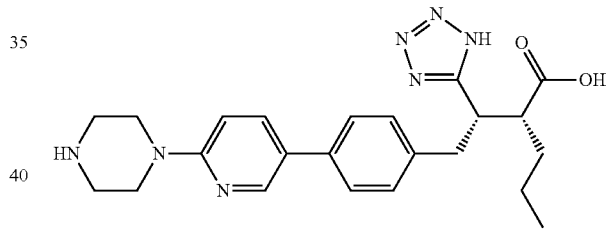

(2R)-2-[(1S)-2-[4-(6-piperazin-1-ylpyridin-3-yl)phenyl]-1-(1H-tetrazol-5-yl)ethyl]pentanoic acid A solution of (S)-tert-butyl 2-((S)-2-(4-bromophenyl)-1-(1H-tetrazol-5-yl)ethyl)pentanoate (120 mg, 0.29 mmol), potassium phosphate tribasic (0.73 ml, 0.73 mmol), palladium(II) acetate/1,1'-Bis(di-t-butylphosphino)ferrocene/Potassium phosphate mixture (27 mg, 0.029 mmol) and tert-butyl 4-(5-(4,4,5,5-tetramethyl-1,3,2-dioxaborolan-2-yl)pyridin-2-yl)piperazine-1-carboxylate (114 mg, 0.29 mmol) in EtOH (2.4 ml) was flashed with N₂ 4 times. The mixture was heated at 75° C. overnight. LC-MS showed the reaction was completed. The reaction mixture was filtered and evaporated to dryness. The residue was carried to deprotection without purification.

The solid obtained above (170 mg, 0.287 mmol) was dissolved in DCM (1.0 ml) and thioanisole (1.0 ml, 8.4 mmol). TFA (1.0 ml, 9.09 mmol) was added and stirred at RT overnight. LC-MS showed that all of SM was gone. The solvent was removed by rotovap and the residue was triturated by Hexane (8 ml×3), and to the residue oil was then added DMSO (9.0 ml), and filtered for HPLC purification to give the desired product. LC-MS m/z [M+H]+ 436.36

EXAMPLE 58

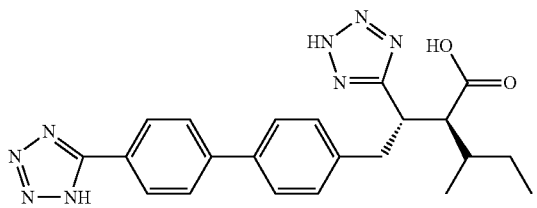 [SMILES: CCC(C)[C@H](C(=O)O)[C@H](Cc1ccc(-c2ccc(-c3nnn[nH]3)cc2)cc1)c1nn[nH]n1]

(2S,3S)-2-((S)-2-(4'-(1H-tetrazol-5-yl)-[1,1'-biphenyl]-4-yl)-1-(2H-tetrazol-5-yl)ethyl)-3-methylpentanoic acid Step A: (2S,3S)-tert-butyl 2-((S)-2-(4'-(1H-tetrazol-5-yl)-[1,1'-biphenyl]-4-yl)-1-(2H-tetrazol-5-yl)ethyl)-3-methylpentanoate To a flask charged with (2S,3R)-tert-butyl 2-((S)-2-(4-bromophenyl)-1-(1H-tetrazol-5-yl)ethyl)-3-methylpentanoate (20 mg, 0.049 mmol) was added tetrakis(triphenylphosphine) palladium(0) (4.4 mg, 3.8 μmol), 5-(4-(4,4,5,5-tetramethyl-1,3,2-dioxaborolan-2-yl)phenyl)-1H-tetrazole (15 mg, 0.057 mmol), and sodium carbonate (15 mg, 0.14 mmol), dioxane (0.4 mL), and water (0.1 mL). The mixture was stirred at 98° C. for overnight. LC-MS showed product. After cooling, the mixture was diluted with EtOAc, washed with 1N HCl and brine. The organic layer was concentrated down to give the crude product. LC-MS m/z [M+H]$^+$ 475.47

Step B: (2S,3S)-2-((S)-2-(4'-(1H-tetrazol-5-yl)-[1,1'-biphenyl]-4-yl)-1-(2H-tetrazol-5-yl)ethyl)-3-methylpentanoic acid To a flask charged with the above crude product was added thioanisol (0.2 mL, 1.7 mmol) and TFA (1 mL, 13 mmol). The mixture was allowed to sit at RT for 2 hours. LC showed complete reaction. The reaction was concentrated, and the residue was purified by HPLC with ACN and water (with 0.05% TFA). LC-MS m/z [M+H]$^+$ 433.30

The following compounds were prepared following the same general procedure of EXAMPLE 58:

| Ex. No. | Structure | Name | Calc'd Mass [M + H]$^+$ | LC/MS m/e [M + H]$^+$ |
|---|---|---|---|---|
| 59 | 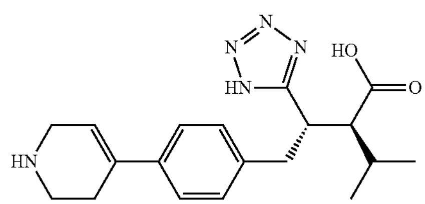 [SMILES: CC(C)[C@H](C(=O)O)[C@H](Cc1ccc(C2=CCNCC2)cc1)c1nnn[nH]1] | (2S,3S)-2-isopropyl-4-(4-(1,2,3,6-tetrahydropyridin-4-yl)phenyl)-3-(1H-tetrazol-5-yl)butanoic acid | 354.4 | 354.2 |
| 60 | 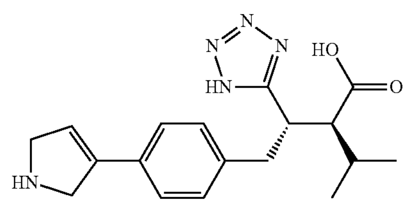 [SMILES: CC(C)[C@H](C(=O)O)[C@H](Cc1ccc(C2=CCNC2)cc1)c1nnn[nH]1] | (2S,3S)-4-(4-(2,5-dihydro-1H-pyrrol-3-yl)phenyl)-2-isopropyl-3-(1H-tetrazol-5-yl)butanoic acid | 342.4 | 342.4 |
| 61 | 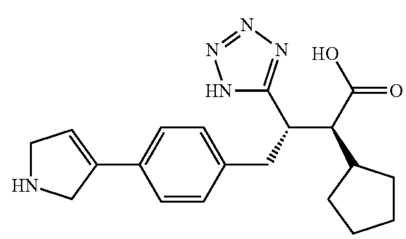 [SMILES: O=C(O)[C@@H](C1CCCC1)[C@H](Cc1ccc(C2=CCNC2)cc1)c1nnn[nH]1] | (2S,3S)-2-cyclopentyl-4-(4-(2,5-dihydro-1H-pyrrol-3-yl)phenyl)-3-(1H-tetrazol-5-yl)butanoic acid | 368.5 | 368.4 |
| 62 | 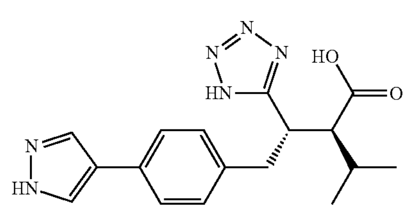 [SMILES: CC(C)[C@H](C(=O)O)[C@H](Cc1ccc(-c2cn[nH]c2)cc1)c1nnn[nH]1] | (2S,3S)-4-(4-(1H-pyrazol-4-yl)phenyl)-2-isopropyl-3-(1H-tetrazol-5-yl)butanoic acid | 341.4 | 341.2 |

| Ex. No. | Structure | Name | Calc'd Mass [M + H]+ | LC/MS m/e [M + H]+ |
|---|---|---|---|---|
| 63 | 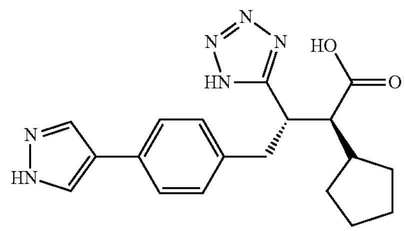 [SMILES: O=C(O)[C@@H](C1CCCC1)[C@H](Cc1ccc(-c2cn[nH]c2)cc1)c1nnn[nH]1] | (2S,3S)-4-(4-(1H-pyrazol-4-yl)phenyl)-2-cyclopentyl-3-(1H-tetrazol-5-yl)butanoic acid | 367.4 | 367.2 |
| 64 | 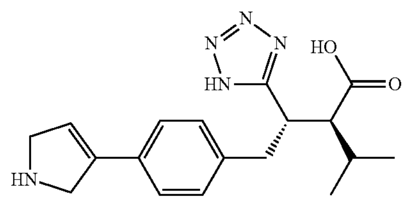 [SMILES: CC(C)[C@H](C(=O)O)[C@H](Cc1ccc(C2=CCNC2)cc1)c1nnn[nH]1] | (2S,3S)-4-(6-(2,5-dihydro-1H-pyrrol-3-yl)pyridin-3-yl)-2-isopropyl-3-(1H-tetrazol-5-yl)butanoic acid | 342.4 | 343.1 |
| 65 | 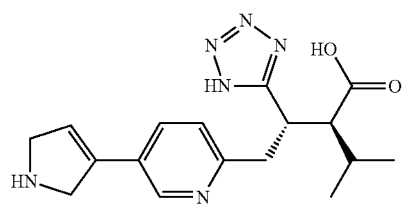 [SMILES: CC(C)[C@H](C(=O)O)[C@H](Cc1ccc(C2=CCNC2)cn1)c1nnn[nH]1] | (2S,3S)-4-(5-(2,5-dihydro-1H-pyrrol-3-yl)pyridin-2-yl)-2-isopropyl-3-(1H-tetrazol-5-yl)butanoic acid | 343.4 | 343.2 |
| 66 | 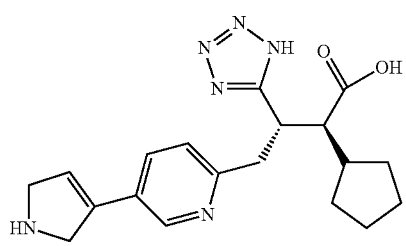 [SMILES: O=C(O)[C@@H](C1CCCC1)[C@H](Cc1ccc(C2=CCNC2)cn1)c1nnn[nH]1] | (2S,3S)-2-cyclopentyl-4-(5-(2,5-dihydro-1H-pyrrol-3-yl)pyridin-2-yl)-3-(1H-tetrazol-5-yl)butanoic acid | 369.5 | 369.2 |
| 67 | 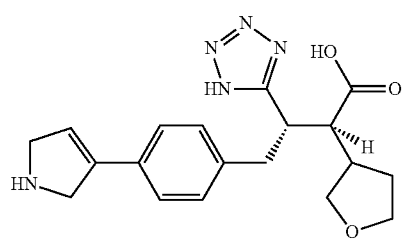 [SMILES: O=C(O)[C@@H](C1CCOC1)[C@H](Cc1ccc(C2=CCNC2)cc1)c1nnn[nH]1] | (2R,3S)-4-(4-(2,5-dihydro-1H-pyrrol-3-yl)phenyl)-2-(tetrahydrofuran-3-yl)-3-(1H-tetrazol-5-yl)butanoic acid | 370.4 | 370.3 |
| 68 | 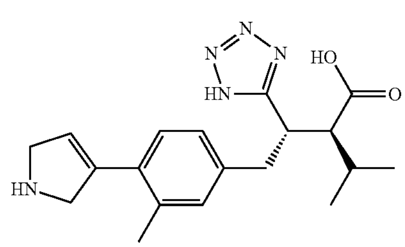 [SMILES: Cc1cc(C[C@H](c2nnn[nH]2)[C@@H](C(=O)O)C(C)C)ccc1C1=CCNC1] | (2S,3S)-4-(4-(2,5-dihydro-1H-pyrrol-3-yl)-3-methylphenyl)-2-isopropyl-3-(1H-tetrazol-5-yl)butanoic acid | 356.4 | 356.2 |

-continued

| Ex. No. | Structure | Name | Calc'd Mass [M + H]+ | LC/MS m/e [M + H]+ |
|---|---|---|---|---|
| 69 | 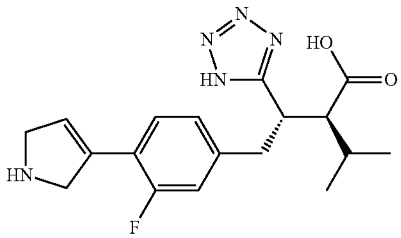 [SMILES: CC(C)[C@H](C(=O)O)[C@H](Cc1ccc(C2=CCNC2)c(F)c1)c1nnn[nH]1] | (2S,3S)-4-(4-(2,5-dihydro-1H-pyrrol-3-yl)-3-fluorophenyl)-2-isopropyl-3-(1H-tetrazol-5-yl)butanoic acid | 360.4 | 360.0 |
| 70 | 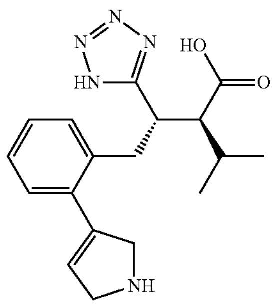 [SMILES: CC(C)[C@H](C(=O)O)[C@H](Cc1ccccc1C1=CCNC1)c1nnn[nH]1] | (2S,3S)-4-(2-(2,5-dihydro-1H-pyrrol-3-yl)phenyl)-2-isopropyl-3-(1H-tetrazol-5-yl)butanoic acid | 342.4 | 342.2 |
| 71 | 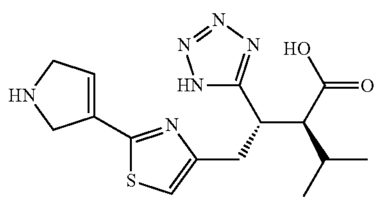 [SMILES: CC(C)[C@H](C(=O)O)[C@H](Cc1csc(C2=CCNC2)n1)c1nnn[nH]1] | (2S,3S)-4-(2-(2,5-dihydro-1H-pyrrol-3-yl)thiazol-4-yl)-2-isopropyl-3-(1H-tetrazol-5-yl)butanoic acid | 349.4 | 349.1 |
| 72 | 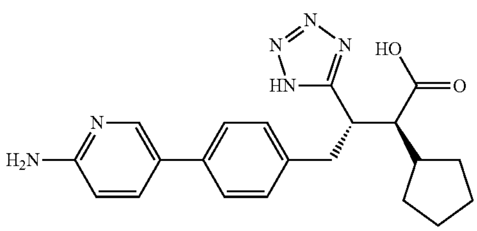 [SMILES: Nc1ccc(-c2ccc(C[C@H](c3nnn[nH]3)[C@@H](C(=O)O)C3CCCC3)cc2)cn1] | (2S,3S)-4-(4-(6-aminopyridin-3-yl)phenyl)-2-cyclopentyl-3-(1H-tetrazol-5-yl)butanoic acid | 393.5 | 393.2 |
| 73 | 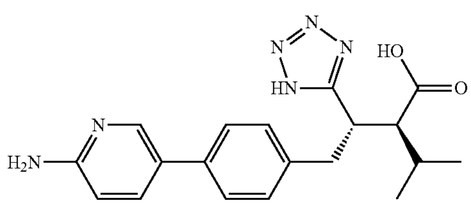 [SMILES: CC(C)[C@H](C(=O)O)[C@H](Cc1ccc(-c2ccc(N)nc2)cc1)c1nnn[nH]1] | (2S,3S)-4-(4-(6-aminopyridin-3-yl)phenyl)-2-isopropyl-3-(1H-tetrazol-5-yl)butanoic acid | 367.4 | 367.3 |
| 74 | 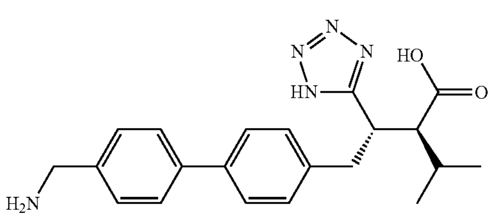 [SMILES: CC(C)[C@H](C(=O)O)[C@H](Cc1ccc(-c2ccc(CN)cc2)cc1)c1nnn[nH]1] | (2S,3S)-4-(4'-(aminomethyl)-[1,1'-biphenyl]-4-yl)-2-isopropyl-3-(1H-tetrazol-5-yl)butanoic acid | 380.5 | 380.3 |

| Ex. No. | Structure | Name | Calc'd Mass [M + H]+ | LC/MS m/e [M + H]+ |
|---|---|---|---|---|
| 75 | 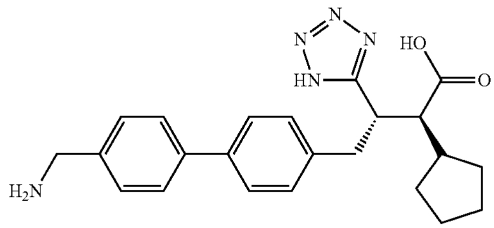 [SMILES: NCc1ccc(-c2ccc(C[C@H](c3nnn[nH]3)[C@@H](C(=O)O)C3CCCC3)cc2)cc1] | (2S,3S)-4-(4'-(aminomethyl)-[1,1'-biphenyl]-4-yl)-2-cyclopentyl-3-(1H-tetrazol-5-yl)butanoic acid | 406.5 | 406.4 |
| 76 | 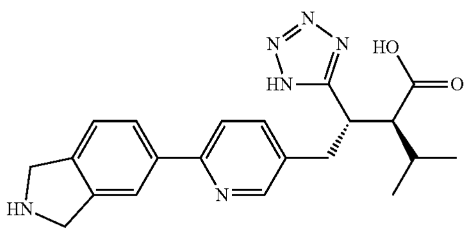 [SMILES: CC(C)[C@H](C(=O)O)[C@H](Cc1ccc(-c2ccc3c(c2)CNC3)nc1)c1nnn[nH]1] | (2S,3S)-4-(6-(isoindolin-5-yl)pyridin-3-yl)-2-isopropyl-3-(1H-tetrazol-5-yl)butanoic acid | 393.5 | 393.2 |
| 77 | 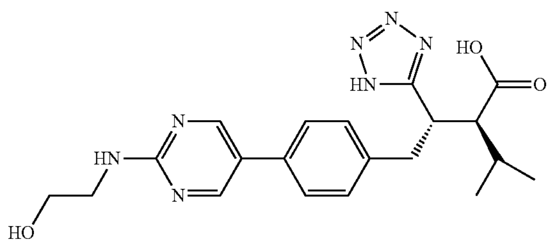 [SMILES: CC(C)[C@H](C(=O)O)[C@H](Cc1ccc(-c2cnc(NCCO)nc2)cc1)c1nnn[nH]1] | (2S,3S)-4-(4-(2-((2-hydroxyethyl)amino)pyrimidin-5-yl)phenyl)-2-isopropyl-3-(1H-tetrazol-5-yl)butanoic acid | 412.5 | 412.2 |

EXAMPLE 78

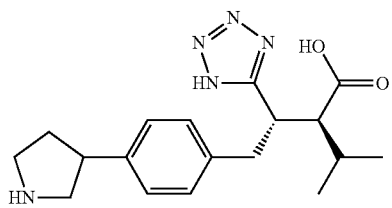 [SMILES: CC(C)[C@H](C(=O)O)[C@H](Cc1ccc(C2CCNC2)cc1)c1nnn[nH]1]

(2S,3S)-2-isopropyl-4-(4-(pyrrolidin-3-yl)phenyl)-3-(1H-tetrazol-5-yl)butanoic acid Step A: tert-butyl 3-(4-((2S,3S)-3-(tert-butoxycarbonyl)-4-methyl-2-(1H-tetrazol-5-yl)pentyl)phenyl)-2,5-dihydro-1H-pyrrole-1-carboxylate The intermediate was prepared from (2S,3S)-tert-butyl 4-(4-bromophenyl)-2-isopropyl-3-(1H-tetrazol-5-yl)butanoate and tert-butyl 3-(4,4,5,5-tetramethyl-1,3,2-dioxaborolan-2-yl)-2,5-dihydro-1H-pyrrole-1-carboxylate following step A of EXAMPLE 45. LC-MS m/z [M+H]+ 498.44

Step B: tert-butyl 3-(4-((2S,3S)-3-(tert-butoxycarbonyl)-4-methyl-2-(1H-tetrazol-5-yl)pentyl)phenyl)pyrrolidine-1-carboxylate The product above (95 mg, 0.19 mmol) was treated with Pd—C (20 mg, 0.19 mmol) in MeOH under an atmosphere of hydrogen for 16 hours. LC showed complete reaction. The reaction was filtered and concentrated to give the crude product. LC-MS m/z [M+H]+ 500.34

Step C: (2S,3S)-2-isopropyl-4-(4-(pyrrolidin-3-yl)phenyl)-3-(1H-tetrazol-5-yl)butanoic acid To a flask charged with crude tert-butyl 3-(4-((2S,3S)-3-(tert-butoxycarbonyl)-4-methyl-2-(1H-tetrazol-5-yl)pentyl)phenyl)pyrrolidine-1-carboxylate (80 mg, 0.15 mmol) was added thioanisol (0.2 mL, 1.7 mmol) and TFA (2 mL, 26 mmol). The mixture was allowed to stir at RT for 3 hours. LC showed complete reaction. The reaction was concentrated, and the residue was purified by purified by HPLC with ACN and water (with 0.05% TFA). LC-MS m/z [M+H]+ 370.28

The following compounds were prepared following the same procedure as EXAMPLE 78:

| Ex. No. | Structure | Name | Calc'd Mass [M + H]+ | LC/MS m/e [M + H]+ |
|---|---|---|---|---|
| 79 | 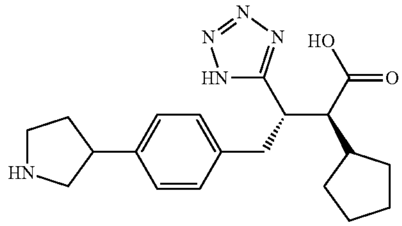 [SMILES: O=C(O)[C@@H](C1CCCC1)[C@H](Cc1ccc(C2CCNC2)cc1)c1nnn[nH]1] | 3-(4-((2S,3S)-3-carboxy-3-cyclopentyl-2-(1H-tetrazol-5-yl)propyl)phenyl)pyrrolidin-1-ium | 370.5 | 370.3 |
| 80 | 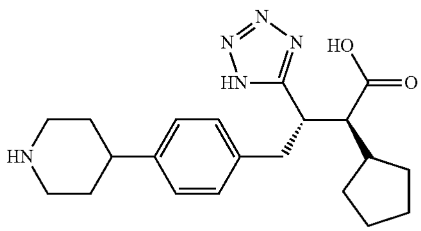 [SMILES: O=C(O)[C@@H](C1CCCC1)[C@H](Cc1ccc(C2CCNCC2)cc1)c1nnn[nH]1] | 4-(4-((2S,3S)-3-carboxy-3-cyclopentyl-2-(1H-tetrazol-5-yl)propyl)phenyl)piperidine | 384.5 | 384.3 |
| 81 | 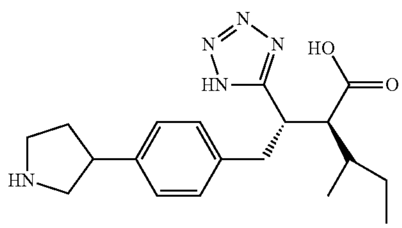 [SMILES: CCC(C)[C@H](C(=O)O)[C@H](Cc1ccc(C2CCNC2)cc1)c1nnn[nH]1] | (2S,3S)-3-methyl-2-((1S)-2-(4-(pyrrolidin-3-yl)phenyl)-1-(1H-tetrazol-5-yl)ethyl)pentanoic acid | 358.5 | 358.2 |

EXAMPLE 82

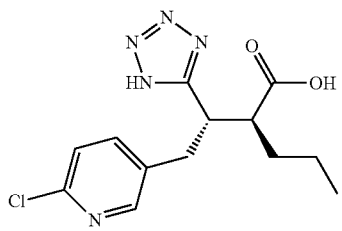 [SMILES: CCC[C@H](C(=O)O)[C@H](Cc1ccc(Cl)nc1)c1nnn[nH]1]

(S)-2-((S)-2-(6-chloropyridin-3-yl)-1-(1H-tetrazol-5-yl)ethyl)pentanoic acid

Step A: (S)-2-((S)-2-(6-chloropyridin-3-yl)-1-(1-((2-(trimethylsilyl)ethoxy)methyl)-1H-tetrazol-5-yl)ethyl)pentanoic acid In a 25 ml RB flask under $N_2$, diisopropylamine (1.42 ml, 10 mmol), was dissolved in 10 ml THF and cooled to −78° C. n-BuLi in hexane (4.0 ml, 10 mmol) was added. The LDA solution (0.65 M) was stirred for 15 mins at −15° C. before using it. In another 25 ml RB flask, (S)-2-((1-((2-(trimethylsilyl)ethoxy)methyl)-1H-tetrazol-5-yl)methyl)pentanoic acid (92 mg, 0.293 mmol) was added to THF (5 ml) then cooled to −78° C. and then to the reaction mixture was added the above LDA in THF (1.12 ml, 0.73 mmol). The reaction mixture was stirred for 45 mins at −78° C. then 2-chloro-5-chloromethylpyridine (47 mg, 0.29 mmol suspended in 4 ml THF) was added. The reaction turned orange in color and was stirred at −78° C. for 1 hr. The reaction mixture was quenched with saturated $NH_4Cl$ (4 ml) and extracted with EtOAc (2×10 ml). The organic layer was dried over $Na_2SO_4$, filtered and concentrated. The residue was purified by reverse phase HPLC with ACN and water buffered with 0.05% TFA. LC-MS [M+1]: 440.39.

Step B: (S)-2-((S)-2-(6-chloropyridin-3-yl)-1-(1H-tetrazol-5-yl)ethyl)pentanoic acid (S)-2-((S)-2-(6-chloropyridin-3-yl)-1-(1-((2-(trimethylsilyl)ethoxy)methyl)-1H-tetrazol-5-yl)ethyl)pentanoic acid (10 mg, 0.023 mmol) was heated in HCl (1 ml, 2M)/EtOH (2 ml) at 60° C. for 9 hrs. The reaction was cooled and concentrated, then the residue was purified by reverse phase HPLC with ACN and water buffered with 0.05% TFA. LC-MS [M+1]:310.19.

The following compounds were prepared following the same procedure as EXAMPLE 82.

| Ex. No. | Structure | IUPAC Name | Calc'd Mass [M + H]+ | LC/MS m/e [M + H]+ |
|---|---|---|---|---|
| 83 | 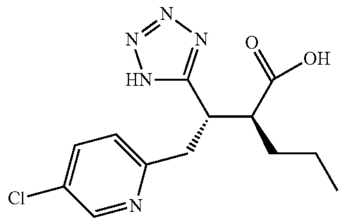 [SMILES: CCC[C@H](C(=O)O)[C@H](Cc1ccc(Cl)cn1)c1nnn[nH]1] | (S)-2-((S)-2-(5-chloropyridin-2-yl)-1-(1H-tetrazol-5-yl)ethyl)pentanoic acid | 310.11 | 310.26 |
| 84 | 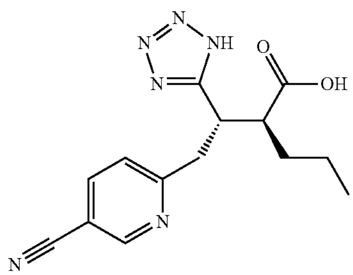 [SMILES: CCC[C@H](C(=O)O)[C@H](Cc1ccc(C#N)cn1)c1nnn[nH]1] | (2S)-2-[(1S)-2-(5-cyanopyridin-2-yl)-1-(1H-tetrazol-5-yl)ethyl]pentanoic acid | 301.14 | 301.06 |
| 85 | 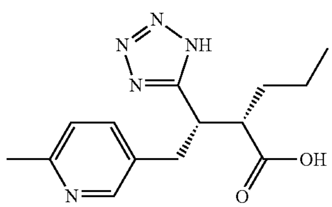 [SMILES: CCC[C@H](C(=O)O)[C@H](Cc1ccc(C)nc1)c1nnn[nH]1] | (2S)-2-[(1S)-2-(6-methylpyridin-3-yl)-1-(1H-tetrazol-5-yl)ethyl]pentanoic acid | 290.16 | 290.11 |
| 86 | 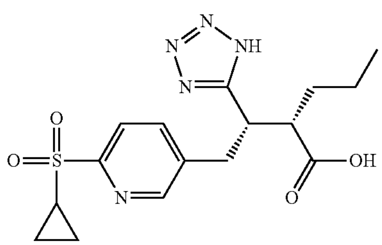 [SMILES: CCC[C@H](C(=O)O)[C@H](Cc1ccc(S(=O)(=O)C2CC2)nc1)c1nnn[nH]1] | (2S)-2-[(1S)-2-[6-(cyclopropylsulfonyl)pyridin-3-yl]-1-(1H-tetrazol-5-yl)ethyl]pentanoic acid | 380.14 | 380.16 |
| 87 | 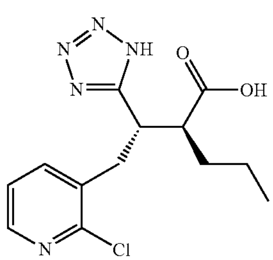 [SMILES: CCC[C@H](C(=O)O)[C@H](Cc1cccnc1Cl)c1nnn[nH]1] | (2S)-2-[(1S)-2-(2-chloropyridin-3-yl)-1-(1H-tetrazol-5-yl)ethyl]pentanoic acid | 310.11 | 310.03 |
| 88 | 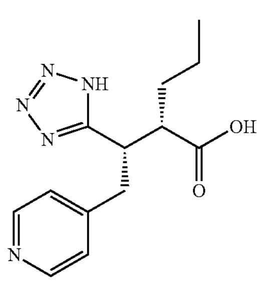 [SMILES: CCC[C@H](C(=O)O)[C@H](Cc1ccncc1)c1nnn[nH]1] | (2S)-2-[(1S)-2-pyridin-4-yl-1-(1H-tetrazol-5-yl)ethyl]pentanoic acid | 276.15 | 276.10 |

| Ex. No. | Structure | IUPAC Name | Calc'd Mass [M + H]+ | LC/MS m/e [M + H]+ |
|---|---|---|---|---|
| 89 | 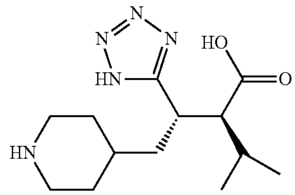 [SMILES: CC(C)[C@H](C(=O)O)[C@H](CC1CCNCC1)c1nnn[nH]1] | (2S,3S)-2-isopropyl-4-(piperidin-4-yl)-3-(1H-tetrazol-5-yl)butanoic acid | 282.4 | 282.1 |
| 90 | 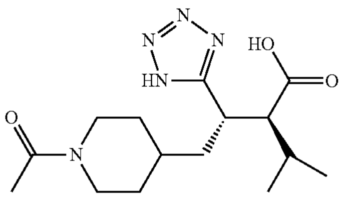 [SMILES: CC(=O)N1CCC(C[C@H](c2nnn[nH]2)[C@@H](C(=O)O)C(C)C)CC1] | (2S,3S)-4-(1-acetylpiperidin-4-yl)-2-isopropyl-3-(1H-tetrazol-5-yl)butanoic acid | 324.4 | 324.1 |
| 91 | 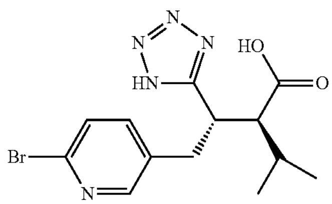 [SMILES: CC(C)[C@H](C(=O)O)[C@H](Cc1ccc(Br)nc1)c1nnn[nH]1] | (2S,3S)-4-(6-bromopyridin-3-yl)-2-isopropyl-3-(1H-tetrazol-5-yl)butanoic acid | 355.2 | 355.9 |
| 92 | 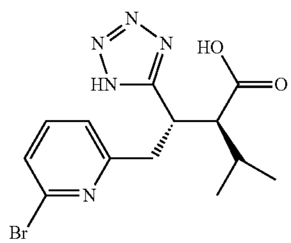 [SMILES: CC(C)[C@H](C(=O)O)[C@H](Cc1cccc(Br)n1)c1nnn[nH]1] | (2S,3S)-4-(6-bromopyridin-2-yl)-2-isopropyl-3-(1H-tetrazol-5-yl)(butanoic acid | 355.2 | 356.0 |

EXAMPLE 93

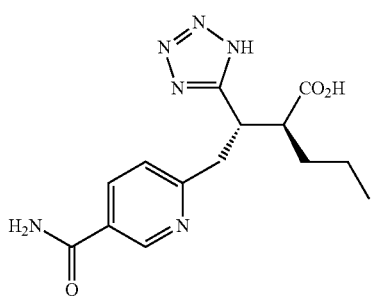 [SMILES: CCC[C@H](C(=O)O)[C@H](Cc1ccc(C(N)=O)cn1)c1nnn[nH]1]

(S)-2-((S)-2-(5-carbamoylpyridin-2-yl)-1-(1H-tetrazol-5-yl)ethyl) pentanoic acid A mixture of (S)-2-((S)-2-(5-cyanopyridin-2-yl)-1-(1H-tetrazol-5-yl)ethyl)pentanoic acid (8 mg, 0.027 mmol) and sulfuric acid (400 μL, 7.5 mmol) was stirred at RT over the weekend. To the mixture was added ice, and the mixture was neutralized with aq. KOH (5 N). EtOAc was added for partitioning while pH was 4-5. The organic was dried over $Na_2SO_4$, filtered, and evaporated to dryness. The crude was purified by reverse phase with C-18 prep. HPLC to obtain product, (S)-2-((S)-2-(5-carbamoylpyridin-2-yl)-1-(1H-tetrazol-5-yl)ethyl) pentanoic acid. LC-MS m/z 319.06 (calc. m/z 319.15).

EXAMPLE 94

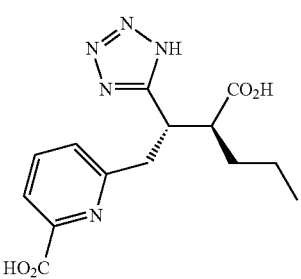 [SMILES: CCC[C@H](C(=O)O)[C@H](Cc1cccc(C(=O)O)n1)c1nnn[nH]1]

Step A: (S)-2-((S)-2-(6-(methoxycarbonyl)pyridin-2-yl)-1-(1-((2-(trimethylsilyl)ethoxy)methyl)-1H-tetrazol-5-yl)ethyl)pentanoic acid To a solution of (S)-2-((1-((2-(trimethylsilyl)ethoxy)methyl)-1H-tetrazol-5-yl)methyl)pentanoic acid (93 mg, 0.30 mmol) in THF was added lithium diisopropylamide (0.37 mL, 0.74 mmol) at −78° C. The mixture was allowed to stir at −78° C. for 40 minutes, and then to the mixture was added methyl 6-(bromomethyl)picolinate (81 mg, 0.35 mmol) in THF. The reaction was warmed up to RT naturally and stirred overnight. To the mixture was added sat. aq. NH$_4$Cl and EtOAc for partitioning. The organic layer was separated, dried over Na$_2$SO$_4$, and evaporated to dryness. The crude material was used directly in step B.

Step B: (S)-2-((S)-2-(6-(methoxycarbonyl)pyridin-2-yl)-1-(1-((2-(trimethylsilyl)ethoxy)methyl)-1H-tetrazol-5-yl)ethyl)pentanoic acid In a vial, half of the crude (67 mg, 0.14 mmol) was dissolved in EtOH (1.5 ml)/1.5 ml 1N HCl, and heated at 60° C. overnight. The reaction was concentrated and the residue was purified by reverse phase C18 HPLC to obtain the product, 6-((2S,3)-3-carboxy-2-(1H-tetrazol-5-yl)hexyl)picolinic acid. LC-MS m/z [M+H]$^+$ 320.04 (calc. m/z 320.14).

EXAMPLE 95

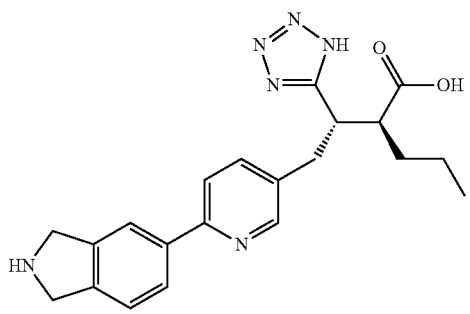 [SMILES: CCC[C@H](C(=O)O)[C@H](Cc1ccc(-c2ccc3c(c2)CNC3)nc1)c1nnn[nH]1]

5-(5-((2S,3S)-3-carboxy-2-(1H-tetrazol-5-yl)hexyl)pyridin-2-yl)isoindolin-2-ium

Step A: tert-butyl 5-(5-((2S,3S)-3-(tert-butoxycarbonyl)-2-(1H-tetrazol-5-yl)hex-5-en-1-yl)pyridin-2-yl)isoindoline-2-carboxylate In a 5 ml microwave tube, (S)-tert-butyl 2-((S)-2-(6-bromopyridin-3-yl)-1-(1H-tetrazol-5-yl)ethyl)pent-4-enoate (90 mg, 0.22 mmol) was dissolved in ethanol (2 ml)/water (1 ml) and to which was added tert-butyl 5-(4,4,5,5-tetramethyl-1,3,2-dioxaborolan-2-yl)isoindoline-2-carboxylate, potassium phosphate tribasic (190 mg, 0.88 mmol). The tube was capped and degassed by vacuum and purged with N$_2$. The tube was uncapped and 1,1'-bis(di-tert-butylphosphino)ferrocene palladium dichloride (14 mg, 0.022 mmol) was added then the tube was recapped and degassed again. The tube was microwaved at 100° C. for ½ hr. The reaction was filtered and concentrated. The residue was purified by reverse phase HPLC with ACN and water buffered with 0.05% TFA. LC-MS [M+1]: 547.39.

Step B: tert-butyl 5-(5-((2S,3S)-3-(tert-butoxycarbonyl)-2-(1H-tetrazol-5-yl)hexyl)pyridin-2-yl)isoindoline-2-carboxylate In a 100 ml RB flask equipped with a three way stopcock attached to a balloon of H$_2$, tert-butyl 5-(5-((2S,3S)-3-(tert-butoxycarbonyl)-2-(1H-tetrazol-5-yl)hex-5-en-1-yl)pyridin-2-yl)isoindoline-2-carboxylate (57 mg, 0.10 mmol) was dissolved in MeOH (5 ml) and Pd—C (20 mg, 0.19 mmol) was added. The reaction was vacuumed and flushed with H$_2$ (3×) then stirred under H$_2$ at RT for 1.5 hr. The reaction was filtered and concentrated to yield tert-butyl 5-(5-((2S,3S)-3-(tert-butoxycarbonyl)-2-(1H-tetrazol-5-yl)hexyl)pyridin-2-yl)isoindoline-2-carboxylate. LC-MS [M+1]: 549.55.

Step C: 5-(5-((2S,3S)-3-carboxy-2-(1H-tetrazol-5-yl)hexyl)pyridin-2-yl)isoindolin-2-ium 2,2,2-trifluoroacetate In a 10 ml RB flask containing tert-butyl 5-(5-((2S,3S)-3-(tert-butoxycarbonyl)-2-(1H-tetrazol-5-yl)hexyl)pyridin-2-yl)isoindoline-2-carboxylate (57 mg, 0.10 mmol) thioanisole (1 ml, 8.4 mmol) was added followed by TFA (2 mL, 26 mmol). The reaction mixture was stirred at RT for 2 hrs. The reaction was concentrated and the residue was purified by reverse phase HPLC with ACN and water buffered with 0.05% TFA. LC-MS [M+1]: 393.35

EXAMPLE 96

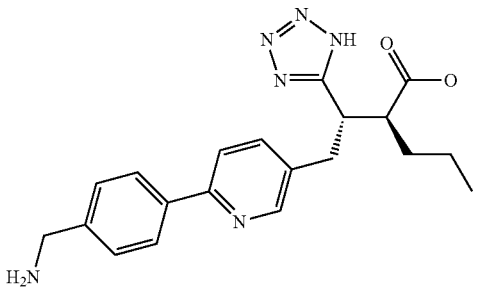 [SMILES: CCC[C@H](C(=O)O)[C@H](Cc1ccc(-c2ccc(CN)cc2)nc1)c1nnn[nH]1]

(4-(5-((2S,3S)-3-carboxy-2-(1H-tetrazol-5-yl)hexyl)pyridin-2-yl)phenyl)methanaminium

Step A. (S)-2-((S)-2-(6-(4-(((tert-butoxycarbonyl)amino)methyl)phenyl)pyridin-3-yl)-1-(1-((2-(trimethylsilyl)ethoxy)methyl)-1H-tetrazol-5-yl)ethyl)pentanoic acid In a 5 ml microwave tube, (S)-2-((S)-2-(6-chloropyridin-3-yl)-1-(1-((2-(trimethylsilyl)ethoxy)methyl)-1H-tetrazol-5-yl)ethyl)pentanoic acid (50 mg, 0.114 mmol) was dissolved in ethanol (1.5 mL)/water (0.5 mL) and then 4-((n-BOC-amino)methyl)phenylboronic acid (43 mg, 0.17 mmol) and potassium phosphate tribasic (96 mg, 0.46 mmol) were added. The tube was capped and degassed by vacuum and purged with N$_2$. The tube was uncapped and 1,1'-bis(di-tert-butylphosphino)ferrocene palladium dichloride (14.8 mg, 0.023 mmol) was added then the tube was capped and degassed again. The reaction was microwaved at 100° C. for 1.5 hr. The reaction was filtered and concentrated. The residue was purified by reverse phase HPLC with ACN and water buffered with 0.05% TFA to yield (S)-2-

((S)-2-(6-(4-(((tert-butoxycarbonyl)amino)methyl)phenyl)pyridin-3-yl)-1-(1-((2-(trimethylsilyl)ethoxy)methyl)-1H-tetrazol-5-yl)ethyl)pentanoic acid. LC-MS [M+1]: 611.56

Step B: (S)-2-((S)-2-(6-(4-(aminomethyl)phenyl)pyridin-3-yl)-1-(1H-tetrazol-5-yl)ethyl)pentanoic acid To a 25 ml RB flask charged with (S)-2-((S)-2-(6-(4-(((tert butoxycarbonyl)amino)methyl)phenyl) pyridin-3-yl)-1-(1-((2-(trimethylsilyl)ethoxy)methyl)-1H-tetrazol-5-yl)ethyl)pentanoic acid (40 mg, 0.065 mmol) was added thioanisole (0.5 ml, 4.23 mmol) followed by TFA (1 mL). The reaction was stirred for 2 hrs. LCMS showed product peak. The reaction was concentrated and the residue was purified by reverse phase HPLC with ACN and water buffered with 0.05% TFA to yield (S)-2-((S)-2-(6-(4-(aminomethyl)phenyl)pyridin-3-yl)-1-(1H-tetrazol-5-yl)ethyl)pentanoic acid. LC-MS [M+1]: 381.34

EXAMPLE 97

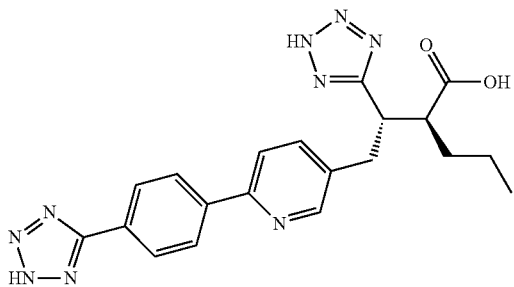 [SMILES: CCC[C@H](C(=O)O)[C@H](Cc1ccc(-c2ccc(-c3nn[nH]n3)cc2)nc1)c1nn[nH]n1]

(S)-2-((S)-2-(6-(4-(2H-tetrazol-5-yl)phenyl)pyridin-3-yl)-1-(1H-tetrazol-5-yl)ethyl)pentanoic acid The compound was prepared following the same procedure as EXAMPLE 96 from a mixture of 5-(4-(4,4,5,5-tetramethyl-1,3,2-dioxaborolan-2-yl)phenyl)-2H-tetrazole, (5)-2-((S)-2-(6-chloropyridin-3-yl)-1-(1-((2-(trimethylsilyl)ethoxy)methyl)-1H-tetrazol-5-yl)ethyl)pentanoic acid, potassium phosphate tribasic and 1,1'-bis(di-tert-butylphosphino)ferrocene palladium dichloride in EtOH-water (1.5: 0.5 ml). LC-MS [M+1]: 420.30

EXAMPLE 98

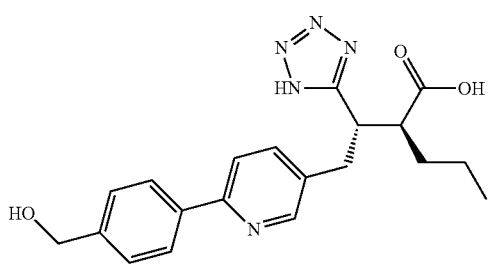 [SMILES: CCC[C@H](C(=O)O)[C@H](Cc1ccc(-c2ccc(CO)cc2)nc1)c1nnn[nH]1]

(S)-2-((S)-2-(5-(4-(hydroxymethyl)phenyl)pyridin-2-yl)-1-(1H-tetrazol-5-yl)ethyl)pentanoic acid The compound was prepared following the same procedure as EXAMPLE 96 from a mixture of (S)-2-((S)-2-(5-bromopyridin-2-yl)-1-(1-((2-(trimethylsilyl)ethoxy)methyl)-1H-tetrazol-5-yl)ethyl)pentanoic acid, (4-(4,4,5,5-tetramethyl-1,3,2-dioxaborolan-2-yl)phenyl)methanol, potassium phosphate tribasic and 1,1'-bis(di-tert-butylphosphino)ferrocene palladium dichloride in EtOH-water (2: 0.4 ml). LC-MS [M+1]: 382.33

EXAMPLE 99

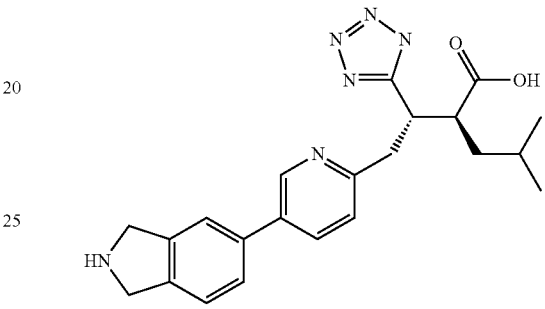

(S)-2-((S)-2-(5-(isoindolin-5-yl)pyridin-2-yl)-1-(1H-tetrazol-5-yl)ethyl)-4-methylpentanoic acid Step A: tert-butyl 5-(6-(hydroxymethyl)pyridin-3-yl)isoindoline-2-carboxylate To a 25 mL microwave vial with a stir bar was added tert-butyl 5-(4,4,5,5-tetramethyl-1,3,2-dioxaborolan-2-yl)isoindoline-2-carboxylate (260 mg, 0.75 mmol), (5-bromopyridin-2-yl)methanol (212 mg, 1.13 mmol), 1,1'-bis(di-tert-butylphosphino)ferrocene palladium dichloride (49 mg, 0.075 mmol), and K$_3$PO$_4$ (480 mg, 2.3 mmol). The vial was sealed, and then EtOH (4 ml) and water (2 ml) were added. The mixture was flushed with nitrogen, and then heated to 100° C. for 30 minutes. LC showed very good reaction. The reaction was diluted with 1 mL of water, and the organic layer was diluted with EtOAc (5 mL). The crude solution was sucked out with a syringe. The solution was evaporated on a rotavapor, and the residue was dissolved in DCM and injected onto a 24 G ISCO column. The desired product was isolated by MPLC with hexane and EtOAc gradient. The product was eluted at about 100% EtOAc. It was a yellow solid. LC-MS [M+1]: 327.2

Step B: tert-butyl 5-(6-(((methylsulfonyl)oxy)methyl)pyridin-3-yl)isoindoline-2-carboxylate To a solution of tert-butyl 5-(6-(hydroxymethyl)pyridin-3-yl)isoindoline-2-carboxylate (200 mg, 0.61 mmol) in DCM (15 ml) was added TEA (0.085 ml, 0.61 mmol) and methanesulfonyl chloride (0.048 ml, 0.61 mmol) at 0° C. The ice bath was removed when all reagents were added. TLC showed fairly clean reaction after 2 hours at RT. The reaction was diluted with 30 mL of DCM, washed with aq. NH$_4$Cl, and separated. The solution was dried over sodium sulfate, filtered and concentrated to give a light yellow foam.

The form turned pink in a few minutes. It was used in the next alkylation step without further purification. LC-MS [M+1]: 405.3

Step C: tert-butyl 5-(6-(chloromethyl)pyridin-3-yl) isoindoline-2-carboxylate

To a solution of tert-butyl 5-(6-(((methylsulfonyl)oxy) methyl)pyridin-3-yl)isoindoline-2-carboxylate (400 mg, 0.99 mmol) in acetonitrile (10 ml) was added lithium chloride (126 mg, 3.0 mmol). The mixture was allowed to stir at RT for 20 hours. LC showed very clean conversion. The reaction was diluted with DCM to precipitate all the solids. The solids were filtered off, and the filtrate was concentrated. The residue was loaded onto a 24 G ISCO column, and separated by MPLC with hexane and EtOAc. The product was a colorless oil. LC-MS [M+1]: 345.2

Step D: (S)-2-((S)-2-(5-(2-(tert-butoxycarbonyl) isoindolin-5-yl)pyridin-2-yl)-1-(1-((2-(trimethylsilyl) ethoxy)methyl)-1H-tetrazol-5-yl)ethyl)-4-methyl-pentanoic acid To a solution of (S)-4-methyl-2-((2-((2-(trimethylsilyl) ethoxy)methyl)-2H-tetrazol-5-yl)methyl)pentanoic acid (110 mg, 0.34 mmol) in THF (6 ml) was added LDA (1.2 ml, 0.84 mmol). The mixture was allowed to stir at −78° C. for 45 minutes before tert-butyl 5-(5-(chloromethyl)pyridin-2-yl)isoindoline-2-carboxylate (115 mg, 0.34 mmol) in 2 mL THF was added in. LC showed a small amount of the desired product. The reaction was quenched with aq. $NH_4Cl$, extracted with EtOAc, and separated. The solution was dried over sodium sulfate, filtered, and concentrated. The residue was dissolved in MeOH, and purified by Gilson HPLC with ACN and water (with 0.05% TFA) to give a small amount of the desired product. LC-MS [M+1]: 637.4

Step E: (S)-2-((S)-2-(5-(isoindolin-5-yl)pyridin-2-yl)-1-(1H-tetrazol-5-yl)ethyl)-4-methylpentanoic acid To a solution of (S)-2-((S)-2-(5-(2-(tert-butoxycarbonyl) isoindolin-5-yl)pyridin-2-yl)-1-(2-((2-(trimethylsilyl) ethoxy)methyl)-2H-tetrazol-5-yl)ethyl)-4-methylpentanoic acid (65 mg, 0.10 mmol) in DCM (5 ml) was added TFA (1.0 mL, 13 mmol). The mixture was stirred at room temperature under $N_2$ for 2 hours. The mixture was concentrated under reduced pressure and purified by Gilson (Water, Sunfire Prep C18 OBD 5 uL 19×100 mm column, 0%→40% MeCN in 20 min run, 10 mL/min) to give desire compound. LC-MS [M+1]: 407.3

EXAMPLE 100

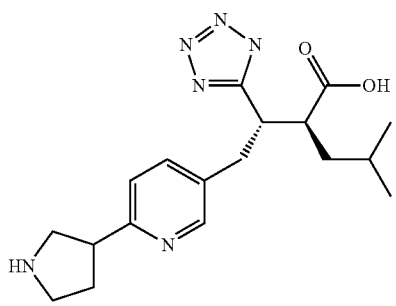 [SMILES: CC(C)C[C@H](C(=O)O)[C@H](Cc1ccc(C2CCNC2)nc1)c1nnn[nH]1]

(2S)-4-methyl-2-((1S)-2-(6-(pyrrolidin-3-yl)pyridin-3-yl)-1-(1H-tetrazol-5-yl)ethyl)pentanoic acid Step A: (S)-2-((S)-2-(6-(1-(tert-butoxycarbonyl)-2, 5-dihydro-1H-pyrrol-3-yl)pyridin-3-yl)-1-(2-((2-(trimethylsilyl)ethoxy)methyl)-2H-tetrazol-5-yl) ethyl)-4-methylpentanoic acid A solution of (S)-2-((S)-2-(6-bromopyridin-3-yl)-1-(2-((2-(trimethylsilyl)ethoxy)methyl)-2H-tetrazol-5-yl)ethyl)-4-methylpentanoic acid (70 mg, 0.14 mmol), 1,1'-bis(di-tert-butylphosphino)ferrocene palladium dichloride (18 mg, 0.028 mmol), $K_3PO_4$ (0.49 mL, 0.49 mmol) and tert-butyl 3-(4,4,5,5-tetramethyl-1,3,2-dioxaborolan-2-yl)-2,5-di-hydro-1H-pyrrole-1-carboxylate (104 mg, 0.35 mmol) in ethanol (2 mL) was flashed with $N_2$ 4 times. The reaction mixture was stirred at 75° C. under $N_2$ overnight. A small amount of water was added and the organic was extracted with EtOAc 3 times. The organic was concentrated under vacuum. The crude was dissolved in ACN and water and purified by Gilson, Water, Sunfire Prep C18 OBD 5 µL 19×100 mm column, 10%→100% MeCN in 12 min. LC-MS [M+1]: 587.34

Step B: (2S)-2-((1S)-2-(6-(1-(tert-butoxycarbonyl) pyrrolidin-3-yl)pyridin-3-yl)-1-(1-((2-(trimethylsilyl) ethoxy)methyl)-1H-tetrazol-5-yl)ethyl)-4-methyl-pentanoic acid A solution of (S)-2-((S)-2-(6-(1-(tert-butoxycarbonyl)-2, 5-dihydro-1H-pyrrol-3-yl)pyridin-3-yl)-1-(2-((2-(trimethyl-silyl)ethoxy)methyl)-2H-tetrazol-5-yl)ethyl)-4-methylpen-tanoic acid (26 mg, 0.044 mmol) and Pd—C (9.4 mg, 8.9 µmol) in Ethanol (1 ml) was degassed and flashed with $N_2$ 3× then $H_2$ 4×. The mixture was stirred under $H_2$ for 2 hours. The crude UPLC indicated the desired MS. The mixture was filtered and concentrated under vacuum. The crude was taken on as is for the next step. LC-MS [M+1]: 589.36

Step C: (2S)-4-methyl-2-((1S)-2-(6-(pyrrolidin-3-yl) pyridin-3-yl)-1-(1H-tetrazol-5-yl)ethyl)pentanoic acid A solution of (2S)-2-((1S)-2-(6-(1-(tert-butoxycarbonyl) pyrrolidin-3-yl)pyridin-3-yl)-1-(2-((2-(trimethylsilyl) ethoxy)methyl)-2H-tetrazol-5-yl)ethyl)-4-methylpentanoic acid (25 mg, 0.042 mmol) and HCl (1 mL, 1.0 mmol) in ethanol (1 ml) was heated at 60° C. for 1 hr. The crude UPLC indicated a desired peak at 359 m/z. The solution was directly injected into Gilson (Water, Sunfire Prep C18 OBD 5 µL 19×100 mm column, 0%→50% MeCN in 12 min run) to give the desired compound. LC-MS [M+1]: 359.2

The following compounds were prepared according to the same procedure as EXAMPLE 100.

| EX. NO. | Structure | Name | Calc'd mass [M + H]+ | MS found |
|---|---|---|---|---|
| 101 | 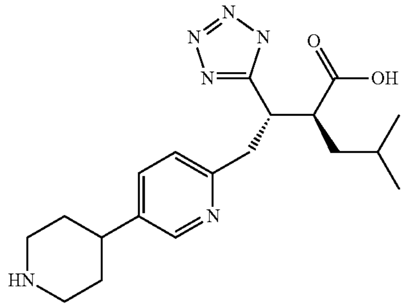 [SMILES: CC(C)C[C@H](C(=O)O)[C@H](Cc1ccc(C2CCNCC2)cn1)c1nnn[nH]1] | (S)-4-methyl-2-((S)-2-(5-(piperidin-4-yl)pyridin-2-yl)-1-(1H-tetrazol-5-yl)ethyl)pentanoic acid | 373.24 | 373.40 |
| 102 | 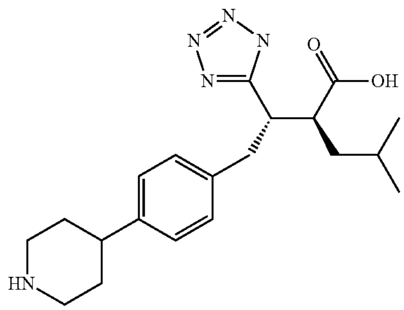 [SMILES: CC(C)C[C@H](C(=O)O)[C@H](Cc1ccc(C2CCNCC2)cc1)c1nnn[nH]1] | (S)-4-methyl-2-((S)-2-(4-(piperidin-4-yl)phenyl)-1-(1H-tetrazol-5-yl)ethyl)pentanoic acid | 372.24 | 372.34 |
| 103 | 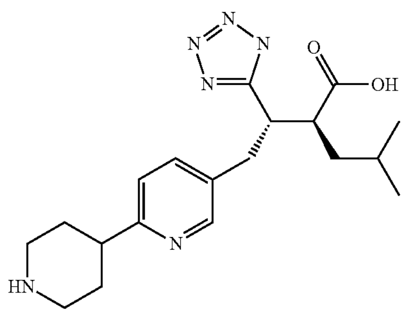 [SMILES: CC(C)C[C@H](C(=O)O)[C@H](Cc1ccc(C2CCNCC2)nc1)c1nnn[nH]1] | (S)-4-methyl-2-((S)-2-(6-(piperidin-4-yl)pyridin-3-yl)-1-(1H-tetrazol-5-yl)ethyl)pentanoic acid | 373.2 | 373.2 |
| 104 | 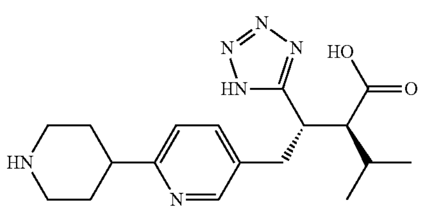 [SMILES: CC(C)[C@H](C(=O)O)[C@H](Cc1ccc(C2CCNCC2)nc1)c1nnn[nH]1] | (2S,3S)-2-isopropyl-4-(6-(piperidin-4-yl)pyridin-3-yl)-3-(1H-tetrazol-5-yl)butanoic acid | 359.4 | 359.2 |
| 105 | 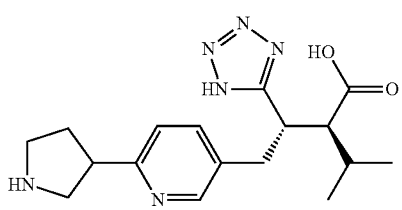 [SMILES: CC(C)[C@H](C(=O)O)[C@H](Cc1ccc(C2CCNC2)nc1)c1nnn[nH]1] | (2S,3S)-2-isopropyl-4-(6-(pyrrolidin-3-yl)pyridin-3-yl)-3-(1H-tetrazol-5-yl)butanoic acid | 345.4 | 345.2 |
| 106 | 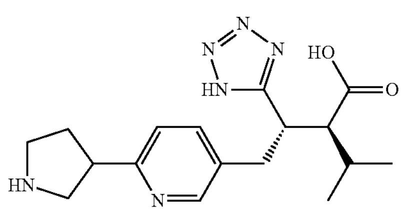 [SMILES: CC(C)[C@H](C(=O)O)[C@H](Cc1ccc(C2CCNC2)nc1)c1nnn[nH]1] | (2S,3S)-2-isopropyl-4-(5-(pyrrolidin-3-yl)pyridin-2-yl)-3-(1H-tetrazol-5-yl)butanoic acid | 343.4 | 343.2 |

| EX. NO. | Structure | Name | Calc'd mass [M + H]+ | MS found |
|---|---|---|---|---|
| 107 | 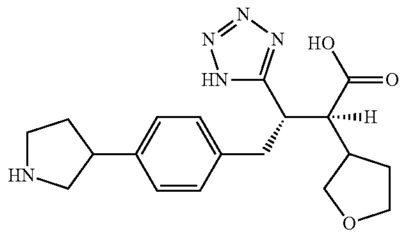 [SMILES: O=C(O)[C@@H](C1CCOC1)[C@H](Cc1ccc(C2CCNC2)cc1)c1nnn[nH]1] | (2R,3S)-4-(4-(pyrrolidin-3-yl)phenyl)-2-(tetrahydrofuran-3-yl)-3-(1H-tetrazol-5-yl)butanoic acid | 372.4 | 372.2 |
| 108 | 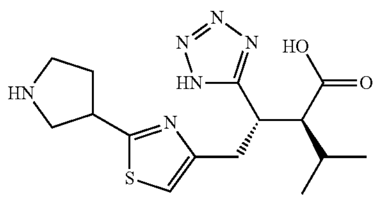 | (2S,3S)-2-isopropyl-4-(2-(pyrrolidin-3-yl)thiazol-4-yl)-3-(1H-tetrazol-5-yl)butanoic acid | 351.4 | 350.9 |
| 109 | 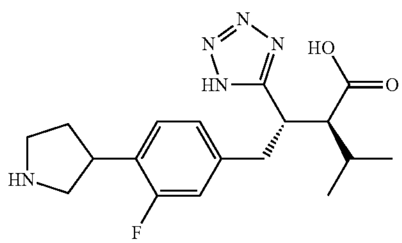 [SMILES: CC(C)[C@H](C(=O)O)[C@H](Cc1ccc(C2CCNC2)c(F)c1)c1nnn[nH]1] | (2S,3S)-4-(3-fluoro-4-(pyrrolidin-3-yl)phenyl)-2-isopropyl 3-(1H-tetrazol-5-yl)butanoic acid | 362.4 | 362.2 |
| 110 | 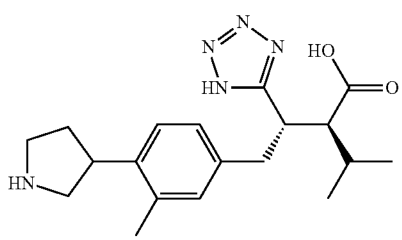 [SMILES: Cc1cc(C[C@H](c2nnn[nH]2)[C@@H](C(=O)O)C(C)C)ccc1C1CCNC1] | (2S,3S)-2-isopropyl-4-(3-methyl-4-(pyrrolidin-3-yl)phenyl)-3-(1H-tetrazol-5-yl)butanoic acid | 358.5 | 358.2 |

EXAMPLE 111

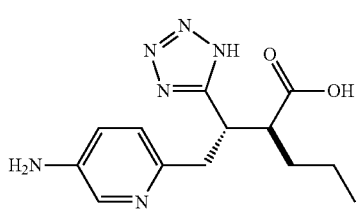 [SMILES: CCC[C@H](C(=O)O)[C@H](Cc1ccc(N)cn1)c1nnn[nH]1]

(S)-2-((S)-2-(5-aminopyridin-2-yl)-1-(1H-tetrazol-5-yl)ethyl)pentanoic acid

Step A: (S)-2-((S)-2-(5-aminopyridin-2-yl)-1-(1-((2-(trimethylsilyl)ethoxy)methyl)-1H-tetrazol-5-yl)ethyl)pentanoic acid In a 5 ml MW tube, (S)-2-((S)-2-(5-bromopyridin-2-yl)-1-(1-((2-(trimethylsilyl)ethoxy)methyl)-1H-tetrazol-5-yl)ethyl)pentanoic acid (50 mg, 0.10 mmol) was dissolved in ethylene glycol (1 ml) and then N,N'-dimethylethylenediamine (2.2 µl, 0.021 mmol), copper(I) oxide (1.5 mg, 10 µmol), ammonium hydroxide (0.57 ml, 4.1 mmol) and $K_2CO_3$ (2.8 mg, 0.021 mmol) were added. The tube was capped and heated at 80° C. overnight. LCMS showed the product peak. The reaction was filtered and concentrated. The residue was purified on Gilson Trilution instrument by preparative HPLC reverse phase (C-18) with Phenomenex Luna C18 prep column, 100 Å, 5 µm, 10 mm×30 mm, eluted with 0-45% acetonitrile/water+0.05% TFA in 15 ramp time, to give a brown oil. LC-MS [M+1]: 421.7

Step B: (S)-2-((S)-2-(5-aminopyridin-2-yl)-1-(1H-tetrazol-5-yl)ethyl)pentanoic acid In a 25 ml flask, (S)-2-((S)-2-(5-aminopyridin-2-yl)-1-((2-(trimethylsilyl)ethoxy)methyl)-1H-tetrazol-5-yl)ethyl)pentanoic acid (15 mg, 0.036 mmol) was dissolved in DCM (2 ml) then TFA (0.5 ml, 6.5 mmol) was added. Then the reaction mixture was stirred at RT for 2 hrs. The reaction was concentrated and the residue was purified on Gilson Trilution instrument by preparative HPLC Reverse phase (C-18) with Phenomenex Luna C18 prep column, 100 Å, 5 µm, 10 mm×30 mm, eluted with 0-40% Acetonitrile/Water (0.05% TFA), to give the desired product. LC-MS [M+1]: 291.2

The following compounds were prepared following the same procedure as EXAMPLE 111.

| Ex. No. | Structure | IUPAC Name | Calc'd Mass [M + H]+ | LC/MS m/e [M + H]+ |
|---|---|---|---|---|
| 112 | 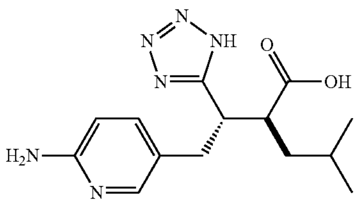 [SMILES: CC(C)C[C@H](C(=O)O)[C@H](Cc1ccc(N)nc1)c1nnn[nH]1] | 2-amino-5-((2S,3S)-3-carboxy-5-methyl-2-(2H-tetrazol-5-yl)hexyl)pyridin-1-ium 2,2,2-trifluoroacetate | 305.2 | 305.2 |
| 113 | 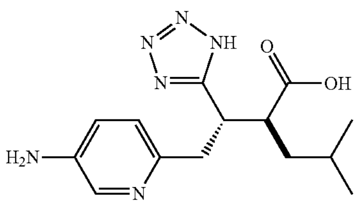 [SMILES: CC(C)C[C@H](C(=O)O)[C@H](Cc1ccc(N)cn1)c1nnn[nH]1] | 5-amino-2-((2S,3S)-3-carboxy-5-methyl-2-(2H-tetrazol-5-yl)hexyl)pyridin-1-ium 2,2,2-trifluoroacetate | 305.2 | 305.2 |
| 114 | 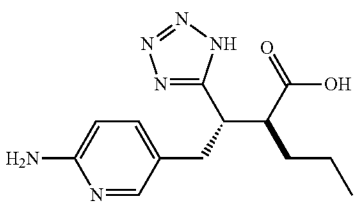 [SMILES: CCC[C@H](C(=O)O)[C@H](Cc1ccc(N)nc1)c1nnn[nH]1] | (S)-2-((S)-2-(6-aminopyridin-3-yl)-1-(1H-tetrazol-5-yl)ethyl)pentanoic acid | 291.2 | 291.2 |
| 115 | 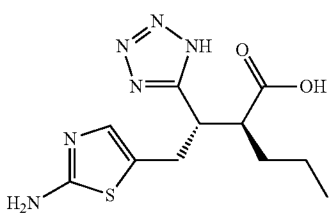 [SMILES: CCC[C@H](C(=O)O)[C@H](Cc1cnc(N)s1)c1nnn[nH]1] | (2S)-2-[(1S)-2-(2-amino-1,3-thiazol-5-yl)-1-(1H-tetrazol-5-yl)ethyl]pentanoic acid | 297.1 | 297.2 |
| 116 | 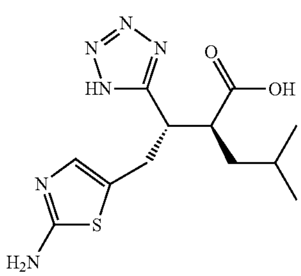 [SMILES: CC(C)C[C@H](C(=O)O)[C@H](Cc1cnc(N)s1)c1nnn[nH]1] | (2S)2-[(1S)-2-(2-amino-1,3-thiazol-5-yl)-1-(1H-tetrazol-5-yl)ethyl]-4-methylpentanoic acid | 311.1 | 311.5 |
| 117 | 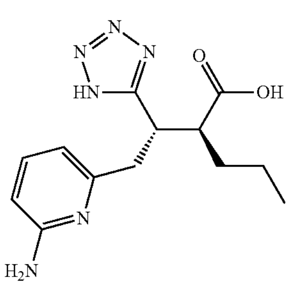 [SMILES: CCC[C@H](C(=O)O)[C@H](Cc1cccc(N)n1)c1nnn[nH]1] | (2S)-2-[(1S)-2-(6-aminopyridin-2-yl)-1-(1H-tetrazol-5-yl)ethyl]pentanoic acid | 291.2 | 291.2 |

-continued

| Ex. No. | Structure | IUPAC Name | Calc'd Mass [M + H]+ | LC/MS m/e [M + H]+ |
|---|---|---|---|---|
| 118 | 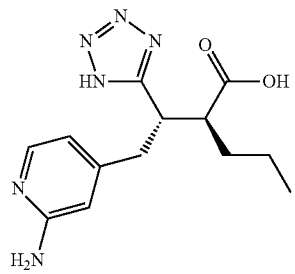 [SMILES: CCC[C@H](C(=O)O)[C@H](Cc1ccnc(N)c1)c1nnn[nH]1] | (2S)-2-[(1S)-2-(2-aminopyridin-4-yl)-1-(1H-tetrazol-5-yl)ethyl]pentanoic acid | 291.2 | 291.1 |
| 119 | 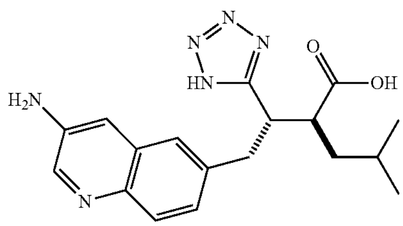 | (S)-2-((S)-2-(3-aminoquinolin-6-yl)-1-(1H-tetrazol-5-yl)ethyl)-4-methylpentanoic acid | 355.2 | 355.2 |
| 120 | 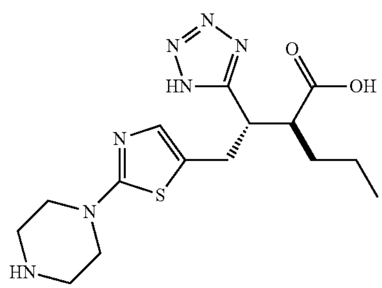 [SMILES: CCC[C@H](C(=O)O)[C@H](Cc1cnc(N2CCNCC2)s1)c1nnn[nH]1] | (S)-2-((S)-2-(2-(piperazin-1-yl)thiazol-5-yl)-1-(1H-tetrazol-5-yl)ethyl)pentanoic acid | 366.2 | 366.6 |
| 121 | 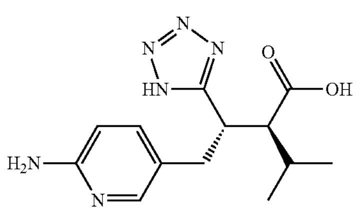 [SMILES: CC(C)[C@H](C(=O)O)[C@H](Cc1ccc(N)nc1)c1nnn[nH]1] | (2S,3S)-4-(6-aminopyridin-3-yl)-2-isopropyl-3-(1H-tetrazol-5-yl)butanoic acid | 291.3 | 291.1 |
| 122 | 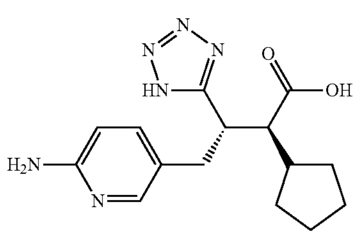 [SMILES: Nc1ccc(C[C@H](c2nnn[nH]2)[C@@H](C(=O)O)C2CCCC2)cn1] | (2S,3S)-4-(6-aminopyridin-3-yl)-2-cyclopentyl-3-(1H-tetrazol-5-yl)butanoic acid | 317.2 | 317.1 |
| 123 | 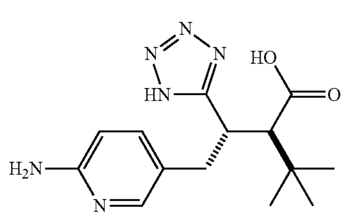 | (2R,3S)-4-(6-aminopyridin-3-yl)-2-(tert-butyl)-3-(1H-tetrazol-5-yl)butanoic acid | 305.2 | 305.1 |

| Ex. No. | Structure | IUPAC Name | Calc'd Mass [M + H]+ | LC/MS m/e [M + H]+ |
|---|---|---|---|---|
| 124 | 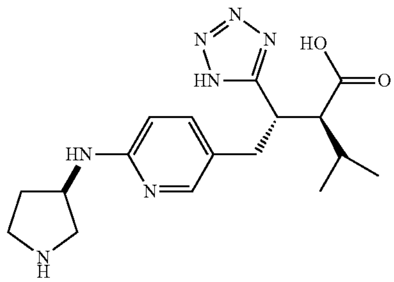 | (2S,3S)-2-isopropyl-4-(6-((R)-pyrrolidin-3-ylamino)pyridin-3-yl)-3-(1H-tetrazol-5-yl)butanoic acid | 360.4 | 360.2 |
| 125 | 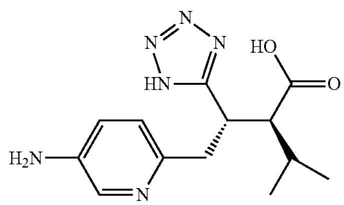 [SMILES: CC(C)[C@H](C(=O)O)[C@H](Cc1ccc(N)cn1)c1nnn[nH]1] | (2S,3S)-4-(5-aminopyridin-2-yl)-2-isopropyl-3-(1H-tetrazol-5-yl)butanoic acid | 291.3 | 291.2 |
| 126 | 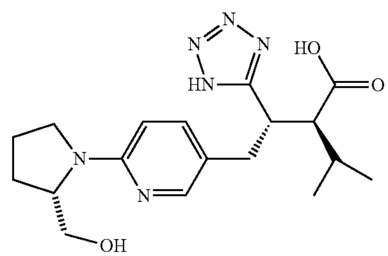 [SMILES: CC(C)[C@H](C(=O)O)[C@H](Cc1ccc(N2CCC[C@H]2CO)nc1)c1nnn[nH]1] | (2S,3S)-4-(6-((S)-2-(hydroxymethyl)pyrrolidin-1-yl)pyridin-3-yl)-2-isopropyl-3-(1H-tetrazol-5-yl)butanoic acid | 375.4 | 375.2 |
| 127 | 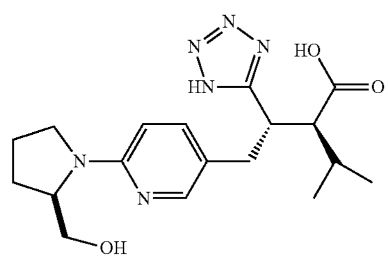 [SMILES: CC(C)[C@H](C(=O)O)[C@H](Cc1ccc(N2CCC[C@@H]2CO)nc1)c1nnn[nH]1] | (2S,3S)-4-(6-((R)-2-(hydroxymethyl)pyrrolidin-1-yl)pyridin-3-yl)-2-isopropyl-3-(1H-tetrazol-5-yl)butanoic acid | 375.4 | 375.2 |

EXAMPLE 128

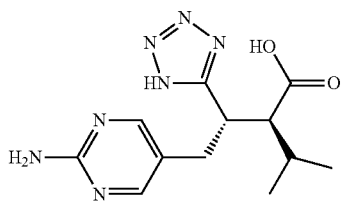 [SMILES: CC(C)[C@H](C(=O)O)[C@H](Cc1cnc(N)nc1)c1nnn[nH]1]

(2S,3S)-4-(2-aminopyrimidin-5-yl)-2-isopropyl-3-(1H-tetrazol-5-yl)butanoic acid

Step A: (2S,3S)-4-(2-aminopyrimidin-5-yl)-2-isopropyl-3-(1-((2-(trimethylsilyl)ethoxy)methyl)-1H-tetrazol-5-yl)butanoic acid Ammonium hydroxide (0.85 ml, 6.4 mmol) was added to a stirred, room temperature mixture of (2S,3S)-4-(2-chloropyrimidin-5-yl)-2-isopropyl-3-(1-((2-(trimethylsilyl)ethoxy)methyl)-1H-tetrazol-5-yl)butanoic acid (70 mg, 0.16 mmol) and dioxane (0.2 mL) in a vial and the mixture was stirred at 65° C. overnight. The reaction mixture was neutralized to pH~7 with 1N HCl, and concentrated down. The residue was purified by column chromatography on a C18 column, eluting with acetonitrile/water+0.1% TFA (0~95~30%) to give the product. LC-MS m/z [M+1]+ 422.23

Step B: (2S,3S)-4-(2-aminopyrimidin-5-yl)-2-isopropyl-3-(1H-tetrazol-5-yl)butanoic acid To a solution of (2S,3S)-4-(2-aminopyrimidin-5-yl)-2-isopropyl-3-(1-((2-(trimethylsilyl)ethoxy)methyl)-1H-tetrazol-5-yl)butanoic acid (23 mg, 0.039 mmol) in DCM (0.5 mL) was added thioanisole (0.015 ml, 0.13 mmol) followed by TFA (1 mL). Then the reaction mixture was stirred at RT for 3 hrs. The volatiles were evaporated and the residue was purified on a Gilson Trilution instrument by preparative HPLC Reverse phase (C-18), eluted with 5-95% Acetonitrile/Water+0.05% TFA, to give the product. LC-MS [M+1]: 292.09

EXAMPLEs 129 and 130

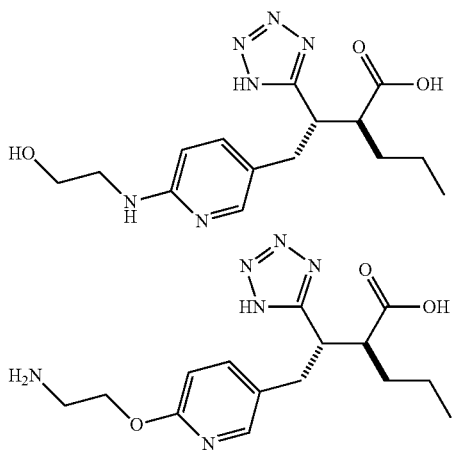

(S)-2-((S)-2-(6-((2-hydroxyethyl)amino)pyridin-3-yl)-1-(1H-tetrazol-5-yl)ethyl)pentanoic acid & (S)-2-((S)-2-(6-(2-aminoethoxy)pyridin-3-yl)-1-(1H-tetrazol-5-yl)ethyl)pentanoic acid Step A: (S)-2-((S)-2-(6-((2-hydroxyethyl)amino)pyridin-3-yl)-1-(1-((2-(trimethylsilyl)ethoxy)methyl)-1H-tetrazol-5-yl)ethyl)pentanoic acid & (S)-2-((S)-2-(6-(2-aminoethoxy)pyridin-3-yl)-1-(1-((2-(trimethylsilyl)ethoxy)methyl)-1H-tetrazol-5-yl)ethyl)pentanoic acid In a 5 ml MW tube, (S)-2-((S)-2-(6-bromopyridin-3-yl)-1-(1-((2-(trimethylsilyl)ethoxy)methyl)-1H-tetrazol-5-yl)ethyl)pentanoic acid (50 mg, 0.10 mmol), 2-aminoethanol (9.3 µl, 0.16 mmol), $Cs_2CO_3$ (67 mg, 0.21 mmol) and Buchwald preformed ketone (8.2 mg, 0.021 mmol) were suspended in DMF (1 mL), and then degassed and backfilled and sealed under $N_2$. The reaction mixture was microwaved at 100° C. for 1 hr. The reaction was filtered and concentrated. The residue was purified on Gilson Trilution instrument by preparative HPLC Reverse phase (C-18) with Phenomenex Luna C18 prep column, 100 Å, 5 µm, 10 mm×30 mm, eluted with 10-90% in 15 mins ramp time Acetonitrile/Water with 0.05% TFA. LC-MS m/z $[M+1]^+$ 465.29

Step B: (S)-2-((S)-2-(6-((2-hydroxyethyl)amino)pyridin-3-yl)-1-(1H-tetrazol-5-yl)ethyl)pentanoic acid & (S)-2-((S)-2-(6-(2-aminoethoxy)pyridin-3-yl)-1-(1H-tetrazol-5-yl)ethyl)pentanoic acid The material obtained above was treated with TFA (1 mL) in DCM (1 mL) for 2 hours at RT. The reaction was concentrated, and the residue was purified by preparative HPLC Reverse phase (C-18) with Phenomenex Luna C18 prep column, 100 Å, 5 µm, 10 mm×30 mm, eluted with 0-40% in 15 mins ramp time acetonitrile/water with 0.05% TFA.

EXAMPLE 129: LC-MS [M+1]: 335.63
EXAMPLE 130: LC-MS [M+1]: 335.38

The following compounds are prepared following the same procedure as EXAMPLES 129 and 130.

| Ex. NO. | Structure | IUPAC Name | Calc'd Mass [M + H]+ | LC/MS m/e [M + H]+ |
|---|---|---|---|---|
| 131 | 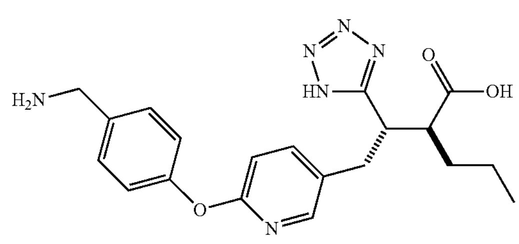 | (S)-2-((S)-2-(6-(4-(aminomethyl)phenoxy)pyridin-3-yl)-1-(1H-tetrazol-5-yl)ethyl)pentanoic acid | 397.19 | 397.32 |
| 132 | 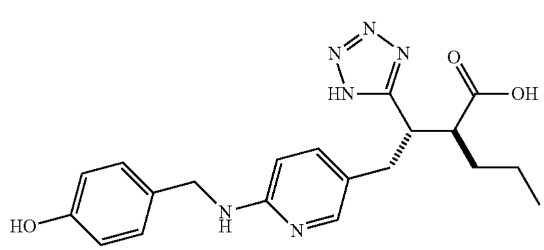 | (S)-2-((S)-2-(6-((4-hydroxybenzyl)amino)pyridin-3-yl)-1-(1H-tetrazol-5-yl)ethyl)pentanoic acid | 397.19 | 397.32 |

-continued

| Ex. NO. | Structure | IUPAC Name | Calc'd Mass [M + H]+ | LC/MS m/e [M + H]+ |
|---|---|---|---|---|
| 133 | 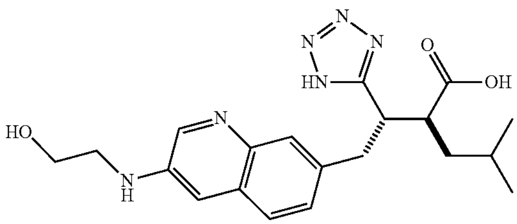 | (S)-2-((S)-2-(3-((2-hydroxyethyl)amino)quinolin-7-yl)-1-(1H-tetrazol-5-yl)ethyl)-4-methylpentanoic acid | 297.1 | 297.2 |
| 134 | 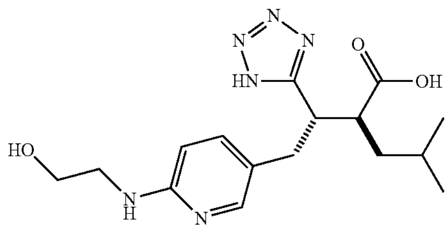 | (S)-2-((S)-2-(6-((2-hydroxyethyl)amino)pyridin-3-yl)-1-(1H-tetrazol-5-yl)ethyl)-4-methylpentanoic acid | 349.2 | 349.2 |
| 135 | 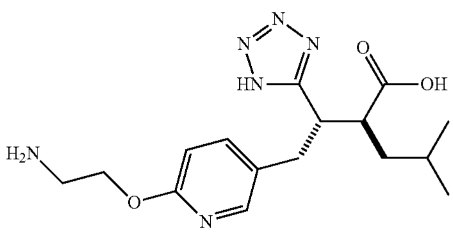 | (S)-2-((S)-2-(6-(2-aminoethoxy)pyridin-3-yl)-1-(1H-tetrazol-5-yl)ethyl)-4-methylpentanoic acid | 349.2 | 349.2 |
| 136 | 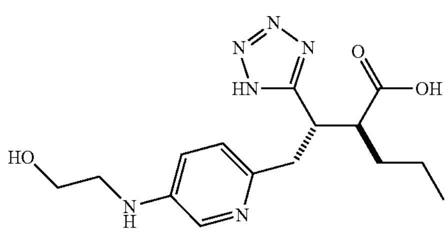 | (S)-2-((S)-2-(5-((2-hydroxyethyl)amino)pyridin-2-yl)-1-(1H-tetrazol-5-yl)ethyl)pentanoic acid | 335.2 | 335.1 |
| 137 | 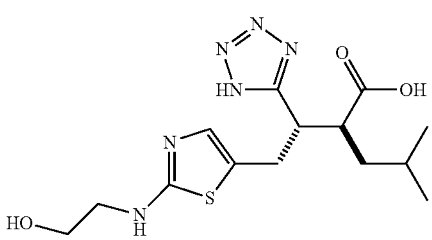 | (S)-2-((S)-2-(2-((2-hydroxyethyl)amino)thiazol-5-yl)-1-(1H-tetrazol-5-yl)ethyl)-4-methylpentanoic acid | 355.2 | 355.2 |
| 138 | 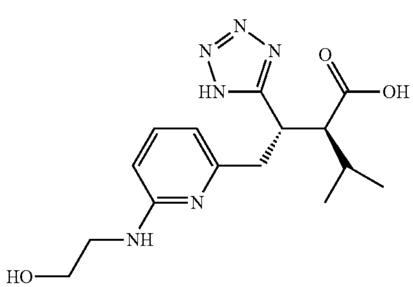 [SMILES: CC(C)[C@H](C(=O)O)[C@H](Cc1cccc(NCCO)n1)c1nnn[nH]1] | (2S,3S)-4-(6-((2-hydroxyethyl)amino)pyridin-2-yl)-2-isopropyl-3-(1H-tetrazol-5-yl)butanoic acid | 335.4 | 335.1 |

| Ex. NO. | Structure | IUPAC Name | Calc'd Mass [M + H]+ | LC/MS m/e [M + H]+ |
|---|---|---|---|---|
| 139 | 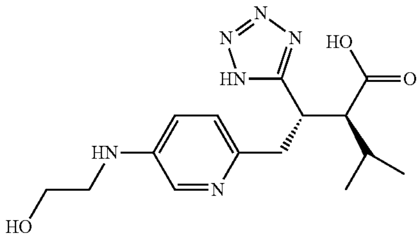 [SMILES: CC(C)[C@H](C(=O)O)[C@H](Cc1ccc(NCCO)cn1)c1nnn[nH]1] | (2S,3S)-4-(5-((2-hydroxyethyl)amino)pyridin-2-yl)-2-isopropyl-3-(1H-tetrazol-5-yl)butanoic acid | 335.4 | 335.1 |
| 140 | 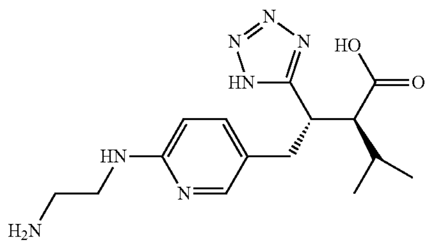 [SMILES: CC(C)[C@H](C(=O)O)[C@H](Cc1ccc(NCCN)nc1)c1nnn[nH]1] | (2S,3S)-4-(6-((2-aminoethyl)amino)pyridin-3-yl)-2-isopropyl-3-(1H-tetrazol-5-yl)butanoic acid | 334.4 | 334.2 |
| 141 | 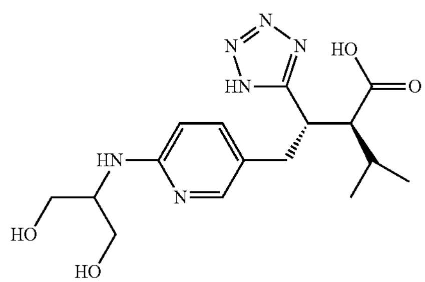 [SMILES: CC(C)[C@H](C(=O)O)[C@H](Cc1ccc(NC(CO)CO)nc1)c1nnn[nH]1] | (2S,3S)-4-(6-((1,3-dihydroxypropan-2-yl)amino)pyridin-3-yl)-2-isopropyl-3-(1H-tetrazol-5-yl)butanoic acid | 365.4 | 365.2 |
| 142 | 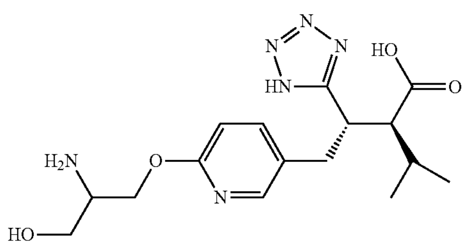 [SMILES: CC(C)[C@H](C(=O)O)[C@H](Cc1ccc(OCC(N)CO)nc1)c1nnn[nH]1] | (2S,3S)-4-(6-(2-amino-3-hydroxypropoxy)pyridin-3-yl)-2-isopropyl-3-(1H-tetrazol-5-yl)butanoic acid | 365.4 | 365.2 |

EXAMPLE 143

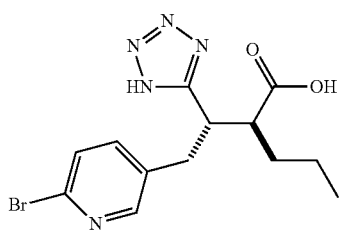

(S)-tert-butyl 2-((S)-2-(6-bromopyridin-3-yl)-1-(1H-tetrazol-5-yl)ethyl)pentanoate To a flask charged with (S)-tert-butyl 2-((S)-2-(6-bromopyridin-3-yl)-1-(1H-tetrazol-5-yl)ethyl)pentanoate (86 mg, 0.21 mmol) was added thioanisole (1 mL, 8.4 mmol) and TFA (2 mL). The mixture was allowed to stir for 3 hours at RT. The reaction was concentrated and then the residue was purified on Gilson Trilution instrument by preparative HPLC Reverse phase (C-18) with Phenomenex Luna C18 prep column, 100 Å, 5 μm, 10 mm×30 mm, eluted with acetonitrile/water+0.05% TFA. LC-MS [M+1]: 354.2

EXAMPLE 144

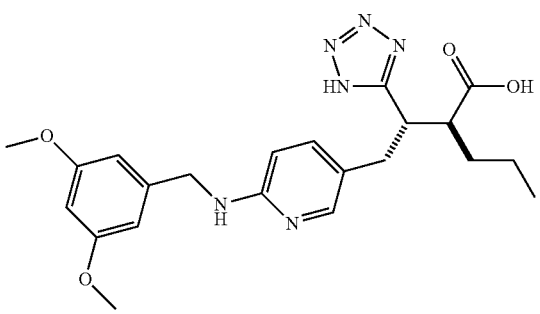 [SMILES: CCC[C@H](C(=O)O)[C@H](Cc1ccc(NCc2cc(OC)cc(OC)c2)nc1)c1nnn[nH]1]

(S)-2-((S)-2-(6-((3,5-dimethoxybenzyl)amino)pyridin-3-yl)-1-(1H-tetrazol-5-yl)ethyl)pentanoic acid Step A: (S)-tert-butyl 2-((S)-2-(6-((3,5-dimethoxybenzyl)amino)pyridin-3-yl)-1-(1H-tetrazol-5-yl)ethyl)pent-4-enoate In a 5 ml MW tube, (S)-tert-butyl 2-((S)-2-(6-bromopyridin-3-yl)-1-(1H-tetrazol-5-yl)ethyl)pent-4-enoate (90 mg, 0.22 mmol), (3,5-dimethoxyphenyl)methanamine (55 mg, 0.33 mmol), Buckwald CuI—2-isobutyrylcyclohexanone precatalyst (18 mg, 0.044 mmol) and $Cs_2CO_3$ (140 mg, 0.44 mmol) were suspended in DMF (1 mL) then degassed and backfilled and sealed under $N_2$. The reaction was microwaved at 100° C. for 0.5 hr. The reaction was filtered and concentrated. The residue was purified on Gilson Trilution instrument by preparative HPLC Reverse phase (C-18) with Phenomenex Luna C18 prep column, 100 Å, 5 µm, 10 mm×30 mm, eluted with 10-100% in 12 mins Acetonitrile/Water+0.05% TFA, isolated peak to give a cream foam. LC-MS [M+1]: 495.41

Step B: (S)-2-((S)-2-(6-((3,5-dimethoxybenzyl)amino)pyridin-3-yl)-1-(1H-tetrazol-5-yl)ethyl)pentanoic acid In a 25 ml RB flask, a mixture of (S)-tert-butyl 2-((S)-2-(6-((3,5-dimethoxybenzyl)amino)pyridin-3-yl)-1-(1H-tetrazol-5-yl)ethyl)pent-4-enoate (18 mg, 0.036 mmol) and Pd—C (3.9 mg, 0.036 mmol) was dissolved in MeOH, and then degassed and backfilled with $H_2$. The reaction was stirred under a balloon of hydrogen at RT. After 3 hrs, LC-MS showed hydrogenation of double bond, but the 3,5-dimethoxybenzyl group was still attached. The reaction mixture was filtered and concentrated in vacuum. To the residue was added thioanisole (1.0 ml, 8.4 mmol) followed by TFA (2.0 ml, 26 mmol). The residue was purified on Gilson HPLC (C-18), eluted with 10-100% acetonitrile/water+0.05% TFA, to furnish the product. LC-MS [M+1]: 441.37

EXAMPLE 145

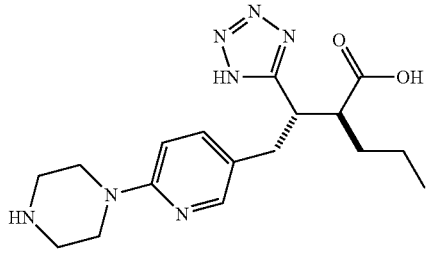 [SMILES: CCC[C@H](C(=O)O)[C@H](Cc1ccc(N2CCNCC2)nc1)c1nnn[nH]1]

(S)-2-((S)-2-(6-(piperazin-1-yl)pyridin-3-yl)-1-(1H-tetrazol-5-yl)ethyl)pentanoic acid Step A: tert-butyl 4-(5-((2S,3S)-3-(tert-butoxycarbonyl)-2-(1H-tetrazol-5-yl)hex-5-en-1-yl)pyridin-2-yl)piperazine-1-carboxylate In a 5 ml microwave tube, (S)-tert-butyl 2-((S)-2-(6-bromopyridin-3-yl)-1-(1H-tetrazol-5-yl)ethyl)pent-4-enoate (90 mg, 0.22 mmol), tert-butyl piperazine-1-carboxylate (49 mg, 0.26 mmol), sodium tert-butoxide (42 mg, 0.44 mmol) and chloro(2-dicyclohexylphosphino-2',6'-di-propoxy-1,1'-biphenyl)[2-(2-aminoethylphenyl)]palladium(II), methyl-t-butylether adduct (9.0 mg, 0.011 mmol) were suspended in THF (1 ml) then degassed and backfilled and sealed under $N_2$. The reaction was microwaved at 100° C. for 0.5 hr. LC-MS showed product peak. The residue was purified on Gilson Trilution instrument by preparative HPLC Reverse phase (C-18) with Phenomenex Luna C18 prep column, 100 Å, 5 µm, 10 mm×30 mm, eluted with 10-100% acetonitrile/water+0.05% TFA, to give a cream color foam. LC-MS [M+1]: 441.37

Step B: (S)-2-((S)-2-(6-(piperazin-1-yl)pyridin-3-yl)-1-(1H-tetrazol-5-yl)ethyl)pentanoic acid In a 100 ml RB flask equipped with a three way stopcock attached to a balloon of $H_2$, tert-butyl 4-(5-((2S,3S)-3-(tert-butoxycarbonyl)-2-(1H-tetrazol-5-yl)hex-5-en-1-yl)pyridin-2-yl)piperazine-1-carboxylate (30 mg, 0.058 mmol) was dissolved in MeOH (5 ml) and Pd/C (12 mg, 0.11 mmol) was added. The reaction was vacuumed and flushed with $H_2$ (3×) from a balloon then stirred under $H_2$ at RT for 1.5 hrs. LC-MS showed hydrogenated product. The reaction was filtered and concentrated. The resulting crude was further treated with thioanisole (1 ml, 8.4 mmol) followed by TFA (2 ml, 26 mmol). After 2 hrs at RT, LC showed the product peak. The reaction was concentrated, and the residue was purified on Gilson HPLC (C-18), eluted with 10-100% Acetonitrile/Water+0.05% TFA, to furnish the product. LC-MS [M+1]: 360.20

EXAMPLE 146

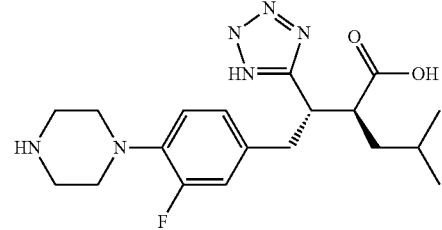 [SMILES: CC(C)C[C@H](C(=O)O)[C@H](Cc1ccc(N2CCNCC2)c(F)c1)c1nn[nH]n1]

(S)-2-((S)-2-(3-fluoro-4-(piperazin-1-yl)phenyl)-1-(2H-tetrazol-5-yl)ethyl)-4-methylpentanoic acid The compound was prepared following the same procedure as EXAMPLE 145. LC-MS m/z [M+1]: 391.25 (calc. m/z 391.23).

EXAMPLE 147

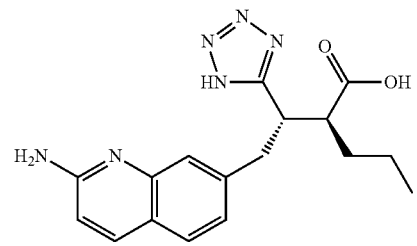 [SMILES: CCC[C@H](C(=O)O)[C@H](Cc1ccc2ccc(N)nc2c1)c1nnn[nH]1]

(S)-2-((S)-2-(2-aminoquinolin-7-yl)-1-(1H-tetrazol-5-yl)ethyl)pentanoic acid

Step A. (2-chloroquinolin-7-yl)methanol

In a 25 ml RB flask, 2-chloroquinoline-7-carboxylic acid (560 mg, 2.7 mmol) was dissolved in THF (50 ml) and cooled to −20° C. then TEA (0.75 ml, 5.4 mmol) was added followed by isobutyl chloroformate (0.42 ml, 3.2 mmol). The reaction mixture was stirred for 20 min, then filtered and rinsed with THF (10 ml). The filtrate was cooled to −15° C. and to this was added NaBH₄ (510 mg, 13 mmol). The mixture was stirred at 0° C. for 3 hrs. The reaction was quenched with sat'd aqueous ammonium chloride (10 ml) and extracted ethyl acetate (3×). The combined organic layer was washed with brine, dried over NaSO₄, filtered and evaporated to dryness. The residue was purified by MPLC ISCO Combi-flash with 0-50% EtOAc/hexane to yield (2-chloroquinolin-7-yl)methanol. LC-MS [M+1]: 193.9

Step B: 7-(bromomethyl)-2-chloroquinoline

In a 25 ml RB flask, (2-chloroquinolin-7-yl)methanol (250 mg, 1.3 mmol) was dissolved in DCM (10 ml) and cooled to 0° C. then triphenylphosphine (340 mg, 1.3 mmol) was added, followed by carbon tetrabromide (430 mg, 1.3 mmol). The reaction was stirred for 30 mins, then warmed up to RT and stirred overnight. When LCMS showed SM still present, more triphenylphosphine (340 mg, 1.23 mmol) and carbon tetrabromide (430 mg, 1.3 mmol) were added then stirred at RT overnight. The reaction was concentrated and the residue was purified by MPLC ISCO Combi-flash with 0-50% EtOAc/hexane to yield 7-(bromomethyl)-2-chloroquinoline. LC-MS [M+1]: 255.9

Step C: (S)-2-((S)-2-(2-chloroquinolin-7-yl)-1-(1-((2-(trimethylsilyl)ethoxy)methyl)-1H-tetrazol-5-yl)ethyl)pentanoic acid In a 100 ml RB flask under argon, (S)-2-((1-((2-(trimethylsilyl)ethoxy)methyl)-1H-tetrazol-5-yl)methyl)pentanoic acid (280 mg, 0.88 mmol) was dissolved in THF (15 ml) then cooled to −78° C. LDA (3.4 ml, 0.64 M, 2.2 mmol) was added and the reaction mixture was stirred for 45 mins then 7-(bromomethyl)-2-chloroquinoline (230 mg, 0.88 mmol) in THF was added. The reaction mixture was stirred at −78° C. for 5 hrs, and then quenched with sat'd aqueous NH₄Cl (3 ml) and extracted with EtOAc 2×, dried (Na₂SO₄) filtered and concentrated. The residue was purified by preparative MPLC Reverse phase (C-18) with ACN and water buffered with 0.05% TFA to yield (S)-2-((S)-2-(2-chloroquinolin-7-yl)-1-(1-((2-(trimethylsilyl)ethoxy)methyl)-1H-tetrazol-5-yl)ethyl)pentanoic acid. LC-MS [M+1]:490

Step D: (S)-2-((S)-2-(2-aminoquinolin-7-yl)-1-(1-((2-(trimethylsilyl)ethoxy)methyl)-1H-tetrazol-5-yl)ethyl)pentanoic acid In a 5 ml MW tube, (S)-2-((S)-2-(2-chloroquinolin-7-yl)-1-(1-((2-(trimethylsilyl)ethoxy)methyl)-1H-tetrazol-5-yl)ethyl)pentanoic acid (70 mg, 0.14 mmol) was dissolved in ethylene glycol (1 ml) and added copper(I) oxide (2.0 mg, 0.014 mmol), N,N'-dimethylethylenediamine (3.1 µl, 0.029 mmol), K₂CO₃ (4.0 mg, 0.029 mmol) and ammonium hydroxide (0.80 ml, 5.7 mmol). The mixture was capped, degassed and purged with N₂ then heated at 80° C. overnight. LCMS showed the product peak. The reaction was filtered, concentrated then purified by reverse phase HPLC with ACN and water buffered with 0.05% TFA to yield (S)-2-((S)-2-(2-aminoquinolin-7-yl)-1-(1-((2-(trimethylsilyl)ethoxy)methyl)-1H-tetrazol-5-yl)ethyl)pentanoic acid. LC-MS [M+1]: 471.3

Step E: (S)-2-((S)-2-(2-aminoquinolin-7-yl)-1-(1H-tetrazol-5-yl)ethyl)pentanoic acid In a 5 ml MW tube (S)-2-((S)-2-(2-aminoquinolin-7-yl)-1-(1-((2-(trimethylsilyl)ethoxy)methyl)-1H-tetrazol-5-yl)ethyl)pentanoic acid (8.4 mg, 0.018 mmol) was dissolved in EtOH (1.5 ml) and HCl (1.5 ml, 1.5 mmol) was added. The tube was capped and was heated to 60° C. overnight. The reaction was concentrated then the residue was purified by reverse phase HPLC with ACN and water buffered with 0.05% TFA to yield (S)-2-((S)-2-(2-aminoquinolin-7-yl)-1-(1H-tetrazol-5-yl)ethyl)pentanoic acid. LC-MS [M+1]: 341.2

EXAMPLE 148

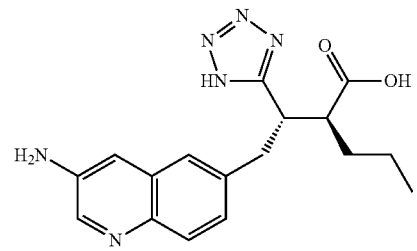 [SMILES: CCC[C@H](C(=O)O)[C@H](Cc1ccc2ncc(N)cc2c1)c1nnn[nH]1]

3-amino-6-((2S,3S)-3-carboxy-2-(1H-tetrazol-5-yl)hexyl)quinolin-1-ium

3-Amino-6-((2S,3S)-3-carboxy-2-(1H-tetrazol-5-yl)hexyl)quinolin-1-ium 2,2,2-trifluoroacetate was prepared as EXAMPLE 147 with 3-bromo-6-(chloromethyl)quinoline. LC-MS [M+1]: 341.2

EXAMPLE 149

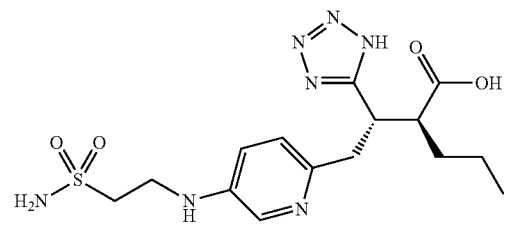 [SMILES: CCC[C@H](C(=O)O)[C@H](Cc1ccc(NCCS(N)(=O)=O)cn1)c1nnn[nH]1]

2-((2S,3S)-3-carboxy-2-(1H-tetrazol-5-yl)hexyl)-5-((2-sulfamoylethyl)amino)pyridin-1-ium Step A: S)-2-((S)-2-(5-((2-sulfamoylethyl)amino)pyridin-2-yl)-1-(1-((2-(trimethylsilyl)ethoxy)methyl)-1H-tetrazol-5-yl)ethyl)pentanoic acid In a 5 ml MW tube, (S)-2-((S)-2-(5-bromopyridin-2-yl)-1-(1-((2-(trimethylsilyl)ethoxy)methyl)-1H-tetrazol-5-yl)

ethyl)pentanoic acid (150 mg, 0.31 mmol), Brettphos palladacycle (12 mg, 0.015 mmol), sodium tert-butoxide (60 mg, 0.62 mmol) and 2-aminoethanesulfonamide (95 mg, 0.76 mmol) were dissolved in THF (2 ml). The tube was then sealed, degassed and purged with nitrogen. The reaction was stirred at room temperature for 72 hrs. The reaction was filtered and concentrated then the residue was purified by reverse phase HPLC with ACN and water buffered with 0.05% TFA to yield (S)-2-((S)-2-(5-((2-sulfamoylethyl)amino)pyridin-2-yl)-1-(1-((2-(trimethylsilyl)ethoxy)methyl)-1H-tetrazol-5-yl)ethyl)pentanoic acid. LC-MS [M+1]: 528.2.

Step B: 2-((2S,3S)-3-carboxy-2-(1H-tetrazol-5-yl)hexyl)-5-((2-sulfamoylethyl)amino)pyridin-1-ium In a sealed 5 ml MW tube, (S)-2-((S)-2-(5-((2-sulfamoylethyl)amino)pyridin-2-yl)-1-(1-((2-(trimethylsilyl)ethoxy)methyl)-1H-tetrazol-5-yl)ethyl)pentanoic acid (14 mg, 0.027 mmol) was dissolved in EtOH (2 ml) and 1N HCl (2 ml, 2.0 mmol) was added. The reaction mixture was heated to 60° C. for 16 hrs. The reaction was filtered and concentrated then the residue was purified by reverse phase HPLC with ACN and water buffered with 0.05% TFA to yield 2-((2S,3S)-3-carboxy-2-(1H-tetrazol-5-yl)hexyl)-5-((2-sulfamoylethyl)amino)pyridin-1-ium 2,2,2-trifluoroacetate. LC-MS [M+1]$^+$ 398.1

EXAMPLE 150

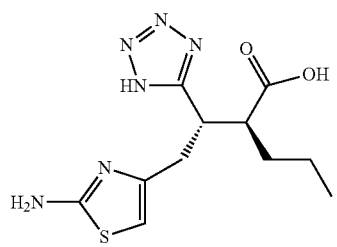 [SMILES: CCC[C@H](C(=O)O)[C@H](Cc1csc(N)n1)c1nnn[nH]1]

4-((2S,3S)-3-carboxy-2-(1H-tetrazol-5-yl)hexyl)thiazol-2-aminium

Step A: 2-bromo-4-(bromomethyl)thiazole

In a 25 ml RB flask, (2-bromothiazol-4-yl)methanol (1.9 g, 9.8 mmol) was dissolved in DCM (20 ml) then cooled to 0° C. and triphenylphosphine (2.6 g, 9.8 mmol) followed by carbon tetrabromide (3.2 g, 9.8 mmol) were added. The reaction mixture was stirred for 30 mins, then warmed up to RT for 16 hrs. LCMS showed SM still present. Additional triphenylphosphine (2.6 g, 9.8 mmol) and carbon tetrabromide (3.2 g, 9.8 mmol) were added then stirred at RT for another 16 hrs. The reaction was concentrated and the residue was purified by MPLC ISCO Combi-flash on ISCO Redi-Sep 40 g column with EtOAc/hexane to give 2-bromo-4-(bromomethyl)thiazole. LC-MS [M+1]$^+$ 258.2.

Step B: (S)-2-((S)-2-(2-bromothiazol-4-yl)-1-(1-((2-(trimethylsilyl)ethoxy)methyl)-1H-tetrazol-5-yl)ethyl)pentanoic acid In a 25-ml RB flask under N$_2$, diisopropylamine (1.7 ml, 11 mmol) was dissolved in THF (10 ml) then cooled to −78° C. n-BuLi in hexane (4.0 ml, 10 mmol, 2.5M) was added and the reaction mixture stirred for 15 mins. In another 100 ml RB flask under argon, (S)-2-((1-((2-(trimethylsilyl)ethoxy)methyl)-1H-tetrazol-5-yl)methyl)pentanoic acid (540 mg, 1.7 mmol) was dissolved in THF (15 ml) then cooled to −78° C. To the flask was added LDA (6.7 ml, 4.3 mmol) prepared above. The reaction mixture was stirred for 45 mins and 2-bromo-4-(bromomethyl)thiazole (530 mg, 2.1 mmol) in THF was added. The reaction mixture was stirred at −78° C. for 5 hrs, and then quenched with NH$_4$Cl solution and extracted with EtOAc 2 times, dried with Na$_2$SO$_4$, filtered and concentrated. The residue was purified by reverse phase HPLC with ACN and water buffered with 0.05% TFA to yield (S)-2-((S)-2-(2-bromothiazol-4-yl)-1-(1-((2-(trimethylsilyl)ethoxy)methyl)-1H-tetrazol-5-yl)ethyl)pentanoic acid. LC-MS [M+2]$^+$ 492.6

Step C: (S)-2-((S)-2-(2-aminothiazol-5-yl)-1-(1-((2-(trimethylsilyl)ethoxy)methyl)-1H-tetrazol-5-yl)ethyl)pentanoic acid To a 5 ml MW tube (S)-2-((S)-2-(2-bromothiazol-5-yl)-1-(1-((2-(trimethylsilyl)ethoxy)methyl)-1H-tetrazol-5-yl)ethyl)pentanoic acid (64 mg, 0.13 mmol) was dissolved in ethylene glycol (1 ml) and then copper(i) oxide (6 mg, 0.042 mmol), N,N'-dimethylethylenediamine (2.8 μl, 0.026 mmol), K$_2$CO$_3$ (6 mg, 0.043 mmol) and ammonium hydroxide (0.72 ml, 5.2 mmol) were added. The tube was degassed and purged with N$_2$ then capped and heated at 80° C. for 16 hrs. The reaction was filtered and concentrated. The residue was purified by reverse phase HPLC with ACN and water buffered with 0.05% TFA to yield (S)-2-((S)-2-(2-aminothiazol-5-yl)-1-(1-((2-(trimethylsilyl)ethoxy)methyl)-1H-tetrazol-5-yl)ethyl)pentanoic acid. LC-MS m/z [M+1]$^+$ 427

Step D: 4-((2S,3S)-3-carboxy-2-(1H-tetrazol-5-yl)hexyl)thiazol-2-aminium

In a 5 ml MW tube, (S)-2-((S)-2-(2-aminothiazol-5-yl)-1-(1-((2-(trimethylsilyl)ethoxy)methyl)-1H-tetrazol-5-yl)ethyl)pentanoic acid (10 mg, 0.023 mmol) was dissolved in EtOH (2 ml) and then 1N HCl (2 ml, 2.0 mmol) was added. The tube was capped and heated at 60° C. for 16 hrs. The residue was purified by reverse phase HPLC with ACN and water buffered with 0.05% TFA to yield 4-((2S,3S)-3-carboxy-2-(1H-tetrazol-5-yl)hexyl)thiazol-2-aminium. LC-MS m/z [M+1]$^+$ 297.

EXAMPLE 151

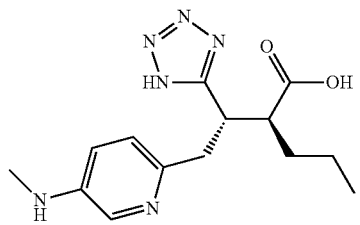 [SMILES: CCC[C@H](C(=O)O)[C@H](Cc1ccc(NC)cn1)c1nnn[nH]1]

S)-2-((S)-2-(5-(methylamino)pyridin-2-yl)-1-(1H-tetrazol-5-yl)ethyl)pentanoic acid Step A: (S)-2-((S)-2-(5-(methylamino)pyridin-2-yl)-1-(1-((2-(trimethylsilyl)ethoxy)methyl)-1H-tetrazol-5-yl)ethyl)pentanoic acid In a sealed 5 ml MW tube, (S)-2-((S)-2-(5-bromopyridin-2-yl)-1-(1-((2-(trimethylsilyl)ethoxy)methyl)-1H-tetrazol- 5-yl)ethyl)pentanoic acid (55 mg, 0.11 mmol), sodium tert-butoxide (22 mg, 0.23 mmol), Brettphos palladacycle (4.5 mg, 5.7 µmol) and methylamine in THF (0.11 ml, 0.23 mmol) were degassed and purged with $N_2$ then stirred at RT for 72 hrs. The reaction was filtered, the residue was purified by reverse phase HPLC with ACN and water buffered with 0.05% TFA to yield (S)-2-((S)-2-(5-(methylamino)pyridin-2-yl)-1-(1-((2-(trimethylsilyl)ethoxy)methyl)-1H-tetrazol-5-yl)ethyl)pentanoic acid. LC-MS m/z [M+1]$^+$435.

Step B: S)-2-((S)-2-(5-(methylamino)pyridin-2-yl)-1-(1H-tetrazol-5-yl)ethyl)pentanoic acid In a sealed 5 ml MW tube, (S)-2-((S)-2-(5-(methylamino)pyridin-2-yl)-1-(1-((2-(trimethylsilyl)ethoxy)methyl)-1H-tetrazol-5-yl)ethyl)pentanoic acid (50 mg, 0.12 mmol) was dissolved in ethanol (2 ml). Then 1N HCl (2 ml, 2.0 mmol) was added and the reaction mixture was stirred at 60° C. for 16 hrs. The reaction was concentrated and the residue was purified by reverse phase HPLC with ACN and water buffered with 0.05% TFA to yield S)-2-((S)-2-(5-(methylamino)pyridin-2-yl)-1-(1H-tetrazol-5-yl)ethyl)pentanoic acid. LC-MS m/z [M+1]$^+$ 305.1

EXAMPLE 152

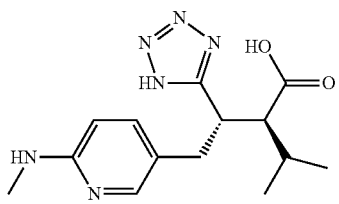 [SMILES: CNc1ccc(C[C@H](c2nnn[nH]2)[C@@H](C(=O)O)C(C)C)cn1]

(2S,3S)-2-isopropyl-4-(6-(methylamino)pyridin-3-yl)-3-(1H-tetrazol-5-yl)butanoic acid The product was prepared following the same procedure as EXAMPLE 151. LC-MS m/z [M+1]$^+$ 305.1

EXAMPLE 153

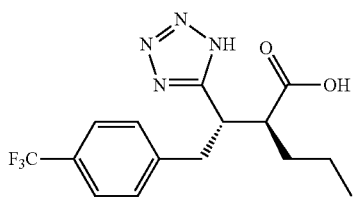 [SMILES: CCC[C@H](C(=O)O)[C@H](Cc1ccc(C(F)(F)F)cc1)c1nnn[nH]1]

(S)-2-((S)-1-(1H-tetrazol-5-yl)-2-(4-(trifluoromethyl)phenyl)ethyl)pentanoic acid Step A: (S)-2-((S)-2-(4,4,5,5-tetramethyl-1,3,2-dioxaborolan-2-yl)-1-(1-((2-(trimethylsilyl)ethoxy)methyl)-1H-tetrazol-5-yl)ethyl)pentanoic acid To a solution of (S)-2-((1-((2-(trimethylsilyl)ethoxy)methyl)-1H-tetrazol-5-yl)methyl)pentanoic acid (310 mg, 1.0 mmol) in THF was added lithium diisopropylamide (1.25 ml, 2.5 mmol). The mixture was allowed to stir at −78° C. for 40 minutes, and then 2-(iodomethyl)-4,4,5,5-tetramethyl-1,3,2-dioxaborolane (540 mg, 2.0 mmol) was added. The reaction was warmed up to RT naturally and stirred overnight. To the mixture was added sat. aq. $NH_4Cl$ and EtOAc for partitioning. The organic layer was separated, dried over $Na_2SO_4$, and evaporated to dryness. The crude was used directly in the next step.

Step B: (S)-methyl 2-((S)-2-(4,4,5,5-tetramethyl-1,3,2-dioxaborolan-2-yl)-1-(1-((2-(trimethylsilyl)ethoxy)methyl)-1H-tetrazol-5-yl)ethyl)pentanoate The crude of (S)-2-((S)-2-(4,4,5,5-tetramethyl-1,3,2-dioxaborolan-2-yl)-1-(1-((2-(trimethylsilyl)ethoxy)methyl)-1H-tetrazol-5-yl)ethyl)pentanoic acid (430 mg, 0.95 mmol) was dissolved in Toluene (2 ml) and MeOH (1 ml). TMS-Diazomethane (0.95 ml, 1.9 mmol) was added slowly and the reaction stirred overnight. The solvent was evaporated in high vacuum. The crude material was used directly in Step C.

Step C: potassium trifluoro((2S,3S)-3-(methoxycarbonyl)-2-(1-((2-(trimethylsilyl)ethoxy)methyl)-1H-tetrazol-5-yl)hexyl)borate To a methanol solution of (S)-methyl 2-((S)-2-(4,4,5,5-tetramethyl-1,3,2-dioxaborolan-2-yl)-1-(1-((2-(trimethylsilyl)ethoxy)methyl)-1H-tetrazol-5-yl)ethyl)pentanoate (100 mg, 0.21 mmol) was added 4.5 M potassium bifluoride (160 µL, 0.70 mmol) slowly and the reaction stirred at RT for 1 hour. The solvent was removed in vacuo and acetone was added and the suspension stirred for 15 min at RT. The mixture was filtered, and the filtrate was evaporated to dry to obtain the crude material.

Step D: (S)-methyl 2-((S)-2-(4-(trifluoromethyl)phenyl)-1-(1-((2-(trimethylsilyl)ethoxy)methyl)-1H-tetrazol-5-yl)ethyl)pentanoate In the reaction vessel cesium carbonate (87 mg, 0.27 mmol) and Ad2nBuP Biphenyl Precatalyst (6.0 mg, 8.9 µmol) were combined with water (0.05 ml) and potassium trifluoro((2S,3S)-3-(methoxycarbonyl)-2-(1-((2-(trimethylsilyl)ethoxy)methyl)-1H-tetrazol-5-yl)hexyl)borate (39 mg, 0.087 mmol), and 1-bromo-4-(trifluoromethyl)benzene (20 mg, 0.089 mmol) in toluene. The mixture was degassed and then heated at 100° C. overnight. The mixture was cooled, diluted with EtOAc, washed with water, brine, dried over $MgSO_4$, and filtered. The solvent was evaporated under reduced pressure to gave 42 mg of crude material. The crude was purified on Silica gel Chromatography with EtOAc-hexane 0-100%, to obtain the product, (S)-methyl 2-((S)-2-(4-(trifluoromethyl)phenyl)-1-(1-((2-(trimethylsilyl)ethoxy)methyl)-1H-tetrazol-5-yl)ethyl)pentanoate. LC-MS m/z [M+1]$^+$ 487.15

Step E: (S)-2-((S)-1-(1H-tetrazol-5-yl)-2-(4-(trifluoromethyl)phenyl)ethyl)pentanoic acid A solution of (S)-methyl 2-((S)-2-(4-(trifluoromethyl)phenyl)-1-(1-((2-(trimethylsilyl)ethoxy)methyl)-1H-tetrazol-5-yl)ethyl)pentanoate (15 mg, 0.031 mmol), and Lithium hydroxide (15 mg, 0.62 mmol) in MeOH—$H_2O$ (1:1) was stirred at 55° C. overnight. After being cooled, EtOAc and $H_2O$ were added and the solution was adjusted to pH<4 by 1N HCl. The organic was evaporated to dryness to obtain the crude. The crude was dissolved in EtOH (0.5 ml)/0.5 ml 1N HCl, and heated at 60° C. overnight. The reaction was concentrated and the residue was purified by reverse phase C18 HPLC, ACN-H$_2$O (0.05% TFA) gradient to obtain the product, (S)-2-((S)-1-(1H-tetrazol-5-yl)-2-(4-(trifluoromethyl)phenyl)ethyl)pentanoic acid. LC-MS: m/z [M+H]$^+$ 343.09 (calc. m/z 343.14).

EXAMPLE 154

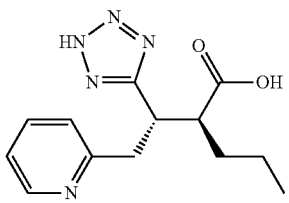 [SMILES: CCC[C@H](C(=O)O)[C@H](Cc1ccccn1)c1nn[nH]n1]

(S)-2-((S)-2-(pyridin-2-yl)-1-(1H-tetrazol-5-yl)ethyl)pentanoic acid

The compound was prepared according to the above EXAMPLE 153 with 2-bromopyridine as coupling partner in Step D. (S)-2-((S)-2-(pyridin-2-yl)-1-(1H-tetrazol-5-yl)ethyl)pentanoic acid, LC-MS: m/z [M+H]$^+$ 276.14 (calc. m/z 276.15).

EXAMPLE 155

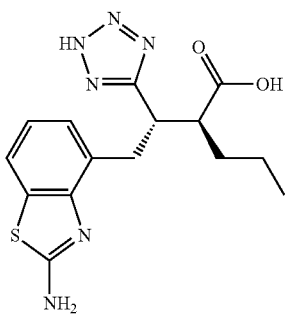 [SMILES: CCC[C@H](C(=O)O)[C@H](Cc1cccc2sc(N)nc12)c1nn[nH]n1]

(S)-2-((S)-2-(2-aminobenzo[d]thiazol-4-yl)-1-(2H-tetrazol-5-yl)ethyl)pentanoic acid Step A: (S)-tert-butyl 2-((S)-2-(2-aminobenzo[d]thiazol-4-yl)-1-(1-((2-(trimethylsilyl)ethoxy)methyl)-1H-tetrazol-5-yl)ethyl)pentanoate In a 5 ml microwave tube, potassium ((2S,3S)-3-(tert-butoxycarbonyl)-2-(1-((2-(trimethylsilyl)ethoxy)methyl)-1H-tetrazol-5-yl)hexyl)trifluoroborate (200 mg, 0.40 mmol) was dissolved in toluene (1.8 mL)/water (175 µl). Then 4-bromobenzo[d]thiazol-2-amine (70 mg, 0.31 mmol), cesium carbonate (300 mg, 0.92 mmol), and Ad2nBuP biphenyl Precatalyst (29 mg, 0.043 mmol) were added. The tube was sealed, degassed and purged with N$_2$ (3×) then heated to 100° C. for 16 hrs. The reaction was cooled and poured into water then extracted with EtOAc (2×). The EtOAc layer was washed with brine, dried over Na$_2$SO$_4$, and then filtered and concentrated. The residue was purified by MPLC with 0-100% EtOAc/hexane to yield (S)-tert-butyl 2-((S)-2-(2-aminobenzo[d]thiazol-4-yl)-1-(1-((2-(trimethylsilyl)ethoxy)methyl)-1H-tetrazol-5-yl)ethyl)pentanoate. LC-MS [M+1]: 533.25.

Step B: (S)-2-((S)-2-(2-aminobenzo[d]thiazol-4-yl)-1-(2H-tetrazol-5-yl)ethyl)pentanoic acid To a 25 mL RB flask charged with (S)-tert-butyl 2-((S)-2-(2-aminobenzo[d]thiazol-4-yl)-1-(1-((2-(trimethylsilyl)ethoxy)methyl)-1H-tetrazol-5-yl)ethyl)pentanoate (44 mg, 0.083 mmol) was added TFA (1.8 mL) and water (0.18 mL). The mixture was allowed to stir at RT for 2 hours. The desired product was purified by preparative HPLC Reverse phase (C-18) with Phenomenex Luna C18 prep column, 100 Å, 5 µm, 10 mm×30 mm, eluted with 10-100% acetonitrile/water+0.05% TFA. LC-MS [M+1]: 346.12

EXAMPLE 156

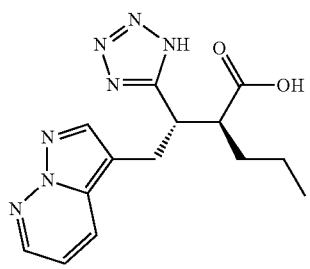 [SMILES: CCC[C@H](C(=O)O)[C@H](Cc1cnn2ncccc12)c1nnn[nH]1]

(S)-2-((S)-2-(pyrazolo[1,5-b]pyridazin-3-yl)-1-(1H-tetrazol-5-yl)ethyl)pentanoic acid The compound was prepared following the same procedure as EXAMPLE 155 with potassium ((2S,3S)-3-(tert-butoxycarbonyl)-2-(1-((2-(trimethylsilyl)ethoxy)methyl)-1H-tetrazol-5-yl)hexyl)trifluoroborate and 3-bromopyrazolo[1,5-b]pyridazine. LC-MS [M+1]:316.1

EXAMPLE 157

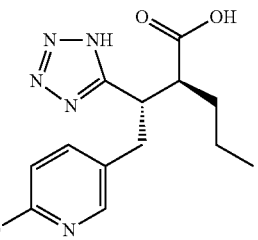

(S)-2-((S)-2-(6-hydroxypyridin-3-yl)-1-(1H-tetrazol-5-yl)ethyl)pentanoic acid

Step A: (S)-2-((S)-2-(6-hydroxypyridin-3-yl)-1-(1-((2-(trimethylsilyl)ethoxy)methyl)-1H-tetrazol-5-yl)ethyl)pentanoic acid In a 5 mL MW tube, (S)-2-((S)-2-(6-bromopyridin-3-yl)-1-(1-((2-(trimethylsilyl)ethoxy)methyl)-1H-tetrazol-5-yl)

ethyl)pentanoic acid (50 mg, 0.10 mmol), KOH (17 mg, 0.31 mmol), Pd₂dba₃ (4.0 mg, 4.3 μmol), and di-tert-butyl(2',4',6'-triisopropyl-3,4,5,6-tetramethyl-[1,1'-biphenyl]-2-yl)phosphine (10 mg, 0.021 mmol) were dissolved in dioxane (0.5 mL)/water (0.5 mL). The tube was sealed, degassed and purged with nitrogen. The mixture was heated at 100° C. for 16 hrs. The reaction was cooled and diluted with water then adjusted to pH 6 with 1N HCl. The reaction mixture was extracted with EtOAc (2×), dried over Na₂SO₄, filtered and concentrated. The residue was purified by reverse phase HPLC with ACN and water buffered with 0.05% TFA to yield (S)-2-((S)-2-(6-hydroxypyridin-3-yl)-1-(1-((2-(trimethylsilyl)ethoxy)methyl)-1H-tetrazol-5-yl)ethyl)pentanoic acid. LCMS [M+1]: 422.6.

Step B: (S)-2-((S)-2-(6-hydroxypyridin-3-yl)-1-(1H-tetrazol-5-yl)ethyl)pentanoic acid The isolated (S)-2-((S)-2-(6-hydroxypyridin-3-yl)-1-(1-((2-(trimethylsilyl)ethoxy)methyl)-1H-tetrazol-5-yl)ethyl)pentanoic acid was stirred in TFA (3 mL)/water (0.3 mL) for 2 hours at RT. The reaction was concentrated and the residue was purified by reverse phase HPLC with ACN and water buffered with 0.05% TFA to yield (S)-2-((S)-2-(6-hydroxypyridin-3-yl)-1-(1H-tetrazol-5-yl)ethyl)pentanoic acid. LCMS [M+1]: 292.1

EXAMPLE 158

(S)-2-((S)-1-(1H-tetrazol-5-yl)-2-(6-(1,3,5-trimethyl-1H-pyrazol-4-yl)pyridin-3-yl)ethyl)pentanoic acid Step A: (S)-tert-butyl 2-((S)-1-(1H-tetrazol-5-yl)-2-(6-(1,3,5-trimethyl-1H-pyrazol-4-yl)pyridin-3-yl)ethyl)pentanoate In a 5 ml microwave tube, (S)-tert-butyl 2-((S)-2-(6-bromopyridin-3-yl)-1-(1H-tetrazol-5-yl)ethyl)pentanoate (30 mg, 0.073 mmol), 1,3,5-trimethyl-4-(4,4,5,5-tetramethyl-1,3,2-dioxaborolan-2-yl)-1H-pyrazole (42 mg, 0.18 mmol), chloro[(di(1-adamantyl)-N-butylphosphine)-2-(2-aminobiphenyl)]palladium(II) (4.9 mg, 7.3 μmol) and K₃PO₄ (62 mg, 0.29 mmol) were dissolved in THF (1 mL)/Water (0.4 mL). Then the tube was degassed and sealed under N₂. The mixture was heated for 16 hrs at 110° C. LC-MS showed product peak M+1=440. The reaction was poured into water and extracted with EtOAc (2×5 mL), then dried over Na₂SO₄, filtered and concentrated to give the crude product, which was used in the next step. LC-MS [M+1]: 440.5

Step B: (S)-2-((S)-1-(1H-tetrazol-5-yl)-2-(6-(1,3,5-trimethyl-1H-pyrazol-4-yl)pyridin-3-yl)ethyl)pentanoic acid To a 25 ml RB flask under N₂ containing (S)-tert-butyl 2-((S)-1-(1H-tetrazol-5-yl)-2-(6-(1,3,5-trimethyl-1H-pyrazol-4-yl)pyridin-3-yl)ethyl)pentanoate (57 mg, 0.13 mmol), was added thioanisole (0.015 ml, 0.13 mmol) followed by TFA (1 mL). Then the reaction mixture was stirred at RT for 3 hrs. The volatiles were evaporated and the residue was purified on Gilson Trilution instrument by preparative HPLC Reverse phase (C-18) with Phenomenex Luna C18 prep column, 100 Å, 5 μm, 10 mm×30 mm, eluted with 10-100% acetonitrile/water+0.05% TFA, to give the product. LC-MS [M+1]: 384.38

The following compounds were prepared following the same procedure as EXAMPLE 158

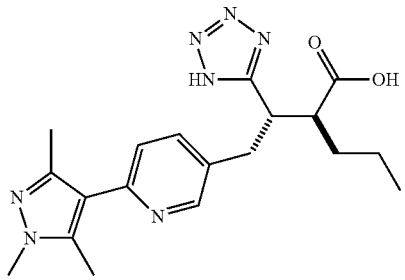

| Ex. No. | Structure | IUPAC Name | Calc'd Mass [M + H]+ | LC/MS m/e [M + H]+ |
|---|---|---|---|---|
| 159 | 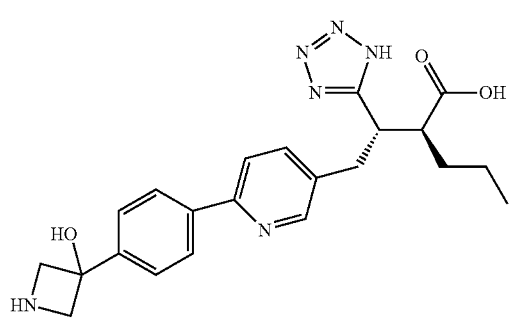 [SMILES: CCC[C@H](C(=O)O)[C@H](Cc1ccc(-c2ccc(C3(O)CNC3)cc2)nc1)c1nnn[nH]1] | (2S)-2-[(1S)-2-{6-[4-(3-hydroxyazetidin-3-yl)phenyl]pyridin-3-yl}-1-(1H-tetrazol-5-yl)ethyl]pentanoic acid | 423.21 | 423.35 |

| Ex. No. | Structure | IUPAC Name | Calc'd Mass [M + H]+ | LC/MS m/e [M + H]+ |
|---|---|---|---|---|
| 160 | 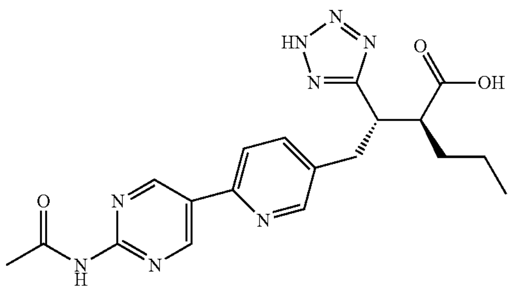 [SMILES: CCC[C@H](C(=O)O)[C@H](Cc1ccc(-c2cnc(NC(C)=O)nc2)nc1)c1nn[nH]n1] | (2S)-2-[(1S)-2-{6-[2-(acetylamino)pyrimidin-5-yl]pyridin-3-yl}-1-(1H-tetrazol-5-yl)ethyl]pentanoic acid | 411.18 | 411.29 |
| 161 | 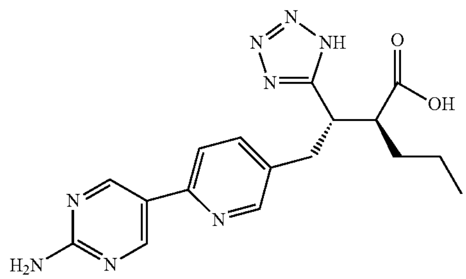 [SMILES: CCC[C@H](C(=O)O)[C@H](Cc1ccc(-c2cnc(N)nc2)nc1)c1nnn[nH]1] | (2S)-2-[(1S)-2-[6-(2-aminopyrimidin-5-yl)pyridin-3-yl]-1-(1H-tetrazol-5-yl)ethyl]pentanoic acid | 369.17 | 369.27 |
| 162 | 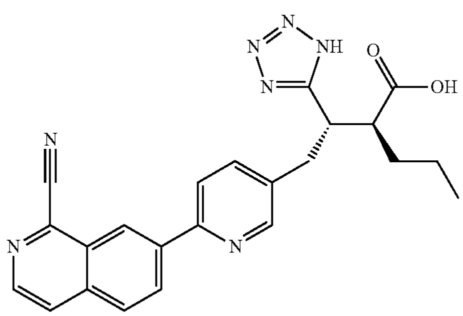 [SMILES: CCC[C@H](C(=O)O)[C@H](Cc1ccc(-c2ccc3ccnc(C#N)c3c2)nc1)c1nnn[nH]1] | (2S)-2-[(1S)-2-[6-(1-cyanoisoquinolin-7-yl)pyridin-3-yl]-1-(1H-tetrazol-5-yl)ethyl]pentanoic acid | 428.18 | 428.28 |
| 163 | 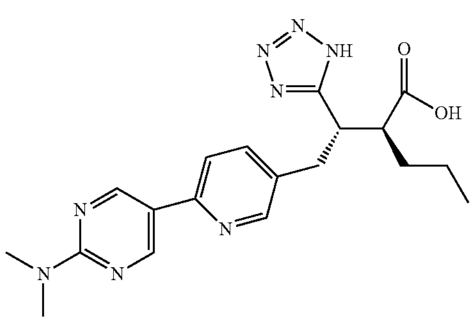 [SMILES: CCC[C@H](C(=O)O)[C@H](Cc1ccc(-c2cnc(N(C)C)nc2)nc1)c1nnn[nH]1] | (2S)-2-[(1S)-2-{6-[2-(dimethylamino)pyrimidin-5-yl]pyridin-3-yl}-1-(1H-tetrazol-5-yl)ethyl]pentanoic acid | 397.20 | 397.30 |
| 164 | 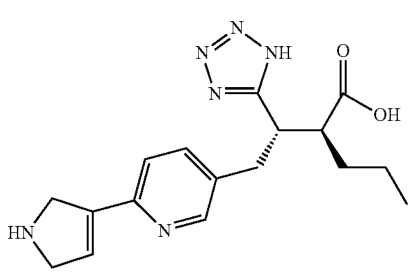 [SMILES: CCC[C@H](C(=O)O)[C@H](Cc1ccc(C2=CCNC2)nc1)c1nnn[nH]1] | (2S)-2-[(1S)-2-[6-(2,5-dihydro-1H-pyrrol-3-yl)pyridin-3-yl]-1-(1H-tetrazol-5-yl)ethyl]pentanoic acid | 343.18 | 343.30 |

-continued

| Ex. No. | Structure | IUPAC Name | Calc'd Mass [M + H]+ | LC/MS m/e [M + H]+ |
|---|---|---|---|---|
| 165 | 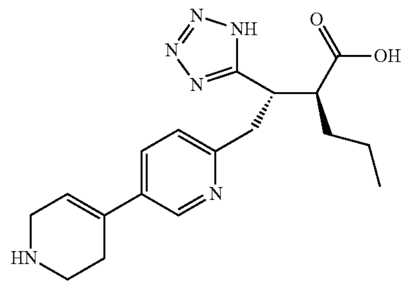 [SMILES: CCC[C@H](C(=O)O)[C@H](Cc1ccc(C2=CCNCC2)cn1)c1nnn[nH]1] | (2S)-2-[(1S)-2-(1',2',3',6'-tetrahydro-3,4'-bipyridin-6-yl)-1-(1H-tetrazol-5-yl)ethyl]pentanoic acid | 357.2 | 357.3 |
| 166 | 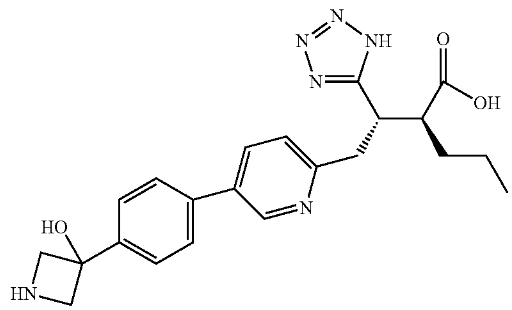 [SMILES: CCC[C@H](C(=O)O)[C@H](Cc1ccc(-c2ccc(C3(O)CNC3)cc2)cn1)c1nnn[nH]1] | (2S)-2-[(1S)-2-{5-[4-(3-hydroxyazetidin-3-yl)phenyl]pyridin-2-yl}-1-(1H-tetrazol-5-yl)ethyl]pentanoic acid | 423.21 | 423.38 |
| 167 | 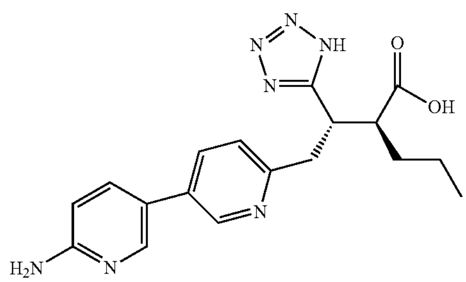 [SMILES: CCC[C@H](C(=O)O)[C@H](Cc1ccc(-c2ccc(N)nc2)cn1)c1nnn[nH]1] | (2S)-2-[(1S)-2-(6'-amino-3,3'-bipyridin-6-yl)-1-(1H-tetrazol-5-yl)ethyl]pentanoic acid | 368.18 | 368.22 |
| 168 | 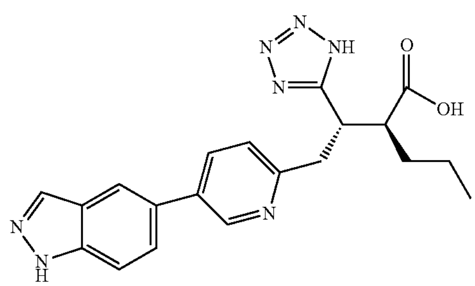 [SMILES: CCC[C@H](C(=O)O)[C@H](Cc1ccc(-c2ccc3[nH]ncc3c2)cn1)c1nnn[nH]1] | (2S)-2-[(1S)-2-[5-(1H-indazol-5-yl)pyridin-2-yl]-1-(1H-tetrazol-5-yl)ethyl]pentanoic acid | 392.18 | 392.18 |
| 169 | 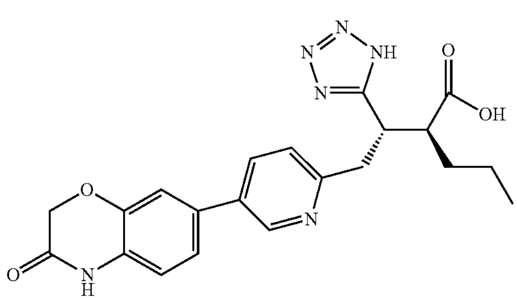 [SMILES: CCC[C@H](C(=O)O)[C@H](Cc1ccc(-c2ccc3c(c2)OCC(=O)N3)cn1)c1nnn[nH]1] | (2S)-2-[(1S)-2-[5-(3-oxo-3,4-dihydro-2H-1,4-benzoxazin-7-yl)pyridin-2-yl]-1-(1H-tetrazol-5-yl)ethyl]pentanoic acid | 423.17 | 423.24 |

| Ex. No. | Structure | IUPAC Name | Calc'd Mass [M + H]+ | LC/MS m/e [M + H]+ |
|---|---|---|---|---|
| 170 | 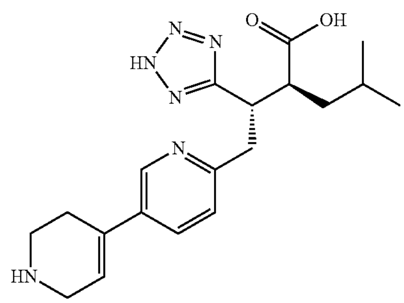 [SMILES: CC(C)C[C@H](C(=O)O)[C@H](Cc1ccc(C2=CCNCC2)cn1)c1nn[nH]n1] | (2S)-4-methyl-2-[(1S)-2-(1',2',3',6'-tetrahydro-3,4'-bipyridin-6-yl)-1-(2H-tetrazol-5-yl)ethyl]pentanoic acid | 371.2 | 371.3 |
| 171 | 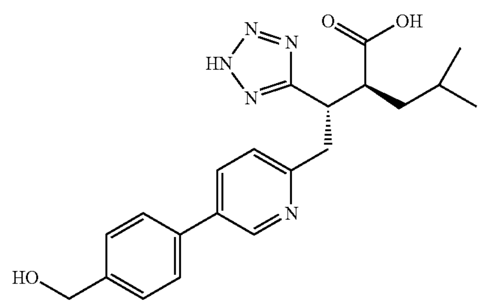 [SMILES: CC(C)C[C@H](C(=O)O)[C@H](Cc1ccc(-c2ccc(CO)cc2)cn1)c1nn[nH]n1] | (2S)-2-[(1S)-2-{5-[4-(hydroxymethyl)phenyl]pyridin-2-yl}-1-(2H-tetrazol-5-yl)ethyl]-4-methylpentanoic acid | 396.2 | 396.3 |
| 172 | 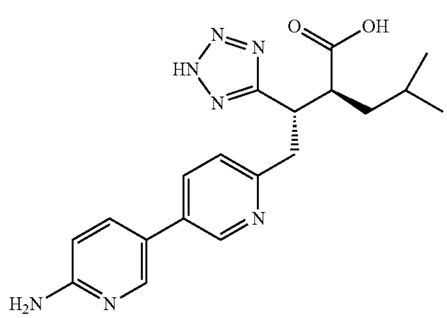 | (2S)-2-[(1S)-2-(6'-amino-3,3'-bipyridin-6-yl)-1-(2H-tetrazol-5-yl)ethyl]-4-methylpentanoic acid | 382.2 | 382.3 |
| 173 | 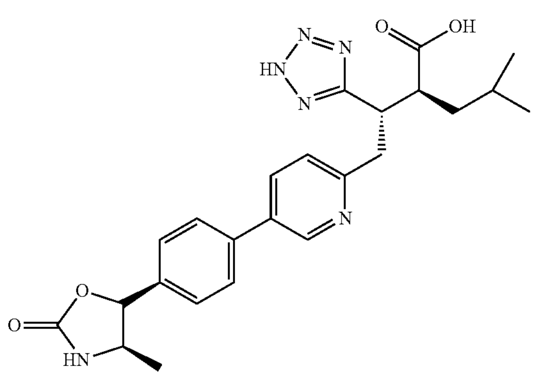 | (2S)-4-methyl-2-[(1S)-2-(5-{4-[(4R,5S)-4-methyl-2-oxo-1,3-oxazolidin-5-yl]phenyl}pyridin-2-yl)-1-(2H-tetrazol-5-yl)ethyl]pentanoic acid | 465.2 | 465.3 |

| Ex. No. | Structure | IUPAC Name | Calc'd Mass [M + H]+ | LC/MS m/e [M + H]+ |
|---|---|---|---|---|
| 174 | 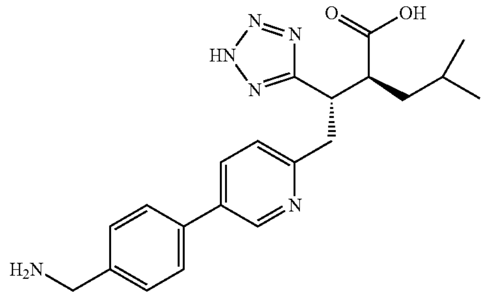 [SMILES: CC(C)C[C@H](C(=O)O)[C@H](Cc1ccc(-c2ccc(CN)cc2)cn1)c1nn[nH]n1] | (2S)-2-[(1S)-2-{5-[4-(aminomethyl)phenyl]pyridin-2-yl}-1-(2H-tetrazol-5-yl)ethyl]-4-methylpentanoic acid | 395.2 | 395.3 |
| 175 | 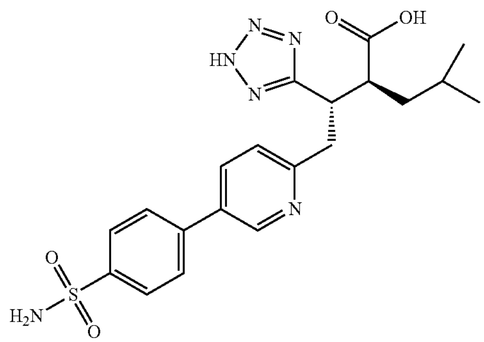 [SMILES: CC(C)C[C@H](C(=O)O)[C@H](Cc1ccc(-c2ccc(S(N)(=O)=O)cc2)cn1)c1nn[nH]n1] | (2S)-4-methyl-2-[(1S)-2-[5-(4-sulfamoylphenyl)pyridin-2-yl]-1-(2H-tetrazol-5-yl)ethyl]pentanoic acid | 445.2 | 445.2 |
| 176 | 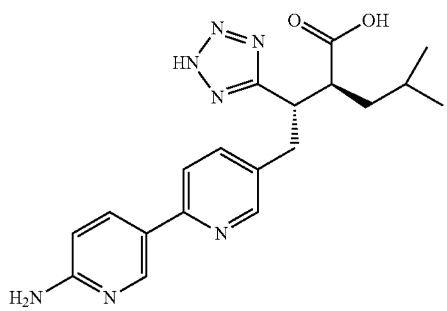 [SMILES: CC(C)C[C@H](C(=O)O)[C@H](Cc1ccc(-c2ccc(N)nc2)nc1)c1nn[nH]n1] | (2S)-2-[(1S)-2-(6'-amino-2,3'-bipyridin-5-yl)-1-(2H-tetrazol-5-yl)ethyl]-4-methylpentanoic acid | 382.2 | 382.3 |
| 177 | 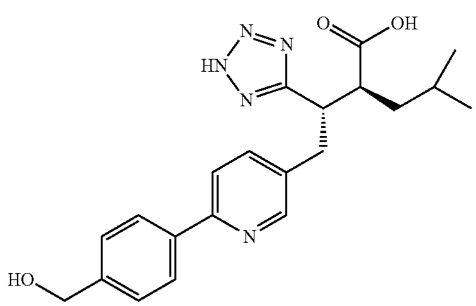 [SMILES: CC(C)C[C@H](C(=O)O)[C@H](Cc1ccc(-c2ccc(CO)cc2)nc1)c1nn[nH]n1] | (2S)-2-[(1S)-2-{6-[4-(hydroxymethyl)phenyl]pyridin-3-yl}-1-(2H-tetrazol-5-yl)ethyl]-4-methylpentanoic acid | 396.2 | 396.2 |
| 178 | 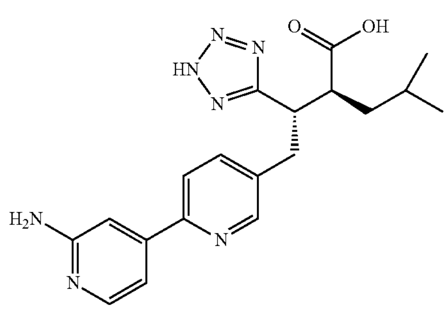 [SMILES: CC(C)C[C@H](C(=O)O)[C@H](Cc1ccc(-c2ccnc(N)c2)nc1)c1nn[nH]n1] | (2S)-2-[(1S)-2-(2'-amino-2,4'-bipyridin-5-yl)-1-(2H-tetrazol-5-yl)ethyl]-4-methylpentanoic acid | 382.2 | 382.2 |

| Ex. No. | Structure | IUPAC Name | Calc'd Mass [M + H]+ | LC/MS m/e [M + H]+ |
|---|---|---|---|---|
| 179 | 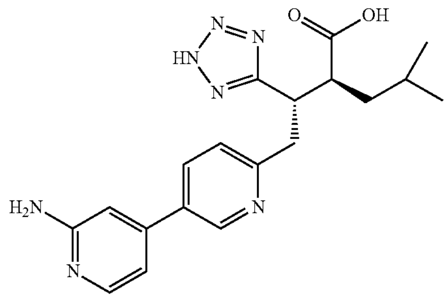 [SMILES: CC(C)C[C@H](C(=O)O)[C@H](Cc1ccc(-c2ccnc(N)c2)cn1)c1nn[nH]n1] | (2S)-2-[(1S)-2-(2'-amino-3,4'-bipyridin-6-yl)-1-(2H-tetrazol-5-yl)ethyl]-4-methylpentanoic acid | 382.2 | 382.2 |
| 180 | 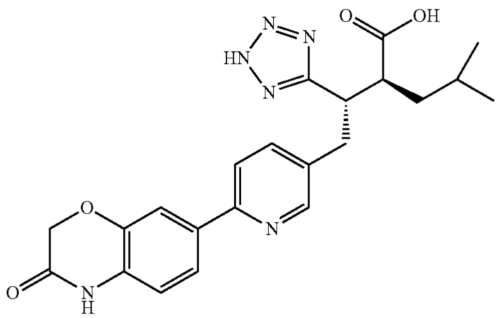 [SMILES: CC(C)C[C@H](C(=O)O)[C@H](Cc1ccc(-c2ccc3c(c2)OCC(=O)N3)nc1)c1nn[nH]n1] | (2S)-4-methyl-2-[(1S)-2-[6-(3-oxo-3,4-dihydro-2H-1,4-benzoxazin-7-yl)pyridin-3-yl]-1-(2H-tetrazol-5-yl)ethyl]pentanoic acid | 437.2 | 437.2 |
| 181 | 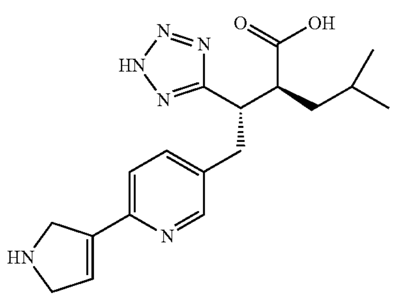 [SMILES: CC(C)C[C@H](C(=O)O)[C@H](Cc1ccc(C2=CCNC2)nc1)c1nn[nH]n1] | (2S)-2-[(1S)-2-[6-(2,5-dihydro-1H-pyrrol-3-yl)pyridin-3-yl]-1-(2H-tetrazol-5-yl)ethyl]-4-methylpentanoic acid | 357.2 | 357.2 |
| 182 | 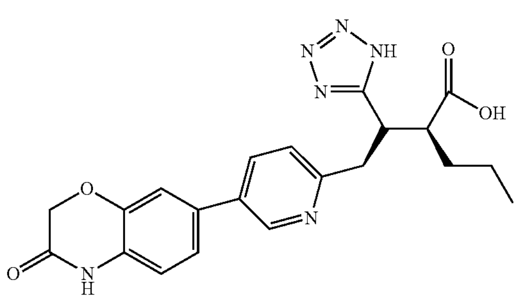 | (2S)-2-[(1R)-2-[5-(3-oxo-3,4-dihydro-2H-1,4-benzoxazin-7-yl)pyridin-2-yl]-1-(1H-tetrazol-5-yl)ethyl]pentanoic acid | 423.2 | 423.3 |

EXAMPLEs 183-188

Parallel synthesis of (2R)-2-[(1R)-2-[4'-substituted phenyl]-1-(2H-tetrazol-5-yl)ethyl]hexanoic acid

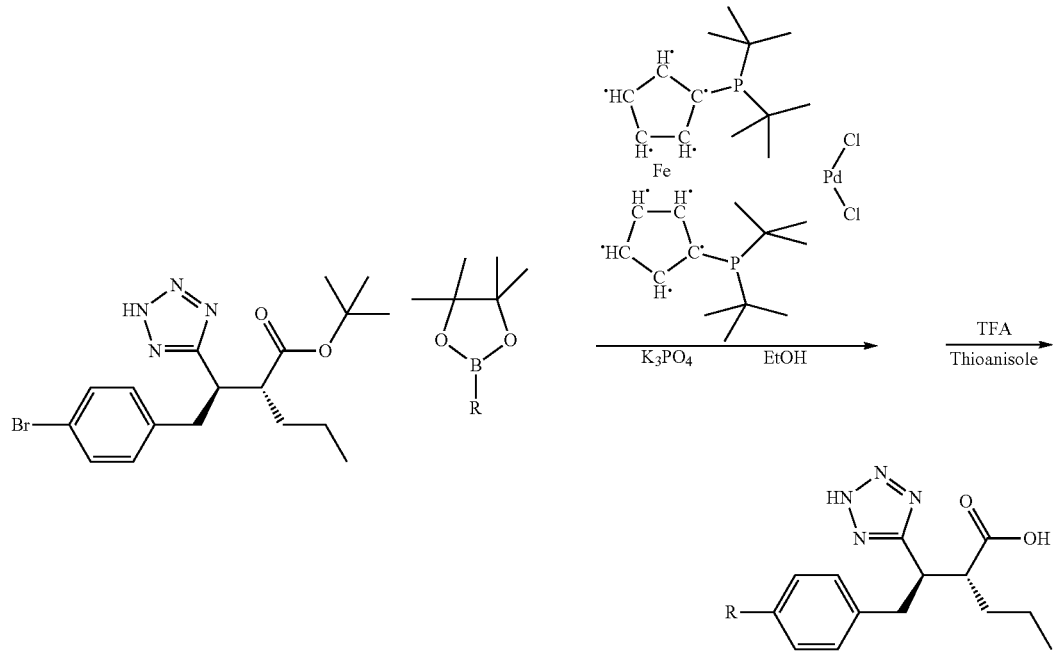

Step A: Palladium Catalyzed C—C Coupling of Arylbromide and Boronic Acids.

Into 2 dram vials were added substituted boronic acid or ester (0.071 mmol), palladium catalyst (3.07 mg, 4.7 µmol) and 189 µL of 1 N degassed aq. K₃PO₄ solution. In glove box, 1 mL of solution of (R)-tert-butyl 2-((R)-2-(4-bromophenyl)-1-(2H-tetrazol-5-yl)ethyl)pentanoate (20 mg, 0.047 mmol) in EtOH were added into each vial. The vials were capped and heated at 70° C. with stirring for 20 hr (overnight). After the vials were cooled down to room temperature, the solvent was removed in GeneVac. Into each residue was added 600 µL of H₂O and 2 mL of DCM. The organic layers were transferred into 2 dram vials. The organic solvent was removed in GeneVac to afford the crude intermediates.

Step B: Removal of the Tert-Butyl Protecting Group Under Acidic Conditions

Into each vial was added a solution of thioanisole (0.3 mL) and DCM (0.3 mL) in TFA (0.3 mL). The vials were agitated at 25° C. for 16 hr. The solvent was removed in a GeneVac. The residues were dissolved in 1.3 mL of DMSO. Each crude mixture was filtered into a 96-well tray and purified by HPLC to afford EXAMPLES 183 to 188.

| Ex. No. | Structure | IUPAC Name | Calc'd Mass [M + H]+ | LC/MS m/e [M + H]+ |
|---|---|---|---|---|
| 183 | 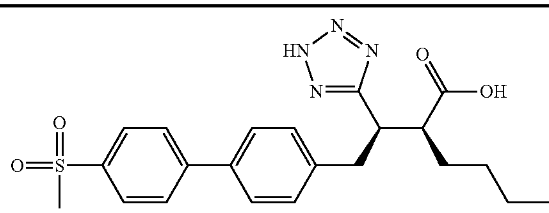 | (2R)-2-[(1R)-2-[4'-(methylsulfonyl)biphenyl-4-yl]-1-(2H-tetrazol-5-yl)ethyl]hexanoic acid | 443.18 | 443.17 |
| 184 | 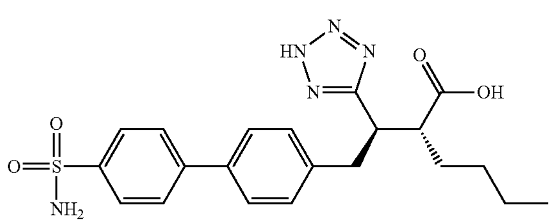 [SMILES: CCCC[C@@H](C(=O)O)[C@@H](Cc1ccc(-c2ccc(S(N)(=O)=O)cc2)cc1)c1nn[nH]n1] | (2R)-2-[(1R)-2-(4'-sulfamoylbiphenyl-4-yl)-1-(2H-tetrazol-5-yl)ethyl]hexanoic acid | 444.17 | 444.16 |

| Ex. No. | Structure | IUPAC Name | Calc'd Mass [M + H]+ | LC/MS m/e [M + H]+ |
|---|---|---|---|---|
| 185 | 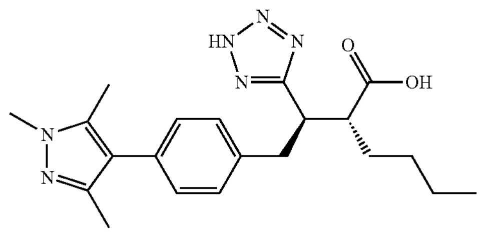 [SMILES: CCCC[C@@H](C(=O)O)[C@@H](Cc1ccc(-c2c(C)nn(C)c2C)cc1)c1nn[nH]n1] | (2R)-2-{(1R)-1-(2H-tetrazol-5-yl)-2-[4-(1,3,5-trimethyl-1H-pyrazol-4-yl)phenyl]ethyl} hexanoic acid | 397.23 | 397.23 |
| 186 | 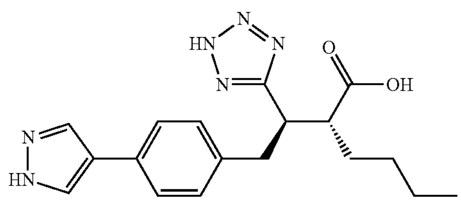 [SMILES: CCCC[C@@H](C(=O)O)[C@@H](Cc1ccc(-c2cn[nH]c2)cc1)c1nn[nH]n1] | (2R)-2-[(1R)-2-[4-(1H-pyrazol-4-yl)phenyl]-1-(2H-tetrazol-5-yl)ethyl] hexanoic acid | 355.19 | 355.18 |
| 187 | 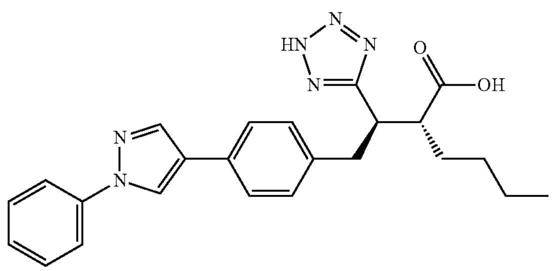 [SMILES: CCCC[C@@H](C(=O)O)[C@@H](Cc1ccc(-c2cnn(-c3ccccc3)c2)cc1)c1nn[nH]n1] | (2R)-2-[(1R)-2-[4-(1-phenyl-1H-pyrazol-4-yl)phenyl]-1-(2H-tetrazol-5-yl)ethyl]hexanoic acid | 431.22 | 431.21 |
| 188 | 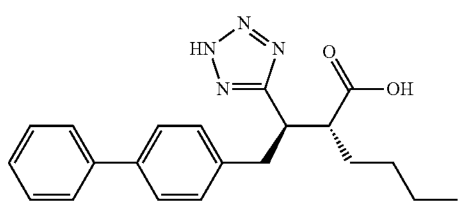 [SMILES: CCCC[C@@H](C(=O)O)[C@@H](Cc1ccc(-c2ccccc2)cc1)c1nn[nH]n1] | (2R)-2-[(1R)-2-biphenyl-4-yl-1-(2H-tetrazol-5-yl)ethyl]hexanoic acid | 365.2 | 365.19 |

EXAMPLEs 189-214

Parallel synthesis of (2S)-2-[(1S)-2-[4'-substituted phenyl]-1-(2H-tetrazol-5-yl)ethyl]hexanoic acid

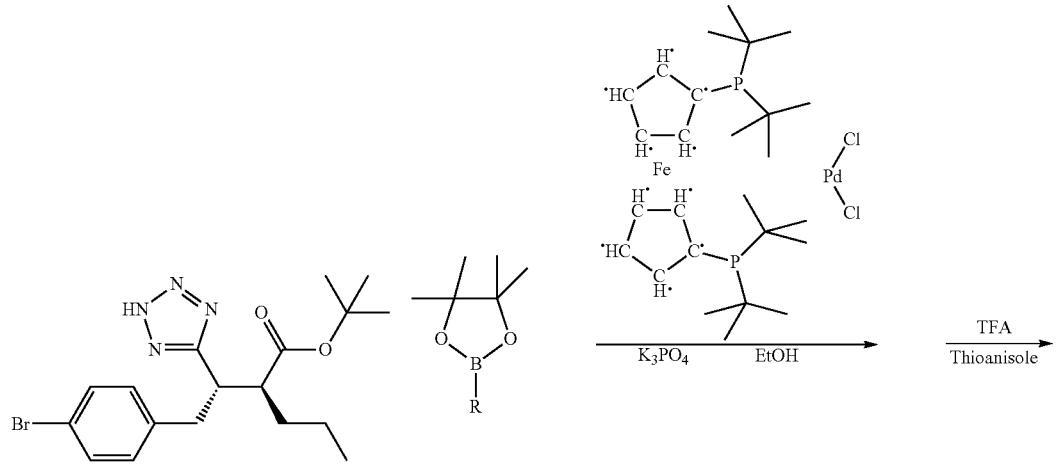

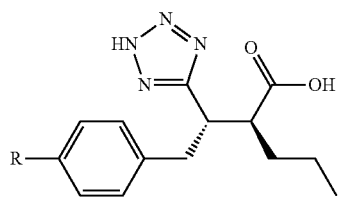

Step A: Palladium Catalyzed C—C Coupling of Arylbromide and Boronic Acids.

Into 2 dram vials was added substituted boronic acid or ester (0.071 mmol), palladium catalyst (3.07 mg, 4.7 μmol) and 189 μL of 1 N degassed aq. K₃PO₄ solution. In glove box, 1 mL of solution of (S)-tert-butyl 2-((S)-2-(4-bromophenyl)-1-(2H-tetrazol-5-yl)ethyl)pentanoate (20 mg, 0.047 mmol) in EtOH was added into each vial. The vials were capped and heated at 70° C. with stirring for 20 hr (overnight). After the vials were cooled down to room temperature, the solvent was removed in GeneVac. Into each residue was added 600 μL of H₂O and 2 mL of DCM. The organic layers were transferred into 2 dram vials. The organic solvent was removed in GeneVac to afford the crude intermediates.

Step B: Removal of the Tert-Butyl Protecting Group Under Acidic Conditions

Into each vial was added a solution of thioanisole (0.3 mL), DCM (0.3 mL) in TFA (0.3 mL). The vials were agitated at 25° C. for 16 hr. The solvent was removed in a GeneVac. The residues were dissolved in 1.3 mL of DMSO. Each crude mixture was filtered into a 96-well tray and purified by HPLC to afford the EXAMPLES 189 to 214.

| Ex. No. | Structure | IUPAC Name | Calc'd Mass [M + H]+ | LC/MS m/e [M + H]+ |
|---|---|---|---|---|
| 189 | 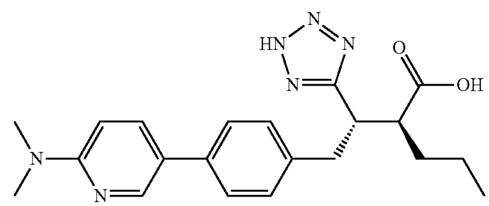 [SMILES: CCC[C@H](C(=O)O)[C@H](Cc1ccc(-c2ccc(N(C)C)nc2)cc1)c1nn[nH]n1] | (2S)-2-[(1S)-2-{4-[6-(dimethylamino)pyridin-3-yl]phenyl}-1-(2H-tetrazol-5-yl)ethyl]pentanoic acid | 395.21 | 395.21 |
| 190 | 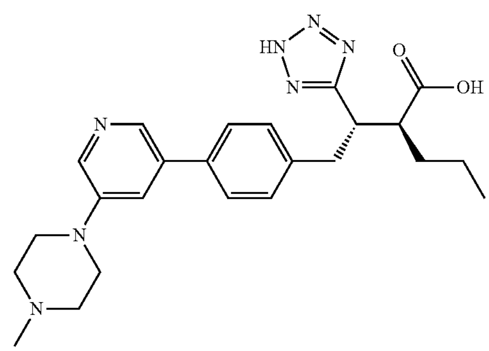 [SMILES: CCC[C@H](C(=O)O)[C@H](Cc1ccc(-c2cncc(N3CCN(C)CC3)c2)cc1)c1nn[nH]n1] | (2S)-2-[(1S)-2-{4-[5-(4-methylpiperazin-1-yl)pyridin-3-yl]phenyl}-1-(2H-tetrazol-5-yl)ethyl]pentanoic acid | 450.26 | 450.25 |
| 191 | 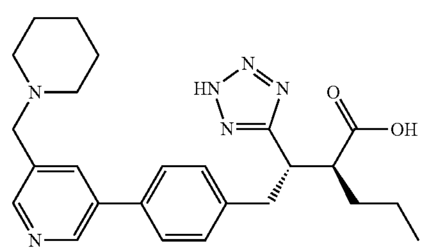 [SMILES: CCC[C@H](C(=O)O)[C@H](Cc1ccc(-c2cncc(CN3CCCCC3)c2)cc1)c1nn[nH]n1] | (2S)-2-[(1S)-2-{4-[5-(piperidin-1-ylmethyl)pyridin-3-yl]phenyl}-1-(2H-tetrazol-5-yl)ethyl]pentanoic acid | 449.27 | 449.26 |
| 192 | 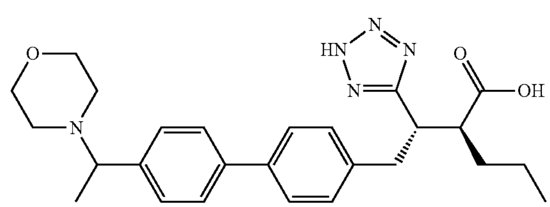 [SMILES: CCC[C@H](C(=O)O)[C@H](Cc1ccc(-c2ccc(C(C)N3CCOCC3)cc2)cc1)c1nn[nH]n1] | (2S)-2-[(1S)-2-[4'-(1-morpholin-4-ylethyl)biphenyl-4-yl]-1-(2H-tetrazol-5-yl)ethyl]pentanoic acid | 464.27 | 464.26 |

-continued

| Ex. No. | Structure | IUPAC Name | Calc'd Mass [M + H]+ | LC/MS m/e [M + H]+ |
|---|---|---|---|---|
| 193 | 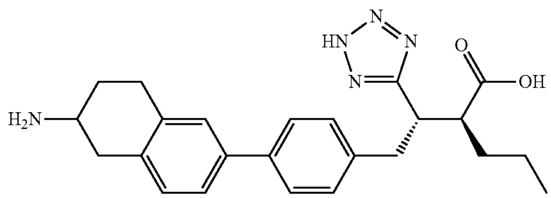 [SMILES: CCC[C@H](C(=O)O)[C@H](Cc1ccc(-c2ccc3c(c2)CCC(N)C3)cc1)c1nn[nH]n1] | (2S)-2-[(1S)-2-[4-(6-amino-5,6,7,8-tetrahydronaphthalen-2-yl)phenyl]-1-(2H-tetrazol-5-yl)ethyl]pentanoic acid | 420.24 | 420.23 |
| 194 | 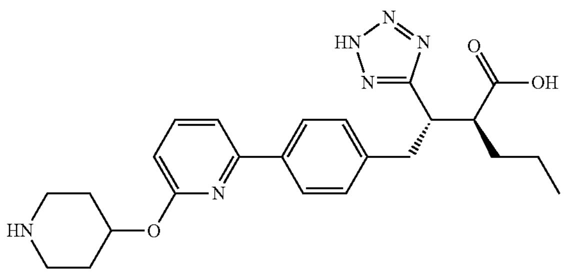 [SMILES: CCC[C@H](C(=O)O)[C@H](Cc1ccc(-c2cccc(OC3CCNCC3)n2)cc1)c1nn[nH]n1] | (2S)-2-[(1S)-2-{4-[6-(piperidin-4-yloxy)pyridin-2-yl]phenyl}-1-(2H-tetrazol-5-yl)ethyl]pentanoic acid | 451.25 | 451.24 |
| 195 | 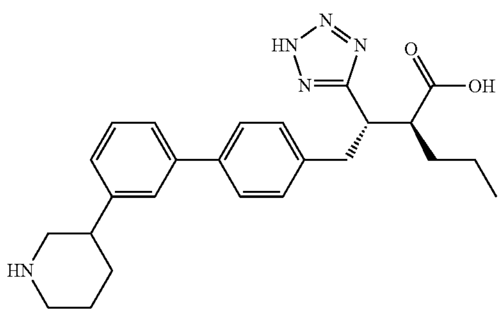 [SMILES: CCC[C@H](C(=O)O)[C@H](Cc1ccc(-c2cccc(C3CCCNC3)c2)cc1)c1nn[nH]n1] | (2S)-2-[(1S)-2-(3'-piperidin-3-ylbiphenyl-4-yl)-1-(2H-tetrazol-5-yl)ethyl]pentanoic acid | 434.26 | 434.25 |
| 196 | 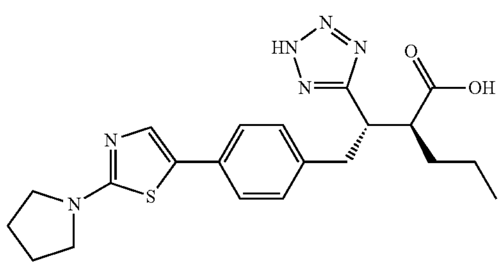 [SMILES: CCC[C@H](C(=O)O)[C@H](Cc1ccc(-c2cnc(N3CCCC3)s2)cc1)c1nn[nH]n1] | (2S)-2-[(1S)-2-[4-(2-pyrrolidin-1-yl-1,3-thiazol-5-yl)phenyl]-1-(2H-tetrazol-5-yl)ethyl]pentanoic acid | 427.19 | 427.18 |
| 197 | 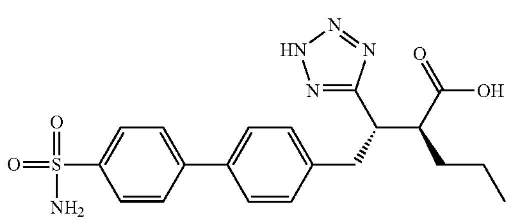 [SMILES: CCC[C@H](C(=O)O)[C@H](Cc1ccc(-c2ccc(S(N)(=O)=O)cc2)cc1)c1nn[nH]n1] | (2S)-2-[(1S)-2-(4'-sulfamoylbiphenyl-4-yl)-1-(2H-tetrazol-5-yl)ethyl]pentanoic acid | 430.15 | 430.15 |
| 198 | 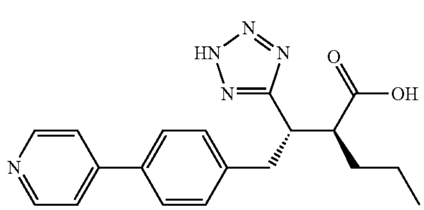 [SMILES: CCC[C@H](C(=O)O)[C@H](Cc1ccc(-c2ccncc2)cc1)c1nn[nH]n1] | (2S)-2-[(1S)-2-(4-pyridin-4-ylphenyl)-1-(2H-tetrazol-5-yl)ethyl]pentanoic acid | 352.18 | 352.17 |

-continued

| Ex. No. | Structure | IUPAC Name | Calc'd Mass [M + H]+ | LC/MS m/e [M + H]+ |
|---|---|---|---|---|
| 199 | 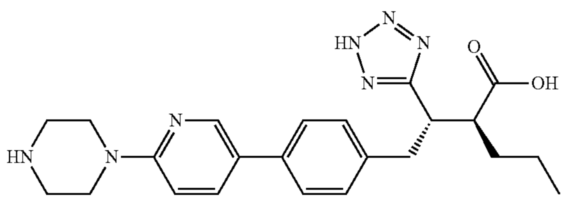 [SMILES: CCC[C@H](C(=O)O)[C@H](Cc1ccc(-c2ccc(N3CCNCC3)nc2)cc1)c1nn[nH]n1] | (2S)-2-[(1S)-2-[4-(6-piperazin-1-ylpyridin-3-yl)phenyl]-1-(2H-tetrazol-5-yl)ethyl]pentanoic acid | 436.25 | 436.24 |
| 200 | 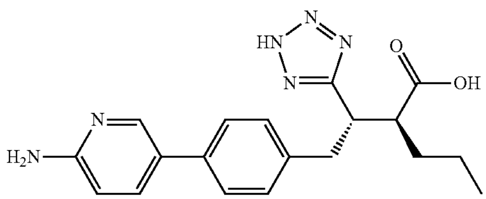 [SMILES: CCC[C@H](C(=O)O)[C@H](Cc1ccc(-c2ccc(N)nc2)cc1)c1nn[nH]n1] | (2S)-2-[(1S)-2-[4-(6-aminopyridin-3-yl)phenyl]-1-(2H-tetrazol-5-yl)ethyl]pentanoic acid | 367.19 | 367.18 |
| 201 | 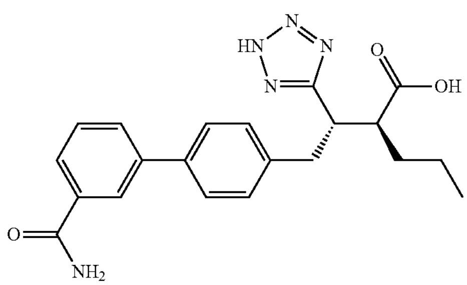 [SMILES: CCC[C@H](C(=O)O)[C@H](Cc1ccc(-c2cccc(C(N)=O)c2)cc1)c1nn[nH]n1] | (2S)-2-[(1S)-2-(3'-carbamoylbiphenyl-4-yl)-1-(2H-tetrazol-5-yl)ethyl]pentanoic acid | 394.19 | 394.18 |
| 202 | 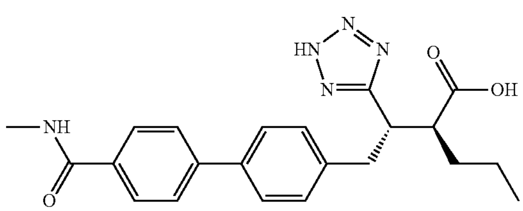 [SMILES: CCC[C@H](C(=O)O)[C@H](Cc1ccc(-c2ccc(C(=O)NC)cc2)cc1)c1nn[nH]n1] | (2S)-2-[(1S)-2-[4'-(methylcarbamoyl)biphenyl-4-yl]-1-(2H-tetrazol-5-yl)ethyl]pentanoic acid | 408.2 | 408.2 |
| 203 | 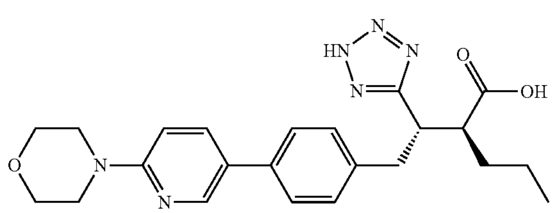 [SMILES: CCC[C@H](C(=O)O)[C@H](Cc1ccc(-c2ccc(N3CCOCC3)nc2)cc1)c1nn[nH]n1] | (2S)-2-[(1S)-2-[4-(6-morpholin-4-ylpyridin-3-yl)phenyl]-1-(2H-tetrazol-5-yl)ethyl]pentanoic acid | 437.23 | 437.22 |
| 204 | 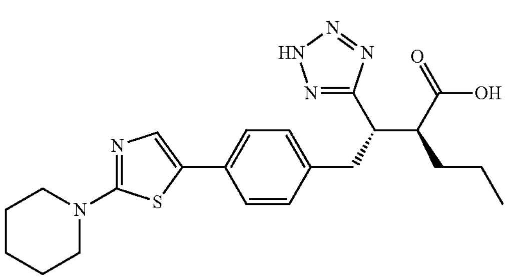 [SMILES: CCC[C@H](C(=O)O)[C@H](Cc1ccc(-c2cnc(N3CCCCC3)s2)cc1)c1nn[nH]n1] | (2S)-2-[(1S)-2-[4-(2-piperidin-1-yl-1,3-thiazol-5-yl)phenyl]-1-(2H-tetrazol-5-yl)ethyl]pentanoic acid | 441.21 | 441.2 |

-continued

| Ex. No. | Structure | IUPAC Name | Calc'd Mass [M + H]+ | LC/MS m/e [M + H]+ |
|---|---|---|---|---|
| 205 | 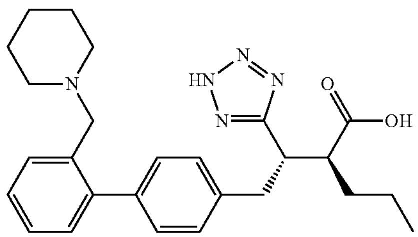 [SMILES: CCC[C@H](C(=O)O)[C@H](Cc1ccc(-c2ccccc2CN2CCCCC2)cc1)c1nn[nH]n1] | (2S)-2-[(1S)-2-[2'-(piperidin-1-ylmethyl)biphenyl-4-yl]-1-(2H-tetrazol-5-yl)ethyl]pentanoic acid | 448.27 | 448.26 |
| 206 | 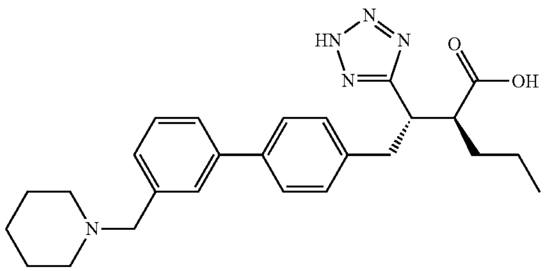 [SMILES: CCC[C@H](C(=O)O)[C@H](Cc1ccc(-c2cccc(CN3CCCCC3)c2)cc1)c1nn[nH]n1] | (2S)-2-[(1S)-2-[3'-(piperidin-1-ylmethyl)biphenyl-4-yl]-1-(2H-tetrazol-5-yl)ethyl]pentanoic acid | 448.27 | 448.26 |
| 207 | 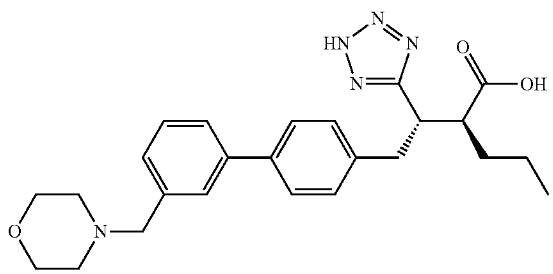 [SMILES: CCC[C@H](C(=O)O)[C@H](Cc1ccc(-c2cccc(CN3CCOCC3)c2)cc1)c1nn[nH]n1] | (2S)-2-[(1S)-2-[3'-(morpholin-4-ylmethyl)biphenyl-4-yl]-1-(2H-tetrazol-5-yl)ethyl]pentanoic acid | 450.25 | 450.24 |
| 208 | 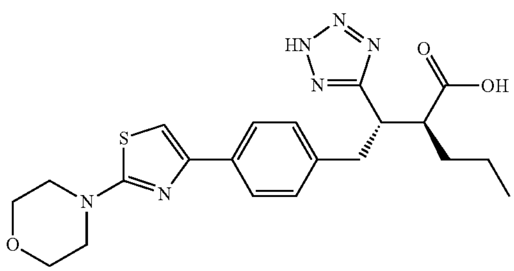 [SMILES: CCC[C@H](C(=O)O)[C@H](Cc1ccc(-c2csc(N3CCOCC3)n2)cc1)c1nn[nH]n1] | (2S)-2-[(1S)-2-[4-(2-morpholin-4-yl-1,3-thiazol-4-yl)phenyl]-1-(2H-tetrazol-5-yl)ethyl]pentanoic acid | 443.19 | 443.18 |
| 209 | 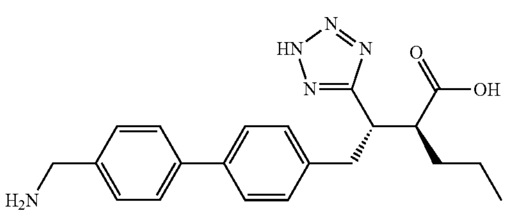 [SMILES: CCC[C@H](C(=O)O)[C@H](Cc1ccc(-c2ccc(CN)cc2)cc1)c1nn[nH]n1] | (2S)-2-[(1S)-2-[4'-(aminomethyl)biphenyl-4-yl]-1-(2H-tetrazol-5-yl)ethyl]pentanoic acid | 380.21 | 380.2 |
| 210 | 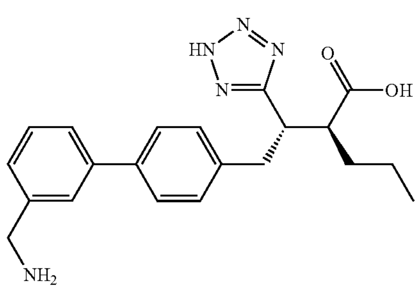 [SMILES: CCC[C@H](C(=O)O)[C@H](Cc1ccc(-c2cccc(CN)c2)cc1)c1nn[nH]n1] | (2S)-2-[(1S)-2-[3'-(aminomethyl)biphenyl-4-yl]-1-(2H-tetrazol-5-yl)ethyl]pentanoic acid | 380.21 | 380.2 |

| Ex. No. | Structure | IUPAC Name | Calc'd Mass [M + H]+ | LC/MS m/e [M + H]+ |
|---|---|---|---|---|
| 211 | 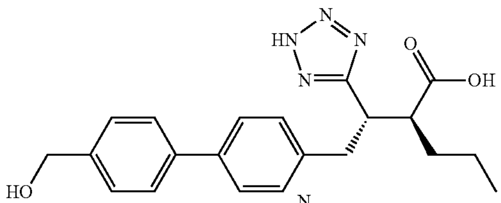 | (2S)-2-[(1S)-2-[4'-(hydroxymethyl)biphenyl-4-yl]-1-(2H-tetrazol-5-yl)ethyl]pentanoic acid | 381.19 | 381.18 |
| 212 | 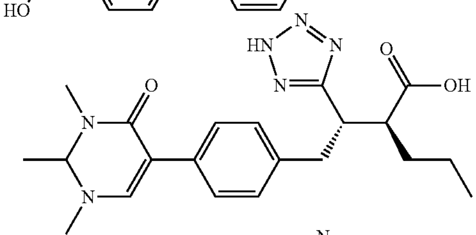 | (2S)-2-[(1S)-2-[4-(1,3-dimethyl-2,4-dioxo-1,2,3,4-tetrahydropyrimidin-5-yl)phenyl]-1-(2H-tetrazol-5-yl)ethyl]pentanoic acid | 413.19 | 413.19 |
| 213 | 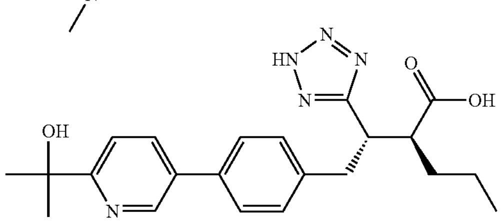 | (2S)-2-[(1S)-2-{4-[6-(1-hydroxy-1-methylethyl)pyridin-3-yl]phenyl}-1-(2H-tetrazol-5-yl)ethyl]pentanoic acid | 410.22, | 410.21 |
| 214 | 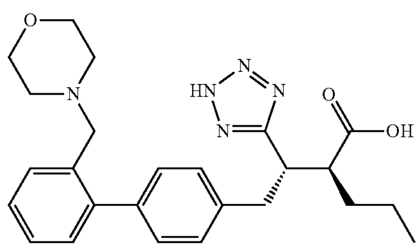 [SMILES: CCC[C@H](C(=O)O)[C@H](Cc1ccc(-c2ccccc2CN2CCOCC2)cc1)c1nn[nH]n1] | (2S)-2-[(1S)-2-[2'-(morpholin-4-ylmethyl)biphenyl-4-yl]-1-(2H-tetrazol-5-yl)ethyl]pentanoic acid | 450.25 | 450.24 |

EXAMPLEs 215-224

Parallel synthesis of (2S)-2-[(1S)-2-[4'-amino substituted phenyl]-1-(2H-tetrazol-5-yl)ethyl]hexanoic acid:

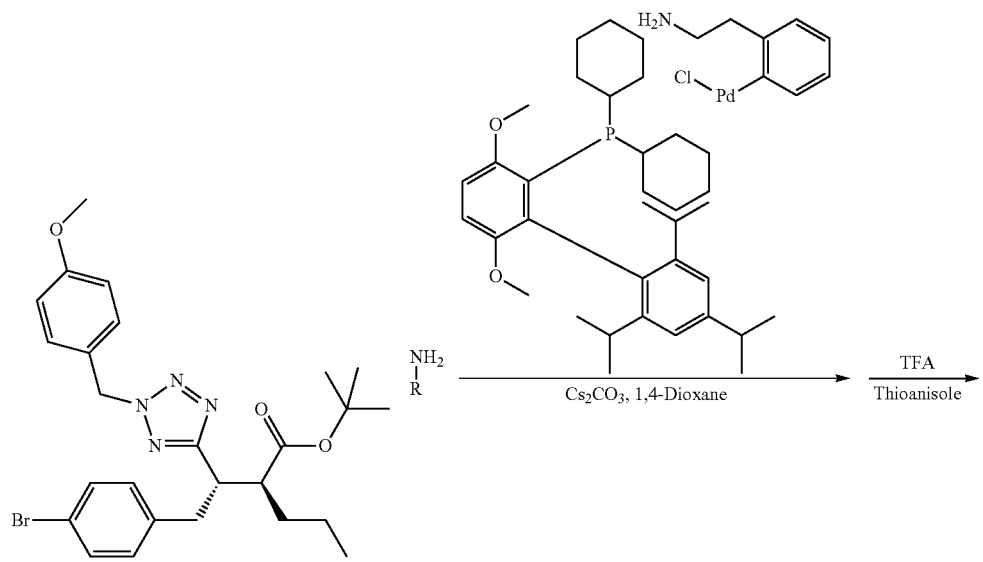

-continued

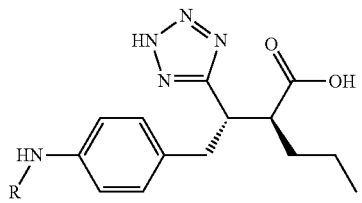

Step A: Palladium Catalyzed C—N Coupling of Arylbromide and Primary Amines.

Into 2 dram vials were added substituted primary amines (0.15 mmol), palladium catalyst (4.07 mg, 5.1 µmol) and cesium carbonate (66.5 mg, 0.2 mmol). In glove box, 1 mL of solution of (S)-tert-butyl 2-((S)-2-(4-bromophenyl)-1-(2-(4-methylbenzyl)-2H-tetrazol-5-yl)ethyl)pentanoate (27 mg, 0.051 mmol) in 1,4-Dioxane was added into each vial. The vials were capped and heated at 90° C. with stirring for 20 hr (overnight). After the vials were cooled down to room temperature, the solvent was removed in GeneVac. Into each residue was added 600 µL of H₂O and 2 mL of DCM. The organic layers were transferred into 2 dram vials. The organic solvent was removed in GeneVac to afford the crude intermediates.

Step B: Removal of the Tert-Butyl and p-Methoxybenzyl (PMB) Protecting Group Under Acidic Conditions.

Into each vial was added a solution of thioanisole (0.3 mL), and DCM (0.3 mL) in TFA (0.3 mL). The vials were agitated at 25° C. for 16 hr. The solvent was removed in a GeneVac. Into each vial was added a solution of thioanisole (0.3 mL), and DCM (0.3 mL) in TFA (0.3 mL). The vials were agitated at 55° C. for 16 hr. The solvent was removed in a GeneVac. The residues were dissolved in 1.3 mL of DMSO. Each crude mixture was filtered into a 96-well tray and purified by HPLC to afford the EXAMPLES 215 to 224.

| Ex. No. | Structure | IUPAC Name | Calc'd Mass [M + H]+ | LC/MS m/e [M + H]+ |
|---|---|---|---|---|
| 215 | 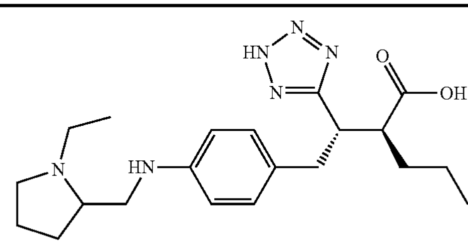 | (2S)-2-[(1S)-2-(4-{[(1-ethylpyrrolidin-2-yl)methyl]amino}phenyl)-1-(2H-tetrazol-5-yl)ethyl]pentanoic acid | 401.27 | 401.26 |
| 216 | 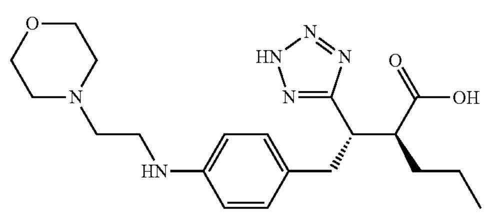 [SMILES: CCC[C@H](C(=O)O)[C@H](Cc1ccc(NCCN2CCOCC2)cc1)c1nn[nH]n1] | (2S)-2-[(1S)-2-{4-[(2-morpholin-4-ylethyl)amino]phenyl}-1-(2H-tetrazol-5-yl)ethyl]pentanoic acid | 403.25 | 403.24 |
| 217 | 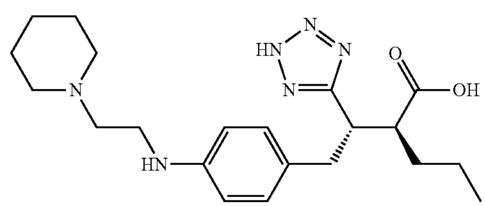 [SMILES: CCC[C@H](C(=O)O)[C@H](Cc1ccc(NCCN2CCCCC2)cc1)c1nn[nH]n1] | (2S)-2-[(1S)-2-{4-[(2-piperidin-1-ylethyl)amino]phenyl}-1-(2H-tetrazol-5-yl)ethyl]pentanoic acid | 401.27 | 401.26 |
| 218 | 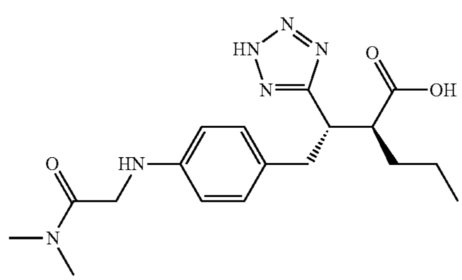 [SMILES: CCC[C@H](C(=O)O)[C@H](Cc1ccc(NCC(=O)N(C)C)cc1)c1nn[nH]n1] | (2S)-2-[(1S)-2-(4-{[2-(dimethylamino)-2-oxoethyl]amino}phenyl)-1-(2H-tetrazol-5-yl)ethyl]pentanoic acid | 375.21 | 375.21 |

| Ex. No. | Structure | IUPAC Name | Calc'd Mass [M + H]+ | LC/MS m/e [M + H]+ |
|---|---|---|---|---|
| 219 | 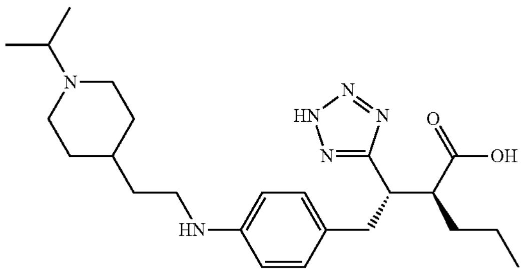 [SMILES: CCC[C@H](C(=O)O)[C@H](Cc1ccc(NCCC2CCN(C(C)C)CC2)cc1)c1nn[nH]n1] | (2S)-2-[(1S)-2-[4-({2-[4-(1-methylethyl)piperazin-1-yl]ethyl}amino)phenyl]-1-(2H-tetrazol-5-yl)ethyl]pentanoic acid | 444.31 | 444.3 |
| 220 | 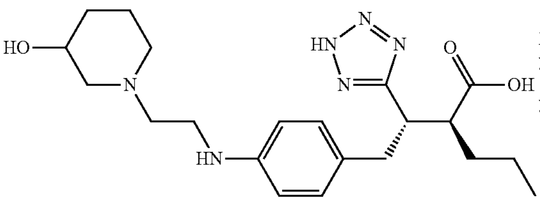 [SMILES: CCC[C@H](C(=O)O)[C@H](Cc1ccc(NCCN2CCCC(O)C2)cc1)c1nn[nH]n1] | (2S)-2-[(1S)-2-(4-{[2-(3-hydroxypiperidin-1-yl)ethyl]amino}phenyl)-1-(2H-tetrazol-5-yl)ethyl]pentanoic acid | 417.26 | 417.25 |
| 221 | 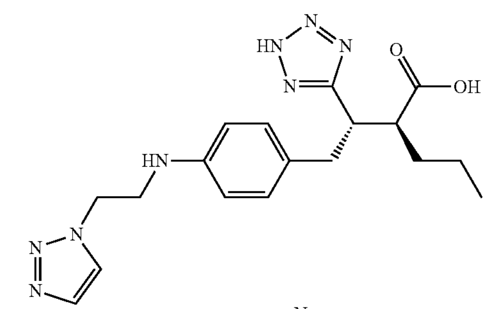 | (2S)-2-[(1S)-1-(2H-tetrazol-5-yl)-2-(4-{[2-(1H-1,2,3-triazol-1-yl)ethyl]amino}phenyl)ethyl]pentanoic acid | 385.21 | 385.2 |
| 222 | 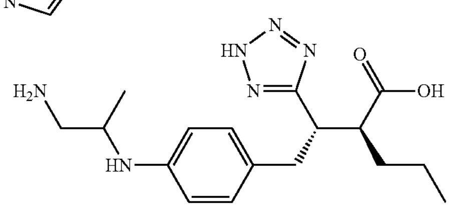 | (2S)-2-[(1S)-2-{4-[(2-amino-1-methylethyl)amino]phenyl}-1-(2H-tetrazol-5-yl)ethyl]pentanoic acid | 347.22 | 347.21 |
| 223 | 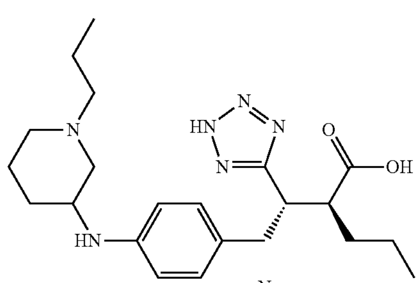 | (2S)-2-[(1S)-2-{4-[(1-propylpiperidin-3-yl)amino]phenyl}-1-(2H-tetrazol-5-yl)ethyl]pentanoic acid | 415.28 | 415.27 |
| 224 | 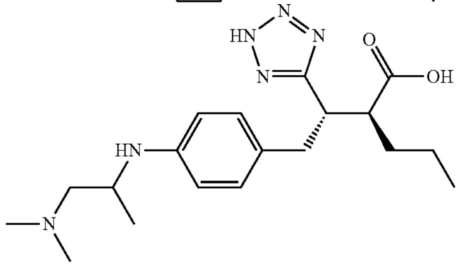 | (2S)-2-[(1S)-2-(4-{[2-(dimethylamino)-1-methylethyl]amino}phenyl)-1-(2H-tetrazol-5-yl)ethyl]pentanoic acid | 375.25 | 375.24 |

EXAMPLEs 225-232

Parallel synthesis of (2S)-2-[(1S)-2-[4'-aminosubstituted phenyl]-1-(2H-tetrazol-5-yl)ethyl]hexanoic acid

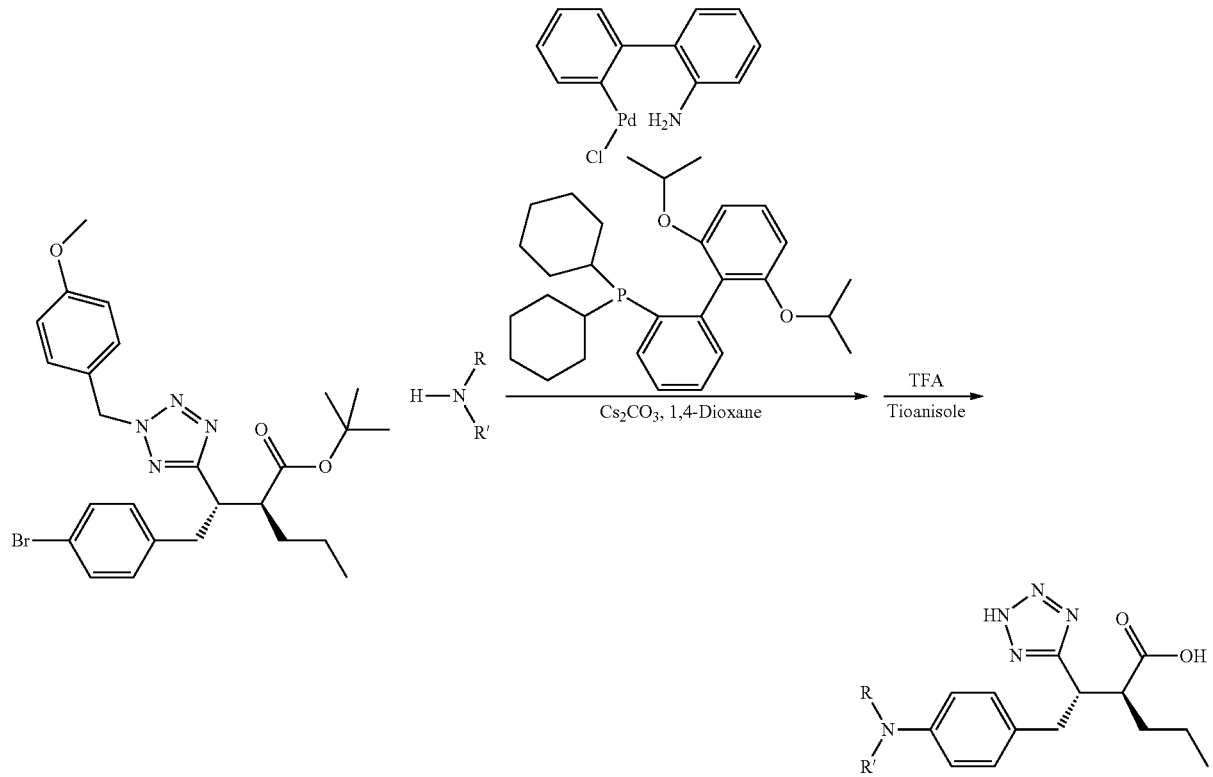

Step A: Palladium Catalyzed C—N Coupling of Arylbromide and Secondary Amines

Into 2 dram vials were added substituted primary amines (0.15 mmol), palladium catalyst (4.07 mg, 5.1 µmol) and cesium carbonate (66.5 mg, 0.2 mmol). In glove box, 1 mL of solution of (S)-tert-butyl 2-((S)-2-(4-bromophenyl)-1-(2-(4-methylbenzyl)-2H-tetrazol-5-yl)ethyl)pentanoate (27 mg, 0.051 mmol) in 1,4-Dioxane were added into each vial. The vials were capped and heated at 90° C. with stirring for 20 hr (overnight). After the vials were cooled down to room temperature, the solvent was removed in GeneVac. Into each residue was added 600 µL of $H_2O$ and 2 mL of DCM. The organic layers were transferred into 2 dram vials. The organic solvent was removed in GeneVac to afford the crude intermediates.

Step B: Removal of the Tert-Butyl and p-Methoxybenzyl (PMB) Protecting Group Under Acidic Conditions Into each vial was added a solution of thioanisole (0.3 mL), and DCM (0.3 mL) in TFA (0.3 mL). The vials were agitated at 25° C. for 16 hr. The solvent was removed in a GeneVac. Into each vial was added a solution of thioanisole (0.3 mL), and DCM (0.3 mL) in TFA (0.3 mL). The vials were agitated at 55° C. for 16 hr. The solvent was removed in a GeneVac. The residues were dissolved in 1.3 mL of DMSO. Each crude mixture was filtered into a 96-well tray and purified by HPLC to afford the EXAMPLES 225 to 232.

| Ex. No. | Structure | IUPAC Name | Calc'd Mass [M + H]+ | LC/MS m/e [M + H]+ |
|---|---|---|---|---|
| 225 | 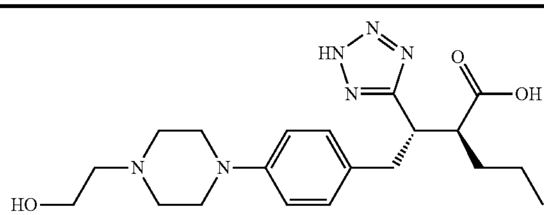 | (2S)-2-[(1S)-2-{4-[4-(2-hydroxyethyl)piperazin-1-yl]phenyl}-1-(2H-tetrazol-5-yl)ethyl]pentanoic acid | 403.25 | 403.24 |

-continued

| Ex. No. | Structure | IUPAC Name | Calc'd Mass [M + H]+ | LC/MS m/e [M + H]+ |
|---|---|---|---|---|
| 226 | 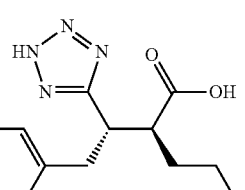 | (2S)-2-[(1S)-2-[4-(4-phenylpiperazin-1-yl)phenyl]-1-(2H-tetrazol-5-yl)ethyl]pentanoic acid | 435.25 | 435.24 |
| 227 | 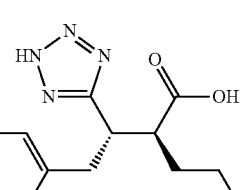 | (2S)-2-[(1S)-2-[4-(4-pyridin-4-ylpiperazin-1-yl)phenyl]-1-(2H-tetrazol-5-yl)ethyl]pentanoic acid | 436.25 | 436.24 |
| 228 | 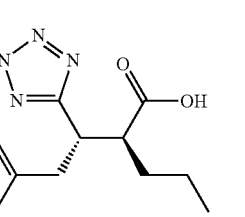 | (2S)-2-[(1S)-2-[4-(4-acetylpiperazin-1-yl)phenyl]-1-(2H-tetrazol-5-yl)ethyl]pentanoic acid | 401.23 | 401.22 |
| 229 | 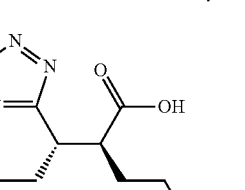 | (2S)-2-[(1S)-2-{4-[(3R)-3-aminopiperidin-1-yl]phenyl}-1-(2H-tetrazol-5-yl)ethyl]pentanoic acid | 373.23 | 373.23 |
| 230 | 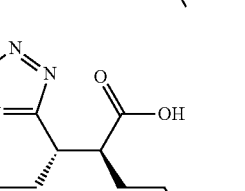 | (2S)-2-[(1S)-2-{4-[(3S)-3-aminopiperidin-1-yl]phenyl}-1-(2H-tetrazol-5-yl)ethyl]pentanoic acid | 373.23 | 373.23 |
| 231 | 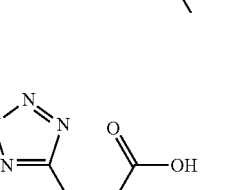 | (2S)-2-[(1S)-2-[4-(4-methylpiperazin-1-yl)phenyl]-1-(2H-tetrazol-5-yl)ethyl]pentanoic acid | 373.23 | 373.23 |
| 232 | 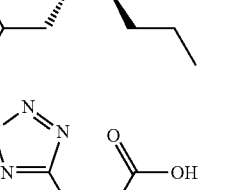 | (2S)-2-[(1S)-2-[4-(hexahydropyrrolo[1,2-a]pyrazin-2(1H)-yl)phenyl]-1-(2H-tetrazol-5-yl)ethyl]pentanoic acid | 399.25 | 399.24 |

EXAMPLEs 233-250
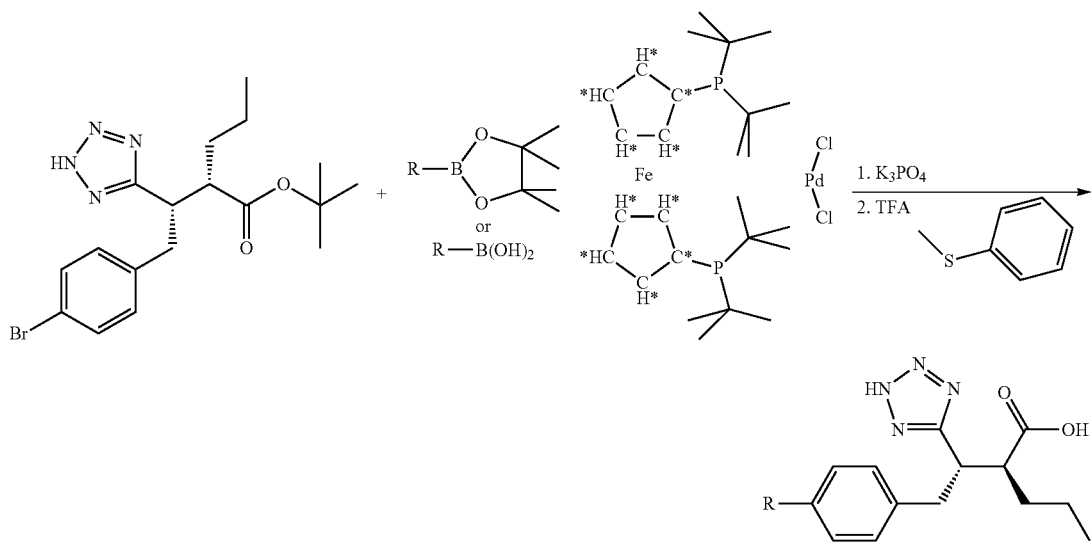
| Ex. No. | Structure | IUPAC Name | Calc'd Mass [M + H]+ | LC/MS m/e [M + H]+ |
|---|---|---|---|---|
| 233 | 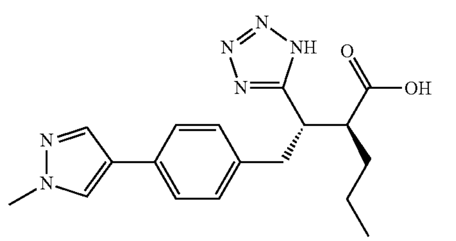 [SMILES: CCC[C@H](C(=O)O)[C@H](Cc1ccc(-c2cnn(C)c2)cc1)c1nnn[nH]1] | (2S)-2-[(1S)-2-[4-(1-methyl-1H-pyrazol-4-yl)phenyl]-1-(1H-tetrazol-5-yl)ethyl]pentanoic acid | 355.19 | 355.18 |
| 234 | 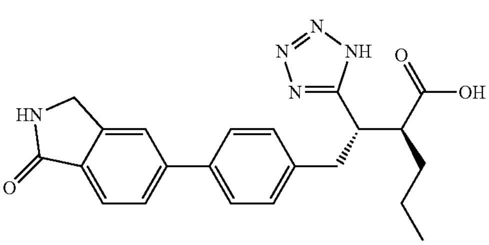 [SMILES: CCC[C@H](C(=O)O)[C@H](Cc1ccc(-c2ccc3c(c2)CNC3=O)cc1)c1nnn[nH]1] | (2S)-2-[(1S)-2-[4-(1-oxo-2,3-dihydro-1H-isoindol-5-yl)phenyl]-1-(1H-tetrazol-5-yl)ethyl]pentanoic acid | 406.19 | 406.18 |
| 235 | 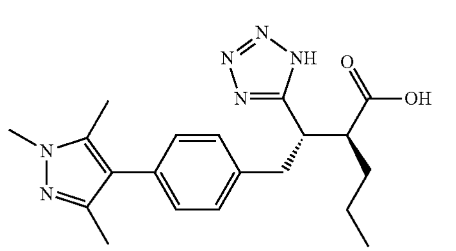 [SMILES: CCC[C@H](C(=O)O)[C@H](Cc1ccc(-c2c(C)nn(C)c2C)cc1)c1nnn[nH]1] | (2S)-2-{(1S)-1-(1H-tetrazol-5-yl)-2-[4-(1,3,5-trimethyl-1H-pyrazol-4-yl)phenyl]ethyl}pentanoic acid | 383.22 | 383.21 |

| Ex. No. | Structure | IUPAC Name | Calc'd Mass [M + H]+ | LC/MS m/e [M + H]+ |
|---|---|---|---|---|
| 236 | 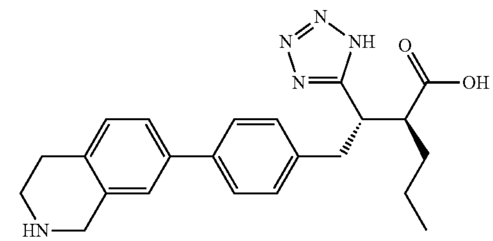 [SMILES: CCC[C@H](C(=O)O)[C@H](Cc1ccc(-c2ccc3c(c2)CNCC3)cc1)c1nnn[nH]1] | (2S)-2-[(1S)-2-[4-(1,2,3,4-tetrahydroisoquinolin-7-yl)phenyl]-1-(1H-tetrazol-5-yl)ethyl]pentanoic acid | 406.22 | 406.22 |
| 237 | 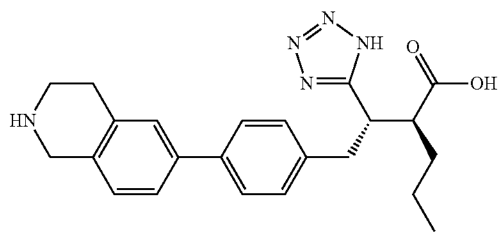 [SMILES: CCC[C@H](C(=O)O)[C@H](Cc1ccc(-c2ccc3c(c2)CCNC3)cc1)c1nnn[nH]1] | (2S)-2-[(1S)-2-[4-(1,2,3,4-tetrahydroisoquinolin-6-yl)phenyl]-1-(1H-tetrazol-5-yl)ethyl]pentanoic acid | 406.22 | 406.22 |
| 238 | 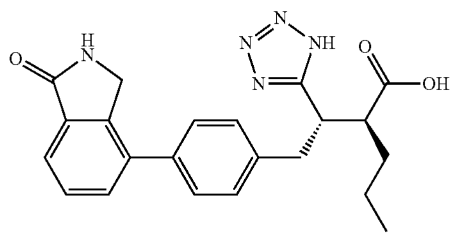 [SMILES: CCC[C@H](C(=O)O)[C@H](Cc1ccc(-c2cccc3c2CNC3=O)cc1)c1nnn[nH]1] | (2S)-2-[(1S)-2-[4-(1-oxo-2,3-dihydro-1H-isoindol-4-yl)phenyl]-1-(1H-tetrazol-5-yl)ethyl]pentanoic acid | 406.19 | 406.18 |
| 239 | 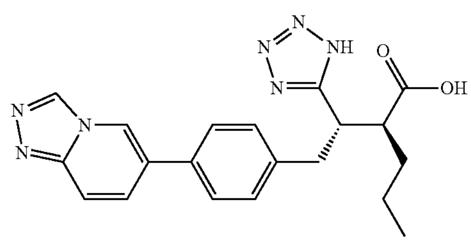 [SMILES: CCC[C@H](C(=O)O)[C@H](Cc1ccc(-c2ccc3nncn3c2)cc1)c1nnn[nH]1] | (2S)-2-[(1S)-1-(1H-tetrazol-5-yl)-2-(4-[1,2,4]triazolo[4,3-a]pyridin-6-ylphenyl)ethyl]pentanoic acid | 392.18 | 392.3 |
| 240 | 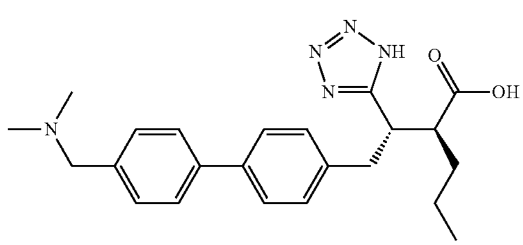 [SMILES: CCC[C@H](C(=O)O)[C@H](Cc1ccc(-c2ccc(CN(C)C)cc2)cc1)c1nnn[nH]1] | (2S)-2-[(1S)-2-{4'-[(dimethylamino)methyl]biphenyl-4-yl}-1-(1H-tetrazol-5-yl)ethyl]pentanoic acid | 408.24 | 408.23 |
| 241 | 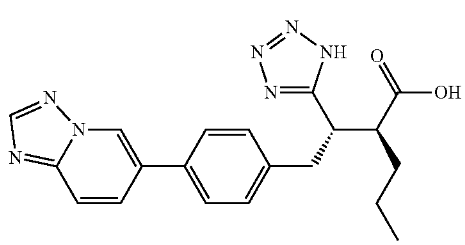 [SMILES: CCC[C@H](C(=O)O)[C@H](Cc1ccc(-c2ccc3ncnn3c2)cc1)c1nnn[nH]1] | (2S)-2-[(1S)-1-(1H-tetrazol-5-yl)-2-(4-[1,2,4]triazolo[1,5-a]pyridin-6-ylphenyl)ethyl]pentanoic acid | 392.18 | 392.18 |

-continued

| Ex. No. | Structure | IUPAC Name | Calc'd Mass [M + H]+ | LC/MS m/e [M + H]+ |
|---|---|---|---|---|
| 242 | 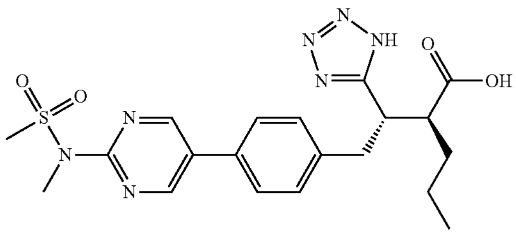 [SMILES: CCC[C@H](C(=O)O)[C@H](Cc1ccc(-c2cnc(N(C)S(C)(=O)=O)nc2)cc1)c1nnn[nH]1] | (2S)-2-[(1S)-2-(4-{2-[methyl(methylsulfonyl)amino]pyrimidin-5-yl}phenyl)-1-(1H-tetrazol-5-yl)ethyl]pentanoic acid | 460.18 | 460.17 |
| 243 | 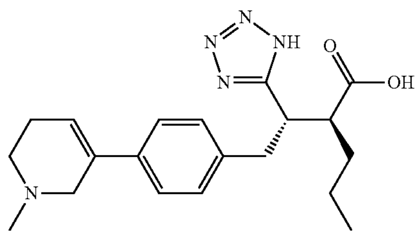 [SMILES: CCC[C@H](C(=O)O)[C@H](Cc1ccc(C2=CCCN(C)C2)cc1)c1nnn[nH]1] | (2S)-2-[(1S)-2-[4-(1-methyl-1,2,5,6-tetrahydropyridin-3-yl)phenyl]-1-(1H-tetrazol-5-yl)ethyl]pentanoic acid | 370.22 | 370.22 |
| 244 | 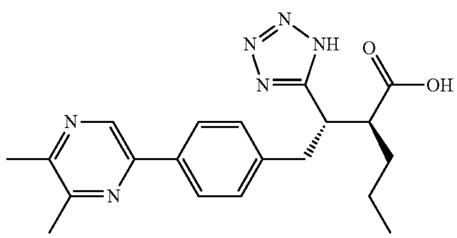 [SMILES: CCC[C@H](C(=O)O)[C@H](Cc1ccc(-c2cnc(C)c(C)n2)cc1)c1nnn[nH]1] | (2S)-2-[(1S)-2-[4-(5,6-dimethylpyrazin-2-yl)phenyl]-1-(1H-tetrazol-5-yl)ethyl]pentanoic acid | 381.2 | 381.2 |
| 245 | 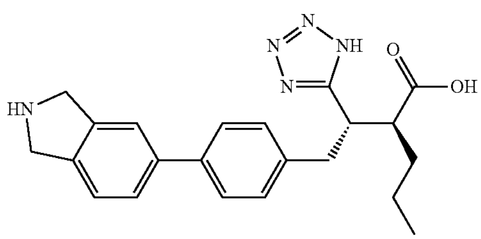 [SMILES: CCC[C@H](C(=O)O)[C@H](Cc1ccc(-c2ccc3c(c2)CNC3)cc1)c1nnn[nH]1] | (2S)-2-[(1S)-2-[4-(2,3-dihydro-1H-isoindol-5-yl)phenyl]-1-(1H-tetrazol-5-yl)ethyl]pentanoic acid | 392.21 | 392.2 |
| 246 | 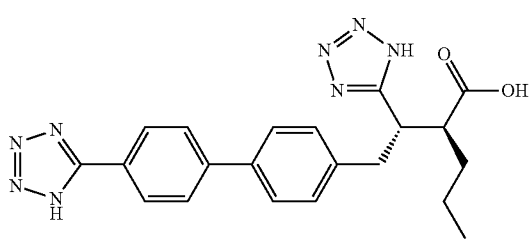 [SMILES: CCC[C@H](C(=O)O)[C@H](Cc1ccc(-c2ccc(-c3nnn[nH]3)cc2)cc1)c1nnn[nH]1] | (2S)-2-{(1S)-1-(1H-tetrazol-5-yl)-2-[4'-(1H-tetrazol-5-yl)biphenyl-4-yl]ethyl}pentanoic acid | 419.19 | 419.19 |
| 247 | 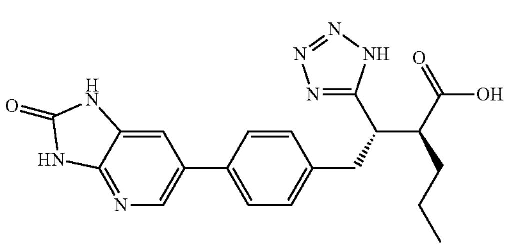 [SMILES: CCC[C@H](C(=O)O)[C@H](Cc1ccc(-c2cnc3[nH]c(=O)[nH]c3c2)cc1)c1nnn[nH]1] | (2S)-2-[(1S)-2-[4-(2-oxo-2,3-dihydro-1H-imidazo[4,5-b]pyridin-6-yl)phenyl]-1-(1H-tetrazol-5-yl)ethyl]pentanoic acid | 408.18 | 408.17 |

| Ex. No. | Structure | IUPAC Name | Calc'd Mass [M + H]+ | LC/MS m/e [M + H]+ |
|---|---|---|---|---|
| 248 | 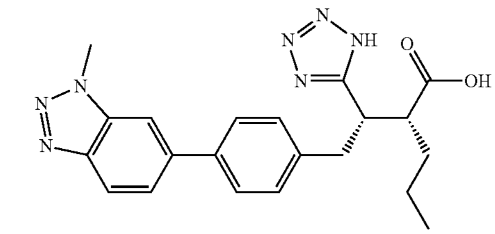 [SMILES: CCC[C@@H](C(=O)O)[C@H](Cc1ccc(-c2ccc3nnn(C)c3c2)cc1)c1nnn[nH]1] | (2R)-2-[(1S)-2-[4-(1-methyl-1H-benzotriazol-6-yl)phenyl]-1-(1H-tetrazol-5-yl)ethyl]pentanoic acid | 406.2 | 406.19 |
| 249 | 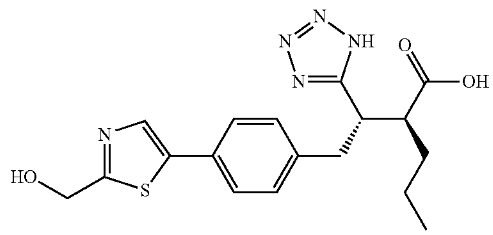 [SMILES: CCC[C@H](C(=O)O)[C@H](Cc1ccc(-c2cnc(CO)s2)cc1)c1nnn[nH]1] | (2S)-2-[(1S)-2-{4-[2-(hydroxymethyl)-1,3-thiazol-5-yl]phenyl-1-(1H-tetrazol-5-yl)ethyl]pentanoic acid | 388.14 | 388.14 |
| 250 | 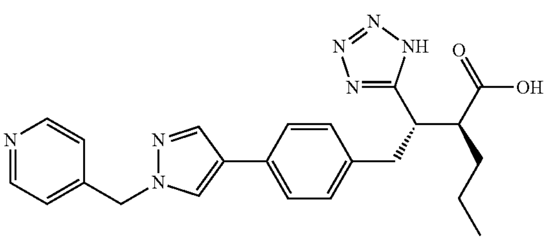 [SMILES: CCC[C@H](C(=O)O)[C@H](Cc1ccc(-c2cnn(Cc3ccncc3)c2)cc1)c1nnn[nH]1] | (2S)-2-[(1S)-2-{4-[1-(pyridin-4-ylmethyl)-1H-pyrazol-4-yl]phenyl}-1-(1H-tetrazol-5-yl)ethyl]pentanoic acid | 432.21 | 432.21 |

EXAMPLEs 251-257

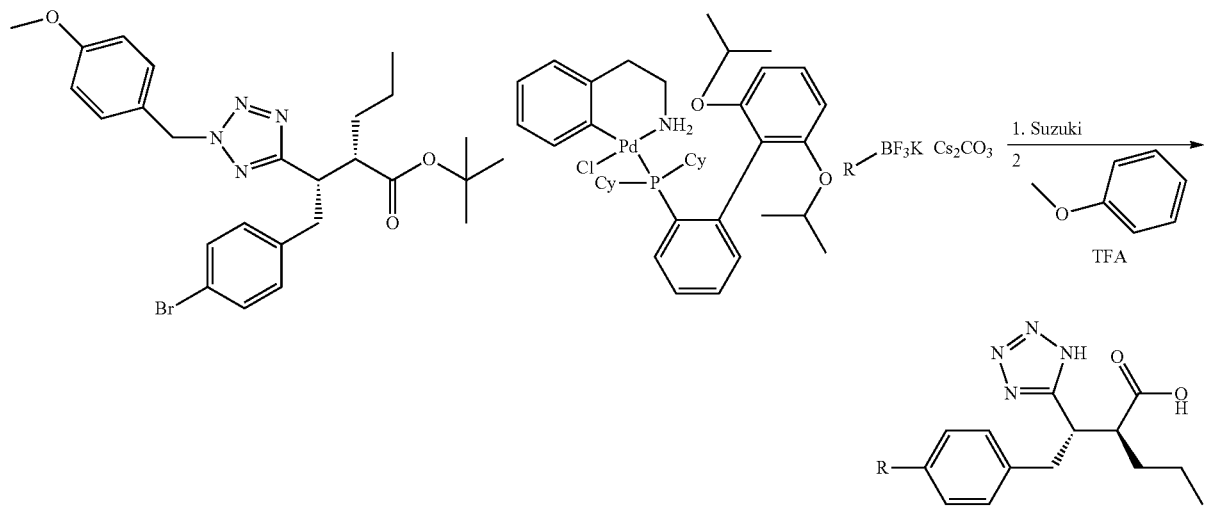

Step 1:

In vials (S)-tert-butyl 2-((S)-2-(4-bromophenyl)-1-(2-(4-methoxybenzyl)-2H-tetrazol-5-yl)ethyl)pentanoate (30 mg, 0.057 mmol), potassium R-trifuoroborate (0.085 mmol) and RuPhos Indoline Preformed Catalyst (4.13 mg, 5.67 μmol) were combined. This mixture was then evacuated and back-filled with N₂ (3 times). Then in glovebox, cesium carbonate (83 mg, 0.255 mmol) was added into vials, followed by degassed Toluene (900 μl) and Water (100 μl). This mixture was then heated at 85° C. for 24 hr. UPLC showed the product formation. The solvent was evaporated in GeneVac. 700 μL of water and 2.4 mL of EtOAc were added into the vials. The organic layers were transferred into 2 dram vials and concentrated to dryness under vacuum.

Step 2:

A solution of anisole (30.6 mg, 0.283 mmol), 0.4 mL of TFA and 0.4 mL of DCM was added into the residues. The solution was shaken at room temperature over a weekend. The vials were heated at 50° C. for 48 hr. The mixtures were concentrated in GeneVac. 1.4 mL of DMSO was added into each vial. The crude solution was filtered through a filter plate and purified by HPLC.

| Ex. No. | Structure | IUPAC Name | Calc'd Mass [M + H]+ | LC/MS m/e [M + H]+ |
|---|---|---|---|---|
| 251 | 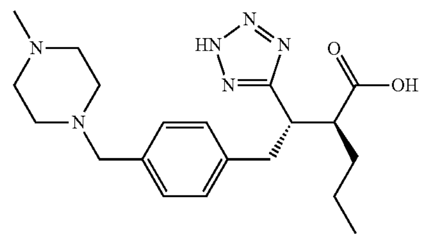 [SMILES: CCC[C@H](C(=O)O)[C@H](Cc1ccc(CN2CCN(C)CC2)cc1)c1nn[nH]n1] | (2S)-2-[(1S)-2-{4-[(4-methylpiperazin-1-yl)methyl]phenyl}-1-(2H-tetrazol-5-yl)ethyl]pentanoic acid | 387.25 | 387.24 |
| 252 | 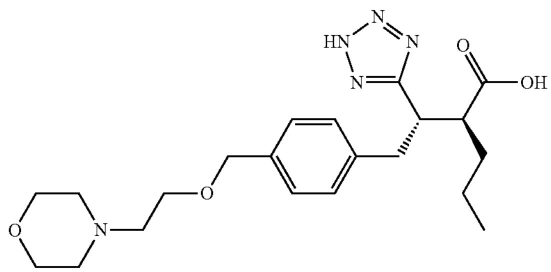 [SMILES: CCC[C@H](C(=O)O)[C@H](Cc1ccc(COCCN2CCOCC2)cc1)c1nn[nH]n1] | (2S)-2-[(1S)-2-{4-[(2-morpholin-4-ylethoxy)methyl]phenyl}-1-(2H-tetrazol-5-yl)ethyl]pentanoic acid | 418.25, | 418.24 |
| 253 | 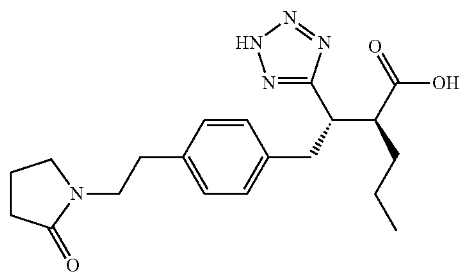 [SMILES: CCC[C@H](C(=O)O)[C@H](Cc1ccc(CCN2CCCC2=O)cc1)c1nn[nH]n1] | (2S)-2-[(1S)-2-{4-[2-(2-oxopyrrolidin-1-yl)ethyl]phenyl}-1-(2H-tetrazol-5-yl)ethyl]pentanoic acid | 386.22 | 386.21 |
| 254 | 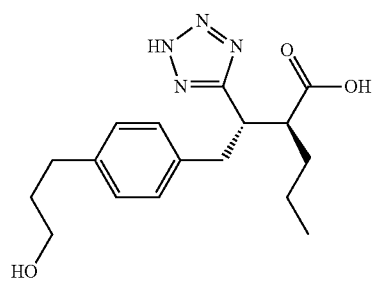 [SMILES: CCC[C@H](C(=O)O)[C@H](Cc1ccc(CCCO)cc1)c1nn[nH]n1] | (2S)-2-[(1S)-2-[4-(3-hydroxypropyl)phenyl]-1-(2H-tetrazol-5-yl)ethyl]pentanoic acid | 333.19 | 333.18 |
| 255 | 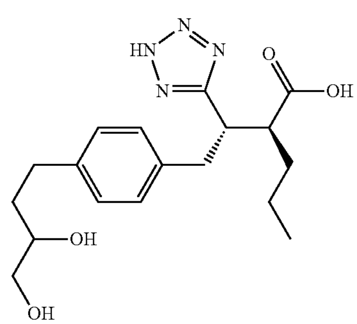 [SMILES: CCC[C@H](C(=O)O)[C@H](Cc1ccc(CCC(O)CO)cc1)c1nn[nH]n1] | (2S)-2-[(1S)-2-[4-(3,4-dihydroxybutyl)phenyl]-1-(2H-tetrazol-5-yl)ethyl]pentanoic acid | 363.2 | 363.2 |

| Ex. No. | Structure | IUPAC Name | Calc'd Mass [M + H]+ | LC/MS m/e [M + H]+ |
|---|---|---|---|---|
| 256 | 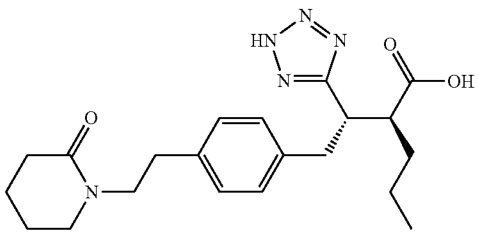 [SMILES: CCC[C@H](C(=O)O)[C@H](Cc1ccc(CCN2CCCCC2=O)cc1)c1nn[nH]n1] | (2S)-2-[(1S)-2-{4-[2-(2-oxopiperidin-1-yl)ethyl]phenyl}-1-(2H-tetrazol-5-yl)ethyl]pentanoic acid | 400.23 | 400.23 |
| 257 | 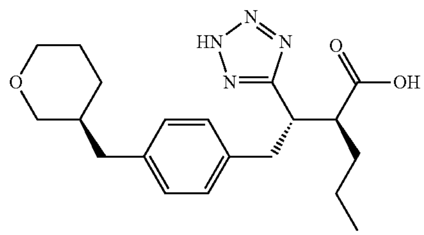 [SMILES: CCC[C@H](C(=O)O)[C@H](Cc1ccc(C[C@@H]2CCCOC2)cc1)c1nn[nH]n1] | (2S)-2-[(1S)-2-{4-[(3S)-tetrahydro-2H-pyran-3-ylmethyl]phenyl}-1-(2H-tetrazol-5-yl)ethyl]pentanoic acid | 373.22 | 373.22 |

EXAMPLE 258

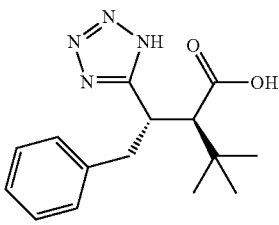 [SMILES: CC(C)(C)[C@H](C(=O)O)[C@H](Cc1ccccc1)c1nnn[nH]1]

(2R,3S)-2-(tert-butyl)-4-phenyl-3-(1H-tetrazol-5-yl)butanoic acid

Step A: (R)-4-benzyl-3-(3,3-dimethylbutanoyl)oxazolidin-2-one

A solution of the (R)-4-benzyloxazolidin-2-one (6.6 g, 37 mmol) in THF (50 mL) was cooled to −78° C., then n-BuLi was added dropwise. The mixture was stirred for 15 minutes, then the 3,3-dimethylbutanoyl chloride in 10 mL THF was added dropwise. The mixture was stirred for 30 minutes at −78° C., then the cold bath was removed and the mixture stirred for an additional hour while warming to RT. The reaction was quenched with 20 mL sat. $NH_4Cl$ (aq), and then THF was removed in vacuo. Water (20 mL) was added to the residue, and the aqueous layer extracted with 2×100 mL $Et_2O$. The combined organic extracts were washed with 50 mL 0.5 N NaOH (aq) and 50 mL brine, then dried with $Na_2SO_4$, and concentrated in vacuo to provided (R)-4-benzyl-3-(3,3-dimethylbutanoyl)oxazolidin-2-one.

Step B: (R)-tert-butyl 3-((R)-4-benzyl-2-oxooxazolidine-3-carbonyl)-4,4-dimethylpentanoate To a solution of (R)-4-benzyl-3-(3,3-dimethylbutanoyl) oxazolidin-2-one (12 g, 43.6 mmol) in THF (100 ml) was added NaHMDS (47.9 ml, 47.9 mmol) at −78° C. and the resulting solution was stirred at −78° C. for 1 hr. Then a solution of tert-butyl 2-bromoacetate (19 ml, 130 mmol) in 5 mL THF was added slowly, and the resulting solution was stirred for 1 hr, then slowly warmed to RT. Then, the reaction mixture was diluted with $NH_4Cl$/water, transferred to a separatory funnel, and extracted with ethyl acetate. The organic layer was dried with $MgSO_4$, evaporated and purified using 0 to 100% ethyl acetate in hexanes (120 gm redisep column was used) to provide the product.

Step C: (R)-3-((R)-4-benzyl-2-oxooxazolidine-3-carbonyl)-4,4-dimethylpentanoic acid To a solution of (R)-tert-butyl 3-((R)-4-benzyl-2-oxooxazolidine-3-carbonyl)-4,4-dimethylpentanoate (3.3 g, 8.5 mmol) in DCM (4 ml) was added TFA (4 ml, 52 mmol) at 0° C. Then, the ice bath was removed, and the reaction mixture was stirred at RT for 15 min. The reaction mixture was diluted with ethyl acetate, transferred to a separatory funnel, washed with saturated $NaHCO_3$, then with brine. The organic layer was dried with $MgSO_4$, and crude was taken directly to the next step without further purification.

Step D: (R)-3-((R)-4-benzyl-2-oxooxazolidine-3-carbonyl)-4,4-dimethylpentanamide To a solution of (R)-3-((R)-4-benzyl-2-oxooxazolidine-3-carbonyl)-4,4-dimethylpentanoic acid (2.8 g, 8.5 mmol) in THF (20 ml) was added DIEA (1.8 ml, 10 mmol), HATU (3.9 g, 10.2 mmol) and ammonium chloride (0.91 g, 17 mmol) at 0° C. The ice bath was removed and the resulting mixture was stirred at RT for 2 hrs. The reaction mixture was diluted with ethyl acetate, transferred to a separatory funnel, washed with saturated $NaHCO_3$, then with brine. The organic layer was dried with $MgSO_4$, evaporated and purified using 0 to 100% ethyl acetate in hexanes (40 gm redisep column was used) to provide the product.

Step E: (R)-3-((R)-4-benzyl-2-oxooxazolidine-3-carbonyl)-4,4-dimethylpentanenitrile To a solution of (R)-3-((R)-4-benzyl-2-oxooxazolidine-3-carbonyl)-4,4-dimethylpentanamide (3.0 g, 9.0 mmol) in DCM (24 ml) was added pyridine (2.2 ml, 27 mmol) followed by TFAA (1.9 ml, 14 mmol) at 0° C. Then the ice bath was removed and the resulting mixture was stirred at RT for 1 hr. The reaction mixture was diluted with ethyl acetate, transferred to a separatory funnel, washed with saturated NaHCO₃, then with brine. The organic layer was dried with MgSO₄, evaporated and purified using 0 to 100% ethyl acetate in hexanes (40 gm redisep column was used) to provide the product.

Step F: (R)-3-((R)-2-((1H-tetrazol-5-yl)methyl)-3,3-dimethylbutanoyl)-4-benzyloxazolidin-2-one To a solution of (R)-3-((R)-4-benzyl-2-oxooxazolidine-3-carbonyl)-4,4-dimethylpentanenitrile (1.8 g, 5.7 mmol) in toluene (20 ml) was added dibutylstannanone (0.43 g, 1.7 mmol) and azidotrimethylsilane (2.3 ml, 17 mmol), and the resulting mixture was heated at 110° C. for 12 hr. The reaction was evaporated to dryness and purified using 0 to 100% ethyl acetate in hexanes to provide the product.

Step G: (R)-4-benzyl-3-((R)-3,3-dimethyl-2-((1-((2-(trimethylsilyl)ethoxy)methyl)-1H-tetrazol-5-yl)methyl)butanoyl)oxazolidin-2-one To a solution of (R)-3-((R)-2-((1H-tetrazol-5-yl)methyl)-3,3-dimethylbutanoyl)-4-benzyloxazolidin-2-one (1.9 g, 5.4 mmol) in acetonitrile was added DIEA (1.9 ml, 11 mmol) at 0° C., and the resulting solution was stirred for 10 min. (2-(chloromethoxy)ethyl)trimethylsilane (1.2 ml, 6.5 mmol) was added and the resulting solution was slowly warmed to RT. The reaction mixture was diluted with ethyl acetate, transferred to a separatory funnel, washed with saturated NaHCO₃, then with brine. The organic layer was dried with MgSO₄, evaporated and two regioisomers were separated using 0 to 100% ethyl acetate in hexanes (40 gm redisep column was used) to give the product.

Step H: (R)—S-ethyl 3,3-dimethyl-2-((2-((2-(trimethylsilyl)ethoxy)methyl)-2H-tetrazol-5-yl)methyl)butanethioate To a solution of ethanethiol (0.83 ml, 11.2 mmol) in THF (16 ml) was added n-BuLi (3.73 ml, 8.2 mmol) at −78° C. The resulting mixture was slowly warmed to 0° C., and stirred for 15 min. Then a precooled (−78° C.) solution of (R)-4-benzyl-3-((R)-3,3-dimethyl-2-((1-((2-(trimethylsilyl)ethoxy)methyl)-1H-tetrazol-5-yl)methyl)butanoyl)oxazolidin-2-one (1.6 g, 3.28 mmol) was added and the resulting mixture was stirred at 0° C. for 12 hr. Then, the reaction mixture was diluted with 1 N NaOH, and extracted with ether. The crude product was purified using 0 to 100% ethyl acetate in hexanes to provide the product.

Step I: (R)-3,3-dimethyl-2-((1-((2-(trimethylsilyl)ethoxy)methyl)-1H-tetrazol-5-yl)methyl)butanoic acid (R)—S-ethyl 3,3-dimethyl-2-((2-((2-(trimethylsilyl)ethoxy)methyl)-2H-tetrazol-5-yl)methyl)butanethioate (800 mg, 2.1 mmol) in water/EtOH was added to a stirred room temperature mixture of lithium hydroxide (260 mg, 11 mmol), H₂O₂ (0.38 ml, 4.3 mmol) and the mixture was stirred at 75° C. over the weekend. LC-MS showed the reaction was completed. After cooling, the reaction mixture was acidified to pH~3 by 1N HCl, extracted with EtOAc, washed with saturated Na₂S₂O₃ and brine. The organic layer was dried over MgSO₄, filtered and concentrated to dryness to give the product.

Step J: (2R,3R)-2-(tert-butyl)-4-phenyl-3-(1-((2-(trimethylsilyl)ethoxy)methyl)-1H-tetrazol-5-yl)butanoic acid and (2R,3S)-2-(tert-butyl)-4-phenyl-3-(1-((2-(trimethylsilyl)ethoxy)methyl)-1H-tetrazol-5-yl)butanoic acid To a solution of diisopropylamine (0.50 ml, 3.5 mmol) in tetrahydrofuran (5 ml) was added n-BuLi (1.3 ml, 3.5 mmol) at −5° C. Then the resulting solution was slowly warmed to RT, then cooled to −78° C. and a solution of (R)-2-cyclopentyl-3-(1-((2-(trimethylsilyl)ethoxy)methyl)-1H-tetrazol-5-yl)propanoic acid (500 mg, 1.47 mmol) in 1 ml THF was added. The resulting mixture was stirred for 1 hr, then a solution of benzyl bromide (480 mg, 1.9 mmol) in 1 mL THF was added. The reaction mixture was slowly warmed to RT over 12 hrs. The reaction mixture was diluted with saturated ammonium chloride, and then was extracted with ethyl acetate. The crude product was purified using 0 to 100% ethyl acetate in hexanes to provide a mixture of 2 products.

Step K: (2R,3S)-2-(tert-butyl)-4-phenyl-3-(1H-tetrazol-5-yl)butanoic acid

To a solution of above products (50 mg, 0.119 mmol) in ethanol (1 ml) was added HCl (1 ml, 2.0 mmol), and the resulting solution was heated at 70° C. for 1 hr. The reaction mixture was evaporated to dryness and separated by reverse phase HPLC to afford the product. LC-MS m/z [M+1]⁺: 289.06.

EXAMPLE 259

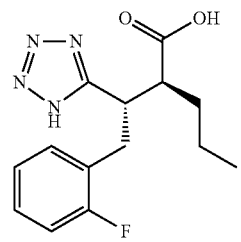 [SMILES: CCC[C@H](C(=O)O)[C@H](Cc1ccccc1F)c1nnn[nH]1]

(S)-2-((S)-2-(2-fluorophenyl)-1-(1H-tetrazol-5-yl)ethyl)pentanoic acid

Step A: (S)-2-((S)-2-(2-fluorophenyl)-1-(1-((2-(trimethylsilyl)ethoxy)methyl)-1H-tetrazol-5-yl)ethyl)pentanoic acid To a solution of (S)-2-((1-((2-(trimethylsilyl)ethoxy)methyl)-1H-tetrazol-5-yl)methyl)pentanoic acid (200 mg, 0.64 mmol) in THF (2.0 ml) at −78° C., was added dropwise lithium diisopropylamide (0.80 ml, 1.6 mmol) and then the reaction mixture was stirred at −78° C. for 0.5 hr. 1-(chloromethyl)-2-fluorobenzene (0.151 ml, 1.272 mmol) was added and the reaction mixture was stirred at −78° C. for 2 hours, then RT overnight. The reaction mixture was quenched with 3 ml of saturated NH₄Cl, extracted with EtOAc (10 ml×3), and then the combined organic layers were dried over MgSO₄, filtered and evaporated to dryness to give the crude oil which was used directly in the next step.

Step B: (S)-2-((S)-2-(2-fluorophenyl)-1-(1H-tetrazol-5-yl)ethyl)pentanoic acid

In a 25 mL sealed microwave tube (S)-2-((S)-2-(2-fluorophenyl)-1-(1-((2-(trimethylsilyl)ethoxy)methyl)-1H-tetrazol-5-yl)ethyl)pentanoic acid (270 mg, 0.64 mmol) was dissolved in ethanol (3.0 ml)/hydrogen chloride 1N (3.0 ml, 3.0 mmol) and heated at 60° C. overnight. The reaction was concentrated and to the residue was added DMSO (7.5 ml). The reaction mixture was purified by C18 reverse phase preparatory HPLC to afford the TFA salt of desired compound. LC-MS m/z [M+1]⁺ 293.07

The following compounds were prepared according to the general procedure of EXAMPLE 259.

| Ex. No | Structure | IUPAC Name | Calc'd Mass $[M + H]^+$ | LC/MS m/e $[M + H]^+$ |
|---|---|---|---|---|
| 260 | 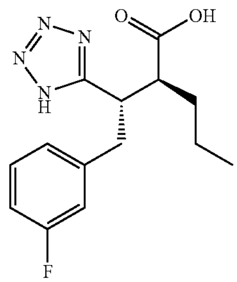 [SMILES: CCC[C@H](C(=O)O)[C@H](Cc1cccc(F)c1)c1nnn[nH]1] | (2S)-2-[(1S)-2-(3-fluorophenyl)-1-(1H-tetrazol-5-yl)ethyl]pentanoic acid | 293.14 | 293.10 |
| 261 | 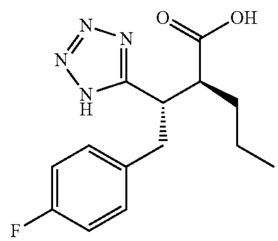 [SMILES: CCC[C@H](C(=O)O)[C@H](Cc1ccc(F)cc1)c1nnn[nH]1] | (2S)-2-[(1S)-2-(4-fluorophenyl)-1-(1H-tetrazol-5-yl)ethyl]pentanoic acid | 293.14 | 293.08 |
| 262 | 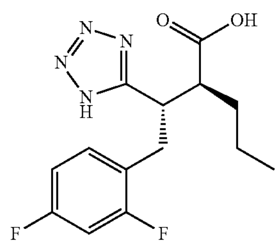 [SMILES: CCC[C@H](C(=O)O)[C@H](Cc1ccc(F)cc1F)c1nnn[nH]1] | (2S)-2-[(1S)-2-(2,4-difluorophenyl)-1-(1H-tetrazol-5-yl)ethyl]pentanoic acid | 311.13 | 311.04 |
| 263 | 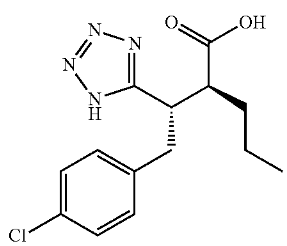 [SMILES: CCC[C@H](C(=O)O)[C@H](Cc1ccc(Cl)cc1)c1nnn[nH]1] | (2S)-2-[(1S)-2-(4-chlorophenyl)-1-(1H-tetrazol-5-yl)ethyl]pentanoic acid | 309.11 | 309.05 |
| 264 | 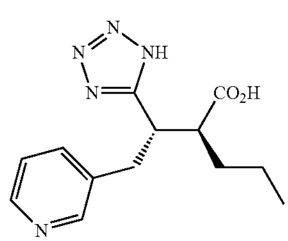 [SMILES: CCC[C@H](C(=O)O)[C@H](Cc1cccnc1)c1nnn[nH]1] | (S)-2-((S)-2-(pyridin-3-yl)-1-(1H-tetrazol-5-yl)ethyl)pentanoic acid | 276.15 | 276.14 |

-continued

| Ex. No | Structure | IUPAC Name | Calc'd Mass [M + H]+ | LC/MS m/e [M + H]+ |
|---|---|---|---|---|
| 265 | 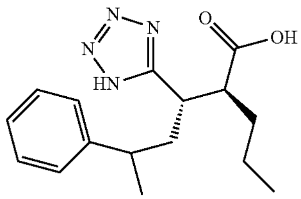 [SMILES: CCC[C@H](C(=O)O)[C@H](CC(C)c1ccccc1)c1nnn[nH]1] | (2S,3S,5R)-5-phenyl-2-propyl-3-(1H-tetrazol-5-yl) hexanoic acid | 303.18 | 303.13 |
| 266 | 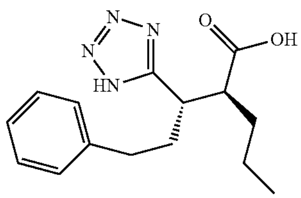 [SMILES: CCC[C@H](C(=O)O)[C@H](CCc1ccccc1)c1nnn[nH]1] | (2S,3S)-5-phenyl-2-propyl-3-(1H-tetrazol-5-yl)pentanoic acid | 289.17 | 289.12 |
| 267 | 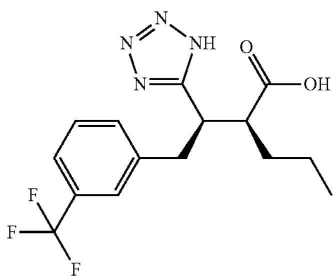 [SMILES: CCC[C@H](C(=O)O)[C@@H](Cc1cccc(C(F)(F)F)c1)c1nnn[nH]1] | (2S)-2-{(1S)-1-(1H-tetrazol-5-yl)-2-[3-(trifluoromethyl)phenyl]ethyl} pentanoic acid | 343.14 | 343.11 |
| 268 | 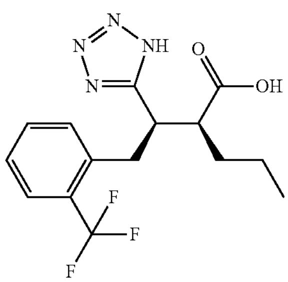 [SMILES: CCC[C@H](C(=O)O)[C@@H](Cc1ccccc1C(F)(F)F)c1nnn[nH]1] | (2S)-2-{(1S)-1-(1H-tetrazol-5-yl)-2-[2-(trifluoromethyl)phenyl]ethyl} pentanoic acid | 343.14 | 343.06 |
| 269 | 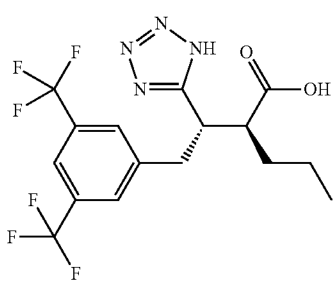 [SMILES: CCC[C@H](C(=O)O)[C@H](Cc1cc(C(F)(F)F)cc(C(F)(F)F)c1)c1nnn[nH]1] | (2S)-2-[(1S)-2-[3,5-bis(trifluoromethyl)phenyl]-1-(1H-tetrazol-5-yl) ethyl]pentanoic acid | 411.13 | 411.12 |
| 270 | 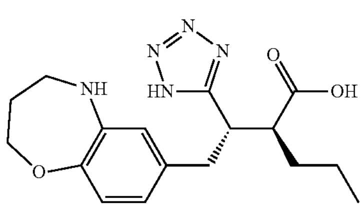 [SMILES: CCC[C@H](C(=O)O)[C@H](Cc1ccc2c(c1)NCCCO2)c1nnn[nH]1] | (2S)-2-[(1S)-2-(2,3,4,5-tetrahydro-1,4-benzoxazepin-7-yl)-1-(1H-tetrazol-5-yl) ethyl]pentanoic acid | 346.19 | 346.18 |

| Ex. No | Structure | IUPAC Name | Calc'd Mass [M + H]+ | LC/MS m/e [M + H]+ |
|---|---|---|---|---|
| 271 | 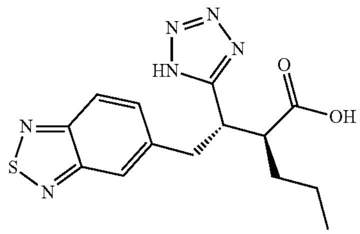 [SMILES: CCC[C@H](C(=O)O)[C@H](Cc1ccc2nsnc2c1)c1nnn[nH]1] | (2S)-2-[(1S)-2-(2,1,3-benzothiadiazol-5-yl)-1-(1H-tetrazol-5-yl)ethyl]pentanoic acid | 333.11 | 333.11 |
| 272 | 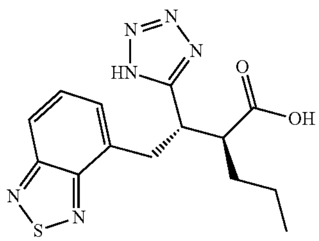 [SMILES: CCC[C@H](C(=O)O)[C@H](Cc1cccc2nsnc12)c1nnn[nH]1] | (2S)-2-[(1S)-2-(2,1,3-benzothiadiazol-4-yl)-1-(1H-tetrazol-5-yl)ethyl]pentanoic acid | 333.11 | 332.98 |
| 273 | 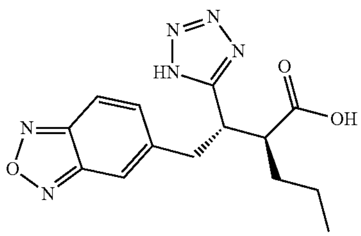 [SMILES: CCC[C@H](C(=O)O)[C@H](Cc1ccc2nonc2c1)c1nnn[nH]1] | (2S)-2-[(1S)-2-(2,1,3-benzoxadiazol-5-yl)-1-(1H-tetrazol-5-yl)ethyl]pentanoic acid | 317.14 | 317.15 |
| 274 | 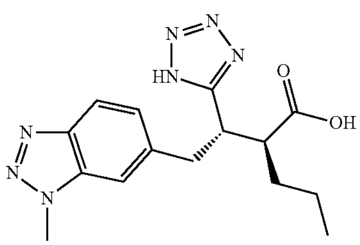 [SMILES: CCC[C@H](C(=O)O)[C@H](Cc1ccc2nnn(C)c2c1)c1nnn[nH]1] | (2S)-2-[(1S)-2-(1-methyl-1H-benzotriazol-5-yl)-1-(1H-tetrazol-5-yl)ethyl]pentanoic acid | 330.17 | 330.15 |

EXAMPLE 275

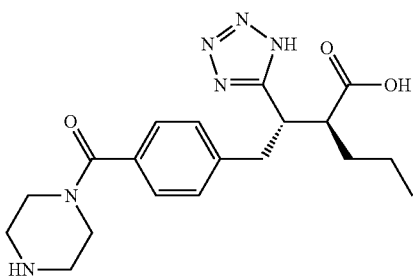 [SMILES: CCC[C@H](C(=O)O)[C@H](Cc1ccc(C(=O)N2CCNCC2)cc1)c1nnn[nH]1]

(2S)-2-[(1S)-2-[4-(piperazin-1-ylcarbonyl)phenyl]-1-(1H-tetrazol-5-yl)ethyl]pentanoic acid Step A: tert-butyl 4-(4-((2S,3S)-3-(tert-butoxycarbonyl)-2-(1-(4-methoxybenzyl)-1H-tetrazol-5-yl)hexyl)benzoyl)piperazine-1-carboxylate A mixture of 4-((2S,3S)-3-(tert-butoxycarbonyl)-2-(1-(4-methoxybenzyl)-1H-tetrazol-5-yl)hexyl)benzoic acid (60 mg, 0.12 mmol), HATU (69 mg, 0.18 mmol), tert-butyl piperidin-4-ylcarbamate (73 mg, 0.36 mmol), and Hunig's Base (0.11 ml, 0.61 mmol) in DMF (1.0 ml) was stirred overnight. LCMS showed that the reaction was complete. The reaction mixture was worked up with EtOAc (3×10 ml)/Bicarbonate, washed with brine (3×10 ml), dried over MgSO4, and evaporated to get the crude product which was used as directed for next step.

Step B: (2S)-2-[(1S)-2-[4-(piperazin-1-ylcarbonyl)phenyl]-1-(1H-tetrazol-5-yl)ethyl]pentanoic acid A reaction mixture of tert-butyl 4-(4-((2S,3S)-3-(tert-butoxycarbonyl)-2-(1-(4-methoxybenzyl)-1H-tetrazol-5-yl)hexyl)benzoyl)piperazine-1-carboxylate (190 mg, 0.29 mmol), 2,2,2-trifluoroacetic acid (600 μL, 7.8 mmol), and methyl(phenyl)sulfane (600 μL, 7.7 mmol) was stirred at 50° C. overnight. The reaction was cooled to RT, and rotavapored to dryness. The residue was dissolved in DMSO and purified by reverse phase HPLC to afford the desired product. LC-MS m/z [M+1]+ 387.24

The following compounds were prepared according to the general procedure of EXAMPLE 275.

| Ex. No | Structure | IUPAC Name | Calc'd Mass [M + H]+ | LC/MS m/e [M + H]+ |
|---|---|---|---|---|
| 276 | 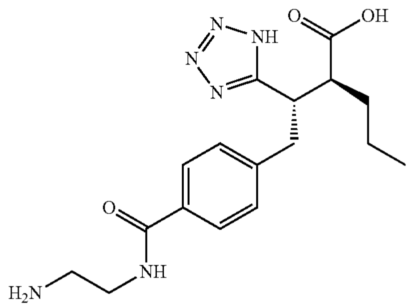 [SMILES: CCC[C@H](C(=O)O)[C@H](Cc1ccc(C(=O)NCCN)cc1)c1nnn[nH]1] | (2S)-2-[(1S)-2-{4-[(2-aminoethyl)carbamoyl]phenyl}-1-(1H-tetrazol-5-yl)ethyl]pentanoic acid | 361.2 | 361.23 |
| 277 | 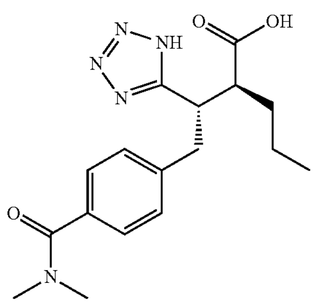 [SMILES: CCC[C@H](C(=O)O)[C@H](Cc1ccc(C(=O)N(C)C)cc1)c1nnn[nH]1] | (2S)-2-[(1S)-2-[4-(dimethylcarbamoyl)phenyl]-1-(1H-tetrazol-5-yl)ethyl]pentanoic acid | 346.19 | 346.19 |
| 278 | 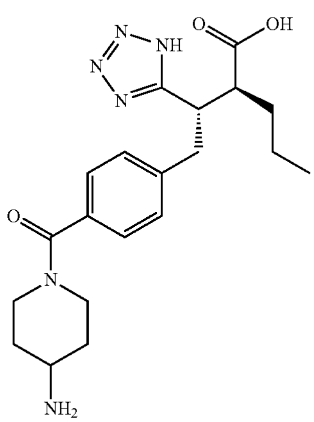 [SMILES: CCC[C@H](C(=O)O)[C@H](Cc1ccc(C(=O)N2CCC(N)CC2)cc1)c1nnn[nH]1] | (2S)-2-[(1S)-2-{4-[(4-aminopiperidin-1-yl)carbonyl]phenyl}-1-(1H-tetrazol-5-yl)ethyl]pentanoic acid | 401.23 | 401.27 |
| 279 | 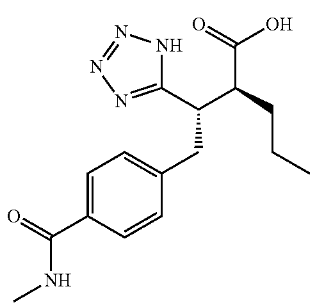 [SMILES: CCC[C@H](C(=O)O)[C@H](Cc1ccc(C(=O)NC)cc1)c1nnn[nH]1] | (2S)-2-[(1S)-2-[4-(methylcarbamoyl)phenyl]-1-(1H-tetrazol-5-yl)ethyl]pentanoic acid | 332.17 | 332.17 |

-continued

| Ex. No | Structure | IUPAC Name | Calc'd Mass [M + H]+ | LC/MS m/e [M + H]+ |
|---|---|---|---|---|
| 280 | 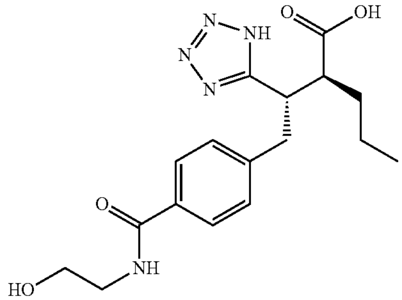 [SMILES: CCC[C@H](C(=O)O)[C@H](Cc1ccc(C(=O)NCCO)cc1)c1nnn[nH]1] | (2S)-2-[(1S)-2-{4-[(2-hydroxyethyl)carbamoyl]phenyl}-1-(1H-tetrazol-5-yl)ethyl]pentanoic acid | 362.18 | 362.18 |
| 281 | 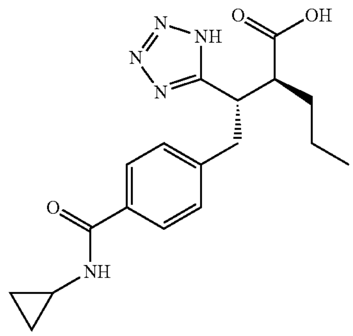 [SMILES: CCC[C@H](C(=O)O)[C@H](Cc1ccc(C(=O)NC2CC2)cc1)c1nnn[nH]1] | (2S)-2-[(1S)-2-[4-(cyclopropylcarbamoyl)phenyl]-1-(1H-tetrazol-5-yl)ethyl]pentanoic acid | 358.19 | 358.23 |
| 282 | 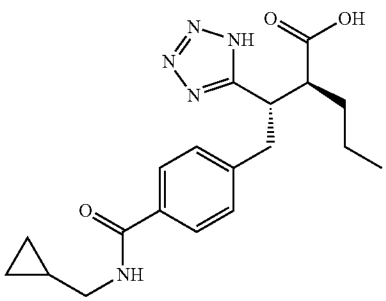 [SMILES: CCC[C@H](C(=O)O)[C@H](Cc1ccc(C(=O)NCC2CC2)cc1)c1nnn[nH]1] | (2S)-2-[(1S)-2-{4-[(cyclopropylmethyl)carbamoyl]phenyl}-1-(1H-tetrazol-5-yl)ethyl]pentanoic acid | 372.2 | 372.23 |

EXAMPLE 283

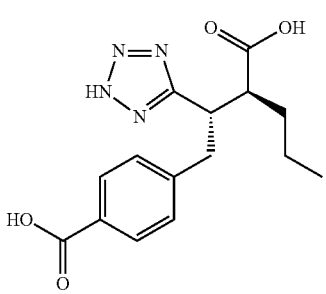 [SMILES: CCC[C@H](C(=O)O)[C@H](Cc1ccc(C(=O)O)cc1)c1nn[nH]n1]

4-((2S,3S)-3-carboxy-2-(2H-tetrazol-5-yl)hexyl)benzoic acid

To a solution of 4-((2S,3S)-3-(tert-butoxycarbonyl)-2-(1-(4-methoxybenzyl)-1H-tetrazol-5-yl)hexyl)benzoic acid compound with 4-((2S,3S)-3-(tert-butoxycarbonyl)-2-(2-(4-methoxybenzyl)-2H-tetrazol-5-yl)hexyl)benzoic acid (20 mg total, 0.040 mmol) in DCM (0.50 mL) was added TFA (0.50 mL) and thioanisole (0.50 mL, 4.2 mmol). The mixture was allowed to stir for 1 hour at 50° C. The solvent was removed, and the residue was dissolved In DMSO, and the desired product was purified by reverse-phase HPLC. LC-MS m/z [M+1]+ 319.11

EXAMPLE 284

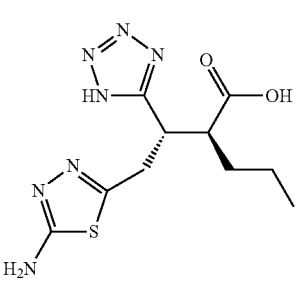 [SMILES: CCC[C@H](C(=O)O)[C@H](Cc1nnc(N)s1)c1nnn[nH]1]

(S)-2-((S)-2-(5-amino-1,3,4-thiadiazol-2-yl)-1-(1H-tetrazol-5-yl)ethyl)pentanoic acid Step A: 2-bromo-5-(bromomethyl)-1,3,4-thiadiazole To the mixture of 2-bromo-5-methyl-1,3,4-thiadiazole (3.6 g, 20 mmol) in CCl₄ (320 ml) was added 1-bromopyrrolidine-2,5-dione (3600 mg, 20 mmol) and (E)-2,2'-(diazene-1,2-diyl)bis(2-methylpropanenitrile) (190 mg, 1.2 mmol). The resulting mixture was heated at reflux for 4.5 hrs. After filtration through celite and washing of the pad with DCM, the combined filtrate was concentrated and the residue was purified on silica gel column using EtOAc/hexane as eluting solvents to give 2-bromo-5-(bromomethyl)-1,3,4-thiadiazole. LC/MS: (M+1)⁺: 256.83, 258.84, 260.88.

Step B: (S)-2-((S)-2-(5-bromo-1,3,4-thiadiazol-2-yl)-1-(1-((2-(trimethylsilyl)ethoxy)methyl)-1H-tetrazol-5-yl)ethyl)pentanoic acid To a solution of diisopropylamine (1.3 ml, 8.9 mmol) in THF (8 mL) at −78° C. was added n-butyllithium (3.26 ml, 8.16 mmol), and the resulting solution was stirred at −78° C. for 15 min before being warmed to 0° C. for 5 min. To a solution of (S)-2-((1-((2-(trimethylsilyl)ethoxy)methyl)-1H-tetrazol-5-yl)methyl)pentanoic acid (0.57 g, 1.8 mmol) in THF (10 mL) at −78° C. was added the above prepared LDA (5.9 ml, 3.8 mmol) dropwise. The resulting solution was stirred at −78° C. for 45 min before addition of 2-bromo-5-(bromomethyl)-1,3,4-thiadiazole (0.47 g, 1.8 mmol) in THF (3 mL) dropwise. The resulting mixture was then stirred at −78° C. for 3 hrs. The reaction was quenched by addition of saturated NH₄Cl solution (50 mL), then the mixture was extracted with EtOAc twice, and the combined organic phase was dried over Na₂SO₄, concentrated and the residue was purified on Gilson using 20-100% acetonitrile (0.05% TFA) over 10 mins to give (S)-2-((S)-2-(5-bromo-1,3,4-thiadiazol-2-yl)-1-(1-((2-(trimethylsilyl)ethoxy)methyl)-1H-tetrazol-5-yl)ethyl)pentanoic acid. LC/MS: (M+1)⁺: 491.14; 493.11.

Step C: (S)-2-((S)-2-(5-amino-1,3,4-thiadiazol-2-yl)-1-(1-((2-(trimethylsilyl)ethoxy)methyl)-1H-tetrazol-5-yl)ethyl)pentanoic acid To a solution of (S)-2-((S)-2-(5-bromo-1,3,4-thiadiazol-2-yl)-1-(1-((2-(trimethylsilyl)ethoxy)methyl)-1H-tetrazol-5-yl)ethyl)pentanoic acid (90 mg, 0.18 mmol) (50 mg, 0.103 mmol) in ethylene glycol (1 ml) and was added copper(I) oxide (2.6 mg, 0.018 mmol), n,n'-dimethylethylenediamine (3.9 µl, 0.037 mmol), K₂CO₃ (5.1 mg, 0.037 mmol) and ammonium hydroxide (1.0 ml, 7.3 mmol). The mixture was degassed and purged with N₂ before being heated at 80° C. overnight. After filtration through celite, the filtrate was concentrated and the residue was purified on Gilson using 10-100% acetonitrile (0.05% TFA) to give (S)-2-((S)-2-(5-amino-1,3,4-thiadiazol-2-yl)-1-(1-((2-(trimethylsilyl)ethoxy)methyl)-1H-tetrazol-5-yl)ethyl)pentanoic acid. LC/MS: (M+1)⁺: 428.20.

Step D: (S)-2-((S)-2-(5-amino-1,3,4-thiadiazol-2-yl)-1-(1H-tetrazol-5-yl)ethyl)pentanoic acid (S)-2-((S)-2-(5-amino-1,3,4-thiadiazol-2-yl)-1-(1-((2-(trimethylsilyl)ethoxy)methyl)-1H-tetrazol-5-yl)ethyl)pentanoic acid (17 mg, 0.040 mmol) was treated with TFA (2 ml) and the resulting solution was stirred at RT for 1 hour. After removing the volatiles, the residue was purified on Gilson using 5-35% acetonitrile (0.05% TFA) as gradient to give (S)-2-((S)-2-(5-amino-1,3,4-thiadiazol-2-yl)-1-(1H-tetrazol-5-yl)ethyl)pentanoic acid. LC/MS: (M+1)⁺: 298.07.

EXAMPLE 285

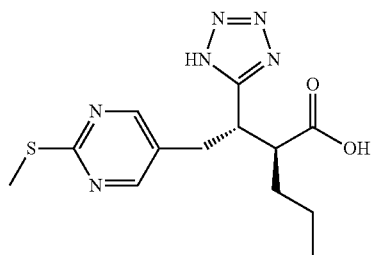 [SMILES: CCC[C@H](C(=O)O)[C@H](Cc1cnc(SC)nc1)c1nnn[nH]1]

(S)-2-((S)-2-(2-(methylthio)pyrimidin-5-yl)-1-(1H-tetrazol-5-yl)ethyl)pentanoic acid Step A: (2-(methylthio)pyrimidin-5-yl)methanol To the solution of methyl 2-(methylthio)pyrimidine-5-carboxylate (3.1 g, 17 mmol) in toluene (100 ml) at −78° C. was added DIBAL-H (42 ml, 42 mmol) dropwise. The resulting solution was stirred at −78° C. for 30 min then warmed to 0° C. for 30 min. The reaction was quenched by addition of MeOH (2 mL), sat. Na₂SO₄ (50 ml), and 1N NaOH (20 mL). The mixture was stirred at RT overnight. After filtration, the filtrate was extracted with EtOAc and DCM. The combined organic phase was dried over Na₂SO₄, concentrated and the residue was purified on silica gel column using EtOAc/hexane as eluting solvents to give (2-(methylthio)pyrimidin-5-yl)methanol. LC/MS: (M+1)⁺: 156.96.

Step B: 5-(bromomethyl)-2-(methylthio)pyrimidine

To the solution of (2-(methylthio)pyrimidin-5-yl)methanol (0.88 g, 5.6 mmol) in DCM (20 ml) at 0° C. was added triphenylphosphine (2.1 g, 7.9 mmol) and carbon tetrabromide (2.6 g, 7.9 mmol). The resulting solution was stirred at 0° C. for 1 hour. The reaction mixture was purified on silica gel column using EtOAc/hexane as eluting solvents to give 5-(bromomethyl)-2-(methylthio)pyrimidine. LC/MS: (M+1)⁺: 218.90; 220.90.

Step C: (S)-2-((S)-2-(2-(methylthio)pyrimidin-5-yl)-1-(1-((2-(trimethylsilyl)ethoxy)methyl)-1H-tetrazol-5-yl)ethyl)pentanoic acid To a solution of diisopropylamine (2.7 ml, 19 mmol) in THF (6 mL) at −78° C. was added n-butyllithium (11 ml, 18 mmol), and the resulting solution was stirred at −78° C. for 15 min before warmed to 0° C. for 5 min. To a solution of (S)-2-((1-((2-(trimethylsilyl)ethoxy)methyl)-1H-tetrazol-5-yl)methyl)pentanoic acid (1.7 g, 5.4 mmol) in THF (25 ml) at −78° C. was added the above prepared LDA (13 ml, 11 mmol) dropwise. The resulting solution was stirred at −78° C. for 45 min before addition of 5-(bromomethyl)-2-(methylthio)pyrimidine (1.2 g, 5.4 mmol) in THF (20 mL). The resulting mixture was then stirred at −78° C. overnight. The reaction was quenched by addition of sat. NH₄Cl solution (100 mL), them the mixture was extracted with EtOAc twice, the combined organic phase was dried over Na₂SO₄, concentrated and the residue was purified on reverse phase MPLC (C18, 130 g) using 10-100% acetonitrile (0.05% TFA) as gradient to give (S)-2-((S)-2-(2-(methylthio)pyrimidin-5-yl)-1-(1-((2-(trimethylsilyl)ethoxy)methyl)-1H-tetrazol-5-yl)ethyl)pentanoic acid. LC/MS: (M+1)⁺:453.15.

Step D: (S)-2-((S)-2-(2-(methylthio)pyrimidin-5-yl)-1-(1H-tetrazol-5-yl)ethyl)pentanoic acid To a solution of (S)-2-((S)-2-(2-(methylthio)pyrimidin-5-yl)-1-(1-((2-(trimethylsilyl)ethoxy)methyl)-1H-tetrazol-5-yl)ethyl)pentanoic acid (30 mg, 0.066 mmol) in CH₂Cl₂ (1 ml) was added TFA (2 mL, 26 mmol), then the resulting solution was stirred at RT for 2 hours. After concentration the residue was purified on Gilson using 3-50% acetonitrile (0.05% TFA) as gradient to give (S)-2-((S)-2-(2-(methylthio)pyrimidin-5-yl)-1-(1H-tetrazol-5-yl)ethyl)pentanoic acid. LC/MS: (M+1)⁺: 323.04.

EXAMPLE 286

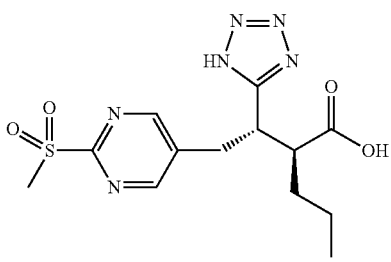 [SMILES: CCC[C@H](C(=O)O)[C@H](Cc1cnc(S(C)(=O)=O)nc1)c1nnn[nH]1]

(S)-2-((S)-2-(2-(methylsulfonyl)pyrimidin-5-yl)-1-(1H-tetrazol-5-yl)ethyl)pentanoic acid Step A: (S)-2-((S)-2-(2-(methylsulfonyl)pyrimidin-5-yl)-1-(1-((2-(trimethylsilyl)ethoxy)methyl)-1H-tetrazol-5-yl)ethyl)pentanoic acid To a solution of (S)-2-((S)-2-(2-(methylthio)pyrimidin-5-yl)-1-(1-((2-(trimethylsilyl)ethoxy)methyl)-1H-tetrazol-5-yl)ethyl)pentanoic acid (1.6 g, 3.6 mmol) in CH₂Cl₂ (30 ml) at 0° C. was added m-CPBA (2.2 g, 9.1 mmol), then the resulting solution was stirred at RT overnight. A solution of thiosulphate (2.0 g) in water (5 mL) was added and the mixture was stirred at RT for 1 hour. The mixture was partitioned between sat. NH₄Cl and DCM, the aqueous phase was extracted with DCM four times, the combined organic phase was dried over Na₂SO₄, concentrated and the residue was purified on reverse phase MPLC (C18, 130 g) using 10-50% acetonitrile (0.05% TFA) as gradient to give (S)-2-((S)-2-(2-(methylsulfonyl)pyrimidin-5-yl)-1-(1-((2-(trimethylsilyl)ethoxy)methyl)-1H-tetrazol-5-yl)ethyl)pentanoic acid. LC/MS: (M+1)⁺: 485.12.

Step B: (S)-2-((S)-2-(2-(methylsulfonyl)pyrimidin-5-yl)-1-(1H-tetrazol-5-yl)ethyl)pentanoic acid To a solution of (S)-2-((S)-2-(2-(methylsulfonyl)pyrimidin-5-yl)-1-(1-((2-(trimethylsilyl)ethoxy)methyl)-1H-tetrazol-5-yl)ethyl)pentanoic acid (100 mg, 0.21 mmol) in TFA (2 ml) was added water (0.2 ml), and the resulting solution was stirred at RT for 1 hour. After removing the volatile, the residue was purified on reverse phase HPLC using 5-50% acetonitrile (0.05% TFA)/water (0.05% TFA) as mobile phase to give (S)-2-((S)-2-(2-(methylsulfonyl)pyrimidin-5-yl)-1-(1H-tetrazol-5-yl)ethyl)pentanoic acid. LC/MS: (M+1)⁺: 355.07.

EXAMPLE 287

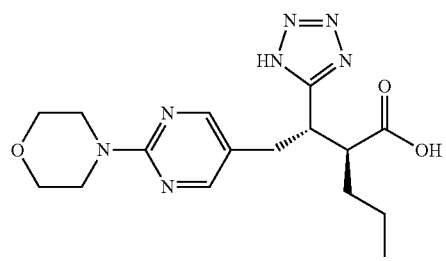 [SMILES: CCC[C@H](C(=O)O)[C@H](Cc1cnc(N2CCOCC2)nc1)c1nnn[nH]1]

(S)-2-((S)-2-(2-morpholinopyrimidin-5-yl)-1-(1H-tetrazol-5-yl)ethyl)pentanoic acid Step A: (S)-2-((S)-2-(2-morpholinopyrimidin-5-yl)-1-(1-((2-(trimethylsilyl)ethoxy)methyl)-1H-tetrazol-5-yl)ethyl)pentanoic acid To the solution of (S)-2-((S)-2-(2-(methylsulfonyl)pyrimidin-5-yl)-1-(1-((2-(trimethylsilyl)ethoxy)methyl)-1H-tetrazol-5-yl)ethyl)pentanoic acid (51 mg, 0.10 mmol) and morpholine (0.037 ml, 0.42 mmol) in DMF (1 ml) was added K₂CO₃ (29 mg, 0.21 mmol) and the resulting mixture was heated at 100° C. for 23 hrs. The mixture was purified on Gilson using 10-90% acetonitrile (0.05% TFA) to give (S)-2-((S)-2-(2-morpholinopyrimidin-5-yl)-1-(1-((2-(trimethylsilyl)ethoxy)methyl)-1H-tetrazol-5-yl)ethyl)pentanoic acid. LC/MS: (M+1)⁺: 492.19.

Step B: (S)-2-((S)-2-(2-morpholinopyrimidin-5-yl)-1-(1H-tetrazol-5-yl)ethyl)pentanoic acid To the solution of (S)-2-((S)-2-(2-morpholinopyrimidin-5-yl)-1-(1-((2-(trimethylsilyl)ethoxy)methyl)-1H-tetrazol-5-yl)ethyl)pentanoic acid (37 mg, 0.075 mmol) in TFA (2 ml) was added water (0.2 mL), and the resulting solution was stirred at RT for 2 hrs. After removing the volatile, the residue was purified on Gilson using 5-50% acetonitrile (0.05% TFA) to give (S)-2-((S)-2-(2-morpholinopyrimidin-5-yl)-1-(1H-tetrazol-5-yl)ethyl)pentanoic acid. LC/MS: (M+1)⁺: 362.14.

EXAMPLE 288

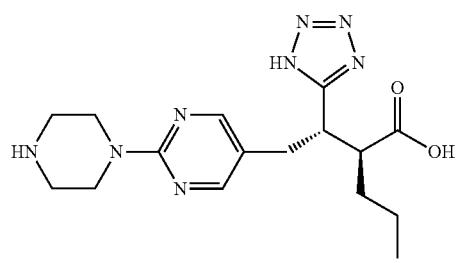 [SMILES: CCC[C@H](C(=O)O)[C@H](Cc1cnc(N2CCNCC2)nc1)c1nnn[nH]1]

(S)-2-((S)-2-(2-(piperazin-1-yl)pyrimidin-5-yl)-1-(1H-tetrazol-5-yl)ethyl)pentanoic acid Step A: (S)-2-((S)-2-(2-(4-((benzyloxy)carbonyl)piperazin-1-yl)pyrimidin-5-yl)-1-(1-((2-(trimethylsilyl)ethoxy)methyl)-1H-tetrazol-5-yl)ethyl)pentanoic acid To a solution of (S)-2-((S)-2-(2-(methylsulfonyl)pyrimidin-5-yl)-1-(1-((2-(trimethylsilyl)ethoxy)methyl)-1H-tetrazol-5-yl)ethyl)pentanoic acid (58 mg, 0.12 mmol) and benzyl piperazine-1-carboxylate (160 mg, 0.72 mmol) in DMF (1 ml) was added $K_2CO_3$ (33 mg, 0.24 mmol), and the resulting mixture was heated at 100° C. for 23 hours. The mixture was purified on Gilson using 10-90% acetonitrile (0.05% TFA) to give (S)-2-((S)-2-(2-(4-((benzyloxy)carbonyl)piperazin-1-yl)pyrimidin-5-yl)-1-(1-((2-(trimethylsilyl)ethoxy)methyl)-1H-tetrazol-5-yl)ethyl)pentanoic acid. LC/MS: (M+1)$^+$: 625.19.

Step B: (S)-2-((S)-2-(2-(piperazin-1-yl)pyrimidin-5-yl)-1-(1-((2-(trimethylsilyl)ethoxy)methyl)-1H-tetrazol-5-yl)ethyl)pentanoic acid To the solution of (S)-2-((S)-2-(2-(4-((benzyloxy)carbonyl)piperazin-1-yl)pyrimidin-5-yl)-1-(1-((2-(trimethylsilyl)ethoxy)methyl)-1H-tetrazol-5-yl)ethyl)pentanoic acid (15 mg, 0.024 mmol) in MeOH (10 ml) was added 10% Pd/C (26 mg, 0.024 mmol), and the resulting mixture was hydrogenated at RT via $H_2$ balloon for 2 hrs. The mixture was filtered through celite under $N_2$ and the filtrate was concentrated to give (S)-2-((S)-2-(2-(piperazin-1-yl)pyrimidin-5-yl)-1-(1-((2-(trimethylsilyl)ethoxy)methyl)-1H-tetrazol-5-yl)ethyl)pentanoic acid. LC/MS: (M+1)$^+$: 491.27.

Step C: (S)-2-((S)-2-(2-(piperazin-1-yl)pyrimidin-5-yl)-1-(1H-tetrazol-5-yl)ethyl)pentanoic acid To a solution of (S)-2-((S)-2-(2-(piperazin-1-yl)pyrimidin-5-yl)-1-(1-((2-(trimethylsilyl)ethoxy)methyl)-1H-tetrazol-5-yl)ethyl)pentanoic acid (15 mg, 0.031 mmol) in TFA (2 ml) was added water (0.2 mL). The resulting solution was stirred at RT for 2 hrs. After removing the volatile, the residue was purified on Gilson using 5-50% acetonitrile (0.05% TFA) to give (S)-2-((S)-2-(2-(piperazin-1-yl)pyrimidin-5-yl)-1-(1H-tetrazol-5-yl)ethyl)pentanoic acid. LC/MS: (M+1)$^+$: 361.25.

(S)-2-((S)-2-(2-(piperidin-4-yloxy)pyrimidin-5-yl)-1-(1H-tetrazol-5-yl)ethyl)pentanoic acid Step A: (S)-2-((S)-2-(2-((1-((benzyloxy)carbonyl)piperidin-4-yl)oxy)pyrimidin-5-yl)-1-(1-((2-(trimethylsilyl)ethoxy)methyl)-1H-tetrazol-5-yl)ethyl)pentanoic acid To a solution of benzyl 4-hydroxypiperidine-1-carboxylate (36 mg, 0.15 mmol) in DMF (3 ml) was added NaH (24 mg, 0.61 mmol) at 0° C. The resulting mixture was stirred at 0° C. for 30 min before addition of (S)-2-((S)-2-(2-(methylsulfonyl)pyrimidin-5-yl)-1-(1-((2-(trimethylsilyl)ethoxy)methyl)-1H-tetrazol-5-yl)ethyl)pentanoic acid (74 mg, 0.15 mmol). The mixture was then stirred at 0° C. for 3 hrs. After quenching with water, the solution was purified on Gilson using 30-100% acetonitrile (0.05% TFA) to give (S)-2-((S)-2-(2-((1-((benzyloxy)carbonyl)piperidin-4-yl)oxy)pyrimidin-5-yl)-1-(1-((2-(trimethylsilyl)ethoxy)methyl)-1H-tetrazol-5-yl)ethyl)pentanoic acid. LC/MS: (M+1)$^+$: 640.25.

Step B: (S)-2-((S)-2-(2-(piperidin-4-yloxy)pyrimidin-5-yl)-1-(1-((2-(trimethylsilyl)ethoxy)methyl)-1H-tetrazol-5-yl)ethyl)pentanoic acid To a solution of (S)-2-((S)-2-(2-((1-((benzyloxy)carbonyl)piperidin-4-yl)oxy)pyrimidin-5-yl)-1-(1-((2-(trimethylsilyl)ethoxy)methyl)-1H-tetrazol-5-yl)ethyl)pentanoic acid (64 mg, 0.10 mmol) in MeOH (10 ml) was added 10% Pd/C (11 mg, 10 μmol). The resulting mixture was hydrogenated at RT via $H_2$ balloon for 2 hrs. The mixture was filtered through celite under $N_2$ and the filtrate was concentrated to give (S)-2-((S)-2-(2-(piperidin-4-yloxy)pyrimidin-5-yl)-1-(1-((2-(trimethylsilyl)ethoxy)methyl)-1H-tetrazol-5-yl)ethyl)pentanoic acid. LC/MS: (M+1)$^+$: 506.18.

Step C: (S)-2-((S)-2-(2-(piperidin-4-yloxy)pyrimidin-5-yl)-1-(1H-tetrazol-5-yl)ethyl)pentanoic acid The solution of (S)-2-((S)-2-(2-(piperidin-4-yloxy)pyrimidin-5-yl)-1-(1-((2-(trimethylsilyl)ethoxy)methyl)-1H-tetrazol-5-yl)ethyl)pentanoic acid (51 mg, 0.10 mmol) in TFA (2 mL, 26 mmol) and water (0.2 ml) was stirred at RT for 2 hrs. The solution was concentrated and the residue was purified on Gilson using 5-50% acetonitrile (0.05% TFA) to give (S)-2-((S)-2-(2-(piperidin-4-yloxy)pyrimidin-5-yl)-1-(1H-tetrazol-5-yl)ethyl)pentanoic acid. LC/MS: (M+1)$^+$: 376.22.

EXAMPLE 289

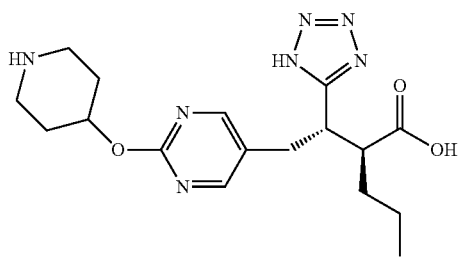 [SMILES: CCC[C@H](C(=O)O)[C@H](Cc1cnc(OC2CCNCC2)nc1)c1nnn[nH]1]

EXAMPLE 290

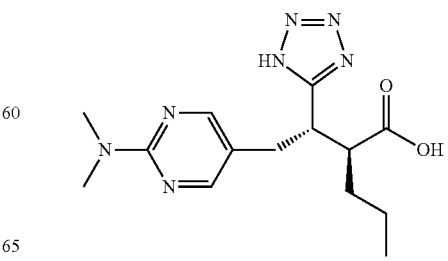

(S)-2-((S)-2-(2-(dimethylamino)pyrimidin-5-yl)-1-(1H-tetrazol-5-yl)ethyl)pentanoic acid Step A: (S)-2-((S)-2-(2-(dimethylamino)pyrimidin-5-yl)-1-(1-((2-(trimethylsilyl)ethoxy)methyl)-1H-tetrazol-5-yl)ethyl)pentanoic acid To a solution of (S)-2-((S)-2-(2-(methylsulfonyl)pyrimidin-5-yl)-1-(1-((2-(trimethylsilyl)ethoxy)methyl)-1H-tetrazol-5-yl)ethyl)pentanoic acid (74 mg, 0.15 mmol) and benzyl 4-aminopiperidine-1-carboxylate (14 mg, 0.61 mmol) in DMF (1 ml) was added K$_2$CO$_3$ (42 mg, 0.30 mmol), and the resulting mixture was heated at 100° C. for 23 hrs. The mixture was purified on Gilson using 10-90% acetonitrile (0.05% TFA) to give (S)-2-((S)-2-(2-(dimethylamino)pyrimidin-5-yl)-1-(1-((2-(trimethylsilyl)ethoxy)methyl)-1H-tetrazol-5-yl)ethyl)pentanoic acid. LC/MS: (M+1)$^+$: 450.26.

Step B: (S)-2-((S)-2-(2-(dimethylamino)pyrimidin-5-yl)-1-(1H-tetrazol-5-yl)ethyl)pentanoic acid To a solution of (S)-2-((S)-2-(2-(dimethylamino)pyrimidin-5-yl)-1-(1-((2-(trimethylsilyl)ethoxy)methyl)-1H-tetrazol-5-yl)ethyl)pentanoic acid (20 mg, 0.044 mmol) in TFA (2 ml) was added water (0.2 mL), then the resulting solution was stirred at RT for 2 hrs. After removing the volatile, the residue was purified on Gilson using 5-50% acetonitrile (0.05% TFA) to give (S)-2-((S)-2-(2-(dimethylamino)pyrimidin-5-yl)-1-(1H-tetrazol-5-yl)ethyl)pentanoic acid. LC/MS: (M+1)$^+$: 320.10.

EXAMPLE 291

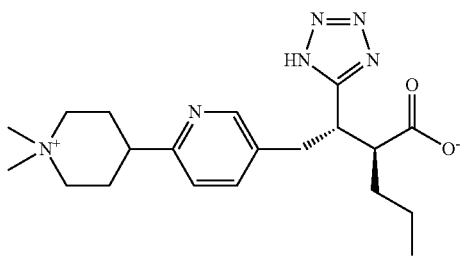 [SMILES: CCC[C@H](C(=O)[O-])[C@H](Cc1ccc(C2CC[N+](C)(C)CC2)nc1)c1nnn[nH]1]

(S)-2-((S)-2-(6-(1,1-dimethylpiperidin-1-ium-4-yl)pyridin-3-yl)-1-(1H-tetrazol-5-yl)ethyl)pentanoate Step A: 1,1-dimethyl-4-(4,4,5,5-tetramethyl-1,3,2-dioxaborolan-2-yl)-1,2,3,6-tetrahydropyridin-1-ium To a solution of 1-methyl-4-(4,4,5,5-tetramethyl-1,3,2-dioxaborolan-2-yl)-1,2,3,6-tetrahydropyridine (0.86 g, 3.8 mmol) in acetone (20 ml) was added MeI (0.26 ml, 4.2 mmol). The resulting solution was stirred at RT for 1 hour. The mixture was concentrated to give 1,1-dimethyl-4-(4,4,5,5-tetramethyl-1,3,2-dioxaborolan-2-yl)-1,2,3,6-tetrahydropyridin-1-ium. LC-MS M$^+$:238.15.

Step B: 5-((2S,3S)-3-carboxy-2-(1-((2-(trimethylsilyl)ethoxy)methyl)-1H-tetrazol-5-yl)hexyl)-1',1'-dimethyl-1',2',3',6'-tetrahydro-[2,4'-bipyridin]-1'-ium To a solution of 1,1-dimethyl-4-(4,4,5,5-tetramethyl-1,3,2-dioxaborolan-2-yl)-1,2,3,6-tetrahydropyridin-1-ium (200 mg, 0.54 mmol) and (S)-2-((S)-2-(6-bromopyridin-3-yl)-1-(1-((2-(trimethylsilyl)ethoxy)methyl)-1H-tetrazol-5-yl)ethyl)pentanoic acid (200 mg, 0.41 mmol) in dioxane (3 ml) was added Na$_2$CO$_3$ solution (0.62 ml, 1.2 mmol). The mixture was degassed by N$_2$ via vacuum/N$_2$ three times, PdCl$_2$(dppf) (30 mg, 0.041 mmol) was added and the resulting mixture was degassed again before heated at 100° C. overnight. After filtration the filtrate was concentrated and the residue was purified on reverse phase HPLC using acetonitrile/water (0.1% TFA) as mobile phase to give 5-((2S,3S)-3-carboxy-2-(1-((2-(trimethylsilyl)ethoxy)methyl)-1H-tetrazol-5-yl)hexyl)-1',1'-dimethyl-1',2',3',6'-tetrahydro-[2,4'-bipyridin]-1'-ium. LC-MS M$^+$: 515.33.

Step C: 5-((2S,3S)-3-carboxy-2-(1H-tetrazol-5-yl)hexyl)-1',1'-dimethyl-1',2',3',6'-tetrahydro-[2,4'-bipyridin]-1'-ium To the 5-((2S,3S)-3-carboxy-2-(1-((2-(trimethylsilyl)ethoxy)methyl)-1H-tetrazol-5-yl)hexyl)-1',1'-dimethyl-1',2',3',6'-tetrahydro-[2,4'-bipyridin]-1'-ium (160 mg, 0.31 mmol) was added TFA (2 ml) and the resulting solution was stirred at RT for 1 hour. After concentration the residue was purified on reverse phase HPLC using acetonitrile/water (0.05% TFA) as mobile phase to give 5-((2S,3S)-3-carboxy-2-(1H-tetrazol-5-yl)hexyl)-1',1'-dimethyl-1',2',3',6'-tetrahydro-[2,4'-bipyridin]-1'-ium. LC-MS M$^+$:385.13.

Step D: (S)-2-((S)-2-(6-(1,1-dimethylpiperidin-1-ium-4-yl)pyridin-3-yl)-1-(1H-tetrazol-5-yl)ethyl)pentanoate To a solution of 5-((2S,3S)-3-carboxy-2-(1H-tetrazol-5-yl)hexyl)-1',1'-dimethyl-1',2',3',6'-tetrahydro-[2,4'-bipyridin]-1'-ium (77 mg, 0.20 mmol) in MeOH (10 ml) was added 10% Pd/C (21 mg, 0.020 mmol). The resulting mixture was subjected to hydrogenation via H$_2$ balloon at RT for 1 hour. After filtration through celite under N$_2$, the filtrate was concentrated and the residue was purified on reverse phase HPLC using acetonitrile/water (0.05% TFA) as mobile phase to give (S)-2-((S)-2-(6-(1,1-dimethylpiperidin-1-ium-4-yl)pyridin-3-yl)-1-(1H-tetrazol-5-yl)ethyl)pentanoate. LC-MS M$^+$: 387.19

EXAMPLE 292

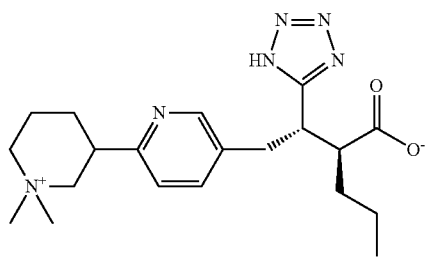 [SMILES: CCC[C@H](C(=O)[O-])[C@H](Cc1ccc(C2CCC[N+](C)(C)C2)nc1)c1nnn[nH]1]

(2S)-2-((1S)-2-(6-(1,1-dimethylpiperidin-1-ium-3-yl)pyridin-3-yl)-1-(1H-tetrazol-5-yl)ethyl)pentanoate Step A: 5-(4,4,5,5-tetramethyl-1,3,2-dioxaborolan-2-yl)-1,2,3,6-tetrahydropyridine To a solution of tert-butyl 3-(4,4,5,5-tetramethyl-1,3,2-dioxaborolan-2-yl)-5,6-dihydropyridine-1(2H)-carboxylate (102 mg, 0.33 mmol) in $CH_2Cl_2$ (2 ml) was added TFA (2 ml, 26.0 mmol) at RT and the resulting solution was stirred at RT for 1 hour. After concentration the residue was lyophilized from acetonitrile/water to give 5-(4,4,5,5-tetramethyl-1,3,2-dioxaborolan-2-yl)-1,2,3,6-tetrahydropyridine 2,2,2-trifluoroacetate. LCMS $(M+1)^+$: 210.13

Step B: 1,1-dimethyl-5-(4,4,5,5-tetramethyl-1,3,2-dioxaborolan-2-yl)-1,2,3,6-tetrahydropyridin-1-ium To a solution of 5-(4,4,5,5-tetramethyl-1,3,2-dioxaborolan-2-yl)-1,2,3,6-tetrahydropyridine 2,2,2-trifluoroacetate (0.11 g, 0.33 mmol) in THF (10 ml) was added $Na_2CO_3$ (0.14 g, 1.3 mmol) and MeI (0.083 ml, 1.3 mmol). The resulting mixture was stirred at RT for 4 hours. The mixture was concentrated to give 1,1-dimethyl-5-(4,4,5,5-tetramethyl-1,3,2-dioxaborolan-2-yl)-1,2,3,6-tetrahydropyridin-1-ium. LCMS $M^+$: 238.11

Step C: 5-((2S,3S)-3-carboxy-2-(1-((2-(trimethylsilyl)ethoxy)methyl)-1H-tetrazol-5-yl)hexyl)-1',1'-dimethyl-1',2',5',6'-tetrahydro-[2,3'-bipyridin]-1'-ium To a solution of 1,1-dimethyl-5-(4,4,5,5-tetramethyl-1,3,2-dioxaborolan-2-yl)-1,2,3,6-tetrahydropyridin-1-ium (77 mg, 0.32 mmol) and (S)-2-((S)-2-(6-bromopyridin-3-yl)-1-(1-((2-(trimethylsilyl)ethoxy)methyl)-1H-tetrazol-5-yl)ethyl)pentanoic acid (120 mg, 0.25 mmol) in dioxane (6 ml) was added $Na_2CO_3$ solution (0.37 ml, 0.74 mmol). The mixture was degassed by $N_2$ via vacuum/$N_2$ three times, then $PdCl_2$(dppf) (18 mg, 0.025 mmol) was added and the resulting mixture was degassed again before being heated at 100° C. overnight. After filtration the filtrate was concentrated and the residue was purified on reverse phase MPLC using acetonitrile/water (0.05% TFA) as mobile phase to give 5-((2S,3S)-3-carboxy-2-(1-((2-(trimethylsilyl)ethoxy)methyl)-1H-tetrazol-5-yl)hexyl)-1',1'-dimethyl-1',2',5',6'-tetrahydro-[2,3'-bipyridin]-1'-ium. LCMS $M^+$: 515.32.

Step D: 3-(5-((2S,3S)-3-carboxy-2-(1-((2-(trimethylsilyl)ethoxy)methyl)-1H-tetrazol-5-yl)hexyl)pyridin-2-yl)-1,1-dimethylpiperidin-1-ium To a solution of 5-((2S,3S)-3-carboxy-2-(1-((2-(trimethylsilyl)ethoxy)methyl)-1H-tetrazol-5-yl)hexyl)-1',1'-dimethyl-1',2',5',6'-tetrahydro-[2,3'-bipyridin]-1'-ium (52 mg, 0.10 mmol) in MeOH (15 ml) was added 10% Pd/C (11 mg, 10 μmol). The resulting mixture was subjected to hydrogenation with $H_2$ balloon at RT for 2 hrs. After filtration through celite under $N_2$, the filtrate was concentrated and the residue was purified on reverse phase HPLC using acetonitrile/water (0.05% TFA) as mobile phase to give 3-(5-((2S,3S)-3-carboxy-2-(1-((2-(trimethylsilyl)ethoxy)methyl)-1H-tetrazol-5-yl)hexyl)pyridin-2-yl)-1,1-dimethylpiperidin-1-ium. LC-MS $M^+$: 517.33.

Step E: (2S)-2-((1S)-2-(6-(1,1-dimethylpiperidin-1-ium-3-yl)pyridin-3-yl)-1-(1H-tetrazol-5-yl)ethyl)pentanoate To a solution of 3-(5-((2S,3S)-3-carboxy-2-(1-((2-(trimethylsilyl)ethoxy)methyl)-1H-tetrazol-5-yl)hexyl)pyridin-2-yl)-1,1-dimethylpiperidin-1-ium (24 mg, 0.046 mmol) in TFA (2 mL, 26 mmol) was added water (0.2 mL). The resulting solution was stirred at RT for 2 hrs. After concentration the residue was purified on reverse phase HPLC using acetonitrile/water (0.05% TFA) to give (2S)-2-((1S)-2-(6-(1,1-dimethylpiperidin-1-ium-3-yl)pyridin-3-yl)-1-(1H-tetrazol-5-yl)ethyl)pentanoate. LCMS $M^+$: 387.22.

EXAMPLE 293

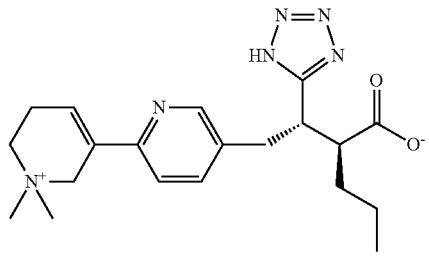 [SMILES: CCC[C@H](C(=O)[O-])[C@H](Cc1ccc(C2=CCC[N+](C)(C)C2)nc1)c1nnn[nH]1]

(S)-2-((S)-2-(1',1'-dimethyl-1',2',5',6'-tetrahydro-[2,3'-bipyridin]-1'-ium-5-yl)-1-(1H-tetrazol-5-yl)ethyl)pentanoate To a solution of 5-((2S,3S)-3-carboxy-2-(1-((2-(trimethylsilyl)ethoxy)methyl)-1H-tetrazol-5-yl)hexyl)-1',1'-dimethyl-1',2',5',6'-tetrahydro-[2,3'-bipyridin]-1'-ium (EXAMPLE 292, step D) (13 mg, 0.025 mmol) in TFA (2 mL, 26.0 mmol) was added water (0.2 mL). The resulting solution was stirred at RT for 2 hrs. The reaction solution was concentrated and the residue was purified on reverse phase HPLC using acetonitrile/water (0.05% TFA) to give (S)-2-((S)-2-(1',1'-dimethyl-1',2',5',6'-tetrahydro-[2,3'-bipyridin]-1'-ium-5-yl)-1-(1H-tetrazol-5-yl)ethyl)pentanoate. LC-MS $M^+$: 385.19.

EXAMPLE 294

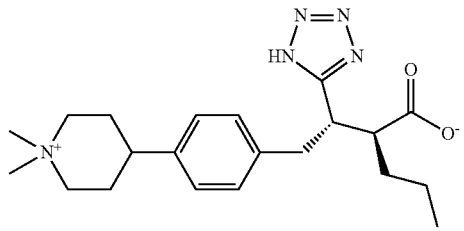 [SMILES: CCC[C@H](C(=O)[O-])[C@H](Cc1ccc(C2CC[N+](C)(C)CC2)cc1)c1nnn[nH]1]

(S)-2-((S)-2-(4-(1,1-dimethylpiperidin-1-ium-4-yl)phenyl)-1-(1H-tetrazol-5-yl)ethyl)pentanoate Step A: (S)-2-((S)-2-(4-bromophenyl)-1-(1-((2-(trimethylsilyl)ethoxy)methyl)-1H-tetrazol-5-yl)ethyl)pentanoic acid To a solution of diisopropylamine (6.3 ml, 44 mmol) in THF (12 mL) at −78° C. was added n-butyllithium (25 ml, 40 mmol), and the resulting solution was stirred at −78° C. for 15 min before warmed to 0° C. To a solution of (S)-2-((1-((2-(trimethylsilyl)ethoxy)methyl)-1H-tetrazol-5-yl)methyl)pentanoic acid (2.8 g, 8.9 mmol) in THF (30 mL) at −78° C. was added above prepared LDA (20 ml, 19 mmol) dropwise. The resulting solution was stirred at −78° C. for 45 min before addition of 1-bromo-4-(bromomethyl)benzene (2.2 g, 8.9 mmol) in THF (20 mL). The resulting mixture was then stirred at −78° C. overnight. The reaction was quenched by addition of sat. NH₄Cl solution (100 mL), then the mixture was extracted with EtOAc twice, the combined organic phase was dried over Na₂SO₄, concentrated and the residue was purified on silica gel column using MeOH/DCM as eluting solvents to give (S)-2-((S)-2-(4-bromophenyl)-1-(1-((2-(trimethylsilyl)ethoxy)methyl)-1H-tetrazol-5-yl)ethyl)pentanoic acid. LCMS (M+1)⁺: 483.07.

Step B: 4-(4-((2S,3S)-3-carboxy-2-(1-((2-(trimethylsilyl)ethoxy)methyl)-1H-tetrazol-5-yl)hexyl)phenyl)-1,1-dimethyl-1,2,3,6-tetrahydropyridin-1-ium To a solution of 1,1-dimethyl-4-(4,4,5,5-tetramethyl-1,3,2-dioxaborolan-2-yl)-1,2,3,6-tetrahydropyridin-1-ium (200 mg, 0.54 mmol) and (S)-2-((S)-2-(4-bromophenyl)-1-(1-((2-(trimethylsilyl)ethoxy)methyl)-1H-tetrazol-5-yl)ethyl)pentanoic acid (200 mg, 0.41 mmol) in dioxane (3 ml) was added Na₂CO₃ solution (0.621 ml, 1.241 mmol). The mixture was degassed by N₂ via vacuum/N₂ three times, and PdCl₂(dppf) (30 mg, 0.041 mmol) was added and the resulting mixture was degassed again before being heated at 100° C. overnight. After filtration the filtrate was concentrated and the residue was purified on reverse phase HPLC using acetonitrile/water (0.05% TFA) to give 4-(4-((2S,3S)-3-carboxy-2-(1-((2-(trimethylsilyl)ethoxy)methyl)-1H-tetrazol-5-yl)hexyl)phenyl)-1,1-dimethyl-1,2,3,6-tetrahydropyridin-1-ium. LCMS M⁺: 514.21.

Step C: 4-(4-((2S,3S)-3-carboxy-2-(1-((2-(trimethylsilyl)ethoxy)methyl)-1H-tetrazol-5-yl)hexyl)phenyl)-1,1-dimethylpiperidin-1-ium To a solution of 4-(4-((2S,3S)-3-carboxy-2-(1-((2-(trimethylsilyl)ethoxy)methyl)-1H-tetrazol-5-yl)hexyl)phenyl)-1,1-dimethyl-1,2,3,6-tetrahydropyridin-1-ium (70 mg, 0.14 mmol) in MeOH (10 ml) was added 10% Pd/C (14.5 mg, 0.014 mmol). The resulting mixture was hydrogenated with H₂ Balloon at RT overnight. After filtration the filtrate was concentrated to give 4-(4-((2S,3S)-3-carboxy-2-(1-((2-(trimethylsilyl)ethoxy)methyl)-1H-tetrazol-5-yl)hexyl)phenyl)-1,1-dimethylpiperidin-1-ium. LCMS M⁺: 516.22.

Step D: (S)-2-((S)-2-(4-(1,1-dimethylpiperidin-1-ium-4-yl)phenyl)-1-(1H-tetrazol-5-yl)ethyl)pentanoate To a solution of 4-(4-((2S,3S)-3-carboxy-2-(1-((2-(trimethylsilyl)ethoxy)methyl)-1H-tetrazol-5-yl)hexyl)phenyl)-1,1-dimethylpiperidin-1-ium (70 mg, 0.14 mmol) in TFA (2 ml) was added water (0.2 mL), and the resulting solution was stirred at RT for 1 hour. After removing the volatile, the residue was purified on reverse phase HPLC using acetonitrile/water (0.05% TFA) as mobile phase to give (S)-2-((S)-2-(4-(1,1-dimethylpiperidin-1-ium-4-yl)phenyl)-1-(1H-tetrazol-5-yl)ethyl)pentanoate. LCMS M⁺: 386.23.

EXAMPLE 295

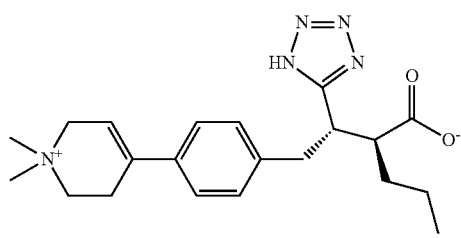 [SMILES: CCC[C@H](C(=O)[O-])[C@H](Cc1ccc(C2=CC[N+](C)(C)CC2)cc1)c1nnn[nH]1]

(S)-2-((S)-2-(4-(1,1-dimethyl-1,2,3,6-tetrahydropyridin-1-ium-4-yl)phenyl)-1-(1H-tetrazol-5-yl)ethyl) pentanoate To a solution of 4-(4-((2S,3S)-3-carboxy-2-(1-((2-(trimethylsilyl)ethoxy)methyl)-1H-tetrazol-5-yl)hexyl)phenyl)-1,1-dimethyl-1,2,3,6-tetrahydropyridin-1-ium (16 mg, 0.031 mmol) in TFA (2 ml) was added water (0.2 mL) and the resulting solution was stirred at RT for 1 hour. After removing the volatile, the residue was purified on reverse phase using acetonitrile/water (0.05% TFA) as mobile phase to give (S)-2-((S)-2-(4-(1,1-dimethyl-1,2,3,6-tetrahydropyridin-1-ium-4-yl)phenyl)-1-(1H-tetrazol-5-yl)ethyl)pentanoate. LCMS M⁺: 384.23.

EXAMPLE 296

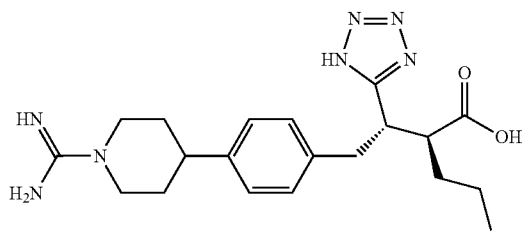 [SMILES: CCC[C@H](C(=O)O)[C@H](Cc1ccc(C2CCN(C(=N)N)CC2)cc1)c1nnn[nH]1]

(S)-2-((S)-2-(4-(1-carbamimidoylpiperidin-4-yl)phenyl)-1-(1H-tetrazol-5-yl)ethyl)pentanoic acid Step A: (S)-2-((S)-2-(4-(1-(tert-butoxycarbonyl)-1,2,3,6-tetrahydropyridin-4-yl)phenyl)-1-(1-((2-(trimethylsilyl)ethoxy)methyl)-1H-tetrazol-5-yl)ethyl)pentanoic acid A mixture of tert-butyl 4-(4,4,5,5-tetramethyl-1,3,2-dioxaborolan-2-yl)-5,6-dihydropyridine-1(2H)-carboxylate (320 mg, 1.02 mmol) and (S)-2-((S)-2-(4-bromophenyl)-1-(1-((2-(trimethylsilyl)ethoxy)methyl)-1H-tetrazol-5-yl)ethyl)pentanoic acid (410 mg, 0.85 mmol) and Na₂CO₃ (1.3 ml, 2.6 mmol) in dioxane (6 ml) was degassed by bubbling N₂ for 20 min before addition of PdCl₂(dppf) (62 mg, 0.085 mmol). The resulting mixture was heated at 100° C. overnight. After filtration the filtrate was concentrated and the residue was purified on reverse phase MPLC using acetonitrile/water (0.05% TFA) as mobile phase to give (S)-2-((S)-2-(4-(1-(tert-butoxycarbonyl)-1,2,3,6-tetrahydropyridin-4-yl)phenyl)-1-(1-((2-(trimethylsilyl)ethoxy)methyl)-1H-tetrazol-5-yl)ethyl)pentanoic acid. LCMS (M+1)⁺: 586.26.

Step B: (S)-2-((S)-2-(4-(1-(tert-butoxycarbonyl)piperidin-4-yl)phenyl)-1-(1-((2-(trimethylsilyl)ethoxy)methyl)-1H-tetrazol-5-yl)ethyl)pentanoic acid To a solution of (S)-2-((S)-2-(4-(1-(tert-butoxycarbonyl)-1,2,3,6-tetrahydropyridin-4-yl)phenyl)-1-(1-((2-(trimethylsilyl)ethoxy)methyl)-1H-tetrazol-5-yl)ethyl)pentanoic acid (500 mg, 0.85 mmol) in MeOH (20 ml) was added 10% Pd/C (90 mg, 0.085 mmol). The resulting mixture was subjected to hydrogenation via a H₂ balloon at RT overnight. After filtration through celite under N₂ the filtrate was concentrated and the residue was purified on silica gel column using MeOH/DCM as eluting solvents to give (S)-2-((S)-2-(4-(1-(tert-butoxycarbonyl)piperidin-4-yl)phenyl)-1-(1-((2-(trimethylsilyl)ethoxy)methyl)-1H-tetrazol-5-yl)ethyl)pentanoic acid. LCMS (M+1)+: 588.29.

Step C: (S)-2-((S)-2-(4-(piperidin-4-yl)phenyl)-1-(1H-tetrazol-5-yl)ethyl)pentanoic acid To a solution of (S)-2-((S)-2-(4-(1-(tert-butoxycarbonyl)piperidin-4-yl)phenyl)-1-(1-((2-(trimethylsilyl)ethoxy)methyl)-1H-tetrazol-5-yl)ethyl)pentanoic acid (0.46 g, 0.78 mmol) in TFA (3 ml) was added water (0.3 ml). The resulting solution was stirred at RT for 0.5 hour. The reaction solution was purified on reverse phase HPLC using acetonitrile/water (0.05% TFA) as mobile phase to give (S)-2-((S)-2-(4-(piperidin-4-yl)phenyl)-1-(1H-tetrazol-5-yl)ethyl)pentanoic acid. LCMS (M+1)+: 358.16.

Step D: (S)-2-((S)-2-(4-(1-carbamimidoylpiperidin-4-yl)phenyl)-1-(1H-tetrazol-5-yl)ethyl)pentanoic acid To a solution of (S)-2-((S)-2-(4-(piperidin-4-yl)phenyl)-1-(1H-tetrazol-5-yl)ethyl)pentanoic acid (100 mg, 0.29 mmol) in DMF (2 ml) was added 1H-pyrazole-1-carboxamidine hydrochloride (63 mg, 0.43 mmol) and DIEA (0.20 ml, 1.2 mmol). The resulting solution was stirred at RT overnight. The mixture was purified on reverse phase using acetonitrile/water (0.1% formic acid) as mobile phase to give (S)-2-((S)-2-(4-(1-carbamimidoylpiperidin-4-yl)phenyl)-1-(1H-tetrazol-5-yl)ethyl)pentanoic acid. LCMS (M+1)+: 400.12.

EXAMPLE 297

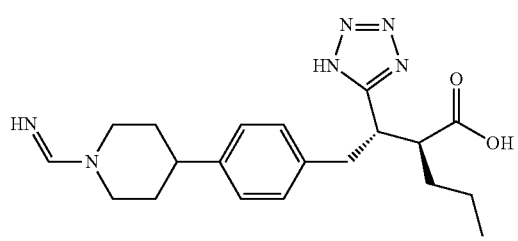 [SMILES: CCC[C@H](C(=O)O)[C@H](Cc1ccc(C2CCN(C=N)CC2)cc1)c1nnn[nH]1]

(S)-2-((S)-2-(4-(1-(iminomethyl)piperidin-4-yl)phenyl)-1-(1H-tetrazol-5-yl)ethyl)pentanoic acid To a solution of (S)-2-((S)-2-(4-(piperidin-4-yl)phenyl)-1-(1H-tetrazol-5-yl)ethyl)pentanoic acid (130 mg, 0.35 mmol) in DMF (1 ml) was added ethyl formimidate hydrochloride (58 mg, 0.53 mmol) and DIEA (0.25 ml, 1.4 mmol). The resulting solution was stirred at RT overnight. The mixture was purified on reverse phase HPLC using acetonitrile/water (0.1% formic acid) as mobile phase to give (S)-2-((S)-2-(4-(1-(iminomethyl)piperidin-4-yl)phenyl)-1-(1H-tetrazol-5-yl)ethyl)pentanoic acid. LCMS (M+1)+: 385.26.

EXAMPLE 298

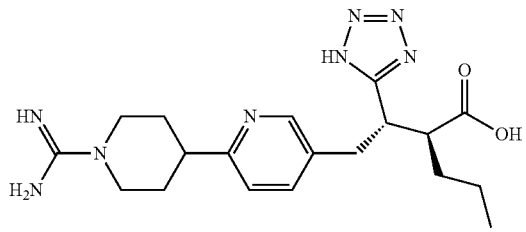 [SMILES: CCC[C@H](C(=O)O)[C@H](Cc1ccc(C2CCN(C(=N)N)CC2)nc1)c1nnn[nH]1]

(S)-2-((S)-2-(6-(1-carbamimidoylpiperidin-4-yl)pyridin-3-yl)-1-(1H-tetrazol-5-yl)ethyl)pentanoic acid Step A: (S)-2-((S)-2-(1'-(tert-butoxycarbonyl)-1',2',3',6'-tetrahydro-[2,4'-bipyridin]-5-yl)-1-(1-((2-(trimethylsilyl)ethoxy)methyl)-1H-tetrazol-5-yl)ethyl)pentanoic acid A solution of tert-butyl 4-(4,4,5,5-tetramethyl-1,3,2-dioxaborolan-2-yl)-5,6-dihydropyridine-1(2H)-carboxylate (470 mg, 1.5 mmol), (S)-2-((S)-2-(6-bromopyridin-3-yl)-1-(1-((2-(trimethylsilyl)ethoxy)methyl)-1H-tetrazol-5-yl)ethyl)pentanoic acid (570 mg, 1.2 mmol) and Na$_2$CO$_3$ (2.3 ml, 4.7 mmol) in 1,4-dioxane (15 ml) was bubbled with N$_2$ for 15 min before addition of PdCl$_2$(dppf) (86 mg, 0.12 mmol). The resulting mixture was heated at 100° C. overnight. After filtration through celite, the filtrate was concentrated and the residue was purified on reverse phase MPLC using acetonitrile/water (0.05% TFA) as mobile phase to give (S)-2-((S)-2-(1'-(tert-butoxycarbonyl)-1',2',3',6'-tetrahydro-[2,4'-bipyridin]-5-yl)-1-(1-((2-(trimethylsilyl)ethoxy)methyl)-1H-tetrazol-5-yl)ethyl)pentanoic acid. LCMS (M+1)+: 587.39.

Step B: (S)-2-((S)-2-(6-(1-(tert-butoxycarbonyl)piperidin-4-yl)pyridin-3-yl)-1-(1-((2-(trimethylsilyl)ethoxy)methyl)-1H-tetrazol-5-yl)ethyl)pentanoic acid To a solution of (S)-2-((S)-2-(1'-(tert-butoxycarbonyl)-1',2',3',6'-tetrahydro-[2,4'-bipyridin]-5-yl)-1-(1-((2-(trimethylsilyl)ethoxy)methyl)-1H-tetrazol-5-yl)ethyl)pentanoic acid (0.58 g, 1.0 mmol) in MeOH (30 ml) was added 10% Pd/C (0.10 g, 0.099 mmol). The resulting mixture was subjected to hydrogenation at RT via H$_2$ balloon for 5 hrs. The mixture was filtered through celite under N$_2$, and the filtrate was concentrated to give (S)-2-((S)-2-(6-(1-(tert-butoxycarbonyl)piperidin-4-yl)pyridin-3-yl)-1-(1-((2-(trimethylsilyl)ethoxy)methyl)-1H-tetrazol-5-yl)ethyl)pentanoic acid. LCMS (M+1)+: 589.25.

Step C: (S)-2-((S)-2-(6-(piperidin-4-yl)pyridin-3-yl)-1-(1H-tetrazol-5-yl)ethyl)pentanoic acid To a solution of (S)-2-((S)-2-(6-(1-(tert-butoxycarbonyl)piperidin-4-yl)pyridin-3-yl)-1-(1-((2-(trimethylsilyl)ethoxy)methyl)-1H-tetrazol-5-yl)ethyl)pentanoic acid (0.37 g, 0.63 mmol) in TFA (2 ml) was added water (0.2 ml). The resulting solution was stirred at RT for 1 hour, then the solution was concentrated and the residue was purified on reverse phase HPLC using acetonitrile/water (0.05% TFA)

as mobile phase to give (S)-2-((S)-2-(6-(piperidin-4-yl)pyridin-3-yl)-1-(1H-tetrazol-5-yl)ethyl)pentanoic acid. LCMS (M+1)⁺: 359.15.

Step D: (S)-2-((S)-2-(6-(1-carbamimidoylpiperidin-4-yl)pyridin-3-yl)-1-(1H-tetrazol-5-yl)ethyl)pentanoic acid To a solution of (S)-2-((S)-2-(6-(piperidin-4-yl)pyridin-3-yl)-1-(1H-tetrazol-5-yl)ethyl)pentanoic acid (120 mg, 0.33 mmol) in DMF (2 ml) was added 1H-pyrazole-1-carboxamidine hydrochloride (73 mg, 0.50 mmol) and DIEA (0.46 ml, 2.7 mmol). The resulting solution was stirred at RT overnight. The mixture was purified on reverse phase HPLC using acetonitrile/water (0.05% TFA) as mobile phase to give (S)-2-((S)-2-(6-(1-carbamimidoylpiperidin-4-yl)pyridin-3-yl)-1-(1H-tetrazol-5-yl)ethyl)pentanoic acid. LCMS (M+1)⁺: 401.15.

EXAMPLE 299

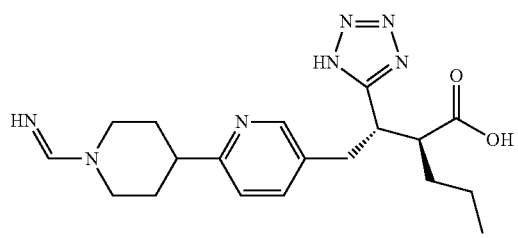 [SMILES: CCC[C@H](C(=O)O)[C@H](Cc1ccc(C2CCN(C=N)CC2)nc1)c1nnn[nH]1]

(S)-2-((S)-2-(6-(1-(iminomethyl)piperidin-4-yl)pyridin-3-yl)-1-(1H-tetrazol-5-yl)ethyl)pentanoic acid To a solution of (S)-2-((S)-2-(6-(piperidin-4-yl)pyridin-3-yl)-1-(1H-tetrazol-5-yl)ethyl)pentanoic acid (35 mg, 0.098 mmol) in DMF (1 ml) was added ethyl formimidate hydrochloride (16 mg, 0.15 mmol) and DIEA (0.14 ml, 0.78 mmol). The resulting solution was stirred at RT overnight. The mixture was purified on reverse phase HPLC using acetonitrile/water (0.05% TFA) as mobile phase to give (S)-2-((S)-2-(6-(1-(iminomethyl)piperidin-4-yl)pyridin-3-yl)-1-(1H-tetrazol-5-yl)ethyl)pentanoic acid. LCMS (M+1)⁺: 386.22.

EXAMPLEs 300-338

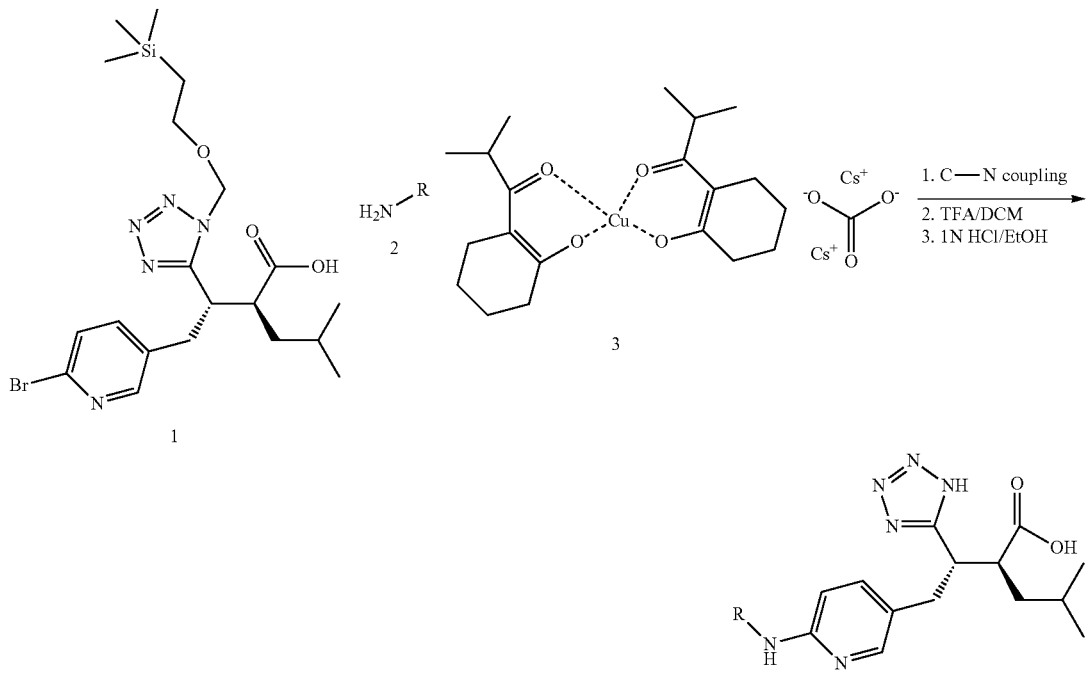

Step 1:

In glovebox, a mixture of (S)-2-((S)-2-(6-bromopyridin-3-yl)-1-(1-((2-(trimethylsilyl)ethoxy)methyl)-1H-tetrazol-5-yl)ethyl)-4-methylpentanoic acid (25 mg, 0.050 mmol), Amine 2 (0.100 mmol), Reactant 3 (3.99 mg, 10.03 μmol), cesium carbonate (49.0 mg, 0.150 mmol) and 600 μL of DMF into 2 dram vials was heated at 100° C. for 16 hr. The vials were cooled down to room temperature and 3 mL of EtOAc was added into each vial. The mixtures were filtered and the solution was concentrated in GeneVac.

Step 2: (De-Boc Reaction for Boc-Containing Amines)

Into the residues were added 2 mL of TFA/DCM. The mixtures were shaken at room temperature for 5 hr and concentrated to dryness.

Step 3: (De-Protection of SEM Group)

1 mL of EtOH and 1 mL of 1N aq. HCl were added into the vials. The mixtures were heated at 60° C. for 16 hr and concentrated in GeneVac. The residues were dissolved in 1.4 mL of DMSO. The crude solution was filtered through a filter plate and purified by HPLC.

The following compounds were made following the above general procedure:

| Ex. No | Structure | IUPAC Name | Calc'd Mass [M + H]+ | LC/MS m/e [M + H]+ |
|---|---|---|---|---|
| 300 | 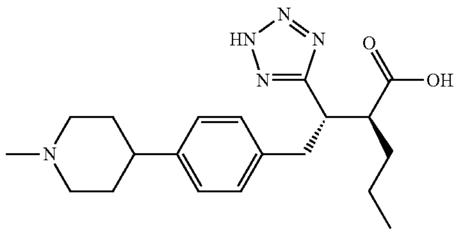 [SMILES: CCC[C@H](C(=O)O)[C@H](Cc1ccc(C2CCN(C)CC2)cc1)c1nn[nH]n1] | (2S)-2-[(1S)-2-[4-(1-methylpiperidin-4-yl)phenyl]-1-(2H-tetrazol-5-yl)ethyl]pentanoic acid | 372.24 | 372.23 |
| 301 | 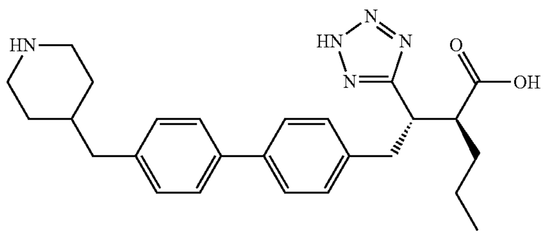 [SMILES: CCC[C@H](C(=O)O)[C@H](Cc1ccc(-c2ccc(CC3CCNCC3)cc2)cc1)c1nn[nH]n1] | (2S)-2-[(1S)-2-[4'-(piperidin-4-ylmethyl)biphenyl-4-yl]-1-(2H-tetrazol-5-yl)ethyl]pentanoic acid | 448.27 | 448.26 |
| 302 | 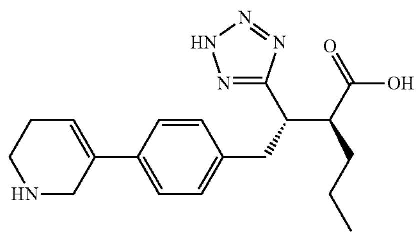 [SMILES: CCC[C@H](C(=O)O)[C@H](Cc1ccc(C2=CCCNC2)cc1)c1nn[nH]n1] | (2S)-2-[(1S)-2-[4-(1,2,5,6-tetrahydropyridin-3-yl)phenyl]-1-(2H-tetrazol-5-yl)ethyl]pentanoic acid | 356.21 | 356.20 |
| 303 | 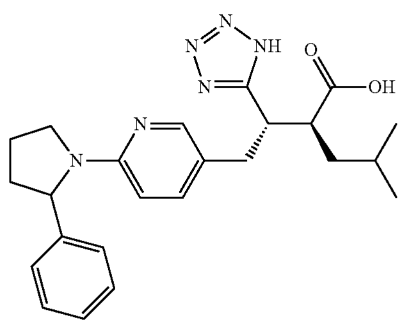 [SMILES: CC(C)C[C@H](C(=O)O)[C@H](Cc1ccc(N2CCCC2c2ccccc2)nc1)c1nnn[nH]1] | (2S)-4-methyl-2-[(1S)-2-[6-(2-phenylpyrrolidin-1-yl)pyridin-3-yl]-1-(1H-tetrazol-5-yl)ethyl]pentanoic acid | 435.25 | 435.24 |
| 304 | 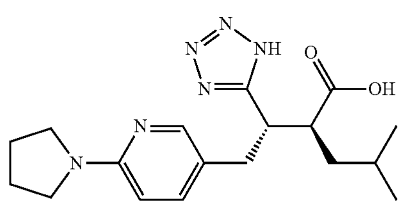 [SMILES: CC(C)C[C@H](C(=O)O)[C@H](Cc1ccc(N2CCCC2)nc1)c1nnn[nH]1] | (2S)-4-methyl-2-[(1S)-2-(6-pyrrolidin-1-ylpyridin-3-yl)-1-(1H-tetrazol-5-yl)ethyl]pentanoic acid | 359.22 | 359.21 |
| 305 | 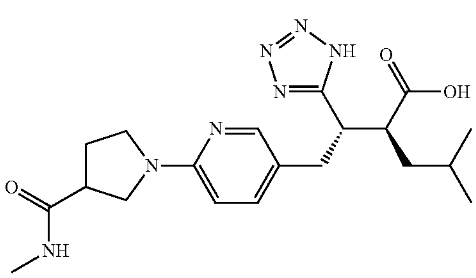 [SMILES: CNC(=O)C1CCN(c2ccc(C[C@H](c3nnn[nH]3)[C@H](CC(C)C)C(=O)O)cn2)C1] | (2S)-4-methyl-2-[(1S)-2-{6-[3-(methylcarbamoyl)pyrrolidin-1-yl]pyridin-3-yl}-1-(1H-tetrazol-5-yl)ethyl]pentanoic acid | 416.24 | 416.23 |

-continued

| Ex. No | Structure | IUPAC Name | Calc'd Mass [M + H]+ | LC/MS m/e [M + H]+ |
|---|---|---|---|---|
| 306 | 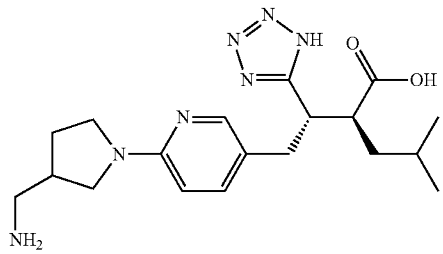 [SMILES: CC(C)C[C@H](C(=O)O)[C@H](Cc1ccc(N2CCC(CN)C2)nc1)c1nnn[nH]1] | (2S)-2-[(1S)-2-{6-[3-(aminomethyl)pyrrolidin-1-yl]pyridin-3-yl}-1-(1H-tetrazol-5-yl)ethyl]-4-methylpentanoic acid | 388.25 | 388.24 |
| 307 | 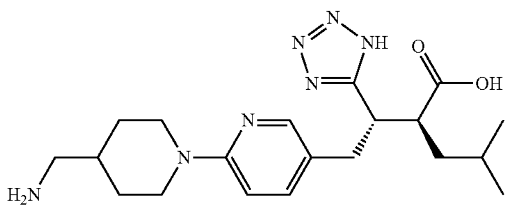 [SMILES: CC(C)C[C@H](C(=O)O)[C@H](Cc1ccc(N2CCC(CN)CC2)nc1)c1nnn[nH]1] | (2S)-2-[(1S)-2-{6-[4-(aminomethyl)piperidin-1-yl]pyridin-3-yl}-1-(1H-tetrazol-5-yl)ethyl]-4-methylpentanoic acid | 402.26 | 402.25 |
| 308 | 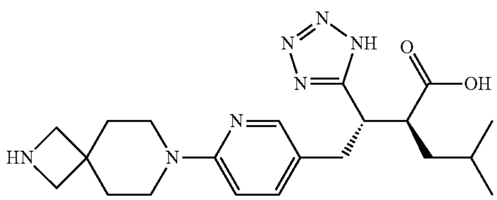 [SMILES: CC(C)C[C@H](C(=O)O)[C@H](Cc1ccc(N2CCC3(CC2)CNC3)nc1)c1nnn[nH]1] | (2S)-2-[(1S)-2-[6-(2,7-diazaspiro[3.5]non-7-yl)pyridin-3-yl]-1-(1H-tetrazol-5-yl)ethyl]-4-methylpentanoic acid | 414.26 | 414.25 |
| 309 | 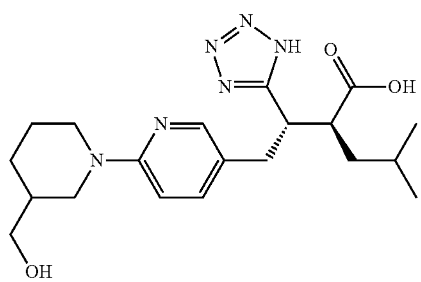 [SMILES: CC(C)C[C@H](C(=O)O)[C@H](Cc1ccc(N2CCCC(CO)C2)nc1)c1nnn[nH]1] | (2S)-2-[(1S)-2-{6-[3-(hydroxymethyl)piperidin-1-yl]pyridin-3-yl}-1-(1H-tetrazol-5-yl)ethyl]-4-methylpentanoic acid | 403.25 | 403.24 |
| 310 | 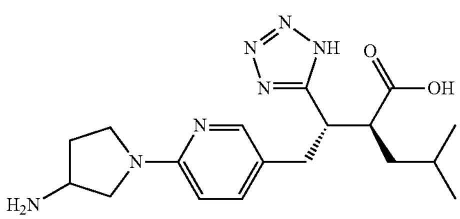 [SMILES: CC(C)C[C@H](C(=O)O)[C@H](Cc1ccc(N2CCC(N)C2)nc1)c1nnn[nH]1] | (2S)-2-[(1S)-2-[6-(3-aminopyrrolidin-1-yl)pyridin-3-yl]-1-(1H-tetrazol-5-yl)ethyl]-4-methylpentanoic acid | 374.23 | 374.22 |
| 311 | 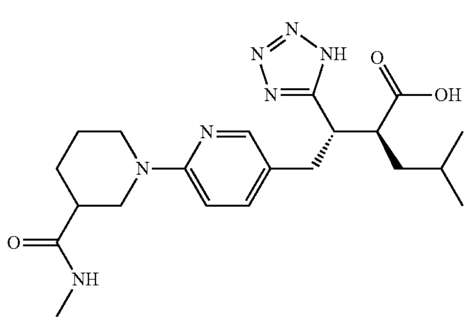 [SMILES: CNC(=O)C1CCCN(c2ccc(C[C@H](c3nnn[nH]3)[C@H](CC(C)C)C(=O)O)cn2)C1] | (2S)-4-methyl-2-[(1S)-2-{6-[3-(methylcarbamoyl)piperidin-1-yl]pyridin-3-yl}-1-(1H-tetrazol-5-yl)ethyl]pentanoic acid | 430.26 | 430.25 |

| Ex. No | Structure | IUPAC Name | Calc'd Mass [M + H]+ | LC/MS m/e [M + H]+ |
|---|---|---|---|---|
| 312 | 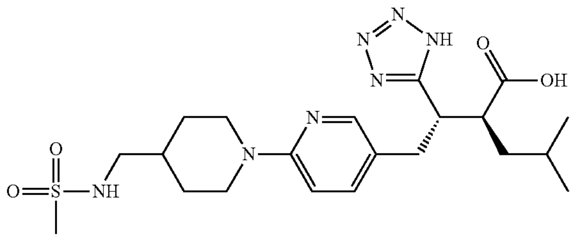 [SMILES: CC(C)C[C@H](C(=O)O)[C@H](Cc1ccc(N2CCC(CNS(C)(=O)=O)CC2)nc1)c1nnn[nH]1] | (2S)-4-methyl-2-[(1S)-2-[6-(4-{[(methylsulfonyl)amino]methyl}piperidin-1-yl)pyridin-3-yl]-1-(1H-tetrazol-5-yl)ethyl]pentanoic acid | 480.24 | 480.23 |
| 313 | 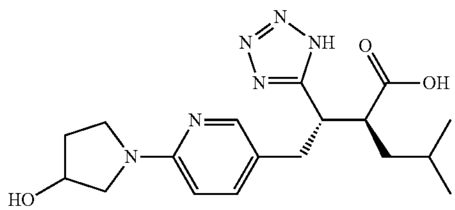 [SMILES: CC(C)C[C@H](C(=O)O)[C@H](Cc1ccc(N2CCC(O)C2)nc1)c1nnn[nH]1] | (2S)-2-[(1S)-2-[6-(3-hydroxypyrrolidin-1-yl)pyridin-3-yl]-1-(1H-tetrazol-5-yl)ethyl]-4-methylpentanoic acid | 375.21 | 375.21 |
| 314 | 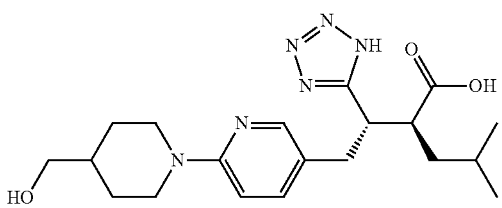 [SMILES: CC(C)C[C@H](C(=O)O)[C@H](Cc1ccc(N2CCC(CO)CC2)nc1)c1nnn[nH]1] | (2S)-2-[(1S)-2-{6-[4-(hydroxymethyl)piperidin-1-yl]pyridin-3-yl}-1-(1H-tetrazol-5-yl)ethyl]-4-methylpentanoic acid | 403.25 | 403.24 |
| 315 | 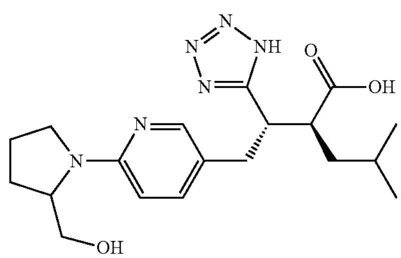 [SMILES: CC(C)C[C@H](C(=O)O)[C@H](Cc1ccc(N2CCCC2CO)nc1)c1nnn[nH]1] | (2S)-2-[(1S)-2-{6-[2-(hydroxymethyl)pyrrolidin-1-yl]pyridin-3-yl}-1-(1H-tetrazol-5-yl)ethyl]-4-methylpentanoic acid | 389.23 | 389.22 |
| 316 | 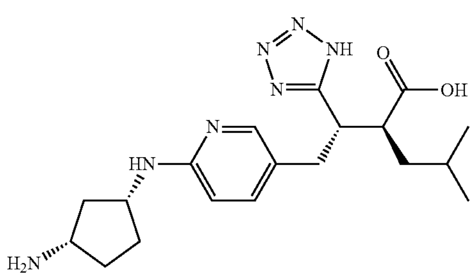 [SMILES: CC(C)C[C@H](C(=O)O)[C@H](Cc1ccc(N[C@@H]2CC[C@H](N)C2)nc1)c1nnn[nH]1] | (2S)-2-[(1S)-2-(6-{[(1R,3S)-3-aminocyclopentyl]amino}pyridin-3-yl)-1-(1H-tetrazol-5-yl)ethyl]-4-methylpentanoic acid | 388.25 | 388.24 |
| 317 | 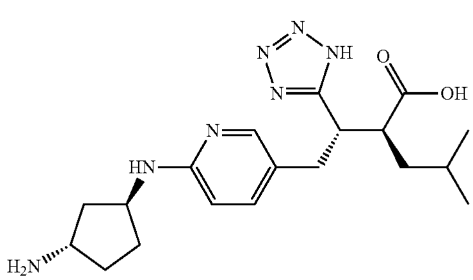 [SMILES: CC(C)C[C@H](C(=O)O)[C@H](Cc1ccc(N[C@H]2CC[C@H](N)C2)nc1)c1nnn[nH]1] | (2S)-2-[(1S)-2-(6-{[(1S,3S)-3-aminocyclopentyl]amino}pyridin-3-yl)-1-(1H-tetrazol-5-yl)ethyl]-4-methylpentanoic acid | 388.25 | 388.24 |

| Ex. No | Structure | IUPAC Name | Calc'd Mass [M + H]+ | LC/MS m/e [M + H]+ |
|---|---|---|---|---|
| 318 | 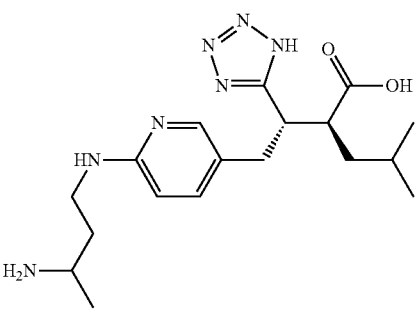 [SMILES: CC(C)C[C@H](C(=O)O)[C@H](Cc1ccc(NCCC(C)N)nc1)c1nnn[nH]1] | (2S)-2-[(1S)-2-{6-[(3-aminobutyl)amino]pyridin-3-yl}-1-(1H-tetrazol-5-yl)ethyl]-4-methylpentanoic acid | 376.25 | 376.24 |
| 319 | 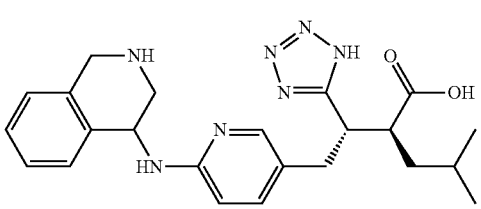 [SMILES: CC(C)C[C@H](C(=O)O)[C@H](Cc1ccc(NC2CNCc3ccccc32)nc1)c1nnn[nH]1] | (2S)-4-methyl-2-[(1S)-2-[6-(1,2,3,4-tetrahydroisoquinolin-4-ylamino)pyridin-3-yl]-1-(1H-tetrazol-5-yl)ethyl]pentanoic acid | 436.25 | 436.24 |
| 320 | 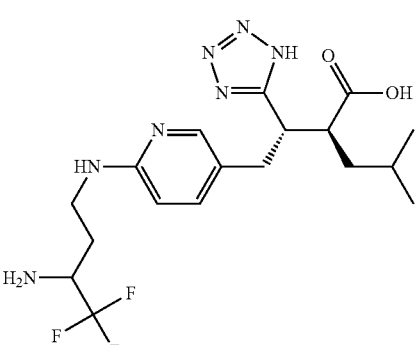 | (2S)-2-[(1S)-2-{6-[(3-amino-4,4,4-trifluorobutyl)amino]pyridin-3-yl}-1-(1H-tetrazol-5-yl)ethyl]-4-methylpentanoic acid | 430.22 | 430.21 |
| 321 | 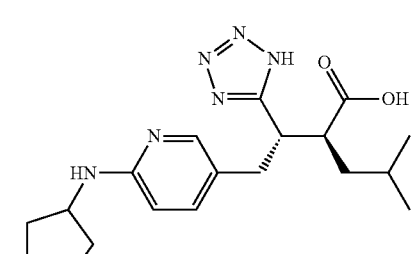 | (2S)-4-methyl-2-[(1S)-2-[6-(pyrrolidin-3-ylamino)pyridin-3-yl]-1-(1H-tetrazol-5-yl)ethyl]pentanoic acid | 374.23 | 374.22 |
| 322 | 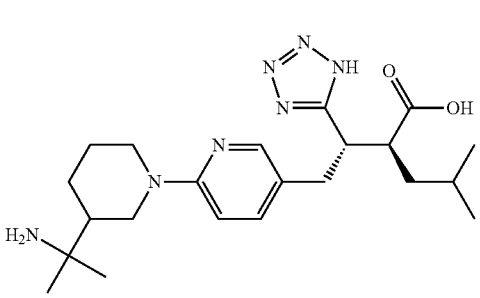 [SMILES: CC(C)C[C@H](C(=O)O)[C@H](Cc1ccc(N2CCCC(C(C)(C)N)C2)nc1)c1nnn[nH]1] | (2S)-2-[(1S)-2-{6-[3-(1-amino-1-methylethyl)piperidin-1-yl]pyridin-3-yl}-1-(1H-tetrazol-5-yl)ethyl]-4-methylpentanoic acid | 430.29 | 430.29 |

-continued

| Ex. No | Structure | IUPAC Name | Calc'd Mass [M + H]+ | LC/MS m/e [M + H]+ |
|---|---|---|---|---|
| 323 | 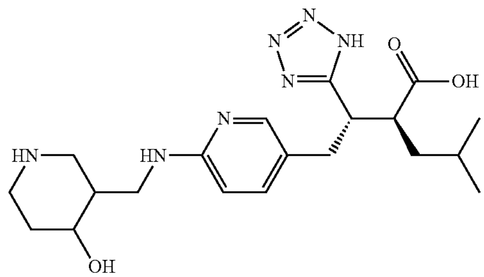 [SMILES: CC(C)C[C@H](C(=O)O)[C@H](Cc1ccc(NCC2CNCCC2O)nc1)c1nnn[nH]1] | (2S)-2-[(1S)-2-(6-{[(4-hydroxypiperidin-3-yl)methyl]amino}pyridin-3-yl)-1-(1H-tetrazol-5-yl)ethyl]-4-methylpentanoic acid | 418.26 | 418.25 |
| 324 | 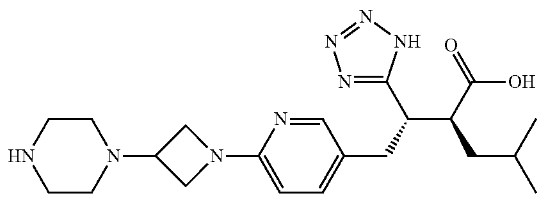 [SMILES: CC(C)C[C@H](C(=O)O)[C@H](Cc1ccc(N2CC(N3CCNCC3)C2)nc1)c1nnn[nH]1] | (2S)-4-methyl-2-[(1S)-2-[6-(3-piperazin-1-ylazetidin-1-yl)pyridin-3-yl]-1-(1H-tetrazol-5-yl)ethyl]pentanoic acid | 429.27 | 429.27 |
| 325 | 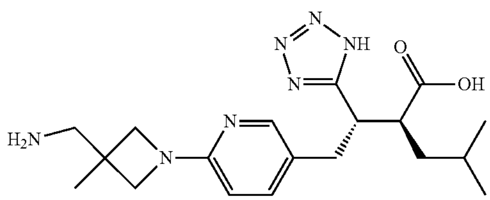 [SMILES: CC(C)C[C@H](C(=O)O)[C@H](Cc1ccc(N2CC(C)(CN)C2)nc1)c1nnn[nH]1] | (2S)-2-[(1S)-2-{6-[3-(aminomethyl)-3-methylazetidin-1-yl]pyridin-3-yl}-1-(1H-tetrazol-5-yl)ethyl]-4-methylpentanoic acid | 388.25 | 388.24 |
| 326 | 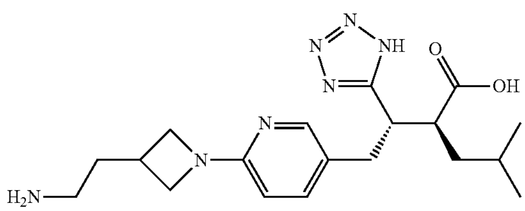 [SMILES: CC(C)C[C@H](C(=O)O)[C@H](Cc1ccc(N2CC(CCN)C2)nc1)c1nnn[nH]1] | (2S)-2-[(1S)-2-{6-[3-(2-aminoethyl)azetidin-1-yl]pyridin-3-yl}-1-(1H-tetrazol-5-yl)ethyl]-4-methylpentanoic acid | 388.25 | 388.24 |
| 327 | 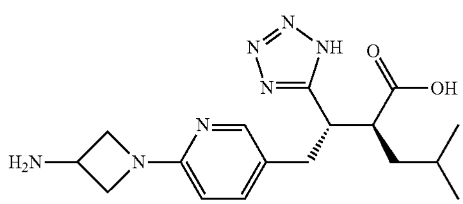 [SMILES: CC(C)C[C@H](C(=O)O)[C@H](Cc1ccc(N2CC(N)C2)nc1)c1nnn[nH]1] | (2S)-2-[(1S)-2-[6-(3-aminoazetidin-1-yl)pyridin-3-yl]-1-(1H-tetrazol-5-yl)ethyl]-4-methylpentanoic acid | 360.21 | 360.21 |
| 328 | 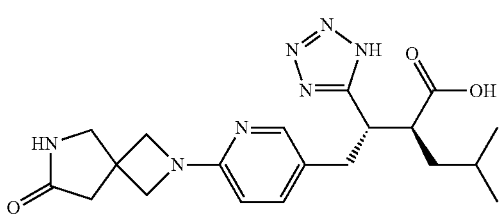 [SMILES: CC(C)C[C@H](C(=O)O)[C@H](Cc1ccc(N2CC3(CNC(=O)C3)C2)nc1)c1nnn[nH]1] | (2S)-4-methyl-2-[(1S)-2-[6-(7-oxo-2,6-diazaspiro[3.4]oct-2-yl)pyridin-3-yl]-1-(1H-tetrazol-5-yl)ethyl]pentanoic acid | 414.23 | 414.22 |
| 329 | 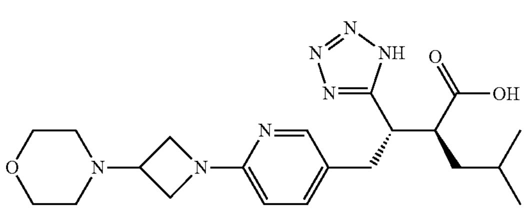 [SMILES: CC(C)C[C@H](C(=O)O)[C@H](Cc1ccc(N2CC(N3CCOCC3)C2)nc1)c1nnn[nH]1] | (2S)-4-methyl-2-[(1S)-2-[6-(3-morpholin-4-ylazetidin-1-yl)pyridin-3-yl]-1-(1H-tetrazol-5-yl)ethyl]pentanoic acid | 430.26 | 430.25 |

| Ex. No | Structure | IUPAC Name | Calc'd Mass [M + H]+ | LC/MS m/e [M + H]+ |
|---|---|---|---|---|
| 330 | 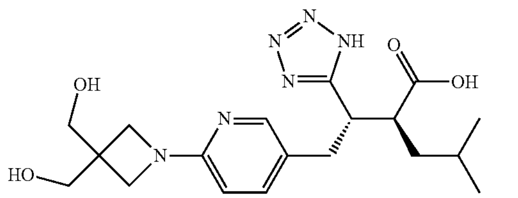 [SMILES: CC(C)C[C@H](C(=O)O)[C@H](Cc1ccc(N2CC(CO)(CO)C2)nc1)c1nnn[nH]1] | (2S)-2-[(1S)-2-{6-[3,3-bis(hydroxymethyl)azetidin-1-yl]pyridin-3-yl}-1-(1H-tetrazol-5-yl)ethyl]-4-methylpentanoic acid | 405.22 | 405.22 |
| 331 | 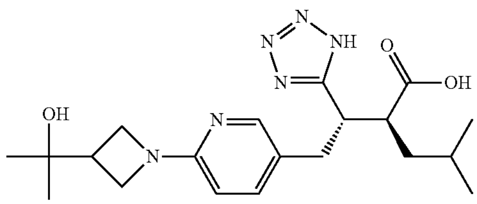 [SMILES: CC(C)C[C@H](C(=O)O)[C@H](Cc1ccc(N2CC(C(C)(C)O)C2)nc1)c1nnn[nH]1] | (2S)-2-[(1S)-2-{6-[3-(1-hydroxy-1-methylethyl)azetidin-1-yl]pyridin-3-yl}-1-(1H-tetrazol-5-yl)ethyl]-4-methylpentanoic acid | 403.25 | 403.24 |
| 332 | 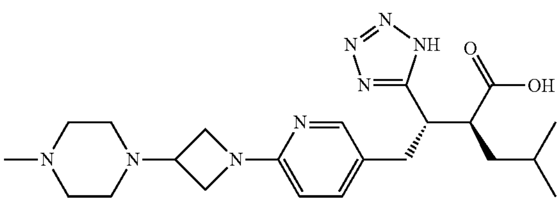 [SMILES: CC(C)C[C@H](C(=O)O)[C@H](Cc1ccc(N2CC(N3CCN(C)CC3)C2)nc1)c1nnn[nH]1] | (2S)-4-methyl-2-[(1S)-2-{6-[3-(4-methylpiperazin-1-yl)azetidin-1-yl]pyridin-3-yl}-1-(1H-tetrazol-5-yl)ethyl]pentanoic acid | 443.29 | 443.28 |
| 333 | 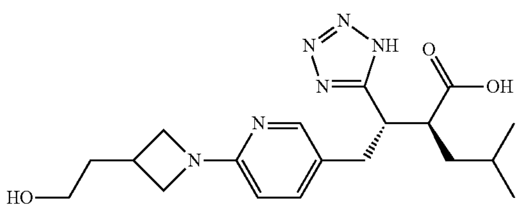 [SMILES: CC(C)C[C@H](C(=O)O)[C@H](Cc1ccc(N2CC(CCO)C2)nc1)c1nnn[nH]1] | (2S)-2-[(1S)-2-{6-[3-(2-hydroxyethyl)azetidin-1-yl]pyridin-3-yl}-1-(1H-tetrazol-5-yl)ethyl]-4-methylpentanoic acid | 389.23 | 389.22 |
| 334 | 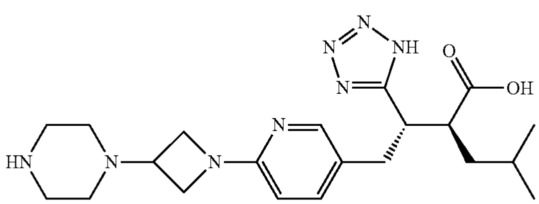 [SMILES: CC(C)C[C@H](C(=O)O)[C@H](Cc1ccc(N2CC(N3CCNCC3)C2)nc1)c1nnn[nH]1] | (2S)-4-methyl-2-[(1S)-2-[6-(3-piperazin-1-ylazetidin-1-yl)pyridin-3-yl]-1-(1H-tetrazol-5-yl)ethyl]pentanoic acid | 429.27 | 429.27 |
| 335 | 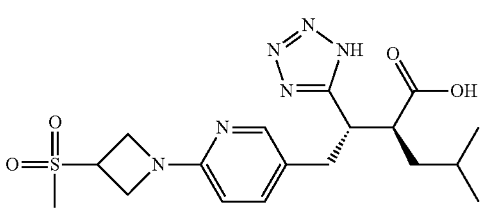 [SMILES: CC(C)C[C@H](C(=O)O)[C@H](Cc1ccc(N2CC(S(C)(=O)=O)C2)nc1)c1nnn[nH]1] | (2S)-4-methyl-2-[(1S)-2-{6-[3-(methylsulfonyl)azetidin-1-yl]pyridin-3-yl}-1-(1H-tetrazol-5-yl)ethyl]pentanoic acid | 423.18 | 423.17 |
| 336 | 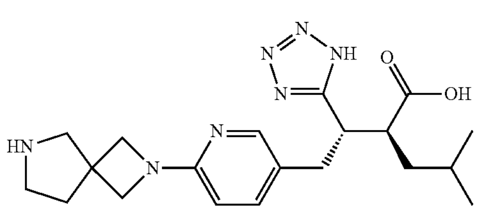 [SMILES: CC(C)C[C@H](C(=O)O)[C@H](Cc1ccc(N2CC3(CCNC3)C2)nc1)c1nnn[nH]1] | (2S)-2-[(1S)-2-[6-(2,6-diazaspiro[3.4]oct-2-yl)pyridin-3-yl]-1-(1H-tetrazol-5-yl)ethyl]-4-methylpentanoic acid | 400.25 | 400.24 |

| Ex. No | Structure | IUPAC Name | Calc'd Mass [M + H]+ | LC/MS m/e [M + H]+ |
|---|---|---|---|---|
| 337 | 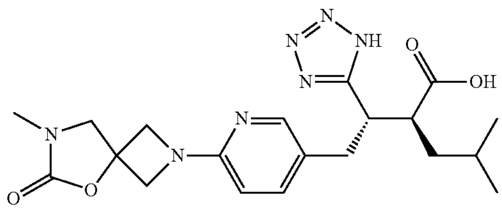 [SMILES: CC(C)C[C@H](C(=O)O)[C@H](Cc1ccc(N2CC3(CN(C)C(=O)O3)C2)nc1)c1nnn[nH]1] | (2S)-4-methyl-2-[(1S)-2-[6-(7-methyl-6-oxo-5-oxa-2,7-diazaspiro[3.4]oct-2-yl)pyridin-3-yl]-1-(1H-tetrazol-5-yl)ethyl]pentanoic acid | 430.22 | 430.21 |
| 338 | 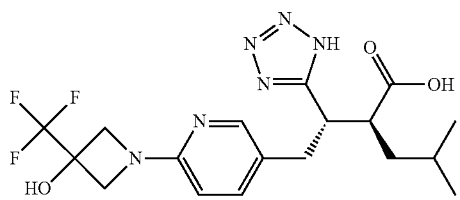 [SMILES: CC(C)C[C@H](C(=O)O)[C@H](Cc1ccc(N2CC(O)(C(F)(F)F)C2)nc1)c1nnn[nH]1] | (2S)-2-[(1S)-2-{6-[3-hydroxy-3-(trifluoromethyl)azetidin-1-yl]pyridin-3-yl}-1-(1H-tetrazol-5-yl)ethyl]-4-methylpentanoic acid | 429.19 | 429.18 |

EXAMPLEs 339-356

Parallel synthesis of (2S)-2-[(1S)-2-[3'-substituted phenyl]-1-(2H-tetrazol-5-yl)ethyl]hexanoic acid

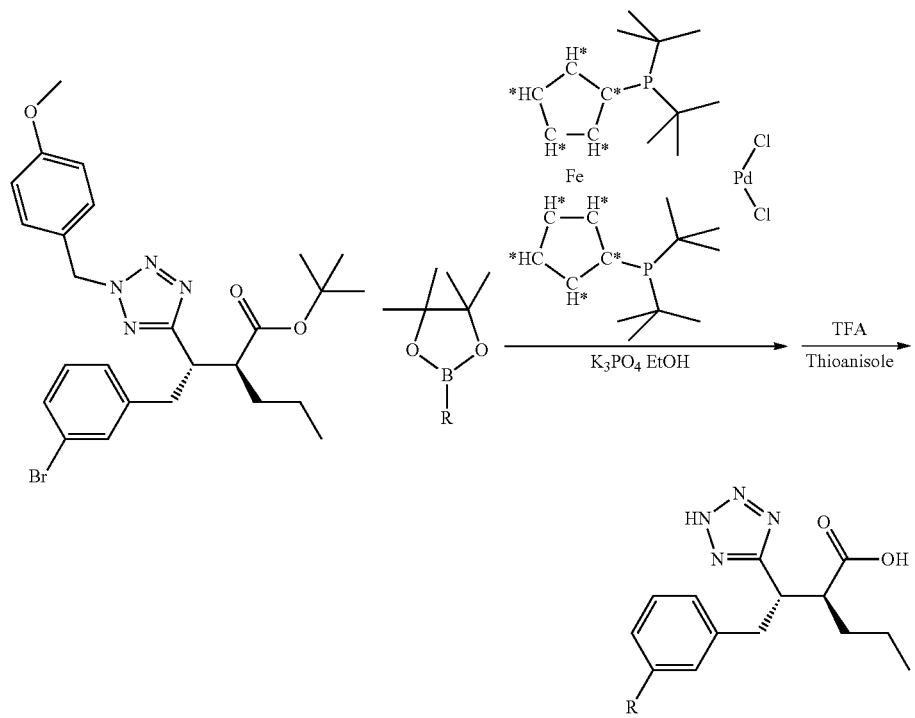

Step A: Palladium Catalyzed C—C Coupling of Arylbromide and Boronic Acids.

Into 2 dram vials were added substituted boronic acid or ester (0.071 mmol), palladium catalyst (3.1 mg, 4.7 μmol) and 189 μL of 1 N degassed aq. K₃PO₄ solution. In glove box, 1 mL of a solution of (S)-tert-butyl 2-((S)-2-(3-bromophenyl)-1-(2-(4-methylbenzyl)-2H-tetrazol-5-yl)ethyl) pentanoate (27 mg, 0.051 mmol) in EtOH were added into each vial. The vials were capped and heated at 75° C. with stirring for 20 hr (overnight). After the vials were cooled down to room temperature, the solvent was removed in GeneVac. Into each residue was added 600 μL of H₂O and 2 mL of DCM. The organic layers were transferred into 2 dram vials. The organic solvent was removed in GeneVac to afford the crude intermediates.

Step B: Removal of the Tert-Butyl and p-Methoxybenzyl (PMB) Protecting Group Under Acidic Conditions.

Into each vial was added a solution of thioanisole (0.3 mL), and DCM (0.3 mL) in TFA (0.3 mL). The vials were agitated at 25° C. for 16 hr. The solvent was removed in a GeneVac. Into each vial was added a solution of thioanisole (0.3 mL), and DCM (0.3 mL) in TFA (0.3 mL). The vials were agitated at 55° C. for 16 hr. The solvent was removed in a GeneVac. The residues were dissolved in 1.3 mL of DMSO. Each crude mixture was filtered into a 96-well tray and purified by HPLC to afford the following EXAMPLES.

| Ex. No | Structure | IUPAC Name | Calc'd Mass [M + H]⁺ | LC/MS m/e [M + H]⁺ |
|---|---|---|---|---|
| 339 | 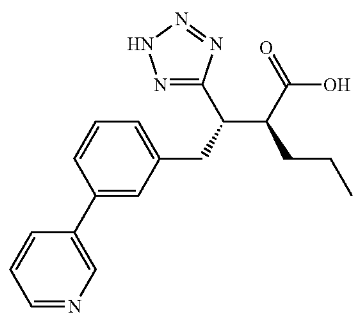 [SMILES: CCC[C@H](C(=O)O)[C@H](Cc1cccc(-c2cccnc2)c1)c1nn[nH]n1] | (2S)-2-[(1S)-2-(3-pyridin-3-ylphenyl)-1-(2H-tetrazol-5-yl)ethyl]pentanoic acid | 352.18 | 352.17 |
| 340 | 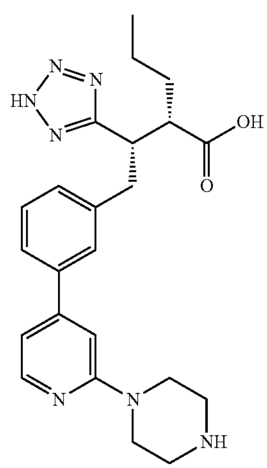 [SMILES: CCC[C@H](C(=O)O)[C@H](Cc1cccc(-c2ccnc(N3CCNCC3)c2)c1)c1nn[nH]n1] | (2S)-2-[(1S)-2-[3-(2-piperazin-1-ylpyridin-4-yl)phenyl]-1-(2H-tetrazol-5-yl)ethyl]pentanoic acid | 436.25 | 436.24 |
| 341 | 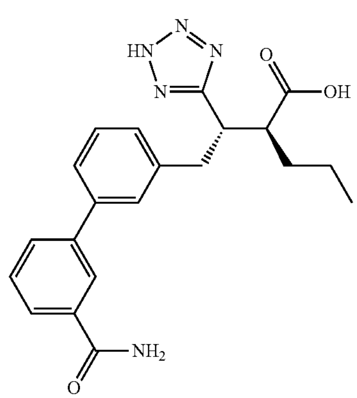 [SMILES: CCC[C@H](C(=O)O)[C@H](Cc1cccc(-c2cccc(C(N)=O)c2)c1)c1nn[nH]n1] | (2S)-2-[(1S)-2-(3'-carbamoylbiphenyl-3-yl)-1-(2H-tetrazol-5-yl)ethyl]pentanoic acid | 394.19 | 394.17 |

| Ex. No | Structure | IUPAC Name | Calc'd Mass [M + H]+ | LC/MS m/e [M + H]+ |
|---|---|---|---|---|
| 342 | 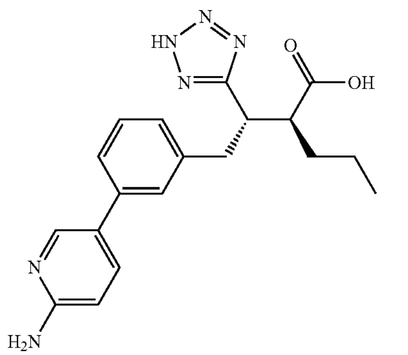 [SMILES: CCC[C@H](C(=O)O)[C@H](Cc1cccc(-c2ccc(N)nc2)c1)c1nn[nH]n1] | (2S)-2-[(1S)-2-[3-(6-aminopyridin-3-yl)phenyl]-1-(2H-tetrazol-5-yl)ethyl]pentanoic acid | 367.19 | 367.18 |
| 343 | 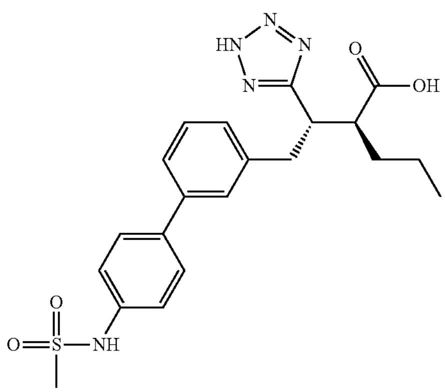 [SMILES: CCC[C@H](C(=O)O)[C@H](Cc1cccc(-c2ccc(NS(C)(=O)=O)cc2)c1)c1nn[nH]n1] | (2S)-2-[(1S)-2-{4'-[(methylsulfonyl)amino]biphenyl-3-yl}-1-(2H-tetrazol-5-yl)ethyl]pentanoic acid | 444.17 | 444.17 |
| 344 | 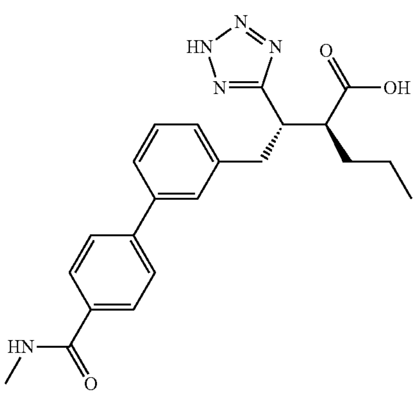 [SMILES: CCC[C@H](C(=O)O)[C@H](Cc1cccc(-c2ccc(C(=O)NC)cc2)c1)c1nn[nH]n1] | (2S)-2-[(1S)-2-[4'-(methylcarbamoyl)biphenyl-3-yl]-1-(2H-tetrazol-5-yl)ethyl]pentanoic acid | 408.2 | 408.19 |
| 345 | 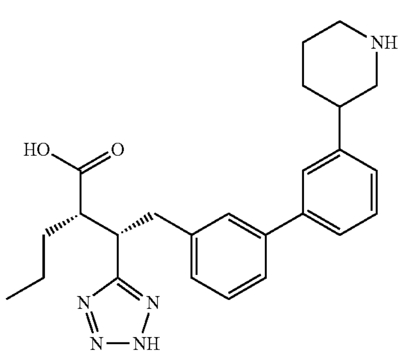 [SMILES: CCC[C@H](C(=O)O)[C@H](Cc1cccc(-c2cccc(C3CCCNC3)c2)c1)c1nn[nH]n1] | (2S)-2-[(1S)-2-(3'-piperidin-3-ylbiphenyl-3-yl)-1-(2H-tetrazol-5-yl)ethyl]pentanoic acid | 434.26 | 434.25 |

-continued

| Ex. No | Structure | IUPAC Name | Calc'd Mass [M + H]+ | LC/MS m/e [M + H]+ |
|---|---|---|---|---|
| 346 | 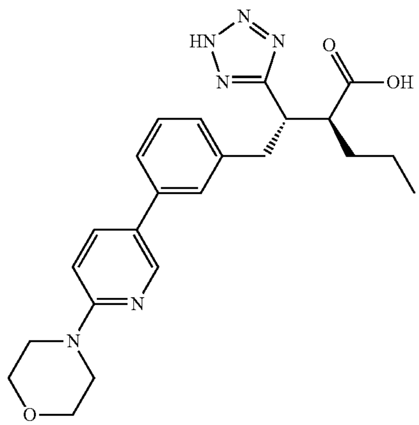 [SMILES: CCC[C@H](C(=O)O)[C@H](Cc1cccc(-c2ccc(N3CCOCC3)nc2)c1)c1nn[nH]n1] | (2S)-2-[(1S)-2-[3-(6-morpholin-4-ylpyridin-3-yl)phenyl]-1-(2H-tetrazol-5-yl)ethyl]pentanoic acid | 437.23 | 437.22 |
| 347 | 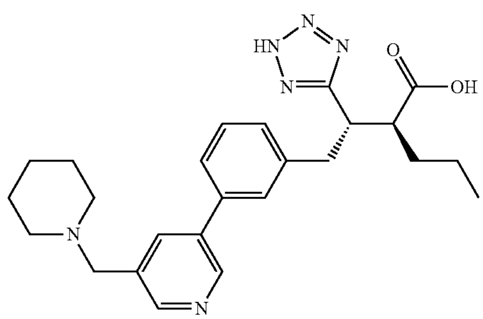 [SMILES: CCC[C@H](C(=O)O)[C@H](Cc1cccc(-c2cncc(CN3CCCCC3)c2)c1)c1nn[nH]n1] | (2S)-2-[(1S)-2-{3-[5-(piperidin-1-ylmethyl)pyridin-3-yl]phenyl}-1-(2H-tetrazol-5-yl)ethyl]pentanoic acid | 449.27 | 449.26 |
| 348 | 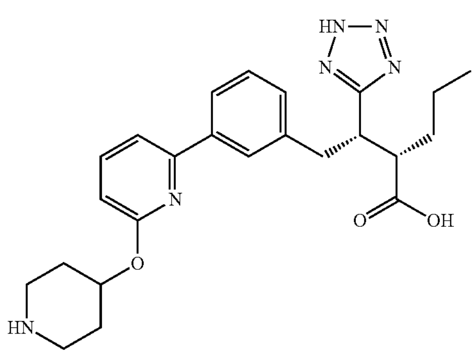 [SMILES: CCC[C@H](C(=O)O)[C@H](Cc1cccc(-c2cccc(OC3CCNCC3)n2)c1)c1nn[nH]n1] | (2S)-2-[(1S)-2-{3-[6-(piperidin-4-yloxy)pyridin-2-yl]phenyl}-1-(2H-tetrazol-5-yl)ethyl]pentanoic acid | 451.25 | 451.24 |
| 349 | 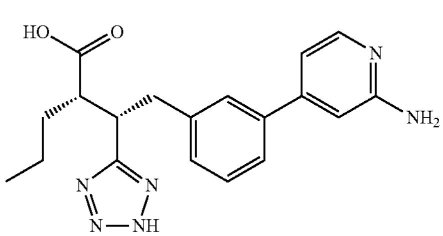 [SMILES: CCC[C@H](C(=O)O)[C@H](Cc1cccc(-c2ccnc(N)c2)c1)c1nn[nH]n1] | (2S)-2-[(1S)-2-[3-(2-aminopyridin-4-yl)phenyl]-1-(2H-tetrazol-5-yl)ethyl]pentanoic acid | 367.19 | 367.19 |

-continued

| Ex. No | Structure | IUPAC Name | Calc'd Mass [M + H]+ | LC/MS m/e [M + H]+ |
|---|---|---|---|---|
| 350 | 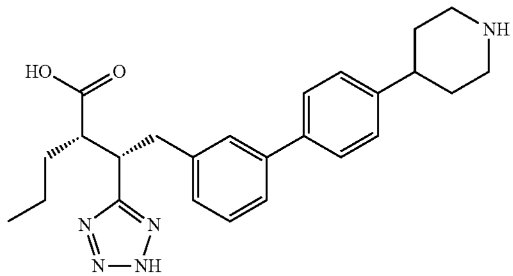 [SMILES: CCC[C@H](C(=O)O)[C@H](Cc1cccc(-c2ccc(C3CCNCC3)cc2)c1)c1nn[nH]n1] | (2S)-2-[(1S)-2-(4'-piperidin-4-ylbiphenyl-3-yl)-1-(2H-tetrazol-5-yl)ethyl]pentanoic acid | 434.26 | 434.25 |
| 351 | 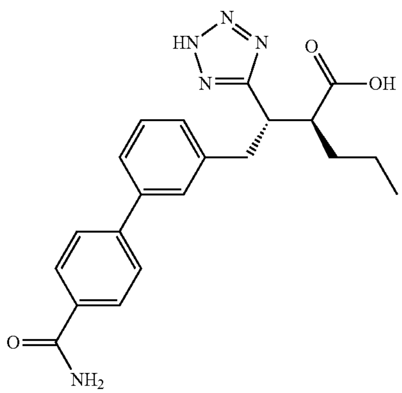 [SMILES: CCC[C@H](C(=O)O)[C@H](Cc1cccc(-c2ccc(C(N)=O)cc2)c1)c1nn[nH]n1] | (2S)-2-[(1)-2-(4'-carbamoylbiphenyl-3-yl)-1-(2H-tetrazol-5-yl)ethyl]pentanoic acid | 394.19 | 394.19 |
| 352 | 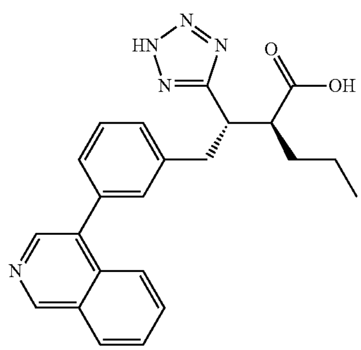 [SMILES: CCC[C@H](C(=O)O)[C@H](Cc1cccc(-c2cncc3ccccc23)c1)c1nn[nH]n1] | (2S)-2-[(1S)-2-(3-isoquinolin-4-ylphenyl)-1-(2H-tetrazol-5-yl)ethyl]pentanoic acid | 402.19 | 402.18 |
| 353 | 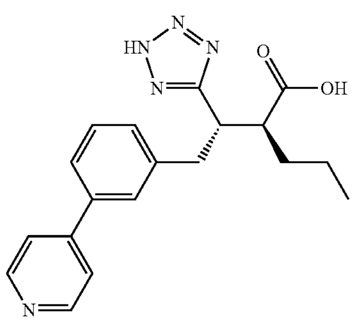 [SMILES: CCC[C@H](C(=O)O)[C@H](Cc1cccc(-c2ccncc2)c1)c1nn[nH]n1] | (2S)-2-[(1S)-2-(3-pyridin-4-ylphenyl)-1-(2H-tetrazol-5-yl)ethyl]pentanoic acid | 352.18 | 352.17 |
| 354 | 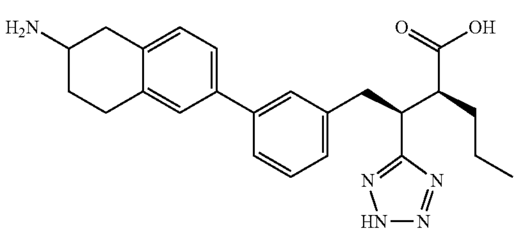 [SMILES: CCC[C@H](C(=O)O)[C@H](Cc1cccc(-c2ccc3c(c2)CCC(N)C3)c1)c1nn[nH]n1] | (2S)-2-[(1S)-2-[3-(6-amino-5,6,7,8-tetrahydronaphthalen-2-yl)phenyl]-1-(2H-tetrazol-5-yl)ethyl]pentanoic acid | 420.24 | 420.23 |

| Ex. No | Structure | IUPAC Name | Calc'd Mass [M + H]+ | LC/MS m/e [M + H]+ |
|---|---|---|---|---|
| 355 | 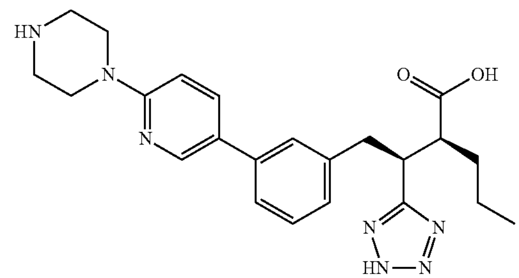 [SMILES: CCC[C@H](C(=O)O)[C@H](Cc1cccc(-c2ccc(N3CCNCC3)nc2)c1)c1nn[nH]n1] | (2S)-2-[(1S)-2-[3-(6-piperazin-1-ylpyridin-3-yl)phenyl]-1-(2H-tetrazol-5-yl)ethyl]pentanoic acid | 436.25 | 436.24 |
| 356 | 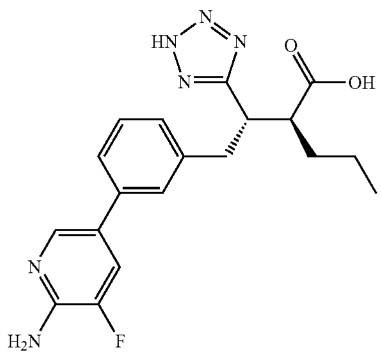 [SMILES: CCC[C@H](C(=O)O)[C@H](Cc1cccc(-c2cnc(N)c(F)c2)c1)c1nn[nH]n1] | (2S)-2-[(1S)-2-[3-(6-amino-5-fluoropyridin-3-yl)phenyl]-1-(2H-tetrazol-5-yl)ethyl]pentanoic acid | 385.18 | 385.19 |
EXAMPLES 357-359
Parallel synthesis of (2S)-2-[(1S)-2-[3'-substituted phenyl]-1-(2H-tetrazol-5-yl)ethyl]hexanoic acid
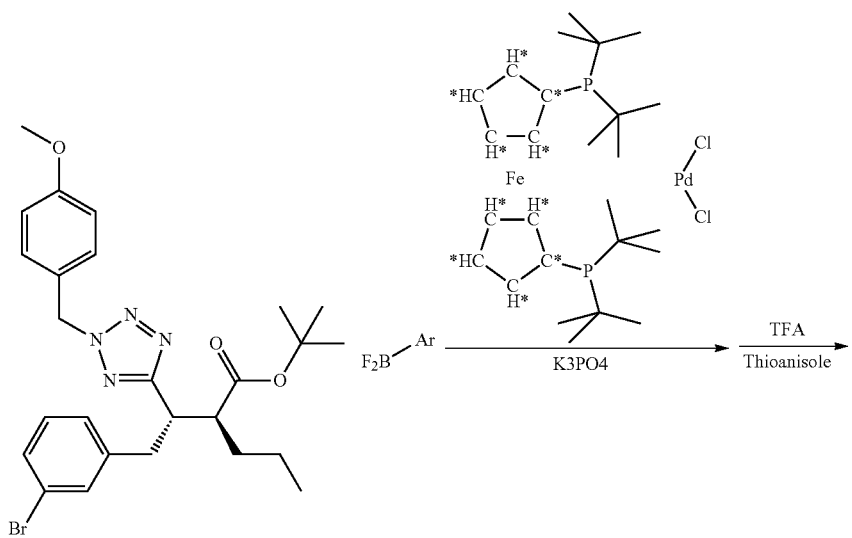

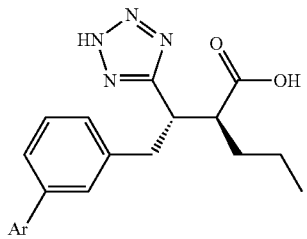

Step A: Palladium Catalyzed C—C Coupling of Arylbromide and Boronic Acids

Into 2 dram vials were added substituted trifluoro boronate (0.071 mmol), palladium catalyst (3.1 mg, 4.7 μmol) and 189 μL of 1 N degassed aq. K₃PO₄ solution. In a glove box, 1 mL of a solution of (S)-tert-butyl 2-((S)-2-(3-bromophenyl)-1-(2-(4-methylbenzyl)-2H-tetrazol-5-yl)ethyl) pentanoate (27 mg, 0.051 mmol) in EtOH was added into each vial. The vials were capped and heated at 75° C. with stirring for 20 hr (overnight). After the vials were cooled down to room temperature, the solvent was removed in GeneVac. Into each residue was added 600 μL of H₂O and 2 mL of DCM. The organic layers were transferred into 2 dram vials. The organic solvent was removed in GeneVac to afford the crude intermediates.

Step B: Removal of the Tert-Butyl & p-Methoxybenzyl (PMB) Protecting Group Under Acidic Conditions Into each vial was added a solution of thioanisole (0.3 mL), DCM (0.3 mL) in TFA (0.3 mL). The vials were agitated at 25° C. for 16 hr. The solvent was removed in a GeneVac. Into each vial was added a solution of thioanisole (0.3 mL), DCM (0.3 mL) in TFA (0.3 mL). The vials were agitated at 55° C. for 16 hr. The solvent was removed in a GeneVac. The residues were dissolved in 1.3 mL of DMSO. Each crude mixture was filtered into a 96-well tray and purified by HPLC to afford the following EXAMPLES.

| Ex. No | Structure | IUPAC Name | Calc'd Mass [M + H]⁺ | LC/MS m/e [M + H]⁺ |
|---|---|---|---|---|
| 357 | 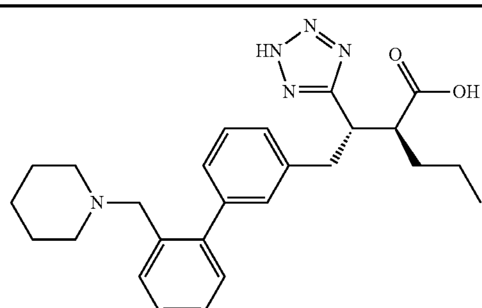 | (2S)-2-[(1S)-2-[2'-(piperidin-1-ylmethyl)biphenyl-3-yl]-1-(2H-tetrazol-5-yl)ethyl]pentanoic acid | 448.27 | 448.25 |
| 358 | 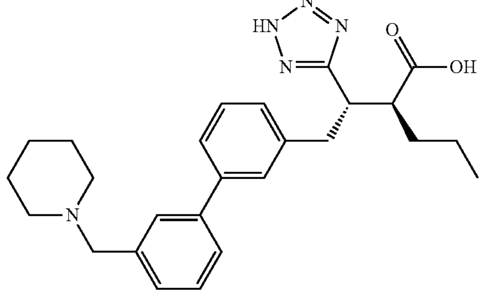 | (2S)-2-[(1S)-2-[3'-(piperidin-1-ylmethyl)biphenyl-3-yl]-1-(2H-tetrazol-5-yl)ethyl]pentanoic acid | 448.27 | 448.25 |
| 359 | 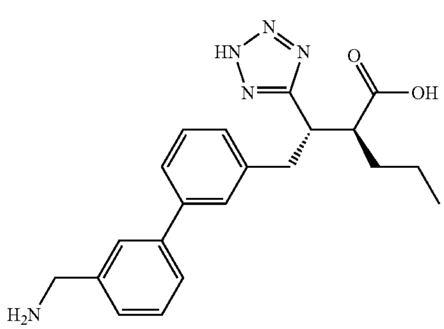 [SMILES: CCC[C@H](C(=O)O)[C@H](Cc1cccc(-c2cccc(CN)c2)c1)c1nn[nH]n1] | (2S)-2-[(1S)-2-[3'-(aminomethyl)biphenyl-3-yl]-1-(2H-tetrazol-5-yl)ethyl]pentanoic acid | 380.21 | 380.2 |

EXAMPLES 360-370

Parallel synthesis of (2S)-2-[(1S)-2-[3'-amino substituted phenyl]-1-(2H-tetrazol-5-yl)ethyl]hexanoic acid

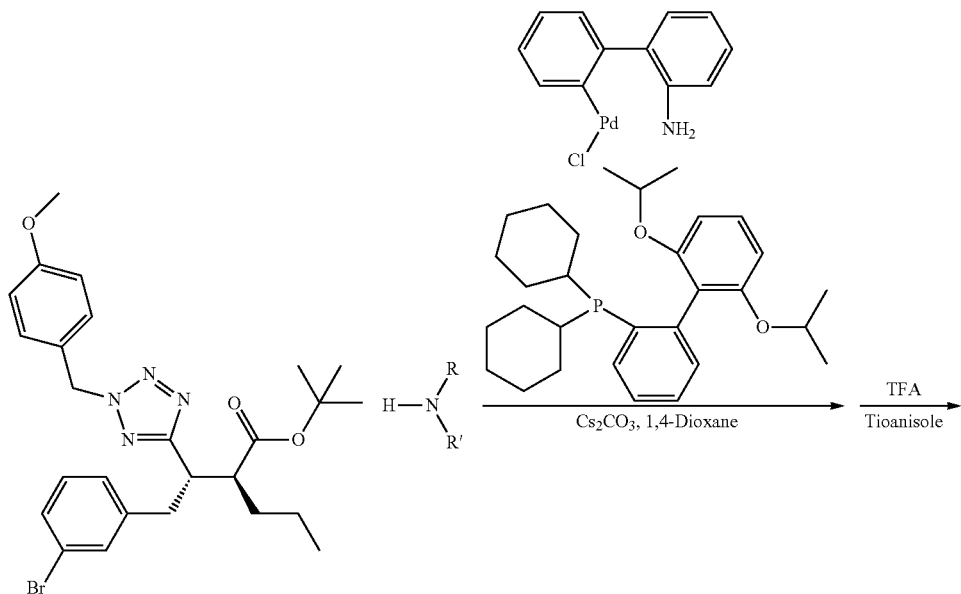

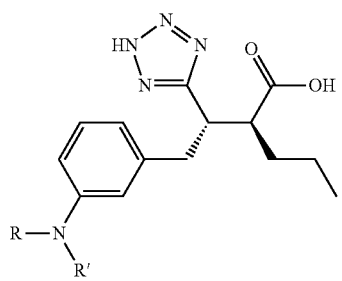

Step A: Palladium Catalyzed C—N Coupling of Arylbromide and Secondary Amines

Into 2 dram vials were added substituted secondary amines (0.15 mmol), palladium catalyst (4.07 mg, 5.1 μmol) and cesium carbonate (66.5 mg, 0.2 mmol). In a glove box, 1 mL of a solution of (S)-tert-butyl 2-((S)-2-(3-bromophenyl)-1-(2-(4-methylbenzyl)-2H-tetrazol-5-yl)ethyl)pentanoate (27 mg, 0.051 mmol) in 1,4-Dioxane was added into each vial. The vials were capped and heated at 90° C. with stirring for 20 hr (overnight). After the vials were cooled down to room temperature, the solvent was removed in GeneVac. Into each residue was added 600 μL of $H_2O$ and 2 mL of DCM. The organic layers were transferred into 2 dram vials. The organic solvent was removed in GeneVac to afford the crude intermediates.

Step B: Removal of the Tert-Butyl and p-Methoxybenzyl (PMB) Protecting Group Under Acidic Conditions Into each vial was added a solution of thioanisole (0.3 mL), and DCM (0.3 mL) in TFA (0.3 mL). The vials were agitated at 25° C. for 16 hr. The solvent was removed in a GeneVac. Into each vial was added a solution of thioanisole (0.3 mL), and DCM (0.3 mL) in TFA (0.3 mL). The vials were agitated at 55° C. for 16 hr. The solvent was removed in a GeneVac. The residues were dissolved in 1.3 mL of DMSO. Each crude mixture was filtered into a 96-well tray and purified by HPLC to afford the following EXAMPLES.

| Ex. No | Structure | IUPAC Name | Calc'd Mass [M + H]⁺ | LC/MS m/e [M + H]⁺ |
|---|---|---|---|---|
| 360 | 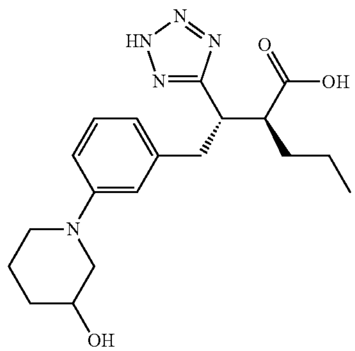 [SMILES: CCC[C@H](C(=O)O)[C@H](Cc1cccc(N2CCCC(O)C2)c1)c1nn[nH]n1] | (2S)-2-[(1S)-2-[3-(3-hydroxypiperidin-1-yl)phenyl]-1-(2H-tetrazol-5-yl)ethyl]pentanoic acid | 374.22 | 374.21 |
| 361 | 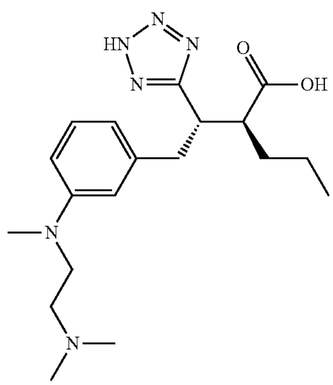 [SMILES: CCC[C@H](C(=O)O)[C@H](Cc1cccc(N(C)CCN(C)C)c1)c1nn[nH]n1] | (2S)-2-[(1S)-2-(3-{[2-(dimethylamino)ethyl](methyl)amino}phenyl)-1-(2H-tetrazol-5-yl)ethyl]pentanoic acid | 375.25 | 375.24 |
| 362 | 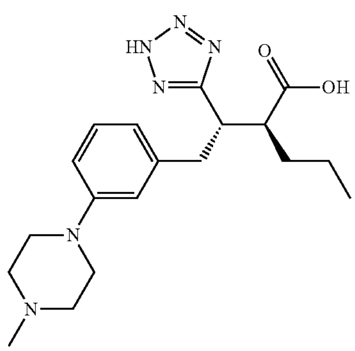 [SMILES: CCC[C@H](C(=O)O)[C@H](Cc1cccc(N2CCN(C)CC2)c1)c1nn[nH]n1] | (2S)-2-[(1S)-2-[3-(4-methylpiperazin-1-yl)phenyl]-1-(2H-tetrazol-5-yl)ethyl]pentanoic acid | 373.23 | 373.22 |
| 363 | 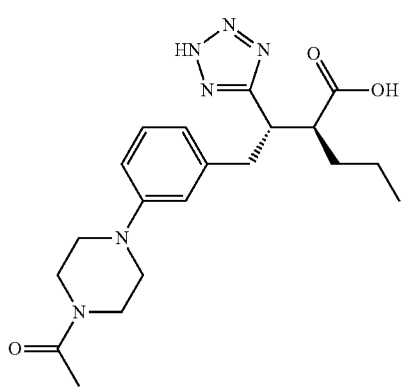 [SMILES: CCC[C@H](C(=O)O)[C@H](Cc1cccc(N2CCN(C(C)=O)CC2)c1)c1nn[nH]n1] | (2S)-2-[(1S)-2-[3-(4-acetylpiperazin-1-yl)phenyl]-1-(2H-tetrazol-5-yl)ethyl]pentanoic acid | 401.23 | 401.22 |

| Ex. No | Structure | IUPAC Name | Calc'd Mass [M + H]+ | LC/MS m/e [M + H]+ |
|---|---|---|---|---|
| 364 | 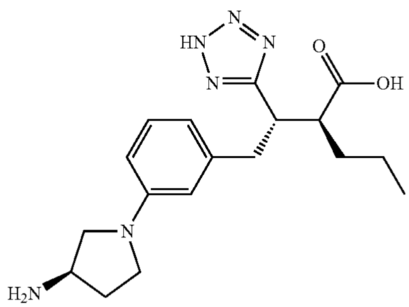 | (2S)-2-[(1S)-2-{3-[(3R)-3-aminopyrrolidin-1-yl]phenyl}-1-(2H-tetrazol-5-yl)ethyl]pentanoic acid | 359.22 | 359.21 |
| 365 | 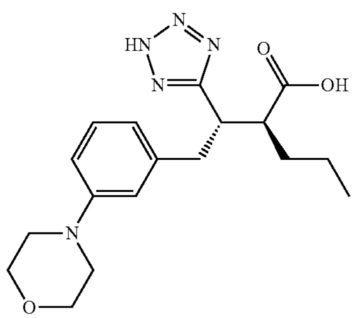 [SMILES: CCC[C@H](C(=O)O)[C@H](Cc1cccc(N2CCOCC2)c1)c1nn[nH]n1] | (2S)-2-[(1S)-2-(3-morpholin-4-ylphenyl)-1-(2H-tetrazol-5-yl)ethyl]pentanoic acid | 360.2 | 360.19 |
| 366 | 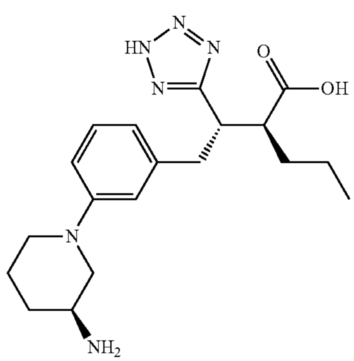 [SMILES: CCC[C@H](C(=O)O)[C@H](Cc1cccc(N2CCC[C@H](N)C2)c1)c1nn[nH]n1] | (2S)-2-[(1S)-2-{3-[(3S)-3-aminopiperidin-1-yl]phenyl}-1-(2H-tetrazol-5-yl)ethyl]pentanoic acid | 373.23 | 373.23 |
| 367 | 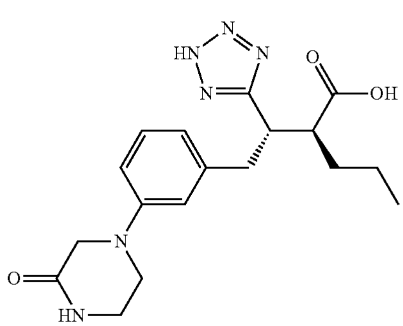 [SMILES: CCC[C@H](C(=O)O)[C@H](Cc1cccc(N2CCNC(=O)C2)c1)c1nn[nH]n1] | (2S)-2-[(1S)-2-[3-(3-oxopiperazin-1-yl)phenyl]-1-(2H-tetrazol-5-yl)ethyl]pentanoic acid | 373.2 | 373.19 |

| Ex. No | Structure | IUPAC Name | Calc'd Mass [M + H]+ | LC/MS m/e [M + H]+ |
|---|---|---|---|---|
| 368 | 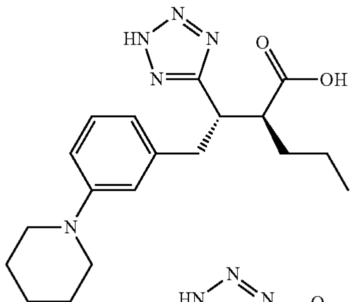 [SMILES: CCC[C@H](C(=O)O)[C@H](Cc1cccc(N2CCCCC2)c1)c1nn[nH]n1] | (2S)-2-[(1S)-2-(3-piperidin-1-ylphenyl)-1-(2H-tetrazol-5-yl)ethyl]pentanoic acid | 358.22 | 358.21 |
| 369 | 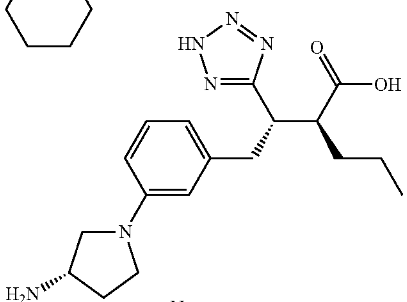 | (2S)-2-[(1S)-2-{3-[(3S)-3-aminopyrrolidin-1-yl]phenyl}-1-(2H-tetrazol-5-yl)ethyl]pentanoic acid | 359.22 | 359.22 |
| 370 | 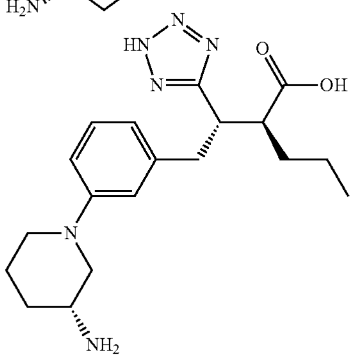 | (2S)-2-[(1S)-2-{3-[(3R)-3-aminopiperidin-1-yl]phenyl}-1-(2H-tetrazol-5-yl)ethyl]pentanoic acid | 373.23 | 373.22 |
EXAMPLES 371-392
Parallel synthesis of (S)-2-(S)-2-(6-O-substituted)pyridin-3-yl)-1-(1H-tetrazol-5-yl)ethyl)-4-methyl-pentanoic acid
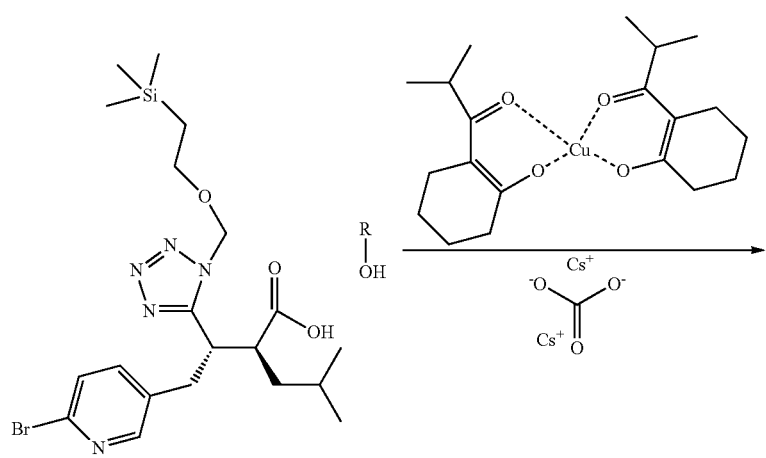

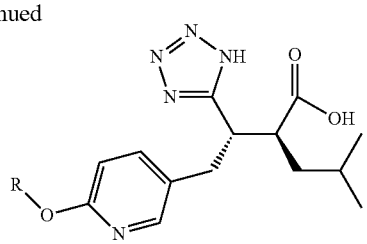

Step A: Copper Catalyzed C—O Coupling of Arylbromide and Phenols

Into 2 dram vials were added substituted phenols (0.15 mmol), copper catalyst (4.07 mg, 5.1 µmol) and cesium carbonate (66.5 mg, 0.2 mmol). In a glove box, 1 mL of a solution of (S)-2-((S)-2-(6-bromopyridin-3-yl)-1-(1-((2-(trimethylsilyl)ethoxy)methyl)-1H-tetrazol-5-yl)ethyl)-4-methylpentanoic acid (25 mg, 0.05 mmol) in DMF was added into each vial. The vials were capped and heated at 100° C. with stirring for 20 hr (overnight). After the vials were cooled down to room temperature, the solvent was removed in GeneVac. Into each residue was added 600 µL of H₂O and 2 mL of DCM. The organic layers were transferred into 2 dram vials. The organic solvent was removed in GeneVac to afford the crude intermediates.

Step B: Removal of the Trimethylsilyl Ethoxy Methyl (SEM) Protecting Group Under Acidic Conditions Into each vial was added a solution of DCM (0.3 mL) in TFA (0.3 mL). The vials were agitated at 25° C. for 8 hr. The solvent was removed in a GeneVac. The residues were dissolved in 1.3 mL of DMSO. Each crude mixture was filtered into a 96-well tray and purified by HPLC to afford the following EXAMPLES.

| Ex. No | Structure | IUPAC Name | Calc'd Mass [M + H]⁺ | LC/MS m/e [M + H]⁺ |
|---|---|---|---|---|
| 371 | 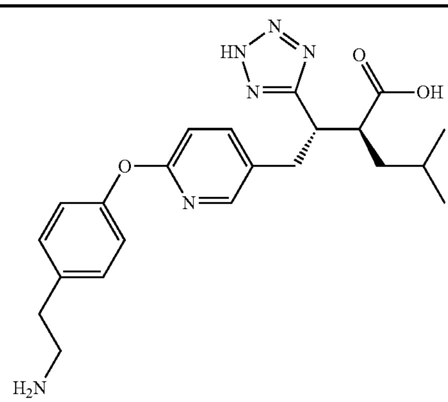 | (2S)-2-[(1S)-2-{6-[4-(2-aminoethyl)phenoxy]pyridin-3-yl}-1-(2H-tetrazol-5-yl)ethyl]-4-methylpentanoic acid | 425.23 | 425.22 |
| 372 | 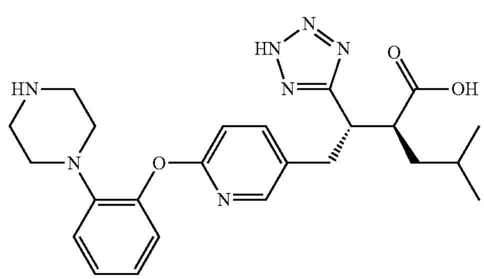 [SMILES: CC(C)C[C@H](C(=O)O)[C@H](Cc1ccc(Oc2ccccc2N2CCNCC2)nc1)c1nn[nH]n1] | (2S)-4-methyl-2-[(1S)-2-[6-(2-piperazin-1-ylphenoxy)pyridin-3-yl]-1-(2H-tetrazol-5-yl)ethyl]pentanoic acid | 466.26 | 466.25 |
| 373 | 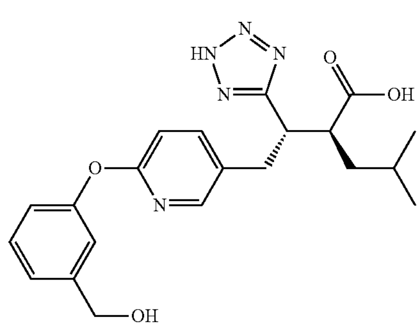 [SMILES: CC(C)C[C@H](C(=O)O)[C@H](Cc1ccc(Oc2cccc(CO)c2)nc1)c1nn[nH]n1] | (2S)-2-[(1S)-2-{6-[3-(hydroxymethyl)phenoxy]pyridin-3-yl}-1-(2H-tetrazol-5-yl)ethyl]-4-methylpentanoic acid | 412.2 | 412.19 |

-continued

| Ex. No | Structure | IUPAC Name | Calc'd Mass [M + H]+ | LC/MS m/e [M + H]+ |
|---|---|---|---|---|
| 374 | 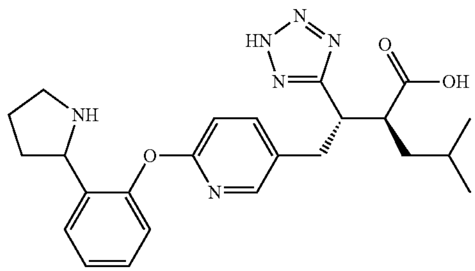 [SMILES: CC(C)C[C@H](C(=O)O)[C@H](Cc1ccc(Oc2ccccc2C2CCCN2)nc1)c1nn[nH]n1] | (2S)-4-methyl-2-[(1S)-2-[6-(2-pyrrolidin-2-ylphenoxy)pyridin-3-yl]-1-(2H-tetrazol-5-yl)ethyl]pentanoic acid | 451.25 | 451.24 |
| 375 | 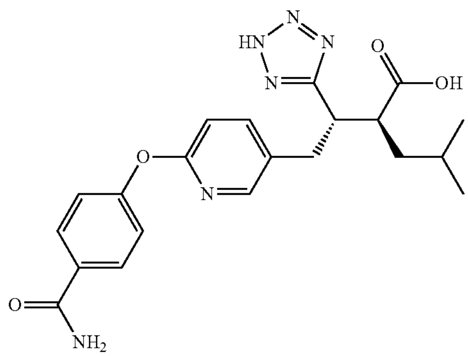 [SMILES: CC(C)C[C@H](C(=O)O)[C@H](Cc1ccc(Oc2ccc(C(N)=O)cc2)nc1)c1nn[nH]n1] | (2S)-2-[(1S)-2-[6-(4-carbamoylphenoxy)pyridin-3-yl]-1-(2H-tetrazol-5-yl)ethyl]-4-methylpentanoic acid | 425.19 | 425.18 |
| 376 | 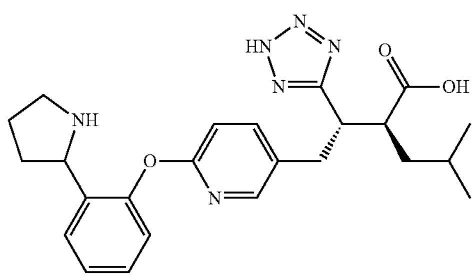 [SMILES: CC(C)C[C@H](C(=O)O)[C@H](Cc1ccc(Oc2ccccc2C2CCCN2)nc1)c1nn[nH]n1] | (2S)-4-methyl-2-[(1S)-2-[6-(2-pyrrolidin-2-ylphenoxy)pyridin-3-yl]-1-(2H-tetrazol-5-yl)ethyl]pentanoic acid | 451.25 | 451.24 |
| 377 | 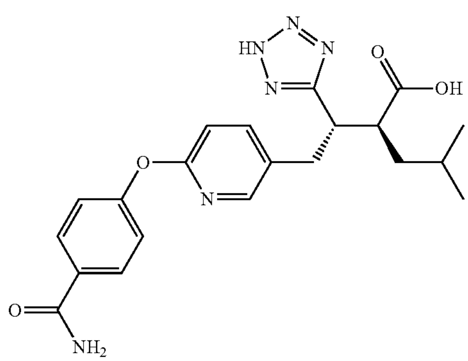 [SMILES: CC(C)C[C@H](C(=O)O)[C@H](Cc1ccc(Oc2ccc(C(N)=O)cc2)nc1)c1nn[nH]n1] | (2S)-2-[(1S)-2-[6-(4-carbamoylphenoxy)pyridin-3-yl]-1-(2H-tetrazol-5-yl)ethyl]-4-methylpentanoic acid | 425.19 | 425.18 |
| 378 | 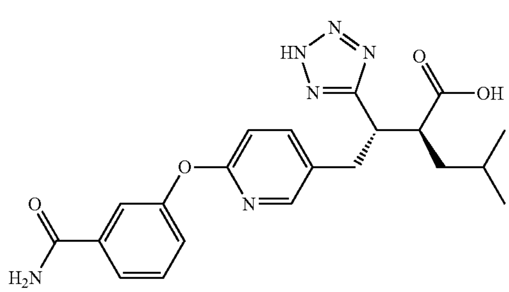 [SMILES: CC(C)C[C@H](C(=O)O)[C@H](Cc1ccc(Oc2cccc(C(N)=O)c2)nc1)c1nn[nH]n1] | (2S)-2-[(1S)-2-[6-(3-carbamoylphenoxy)pyridin-3-yl]-1-(2H-tetrazol-5-yl)ethyl]-4-methylpentanoic acid | 425.19 | 425.18 |

-continued

| Ex. No | Structure | IUPAC Name | Calc'd Mass [M + H]+ | LC/MS m/e [M + H]+ |
|---|---|---|---|---|
| 379 | 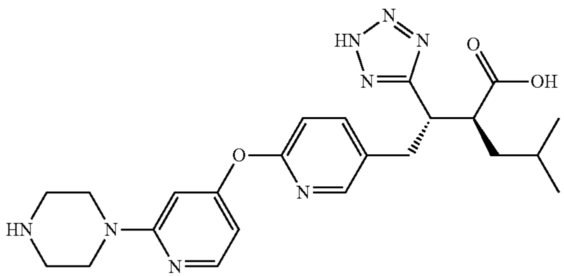 [SMILES: CC(C)C[C@H](C(=O)O)[C@H](Cc1ccc(Oc2ccnc(N3CCNCC3)c2)nc1)c1nn[nH]n1] | (2S)-4-methyl-2-[(1S)-2-{6-[(2-piperazin-1-ylpyridin-4-yl)oxy]pyridin-3-yl}-1-(2H-tetrazol-5-yl)ethyl]pentanoic acid | 467.25 | 467.24 |
| 380 | 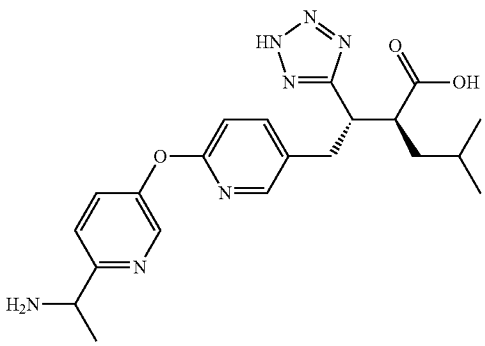 [SMILES: CC(C)C[C@H](C(=O)O)[C@H](Cc1ccc(Oc2ccc(C(C)N)nc2)nc1)c1nn[nH]n1] | (2S)-2-[(1S)-2-(6-{[6-(1-aminoethyl)pyridin-3-yl]oxy}pyridin-3-yl)-1-(2H-tetrazol-5-yl)ethyl]-4-methylpentanoic acid | 426.23 | 426.22 |
| 381 | 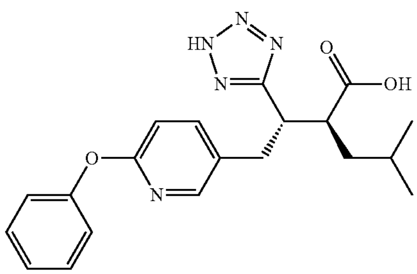 [SMILES: CC(C)C[C@H](C(=O)O)[C@H](Cc1ccc(Oc2ccccc2)nc1)c1nn[nH]n1] | (2S)-4-methyl-2-[(1S)-2-(6-phenoxypyridin-3-yl)-1-(2H-tetrazol-5-yl)ethyl]pentanoic acid | 382.19 | 382.18 |
| 382 | 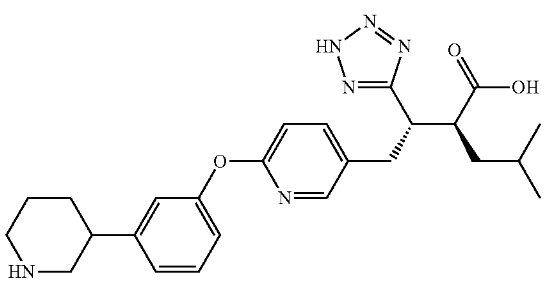 [SMILES: CC(C)C[C@H](C(=O)O)[C@H](Cc1ccc(Oc2cccc(C3CCCNC3)c2)nc1)c1nn[nH]n1] | (2S)-4-methyl-2-[(1S)-2-[6-(3-piperidin-3-ylphenoxy)pyridin-3-yl]-1-(2H-tetrazol-5-yl)ethyl]pentanoic acid | 465.26 | 465.25 |
| 383 | 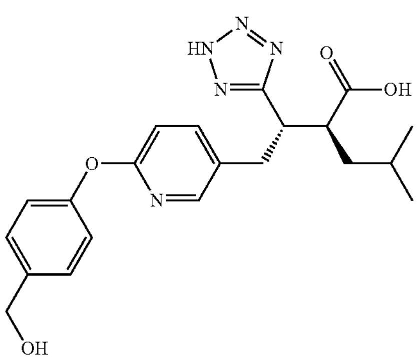 [SMILES: CC(C)C[C@H](C(=O)O)[C@H](Cc1ccc(Oc2ccc(CO)cc2)nc1)c1nn[nH]n1] | (2S)-2-[(1S)-2-{6-[4-(hydroxymethyl)phenoxy]pyridin-3-yl}-1-(2H-tetrazol-5-yl)ethyl]-4-methylpentanoic acid | 412.2 | 412.19 |

-continued

| Ex. No | Structure | IUPAC Name | Calc'd Mass [M + H]+ | LC/MS m/e [M + H]+ |
|---|---|---|---|---|
| 384 | 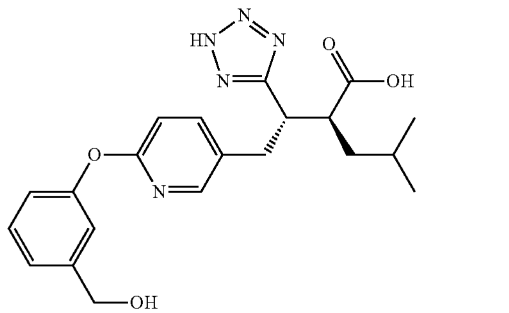 [SMILES: CC(C)C[C@H](C(=O)O)[C@H](Cc1ccc(Oc2cccc(CO)c2)nc1)c1nn[nH]n1] | (2S)-2-[(1S)-2-{6-[3-(hydroxymethyl)phenoxy]pyridin-3-yl}-1-(2H-tetrazol-5-yl)ethyl]-4-methylpentanoic acid | 412.2 | 412.19 |
| 385 | 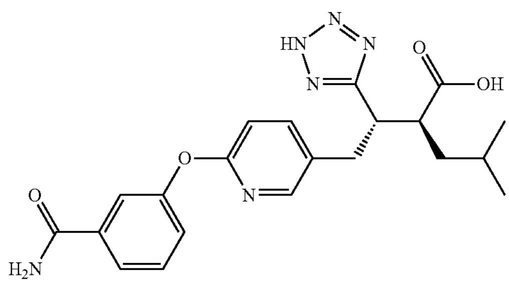 [SMILES: CC(C)C[C@H](C(=O)O)[C@H](Cc1ccc(Oc2cccc(C(N)=O)c2)nc1)c1nn[nH]n1] | (2S)-2-[(1S)-2-[6-(3-carbamoylphenoxy)pyridin-3-yl]-1-(2H-tetrazol-5-yl)ethyl]-4-methylpentanoic acid | 425.19 | 425.18 |
| 386 | 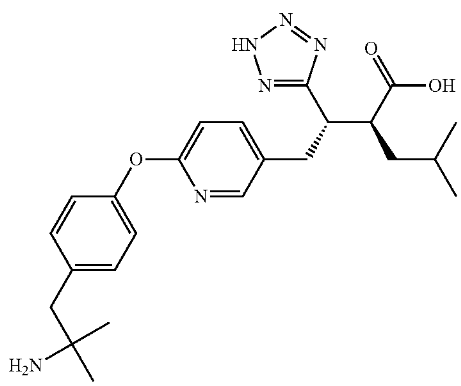 [SMILES: CC(C)C[C@H](C(=O)O)[C@H](Cc1ccc(Oc2ccc(CC(C)(C)N)cc2)nc1)c1nn[nH]n1] | (2S)-2-[(1S)-2-{6-[4-(2-amino-2-methylpropyl)phenoxy]pyridin-3-yl}-1-(2H-tetrazol-5-yl)ethyl]-4-methylpentanoic acid | 453.26 | 453.25 |
| 387 | 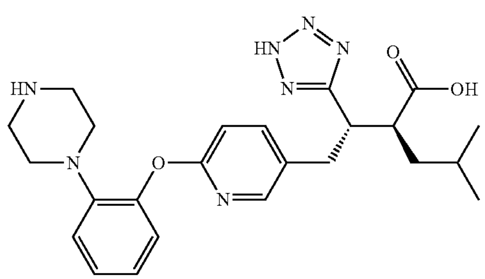 [SMILES: CC(C)C[C@H](C(=O)O)[C@H](Cc1ccc(Oc2ccccc2N2CCNCC2)nc1)c1nn[nH]n1] | (2S)-4-methyl-2-[(1S)-2-[6-(2-piperazin-1-ylphenoxy)pyridin-3-yl]-1-(2H-tetrazol-5-yl)ethyl]pentanoic acid | 466.26 | 466.25 |
| 388 | 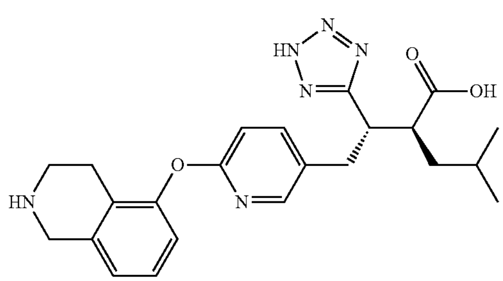 [SMILES: CC(C)C[C@H](C(=O)O)[C@H](Cc1ccc(Oc2cccc3c2CCNC3)nc1)c1nn[nH]n1] | (2S)-4-methyl-2-[(1S)-2-[6-(1,2,3,4-tetrahydroisoquinolin-5-yloxy)pyridin-3-yl]-1-(2H-tetrazol-5-yl)ethyl]pentanoic acid | 437.23 | 437.22 |

-continued

| Ex. No | Structure | IUPAC Name | Calc'd Mass [M + H]+ | LC/MS m/e [M + H]+ |
|---|---|---|---|---|
| 389 | 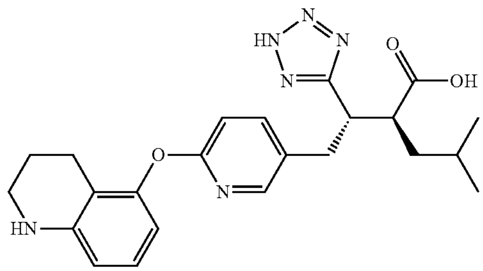 [SMILES: CC(C)C[C@H](C(=O)O)[C@H](Cc1ccc(Oc2cccc3c2CCCN3)nc1)c1nn[nH]n1] | (2S)-4-methyl-2-[(1S)-2-[6-(1,2,3,4-tetrahydroquinolin-5-yloxy)pyridin-3-yl]-1-(2H-tetrazol-5-yl)ethyl]pentanoic acid | 437.23 | 437.22 |
| 390 | 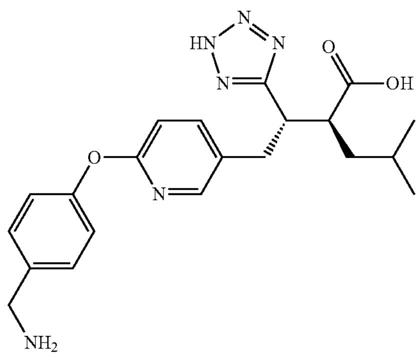 [SMILES: CC(C)C[C@H](C(=O)O)[C@H](Cc1ccc(Oc2ccc(CN)cc2)nc1)c1nn[nH]n1] | (2S)-2-[(1S)-2-{6-[4-(aminomethyl)phenoxy]pyridin-3-yl}-1-(2H-tetrazol-5-yl)ethyl]-4-methylpentanoic acid | 411.21 | 411.2 |
| 391 | 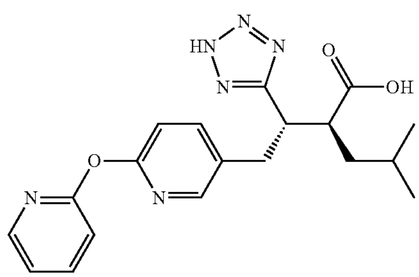 [SMILES: CC(C)C[C@H](C(=O)O)[C@H](Cc1ccc(Oc2ccccn2)nc1)c1nn[nH]n1] | (2S)-4-methyl-2-[(1S)-2-[6-(pyridin-2-yloxy)pyridin-3-yl]-1-(2H-tetrazol-5-yl)ethyl]pentanoic acid | 383.18 | 383.17 |
| 392 | 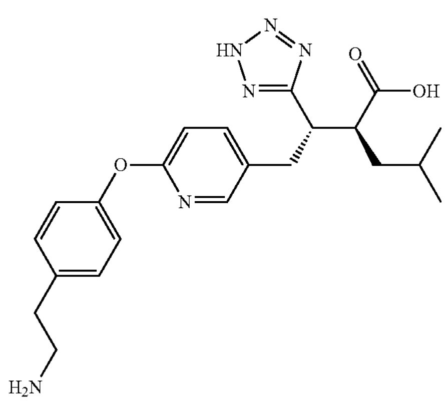 [SMILES: CC(C)C[C@H](C(=O)O)[C@H](Cc1ccc(Oc2ccc(CCN)cc2)nc1)c1nn[nH]n1] | (2S)-2-[(1S)-2-{6-[4-(2-aminoethyl)phenoxy]pyridin-3-yl}-1-(2H-tetrazol-5-yl)ethyl]-4-methylpentanoic acid | 425.23 | 425.22 |

EXAMPLES 393-403

Parallel synthesis of (2S)-2-[(1S)-2-[2'-substituted phenyl]-1-(2H-tetrazol-5-yl)ethyl]hexanoic acid

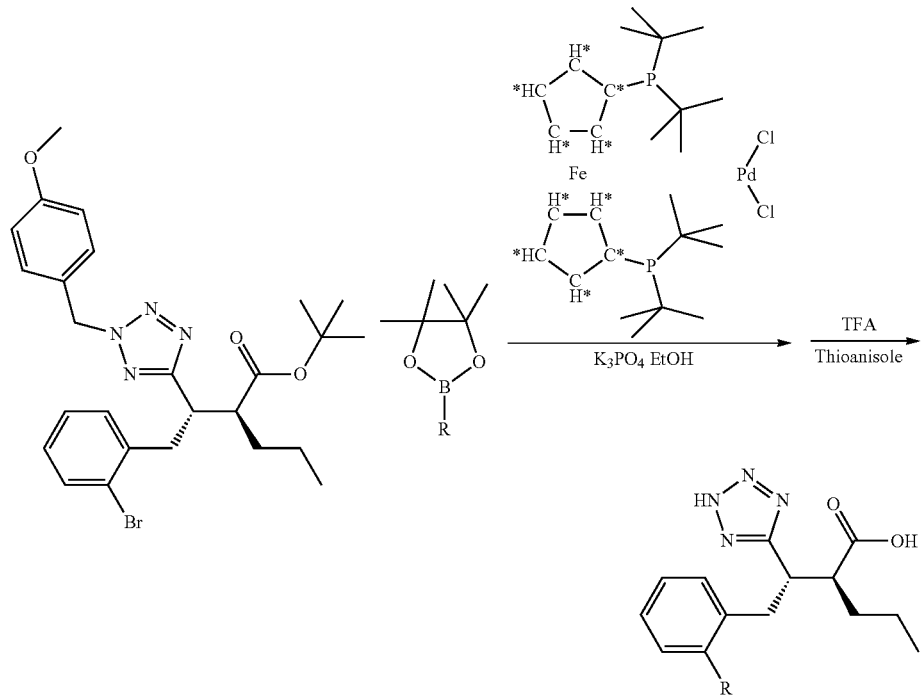

Step A: Palladium Catalyzed C—C Coupling of Arylbromide and Boronic Acids

Into 2 dram vials were added substituted boronic acid or ester (0.071 mmol), palladium catalyst (3.07 mg, 4.7 µmol) and 189 µL of 1 N degassed aq. K₃PO₄ solution. In a glove box, 1 mL of a solution of (S)-tert-butyl 2-((S)-2-(2-bromophenyl)-1-(2-(4-methylbenzyl)-2H-tetrazol-5-yl)ethyl) pentanoate (27 mg, 0.051 mmol) in EtOH was added into each vial. The vials were capped and heated at 75° C. with stirring for 20 hr (overnight). After the vials were cooled down to room temperature, the solvent was removed in GeneVac. Into each residue was added 600 µL of H₂O and 2 mL of DCM. The organic layers were transferred into 2 dram vials. The organic solvent was removed in GeneVac to afford the crude intermediates.

Step B: Removal of the Tert-Butyl and p-Methoxybenzyl (PMB) Protecting Group Under Acidic Conditions Into each vial was added a solution of thioanisole (0.3 mL), and DCM (0.3 mL) in TFA (0.3 mL). The vials were agitated at 25° C. for 16 hr. The solvent was removed in a GeneVac. Into each vial was added a solution of thioanisole (0.3 mL), and DCM (0.3 mL) in TFA (0.3 mL). The vials were agitated at 55° C. for 16 hr. The solvent was removed in a GeneVac. The residues were dissolved in 1.3 mL of DMSO. Each crude mixture was filtered into a 96-well tray and purified by HPLC to afford the following EXAMPLES.

| Ex. No | Structure | IUPAC Name | Calc'd Mass [M + H]⁺ | LC/MS m/e [M + H]⁺ |
|---|---|---|---|---|
| 393 | 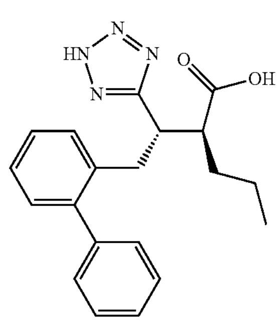 [SMILES: CCC[C@H](C(=O)O)[C@H](Cc1ccccc1-c1ccccc1)c1nn[nH]n1] | (2S)-2-[(1S)-2-biphenyl-2-yl-1-(2H-tetrazol-5-yl)ethyl]pentanoic acid | 351.18 | 351.17 |

| Ex. No | Structure | IUPAC Name | Calc'd Mass [M + H]⁺ | LC/MS m/e [M + H]⁺ |
|---|---|---|---|---|
| 394 | 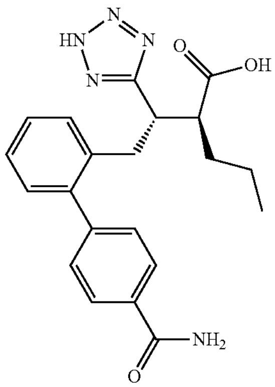 [SMILES: CCC[C@H](C(=O)O)[C@H](Cc1ccccc1-c1ccc(C(N)=O)cc1)c1nn[nH]n1] | (2S)-2-[(1S)-2-(4'-carbamoylbiphenyl-2-yl)-1-(2H-tetrazol-5-yl)ethyl]pentanoic acid | 394.19 | 394.18 |
| 395 | 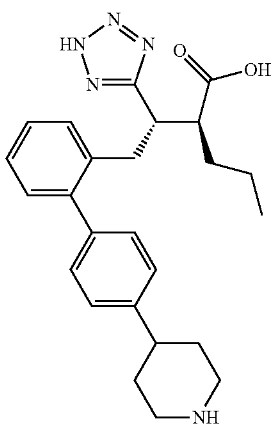 [SMILES: CCC[C@H](C(=O)O)[C@H](Cc1ccccc1-c1ccc(C2CCNCC2)cc1)c1nn[nH]n1] | (2S)-2-[(1S)-2-(4'-piperidin-4-ylbiphenyl-2-yl)-1-(2H-tetrazol-5-yl)ethyl]pentanoic acid | 434.26 | 434.25 |
| 396 | 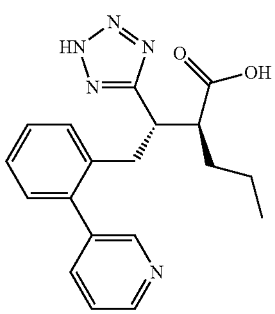 [SMILES: CCC[C@H](C(=O)O)[C@H](Cc1ccccc1-c1cccnc1)c1nn[nH]n1] | (2S)-2-[(1S)-2-(2-pyridin-3-ylphenyl)-1-(2H-tetrazol-5-yl)ethyl]pentanoic acid | 352.18 | 352.17 |
| 397 | 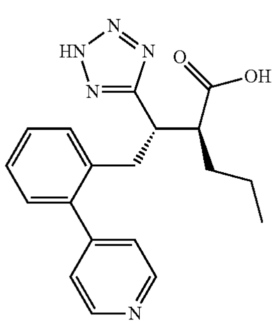 [SMILES: CCC[C@H](C(=O)O)[C@H](Cc1ccccc1-c1ccncc1)c1nn[nH]n1] | (2S)-2-[(1S)-2-(2-pyridin-4-ylphenyl)-1-(2H-tetrazol-5-yl)ethyl]pentanoic acid | 352.18 | 352.17 |

-continued

| Ex. No | Structure | IUPAC Name | Calc'd Mass [M + H]+ | LC/MS m/e [M + H]+ |
|---|---|---|---|---|
| 398 | 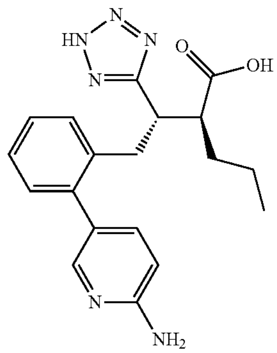 [SMILES: CCC[C@H](C(=O)O)[C@H](Cc1ccccc1-c1ccc(N)nc1)c1nn[nH]n1] | (2S)-2-[(1S)-2-[2-(6-aminopyridin-3-yl)phenyl]-1-(2H-tetrazol-5-yl)ethyl]pentanoic acid | 367.19 | 367.18 |
| 399 | 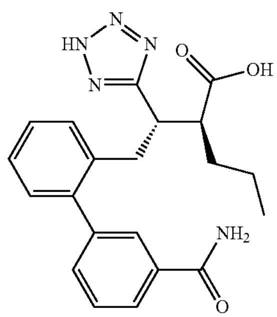 [SMILES: CCC[C@H](C(=O)O)[C@H](Cc1ccccc1-c1cccc(C(N)=O)c1)c1nn[nH]n1] | (2S)-2-[(1S)-2-(3'-carbamoylbiphenyl-2-yl)-1-(2H-tetrazol-5-yl)ethyl]pentanoic acid | 394.19 | 394.19 |
| 400 | 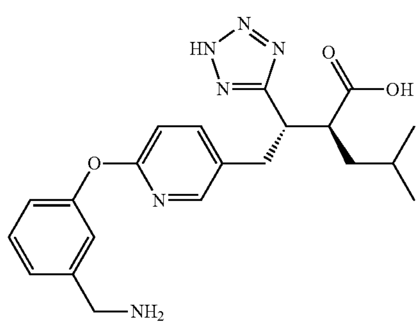 [SMILES: CC(C)C[C@H](C(=O)O)[C@H](Cc1ccc(Oc2cccc(CN)c2)nc1)c1nn[nH]n1] | (2S)-2-[(1S)-2-{6-[3-(aminomethyl)phenoxy]pyridin-3-yl}-1-(2H-tetrazol-5-yl)ethyl]-4-methylpentanoic acid | 411.21 | 411.2 |
| 401 | 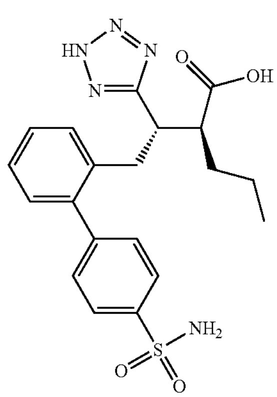 [SMILES: CCC[C@H](C(=O)O)[C@H](Cc1ccccc1-c1ccc(S(N)(=O)=O)cc1)c1nn[nH]n1] | (2S)-2-[(1S)-2-(4'-sulfamoylbiphenyl-2-yl)-1-(2H-tetrazol-5-yl)ethyl]pentanoic acid | 430.15 | 430.14 |

| Ex. No | Structure | IUPAC Name | Calc'd Mass [M + H]+ | LC/MS m/e [M + H]+ |
|---|---|---|---|---|
| 402 | 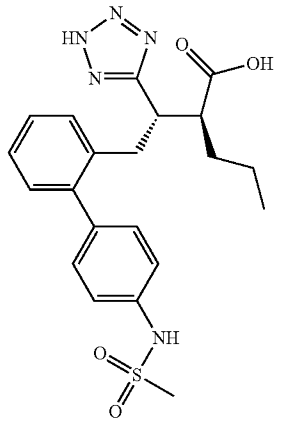 [SMILES: CCC[C@H](C(=O)O)[C@H](Cc1ccccc1-c1ccc(NS(C)(=O)=O)cc1)c1nn[nH]n1] | (2S)-2-[(1S)-2-{4'-[(methylsulfonyl)amino]biphenyl-2-yl}-1-(2H-tetrazol-5-yl)ethyl]pentanoic acid | 444.17 | 444.16 |
| 403 | 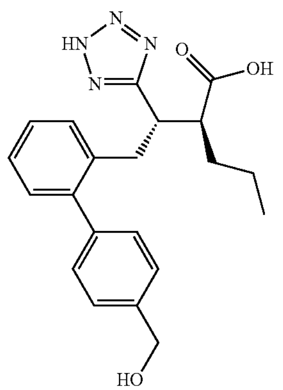 [SMILES: CCC[C@H](C(=O)O)[C@H](Cc1ccccc1-c1ccc(CO)cc1)c1nn[nH]n1] | (2S)-2-[(1S)-2-[4'-(hydroxymethyl)biphenyl-2-yl]-1-(2H-tetrazol-5-yl)ethyl]pentanoic acid | 381.19 | 381.18 |

EXAMPLE 404

(2S)-2-((S)-2-(6-aminopyridin-3-yl)-1-(1H-tetrazol-5-yl)ethyl)-4-phenylpentanoic acid

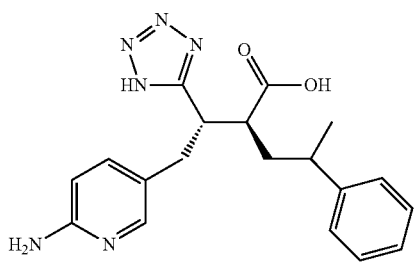 [SMILES: CC(C[C@H](C(=O)O)[C@H](Cc1ccc(N)nc1)c1nnn[nH]1)c1ccccc1]

Step A: (E)-4-phenylpent-3-enoic acid

2-Phenylpropanal (2.1 g, 15.7 mmol), malonic acid (1.792 g, 17.22 mmol) and TEA (2.94 mL, 21.1 mmol) in toluene (25 mL) were refluxed at 100° C. under $N_2$ for 16 hrs. The reaction was diluted with ether and washed with 1M HCl (1×). The ether layer was extracted with 5% aqueous NaOH (3×). The aqueous layer was acidified with 1N HCl to pH 1 then re-extracted with ether (3 times). The ether layer was dried over $Na_2SO_4$, filtered and concentrated to yield (E)-4-phenylpent-3-enoic acid. LC/MS [M+H]+: 177.3.

Step B: 4-phenylpentanoic acid (E)-4-phenylpent-3-enoic acid (2.15 g, 12.20 mmol) was dissolved in MeOH (30 ml) and 10% Pd—C (0.130 g, 1.22 mmol) was added and then stirred under a balloon of $H_2$ for 14 hrs. The catalyst was filtered off and the reaction mixture concentrated to yield 4-phenylpentanoic acid. LC/MS [M+H]+: 179.1

Step C: 4-phenylpentanoic pivalic anhydride 4-phenylpentanoic acid (2.057 g, 11.54 mmol) was dissolved in THF (50 ml) and cooled to −78° C. Hunig's base (2.298 ml, 13.16 mmol) was then added followed by pivaloyl chloride (1.420 ml, 11.54 mmol). The reaction was allowed to warm up to RT for 16 hrs to yield a white suspension. An aliquot was taken and quenched with $NH_3$ in methanol. LC/MS [M+H]+: 178 showed an amide peak indicating the anhydride was formed. The suspension was used as is in the next step.

Step D: (4R,5S)-4-methyl-5-phenyl-3-(4-phenylpentanoyl)oxazolidin-2-one (4R,5S)-4-methyl-5-phenyloxazolidin-2-one (2.045 g, 11.54 mmol) was dissolved in THF (60 ml) and cooled to −78° C. nBuLi in hexane (5.08 ml, 2.5M, 12.69 mmol) was then added and the reaction mixture was stirred for 0.5 hr. 4-Phenylpentanoic pivalic anhydride (3.03 g, 11.54 mmol) in 50 ml THF was then cannulated to the reaction. After stirring at −78° C., the reaction was allowed to warm up to RT and then stirred for 72 hrs. The reaction was quenched with saturated NH$_4$Cl solution (20 ml) then extracted with EtOAc (2×). The organic layer was then washed with saturated brine then dried over Na$_2$SO$_4$, filtered and concentrated. The residue was purified by MPLC with 0-50% EtOAc: hexane to give (4R,5S)-4-methyl-5-phenyl-3-(4-phenylpentanoyl)oxazolidin-2-one. LC/MS [M+H]+: 338.1

Step E: (3S)-3-((4R,5S)-4-methyl-2-oxo-5-phenyloxazolidine-3-carbonyl)-5-phenylhexanenitrile (4R,5S)-4-methyl-5-phenyl-3-(4-phenylpentanoyl)oxazolidin-2-one (1.9 g, 5.63 mmol) was dissolved in THF (45 ml) and cooled to −78° C. LiHMDS in THF (7.32 ml, 1M, 7.32 mmol) was then added and the reaction mixture was stirred for 0.5 hr. Bromoacetonitrile (1.177 ml, 16.89 mmol) was added. The reaction was stirred for 30 mins at −78° C. then allowed to warm up to RT for 16 hrs. The reaction was quenched with saturated NH$_4$Cl solution (15 ml) and extracted with EtOAc (2×), dried over Na$_2$SO$_4$, filtered and concentrated. The residue was purified by MPLC with 0-25% EtOAc: hexane to give (3S)-3-((4R,5S)-4-methyl-2-oxo-5-phenyloxazolidine-3-carbonyl)-5-phenylhexanenitrile. LC/MS [M+H]+: 377.5

Step F: (4R,5S)-3-((2S)-2-((1H-tetrazol-5-yl)methyl)-4-phenylpentanoyl)-4-methyl-5-phenyloxazolidin-2-one (3S)-3-((4R,5S)-4-methyl-2-oxo-5-phenyloxazolidine-3-carbonyl)-5-phenylhexanenitrile (1.461 g, 3.88 mmol) was dissolved in toluene (20 ml) and then dibutyltin oxide (0.097 g, 0.388 mmol) and azidotrimethylsilane (1.030 ml, 7.76 mmol) were added. The reaction was heated to 100° C. for 16 hrs. The reaction was quenched with saturated NH$_4$Cl solution and extracted with EtOAc (2×), dried over Na$_2$SO$_4$, filtered and concentrated. The residue was purified by MPLC with 0-50% ETOAC/hexane to yield (4R,5S)-3-((2S)-2-(1H-tetrazol-5-yl)methyl)-4-phenylpentanoyl)-4-methyl-5-phenyloxazolidin-2-one. LC/MS [M+H]+: 420.2

Step G: (4R,5S)-4-methyl-5-phenyl-3-((2S)-4-phenyl-2-((2-((2-(trimethylsilyl) ethoxy)methyl)-2H-tetrazol-5-yl)methyl)pentanoyl)oxazolidin-2-one (4R,5S)-4-methyl-5-phenyl-3-((2S)-4-phenyl-2-((1-((2-(trimethylsilyl) ethoxy)methyl)-1H-tetrazol-5-yl)methyl)pentanoyl)oxazolidin-2-one (4R,5S)-3-((2S)-2-((1H-tetrazol-5-yl)methyl)-4-phenylpentanoyl)-4-methyl-5-phenyloxazolidin-2-one (960 mg, 2.289 mmol) in acetonitrile (60 ml) was cooled to 0° C. and then Hunig's base (0.799 ml, 4.58 mmol) followed by 2-(trimethylsilyl) ethoxymethyl chloride (0.405 ml, 2.289 mmol) were added. The reaction mixture was stirred at RT and followed by LCMS.

The reaction was poured into water and extracted with EtOAc (2×). The combined EtOAc layers were washed with brine (1x), dried (Na$_2$SO$_4$), filtered and concentrated. The residue was purified by MPLC with 0-50% ETOAC/hexane to yield both regioisomers (4R,5S)-4-methyl-5-phenyl-3-((2S)-4-phenyl-2-((2-((2-(trimethylsilyl) ethoxy)methyl)-2H-tetrazol-5-yl)methyl)pentanoyl)oxazolidin-2-one and (4R,5S)-4-methyl-5-phenyl-3-((2S)-4-phenyl-2-((1-((2-(trimethylsilyl)ethoxy)methyl)-1H-tetrazol-5-yl)methyl)pentanoyl)oxazolidin-2-one. LC/MS [M+H]+: 550.8

Step H: (2S)-4-phenyl-2-((1-((2-(trimethylsilyl)ethoxy)methyl)-1H-tetrazol-5-yl)methyl)pentanoic acid (4R,5S)-4-methyl-5-phenyl-3-((2S)-4-phenyl-2-((1-((2-(trimethylsilyl)ethoxy) methyl)-1H-tetrazol-5-yl)methyl)pentanoyl)oxazolidin-2-one (680.5 mg, 1.238 mmol) was dissolved in THF (10 ml) and cooled to 0° C. To this was added a 0° C. pre-cooled mixture of LiOH—H$_2$O (104 mg, 2.476 mmol) in water (2.5 ml) and H$_2$O$_2$ (1.084 ml, 36%, 12.38 mmol). The reaction mixture was stirred at 0° C. for 1.5 hrs. A solution of sodium bisulfate (234 mg, 2.253 mmol) and sodium sulfite (429 mg, 3.40 mmol) in 10 ml water was added to the reaction at 0° C. then stirred at RT for another 5 mins. The reaction mixture was washed with ether (3×). The aqueous layer was acidified with 1N HCl and extracted with EtOAc (2×), dried over Na$_2$SO$_4$, filtered and concentrated to yield (2S)-4-phenyl-2-((1-((2-(trimethylsilyl)ethoxy)methyl)-1H-tetrazol-5-yl)methyl)pentanoic acid. LC/MS [M+H]+: 391

Step I: (2S)-2-((S)-2-(6-bromopyridin-3-yl)-1-(1-((2-(trimethylsilyl)ethoxy)methyl)-1H-tetrazol-5-yl)ethyl)-4-phenylpentanoic acid (2S)-4-phenyl-2-((1-((2-(trimethylsilyl)ethoxy)methyl)-1H-tetrazol-5-yl)methyl) pentanoic acid (130 mg, 0.333 mmol) was dissolved in THF (10 ml) and cooled to −78° C. Then LDA (1.300 ml, 0.64M, 0.832 mmol) was added. The reaction was stirred for 45 mins then 2-bromo-5-(bromomethyl) pyridine (100 mg, 0.399 mmol) in THF (2 ml) was added. The reaction mixture was stirred at −70° C. for 5 hrs then quenched with saturated aq. NH$_4$Cl solution, extracted with EtOAc (2×), washed with brine (lx), dried (Na$_2$SO$_4$) and concentrated. The residue was purified by reverse phase HPLC with ACN and water buffered with 0.05% TFA to yield (2S)-2-((S)-2-(6-bromopyridin-3-yl)-1-(1-((2-(trimethylsilyl)ethoxy)methyl)-1H-tetrazol-5-yl)ethyl)-4-phenylpentanoic acid. LC/MS [M+H]+: 562.1.

Step J: (2S)-2-((S)-2-(6-aminopyridin-3-yl)-1-(1-((2-(trimethylsilyl)ethoxy)methyl)-1H-tetrazol-5-yl)ethyl)-4-phenylpentanoic acid (2S)-2-((S)-2-(6-bromopyridin-3-yl)-1-(1-((2-(trimethylsilyl) ethoxy) methyl)-1H-tetrazol-5-yl)ethyl)-4-phenylpentanoic acid (67.3 mg, 0.120 mmol), N,N'-dimethylethylenediamine (3.10 µl, 0.029 mmol), copper(I) oxide (1.718 mg, 0.012 mmol), K$_2$CO$_3$ (3.32 mg, 0.024 mmol) and ammonium hydroxide (1500 µl, 10.79 mmol) were added to a 5-ml microwave tube containing ethylene glycol (2 ml). The tube was sealed and heated at 80° C. for 16 hrs. LCMS showed product but a lot of remaining SM. More copper(I) oxide (1.718 mg, 0.012 mmol), NH$_4$OH (0.5 ml), and ethylene glycol (1 ml) were added. The tube was re-capped and heated to 80° C. for another 16 hrs. The reaction was filtered, concentrated and acidified with 1N HCl to pH 5 then extracted with ETOAc:THF mixture. Aqueous layer was re-adjusted to pH 7 and extraction with ETOAc:THF was repeated. Combined organic layers were concentrated. The residue was purified by reverse phase HPLC with ACN and water buffered with 0.05% TFA (2S)-2-((S)-2-(6-aminopyridin-3-yl)-1-(1-((2-(trimethylsilyl)ethoxy) methyl)-1H-tetrazol-5-yl)ethyl)-4-phenylpentanoic acid was isolated. LC/MS [M+H]+: 497.3.

Step K: (2S)-2-((S)-2-(6-aminopyridin-3-yl)-1-(1H-tetrazol-5-yl)ethyl)-4-phenylpentanoic acid (2S)-2-((S)-2-(6-aminopyridin-3-yl)-1-(1-((2-(trimethylsilyl)ethoxy)methyl)-1H-tetrazol-5-yl)ethyl)-4-phenylpentanoic acid (24 mg, 0.048 mmol) was stirred in TFA (2 ml) with water (0.2 ml) for 2 hrs. The reaction was concentrated and the residue was purified by reverse phase HPLC with ACN and water buffered with 0.05% TFA to yield (2S)-2-((S)-2-(6-aminopyridin-3-yl)-1-(1H-tetrazol-5-yl)ethyl)-4-phenylpentanoic acid. LC/MS [M+H]+: 367.1

EXAMPLE 405

(2S,3S)-5-(6-aminopyridin-3-yl)-2-propyl-3-(1H-tetrazol-5-yl)pentanoic acid

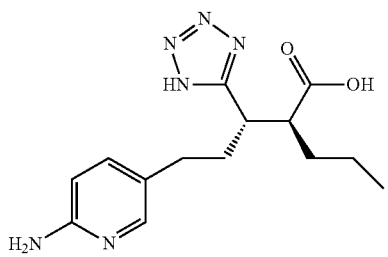 [SMILES: CCC[C@H](C(=O)O)[C@H](CCc1ccc(N)nc1)c1nnn[nH]1]

Step A: Methyl 2-(2-bromopyridin-4-yl)acetate 2-(2-bromopyridin-4-yl)acetic acid (0.9685 g, 4.48 mmol) was dissolved in a mixture of toluene (20 ml)/MeOH (2.50 ml) then cooled to 0° C. Trimethyl-silyldiazomethane (5.60 ml, 11.21 mmol) was added. The reaction was stirred at 0° C. for 1 hr then concentrated to yield methyl 2-(2-bromopyridin-4-yl)acetate. LC/MS [M+H]+: 231.4

Step B: 2-(2-bromopyridin-4-yl)ethanol

Methyl 2-(2-bromopyridin-4-yl)acetate (1.5 g, 6.52 mmol) was dissolved in THF (20 ml) then cooled to 0° C. and then LiAlH4 (3.26 ml, 6.52 mmol) was added. The reaction mixture was stirred at 0° C. for 3 hrs. LCMS showed remaining SM. Additional LiAlH$_4$ (3.26 ml, 6.52 mmol) was added and the reaction mixture stirred for another hour. The reaction was quenched with water (0.5 ml), 15% NaOH (0.5 ml), and more water (1.5 ml). The reaction was diluted with EtOAc and MgSO$_4$ was added. The reaction was stirred then filtered and concentrated to yield 2-(2-bromopyridin-4-yl)ethanol. LC/MS [M+H]+: 202.

Step C: 2-bromo-4-(2-bromoethyl)pyridine

In a 25 ml RB flask, 2-(2-bromopyridin-4-yl)ethanol (1.133 g, 5.61 mmol) was dissolved in DCM (20 ml) and cooled to 0° C. then triphenylphosphine (1.471 g, 5.61 mmol) and CBr$_4$ (1.860 g, 5.61 mmol) were added. The reaction was stirred for 30 mins at 0° C. then warmed up to RT for 16 hr. The reaction was concentrated and the residue was purified by MPLC with 0-50% EtOAc/hexane to yield 2-bromo-4-(2-bromoethyl)pyridine. LC/MS [M+H]+: 265.8.

Step D: 2-bromo-4-(2-iodoethyl)pyridine

To 2-bromo-4-(2-bromoethyl)pyridine (424 mg, 1.60 mmol) in acetone (4 ml) was added sodium iodide (1199 mg, 8.00 mmol) followed by heating at 60° C. for 3 hrs. The reaction was cooled and filtered. The filtrate was concentrated then extracted with EtOAc and washed with brine, dried over NaSO$_4$, filtered and concentrated to yield 2-bromo-4-(2-iodoethyl)pyridine. LC/MS [M+H]+: 313.5

Step E. (2S,3S)-5-(6-bromopyridin-3-yl)-2-propyl-3-(1-((2-(trimethylsilyl)ethoxy) methyl)-1H-tetrazol-5-yl)pentanoic acid (S)-2-((1-((2-(trimethylsilyl)ethoxy)methyl)-1H-tetrazol-5-yl)methyl) pentanoic acid (500 mg, 1.590 mmol) was dissolved in THF (10 ml) and cooled to −78° C. then LDA solution (6.21 ml, 3.98 mmol, 0.64M) was added. The reaction was stirred for 45 mins then 2-bromo-5-(2-iodoethyl)pyridine (498 mg, 1.596 mmol) in THF (1 ml) was added. The reaction mixture was stirred for 5 hrs then allowed to warm up to RT. The reaction was stirred for 16 hrs before quenching with saturated NH$_4$Cl and adjusted to pH=5. The reaction was extracted with ETOAc, dried over Na$_2$SO$_4$, filtered and concentrated. The residue was purified by reverse phase HPLC with ACN and water buffered with 0.05% TFA to yield (2S,3S)-5-(6-bromopyridin-3-yl)-2-propyl-3-(1-((2-(trimethylsilyl) ethoxy) methyl)-1H-tetrazol-5-yl)pentanoic acid. LC/MS [M+H]+: 500.1

Step F: (2S,3S)-5-(6-aminopyridin-3-yl)-2-propyl-3-(1-((2(trimethylsilyl)ethoxy)methyl)-1H-tetrazol-5-yl)pentanoic acid (2S,3S)-5-(6-bromopyridin-3-yl)-2-propyl-3-(1-((2-(trimethylsilyl)ethoxy)methyl)-1H-tetrazol-5-yl)pentanoic acid (37 mg, 0.074 mmol), N,N'-dimethylethylene diamine (1.917 µl, 0.018 mmol), copper(I) oxide (1.062 mg, 7.42 µmol), and K$_2$CO$_3$ (2.052 mg, 0.015 mmol) were suspended in ethylene glycol (0.1 ml) then ammonium hydroxide (0.413 ml, 2.97 mmol) was added. The reaction was purged with N$_2$, capped and heated at 80° C. overnight. LC/MS showed remaining SM. Additional copper(I) oxide (1.062 mg, 7.42 µmol), K$_2$CO$_3$ (2.052 mg, 0.015 mmol) and ammonium hydroxide (0.413 ml, 2.97 mmol) were added and the reaction mixture was heated at 80° C. for another 16 hrs. The reaction was concentrated, adjusted to pH 4, extracted with EtOAc (2×), dried and concentrated. The residue was purified by reverse phase HPLC with ACN and water buffered with 0.05% TFA to yield (2S,3S)-5-(6-aminopyridin-3-yl)-2-propyl-3-(1-((2(trimethylsilyl)ethoxy)methyl)-1H-tetrazol-5-yl)pentanoic acid. LC/MS [M+H]+: 435.3

Step G: 2S,3S)-5-(6-aminopyridin-3-yl)-2-propyl-3-(1H-tetrazol-5-yl)pentanoic acid To (2S,3S)-5-(6-aminopyridin-3-yl)-2-propyl-3-(1-((2-(trimethylsilyl)ethoxy) methyl)-1H-tetrazol-5-yl)pentanoic acid (10 mg, 0.023 mmol) was added TFA (2 ml) and water (0.2 ml). The reaction was stirred at RT for 2 hrs then concentrated. The residue was purified by reverse phase HPLC with ACN and water buffered with 0.05% TFA to yield 2S,3S)-5-(6-aminopyridin-3-yl)-2-propyl-3-(1H-tetrazol-5-yl)pentanoic acid. LC/MS [M+H]+: 305.2

EXAMPLE 406

(2S,3S)-6-(6-aminopyridin-3-yl)-2-propyl-3-(1H-tetrazol-5-yl)hexanoic acid

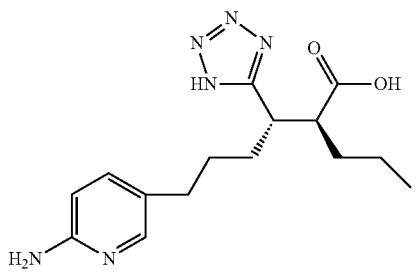 [SMILES: CCC[C@H](C(=O)O)[C@H](CCCc1ccc(N)nc1)c1nnn[nH]1]

Step A: 3-(2-bromopyridin-4-yl)propan-1-ol

Tert-butyl 3-(2-bromopyridin-4-yl)propanoate (0.950 g, 3.32 mmol) was suspended in THF (20 ml) and cooled to 0° C. then LAH (1.660 ml, 3.32 mmol) was added. The reaction mixture was stirred at 0° C. for 1 hr. LCMS showed some SM. Additional LAH (1.660 ml, 3.32 mmol) was added and the reaction mixture stirred for another hour. When TLC showed no SM, the reaction was quenched with water (0.25 ml), 15% NaOH (0.25 ml), and more water (0.75 ml). The reaction mixture was diluted with EtOAc and MgSO4 was added. The mixture was filtered and concentrated to yield 3-(2-bromopyridin-4-yl)propan-1-ol. $^1$H-NMR (500 MHz, CDCl3) δ ppm: 1.92-1.86 (2 H, m), 2.71 (2 H, t, J=7.83 Hz), 3.68-3.67 (2H, m), 7.11-7.06 (1 H, d, J=5.15 Hz), 7.35 (1 H, dd, J=1.49, 0.74 Hz), 8.25 (1 H, d, J=5.07 Hz).

Step B: 2-bromo-4-(3-bromopropyl)pyridine 3-(2-bromopyridin-4-yl)propan-1-ol (636.3 mg, 2.94 mmol) was dissolved in DCM (10 ml) and cooled to 0° C. then triphenylphosphine (772 mg, 2.94 mmol) and CBr4 (977 mg, 2.94 mmol) were added. After stirring for 30 mins at 0° C., the reaction was stirred at RT for 16 hr. The reaction was concentrated and the residue was purified by MPLC with 0-30% EtOAc/hexane to yield 2-bromo-4-(3-bromopropyl)pyridine. LC/MS [M+H]+: 279.9

Step C: 2-bromo-4-(3-iodopropyl)pyridine

To 2-bromo-4-(3-bromopropyl)pyridine (714 mg, 2.56 mmol) in acetone (4 ml) was added sodium iodide (1980 mg, 13.21 mmol) then the reaction mixture was heated to 60° C. for 3 hrs. The reaction was cooled and filtered then concentrated. The residue was taken up with EtOAc and washed with brine, dried over NaSO4, filtered and concentrated to yield 2-bromo-4-(3-iodopropyl)pyridine. LC/MS [M+H]+: 326.3

Step D: (2S,3S)-6-(6-bromopyridin-3-yl)-2-propyl-3-(1-((2(trimethylsilyl)ethoxy)methyl)-1H-tetrazol-5-yl)hexanoic acid (S)-2-((1-((2-(trimethylsilyl)ethoxy)methyl)-1H-tetrazol-5-yl)methyl)pentanoic acid (402.5 mg, 1.280 mmol) was dissolved in THF (10 ml) at −78° C. then LDA (5.00 ml, 0.64M, 3.20 mmol) was added. The reaction mixture was stirred for 45 mins then 2-bromo-5-(3-iodopropyl) pyridine (512 mg, 1.571 mmol) in THF (1 ml) was added. The reaction was stirred at −70° C. for 5 hrs before quenching with aq. saturated NH4Cl. The reaction was acidified to pH 5, extracted with EtOAc (2×), dried over Na2SO4, filtered and concentrated. The residue was purified by reverse phase HPLC with ACN and water buffered with 0.05% TFA to yield (2S,3S)-6-(6-bromopyridin-3-yl)-2-propyl-3-(1-((2(trimethylsilyl)ethoxy)methyl)-1H-tetrazol-5-yl)hexanoic acid. LC/MS [M+H]+: 514.2

Step E: (2S,3S)-6-(6-aminopyridin-3-yl)-2-propyl-3-(1-((2-(trimethylsilyl)ethoxy) methyl)-1H-tetrazol-5-yl)hexanoic acid In a 25 ml microwave tube, (2S,3S)-6-(6-bromopyridin-3-yl)-2-propyl-3-(1-((2-(trimethylsilyl) ethoxy)methyl)-1H-tetrazol-5-yl)hexanoic acid (305 mg, 0.595 mmol), N,N'-dimethylethylenediamine (15 µl, 0.139 mmol), copper(I) oxide (8.52 mg, 0.060 mmol), and K2CO3 (16.45 mg, 0.119 mmol) were suspended in ethylene glycol (3 ml) Ammonium hydroxide (3322 µl, 23.89 mmol) was added. The tube was sealed and heated at 80° C. for 16 hrs. The reaction was cooled and concentrated. The involatile was diluted with water and acidified to pH 5. The mixture was extracted with EtOAc (2×), washed with brine, dried over Na2SO4, filtered and concentrated. The residue was purified by reverse phase HPLC with ACN and water buffered with 0.05% TFA to yield (2S,3S)-6-(6-aminopyridin-3-yl)-2-propyl-3-(1-((2-(trimethylsilyl)ethoxy) methyl)-1H-tetrazol-5-yl)hexanoic acid. LC/MS [M+H]+: 449.3

Step F: (2S,3S)-6-(6-aminopyridin-3-yl)-2-propyl-3-(1H-tetrazol-5-yl)hexanoic acid In a sealed tube, (2S,3S)-6-(6-aminopyridin-3-yl)-2-propyl-3-(1-((2-(trimethyl silyl)ethoxy)methyl)-1H-tetrazol-5-yl)hexanoic acid (130 mg, 0.290 mmol) was dissolved in EtOH (3 ml) then 1N HCl (11.60 ml, 11.60 mmol) was added and the reaction mixture heated at 60° C. for 16 hrs. The reaction was concentrated and the residue was purified by reverse phase HPLC with ACN and water buffered with 0.05% TFA to yield (2S,3S)-6-(6-aminopyridin-3-yl)-2-propyl-3-(1H-tetrazol-5-yl)hexanoic acid. LC/MS [M+H]+: 319.1

EXAMPLE 407

S)-2-((S)-2-(2-chloro-6-((2-hydroxyethyl)amino)pyridin-4-yl)-1-(1H-tetrazol-5-yl)ethyl)-4-methyl-pentanoic acid

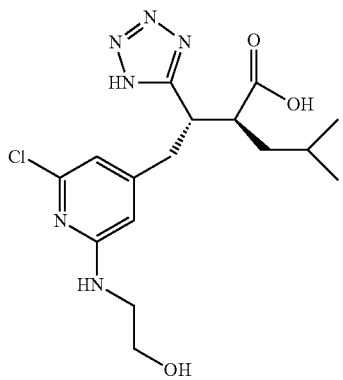 [SMILES: CC(C)C[C@H](C(=O)O)[C@H](Cc1cc(Cl)nc(NCCO)c1)c1nnn[nH]1]

Step A: (S)-2-((S)-2-(2,6-dichloropyridin-4-yl)-1-(1-((2-(trimethylsilyl)ethoxy)methyl)-1H-tetrazol-5-yl)ethyl)-4-methylpentanoic acid (S)-4-methyl-2-((1-((2-(trimethylsilyl)ethoxy) methyl)-1H-tetrazol-5-yl)methyl) pentanoic acid (INTERMEDIATE 30, 483 mg, 1.47 mmol) was dissolved in THF (15 ml) and cooled to −78° C. then LDA (4.38 ml, 3.68 mmol. 0.84 M) was added. The reaction was stirred for 45 mins then 4-(bromomethyl)-2,6-dichloropyridine (425 mg, 1.764 mmol) in THF was added. The reaction mixture was stirred at −78° C. for 5 hrs, then quenched with saturated NH₄Cl solution, extracted with EtOAc (2×) then dried (Na₂SO₄), filtered and concentrated. The residue was purified by reverse phase MPLC with ACN and water buffered with 0.05% TFA to yield (S)-2-((S)-2-(2,6-dichloropyridin-4-yl)-1-(1-((2-(trimethylsilyl)ethoxy) methyl)-1H-tetrazol-5-yl)ethyl)-4-methylpentanoic acid. LC/MS [M+H]+: 488.

Step B: (S)-2-((S)-2-(2,6-dichloropyridin-4-yl)-1-(1-((2-(trimethylsilyl)ethoxy) methyl)-1H-tetrazol-5-yl)ethyl)-4-methylpentanoic acid In a sealed 5 ml MW tube, (S)-2-((S)-2-(2,6-dichloropyridin-4-yl)-1-(1-((2-(trimethylsilyl) ethoxy)methyl)-1H-tetrazol-5-yl)ethyl)-4-methylpentanoic acid (50 mg, 0.102 mmol) was dissolved in DMF (2 ml) then 2-aminoethanol (0.025 ml, 0.409 mmol), Cs₂CO₃ (133 mg, 0.409 mmol) and Buchwald's bis((2-isobutyrylcyclohex-1-en-1-yl)oxy)copper catalyst (40.7 mg, 0.102 mmol) were added. The mixture was degassed and purged with N₂ then heated at 100° C. for 16 hrs. The reaction was filtered and concentrated then stirred in TFA (1 ml):water (0.1 ml) for 2 hr. The volatiles were evaporated and the residue was purified by reverse phase HPLC with ACN and water buffered with 0.05% TFA to yield (S)-2-((S)-2-(2,6-dichloropyridin-4-yl)-1-(1-((2-(trimethylsilyl)ethoxy) methyl)-1H-tetrazol-5-yl)ethyl)-4-methylpentanoic acid. LC/MS [M+H]+: 383.2

EXAMPLE 408

(S)-2-((S)-2-(6-(piperidin-4-yl)pyridin-3-yl)-1-(1H-tetrazol-5-yl)ethyl)pentanoic acid

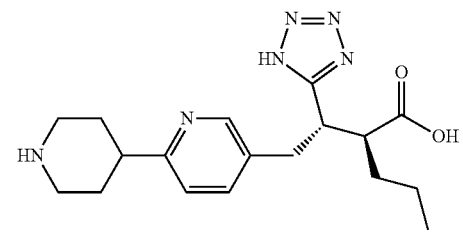 [SMILES: CCC[C@H](C(=O)O)[C@H](Cc1ccc(C2CCNCC2)nc1)c1nnn[nH]1]

Step A: (S)-2-((S)-2-(6-bromopyridin-3-yl)-1-(1-((2-(trimethylsilyl)ethoxy)methyl)-1H-tetrazol-5-yl)ethyl)pentanoic acid To a solution of diisopropylamine (7.04 ml, 49.4 mmol) in THF (8 mL) at −78° C. was added N-butyllithium (18.03 ml, 45.1 mmol). The resulting solution was stirred at −78° C. for 15 min before warming to 0° C. To the solution of (S)-2-((1-((2-(trimethylsilyl)ethoxy)methyl)-1H-tetrazol-5-yl)methyl)pentanoic acid (3.15 g, 10.02 mmol) in THF (50 mL) at −78° C. was added LDA (21.04 ml, 21.04 mmol) dropwise. The resulting solution was stirred at −78° C. for 45 min before addition of 2-bromo-5-(bromomethyl)pyridine (2.51 g, 10.02 mmol) in THF (20 mL). The resulting mixture was then stirred at −78° C. for 3 hr. The reaction was quenched by addition of saturated NH₄Cl solution (50 mL), then the mixture was extracted with EtOAc twice, the combined organic phase was dried over Na₂SO₄, concentrated and the residue was purified on silica gel column using EtOAc (0.2% AcOH)/hexane as eluting solvents to give (S)-2-((S)-2-(6-bromopyridin-3-yl)-1-(1-((2-(trimethylsilyl)ethoxy)methyl)-1H-tetrazol-5-yl)ethyl)pentanoic acid. LC/MS: (M+1)+:484.1 and 486.2.

Step B: (S)-2-((S)-2-(1'-(tert-butoxycarbonyl)-1',2',3',6'-tetrahydro-[2,4'-bipyridin]-5-yl)-1-(1-((2-(trimethylsilyl)ethoxy)methyl)-1H-tetrazol-5-yl)ethyl)pentanoic acid The solution of tert-butyl 4-(4,4,5,5-tetramethyl-1,3,2-dioxaborolan-2-yl)-5,6-dihydropyridine-1(2H)-carboxylate (472 mg, 1.53 mmol), (S)-2-((S)-2-(6-bromopyridin-3-yl)-1-(1-((2-(trimethylsilyl)ethoxy)methyl)-1H-tetrazol-5-yl)ethyl)pentanoic acid (569 mg, 1.17 mmol) and Na₂CO₃ (2.35 ml, 4.70 mmol) in 1,4-Dioxane (15 ml) was bubbled with N₂ for 15 min before addition of PdCl₂(dppf) (86 mg, 0.117 mmol). The resulting mixture was heated at 100° C. overnight. After filtration through celite, the filtrate was concentrated and the residue was purified on reverse phase MPLC using acetonitrile (0.05% TFA)/water (0.05% TFA) as eluting solvents to give (S)-2-((S)-2-(1'-(tert-butoxycarbonyl)-1',2',3',6'-tetrahydro-[2,4'-bipyridin]-5-yl)-1-(1-((2-(trimethylsilyl)ethoxy)methyl)-1H-tetrazol-5-yl)ethyl)pentanoic acid. LC/MS: (M+1)+: 587.39.

Step C: (S)-2-((S)-2-(6-(1-(tert-butoxycarbonyl)piperidin-4-yl)pyridin-3-yl)-1-(1-((2-(trimethylsilyl)ethoxy)methyl)-1H-tetrazol-5-yl)ethyl)pentanoic acid To the solution of (S)-2-((S)-2-(1'-(tert-butoxycarbonyl)-1',2',3',6'-tetrahydro-[2,4'-bipyridin]-5-yl)-1-(1-((2-(trimethylsilyl)ethoxy)methyl)-1H-tetrazol-5-yl)ethyl)pentanoic acid (0.58 g, 0.988 mmol) in MeOH (30 ml) was added 10% Pd/C (0.105 g, 0.099 mmol). The resulting mixture was subjected to hydrogenation at rt via $H_2$ balloon for 5 hr. The mixture was filtered through celite under $N_2$, the filtrate was concentrated to give (S)-2-((S)-2-(6-(1-(tert-butoxycarbonyl)piperidin-4-yl)pyridin-3-yl)-1-(1-((2-(trimethylsilyl)ethoxy)methyl)-1H-tetrazol-5-yl)ethyl)pentanoic acid as a crude. LC/MS: $(M+1)^+$:589.25.

Step D: (S)-2-((S)-2-(6-(piperidin-4-yl)pyridin-3-yl)-1-(1H-tetrazol-5-yl)ethyl)pentanoic acid To the solution of (S)-2-((S)-2-(6-(1-(tert-butoxycarbonyl)piperidin-4-yl)pyridin-3-yl)-1-(1-((2-(trimethylsilyl)ethoxy)methyl)-1H-tetrazol-5-yl)ethyl)pentanoic acid (0.37 g, 0.628 mmol) in TFA (2 ml) was added water (0.2 ml), the resulting solution was stirred at rt for 1 h, the solution was concentrated and the residue was purified on Gilson using acetonitrile (0.05% TFA)/water (0.05% TFA) as eluting solvents to give (S)-2-((S)-2-(6-(piperidin-4-yl)pyridin-3-yl)-1-(1H-tetrazol-5-yl)ethyl)pentanoic acid. LC/MS: $(M+1)^+$: 359.15.

EXAMPLE 409

(2S)-2-((1S)-2-(6-(pyrrolidin-3-yl)pyridin-3-yl)-1-(1H-tetrazol-5-yl)ethyl)pentanoic acid

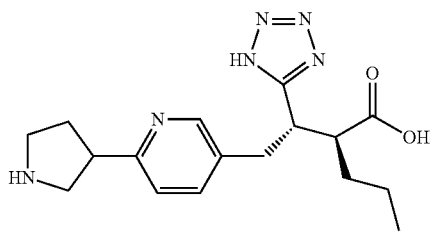 [SMILES: CCC[C@H](C(=O)O)[C@H](Cc1ccc(C2CCNC2)nc1)c1nnn[nH]1]

Step A: (S)-methyl 2-((S)-2-(6-bromopyridin-3-yl)-1-(1-((2-(trimethylsilyl)ethoxy)methyl)-1H-tetrazol-5-yl)ethyl)pentanoate To a solution of (S)-2-((S)-2-(6-bromopyridin-3-yl)-1-(1-((2-(trimethylsilyl)ethoxy)methyl)-1H-tetrazol-5-yl)ethyl)pentanoic acid (0.5 g, 1.032 mmol) in MeOH (30 ml) was added TMS-Diazomethane (5.16 ml, 10.32 mmol) dropwise. The resulting solution was stirred at rt for 20 min before being quenched by addition of acetic acid (1 mL) dropwise. The solution was concentrated to give (S)-methyl 2-((S)-2-(6-bromopyridin-3-yl)-1-(1-((2-(trimethylsilyl)ethoxy)methyl)-1H-tetrazol-5-yl)ethyl)pentanoate. LC/MS: $(M+1)^+$:498.07; 500.07.

Step B: (S)-methyl 2-((S)-2-(6-bromopyridin-3-yl)-1-(1H-tetrazol-5-yl)ethyl)pentanoate To the solution of (S)-methyl 2-((S)-2-(6-bromopyridin-3-yl)-1-(1-((2-(trimethylsilyl)ethoxy)methyl)-1H-tetrazol-5-yl)ethyl)pentanoate (514 mg, 1.031 mmol) in TFA (8 ml) was added water (0.8 mL), and the resulting solution was stirred at rt for 1 hr. The solution was concentrated to give (S)-methyl 2-((S)-2-(6-bromopyridin-3-yl)-1-(1H-tetrazol-5-yl)ethyl)pentanoate. LC/MS: $(M+1)^+$:368.16; 370.16.

Step C: (S)-methyl 2-((S)-2-(6-bromopyridin-3-yl)-1-(1-(4-methoxybenzyl)-1H-tetrazol-5-yl)ethyl)pentanoate To the solution of (S)-methyl 2-((S)-2-(6-bromopyridin-3-yl)-1-(1H-tetrazol-5-yl)ethyl)pentanoate (380 mg, 1.032 mmol) in $CHCl_3$ (4 ml) and water (3 ml) was added $K_2CO_3$ (570 mg, 4.13 mmol), 4-methoxybenzyl chloride (0.169 ml, 1.238 mmol) and tetrabutylammonium chloride, hydrate (61.1 mg, 0.206 mmol). The resulting solution was heated at 40° C. overnight. The mixture was extracted with DCM, and the combined DCM phase was dried over $Na_2SO_4$, concentrated and the residue was purified on silica gel column using EtOAc/hexane as eluting solvents to give (S)-methyl 2-((S)-2-(6-bromopyridin-3-yl)-1-(1-(4-methoxybenzyl)-1H-tetrazol-5-yl)ethyl)pentanoate. LC/MS: $(M+1)^+$: 488.2; 490.2.

Step D: tert-butyl 3-(5-((2S,3S)-2-(1-(4-methoxybenzyl)-1H-tetrazol-5-yl)-3-(methoxycarbonyl)hexyl)pyridin-2-yl)-2,5-dihydro-1H-pyrrole-1-carboxylate A mixture of tert-butyl 3-(4,4,5,5-tetramethyl-1,3,2-dioxaborolan-2-yl)-2,5-dihydro-1H-pyrrole-1-carboxylate (246 mg, 0.833 mmol), (S)-methyl 2-((S)-2-(6-bromopyridin-3-yl)-1-(1-(4-methoxybenzyl)-1H-tetrazol-5-yl)ethyl)pentanoate (339 mg, 0.694 mmol) and $Na_2CO_3$ (1.041 ml, 2.082 mmol) in Dioxane (12 ml) was degassed with $N_2$ for 30 min before addition of $PdCl_2(dppf)$ (50.8 mg, 0.069 mmol). The resulting mixture was heated at 100° C. overnight. After filtration the residue was concentrated and the residue was purified on silica gel column using EtOAc/hexane as eluting solvents to give tert-butyl 3-(5-((2S,3S)-2-((1-(4-methoxybenzyl)-1H-tetrazol-5-yl)-3-(methoxycarbonyl)hexyl)pyridin-2-yl)-2,5-dihydro-1H-pyrrole-1-carboxylate. LC/MS: $(M+1)^+$: 577.44.

Step E: tert-butyl 3-(5-((2S,3S)-2-(1-(4-methoxybenzyl)-1H-tetrazol-5-yl)-3-(methoxycarbonyl)hexyl)pyridin-2-yl)pyrrolidine-1-carboxylate To the solution of tert-butyl 3-(5-((2S,3S)-2-(1-(4-methoxybenzyl)-1H-tetrazol-5-yl)-3-(methoxycarbonyl)hexyl)pyridin-2-yl)-2,5-dihydro-1H-pyrrole-1-carboxylate (395 mg, 0.685 mmol) in MeOH (20 ml) was added 10% Pd/C (72.9 mg, 0.068 mmol). The resulting mixture was hydrogenated at rt via $H_2$ balloon for 3 hr. After filtration through celite under $N_2$, the filtrate was concentrated to give tert-butyl 3-(5-((2S,3S)-2-(1-(4-methoxybenzyl)-1H-tetrazol-5-yl)-3-(methoxycarbonyl)hexyl)pyridin-2-yl)pyrrolidine-1-carboxylate. LC/MS: $(M+1)^+$:579.50.

Step F: (2S)-methyl 2-((1S)-1-(1-(4-methoxybenzyl)-1H-tetrazol-5-yl)-2-(6-(pyrrolidin-3-yl)pyridin-3-yl)ethyl)pentanoate To the solution of tert-butyl 3-(5-((2S,3S)-2-(1-(4-methoxybenzyl)-1H-tetrazol-5-yl)-3-(methoxycarbonyl)hexyl)pyridin-2-yl)pyrrolidine-1-carboxylate (396 mg, 0.684 mmol) in $CH_2Cl_2$ (2 ml) was added TFA (4 mL, 51.9 mmol). The resulting solution was stirred at rt for 1 hr. The solution was concentrated to give (2S)-methyl 2-((1S)-1-(1-(4-methoxybenzyl)-1H-tetrazol-5-yl)-2-(6-(pyrrolidin-3-yl)pyridin-3-yl)ethyl)pentanoate. LC/MS: $(M+1)^+$: 479.38.

Step G: (2S)-2-((1S)-2-(6-(pyrrolidin-3-yl)pyridin-3-yl)-1-(1H-tetrazol-5-yl)ethyl)pentanoic acid To the solution of (2S)-methyl 2-((1S)-1-(1-(4-methoxybenzyl)-1H-tetrazol-5-yl)-2-(6-(pyrrolidin-3-yl)pyridin-3- yl)ethyl)pentanoate (50 mg, 0.084 mmol) in acetic acid (1 ml) was added HCl (1 mL, 12.18 mmol). The resulting solution was heated at 80° C. for 6 hr. After concentration the residue was purified on reverse phase HPLC using acetonitrile (0.1% formic acid)/water (0.1% formic acid) as eluting solvents to give (2S)-2-((1S)-2-(6-(pyrrolidin-3-yl)pyridin-3-yl)-1-(1H-tetrazol-5-yl)ethyl)pentanoic acid. LC/MS: (M+1)+: 345.21.

EXAMPLE 410

(2S)-2-((1S)-2-(6-(1-(iminomethyl)pyrrolidin-3-yl)pyridin-3-yl)-1-(1H-tetrazol-5-yl)ethyl)pentanoic acid

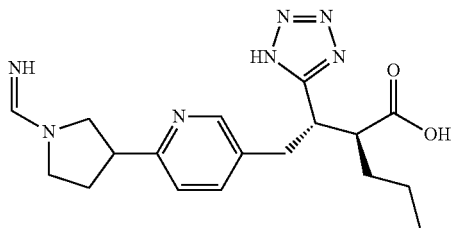 [SMILES: CCC[C@H](C(=O)O)[C@H](Cc1ccc(C2CCN(C=N)C2)nc1)c1nnn[nH]1]

To the solution of (2S)-2-((1S)-2-(6-(pyrrolidin-3-yl)pyridin-3-yl)-1-(1H-tetrazol-5-yl)ethyl)pentanoic acid (50 mg, 0.145 mmol) in DMF (1 ml) was added ethyl formimidate hydrochloride (23.86 mg, 0.218 mmol) and DIEA (0.101 ml, 0.581 mmol). The resulting solution was stirred at rt overnight. The mixture was purified on reverse phase HPLC using acetonitrile (0.05% TFA)/water (0.05% TFA) as eluting solvents to give (2S)-2-((1S)-2-(6-(1-(iminomethyl)pyrrolidin-3-yl)pyridin-3-yl)-1-(1H-tetrazol-5-yl)ethyl)pentanoic acid. LC/MS: (M+1)+: 372.16.

EXAMPLE 411

(2S)-2-((1S)-2-(6-(1-carbamimidoylpyrrolidin-3-yl)pyridin-3-yl)-1-(1H-tetrazol-5-yl)ethyl)pentanoic acid

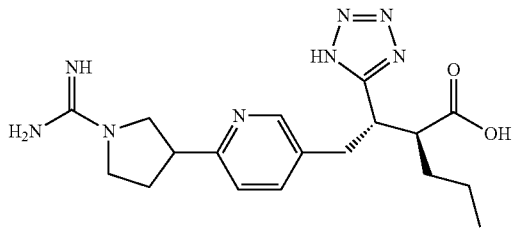 [SMILES: CCC[C@H](C(=O)O)[C@H](Cc1ccc(C2CCN(C(=N)N)C2)nc1)c1nnn[nH]1]

To the solution of (2S)-2-((1S)-2-(6-(pyrrolidin-3-yl)pyridin-3-yl)-1-(1H-tetrazol-5-yl)ethyl)pentanoic acid (50 mg, 0.146 mmol) in DMF (1 ml) was added 1H-pyrazole-1-carboxamidine hydrochloride (32.0 mg, 0.218 mmol) and DIEA (0.102 ml, 0.582 mmol). The resulting solution was stirred at rt overnight. The mixture was purified on reverse phase HPLC using acetonitrile (0.05% TFA)/water (0.05% TFA) as eluting solvents to give (2S)-2-((1S)-2-(6-(1-carbamimidoylpyrrolidin-3-yl)pyridin-3-yl)-1-(1H-tetrazol-5-yl)ethyl)pentanoic acid. LC/MS: (M+1)+: 387.20.

EXAMPLE 412

(S)-2-((S)-2-(4-(piperidin-4-yl)phenyl)-1-(1H-tetrazol-5-yl)ethyl)pentanoic acid

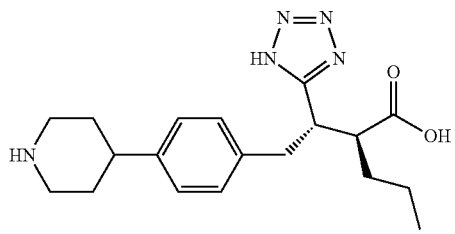 [SMILES: CCC[C@H](C(=O)O)[C@H](Cc1ccc(C2CCNCC2)cc1)c1nnn[nH]1]

Step A: (S)-2-((S)-2-(4-(1-(tert-butoxycarbonyl)-1,2,3,6-tetrahydropyridin-4-yl)phenyl)-1-(1-((2-(trimethylsilyl)ethoxy)methyl)-1H-tetrazol-5-yl)ethyl)pentanoic acid A mixture of tert-butyl 4-(4,4,5,5-tetramethyl-1,3,2-dioxaborolan-2-yl)-5,6-dihydropyridine-1(2H)-carboxylate (316 mg, 1.023 mmol) and (S)-2-((S)-2-(4-bromophenyl)-1-(1-((2-(trimethylsilyl)ethoxy)methyl)-1H-tetrazol-5-yl)ethyl)pentanoic acid (INTERMEDIATE 9, 412 mg, 0.852 mmol) and Na2CO3 (1.28 ml, 2.56 mmol) in dioxane (6 ml) was degassed by bubbling N2 for 20 min before addition of PdCl2(dppf) (62.4 mg, 0.085 mmol). The resulting mixture was heated at 100° C. overnight. After filtration the filtrate was concentrated and the residue was purified on reverse phase MPLC using acetonitrile (0.05% TFA)/water (0.05% TFA) as eluting solvents to give (S)-2-((S)-2-(4-(1-(tert-butoxycarbonyl)-1,2,3,6-tetrahydropyridin-4-yl)phenyl)-1-(1-((2-(trimethylsilyl)ethoxy)methyl)-1H-tetrazol-5-yl)ethyl)pentanoic acid. LC/MS: (M+1)+: 586.26.

Step B: (S)-2-((S)-2-(4-(1-(tert-butoxycarbonyl)piperidin-4-yl)phenyl)-1-(1-((2-(trimethylsilyl)ethoxy)methyl)-1H-tetrazol-5-yl)ethyl)pentanoic acid To the solution of (S)-2-((S)-2-(4-(1-(tert-butoxycarbonyl)-1,2,3,6-tetrahydropyridin-4-yl)phenyl)-1-(1-((2-(trimethylsilyl)ethoxy)methyl)-1H-tetrazol-5-yl)ethyl)pentanoic acid (497 mg, 0.848 mmol) in MeOH (20 ml) was added 10% Pd/C (90 mg, 0.085 mmol). The resulting mixture was subjected to hydrogenation via H2 balloon at rt overnight. After filtration through celite under N2 the filtrate was concentrated and the residue was purified on silica gel column using MeOH/DCM as eluting solvents to give (S)-2-((S)-2-(4-(1-(tert-butoxycarbonyl)piperidin-4-yl)phenyl)-1-(1-((2-(trimethylsilyl)ethoxy)methyl)-1H-tetrazol-5-yl)ethyl)pentanoic acid. LC/MS: (M+1)+:388.29.

Step C. (S)-2-((S)-2-(4-(piperidin-4-yl)phenyl)-1-(1H-tetrazol-5-yl)ethyl)pentanoic acid To the solution of (S)-2-((S)-2-(4-(1-(tert-butoxycarbonyl)piperidin-4-yl)phenyl)-1-(1-((2-(trimethylsilyl)ethoxy)methyl)-1H-tetrazol-5-yl)ethyl)pentanoic acid (0.46 g, 0.783 mmol) in TFA (3 ml) was added Water (0.3 ml), the resulting solution was stirred at rt for 0.5 h. After concentration the residue was purified on reverse phase HPLC using acetonitrile (0.05% TFA)/water (0.05% TFA) to give (S)-2-((S)-2-(4-(piperidin-4-yl)phenyl)-1-(1H-tetrazol-5-yl)ethyl)pentanoic acid. LC/MS: (M+1)⁺: 358.16.

EXAMPLE 413

(2S)-2-((1S)-2-(4-(pyrrolidin-3-yl)phenyl)-1-(1H-tetrazol-5-yl)ethyl)pentanoic acid

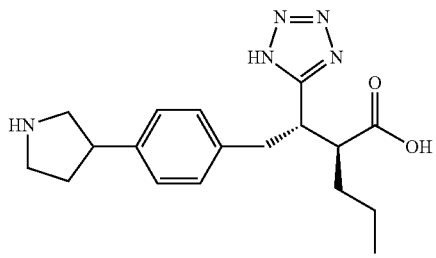 [SMILES: CCC[C@H](C(=O)O)[C@H](Cc1ccc(C2CCNC2)cc1)c1nnn[nH]1]

Step A: (S)-2-((S)-2-(4-(1-(tert-butoxycarbonyl)-2,5-dihydro-1H-pyrrol-3-yl)phenyl)-1-(1-((2-(trimethylsilyl)ethoxy)methyl)-1H-tetrazol-5-yl)ethyl)pentanoic acid A mixture of tert-butyl 3-(4,4,5,5-tetramethyl-1,3,2-dioxaborolan-2-yl)-2,5-dihydro-1H-pyrrole-1-carboxylate (147 mg, 0.496 mmol) and (S)-2-((S)-2-(4-bromophenyl)-1-(1-((2-(trimethylsilyl)ethoxy)methyl)-1H-tetrazol-5-yl)ethyl)pentanoic acid (200 mg, 0.414 mmol) and $Na_2CO_3$ (0.827 ml, 1.66 mmol) in Dioxane (6 ml) was degassed by bubbling $N_2$ for 20 min before addition of $PdCl_2$(dppf) (30.3 mg, 0.041 mmol). The resulting mixture was heated at 100° C. overnight. After filtration the filtrate was concentrated and the residue was purified on reverse phase MPLC using acetonitrile (0.05% TFA)/water (0.05% TFA) as eluting solvents to give (S)-2-((S)-2-(4-(1-(tert-butoxycarbonyl)-2,5-dihydro-1H-pyrrol-3-yl)phenyl)-1-(1-((2-(trimethylsilyl)ethoxy)methyl)-1H-tetrazol-5-yl)ethyl)pentanoic acid. LC/MS: (M+1)⁺: 572.24.

Step B: (2S)-2-((1S)-2-(4-(1-(tert-butoxycarbonyl)pyrrolidin-3-yl)phenyl)-1-(1-((2-(trimethylsilyl)ethoxy)methyl)-1H-tetrazol-5-yl)ethyl)pentanoic acid To the solution of (S)-2-((S)-2-(4-(1-(tert-butoxycarbonyl)-2,5-dihydro-1H-pyrrol-3-yl)phenyl)-1-(1-((2-(trimethylsilyl)ethoxy)methyl)-1H-tetrazol-5-yl)ethyl)pentanoic acid (229 mg, 0.401 mmol) in MeOH (10 ml) was added 10% Pd/C (42.6 mg, 0.040 mmol). The resulting mixture was hydrogenated at rt via $H_2$ balloon overnight. After filtration through celite under $N_2$, the filtrate was concentrated to give (2S)-2-((1S)-2-(4-(1-(tert-butoxycarbonyl)pyrrolidin-3-yl)phenyl)-1-(1-((2-(trimethylsilyl)ethoxy)methyl)-1H-tetrazol-5-yl)ethyl)pentanoic acid. LC/MS: (M+1)⁺: 574.31.

Step C: (2S)-2-((1S)-2-(4-(pyrrolidin-3-yl)phenyl)-1-(1H-tetrazol-5-yl)ethyl)pentanoic acid To the solution of (2S)-2-((1S)-2-(4-(1-(tert-butoxycarbonyl)pyrrolidin-3-yl)phenyl)-1-(1-((2-(trimethylsilyl)ethoxy)methyl)-1H-tetrazol-5-yl)ethyl)pentanoic acid (230 mg, 0.401 mmol) in TFA (3 ml) was added Water (0.3 mL), and the resulting solution was stirred at rt for 1 hr. The mixture was concentrated and the residue was purified on reverse HPLC using acetonitrile (0.05% TFA)/water (0.05% TFA) as eluting solvents to give (2S)-2-((1S)-2-(4-(pyrrolidin-3-yl)phenyl)-1-(1H-tetrazol-5-yl)ethyl)pentanoic acid. LC/MS: (M+1)⁺: 344.17.

EXAMPLE 414

(2S)-2-((1S)-2-(4-(1-carbamimidoylpyrrolidin-3-yl)phenyl)-1-(1H-tetrazol-5-yl)ethyl)pentanoic acid

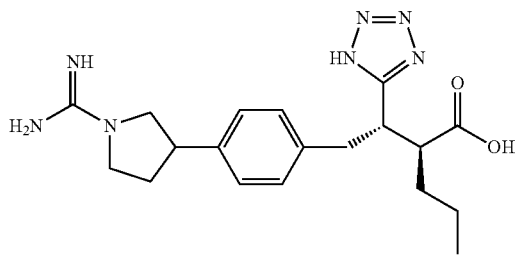 [SMILES: CCC[C@H](C(=O)O)[C@H](Cc1ccc(C2CCN(C(=N)N)C2)cc1)c1nnn[nH]1]

To the solution of (2S)-2-((1S)-2-(4-(pyrrolidin-3-yl)phenyl)-1-(1H-tetrazol-5-yl)ethyl)pentanoic acid (50 mg, 0.146 mmol) in DMF (2 ml) was added 1H-pyrazole-1-carboxamidine hydrochloride (32.1 mg, 0.219 mmol) and DIEA (0.102 ml, 0.584 mmol), and the resulting solution was stirred at rt overnight. The mixture was purified on reverse phase HPLC using acetonitrile (0.05% TFA)/water (0.05% TFA) as eluting solvents to give (2S)-2-((1S)-2-(4-(1-carbamimidoylpyrrolidin-3-yl)phenyl)-1-(1H-tetrazol-5-yl)ethyl)pentanoic acid. LC/MS: (M+1)⁺: 385.86.

EXAMPLE 415

(2S)-2-((1S)-2-(4-(1-(iminomethyl)pyrrolidin-3-yl)phenyl)-1-(1H-tetrazol-5-yl)ethyl)pentanoic acid

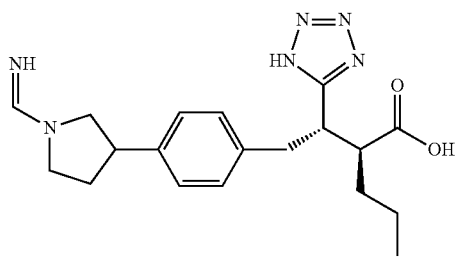 [SMILES: CCC[C@H](C(=O)O)[C@H](Cc1ccc(C2CCN(C=N)C2)cc1)c1nnn[nH]1]

To a solution of (2S)-2-((1S)-2-(4-(pyrrolidin-3-yl)phenyl)-1-(1H-tetrazol-5-yl)ethyl)pentanoic acid (50 mg, 0.146 mmol) in DMF (1 ml) was added ethyl formimidate hydrochloride (23.93 mg, 0.218 mmol) and DIEA (0.102 ml, 0.582 mmol), and the resulting solution was stirred at rt overnight. The mixture was purified on reverse phase HPLC using acetonitrile (0.05% TFA)/water (0.05% TFA) as eluting solvents to give (2S)-2-((1S)-2-(4-(1-(iminomethyl)pyrrolidin-3-yl)phenyl)-1-(1H-tetrazol-5-yl)ethyl)pentanoic acid. LC/MS: (M+1)⁺: 371.20.

EXAMPLE 416

(2S)-2-((1S)-2-(4-(3-hydroxypiperidin-4-yl)phenyl)-1-(1H-tetrazol-5-yl)ethyl)pentanoic acid

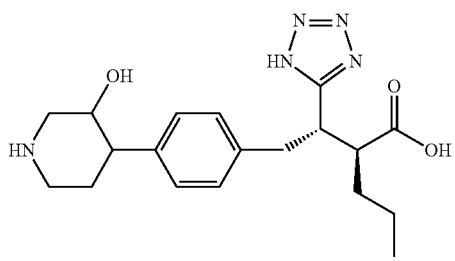 [SMILES: CCC[C@H](C(=O)O)[C@H](Cc1ccc(C2CCNCC2O)cc1)c1nnn[nH]1]

Step A: (S)-2-((S)-2-(4-((3S,4S)-1-(tert-butoxycarbonyl)-3,4-dihydroxypiperidin-4-yl)phenyl)-1-(1-((2-(trimethylsilyl)ethoxy)methyl)-1H-tetrazol-5-yl)ethyl) pentanoic acid (CIS mixture)

To a solution of (S)-2-((S)-2-(4-(1-(tert-butoxycarbonyl)-1,2,3,6-tetrahydropyridin-4-yl)phenyl)-1-(1-((2-(trimethylsilyl)ethoxy)methyl)-1H-tetrazol-5-yl)ethyl)pentanoic acid (330 mg, 0.563 mmol) in acetonitrile (10 ml) and water (5 ml) was added NMO (79 mg, 0.676 mmol) and potassium osmate dihydrate (20.76 mg, 0.056 mmol), and the resulting solution was stirred at rt overnight. Thiosulphate (200 mg) was added and the resulting mixture was stirred at rt for 1 hr. After removing the volatile, the residue was partitioned between saturated NH$_4$Cl (100 mL) and DCM. The mixture was extracted with DCM (3×100 mL), the combined organic phase was dried over Na$_2$SO$_4$, concentrated and the residue was purified on reverse phase MPLC using acetonitrile (0.05% TFA) using acetonitrile (0.05% TFA)/water (0.05% TFA) as eluting solvents to give (S)-2-((S)-2-(4-((3S,4S)-1-(tert-butoxycarbonyl)-3,4-dihydroxypiperidin-4-yl)phenyl)-1-(1-((2-(trimethylsilyl)ethoxy)methyl)-1H-tetrazol-5-yl) ethyl) pentanoic acid (CIS mixture). LC/MS: (M+1)$^+$: 620.29.

Step B: (S)-2-((S)-2-(4-((3S,4S)-3,4-dihydroxypiperidin-4-yl)phenyl)-1-(1H-tetrazol-5-yl)ethyl)pentanoic acid (CIS mixture)

To the solution of (S)-2-((S)-2-(4-((3S,4S)-1-(tert-butoxycarbonyl)-3,4-dihydroxypiperidin-4-yl)phenyl)-1-(1-((2-(trimethylsilyl)ethoxy)methyl)-1H-tetrazol-5-yl)ethyl)pentanoic acid (130 mg, 0.210 mmol) in TFA (3 ml) was added water (0.3 ml), and the resulting solution was stirred at rt for 1 hr. After removing the volatile the residue was purified on reverse phase using acetonitrile (0.05% TFA)/water (0.05% TFA) as eluting solvents to give (S)-2-((S)-2-(4-((3 S,4S)-3,4-dihydroxypiperidin-4-yl)phenyl)-1-(1H-tetrazol-5-yl)ethyl)pentanoic acid (CIS mixture). LC/MS: (M+1)$^+$: 390.24.

Step C: (2S)-2-((1S)-2-(4-(3-hydroxy-1,2,3,6-tetrahydropyridin-4-yl)phenyl)-1-(1H-tetrazol-5-yl)ethyl) pentanoic acid To the solution of (S)-2-((S)-2-(4-((3S,4S)-3,4-dihydroxypiperidin-4-yl)phenyl)-1-(1H-tetrazol-5-yl)ethyl)pentanoic acid (49 mg, 0.126 mmol) in TFA (1 ml) was added triethylsilane (146 mg, 1.258 mmol), and the resulting solution was heated at 80° C. overnight. The volatile was concentrated and the residue was purified on reverse phase HPLC using acetonitrile (0.05% TFA)/water (0.05% TFA) as eluting solvents to give (2S)-2-((1S)-2-(4-(3-hydroxy-1,2,3,6-tetrahydropyridin-4-yl)phenyl)-1-(1H-tetrazol-5-yl) ethyl)pentanoic acid. LC/MS: (M+1)$^+$: 372.33.

Step D: (2S)-2-((1S)-2-(4-(3-hydroxypiperidin-4-yl)phenyl)-1-(1H-tetrazol-5-yl)ethyl)pentanoic acid To the solution of (2S)-2-((1S)-2-(4-(3-hydroxy-1,2,3,6-tetrahydropyridin-4-yl)phenyl)-1-(1H-tetrazol-5-yl)ethyl) pentanoic acid (11 mg, 0.030 mmol) in MeOH (10 ml) was added 10% Pd/C (3.15 mg, 2.96 µmol), and the resulting mixture was hydrogenated at rt via H$_2$ balloon for 3 hr. After filtration through celite the filtrate was concentrated and the residue was purified on reverse HPLC using acetonitrile (0.05% TFA)/water (0.05% TFA) as eluting solvents to give (2S)-2-((1S)-2-(4-(3-hydroxypiperidin-4-yl)phenyl)-1-(1H-tetrazol-5-yl)ethyl)pentanoic acid (racemate). LC/MS: (M+1)$^+$: 374.13.

EXAMPLE 417

(S)-2-((S)-2-(1-methylpyridin-1-ium-4-yl)-1-(1H-tetrazol-5-yl)ethyl)pentanoate

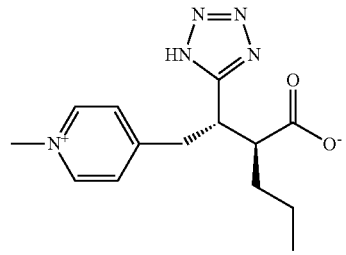 [SMILES: CCC[C@H](C(=O)[O-])[C@H](Cc1cc[n+](C)cc1)c1nnn[nH]1]

Step A: (S)-2-((S)-2-(pyridin-4-yl)-1-(1-((2-(trimethylsilyl)ethoxy)methyl)-1H-tetrazol-5-yl)ethyl) pentanoic acid To a solution of diisopropylamine (0.938 ml, 6.58 mmol) in THF (3 mL) at −78° C. was added N-butyllithium (3.76 ml, 6.01 mmol), and the resulting solution was stirred at −78° C. for 15 min before being warmed to 0° C. To the solution of (S)-2-((1-((2-(trimethylsilyl)ethoxy)methyl)-1H-tetrazol-5-yl)methyl)pentanoic acid (0.42 g, 1.336 mmol) in THF (20 mL) at −78° C. was added LDA (3.77 ml, 2.94 mmol) dropwise. The resulting solution was stirred at −78° C. for 45 min before addition of 4-(bromomethyl)pyridine hydrobromide (0.169 g, 0.668 mmol) in one portion. The resulting mixture was then stirred from −78° C. to rt overnight. The reaction was quenched by addition of saturated NH$_4$Cl solution (50 mL), then the mixture was extracted with EtOAc twice, the combined organic phase was dried over Na$_2$SO$_4$, concentrated and the residue was purified on silica gel column using MeOH/DCM as eluting solvents to give (S)-2-((S)-2-(pyridin-4-yl)-1-(1-((2-(trimethylsilyl)ethoxy)methyl)-1H-tetrazol-5-yl)ethyl)pentanoic acid. LC/MS: (M+1)$^+$: 406.23.

Step B: 4-((2S,3S)-3-(methoxycarbonyl)-2-(1-((2-(trimethylsilyl)ethoxy)methyl)-1H-tetrazol-5-yl)hexyl)-1-methylpyridin-1-ium To the solution of (S)-2-((S)-2-(pyridin-4-yl)-1-(1-((2-(trimethylsilyl)ethoxy)methyl)-1H-tetrazol-5-yl)ethyl)pentanoic acid (46 mg, 0.113 mmol) in acetone (5 ml) was added $K_2CO_3$ (31.4 mg, 0.227 mmol) and MeI (0.021 ml, 0.340 mmol), then the resulting mixture was stirred at rt overnight. The mixture was concentrated and the residue was purified on reverse phase HPLC using acetonitrile (0.05% TFA)/water (0.05% TFA) as eluting solvents to give 4-((2S,3S)-3-(methoxycarbonyl)-2-(1-((2-(trimethylsilyl)ethoxy)methyl)-1H-tetrazol-5-yl)hexyl)-1-methylpyridin-1-ium. LC/MS: $M^+$: 434.24.

Step C: (S)-2-((S)-2-(1-methylpyridin-1-ium-4-yl)-1-(1H-tetrazol-5-yl)ethyl)pentanoate To the solution of 4-((2S,3S)-3-(methoxycarbonyl)-2-(1-((2-(trimethylsilyl)ethoxy)methyl)-1H-tetrazol-5-yl)hexyl)-1-methylpyridin-1-ium (34 mg, 0.078 mmol) in acetic acid (3 ml) was added HCl (6.42 µl, 0.078 mmol), then the resulting solution was heated at 80° C. for 12 hr. After concentration the residue was purified on reverse phase HPLC using acetonitrile (0.05% TFA)/water (0.05% TFA) as eluting solvents to give (S)-2-((S)-2-(1-methylpyridin-1-ium-4-yl)-1-(1H-tetrazol-5-yl)ethyl)pentanoate. LC/MS: $(M+1)^+$: 290.20.

EXAMPLE 418

(2S)-2-((1S)-2-(4-(1,1-dimethylpyrrolidin-1-ium-3-yl)phenyl)-1-(1H-tetrazol-5-yl)ethyl)pentanoate

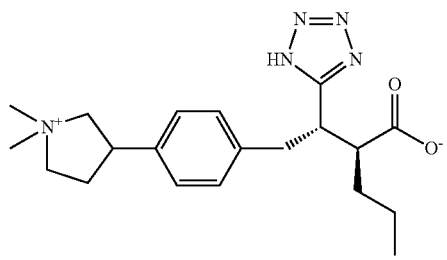 [SMILES: CCC[C@H](C(=O)[O-])[C@H](Cc1ccc(C2CC[N+](C)(C)C2)cc1)c1nnn[nH]1]

Step A: tert-butyl 3-(4-((2S,3S)-3-(tert-butoxycarbonyl)-2-(1-(4-methoxybenzyl)-1H-tetrazol-5-yl)hexyl)phenyl)-2,5-dihydro-1H-pyrrole-1-carboxylate A mixture of tert-butyl 3-(4,4,5,5-tetramethyl-1,3,2-dioxaborolan-2-yl)-2,5-dihydro-1H-pyrrole-1-carboxylate (214 mg, 0.725 mmol) and (S)-tert-butyl 2-((S)-2-(4-bromophenyl)-1-(1-(4-methoxybenzyl)-1H-tetrazol-5-yl)ethyl)pentanoate (320 mg, 0.604 mmol) and $Na_2CO_3$ (1.209 ml, 2.418 mmol) in dioxane (6 ml) was degassed by bubbling $N_2$ for 20 min before addition of $PdCl_2(dppf)$ (44.2 mg, 0.060 mmol). The resulting mixture was heated at 100° C. overnight. After filtration the filtrate was concentrated and the residue was purified on silica gel column using EtOAc/hexane as eluting solvents to give tert-butyl 3-(4-((2S,3S)-3-(tert-butoxycarbonyl)-2-(1-(4-methoxybenzyl)-1H-tetrazol-5-yl)hexyl)phenyl)-2,5-dihydro-1H-pyrrole-1-carboxylate. LC/MS: $(M+1)^+$: 618.32.

Step B: tert-butyl 3-(4-((2S,3S)-3-(tert-butoxycarbonyl)-2-(1-(4-methoxybenzyl)-1H-tetrazol-5-yl)hexyl)phenyl)pyrrolidine-1-carboxylate To the solution of tert-butyl 3-(4-((2S,3S)-3-(tert-butoxycarbonyl)-2-(1-(4-methoxybenzyl)-1H-tetrazol-5-yl)hexyl)phenyl)-2,5-dihydro-1H-pyrrole-1-carboxylate (0.35 g, 0.567 mmol) in MeOH (50 ml) and DCM (10 ml) was added 10% Pd/C (0.060 g, 0.057 mmol), then the resulting mixture was hydrogenated at rt via $H_2$ balloon for 0.5 hr. After filtration through celite under $N_2$, the filtrate was concentrated to give tert-butyl 3-(4-((2S,3S)-3-(tert-butoxycarbonyl)-2-(1-(4-methoxybenzyl)-1H-tetrazol-5-yl)hexyl)phenyl)pyrrolidine-1-carboxylate. LC/MS: $(M+1)^+$:620.37.

Step C: (2S)-2-((1S)-1-(1-(4-methoxybenzyl)-1H-tetrazol-5-yl)-2-(4-(pyrrolidin-3-yl)phenyl)ethyl)pentanoic acid To the solution of tert-butyl 3-(4-((2S,3S)-3-(tert-butoxycarbonyl)-2-(1-(4-methoxybenzyl)-1H-tetrazol-5-yl)hexyl)phenyl)pyrrolidine-1-carboxylate (0.35 g, 0.565 mmol) in $CH_2Cl_2$ (1 ml) was added TFA (4 ml, 51.9 mmol), and the resulting solution was stirred at rt for 1 hr. The solution was concentrated to give (2S)-2-((1S)-1-(1-(4-methoxybenzyl)-1H-tetrazol-5-yl)-2-(4-(pyrrolidin-3-yl)phenyl)ethyl)pentanoic acid. LC/MS: $(M+1)^+$: 464.22.

Step D: 3-(4-((2S,3S)-2-(1-(4-methoxybenzyl)-1H-tetrazol-5-yl)-3-(methoxycarbonyl)hexyl)phenyl)-1,1-dimethylpyrrolidin-1-ium To the solution of (2S)-2-((1S)-1-(1-(4-methoxybenzyl)-1H-tetrazol-5-yl)-2-(4-(pyrrolidin-3-yl)phenyl)ethyl)pentanoic acid (262 mg, 0.565 mmol) in acetone (6 ml) was added $K_2CO_3$ (312 mg, 2.261 mmol) and MeI (0.141 ml, 2.261 mmol), then the resulting mixture was stirred at rt for 5 hr. After concentration, the residue was purified on reverse phase MPLC using acetonitrile (0.05% TFA)/water (0.05% TFA) as eluting solvents to give 3-(4-((2S,3S)-2-(1-(4-methoxybenzyl)-1H-tetrazol-5-yl)-3-(methoxycarbonyl)hexyl)phenyl)-1,1-dimethylpyrrolidin-1-ium. LC/MS: $M^+$: 506.25.

Step E: (2S)-2-((1S)-2-(4-(1,1-dimethylpyrrolidin-1-ium-3-yl)phenyl)-1-(1H-tetrazol-5-yl)ethyl)pentanoate To the solution of 3-(4-((2S,3S)-2-(1-(4-methoxybenzyl)-1H-tetrazol-5-yl)-3-(methoxycarbonyl)hexyl)phenyl)-1,1-dimethylpyrrolidin-1-ium (268 mg, 0.529 mmol) in acetic acid (5 ml) was added HCl (3 mL, 36.5 mmol), then the resulting solution was heated at 80° C. for 2 hr. After concentration the residue was purified on reverse phase HPLC using acetonitrile (0.05% TFA)/water (0.05% TFA) as eluting solvents to give (2R)-2-((1S)-2-(4-(1,1-dimethylpyrrolidin-1-ium-3-yl)phenyl)-1-(1H-tetrazol-5-yl)ethyl)pentanoate (more polar) and (2S)-2-((1S)-2-(4-(1,1-dimethylpyrrolidin-1-ium-3-yl)phenyl)-1-(1H-tetrazol-5-yl)ethyl)pentanoate (less polar). LC/MS: $(M+1)^+$: 372.25.

EXAMPLE 419

(S)-2-((S)-1-(1H-tetrazol-5-yl)-2-(4-((trimethylammonio)methyl)phenyl)ethyl)pentanoate

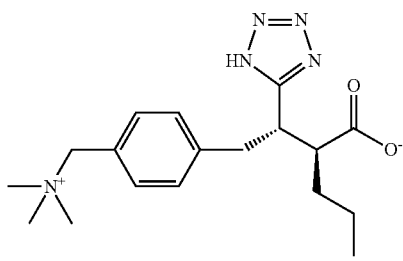 [SMILES: CCC[C@H](C(=O)[O-])[C@H](Cc1ccc(C[N+](C)(C)C)cc1)c1nnn[nH]1]

Step A: (S)-2-((S)-2-(4-cyanophenyl)-1-(1-((2-(trimethylsilyl)ethoxy)methyl)-1H-tetrazol-5-yl)ethyl)pentanoic acid To a solution of diisopropylamine (1.207 ml, 8.47 mmol) in THF (2.85 mL) at −78° C. was added N-butyllithium (4.83 ml, 7.73 mmol), then the resulting solution was stirred at −78° C. for 15 min before being warmed to 0° C. To the solution of (S)-2-((1-((2-(trimethylsilyl)ethoxy)methyl)-1H-tetrazol-5-yl)methyl)pentanoic acid (0.54 g, 1.717 mmol) in THF (8 ml) at −78° C. was added LDA (4.34 ml, 3.78 mmol) dropwise. The resulting solution was stirred at −78° C. for 45 min before addition of 4-(bromomethyl)benzonitrile (0.370 g, 1.889 mmol) in THF (20 mL). The resulting mixture was then stirred at −78° C. overnight. The reaction was quenched by addition of saturated NH$_4$Cl solution (100 mL), then the mixture was extracted with EtOAc twice, the combined organic phase was dried over Na$_2$SO$_4$, concentrated and the residue was purified on silica gel column using MeOH/DCM as eluting solvents to give (S)-2-((S)-2-(4-cyanophenyl)-1-(1-((2-(trimethylsilyl)ethoxy)methyl)-1H-tetrazol-5-yl)ethyl)pentanoic acid. LC/MS: (M+1)$^+$: 430.19.

Step B: (S)-2-((S)-2-(4-(aminomethyl)phenyl)-1-(1-((2-(trimethylsilyl)ethoxy)methyl)-1H-tetrazol-5-yl)ethyl)pentanoic acid To the solution of (S)-2-((S)-2-(4-cyanophenyl)-1-(1-((2-(trimethylsilyl)ethoxy)methyl)-1H-tetrazol-5-yl)ethyl)pentanoic acid (0.36 g, 0.838 mmol) in MeOH (20 ml) was added raney nickel (0.072 g, 0.838 mmol) and TEA (0.350 ml, 2.51 mmol), then the resulting mixture was hydrogenated at 42 psi over the weekend. After filtration through celite under N$_2$, the filtrate was concentrated and the residue was purified on reverse phase MPLC using acetonitrile (0.05% TFA)/water (0.05% TFA) as eluting solvents give (S)-2-((S)-2-(4-(aminomethyl)phenyl)-1-(1-((2-(trimethylsilyl)ethoxy)methyl)-1H-tetrazol-5-yl)ethyl)pentanoic acid. LC/MS: (M+1)$^+$: 434.20.

Step C: 1-(4-((2S,3S)-3-(methoxycarbonyl)-2-(1-((2-(trimethylsilyl)ethoxy)methyl)-1H-tetrazol-5-yl)hexyl)phenyl)-N,N,N-trimethylmethanaminium To the solution of (S)-2-((S)-2-(4-(aminomethyl)phenyl)-1-(1-((2-(trimethylsilyl)ethoxy)methyl)-1H-tetrazol-5-yl)ethyl)pentanoic acid (35 mg, 0.081 mmol) in acetone (2 ml) was added K$_2$CO$_3$ (66.9 mg, 0.484 mmol) and MeI (0.030 ml, 0.484 mmol), then the resulting mixture was stirred at rt overnight. After concentration the residue was purified on reverse phase HPLC using acetonitrile (0.05% TFA)/water (0.05% TFA) as eluting solvents to give 1-(4-((2S,3S)-3-(methoxycarbonyl)-2-(1-((2-(trimethylsilyl)ethoxy)methyl)-1H-tetrazol-5-yl)hexyl)phenyl)-N,N,N-trimethylmethanaminium. M$^+$; 490.26.

Step D: (S)-2-((S)-1-(1H-tetrazol-5-yl)-2-(4-((trimethylammonio)methyl)phenyl)ethyl)pentanoate To the solution of 1-(4-((2S,3S)-3-(methoxycarbonyl)-2-(1-((2-(trimethylsilyl)ethoxy)methyl)-1H-tetrazol-5-yl)hexyl)phenyl)-N,N,N-trimethylmethanaminium (22 mg, 0.045 mmol) in acetic acid (4 ml) was added HCl (2 ml, 24.35 mmol), then the resulting solution was heated at 80° C. for 8 hr. After concentration the residue was purified on reverse phase HPLC using acetonitrile (0.05% TFA)/water (0.05% TFA) as eluting solvents to give (S)-2-((S)-1-(1H-tetrazol-5-yl)-2-(4-((trimethylammonio)methyl)phenyl)ethyl)pentanoate. LC/MS: (M+1)$^+$: 346.17.

EXAMPLES 420 and 421

(2R,3S)-4-(6-aminopyridin-3-yl)-2-(tert-butyl)-3-(1H-tetrazol-5-yl)butanoic acid and (2R,3S)-2-(tert-butyl)-4-(6-hydroxypyridin-3-yl)-3-(1H-tetrazol-5-yl)butanoic acid

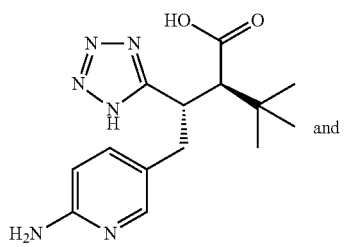

420 and

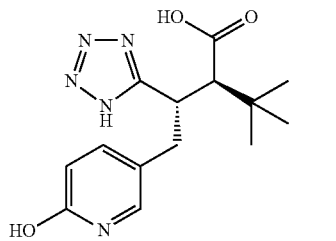

421

Step A: (R)-4-benzyl-3-(3,3-dimethylbutanoyl)oxazolidin-2-one n-Butyllithium (21.3 mL of a 2.5M solution in hexanes; 67.5 mmol) was added to a stirred solution of (R)-4-benzyloxazolidinone (11.9 g; 66.9 mmol) in anhydrous THF (250 mL) at −78° C., under an atmosphere of nitrogen. The mixture was maintained at this temperature for 30 min, then 3,3-dimethylbutanoyl chloride (7.96 ml; 56.4 mmol) was added. After stirring at −78° C. for a further 2 hr, the ice bath was removed and stirring continued for a further 1 hr. The reaction was quenched by the addition of saturated aq. ammonium chloride and the organics extracted into ethyl acetate. The organic phase was separated, washed with 1M NaOH, brine, dried (MgSO$_4$) and the volatiles removed under reduced pressure. The residue was purified by silica gel column chromatography using a 330 g column and MTBE: Heptane 1:4 to 100% DCM as eluent to give the titled compound. LC/MS [M+H]$^+$: 276.41.

Step B: (R)-3-((R)-4-benzyl-2-oxooxazolidine-3-carbonyl)-4,4-dimethylpentanenitrile Sodium hexamethyldisilazide (4.36 mL of a 1.0M solution in toluene) was added to a solution of the acyl oxazolidinone (1.30 g; 4.36 mmol) in anhydrous THF (5 mL) at −78° C., under an atmosphere of nitrogen. When the addition was complete, stirring was maintained at this temperature for 1.5 hr., before the addition of bromoacetonitrile (0.871 ml, 13.07 mmol). The resulting reaction mixture was stirred at −78° C. for 3 hr, before quenching with saturated aq. ammonium chloride followed by the addition of EtOAc. The organic phase was separated, washed with brine, dried (MgSO$_4$) and the volatiles removed under reduced pressure. The residue was purified by silica gel column chromatography using a mixture of hexanes and EtOAc as eluent to give the titled compound.

Step C: (R)-3-((R)-2-((1H-tetrazol-5-yl)methyl)-3,3-dimethylbutanoyl)-4-benzyloxazolidin-2-one Dibutyltin oxide (1.19 g, 4.77 mmol) was added to a mixture of the nitrile (5.00 g, 15.9 mmol) and azidotrimethylsilane (6.33 ml, 47.7 mmol) in anhydrous toluene (50 ml) and the resulting reaction mixture was heated to 110° C. under an atmosphere of nitrogen overnight. After cooling, the reaction was concentrated under reduced pressure and the residue purified by silica gel column chromatography (110 g column) using a gradient of 0 to 100% EtOAc in hexanes as eluent to give the desired tetrazole. LC/MS [M+H]$^+$: 358.76.

Step D: (R)-4-benzyl-3-((R)-3,3-dimethyl-2-((2-((2-(trimethylsilyl)ethoxy)methyl)-2H-tetrazol-5-yl)methyl)butanoyl)oxazolidin-2-one and (R)-4-benzyl-3-((R)-3,3-dimethyl-2-((1-((2-(trimethylsilyl)ethoxy)methyl)-1H-tetrazol-5-yl)methyl)butanoyl)oxazolidin-2-one SEM-Cl (3.33 mL, 18.8 mmol) was added dropwise to a stirred solution of the tetrazole (5.60 g, 15.7 mmol) and Hunigs base (5.47 mL, 31.3 mmol) in anhydrous acetonitrile (50 ml) while cooled in an ice bath under an atmosphere of nitrogen. The resulting reaction mixture was allowed to warm to room temperature overnight. The reaction mixture was partitioned between EtOAc and saturated aq. sodium bicarbonate. The organic phase was separated, washed with brine, dried (MgSO$_4$) and the volatiles removed under reduced pressure. The residue was purified by silica gel column chromatography using a 110 g column and a gradient of EtOAc in hexanes as eluent gave 2-N protected intermediate (LC/MS [M+H]$^+$: 488.60) followed by the desired 1-N protected intermediate (LC/MS [M+H]$^+$: 488.62).

Step E: S-methyl (R)-3,3-dimethyl-2-((1-((2-(trimethylsilyl)ethoxy)methyl)-1H-tetrazol-5-yl)methyl)butanethioate n-Butyllithium (8.53 ml of a 2.5 M solution in hexanes, 21.3 mmol) was added dropwise to a stirred solution of ethanethiol (1.80 g, 29.0 mmol) in anhydrous THF (25 ml) at −78° C., under an atmosphere of nitrogen. When the addition was complete the solution was allowed to warm to ice bath temperature then a solution of the oxazolidinone (4.16 g, 8.53 mmol) in anhydrous THF (5 ml) was added. The resulting reaction mixture was allowed to warm to room temperature overnight. The reaction was quenched by the addition of 1.0M NaOH and the organics extracted into diethyl ether. The organic phase was separated, washed with brine, dried (MgSO$_4$) and the volatiles removed under reduced pressure. The residue was purified by silica gel column chromatography (110 g column) using a gradient of EtOAc in hexanes as eluent to provide the desired thioester.

Step F: (R)-3,3-dimethyl-2-((1-((2-(trimethylsilyl)ethoxy)methyl)-1H-tetrazol-5-yl)methyl)butanoic acid Hydrogen peroxide (2.14 ml of a 35% solution, 24.4 mmol) was added, in three portions, over the course of 10 mins, to a stirred mixture of the thioester (2.60 g, 6.98 mmol) and lithium hydroxide (0.59 g, 24 mmol) in a ethanol (20 mL) and water (10 mL) at 55° C. (oil bath temperature) under an atmosphere of nitrogen. When the addition was complete, the reaction mixture was maintained at this temperature for 1 hr. After cooling, the reaction was acidified to pH=3-5 with 1N HCl and the organics extracted into EtOAc. The organic phase was separated, washed with 10% aq. sodium thiosulfate (×2), brine, dried (MgSO$_4$) and the volatiles removed under reduced pressure to provide the desired acid.

Step G: (2R,3S)-4-(6-bromopyridin-3-yl)-2-(tert-butyl)-3-(1-((2-(trimethylsilyl)ethoxy)methyl)-1H-tetrazol-5-yl)butanoic acid and (2R,3R)-4-(6-bromopyridin-3-yl)-2-(tert-butyl)-3-(1-((2-(trimethylsilyl)ethoxy)methyl)-1H-tetrazol-5-yl)butanoic acid n-Butyllithium (1.29 ml of a 2.5M solution in hexanes, 3.2 mmol) was added dropwise to a stirred solution of the tetrazole-acid (0.48 g, 1.5 mmol) in anhydrous THF (7 mL) at −78° C. under an atmosphere of nitrogen. The solution was maintained at this temperature for 1 hr., then 1-bromo-4-(bromomethyl)pyridine in anhydrous THF (1 mL) was added. The resulting reaction mixture was maintained at −78° C. overnight. The reaction was quenched by the addition of saturated aq. ammonium chloride and the organics extracted into EtOAc. The organic phase was separated, washed with brine, dried (MgSO$_4$) and the volatiles removed under reduced pressure. The residue was purified by silica gel column chromatography (80 g column) to give the desired mixture of diastereomers. LC/MS [M+H]$^+$: 500.59 and 500.61.

Step H: (2R,3S)-4-(6-aminopyridin-3-yl)-2-(tert-butyl)-3-(1-((2-(trimethylsilyl)ethoxy)methyl)-1H-tetrazol-5-yl)butanoic acid and (2R,3S)-2-(tert-butyl)-4-(6-hydroxypyridin-3-yl)-3-(1-((2-(trimethylsilyl)ethoxy)methyl)-1H-tetrazol-5-yl)butanoic acid Ammonium hydroxide (10.8 ml of a 29% aqueous solution, 80 mmol) was added to the diastereoisomeric mixture of tetrazoles (1.00 g, 2.00 mmol), N$^1$, N$^2$-dimethylethane-1,2-diamine 0.022 ml, 0.20 mmol), copper(I) oxide (0.057 g, 0.40 mmol) and potassium carbonate (0.333 g, 2.4 mmol) in ethylene glycol (5 ml) and stirred at 85° C. over a weekend. After cooling, the reaction mixture was concentrated under reduced pressure and the residue purified by C18 column chromatography eluting with a gradient of acetonitrile (containing 0.1% TFA) in water (containing 0.1% TFA) as eluent to give the amino pyridine (LC/MS [M+H]$^+$: 435.67) followed by the hydroxy pyridine (LC/MS [M+H]$^+$: 436.66).

Step I: (2R,3S)-4-(6-aminopyridin-3-yl)-2-(tert-butyl)-3-(1H-tetrazol-5-yl)butanoic acid TFA (1 ml containing 10% water) was added to the protected tetrazole (0.115 g, 0.265 mmol) while cooled in an ice bath. The flask was removed from the ice bath and stirred for 5 min. The volatiles were removed under reduced pressure and the residue purified by reverse phase HPLC using a gradient of acetonitrile (containing 0.1% TFA) in water (containing 0.1% TFA) as eluent to give the TFA salt of the desired product. LC/MS [M+H]$^+$: 305.47

Step J: (2R,3S)-2-(tert-butyl)-4-(6-hydroxypyridin-3-yl)-3-(1H-tetrazol-5-yl)butanoic acid TFA (1 mL containing 10% water) was added to the protected tetrazole (0.03 g, 0.069 mmol) while cooled in an ice bath. The flask was removed from the ice bath and stirred for 5 min. The volatiles were removed under reduced pressure and the residue purified by reverse phase HPLC using a gradient of acetonitrile (containing 0.1% TFA) in water (containing 0.1% TFA) as eluent to give the TFA salt of the desired product. LC/MS [M+H]$^+$: 306.48

EXAMPLE 422

(2R,3S)-2-(tert-butyl)-4-(6-guanidinopyridin-3-yl)-3-(1H-tetrazol-5-yl)butanoic acid

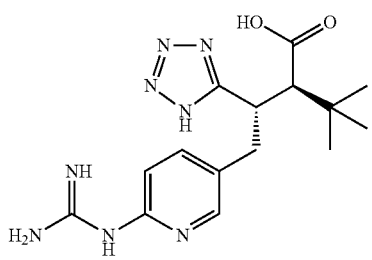 [SMILES: CC(C)(C)[C@H](C(=O)O)[C@H](Cc1ccc(NC(=N)N)nc1)c1nnn[nH]1]

Step A: (2R,3S)-4-(6-((E)-2,3-bis(tert-butoxycarbonyl)guanidino)pyridin-3-yl)-2-(tert-butyl)-3-(1H-tetrazol-5-yl)butanoic acid Mercuric chloride (0.007 g, 0.03 mmol) was added to a mixture of 1,3-bis(tert-butoxycarbonyl)-2-methyl-2-thiopseudourea (0.008 g, 0.03 mmol), the TFA salt of the aminopyridine (0.010 g, 0.02 mmol) and triethylamine (0.008 g, 0.08 mmol) in anhydrous dichloromethane (1 ml) while cooled in an ice bath. The resulting reaction mixture was kept in an ice bath for 30 min, then at room temperature overnight. Additional dichloromethane was added to the white suspension and filtered through a pad of celite. The filtrate was washed with brine, dried (MgSO$_4$) and concentrated under reduced pressure to give the desired product which was used without purification in the nest step (Step B). LC/MS [M+H]$^+$: 547.86

Step B: (2R,3S)-2-(tert-butyl)-4-(6-guanidinopyridin-3-yl)-3-(1H-tetrazol-5-yl)butanoic acid TFA (1 mL containing 10% water) was added to the crude product from the previous step while cooled in an ice bath and the resulting solution was stirred for 15 min. The volatiles were removed under reduced pressure and the residue purified by reverse phase HPLC using a gradient of acetonitrile (containing 0.1% TFA) in water (containing 0.1% TFA) to give the TFA salt of the desired guanidine. LC/MS [M+H]$^+$: 347.56

EXAMPLE 423

(2R,3R)-4-(2-bromobenzo[d]thiazol-4-yl)-2-(tert-butyl)-3-(1H-tetrazol-5-yl)butanoic acid

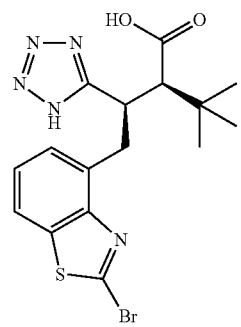 [SMILES: CC(C)(C)[C@H](C(=O)O)[C@@H](Cc1cccc2sc(Br)nc12)c1nnn[nH]1]

Step A: (2R,3R)-4-(2-bromobenzo[d]thiazol-4-yl)-2-(tert-butyl)-3-(1-((2-(trimethylsilyl)ethoxy)methyl)-1H-tetrazol-5-yl)butanoic acid and (2R,3S)-4-(2-bromobenzo[d]thiazol-4-yl)-2-(tert-butyl)-3-(1-((2-(trimethylsilyl)ethoxy)methyl)-1H-tetrazol-5-yl)butanoic acid n-Butyllithium (0.134 ml of a 2.5M solution in hexanes, 0.335 mmol) was added dropwise to a stirred solution of (R)-3,3-dimethyl-2-((1-((2-(trimethylsilyl)ethoxy)methyl)-1H-tetrazol-5-yl)methyl)butanoic acid (0.050 g, 0.15 mmol) in anhydrous THF (1 ml) at −78° C. under an atmosphere of nitrogen. The mixture was maintained at this temperature for 1 hr, then 2-bromo-4-(bromomethyl)benzo[d]thiazole (0.074 g, 0.15 mmol) in anhydrous THF (2 ml) was added and the resulting reaction mixture was stirred at −78° C. overnight. The reaction was quenched by the addition of saturated aq. ammonium chloride and the organics extracted into EtOAc. The organic phase was separated, washed with brine, dried (MgSO$_4$) and the volatiles removed under reduced pressure. The residue was purified by reverse phase HPLC using a gradient of acetonitrile (containing 0.1% TFA) in water (containing 0.1% TFA) to give the (2R,3R)-isomer (LC/MS [M+H]$^+$: 556.49) followed by the (2R,3S)-isomer (LC/MS [M+H]$^+$: 556.50).

Step B: (2R,3R)-4-(2-bromobenzo[d]thiazol-4-yl)-2-(tert-butyl)-3-(1H-tetrazol-5-yl)butanoic acid TFA (3 mL) was added to the protected tetrazole (0.006 g) and the resulting reaction mixture was stirred at room temperature for 30 min. The volatiles were removed under reduced pressure and the residue purified by reverse phase HPLC using a gradient of acetonitrile (containing 0.1% TFA) in water (containing 0.1% TFA) to give the desired product. LC/MS [M+H]$^+$: 426.46.

EXAMPLE 424

(2R,3S)-4-(2-aminobenzo[d]thiazol-4-yl)-2-(tert-butyl)-3-(1H-tetrazol-5-yl)butanoic acid

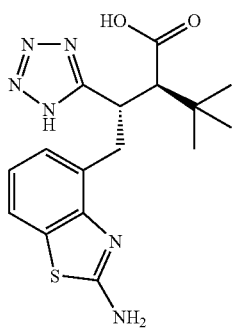 [SMILES: CC(C)(C)[C@H](C(=O)O)[C@H](Cc1cccc2sc(N)nc12)c1nnn[nH]1]

Step A: 2-Bis-(tert-butoxycarbonyl)amino-4-methyl-benzo[d]thiazole

DMAP (0.074 g, 0.61 mmol) was added to a mixture of the amine (1.00 g, 6.09 mmol) and di-tert-butyl dicarbonate (2.66 g, 12.18 mmol) in anhydrous dichloromethane (50 ml) and the resulting reaction mixture stirred at room temperature for 1 hr. The reaction mixture was then washed with an aqueous solution of potassium hydrogen sulfate, brine, then dried (MgSO$_4$) and the volatiles removed under reduced pressure to give a crude product which was used in the next step below, without purification.

Step B: 2-Bis-(tert-butoxycarbonyl)amino-4-bromomethylbenzo[d]thiazole

A mixture of NBS (1.074 g, 6.04 mmol), benzoyl peroxide (0.195 g, 0.604 mmol) and 2-Bis-(tert-butoxycarbonyl)amino-4-methylbenzo[d]thiazole (2.20 g, 6.04 mmol) in carbon tetrachloride (20 mL) was heated to 80° C. for a period of 1 hr. The solvent was removed under reduced pressure, redissolved in EtOAc, washed with water, brine, dried (MgSO$_4$) and the volatiles removed under reduced pressure. Purification of the crude reaction product using silica gel column chromatography gave the desired bromide. LC/MS [M+H]$^+$: 445.50

Step C: (2R,3R)-4-(2-(Bis-(tert-butoxycarbonyl) amino)benzo[d]thiazol-4-yl)-2-(tert-butyl)-3-(1-((2-(trimethylsilyl)ethoxy)methyl)-1H-tetrazol-5-yl) butanoic acid and (2R,3S)-4-(2-(Bis-(tert-butoxycarbonyl)amino)benzo[d]thiazol-4-yl)-2-(tert-butyl)-3-(1-((2-(trimethylsilyl)ethoxy)methyl)-1H-tetrazol-5-yl)butanoic acid n-Butyllithium (0.268 ml of a 2.5M solution in hexanes, 0.67 mmol) was added dropwise to a stirred solution of (R)-3,3-dimethyl-2-((1-((2-(trimethylsilyl)ethoxy)methyl)-1H-tetrazol-5-yl)methyl)butanoic acid (0.100 g, 0.304 mmol) in anhydrous THF (0.5 ml) at −78° C., under an atmosphere of nitrogen. The resulting mixture was maintained at this temperature for 1 hr, before the addition of 2-Bis-(tert-butoxycarbonyl)amino-4-bromomethylbenzo[d] thiazole (0.243 g, 0.548 mmol) in anhydrous THF (2 mL). The reaction was stirred at −78° C. overnight, quenched with saturated aq. ammonium chloride and the organics extracted into EtOAc. The organic phase was separated, washed with brine, dried (MgSO$_4$) and the volatiles removed under reduced pressure. The residue was purified by reverse phase HPLC using a gradient of acetonitrile (containing 0.1% TFA) in water (containing 0.1% TFA) to give the (2R, 3R)-isomer (LC/MS [M+H]$^+$: 692.01) followed by the (2R, 3S)-isomer (LC/MS [M+H]$^+$: 692.01).

Step D: (2R,3S)-4-(2-aminobenzo[d]thiazol-4-yl)-2-(tert-butyl)-3-(1H-tetrazol-5-yl)butanoic acid TFA (1 mL) was added to a mixture of (2R,3S)-4-(2-(Bis-(tert-butoxycarbonyl)amino)benzo[d]thiazol-4-yl)-2-(tert-butyl)-3-(1-((2-(trimethylsilyl)ethoxy)methyl)-1H-tetrazol-5-yl)butanoic acid (0.010 g) and anisole (2 drops from a pipette) in dichloromethane (1 mL). The resulting reaction mixture was stirred at room temperature for 1 hr, then the volatiles removed under reduced pressure. The residue was purified by reverse phase HPLC using a gradient of acetonitrile (containing 0.1% TFA) in water (containing 0.1% TFA) to give the TFA salt of the desired product. LC/MS [M+H]$^+$: 361.41

EXAMPLE 425

(S)-2-((S)-2-(5-bromothiophen-2-yl)-1-(1H-tetrazol-5-yl)ethyl)pentanoic acid

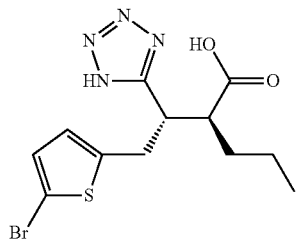 [SMILES: CCC[C@H](C(=O)O)[C@H](Cc1ccc(Br)s1)c1nnn[nH]1]

Step A: (S)-2-((S)-2-(5-bromothiophen-2-yl)-1-(1-((2-(trimethylsilyl)ethoxy)methyl)-1H-tetrazol-5-yl) ethyl)pentanoic acid To a solution of diisopropylamine (0.10 mL, 0.70 mmol)) in 2 mL of THF was added butyllithium (0.28 mL, 0.70 mmol)) at −10 to 0° C. The mixture was stirred at 0 to 5° C. for 30 minutes. After the mixture was cooled to −78° C., (S)-2-((1-((2-(trimethylsilyl)ethoxy)methyl)-1H-tetrazol-5-yl)methyl)pentanoic acid (100 mg, 0.32 mmol) in 0.2 mL of THF was added dropwise and stirred at −78° C. for one hour. 2-bromo-5-(bromomethyl)thiophene (122 mg, 0.477 mmol) in 0.2 mL of THF was added dropwise at −78° C. and stirred at −78° C. for one hour and then gradually warmed up to room temperature and stirred for twenty four hours. The reaction mixture was added to an aqueous solution of NH$_4$Cl and extracted with EtOAc. The organic layer was washed with 1N HCl and brine, dried over MgSO$_4$, filtered and concentrated. The residue was purified by column chromatography on silica gel column, eluting with MeOH/DCM. LC/MS [M+H]+: 491.0.

Step B: (S)-2-((S)-2-(5-bromothiophen-2-yl)-1-(1H-tetrazol-5-yl)ethyl)pentanoic acid TFA (0.5 mL, 0.087 mmol) was added to a stirred room temperature solution of (S)-2-((S)-2-(5-bromothiophen-2-yl)-1-(1-((2-(trimethylsilyl)ethoxy)methyl)-1H-tetrazol-5-yl)ethyl)pentanoic acid (15 mg, 0.031 mmol) in DCM (0.5 mL) and the mixture was stirred at room temperature for three hours. LC-MS showed the reaction was completed. The reaction mixture was concentrated, dissolved in DMSO and purified by HPLC with acetonitrile and water with 0.05% TFA. LC/MS [M+H]+: 361.0

EXAMPLE 426

(3S)-4-(5-bromothiophen-2-yl)-2-(tert-butyl)-3-(1H-tetrazol-5-yl)butanoic acid

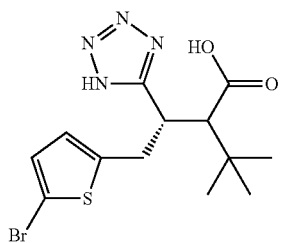 [SMILES: CC(C)(C)C(C(=O)O)[C@H](Cc1ccc(Br)s1)c1nnn[nH]1]

The title compound was prepared in an analogous fashion as that described for (S)-2-((S)-2-(5-bromothiophen-2-yl)-1-(1H-tetrazol-5-yl)ethyl)pentanoic acid (EXAMPLE 425) starting from 3,3-dimethyl-2-((1-((2-(trimethylsilyl)ethoxy)methyl)-1H-tetrazol-5-yl)methyl)butanoic acid. LC/MS [M+H]+: 375.2

EXAMPLE 427

2-((5-((2S,3R)-3-carboxy-4,4-dimethyl-2-(1H-tetrazol-5-yl)pentyl)pyridin-2-yl)amino)ethan-1-aminium 2,2,2-trifluoroacetate

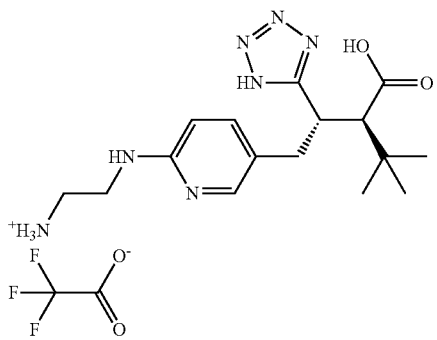

Step A: (2R,3S)-4-(6-((2-aminoethyl)amino)pyridin-3-yl)-2-(tert-butyl)-3-(1-((2-(trimethylsilyl)ethoxy)methyl)-1H-tetrazol-5-yl)butanoic acid In a 5 ml reaction tube, cesium carbonate (98 mg, 0.301 mmol), ethane-1,2-diamine (36.2 mg, 0.602 mmol), Buchwald preformed ketone (11.98 mg, 0.030 mmol) and (2R,3S)-4-(6-bromopyridin-3-yl)-2-(tert-butyl)-3-(1-((2-(trimethylsilyl)ethoxy)methyl)-1H-tetrazol-5-yl)butanoic acid (See EXAMPLES 420 and 421, steps A-G, 50 mg, 0.100 mmol) were suspended in DMF (1.0 mL) then degassed and backfilled and sealed under $N_2$. The reaction was stirred at 100° C. overnight. LC-MS indicated that the reaction completed. The reaction mixture was filtered and concentrated after cooling. The residue was purified by reverse phase C18 column eluting with acetonitrile and water with 0.05% TFA. LC/MS [M+H]+: 478.3

Step B: 2-((5-((2S,3R)-3-carboxy-4,4-dimethyl-2-(1H-tetrazol-5-yl)pentyl)pyridin-2-yl)amino)ethan-1-aminium 2,2,2-trifluoroacetate TFA (0.5 mL, 0.087 mmol) was added to a stirred, room temperature (2R,3S)-4-(6-(2-aminoethyl)amino)pyridin-3-yl)-2-(tert-butyl)-3-(1-((2-(trimethylsilyl)ethoxy)methyl)-1H-tetrazol-5-yl)butanoic acid (26 mg, 0.054 mmol) in DCM (0.5 mL) and the mixture was stirred at room temperature for three hours. LC-MS showed the reaction completed. Concentrated down. Dissolved it in DMSO and purified by HPLC with acetonitrile and water with (0.05% TFA). LC/MS [M+H]+: 348.2

EXAMPLE 428

3-(4-((2S)-3-carboxy-4,4-dimethyl-2-(1H-tetrazol-5-yl)pentyl)phenyl)pyrrolidin-1-ium 2,2,2-trifluoroacetate

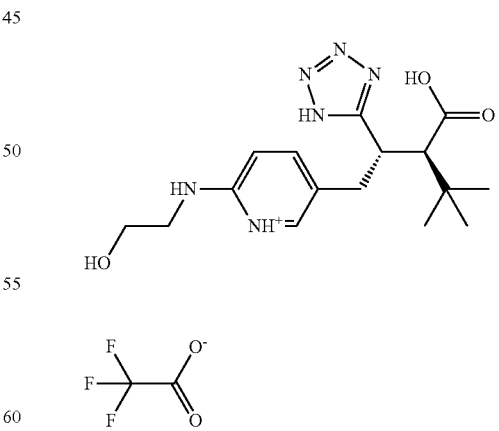

The title compound was prepared in an analogous fashion as that described for 2-((5-((2S,3R)-3-carboxy-4,4-dimethyl-2-(1H-tetrazol-5-yl)pentyl)pyridin-2-yl)amino)ethan-1-aminium 2,2,2-trifluoroacetate (EXAMPLE 427) starting from (2R,3S)-4-(6-bromopyridin-3-yl)-2-(tert-butyl)-3-(1-

((2-(trimethylsilyl)ethoxy)methyl)-1H-tetrazol-5-yl)butanoic acid (See EXAMPLES 420 and 421, steps A-G). LC/MS [M+H]⁺: 349.3

EXAMPLE 429

3-(5-((2S,3R)-3-carboxy-4,4-dimethyl-2-(1H-tetrazol-5-yl)pentyl)pyridin-2-yl)-2,5-dihydro-1H-pyrrol-1-ium 2,2,2-trifluoroacetate

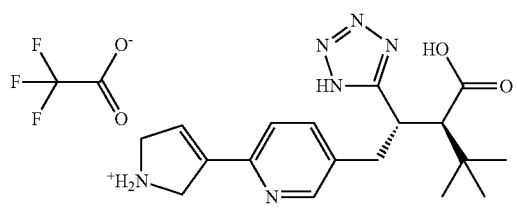 [SMILES: O=C([O-])C(F)(F)F ; CC(C)(C)[C@H](C(=O)O)[C@H](Cc1ccc(C2=CC[NH2+]C2)nc1)c1nnn[nH]1]

Step A: (2R,3S)-4-(6-(1-(tert-butoxycarbonyl)-2,5-dihydro-1H-pyrrol-3-yl)pyridin-3-yl)-2-(tert-butyl)-3-(1-((2-(trimethylsilyl)ethoxy)methyl)-1H-tetrazol-5-yl)butanoic acid Tetrakis palladium (11.13 mg, 9.63 μmol) was added to a stirred, room temperature mixture of tert-butyl 3-(4,4,5,5-tetramethyl-1,3,2-dioxaborolan-2-yl)-2,5-dihydro-1H-pyrrole-1-carboxylate (37 mg, 0.125 mmol), (2R,3S)-4-(6-bromopyridin-3-yl)-2-(tert-butyl)-3-(1-((2-(trimethylsilyl)ethoxy)methyl)-1H-tetrazol-5-yl)butanoic acid (See EXAMPLES 420 and 421, steps A-G) (48 mg, 0.096 mmol) and sodium carbonate (22.45 mg, 0.212 mmol) in dioxane/water under N₂ and the mixture was stirred at 105° C. overnight. LC-MS showed the reaction was completed. After cooling, the mixture was diluted with EtOAc, washed with 1N HCl and brine. The organic layer was dried over MgSO₄, filtered and concentrated. The residue was purified by column chromatography on silica gel column, eluting with CH₂Cl₂/MeOH. LC/MS [M+H]⁺: 587.3

Step B: 3-(5-((2S,3R)-3-carboxy-4,4-dimethyl-2-(1H-tetrazol-5-yl)pentyl)pyridin-2-yl)-2,5-dihydro-1H-pyrrol-1-ium 2,2,2-trifluoroacetate TFA (0.5 mL, 0.087 mmol) was added to a stirred, room temperature mixture of (2R,3S)-4-(6-(1-(tert-butoxycarbonyl)-2,5-dihydro-1H-pyrrol-3-yl)pyridin-3-yl)-2-(tert-butyl)-3-(1-((2-(trimethylsilyl)ethoxy)methyl)-1H-tetrazol-5-yl)butanoic acid (13 mg, 0.022 mmol) and thioanisole (2.62 μL, 0.022 mmol) in a flask and the mixture was stirred at room temperature for three hours. LC-MS showed the reaction completed. The reaction mixture was concentrated, dissolved in DMSO and purified by HPLC with acetonitrile and water with 0.05% TFA. LC/MS [M+H]⁺: 357.3

EXAMPLE 430

3-(5-((2S)-3-carboxy-4,4-dimethyl-2-(1H-tetrazol-5-yl)pentyl)pyridin-2-yl)pyrrolidin-1-ium 2,2,2-trifluoroacetate

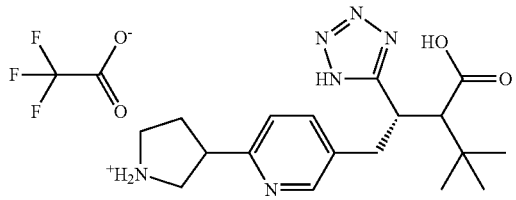 [SMILES: O=C([O-])C(F)(F)F ; CC(C)(C)C(C(=O)O)[C@H](Cc1ccc(C2CC[NH2+]C2)nc1)c1nnn[nH]1]

Step A: (2R,3S)-4-(6-(1-(tert-butoxycarbonyl)pyrrolidin-3-yl)pyridin-3-yl)-2-(tert-butyl)-3-(1-((2-(trimethylsilyl)ethoxy)methyl)-1H-tetrazol-5-yl)butanoic acid Pd—C (8 mg, 7.52 μmol) was added to a room temperature mixture of (2R,3S)-4-(6-(1-(tert-butoxycarbonyl)-2,5-dihydro-1H-pyrrol-3-yl)pyridin-3-yl)-2-(tert-butyl)-3-(1-((2-(trimethylsilyl)ethoxy)methyl)-1H-tetrazol-5-yl) butanoic acid (41 mg, 0.070 mmol) in MeOH and the mixture was stirred at room temperature under H₂ overnight. LC-MS showed the reaction was completed. The reaction mixture was filtered and concentrated to dryness. LC/MS [M+H]⁺: 589.4

Step B: 3-(5-((2S)-3-carboxy-4,4-dimethyl-2-(1H-tetrazol-5-yl)pentyl)pyridin-2-yl)pyrrolidin-1-ium 2,2,2-trifluoroacetate TFA (0.5 mL, 0.087 mmol) was added to a stirred, room temperature mixture of (2R,3S)-4-(6-(1-(tert-butoxycarbonyl)pyrrolidin-3-yl)pyridin-3-yl)-2-(tert-butyl)-3-(1-((2-(trimethylsilyl)ethoxy)methyl)-1H-tetrazol-5-yl)butanoic acid (42 mg, 0.071 mmol) and thioanisole (0.1 mL, 0.845 mmol) in a flask and the mixture was stirred at room temperature for two hours. LC-MS showed the reaction was completed. The reaction mixture was concentrated, dissolved in DMSO and purified by HPLC with acetonitrile and water with 0.05% TFA. LC/MS [M+H]⁺: 358.3

EXAMPLE 431

3-(4-((2S,3R)-3-carboxy-4,4-dimethyl-2-(1H-tetrazol-5-yl)pentyl)phenyl)pyrrolidin-1-ium 2,2,2-trifluoroacetate

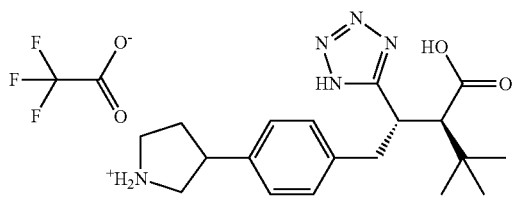 [SMILES: O=C([O-])C(F)(F)F ; CC(C)(C)[C@H](C(=O)O)[C@H](Cc1ccc(C2CC[NH2+]C2)cc1)c1nnn[nH]1]

The title compound was prepared in an analogous fashion as that described for 3-(5-((2S)-3-carboxy-4,4-dimethyl-2-(1H-tetrazol-5-yl)pentyl)pyridin-2-yl)pyrrolidin-1-ium 2,2, 2-trifluoroacetate (EXAMPLE 430) starting from (2R,3S)-4-(4-bromophenyl)-2-(tert-butyl)-3-(1H-tetrazol-5-yl)butanoic acid (prepared in an analogous fashion as described in EXAMPLES 420 and 421, steps A-G, except 4-bromobenzyl bromide is used in place of 2-bromo-5-(bromomethyl)pyridine). LC/MS [M+H]$^+$: 358.3

EXAMPLE 432

3-(4-((2S,3S)-3-carboxy-2-(1H-tetrazol-5-yl)hexyl)phenyl)-3-hydroxypyrrolidin-1-ium 2,2,2-trifluoroacetate

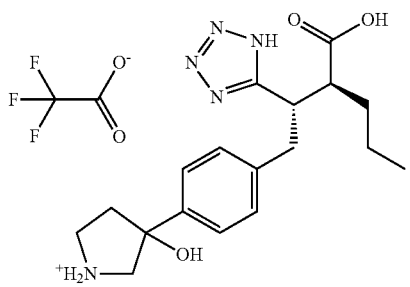 [SMILES: O=C([O-])C(F)(F)F ; CCC[C@H](C(=O)O)[C@H](Cc1ccc(C2(O)CC[NH2+]C2)cc1)c1nnn[nH]1]

Step A: tert-butyl 3-hydroxy-3-(4-((2S,3S)-3-(methoxycarbonyl)-2-(1-((2-(trimethylsilyl)ethoxy)methyl)-1H-tetrazol-5-yl)hexyl)phenyl)pyrrolidine-1-carboxylate In a reaction vessel cesium carbonate (131 mg, 0.401 mmol), and Ad2nBuP Biphenyl Precatalyst (8.95 mg, 0.013 mmol) were combined, followed by potassium trifluoro((2S,3S)-3-(methoxycarbonyl)-2-(1-((2-(trimethylsilyl)ethoxy)methyl)-1H-tetrazol-5-yl)hexyl)borate (60 mg, 0.134 mmol)), and tert-butyl 3-(4-chlorophenyl)-3-hydroxypyrrolidine-1-carboxylate (39.8 mg, 0.134 mmol) in toluene (0.5 mL), and then N$_2$ flushed. This mixture was then evacuated and backfilled with N$_2$ (3 times), then dry, degassed water (0.05 ml) was added to this flask. This mixture was then heated at 100° C. overnight. The mixture was cooled, diluted with EtOAc, washed with H$_2$O and brine, dried over MgSO$_4$, filtered and the solvent was evaporated under reduced pressure. The residue was purified by column chromatography on silica gel column, eluting with EtOAc/isohexane. LC/MS [M+H]$^+$: 604.5

Step B: (2S)-2-((1S)-2-(4-(1-(tert-butoxycarbonyl)-3-hydroxypyrrolidin-3-yl)phenyl)-1-(1-((2-(trimethylsilyl)ethoxy)methyl)-1H-tetrazol-5-yl)ethyl)pentanoic acid LiOH (0.952 mg, 0.040 mmol) was added to a stirred, cooled 0° C. mixture of tert-butyl 3-hydroxy-3-(4-((2S,3S)-3-(methoxycarbonyl)-2-(1-((2-(trimethylsilyl)ethoxy)methyl)-1H-tetrazol-5-yl)hexyl)phenyl)pyrrolidine-1-carboxylate (20 mg, 0.033 mmol) in 0.5 mL dioxane and 0.5 mL of water and the mixture was stirred at room temperature overnight. LC-MS indicated that the reaction was completed. The reaction mixture was acidified it to pH=3 with aq. 1N HCl, then extracted with EtOAc. The organic layer was dried over MgSO$_4$, filtered and concentrated to dryness. LC/MS [M+H]$^+$: 590.3

Step C: 3-(4-((2S,3S)-3-carboxy-2-(1H-tetrazol-5-yl)hexyl)phenyl)-3-hydroxypyrrolidin-1-ium 2,2,2-trifluoroacetate TFA (0.5 mL, 0.087 mmol) was added to a stirred, room temperature (2S)-2-((1S)-2-(4-(1-(tert-butoxycarbonyl)-3-hydroxypyrrolidin-3-yl)phenyl)-1-(1-((2-(trimethylsilyl)ethoxy)methyl)-1H-tetrazol-5-yl)ethyl)pentanoic acid (17 mg, 0.029 mmol) in 0.5 mL of DCM and the mixture was stirred at room temperature for three hours. LC-MS indicated that the reaction was completed. The reaction mixture was concentrated, dissolved in DMSO and purified by HPLC with acetonitrile and water with 0.05% TFA. LC/MS [M+H]$^+$: 360.3

EXAMPLE 433

(S)-2-((S)-2-(4-(2,5-dihydro-1H-pyrrol-3-yl)phenyl)-1-(1H-tetrazol-5-yl)ethyl)-5-(piperidin-4-yl)pentanoic acid compound with 2,2,2-trifluroacetic acid (1:2)

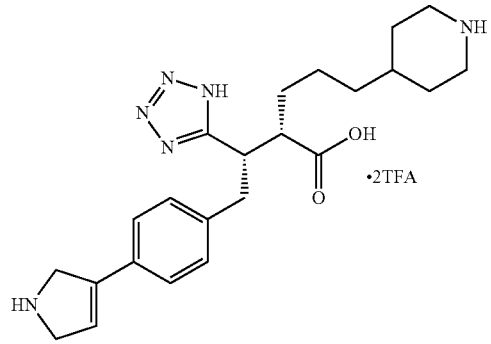 [SMILES: O=C(O)[C@@H](CCCC1CCNCC1)[C@H](Cc1ccc(C2=CCNC2)cc1)c1nnn[nH]1 ; "·2TFA"]

Step A: tert-butyl 4-((4S,5S)-6-(4-bromophenyl)-4-(tert-butoxycarbonyl)-5-(1H-tetrazol-5-yl)hexyl)piperidine-1-carboxylate To a solution of (S)-tert-butyl 4-(4-bromophenyl)-3-(1H-tetrazol-5-yl)butanoate (200 mg, 0.545 mmol) in 5.0 mL of THF was added lithium diisopropylamide in THF (1.362 ml, 1.362 mmol) dropwise at −78° C. under N$_2$. The reaction mixture was stirred for 1.5 hr at −78° C. A solution of tert-butyl 4-(3-iodopropyl)piperidine-1-carboxylate (385 mg, 1.089 mmol) in 0.2 mL of THF was added to the reaction mixture and stirred at −78° C. for 2 hr, then raised to rt for overnight. LC-MS shown no starting material left. The reaction mixture was cooled to 0° C., diluted with 5 mL of THF, followed by 1 mL of saturated aq. NH$_4$Cl. The aqueous phase was extracted with 5 mL of ether. The combined organic phases were dried (MgSO$_4$), concentrated, and chromatographed via silica gel (12 g ISCO cartridge, 0-100% EtOAc in Hexanes) to give the desired product tert-butyl 4-((4S,5S)-6-(4-bromophenyl)-4-(tert-butoxycarbonyl)-5-(1H-tetrazol-5-yl)hexyl)-piperidine-1-carboxylate. LC/MS [M+H]$^+$: 592.63 and 594.63.

Step B: tert-butyl 4-((4S,5S)-4-(tert-butoxycarbonyl)-6-(4-(1-(tert-butoxycarbonyl)-2,5-dihydro-1H-pyrrol-3-yl)phenyl)-5-(1H-tetrazol-5-yl)hexyl)piperidine-1-carboxylate To a stirred mixture of tert-butyl 4-((4S,5S)-6-(4-bromophenyl)-4-(tert-butoxycarbonyl)-5-(1H-tetrazol-5-yl)

hexyl)piperidine-1-carboxylate (0.145 g, 0.245 mmol) and sodium carbonate (0.104 g, 0.979 mmol) in dioxane (4 ml)/water (1 mL) was added tetrakis(triphenylphosphine)Pd (0) (0.028 g, 0.024 mmol) under nitrogen. The reaction mixture was heated in a microwave at 115° C. for 60 min with stirring. LC-MS shown the reaction was completed. After cooling down to rt, the reaction mixture was diluted with 20 mL of EtOAc, then washed with 10 mL of 1N HCl and 20 mL of brine. The organic layer was dried over $MgSO_4$, filtered and concentrated. The residue was purified by column chromatography (ISCO, 80 g column, EtOAc: Hexanes=0-100%) to give product tert-butyl 4-((4S,5S)-4-(tert-butoxycarbonyl)-6-(4-(1-(tert-butoxycarbonyl)-2,5-dihydro-1H-pyrrol-3-yl)phenyl)-5-(1H-tetrazol-5-yl)hexyl)piperidine-1-carboxylate. LC/MS [M+H]: 681.88.

Step C: (S)-2-((S)-2-(4-(2,5-dihydro-1H-pyrrol-3-yl) phenyl)-1-(1H-tetrazol-5-yl)ethyl)-5-(piperidin-4-yl) pentanoic acid 2,2,2-trifluoroacetate (1:2)

To a solution of tert-butyl 4-((4S,5S)-4-(tert-butoxycarbonyl)-6-(4-(1-(tert-butoxycarbonyl)-2,5-dihydro-1H-pyrrol-3-yl)phenyl)-5-(1H-tetrazol-5-yl)hexyl)piperidine-1-carboxylate (35 mg, 0.051 mmol) in DCM (2.0 ml) was added thioanisole (0.5 ml, 4.23 mmol) and TFA (0.5 ml, 6.49 mmol). After 3 hr, LCMS showed that most of SM was gone. The reaction mixture was concentrated with rotavapor, then the residue was dissolved in 2 mL of DMSO, and purified via Gilson (3-60% acetonitrile in $H_2O$) to give the product (S)-2-((S)-2-(4-(2,5-dihydro-1H-pyrrol-3-yl)phenyl)-1-(1H-tetrazol-5-yl)ethyl)-5-(piperidin-4-yl)pentanoic acid. LC/MS $[M+2H]^{2+}$: 213.36.

EXAMPLE 434

(2S)-5-(piperidin-4-yl)-2-((1S)-2-(4-(pyrrolidin-3-yl) phenyl)-1-(1H-tetrazol-5-yl)ethyl)pentanoic acid 2,2,2-trifluoroacetate (1:2)

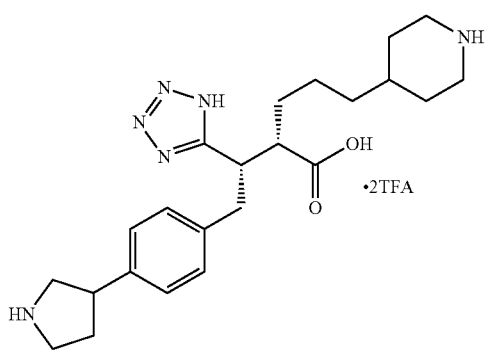 [SMILES: O=C(O)[C@@H](CCCC1CCNCC1)[C@H](Cc1ccc(C2CCNC2)cc1)c1nnn[nH]1 ; "·2TFA"]

To a suspension of Pd—C (13.05 mg, 0.012 mmol) in 10 mL of methanol was added (S)-2-((S)-2-(4-(2,5-dihydro-1H-pyrrol-3-yl)phenyl)-1-(1H-tetrazol-5-yl)ethyl)-5-(piperidin-4-yl)pentanoic acid compound with 2,2,2-trifluoroacetic acid (1:2) (8 mg, 0.012 mmol) and the reaction mixture was stirred at room temperature under $H_2$ overnight. LC-MS showed the reaction was completed. The black suspension was filtered through a celite pad, and the filtrate was concentrated and purified by Gilson (3-60% acetonitrile in $H_2O$) to give the product (2S)-5-(piperidin-4-yl)-2-((1S)-2-(4-(pyrrolidin-3-yl)phenyl)-1-(1H-tetrazol-5-yl)ethyl) pentanoic acid compound with 2,2,2-trifluoroacetic acid (1:2). LC-MS $[M+2H]^{2+}$: 214.38.

EXAMPLE 435

(S)-2-((S)-2-(6-aminopyridin-3-yl)-1-(1H-tetrazol-5-yl)ethyl)-4,4,4-trifluorobutanoic acid

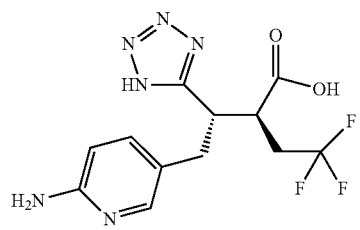 [SMILES: Nc1ccc(C[C@H](c2nnn[nH]2)[C@H](CC(F)(F)F)C(=O)O)cn1]

Step A: 4,4,4-trifluorobutanoic pivalic anhydride 4,4,4-trifluorobutanoic acid (3 g, 21.12 mmol) was dissolved in THF (60 ml) and cooled to −78° C. Then Hunig's Base (4.19 ml, 24 mmol) was added, followed by pivaloyl chloride (2.338 ml, 19 mmol). The reaction was allowed to warm up to room temperature overnight. The 4,4,4-trifluorobutanoic pivalic anhydride solution was used as is without purification.

Step B: (4R,5S)-4-methyl-5-phenyl-3-(4,4,4-trifluorobutanol)oxazolidin-2-one (4R,5S)-4-methyl-5-phenyloxazolidin-2-one (3.40 g, 19.2 mmol) was dissolved in THF (60 ml) and cooled to −78° C. Then n-BuLi in hexane (9.22 ml, 2.5M, 23.04 mmol) was added and the reaction mixture was stirred for 0.5 hr. The 4,4,4-trifluorobutanoic pivalic anhydride (4.34 g, 19.2 mmol) in 60 ml THF was then cannulated to the reaction. The reaction was stirred for 4 hr at −78° C. before quenching with saturated $NH_4Cl$ solution (20 ml). The reaction was extracted with EtOAc (2×). The organic layers were washed with saturated brine then dried over $Na_2SO_4$, filtered and concentrated. The residue was purified by MPLC with 0-25% EtOAc:hexane to give (4R,5S)-4-methyl-5-phenyl-3-(4,4,4-trifluorobutanoyl)oxazolidin-2-one. LC-MS [M+1]: 302.5

Step C: (R)-5,5,5-trifluoro-3-((4R,5S)-4-methyl-2-oxo-5-phenyloxazolidine-3-carbonyl)pentanenitrile (4R,5S)-4-methyl-5-phenyl-3-(4,4,4-trifluorobutanoyl) oxazolidin-2-one (3 g, 9.96 mmol) was dissolved in THF (45 ml) and cooled to −78° C. Then LiHMDS in THF (12.95 ml, 1M, 12.95 mmol) was added and the reaction mixture stirred for 0.5 hr. Bromoacetonitrile (2.081 ml, 29.9 mmol) was added and the reaction mixture stirred for another 0.5 hr then allowed to warm up to RT for 16 hrs. The reaction was quenched with saturated with $NH_4Cl$ solution (15 ml) and extracted with EtOAc (2×), dried over $Na_2SO_4$, filtered and concentrated. The residue was purified by MPLC with 0-25% EtOAc:hexane to give (R)-5,5,5-trifluoro-3-((4R,5S)-4-methyl-2-oxo-5-phenyloxazolidine-3-carbonyl)pentanenitrile. LC-MS [M+1]: 341.2

Step D: (4R,5S)-3-((R)-2-((1H-tetrazol-5-yl) methyl)-4,4,4-trifluorobutanoyl)-4-methyl-5-phenyloxazolidin-2-one (R)-5,5,5-trifluoro-3-((4R,5S)-4-methyl-2-oxo-5-phenyloxazolidine-3-carbonyl)pentanenitrile (1.66 g, 4.88 mmol) was dissolved in toluene (20 ml) and dibutyltin oxide (0.121 g, 0.488 mmol) and azidotrimethylsilane (1.295 ml, 9.76 mmol) were added. The reaction was heated to 100° C. for 16 hrs, then quenched with saturated NH₄Cl solution and extracted with EtOAc (2×), dried over Na₂SO₄, filtered and concentrated. The residue was purified by reverse phase HPLC with ACN and water buffered with 0.05% TFA to yield (4R,5S)-3-((R)-2-((1H-tetrazol-5-yl)methyl)-4,4,4-trifluorobutanoyl)-4-methyl-5-phenyloxazolidin-2-one. LC-MS [M+1]: 384.6.

Step E: (4R,5S)-4-methyl-5-phenyl-3-((R)-4,4,4-trifluoro-2-((4-((2-(trimethylsilyl)ethoxy)methyl)-2H-tetrazol-5-yl)methyl)butanoyl)oxazolidin-2-one (4R,5S)-4-methyl-5-phenyl-3-((R)-4,4,4-trifluoro-2-((1-((2-(trimethylsilyl)ethoxy)methyl)-1H-tetrazol-5-yl)methyl)butanoyl)oxazolidin-2-one (4R,5S)-3-((R)-2-((2H-tetrazol-5-yl)methyl)-4,4,4-trifluorobutanoyl)-4-methyl-5-phenyl oxazolidine-2-one (1.64 g, 4.28 mmol) in acetonitrile (75 ml) was cooled to 0° C. and then Hunig's base (1.494 ml, 8.56 mmol) was added followed by 2-(trimethylsilyl)ethoxymethyl chloride (0.757 ml, 4.28 mmol). The reaction was stirred at room temperature. When the LC-MS showed only product, the reaction was poured into water and extracted with EtOAc (2×50 ml). The organic layer was washed with brine (1×), dried (Na₂SO₄), filtered and concentrated. The residue was purified by MPLC with 0-50% EtOAc:hexane to give both regioisomers (4R,5S)-4-methyl-5-phenyl-3-((R)-4,4,4-trifluoro-2-((2-((2-(trimethylsilyl) ethoxy)methyl)-2H-tetrazol-5-yl)methyl) butanoyl) oxazolidin-2-one and (4R,5S)-4-methyl-5-phenyl-3-((R)-4,4,4-trifluoro-2-((1-((2-(trimethylsilyl)ethoxy)methyl)-1H-tetrazol-5-yl)methyl)butanoyl)oxazolidin-2-one. LC-MS [M+1]: 514.7.

Step F: (R)-4,4,4-trifluoro-2-((1-((2-(trimethylsilyl)ethoxy)methyl)-1H-tetrazol-5-yl)methyl)butanoic acid (4R,5S)-4-methyl-5-phenyl-3-((R)-4,4,4-trifluoro-2-((1-((2-(trimethylsilyl)ethoxy)methyl)-1H-tetrazol-5-yl)methyl) butanoyl)oxazolidin-2-one (1.084 g, 2.111 mmol) was dissolved in THF (15 ml) and cooled to 0° C. To this was added 0° C. pre-cooled mixture of lithium hydroxide monohydrate (0.177 g, 4.22 mmol) in water (4 ml) and H₂O₂ (1.848 ml, 30%, 21.11 mmol). The mixture was stirred at 0° C. for 1.5 hr. When LC-MS showed product peak, a solution of sodium sulfite (1.064 g, 8.44 mmol) and sodium bisulfate (0.593 g, 5.70 mmol) in 5 ml water was added to the reaction at 0° C. then stirred at RT for another 5 mins. The organic layer was separated and the acidic aqueous layer was extracted with ether (2×). The combined organic layers were washed with brine, dried and concentrated. The residue was taken up with ether (20 ml) and extracted with 1N NaOH (2×). The aqueous NaOH layer was acidified with 1N HCl and re-extracted with EtOAc (2×), dried over Na₂SO₄, filtered and concentrated to yield (R)-4,4,4-trifluoro-2-((1-((2-(trimethylsilyl)ethoxy)methyl)-1H-tetrazol-5-yl)methyl)butanoic acid. ¹H-NMR (500 MHz, CDCl3) δ ppm: −0.014 (6H, m), 0.91 (2H, m), 2.70 (1H, m), 2.87 (1H, m), 3.28 (1H, dd, J=16.18, 5.73 Hz), 3.39 (1H, dd, J=16.19, 7.63 Hz), 3.52 (1H, t, J=6.61 Hz), 3.56 (2H, dd, 9.37, 7.52 Hz), 5.72 (2H, m).

Step G: (S)-2-((S)-2-(6-bromopyridin-3-yl)-1-(1-((2-(trimethylsilyl)ethoxy)methyl)-1H-tetrazol-5-yl) ethyl)-4,4,4-trifluorobutanoic acid (R)-4,4,4-trifluoro-2-((1-((2-(trimethylsilyl)ethoxy) methyl)-1H-tetrazol-5-yl)methyl)butanoic acid (490 mg, 1.383 mmol) was dissolved in THF (15 ml) then cooled to −78° C. and then LDA (4.32 ml, 0.64 M, 2.77 mmol) was added. The reaction mixture was stirred for 45 mins then 2-bromo-5-(bromomethyl)pyridine (416 mg, 1.659 mmol) in THF was added. The reaction was stirred at −78° C. for 5 hrs, then quenched with saturated NH₄Cl solution, extracted with EtOAc (2×), dried (Na₂SO₄) then filtered and concentrated. The residue was purified by reverse phase HPLC with ACN and water buffered with 0.05% TFA to yield (S)-2-((S)-2-(6-bromopyridin-3-yl)-1-(1-((2-(trimethylsilyl)ethoxy) methyl)-1H-tetrazol-5-yl)ethyl)-4,4,4-trifluorobutanoic acid. LC-MS [M+2]: 525.6.

Step H: (S)-2-((S)-2-(6-aminopyridin-3-yl)-1-(1H-tetrazol-5-yl)ethyl)-4,4,4-trifluorobutanoic acid In a microwave tube, (S)-2-((S)-2-(6-bromopyridin-3-yl)-1-(1-((2-(trimethylsilyl)ethoxy) methyl)-1H-tetrazol-5-yl) ethyl)-4,4,4-trifluorobutanoic acid (100 mg, 0.191 mmol) was dissolved in ethylene glycol (1 ml) and then copper(I) oxide (2.73 mg, 0.019 mmol), N,N'-dimethylethylenediamine (4.72 μl, 0.044 mmol), K₂CO₃ (5.27 mg, 0.038 mmol) and ammonium hydroxide (1.220 ml, 8.77 mmol) were added. The tube was capped, degassed and purged with N₂ then heated at 80° C. for 16 hr. The reaction was filtered and concentrated then purified by reverse phase HPLC with ACN and water buffered with 0.05% TFA to yield (S)-2-((S)-2-(6-aminopyridin-3-yl)-1-(1-((2-(trimethylsilyl) ethoxy)methyl)-1H-tetrazol-5-yl)ethyl)-4,4,4-trifluorobutanoic acid. LC-MS [M+1]: 461.2

(S)-2-((S)-2-(6-aminopyridin-3-yl)-1-(1-((2-(trimethylsilyl)ethoxy)methyl)-1H-tetrazol-5-yl)ethyl)-4,4,4-trifluorobutanoic acid was dissolved in TFA (3 ml)/H₂O (0.3 ml) and stirred at RT for 16 hr. The residue was purified by reverse phase HPLC with ACN and water buffered with 0.05% TFA to yield (S)-2-((S)-2-(6-aminopyridin-3-yl)-1-(1H-tetrazol-5-yl)ethyl)-4,4,4-trifluorobutanoic acid. LC-MS [M+1]: 331.2

EXAMPLE 436

(S)-4,4,4-trifluoro-2-((S)-2-(6-((2-hydroxyethyl) amino)pyridin-3-yl)-1-(1H-tetrazol-5-yl)ethyl)butanoic acid

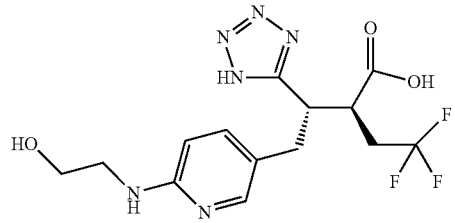 [SMILES: O=C(O)[C@@H](CC(F)(F)F)[C@H](Cc1ccc(NCCO)nc1)c1nnn[nH]1]

In a 5 ml microwave tube, (S)-2-((S)-2-(6-bromopyridin-3-yl)-1-(1-((2-(trimethylsilyl) ethoxy)methyl)-1H-tetrazol-5-yl)ethyl)-4,4,4-trifluorobutanoic acid (EXAMPLE 435, step G, 60 mg, 0.114 mmol), 2-aminoethanol (10.36 μl, 0.172 mmol), Cs₂CO₃ (74.6 mg, 0.229 mmol) and Buchwald's bis((2-isobutyrylcyclohex-1-en-1-yl)oxy)copper catalyst (9.11 mg, 0.023 mmol) were suspended in DMF (1 ml) then degassed, backfilled and sealed under nitrogen. The reaction mixture was heated at 100° C. for 24 hr. The reaction was filtered and concentrated. Then the residue was purified by reverse phase HPLC with ACN and water buffered with 0.05% TFA to yield 1:1 mixture of (S)-2-((S)-2-(6-(2-aminoethoxy)pyridin-3-yl)-1-(1-((2-(trimethylsilyl)ethoxy)methyl)-1H-tetrazol-5-yl)ethyl)-4,4,4-trifluorobutanoic acid and (S)-4,4,4-trifluoro-2-((S)-2-(6-((2-hydroxyethyl)amino)pyridin-3-yl)-1-(1-((2-(trimethylsilyl)ethoxy)methyl)-1H-tetrazol-5-yl)ethyl)butanoic acid. LC/MS [M+H]+: 505.2. The above mixture was stirred in TFA (3 ml) with water (0.3 ml) for 2 hr. The reaction was concentrated and purified by reverse phase HPLC with ACN and water buffered with 0.05% TFA and (S)-4,4,4-trifluoro-2-((S)-2-(6-((2-hydroxyethyl) amino)pyridin-3-yl)-1-(1H-tetrazol-5-yl)ethyl)butanoic acid was isolated. LC/MS [M+H]+: 375.1.

EXAMPLE 437

(S)-2-((S)-2-(isoindolin-5-yl)-1-(1H-tetrazol-5-yl)ethyl)pentanoic acid compound with 2,2,2-trifluoroacetic acid (1:1)

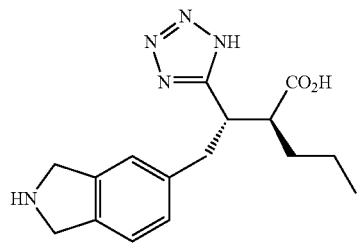 [SMILES: CCC[C@H](C(=O)O)[C@H](Cc1ccc2c(c1)CNC2)c1nnn[nH]1]

To a solution of (S)-2-((1-((2-(trimethylsilyl)ethoxy)methyl)-1H-tetrazol-5-yl)methyl)pentanoic acid (112 mg, 0.356 mmol) in THF was added lithium diisopropylamide (0.445 ml, 0.890 mmol) at −78° C. The mixture was allowed to stir at −78° C. for 40 minutes, and then tert-butyl 5-(bromomethyl)isoindoline-2-carboxylate (122 mg, 0.392 mmol) was added. The reaction was warmed up to rt naturally and stirred overnight. To the mixture was added saturated aq. NH4Cl and EtOAc for partitioning. The organic layer was separated, dried over Na2SO4, and evaporated to dryness. The crude was used directly.

In a vial, the crude material of (S)-2-((S)-2-(2-(tert-butoxycarbonyl)isoindolin-5-yl)-1-(1-((2-(trimethylsilyl)ethoxy)methyl)-1H-tetrazol-5-yl)ethyl)pentanoic acid (~194 mg, 0.355 mmol) was dissolved in EtOH (6 ml)/6 ml 1N HCl, capped and heated at 60° C. overnight.

The reaction mixture was concentrated and the residue was purified by prep. HPLC to obtain the TFA salt of the desired product. LC-MS m/z [M+1]+ 316.17

EXAMPLES 438-447

Parallel synthesis of (2S)-2-[(1S)-2-[3'-fluoro-4'-substituted phenyl]-1-(2H-tetrazol-5-yl)ethyl]-4-methylhexanoic acid

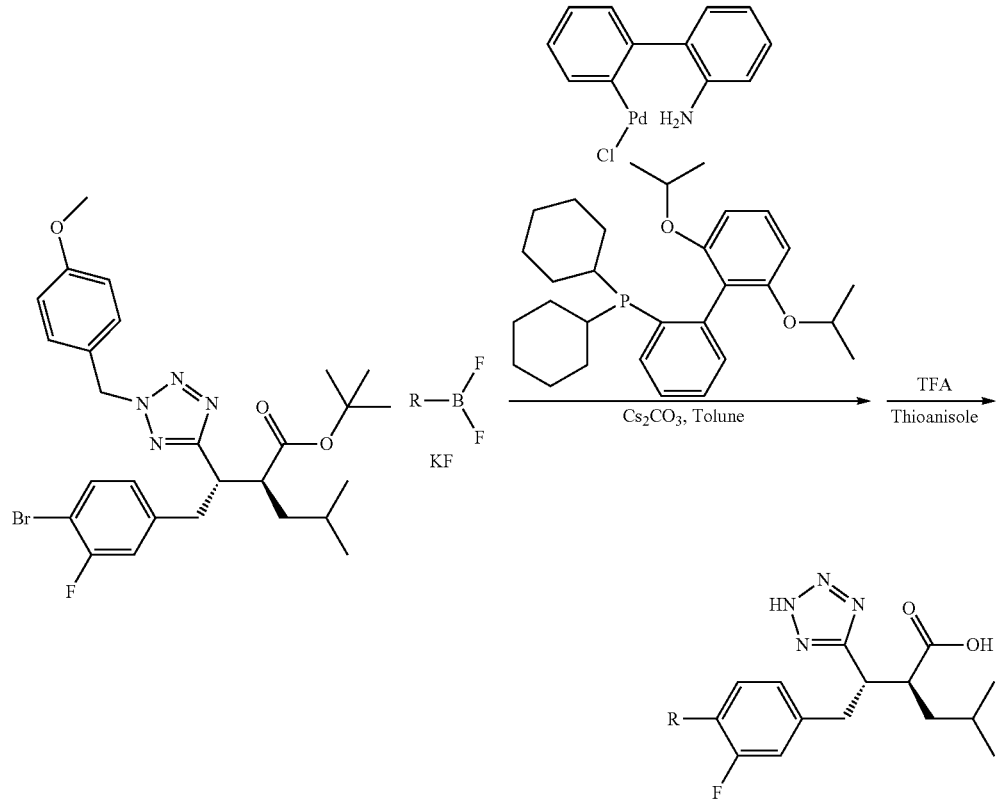

Step A: Palladium Catalyzed C—N Coupling of Arylbromide and Secondary Amines.

Into 2 dram vials were added substituted trifluro borates potassium salts (0.4 mmol) and palladium catalyst (8.2 mg, 10 μmol) and cesium carbonate (66.5 mg, 0.2 mmol). In a glove box, 1 mL of solution of (S)-tert-butyl 2-((S)-2-(4-bromo-3-fluorophenyl)-1-(2-(4-methoxybenzyl)-2H-tetrazol-5-yl)ethyl)-4-methylpentanoate (40 mg, 0.071 mmol) in toluene was added into each vial. The vials were capped and heated at 100° C. with stirring for 20 hr (overnight). After the vials were cooled down to room temperature, the solvent was removed in a Genevac evaporator (Stone Ridge, N.Y.). Into each residue was added 600 μL of H$_2$O and 2 mL of DCM. The organic layers were transferred into 2 dram vials. The organic solvent was removed in the evaporator to afford the crude intermediates.

Step B: Removal of the Tert-Butyl and p-Methoxybenzyl (PMB) Protecting Group Under Acidic Conditions.

Into each vial was added a solution of thioanisole (0.3 mL), DCM (0.3 mL) in TFA (0.3 mL). The vials were agitated at 25° C. for 16 hr. The solvent was removed in a GeneVac evaporator. Into each vial was added a solution of thioanisole (0.3 mL), DCM (0.3 mL) in TFA (0.3 mL). The vials were agitated at 55° C. for 6 hr. The solvent was removed in a Genevac evaporator. The residues were dissolved in 1.3 mL of DMSO. Each crude mixture was filtered into a 96-well tray and purified by HPLC to afford the examples 438 to 447.

| Ex. No. | RBF2.KF | Structure | Name | Calc'd Mass [M + H]$^+$ | LC/MS m/e [M + H]$^+$ |
|---|---|---|---|---|---|
| 438 | 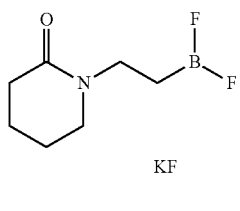 [SMILES: O=C1CCCCN1CCB(F)F ; "KF"] | 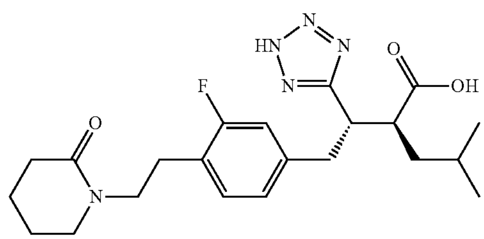 [SMILES: CC(C)C[C@H](C(=O)O)[C@H](Cc1ccc(CCN2CCCCC2=O)c(F)c1)c1nn[nH]n1] | (S)-2-((S)-2-(3-fluoro-4-(2-(2-oxopiperidin-1-yl)ethyl)phenyl)-1-(2H-tetrazol-5-yl)ethyl)-4-methylpentanoic acid | 432.23 | 432.23 |
| 439 | 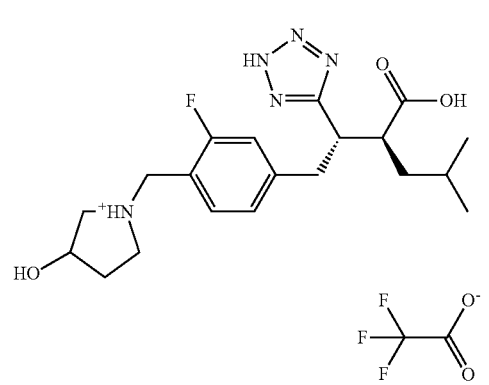 | 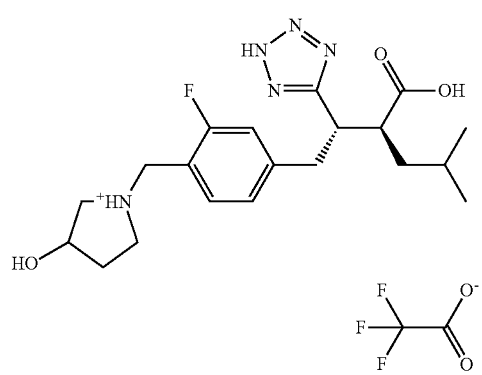 [SMILES: CC(C)C[C@H](C(=O)O)[C@H](Cc1ccc(C[NH+]2CCC(O)C2)c(F)c1)c1nn[nH]n1 ; O=C([O-])C(F)(F)F] | 5-((2S,3S)-3-carboxy-1-(3-fluoro-4-((3-hydroxypyrrolidin-1-yl)methyl)phenyl)-5-methylhexan-2-yl)-2H-tetrazol-3-ium 2,2,2-trifluoroacetate | 406.23 | 406.22 |
| 440 | 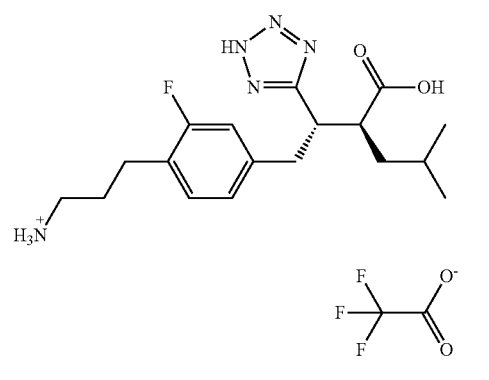 | 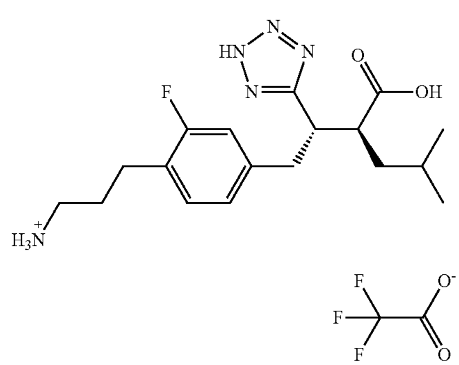 [SMILES: CC(C)C[C@H](C(=O)O)[C@H](Cc1ccc(CCCN)c(F)c1)c1nn[nH]n1 ; O=C([O-])C(F)(F)F] | 5-((2S,3S)-1-(4-(3-aminopropyl)-3-fluorophenyl)-3-carboxy-5-methylhexan-2-yl)-2H-tetrazol-3-ium 2,2,2-trifluoroacetate | 364.21 | 364.21 |

-continued

| Ex. No. | RBF2.KF | Structure | Name | Calc'd Mass [M + H]+ | LC/MS m/e [M + H]+ |
|---|---|---|---|---|---|
| 441 | 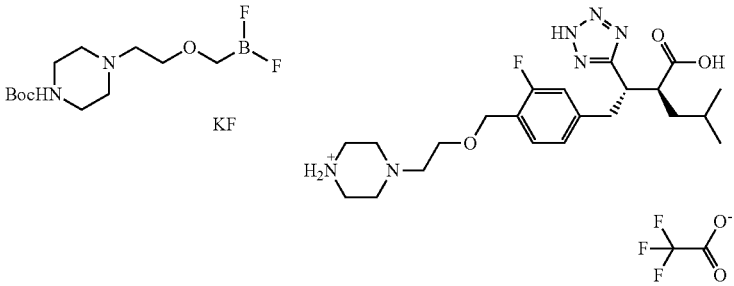 KF | 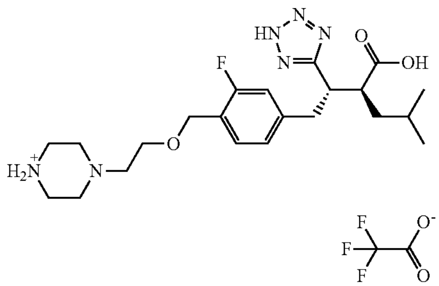 [SMILES: CC(C)C[C@H](C(=O)O)[C@H](Cc1ccc(COCCN2CCNCC2)c(F)c1)c1nn[nH]n1 ; O=C([O-])C(F)(F)F] | 5-((2S,3S)-3-carboxy-1-(3-fluoro-4-((2-(piperazin-1-yl)ethoxy)methyl)phenyl)-5-methylhexan-2-yl)-4422H-tetrazol-3-ium 2,2,2-trifluoroacetate | 449.26 | 449.26 |
| 442 | 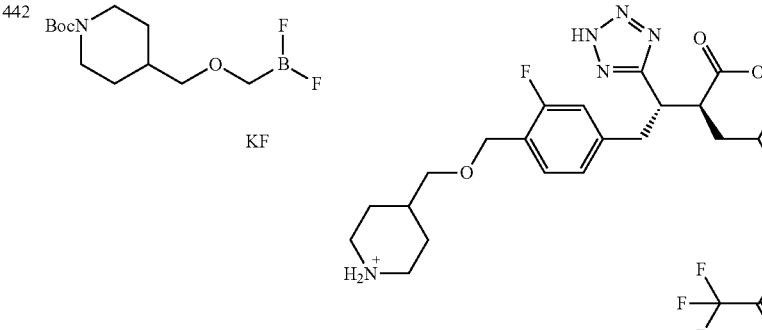 KF | 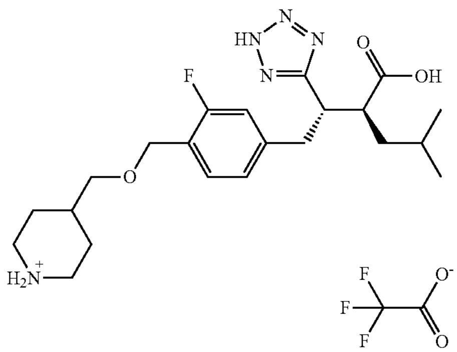 [SMILES: CC(C)C[C@H](C(=O)O)[C@H](Cc1ccc(COCC2CCNCC2)c(F)c1)c1nn[nH]n1 ; O=C([O-])C(F)(F)F] | 5-((2S,3S)-3-carboxy-1-(3-fluoro-4-((piperidin-4-ylmethoxy)methyl)phenyl)-5-methylhexan-2-yl)-2H-tetrazol-3-ium 2,2,2-trifluoroacetate | 434.25 | 434.25 |
| 443 | 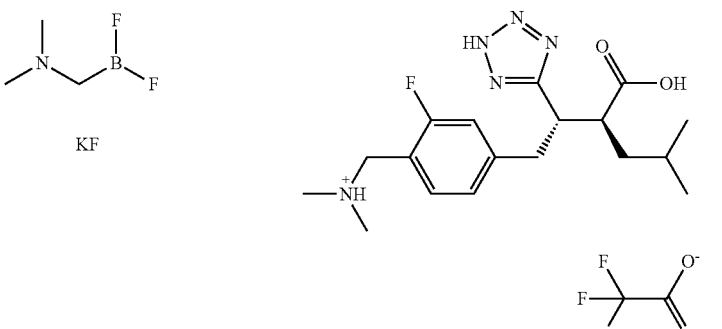 KF | 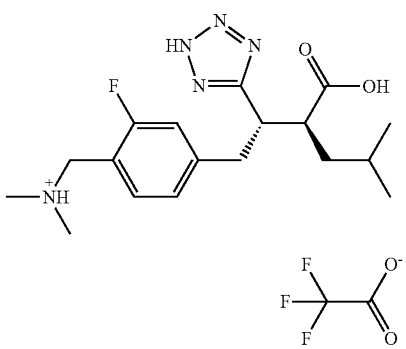 [SMILES: CC(C)C[C@H](C(=O)O)[C@H](Cc1ccc(CN(C)C)c(F)c1)c1nn[nH]n1 ; O=C([O-])C(F)(F)F] | 1-(4-((2S,3S)-3-carboxy-5-methyl-2-(2H-tetrazol-5-yl)hexyl)-2-fluorophenyl)-N,N-dimethylmethan-aminium 2,2,2-trifluoroacetate | 364.21 | 364.21 |
| 444 | 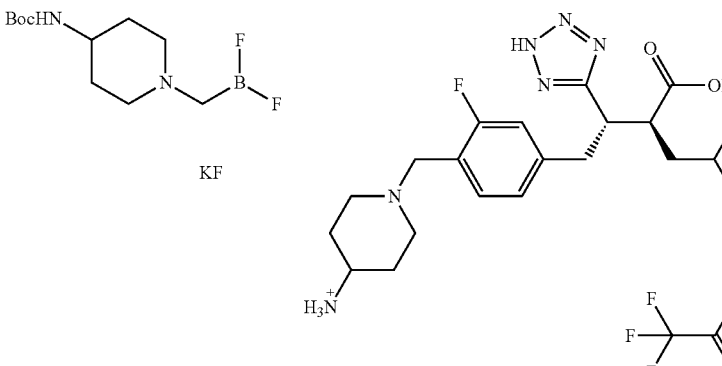 KF | 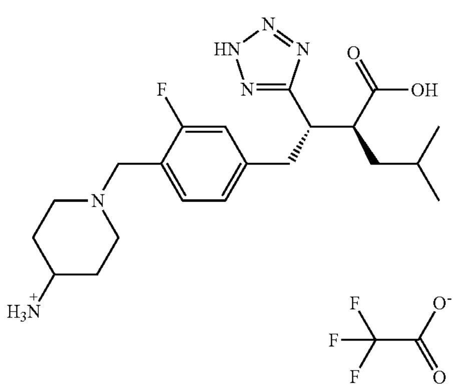 [SMILES: CC(C)C[C@H](C(=O)O)[C@H](Cc1ccc(CN2CCC(N)CC2)c(F)c1)c1nn[nH]n1 ; O=C([O-])C(F)(F)F] | 1-(4-((2S,3S)-3-carboxy-5-methyl-2-(2H-tetrazol-5-yl)hexyl)-2-fluorobenzyl)piperidin-4-aminium 2,2,2-trifluoroacetate | 419.25 | 419.25 |

| Ex. No. | RBF2.KF | Structure | Name | Calc'd Mass [M + H]+ | LC/MS m/e [M + H]+ |
|---|---|---|---|---|---|
| 445 | 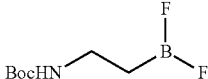 | 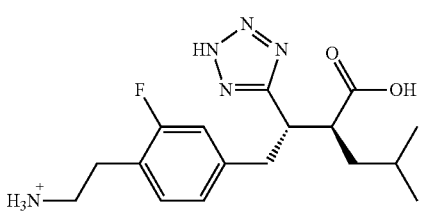 | 2-(4-((2S,3S)-3-carboxy-5-methyl-2-(2H-tetrazol-5-yl)hexyl)-2-fluorophenyl)ethanaminium 2,2,2-trifluoroacetate | 350.19 | 350.19 |
| 446 | 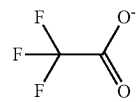 | 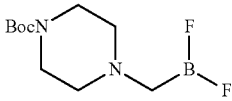 | 4-(4-((2S,3S)-3-carboxy-5-methyl-2-(2H-tetrazol-5-yl)hexyl)-2-fluorobenzyl)piperazin-1-ium 2,2,2-trifluoroacetate | 406.23 | 406.23 |
| 447 | 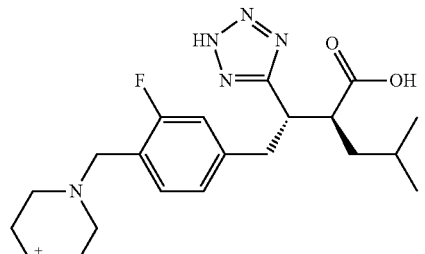 | 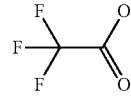 | 4-((4-((2S,3S)-3-carboxy-5-methyl-2-(2H-tetrazol-5-yl)hexyl)-2-fluorobenzyl)oxy)piperidin-1-ium 2,2,2-trifluoroacetate | 420.23 | 420.22 |

EXAMPLES 448-449

Parallel synthesis of (2R)-2-[(1R)-2-[2'-substituted phenyl]-1-(2H-tetrazol-5-yl)ethyl]hexanoic acids

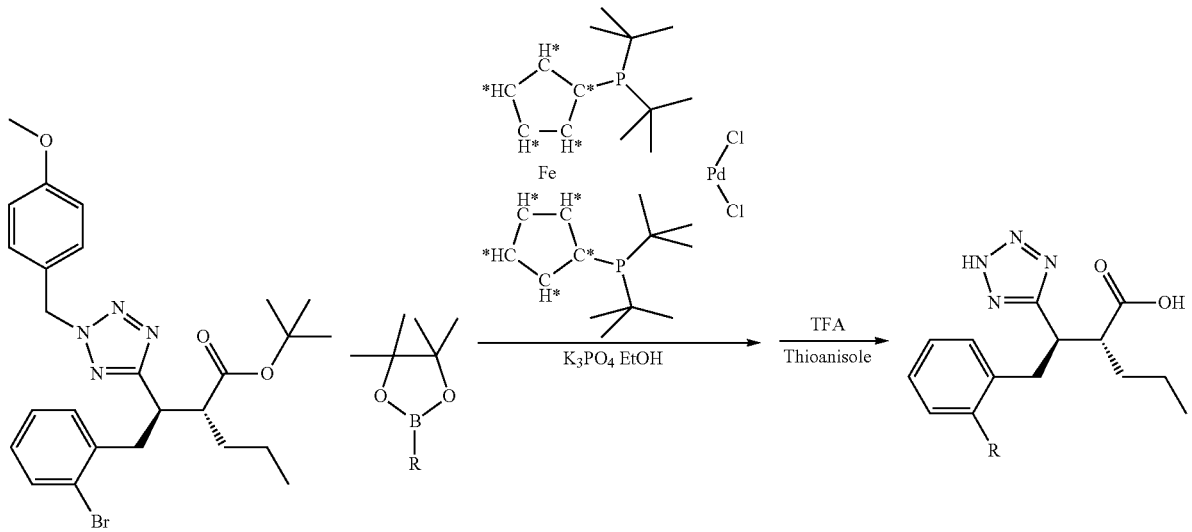

Step A: Palladium Catalyzed C—C Coupling of Arylbromide and Boronic Esters.

Into 2 dram vials were added substituted boronic acid or ester (0.1 mmol) and palladium catalyst (5 mg, 7.6 µmol) and 230 µL of 1 N degassed aq. $K_3PO_4$ solution. In a glove box, 1 mL of a solution of (R)-tert-butyl 2-((R)-2-(2-bromophenyl)-1-(2-(4-methoxybenzyl)-2H-tetrazol-5-yl)ethyl)pentanoate (40 mg, 0.076 mmol) in EtOH was added into each vial. The vials were capped and heated at 75° C. with stirring for 20 hr (overnight). After the vials were cooled down to room temperature, the solvent was removed in a Genevac evaporator. Into each residue was added 600 µL of $H_2O$ and 2 mL of DCM. The organic layers were transferred into 2 dram vials. The organic solvent was removed in the evaporator to afford the crude intermediates.

Step B: Removal of the Tert-Butyl and p-Methoxybenzyl (PMB) Protecting Group Under Acidic Conditions.

Into each vial was added a solution of thioanisole (0.3 mL), DCM (0.3 mL) in TFA (0.3 mL). The vials were agitated at 25° C. for 16 hr. The solvent was removed in a Genevac evaporator. Into each vial was added a solution of thioanisole (0.3 mL), DCM (0.3 mL) in TFA (0.3 mL). The vials were agitated at 55° C. for 6 hr. The solvent was removed in a Genevac evaporator. The residues were dissolved in 1.3 mL of DMSO. Each crude mixture was filtered into a 96-well tray and purified by HPLC to afford the examples 448 to 449.

| Ex. No. | RB(OH)2 | Structure | Name | Calc'd Mass [M + H]+ | LC/MS m/e [M + H]+ |
|---|---|---|---|---|---|
| 448 | | 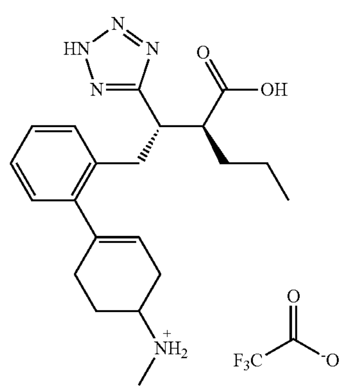 | 2'-((2S,3S)-3-carboxy-2-(2H-tetrazol-5-yl)hexyl)-N-methyl-2,3,4,5-tetrahydro-[1,1'-biphenyl]-4-aminium 2,2,2-trifluoroacetate | 384.23 | 384.23 |

| Ex. No. | RB(OH)2 | Structure | Name | Calc'd Mass [M + H]+ | LC/MS m/e [M + H]+ |
|---|---|---|---|---|---|
| 449 | NHBoc | 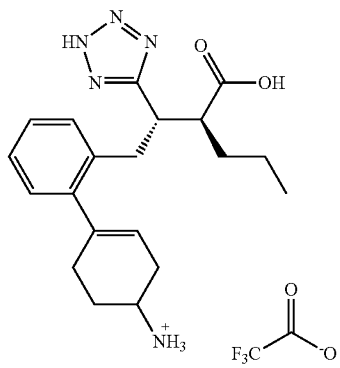 | 2'-((2S,3S)-3-carboxy-2-(2H-tetrazol-5-yl)hexyl)-2,3,4,5-tetrahydro-[1,1'-biphenyl]-4-aminium 2,2,2-trifluoroacetate | 370.22 | 370.22 |

EXAMPLES 450-456

Parallel synthesis of (2R)-2-[(1R)-2-[3-fluoro-4'-substituted phenyl]-1-(2H-tetrazol-5-yl)ethyl]-4-methylhexanoic acid

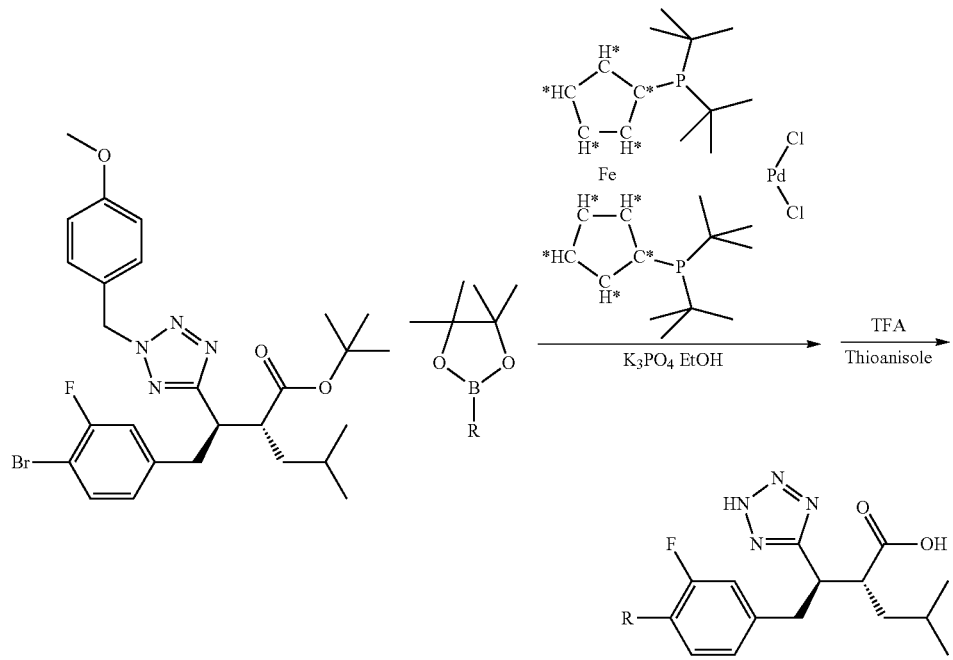

Step A: Palladium Catalyzed C—C Coupling of Arylbromide and Boronic Esters.

Into 2 dram vials were added substituted boronic acid or ester (0.1 mmol) and palladium catalyst (5 mg, 7.6 μmol) and 230 μL of 1 N degassed aq. K₃PO₄ solution. In a glove box, 1 mL of solution of (R)-tert-butyl 2-((R)-2-(4-bromo-3-fluorophenyl)-1-(2-(4-methoxybenzyl)-2H-tetrazol-5-yl)ethyl)-4-methylpentanoate (40 mg, 0.076 mmol) in EtOH was added into each vial. The vials were capped and heated at 75° C. with stirring for 20 hr (overnight). After the vials were cooled down to room temperature, the solvent was removed in Genevac evaporator. Into each residue was added 600 μL of H₂O and 2 mL of DCM. The organic layers were transferred into 2 dram vials. The organic solvent was removed in Genevac evaporator to afford the crude intermediates.

Step B: Removal of the Tert-Butyl & p-Methoxybenzyl (PMB) Protecting Group Under Acidic Conditions.

Into each vial was added a solution of thioanisole (0.3 mL), DCM (0.3 mL) in TFA (0.3 mL). The vials were agitated at 25° C. for 16 hr. The solvent was removed in a Genevac evaporator. Into each vial was added a solution of thioanisole (0.3 mL), DCM (0.3 mL) in TFA (0.3 mL). The vials were agitated at 55° C. for 6 hr. The solvent was removed in a Genevac evaporator. The residues were dissolved in 1.3 mL of DMSO. Each crude mixture was filtered into a 96-well tray and purified by HPLC to afford the examples 450 to 456.

| Ex. No. | RB(OH)2 | Structure | Name | Calc'd Mass [M + H]+ | LC/MS m/e [M + H]+ |
|---|---|---|---|---|---|
| 450 | | 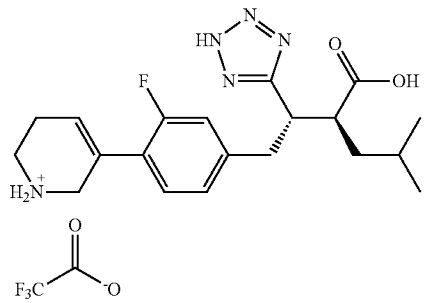 | 5-(4-((2S,3S)-3-carboxy-5-methyl-2-(2H-tetrazol-5-yl)hexyl)-2-fluorophenyl)-1,2,3,6-tetrahydropyridin-1-ium 2,2,2-trifluoroacetate | 388.21 | 388.21 |
| 451 | | 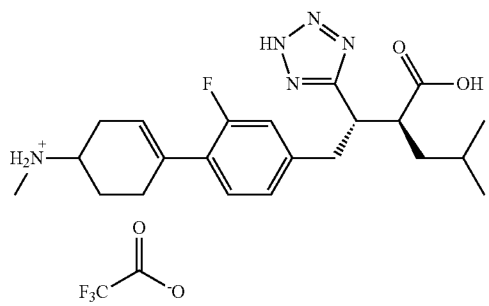 | 4'-((2S,3S)-3-carboxy-5-methyl-2-(2H-tetrazol-5-yl)hexyl)-2'-fluoro-N-methyl-2,3,4,5-tetrahydro-[1,1'-biphenyl]-4-aminium 2,2,2-trifluoroacetate | 416.24 | 416.24 |
| 452 | | 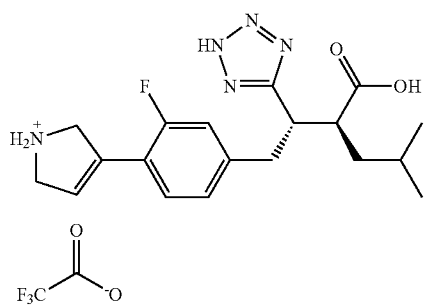 | 3-(4-((2S,3S)-3-carboxy-5-methyl-2-(2H-tetrazol-5-yl)hexyl)-2-fluorophenyl)-2,5-dihydro-1H-pyrrol-1-ium 2,2,2-trifluoroacetate | 374.20 | 374.19 |
| 453 | | 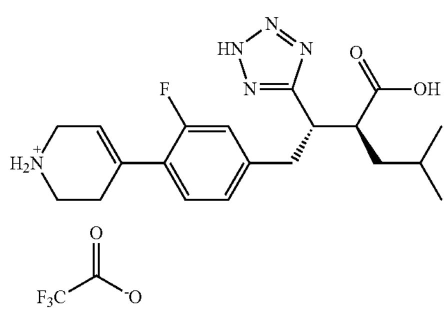 | 4-(4-((2S,3S)-3-carboxy-5-methyl-2-(2H-tetrazol-5-yl)hexyl)-2-fluorophenyl)-1,2,3,6-tetrahydropyridin-1-ium 2,2,2-trifluoroacetate | 402.22 | 402.22 |
| 454 | | 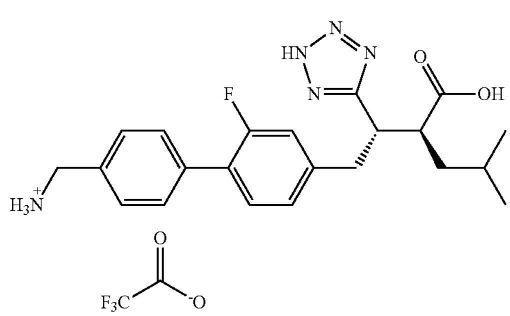 | (4'-((2S,3S)-3-carboxy-5-methyl-2-(2H-tetrazol-5-yl)hexyl)-2'-fluoro-[1,1'-biphenyl]-4-yl)methanaminium 2,2,2-trifluoroacetate | 412.22 | 412.21 |

-continued

| Ex. No. | RB(OH)2 | Structure | Name | Calc'd Mass [M + H]+ | LC/MS m/e [M + H]+ |
|---|---|---|---|---|---|
| 455 | NHBoc pinacol boronate (cyclohexenyl) | H3N+-cyclohexenyl-biphenyl(F)-CH2-CH(tetrazolylmethyl)-CH(iPr)-COOH · F3CCOO− | 4'-((2S,3S)-3-carboxy-5-methyl-2-(2H-tetrazol-5-yl)hexyl)-2'-fluoro-2,3,4,5-tetrahydro-[1,1'-biphenyl]-4-aminium 2,2,2-trifluoroacetate | 402.22 | 402.22 |
| 456 | O=C(NH2)-phenyl-pinacol boronate | H2N(O=C)-phenyl-biphenyl(F)-CH2-CH(tetrazolyl)-CH(iPr)-COOH | (S)-2-((S)-2-(4'-carbamoyl-2-fluoro-[1,1'-biphenyl]-4-yl)-1-(2H-tetrazol-5-yl)ethyl)-4-methylpentanoic acid | 426.20 | 426.19 |

What is claimed:

1. A compound of formula Ia or Ib

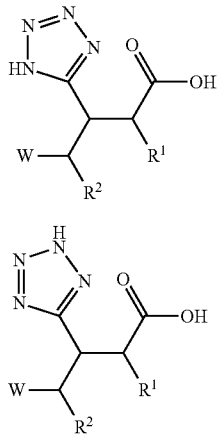

or a pharmaceutically acceptable salt thereof, wherein:

$R_1$ is:
- a) —$C_{2-8}$ alkyl,
- b) —$C_{1-4}$ alkyl substituted with 1, 2, or 3 halo substituents or 1 substituent selected from —$C_{3-6}$cycloalkyl, —CN, —C(=O)NH$_2$, —OH, —$C_{1-3}$alkoxy, phenyl, and HetY,
- c) —$C_{2-6}$alkenyl,
- d) —$C_{3-6}$cycloalkyl, or
- e) HetY, $R^2$ is hydrogen, $C_{1-4}$alkyl, or $C_{1-4}$alkoxy;

HetY is a 4- to 6-membered saturated monocyclic ring with 1 heteroatom ring atom selected from N and O;

W is AryA; HetA; —(CH$_2$)$_{1-2}$-AryA; —CH(CH$_3$)-phenyl; or cyclohexyl substituted with —COOH or —NH$_2$;

AryA is an aromatic ring system selected from:
- a) 5- to 6-membered monocyclic aromatic ring with 0, 1, 2 or 3 heteroatom ring atoms independently selected from N and S, optionally substituted with 1 or 2 substituents R; or
- b) 9- to 11-membered bicyclic aromatic ring system with 1, 2 or 3 heteroatom ring atoms selected from N, O, and S, optionally substituted with 1 substituent R' selected from Br, $C_{1-6}$alkyl, —NH$_2$, and —NHCH$_2$CH$_2$OH;

HetA is a piperidinyl ring optionally substituted with 1 substituent selected from —C(=O)CH$_3$;

each R is independently
halo;
—CF$_3$;
$C_{1-6}$ alkyl optionally substituted with —NR$^x$R$^y$ or 1 or 2 —OH;
$C_{3-6}$ cycloalkenyl optionally substituted with —NR$^x$R$^y$;
—(CH$_2$)$_{0-1}$NHR$^z$;
—CN;
—C(NH$_2$)=NOH;
—C(=O)NR$^x$R$^y$;
—C(=O)NHR$^z$;
—C(=O)OH;
—NR$^x$R$^y$;
—N$^+$(CH$_3$)$_3$;
—NHCH$_2$CH$_2$CH(CF$_3$)NH$_2$;
—NHCH$_2$C(=O)N(CH$_3$)$_2$;
—NHCH$_2$CH$_2$SO$_2$NH$_2$;
—NHC(=NH)NH$_2$;

—OH;
—OR$^z$;
—OCH$_2$CH(NH$_2$)CH$_2$OH;
—SCH$_3$;
—SO$_2$R$^w$;
AryB;
—NH(CH$_2$)$_{0-2}$-AryB;
—O-AryB;
—(CH$_2$)$_{0-2}$-HetB;
—CH$_2$O(CH$_2$)$_{0-2}$-HetB;
—C(=O)-HetB;
—NH(CH$_2$)$_{0-2}$-HetB; or
—O-HetB;
AryB is
  a) a 5- to 6-membered monocyclic aromatic ring with 0, 1, or 2 heteroatom ring atoms independently selected from N and S, optionally substituted with 1, 2 or 3 substituents independently selected from
    F;
    —CH$_3$;
    —CH$_2$NH$_2$;
    —CH$_2$N(CH$_3$)$_2$;
    —CH$_2$CH$_2$NH$_2$;
    —CH$_2$C(CH$_3$)$_2$NH$_2$;
    —CH$_2$OH;
    —C(CH$_3$)$_2$OH;
    —C(=O)NR$^x$R$^y$;
    —NR$^x$R$^y$;
    —NHC(=O)CH$_3$;
    —NHSO$_2$CH$_3$;
    —N(CH$_3$)SO$_2$CH$_3$;
    —OH;
    —OCH$_3$;
    —SO$_2$CH$_3$;
    —SO$_2$NH$_2$;
    —(CH$_2$)$_{0-1}$-AryC;
    —C$_0$-C$_2$alkyl-HetC; and
    —O-HetC;
  b) triazolyl;
  c) tetrazolyl;
  d) 1,3-dimethylpyrimidine-2,4(1H,3H)-dione; or
  e) a 9- to 10-membered bicyclic aromatic ring with 0, 1, 2 or 3 heteroatom ring atoms independently selected from N or O, optionally substituted with Br, —CH$_3$, —CN, —NH$_2$, or oxo;
HetB is
  a) a 4- to 6-membered saturated or monosaturated monocyclic ring with 1 or 2 heteroatom ring atoms independently selected from N and O, optionally substituted with 1, 2, 3, or 4 substituents independently selected from halo; —CF$_3$; C$_{1-6}$ alkyl, C$_{1-6}$aminoalkyl; C$_{1-6}$hydroxyalkyl; —CH(=NH); —C(=NH)NH$_2$; —C(=O)CH$_3$; —C(=O)NHCH$_3$; —C(=O)NHSO$_2$CH$_3$; —NH$_2$;
  —NHSO$_2$CH$_3$, —OH; oxo; —SO$_2$CH$_3$; AryC; or HetC; or
  b) a 8- to 10-membered bicyclic saturated ring system with 1, 2 or 3 ring atoms independently selected from N or O, optionally substituted with 1 or 2 substituents independently selected from —CH$_3$ and oxo; wherein the rings in the bicyclic ring system are fused or spirocyclic;
AryC is phenyl, pyridinyl, or tetrazolyl;
HetC is a 4- to 6-membered saturated monocyclic ring with 1 or 2 heteroatom ring atoms independently selected from N and O, optionally substituted with 1 or 2 substituents selected from —CH$_3$, —OH and oxo;

each R$^x$ and R$^y$ is independently hydrogen or C$_{1-6}$ alkyl;
each R$^z$ is independently —(CH$_2$)$_{0-1}$-C$_{3-6}$cycloalkyl optionally substituted with —NH$_2$;
C$_{1-6}$aminoalkyl; or C$_{1-6}$hydroxyalkyl; and
R$^w$ is selected from C$_{1-8}$alkyl and C$_{3-6}$cycloalkyl.

2. The compound of claim 1, which has the formula Ic or Id

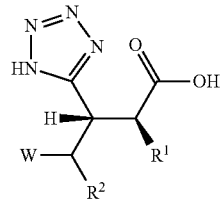

(Ic)

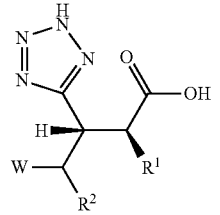

(Id)

or a pharmaceutically acceptable salt thereof.

3. The compound of claim 2, or a pharmaceutically acceptable salt thereof, wherein R$^1$ is —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)CH$_2$CH$_3$, —C(CH$_3$)$_3$, —CH$_2$CH$_2$CH$_2$CH$_2$CH$_3$, —CH(CH$_3$)CH$_2$CH$_2$CH$_3$, —CH$_2$CH$_2$CH$_2$CH(CH$_3$)$_2$, —CH$_2$CH$_2$CH$_2$CH$_2$CH(CH$_3$)$_2$, —CH$_2$CH$_2$F, —CH$_2$CHF$_2$, —CH$_2$CF$_3$, —CH$_2$CH$_2$CH$_2$CF$_3$, —CH$_2$-cyclopropyl, —CH$_2$-cyclopentyl, —CH$_2$CH$_2$-cyclohexyl, —CH$_2$CH$_2$CH$_2$CH$_2$CN, —CH$_2$CH$_2$CH$_2$CH$_2$C(=O)NH$_2$, —CH$_2$CH$_2$CH$_2$CH$_2$OH, —CH$_2$CH$_2$CH$_2$OCH$_3$, —CH$_2$-phenyl, —CH$_2$CH$_2$CH$_2$CH$_2$-phenyl, CH$_2$—CH(CH$_3$)-phenyl, —CH$_2$CH$_2$CH$_2$-piperidinyl, —CH$_2$-oxetanyl, —CH$_2$CH=CH$_2$, —CH$_2$CH$_2$CH=C(CH$_3$)$_2$, cyclopentyl, tetrahydrofuranyl, or tetrahydropyranyl.

4. The compound of claim 3, or a pharmaceutically acceptable salt thereof, wherein W is

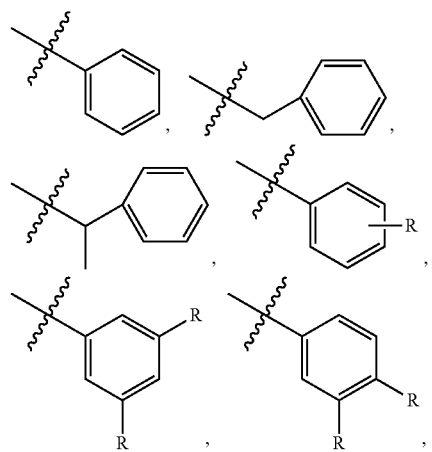

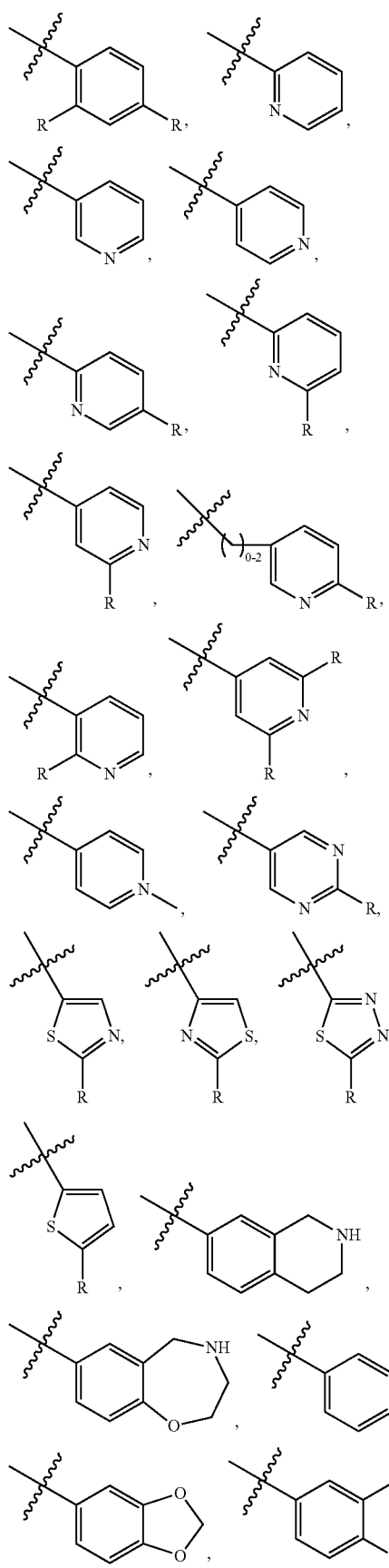
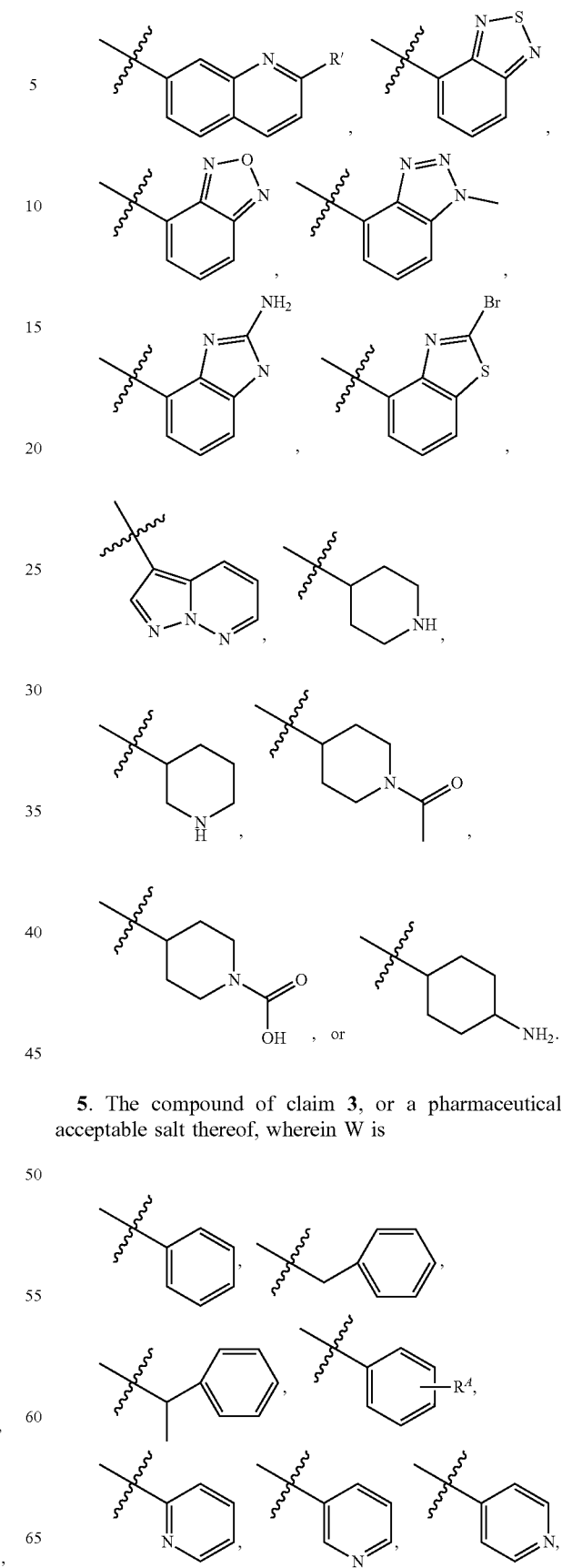
5. The compound of claim 3, or a pharmaceutically acceptable salt thereof, wherein W is

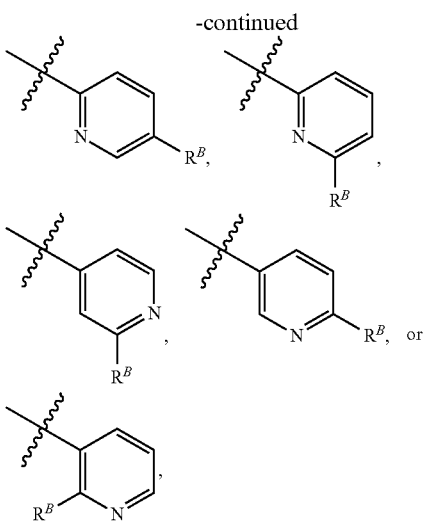

wherein
$R^A$ and $R^B$ are independently Br; F; Cl; —CF$_3$; —CH$_3$; —CH$_2$NH$_2$; —CH$_2$CH$_2$NH$_2$; —CN; —CH$_2$OH; —CONH$_2$; —CONCH$_3$; —CON(CH$_3$)$_2$; —CONH-cyclopropyl; —CONHCH$_2$-cyclopropyl; —CONHCH$_2$CH$_2$NH$_2$; —CONHCH$_2$CH$_2$OH; —COOH; —NH$_2$; —NHCH$_3$; —NHCH$_2$CH$_2$OH; —NHC(=NH)NH$_2$; —OH; —OCH$_2$CH$_2$NH$_2$; —NH-cyclopentyl-NH$_2$; —SO$_2$CH$_3$; —SO$_2$-cyclopropyl; AryB; HetB; —CO-piperazinyl; —CH$_2$-tetrahydropyranyl; —CH$_2$-piperidinyl optionally substituted with —NH$_2$; —NH-pyrrolidinyl; —NHCH$_2$-piperidinyl with —OH; —NH-tetrahydroisoquinolinyl; —O-phenyl substituted with —CONH$_2$, —CH$_2$OH, —CH$_2$NH$_2$, —CH$_2$C(CH$_3$)$_2$NH$_2$, —CH(CH$_3$)NH$_2$, —CH$_2$CH$_2$NH$_2$, piperidinyl, pyrrolidinyl, or piperazinyl; —O-tetrahydroisoquinolinyl; —O-tetrahydroquinolinyl; or —O-pyridinyl optionally substituted with piperazinyl;

AryB is
1) phenyl substituted with —CH$_2$NH$_2$, —CH$_2$N(CH$_3$)$_2$, —CH$_2$OH, —CONH$_2$, —CONHCH$_3$, —NHSO$_2$CH$_3$, —SO$_2$CH$_3$, —SO$_2$NH$_2$, AryC, HetC, —CH$_2$-HetC, or tetrazolyl;
2) pyridinyl optionally substituted with —C(CH$_3$)$_2$OH, —NH$_2$, —N(CH$_3$)$_2$, —NH$_2$ or F;
3) piperazinyl optionally substituted with —CH$_3$, —CH$_2$-piperidinyl, —O-piperidinyl, or morpholinyl;
4) pyrimidinyl substituted with —NH$_2$, —N(CH$_3$)$_2$, —NHCH$_2$CH$_2$OH, —NHCOCH$_3$, —NCH$_3$SO$_2$CH$_3$, or HetC;
5) pyrazinyl substituted with two —CH$_3$;
6) pyrazolyl optionally substituted with 1 to 3 substitutents selected from —CH$_3$, phenyl, and —CH$_2$-pyridinyl;
7) dimethylpyrimidinedione;
8) tetrazolyl;
9) thiazolyl substituted with —CH$_2$OH;
10) 1,2,3,4-tetrahydroquinoline;
11) imidazopyridinone;
12) indazolyl;
13) isoindolinone;
14) isoindolinyl;
15) isoquinolinyl optionally substituted with —CN;
16) methylbenzotriazolyl;
17) benzooxazinone;
18) triazolopyridinyl; or
19) 1,2,3,4-tetrahydronaphthalen-2-amine;

HetB is
1) azetidinyl substituted with —NH$_2$; —CH$_2$NH$_2$; —CH$_2$CH$_2$NH$_2$; —C(CH$_3$)$_2$NH$_2$; —CH$_2$CH$_2$OH; —SO$_2$CH$_3$; morpholinyl; piperazinyl; (CH$_2$OH)$_2$; —CH$_2$NH$_2$ and —CH$_3$; or —OH and —CF$_3$;
2) pyrrolidinyl optionally substituted with —CH$_2$NH$_2$, —CH$_2$OH, —CONHCH$_3$, —NH$_2$, —OH, or AryC;
3) piperidinyl optionally substituted with —CH$_3$, —CH$_2$NH$_2$, —C(CH$_3$)$_2$NH$_2$, —CH$_2$OH, —CONHCH$_3$, —CH$_2$NHSO$_2$CH$_3$, —NH$_2$, —OH, —C(=NH)NH; —C(=NH$_2$)NH$_2$, or —CH=NH;
4) piperazinyl substituted with —CH$_3$, —CH$_2$OH, —CH$_2$CH$_2$OH, —COCH$_3$, =O, or AryC;
5) morpholinyl;
6) dihydropyrrolyl;
7) tetrahydropyridinyl optionally substituted with —CH$_3$;
8) octahydropyrrolo[1,2-a]pyrazine;
9) diazaspirononanyl;
10) diazaspirooctanyl;
11) 2,6-diazaspiro[3.4]octan-7-one; or
12) 7-methyl-5-oxa-2,7-diazaspiro[3.4]octan-6-one;

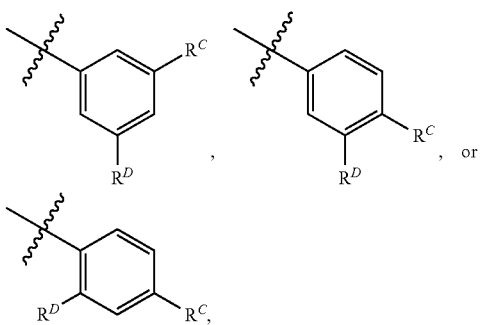

wherein
$R^C$ is F; Br; —CF$_3$; —CH$_2$NH$_2$; pyrrolidinyl; 2,5-dihydro-1H-pyrrole; pyridinyl substituted with —NH$_2$; or piperazinyl;
$R^D$ is F, Br, —CH$_3$, or —CF$_3$;

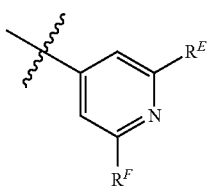

wherein
$R^E$ is Cl, —NH$_2$ or —NHCH$_2$CH$_2$OH;
$R^F$ is Cl;

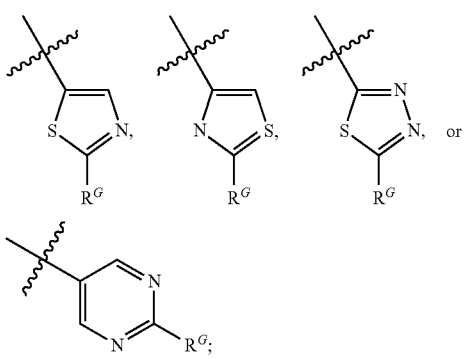

wherein $R^G$ is —$NH_2$, —$N(CH_3)_2$, —$NHCH_2CH_2OH$, —$SCH_3$, —$SO_2CH_3$, morpholinyl, pyrrolidinyl, piperidinyl, piperazinyl, 2,5-dihydro-1H-pyrrole, or —O-piperidinyl; or

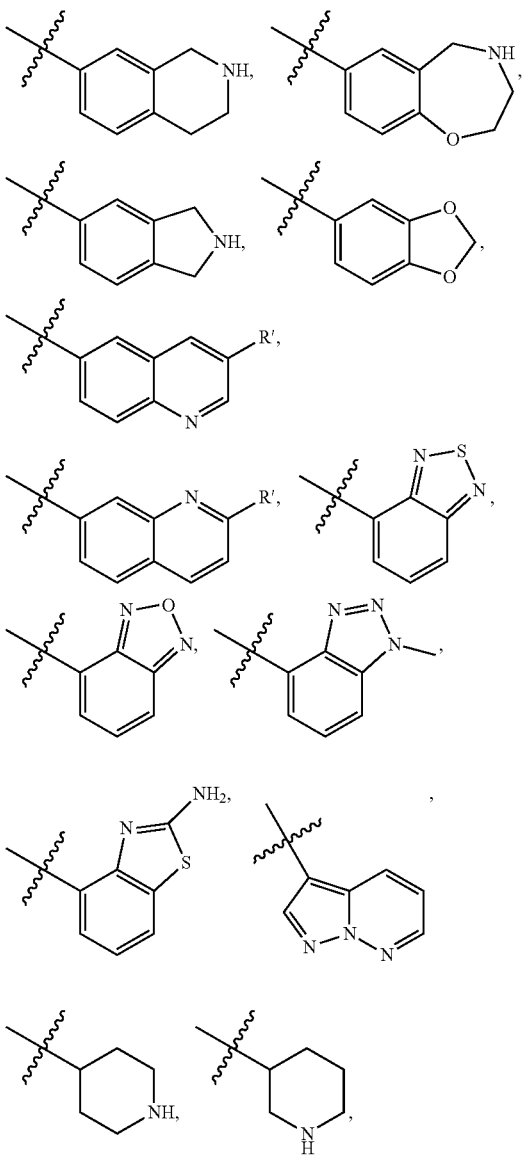

6. The compound of claim 5, or a pharmaceutically acceptable salt thereof, wherein:
$R_1$ is selected from the group consisting of:
 a) —$C_{2-4}$alkyl,
 b) ethyl substituted with three halo substituents, or
 c) —$C_{3-6}$cycloalkyl,
$R^2$ is hydrogen;
W is AryA; —$CH_2$-phenyl; or —$CH(CH_3)$-phenyl;
AryA is an aromatic ring system selected from:
 a) 5- to 6-membered monocyclic aromatic ring with 0, 1, or 2 heteroatom ring atoms independently selected from N and S. optionally substituted with 1 or 2 substituents R; or
 b) 9- to 10-membered bicyclic aromatic ring system with 1, 2 or 3 heteroatom ring atoms selected from N and S, substituted with 1 substituent selected from $C_{1-6}$alkyl and —$NH_2$;
each R is independently fluoro $NHR^z$, —$NR^xR_y$, —NHC(=NH)$NH_2$; —$OR^z$, AryB, —O-AryB, or —$(CH_2)_{0-1}$-HetB;
AryB is a 5- to 6-membered monocyclic aromatic ring with 0, 1, or 2 N ring atoms, optionally substituted with 1 substituent selected from —$CH_2NH_2$, —$CH_2OH$, —C(=O)$NR^xR^Y$, —$NR^xR^y$, —$NHSO_2CH_3$, and HetC;
HetB is a) a 5- to 6-membered saturated or monosaturated monocyclic ring with 1 or 2 N ring atoms, optionally substituted with 1 substituent selected from $C_{1-6}$hydroxyalkyl, —CH(=NH), —C(=NH)$NH_2$, and —OH; or
 b) a 9-membered saturated spirocyclic ring system with 2 N ring atoms;
HetC is a 6-membered saturated monocyclic ring with 1 N ring atom,
each $R^x$ and $R^y$ is independently hydrogen or methyl; and
each $R^z$ is independently $C_{1-6}$aminoalkyl or $C_{1-6}$hydroxyalkyl.

7. The compound of claim 6, or a pharmaceutically acceptable salt thereof, wherein
AryA is a monocyclic ring selected from thiazolyl, phenyl, and pyridinyl, wherein the monocyclic ring optionally substituted with 1 or 2 R substituents; or a bicyclic ring selected from quinolinyl, benzo[d]thiazolyl, and 1H-benzo [d][1,2,3]triazole, wherein the bicyclic is optionally substituted with 1 substituent selected from $C_{1-6}$alkyl and —$NH_2$;
AryB is a monocyclic ring selected from pyrazolyl, phenyl or pyridyl, wherein the monocyclic is optionally substituted with 1 substituent selected from —$CH_2NH_2$, —$CH_2OH$, —C(=O)$NR^xR^y$, —$NR^xR^y$, —$NHSO_2CH_3$, and HetC; and
HetB is a monocyclic ring selected from pyrrolidinyl, dihydropyrrolyl, piperidinyl, or piperazinyl, wherein the monocyclic is optionally substituted with 1 substituent selected from $C_{1-6}$hydroxyalkyl, —CH(=NH), —C(=NH)NH$_2$, and —OH; or diazaspirononanyl.

8. The compound of claim 7, or a pharmaceutically acceptable salt thereof, wherein W is
1) phenyl optionally substituted with
   a) phenyl substituted with —CONH$_2$, —NHSO$_2$CH$_3$, or piperidinyl,
   b) pyridinyl substituted with —NH$_2$,
   c) pyrrolidinyl,
   d) pyrrolidinyl and fluoro,
   e) piperidinyl substituted with —CH=NH,
   f) piperidinyl substituted with —CH(=NH)NH$_2$,
   g) piperizinyl and fluoro,
   h) dihydropyrrolyl,
   i) pyrazolyl, or
   j) —CH$_2$-piperazinyl;
2) —CH$_2$-phenyl;
3) —CH(CH$_3$)-phenyl;
4) pyridinyl optionally substituted with
   a) —NH$_2$,
   b) —NHCH$_3$,
   c) —NHCH$_2$CH$_2$NH$_2$,
   d) —NHCH$_2$CH$_2$OH,
   e) —NHC(=NH)NH$_2$,
   f) pyrrolidinyl optionally substituted with —OH,
   g) piperidinyl optionally substituted with —CH$_2$OH,
   h) phenyl substituted with —CH$_2$NH$_2$ or —CH$_2$OH,
   i) —O-phenyl substituted with —CH$_2$NH$_2$,
   j) pyridinyl substituted with —NH$_2$, or
   k) diazaspirononanyl,
5) thiazolyl substituted with —NH$_2$,
6) quinolinyl substituted with —NH$_2$,
7) benzo[d]thiazolyl substituted with —NH$_2$, or
8) 1H-benzo[d][1,2,3]triazole] substituted with —CH$_3$.

9. The compound of claim 1 having the structure:

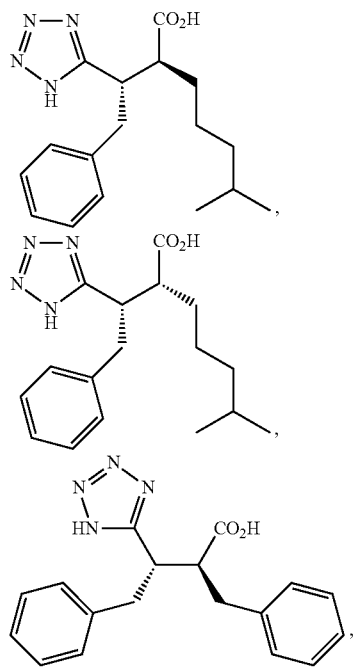

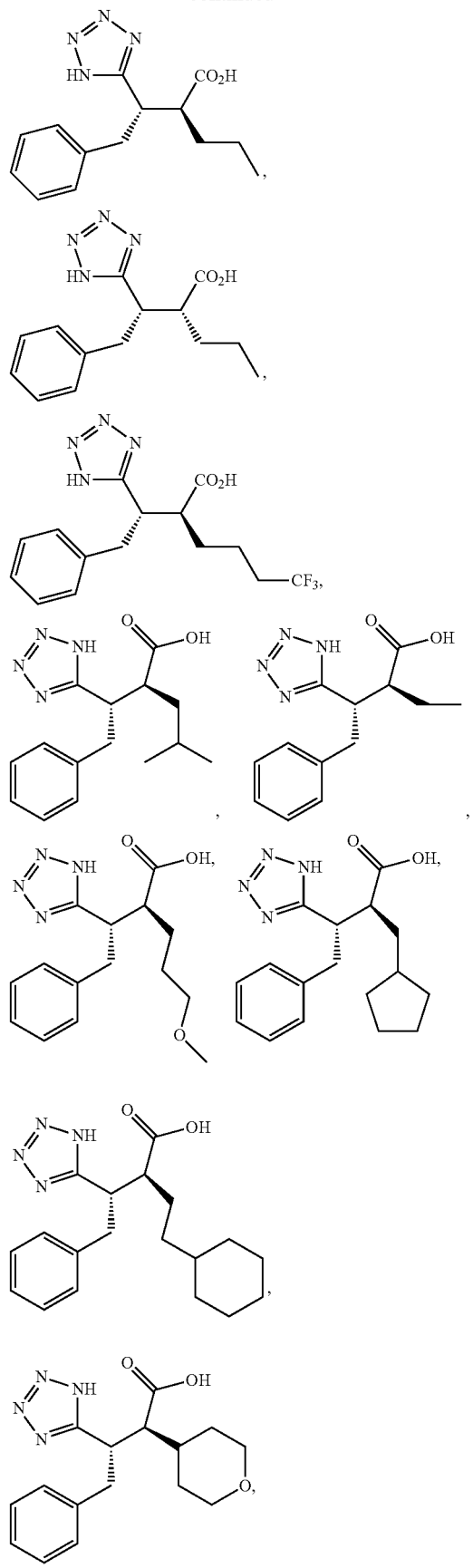

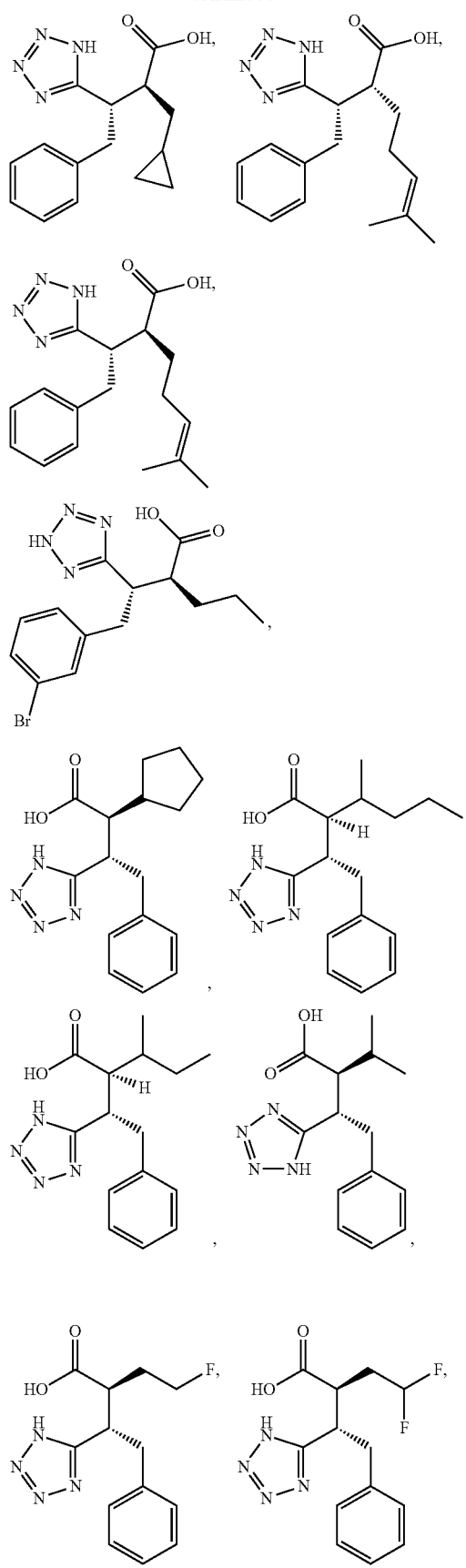
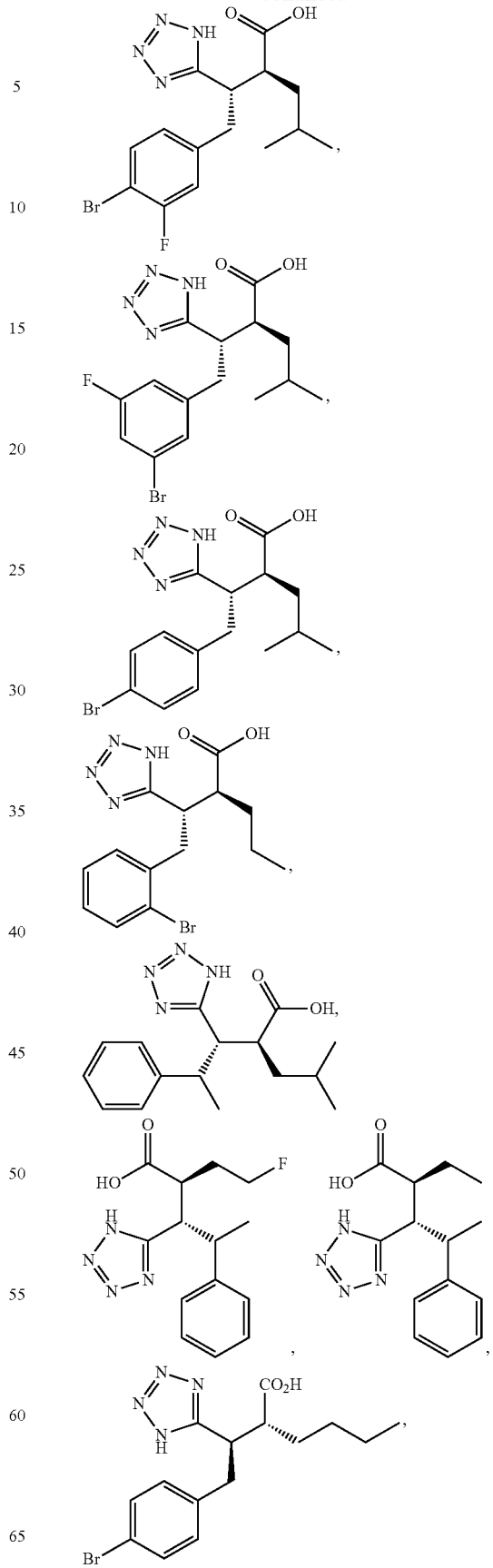

345
-continued
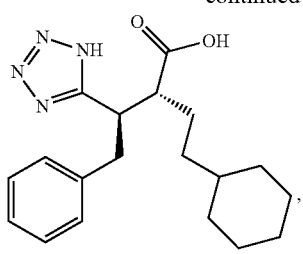
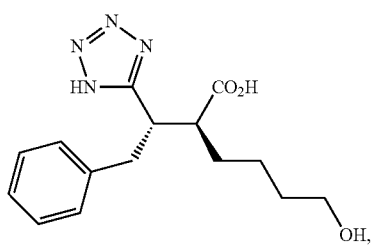
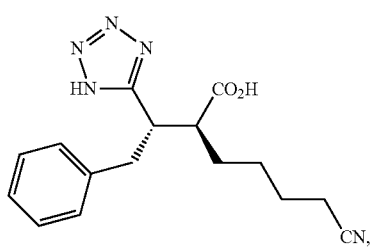
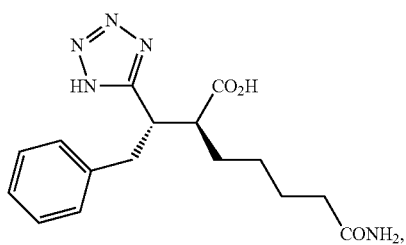
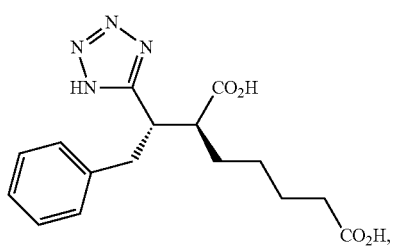
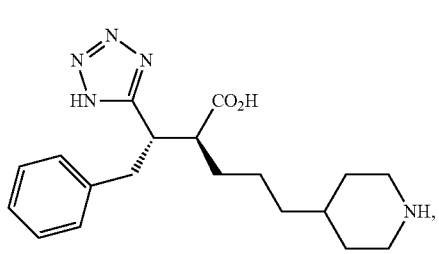
346
-continued
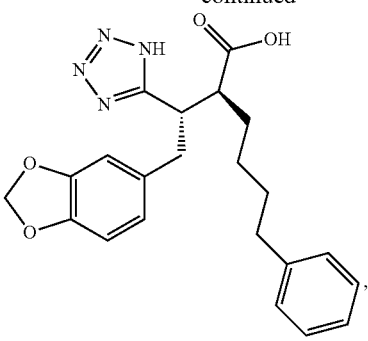
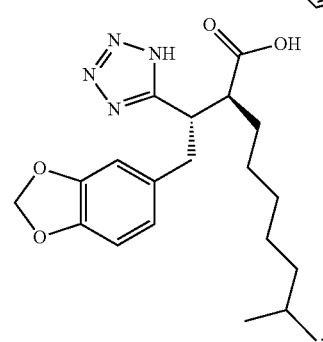
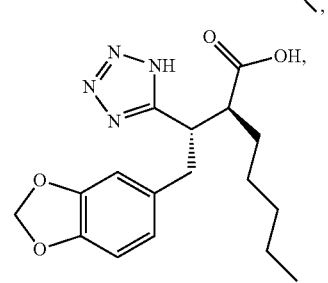
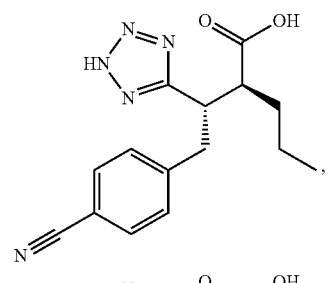
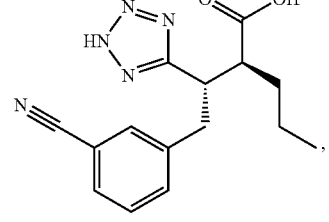
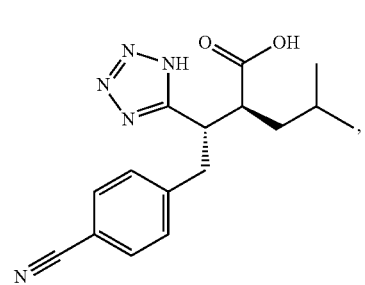

347
-continued
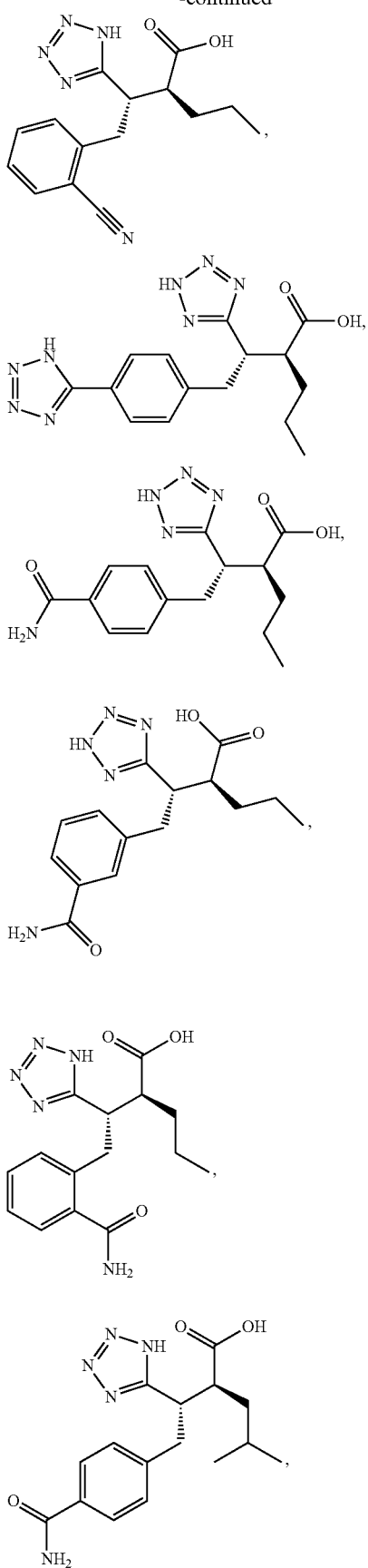
348
-continued
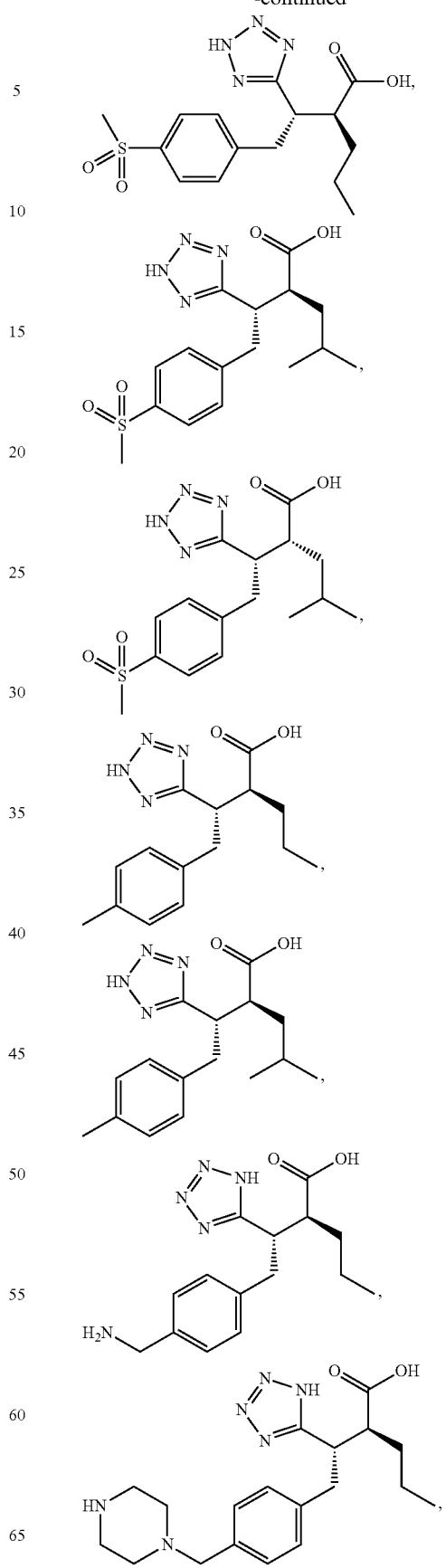

349
-continued
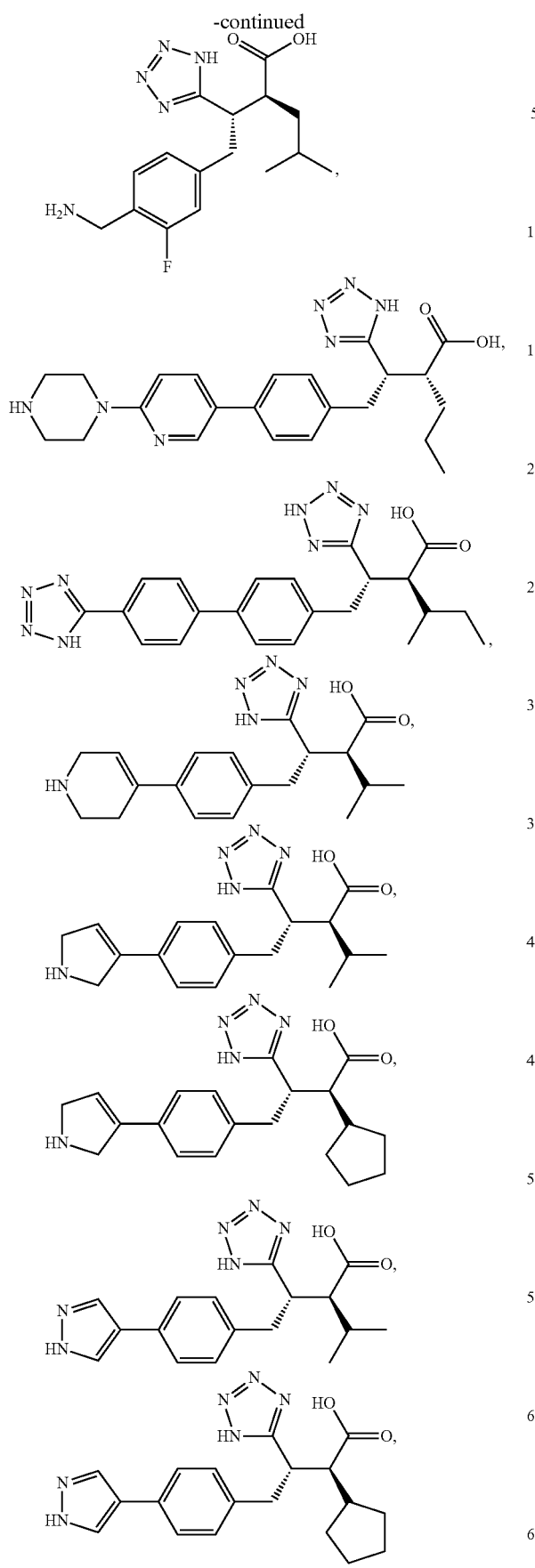
350
-continued
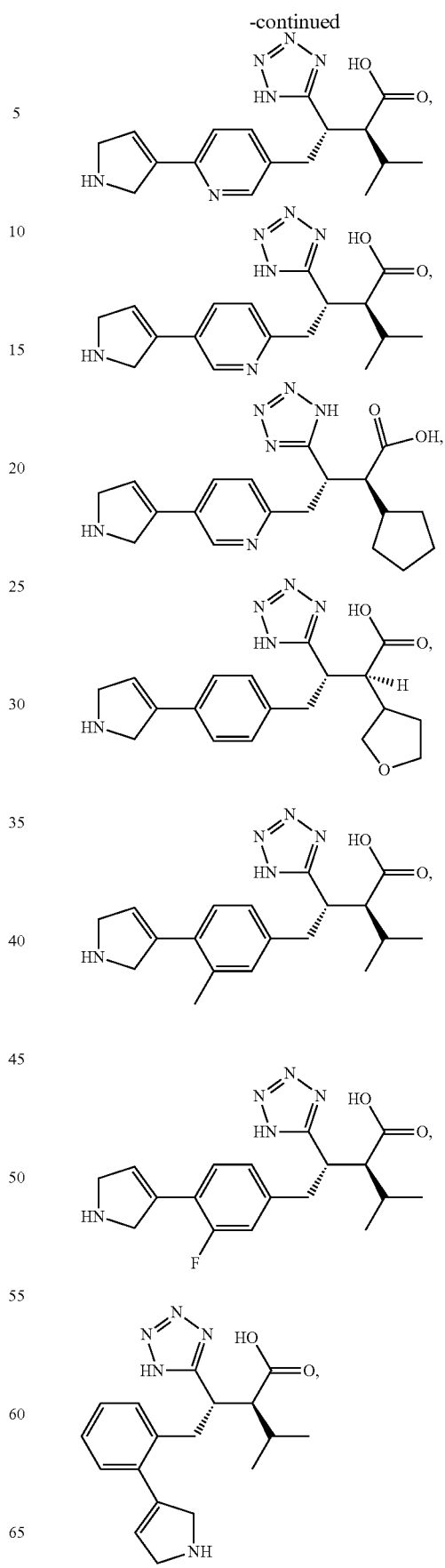

351
-continued
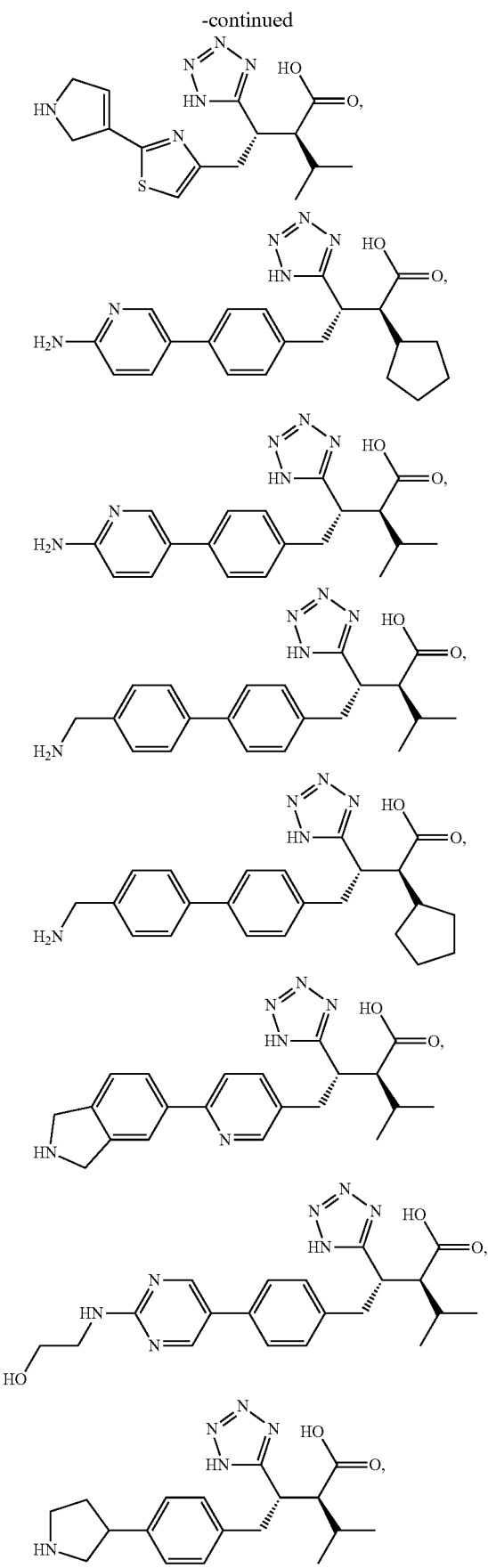
352
-continued
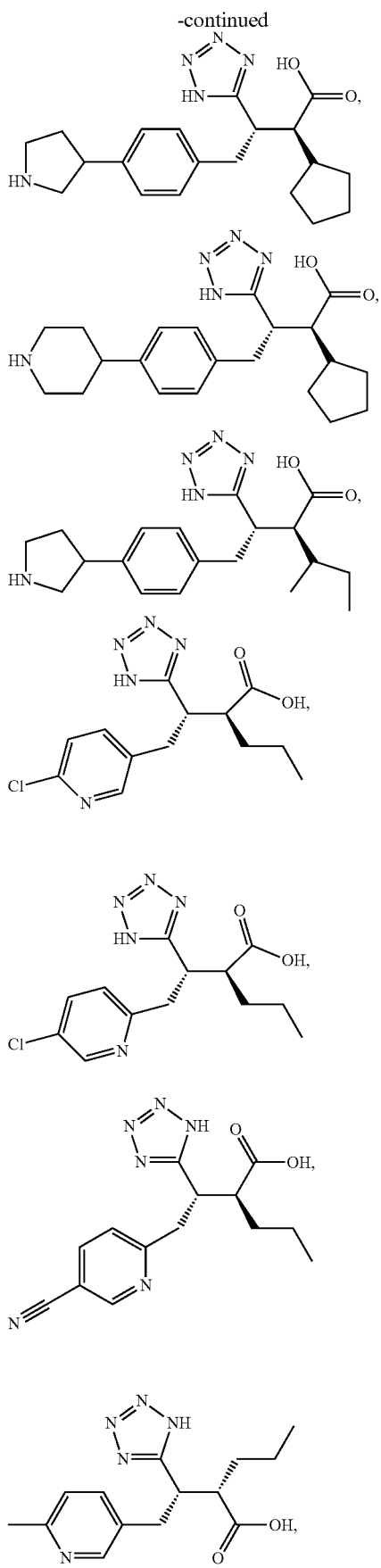

-continued
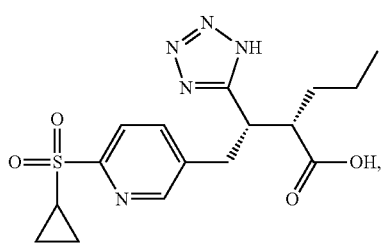
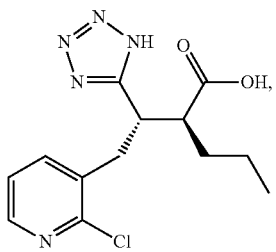
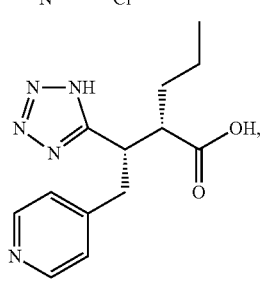
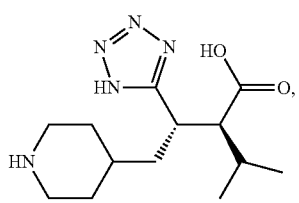
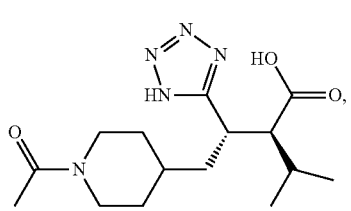
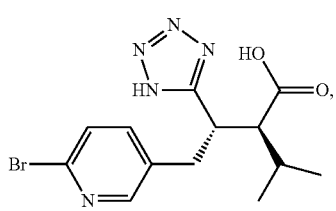
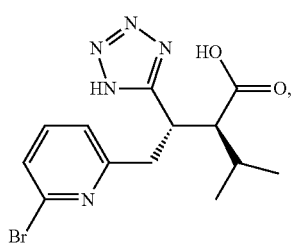
-continued
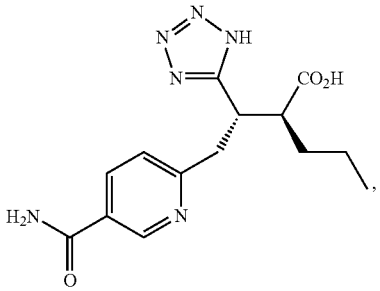
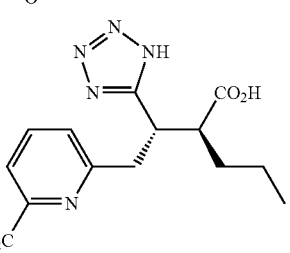
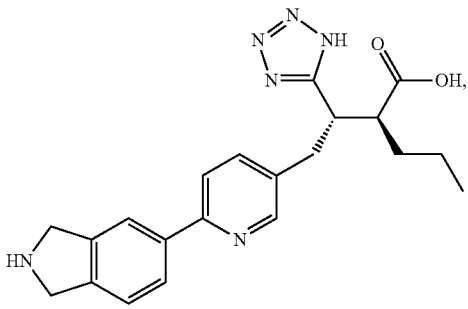
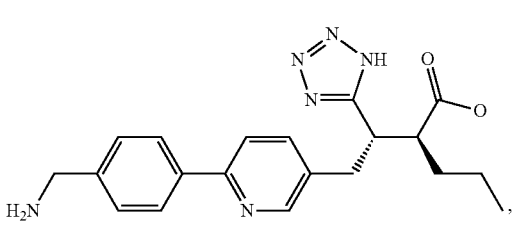
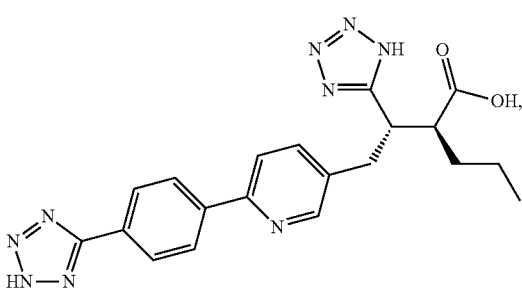
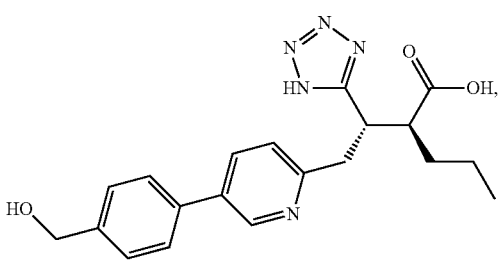

-continued
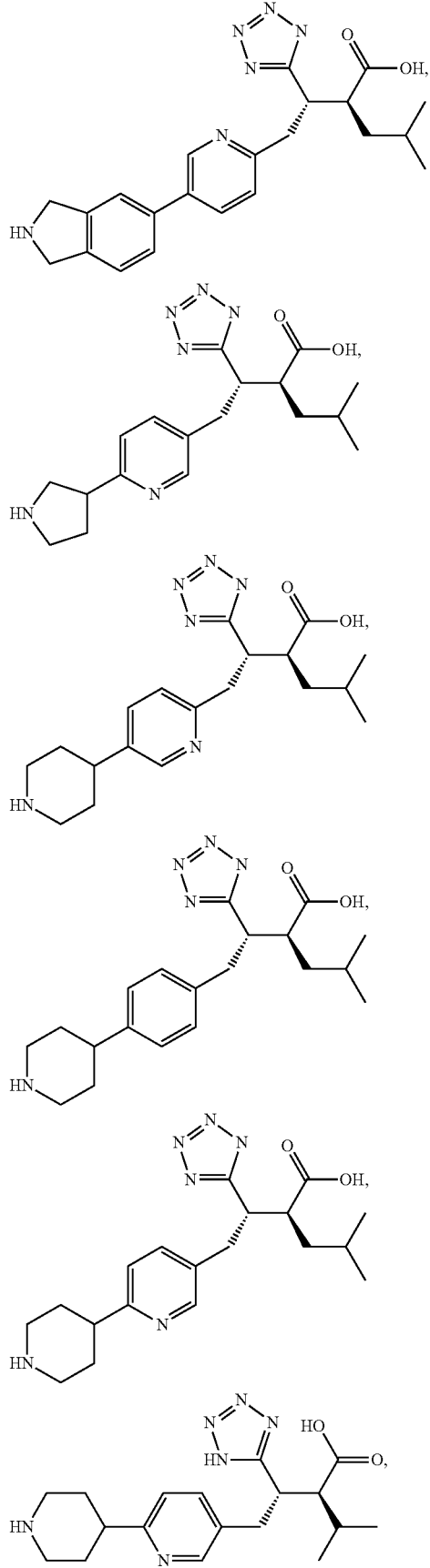
-continued
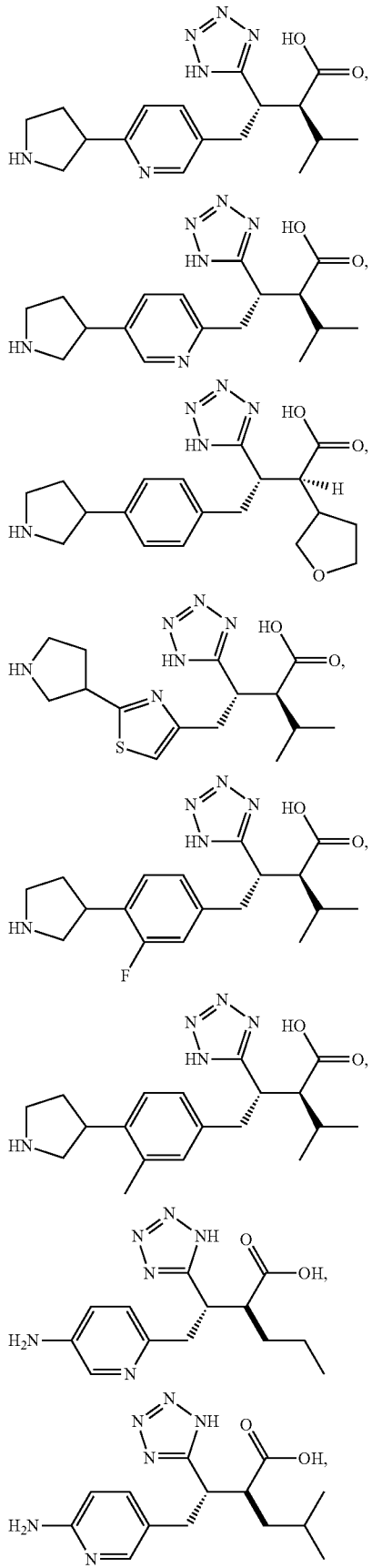

-continued
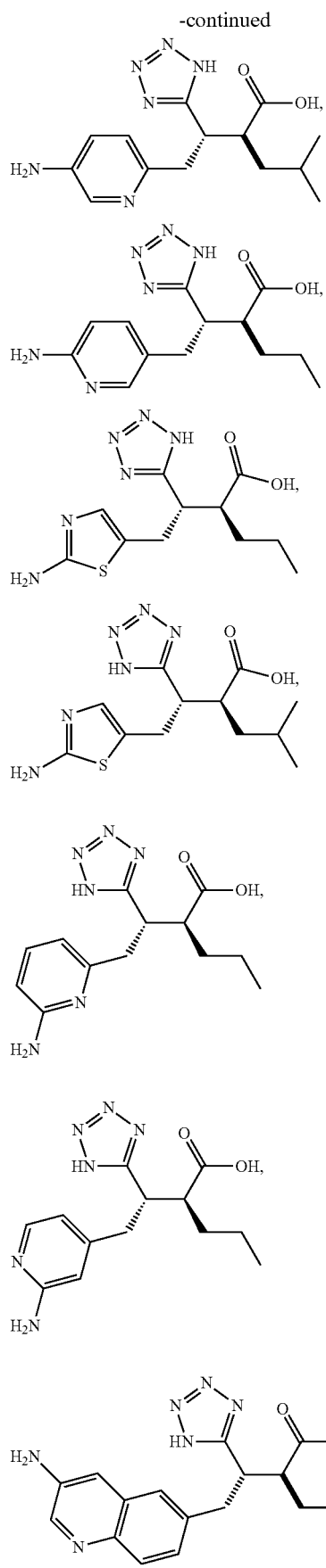
-continued
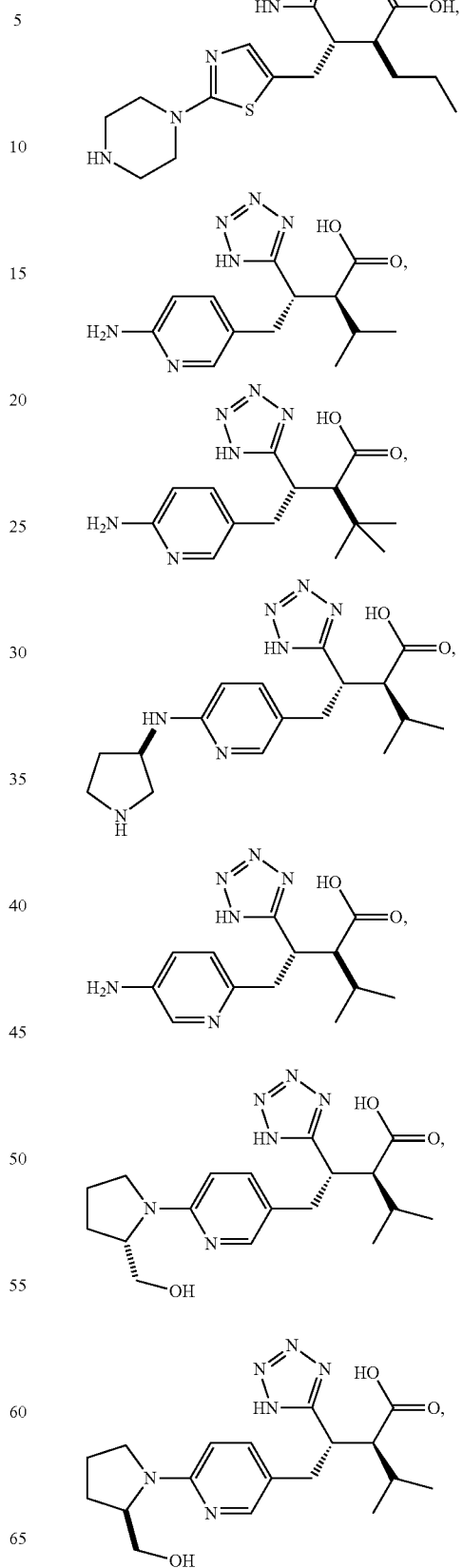

359
-continued
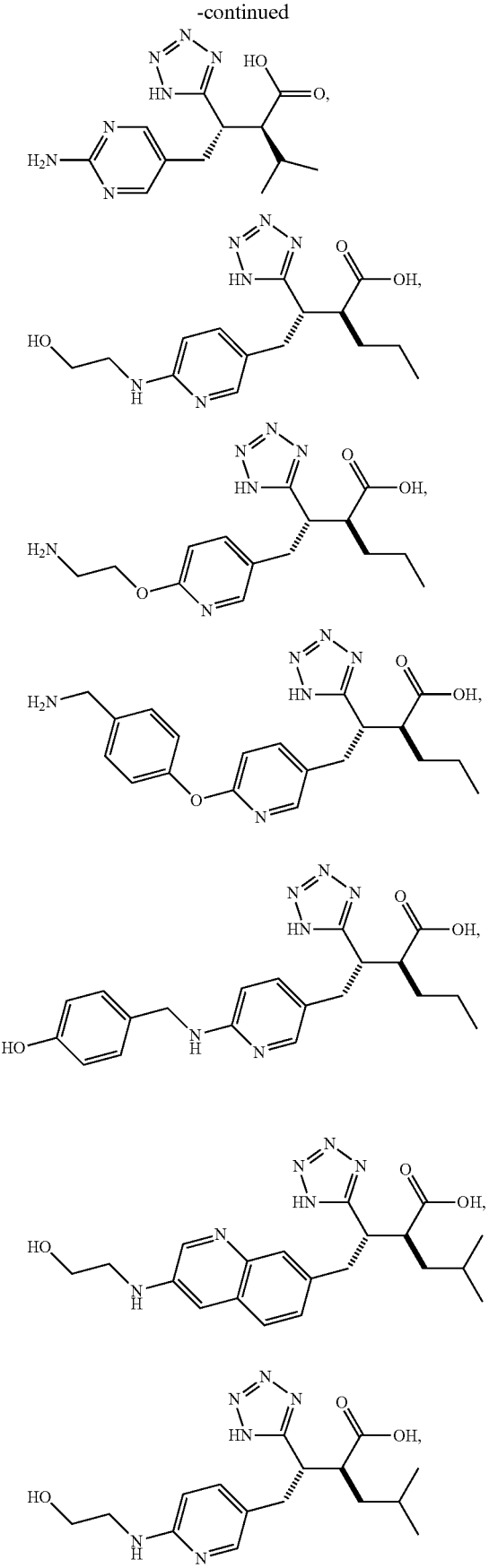
360
-continued
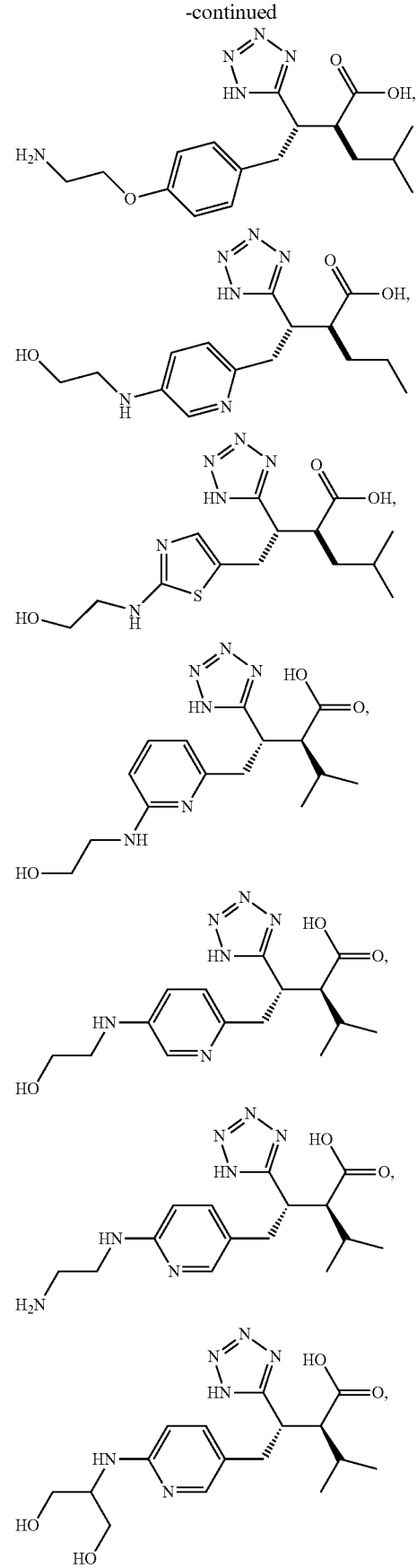

361
-continued
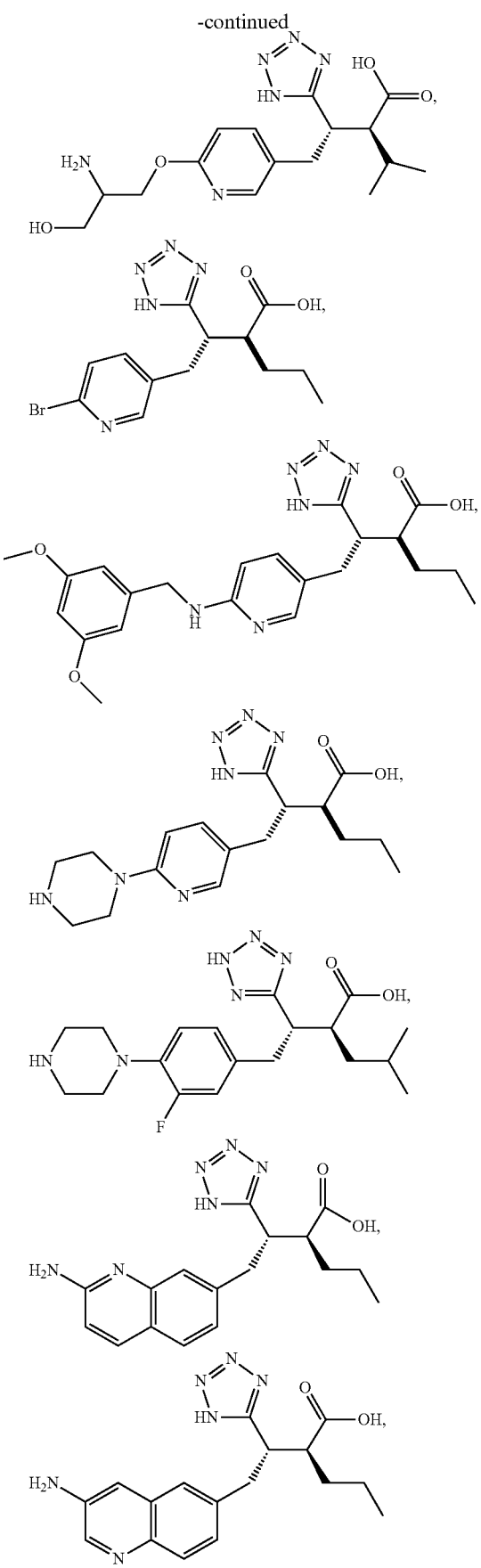
362
-continued
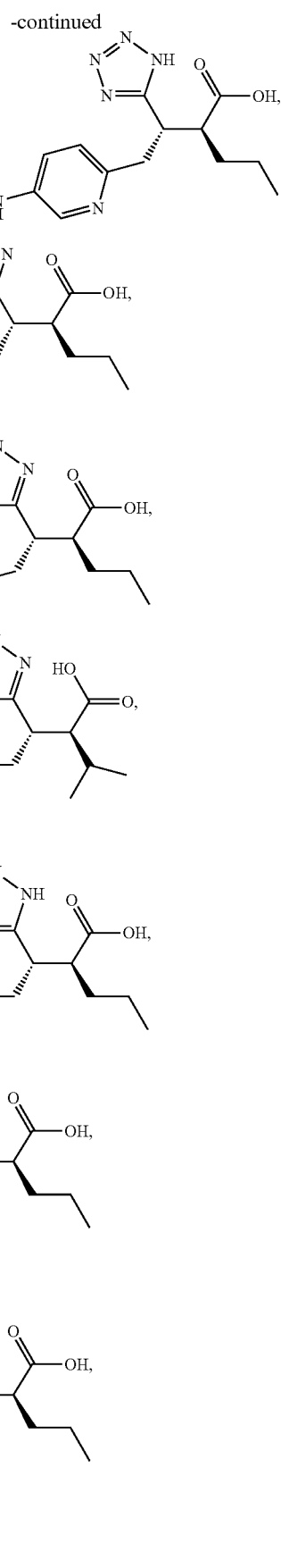

363
-continued
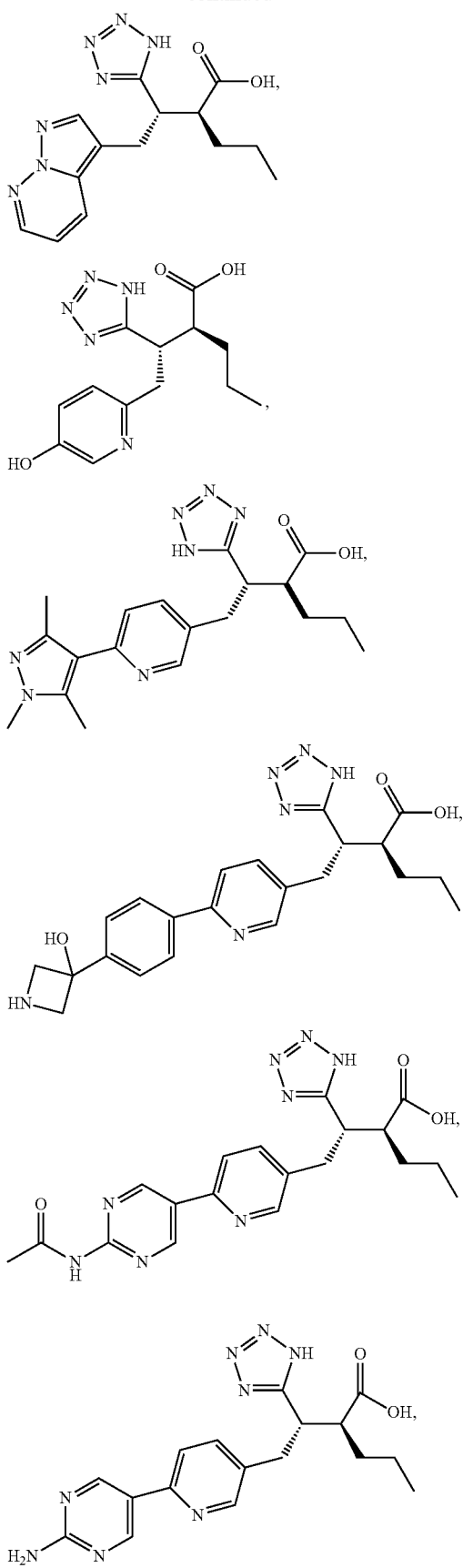
364
-continued
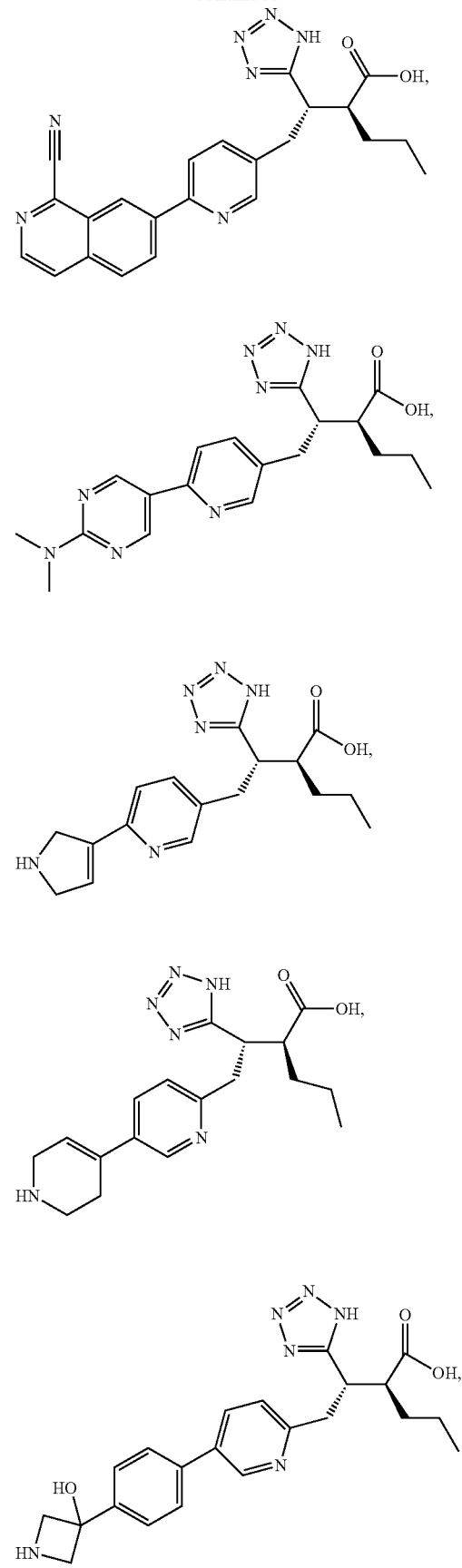

365
-continued
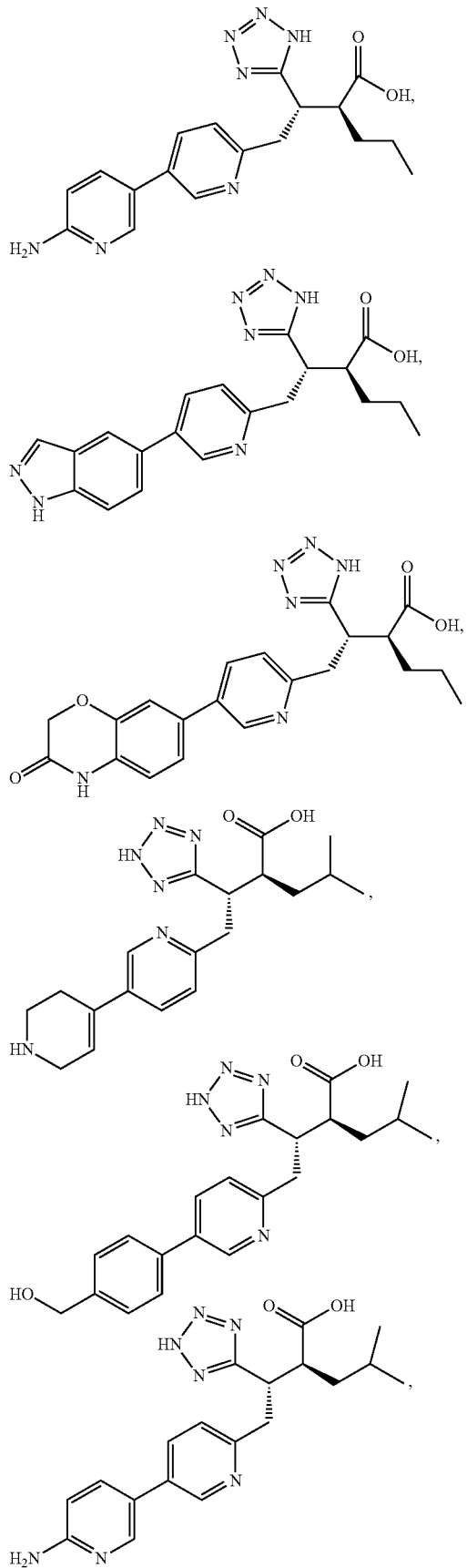
366
-continued
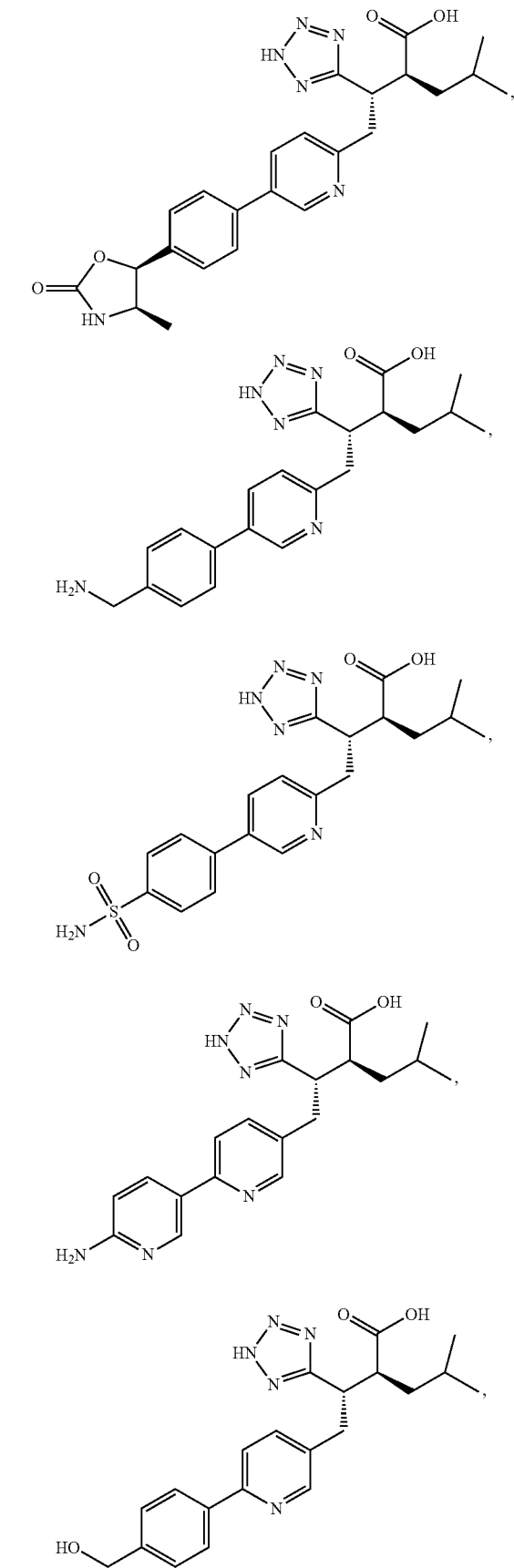

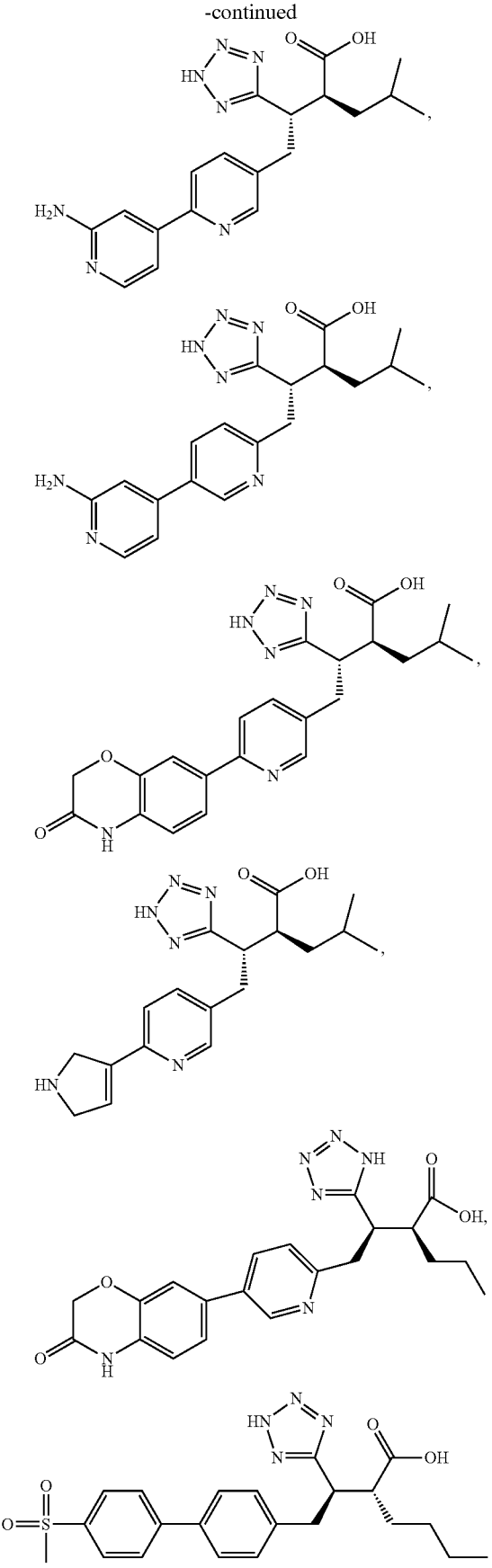
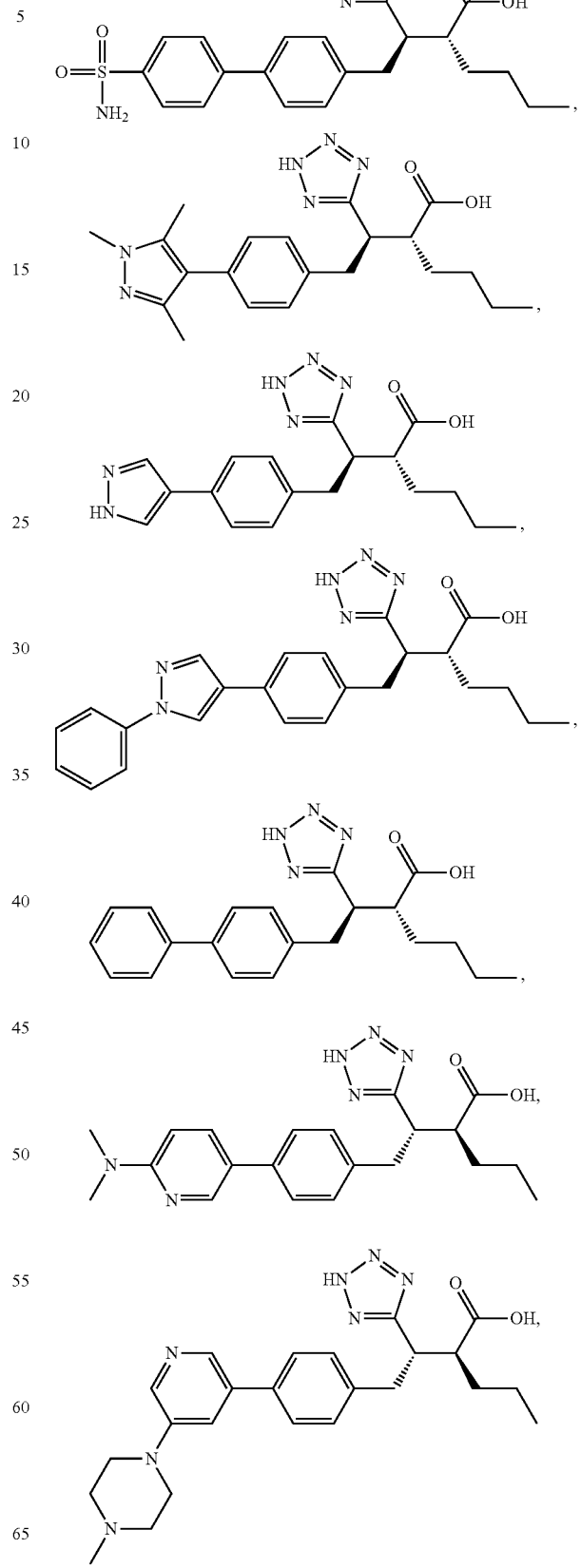

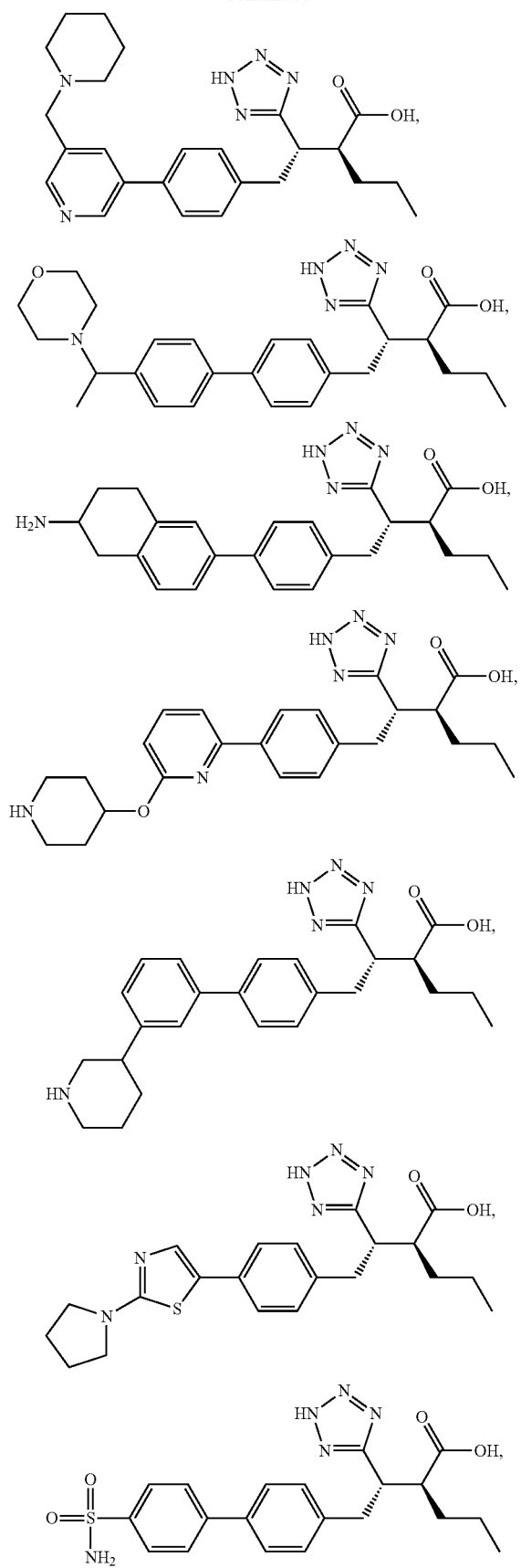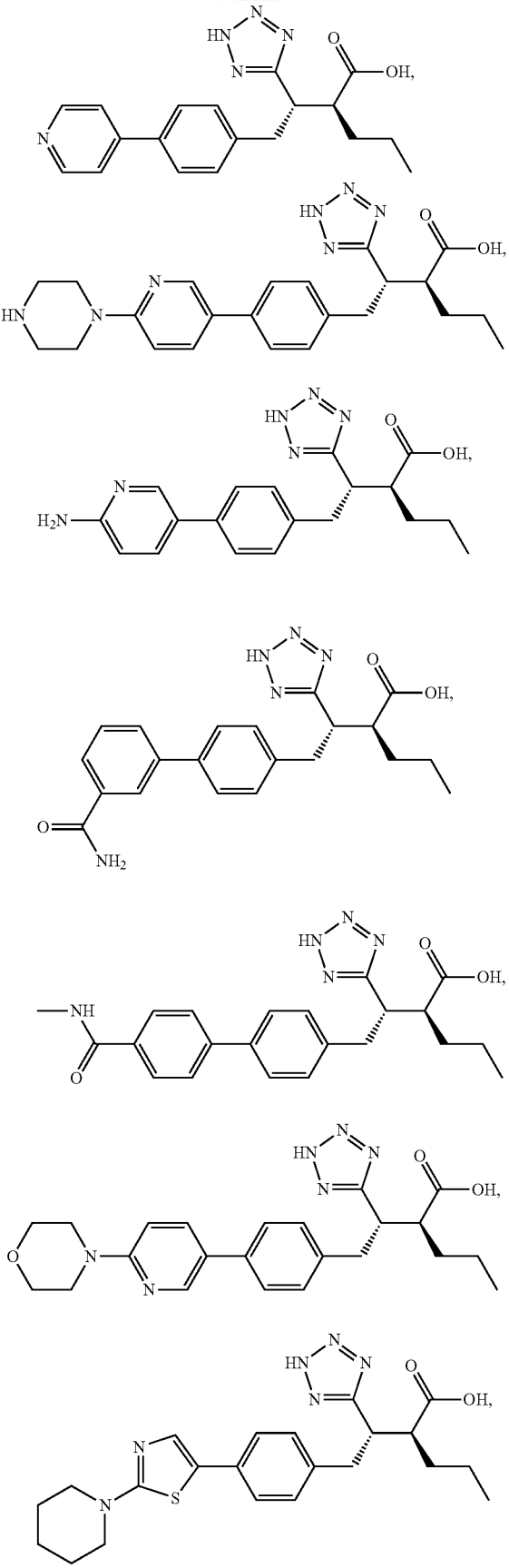

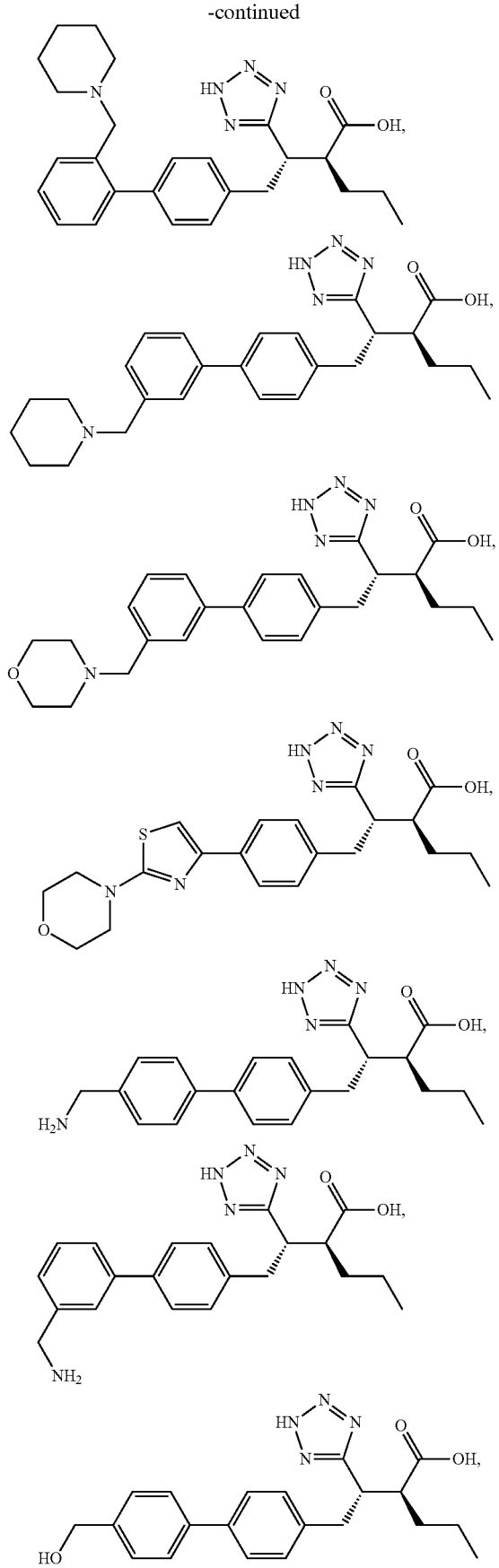
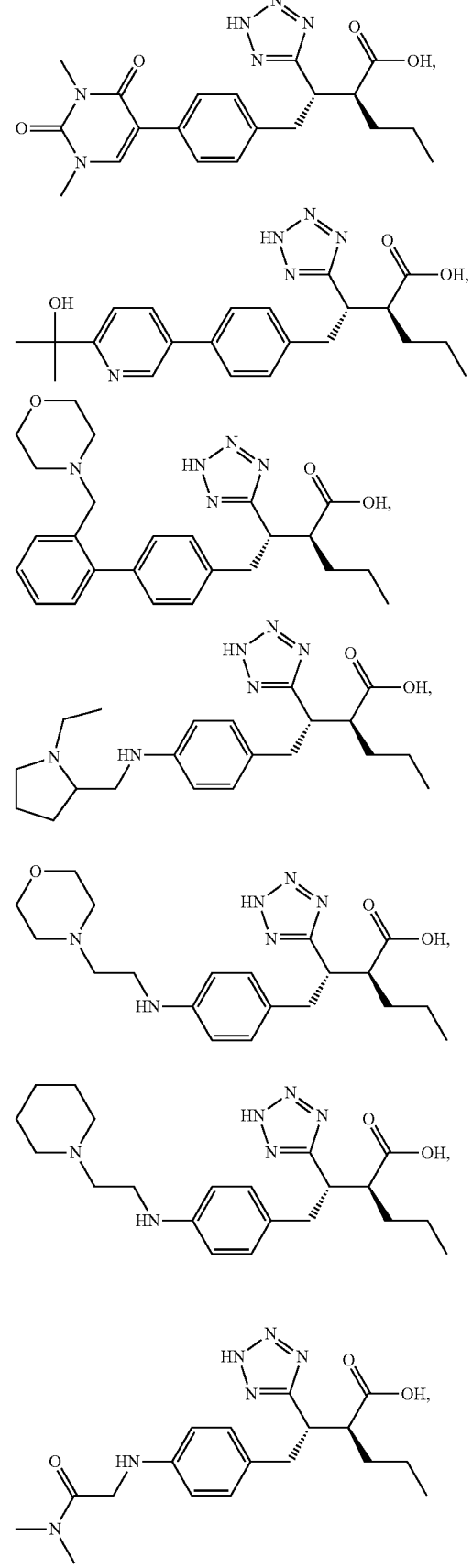

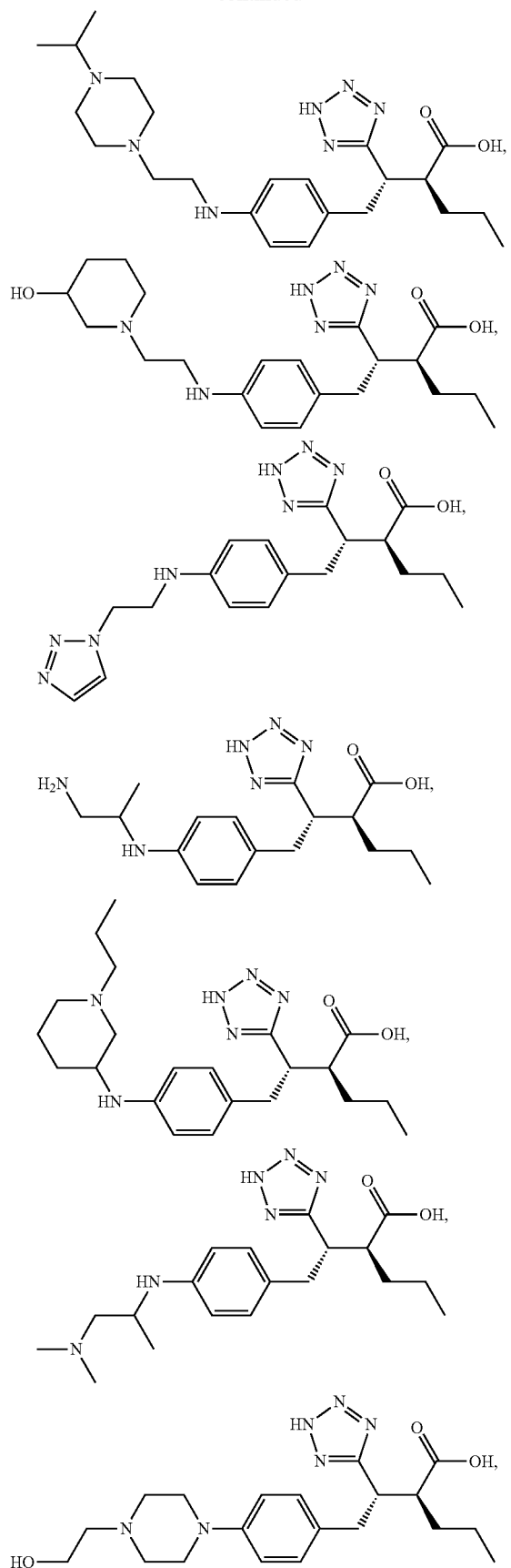
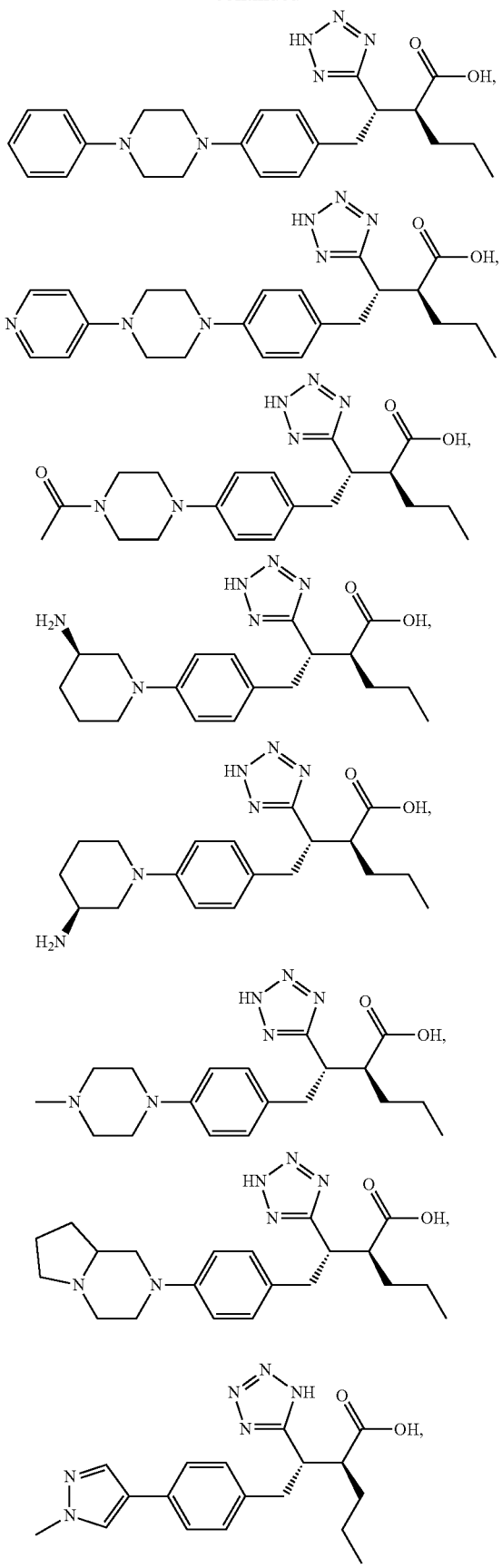

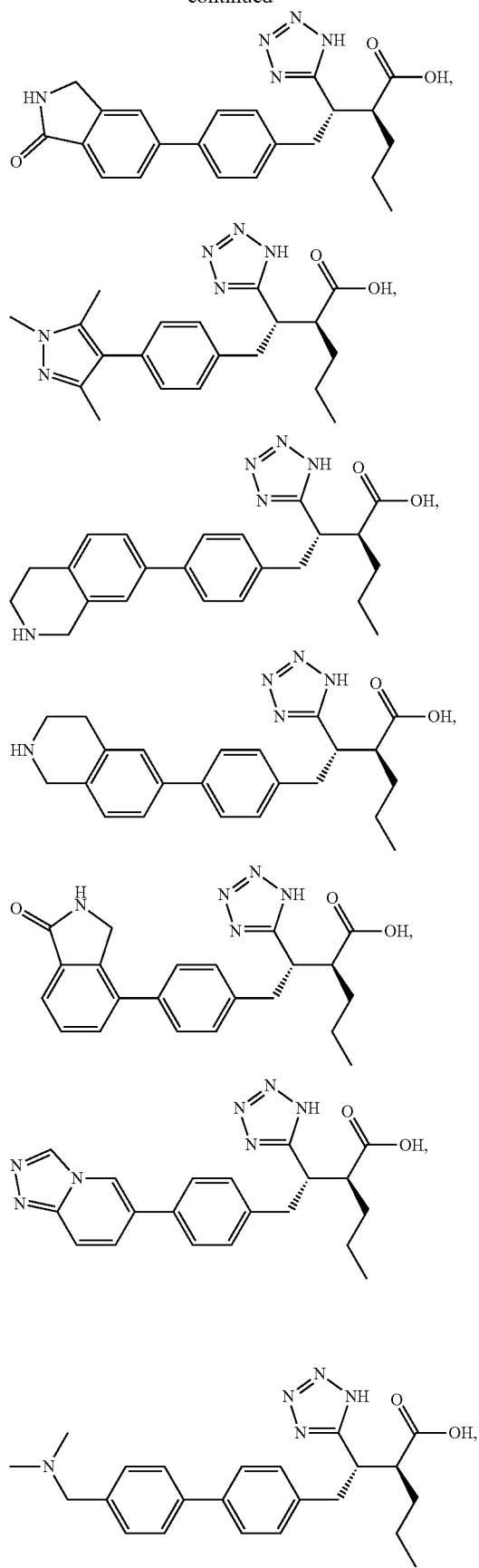
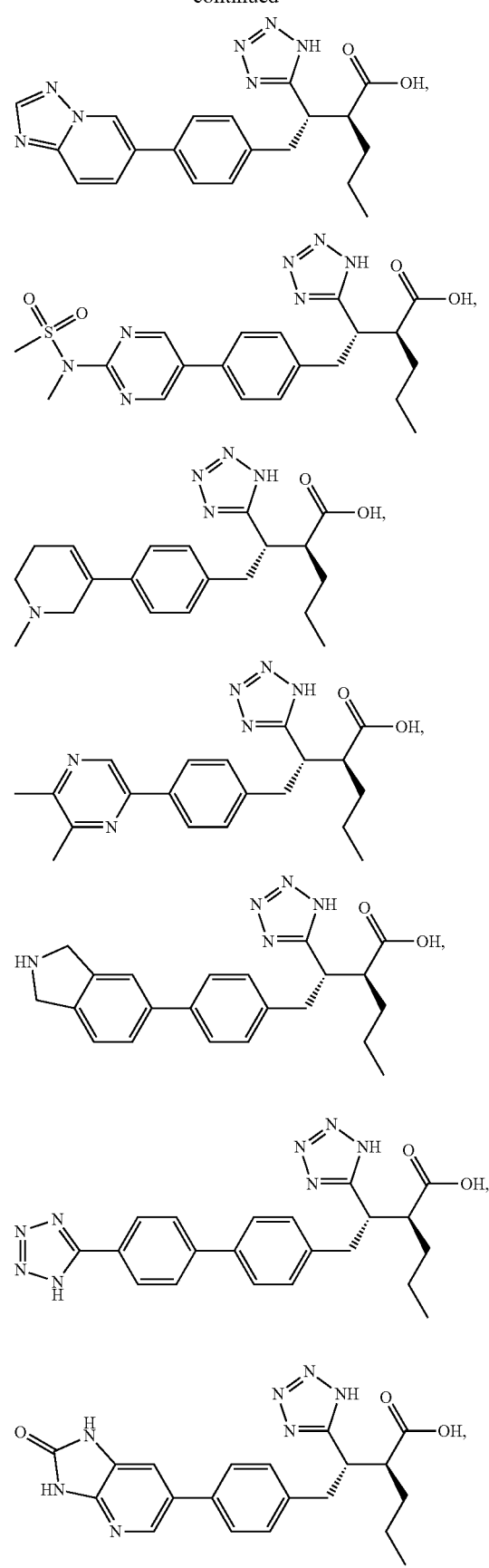

377
-continued
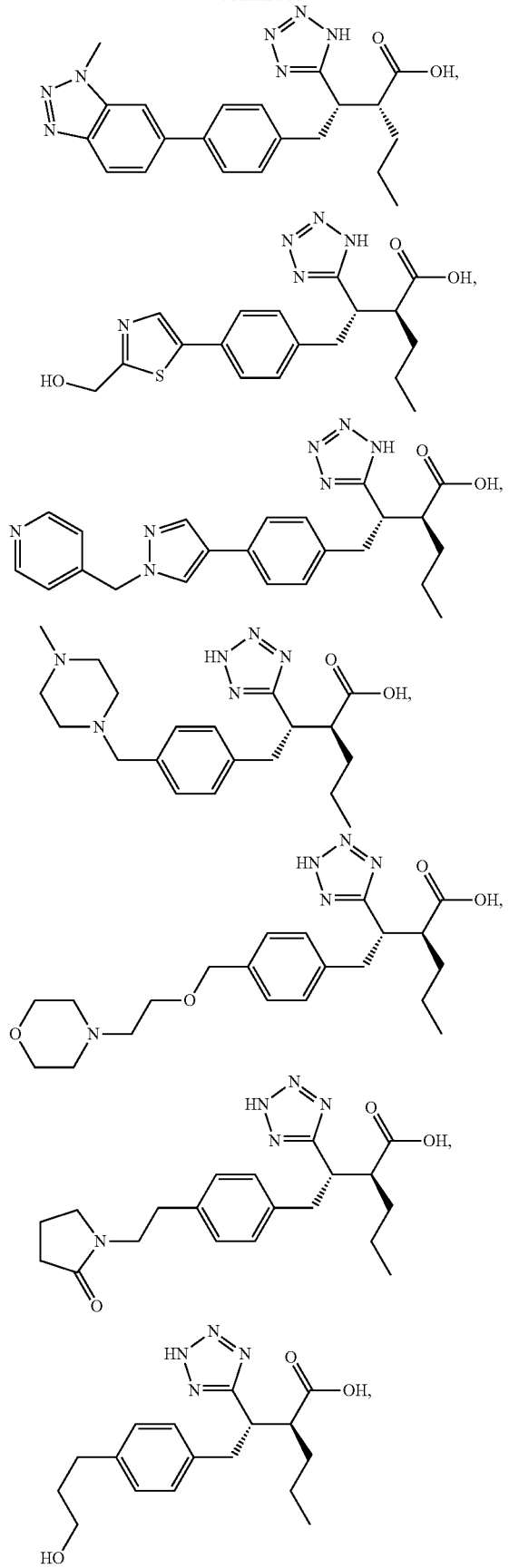
378
-continued
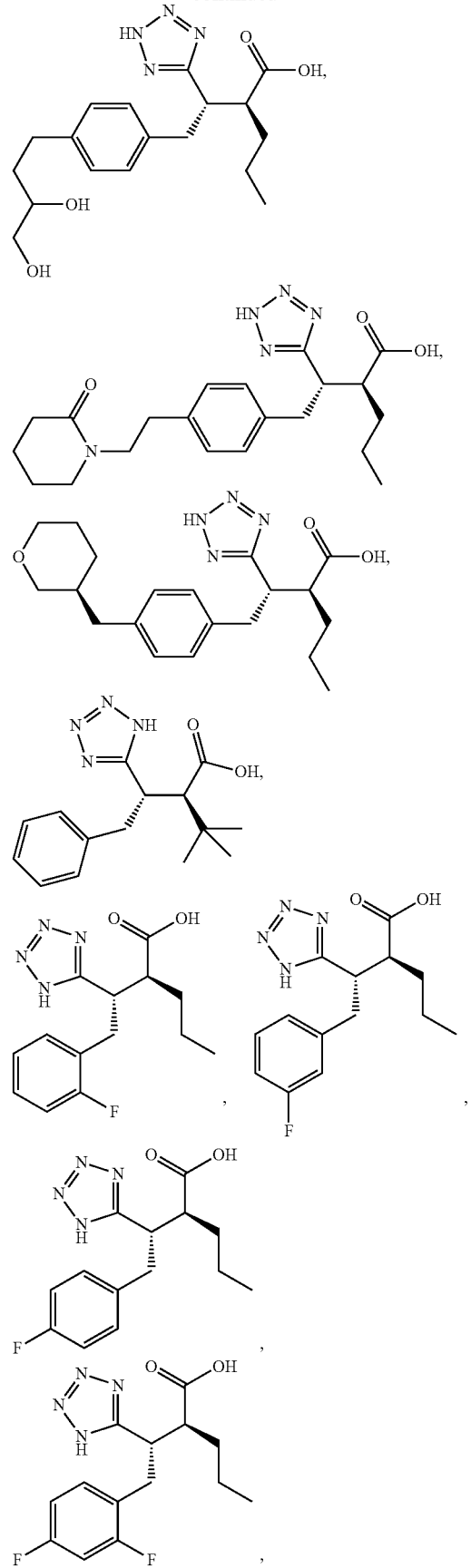

379
-continued
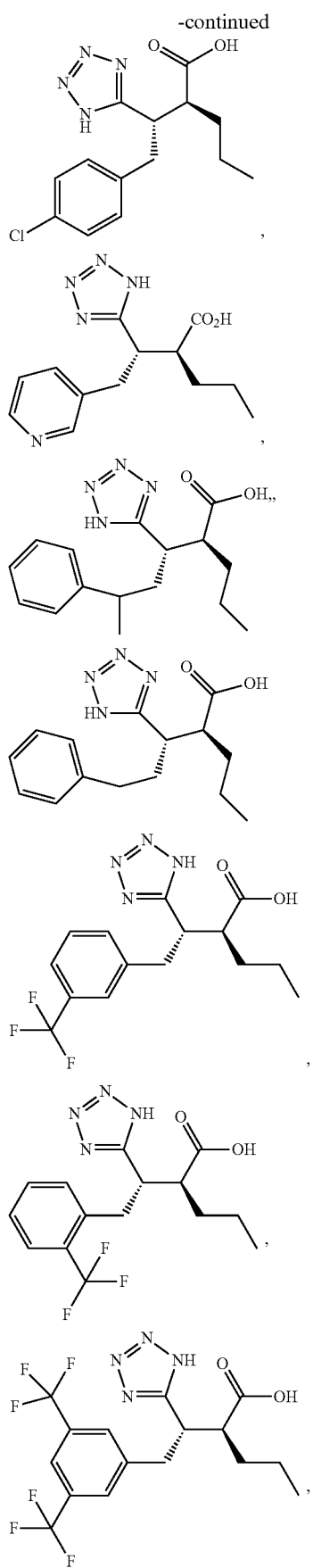
380
-continued
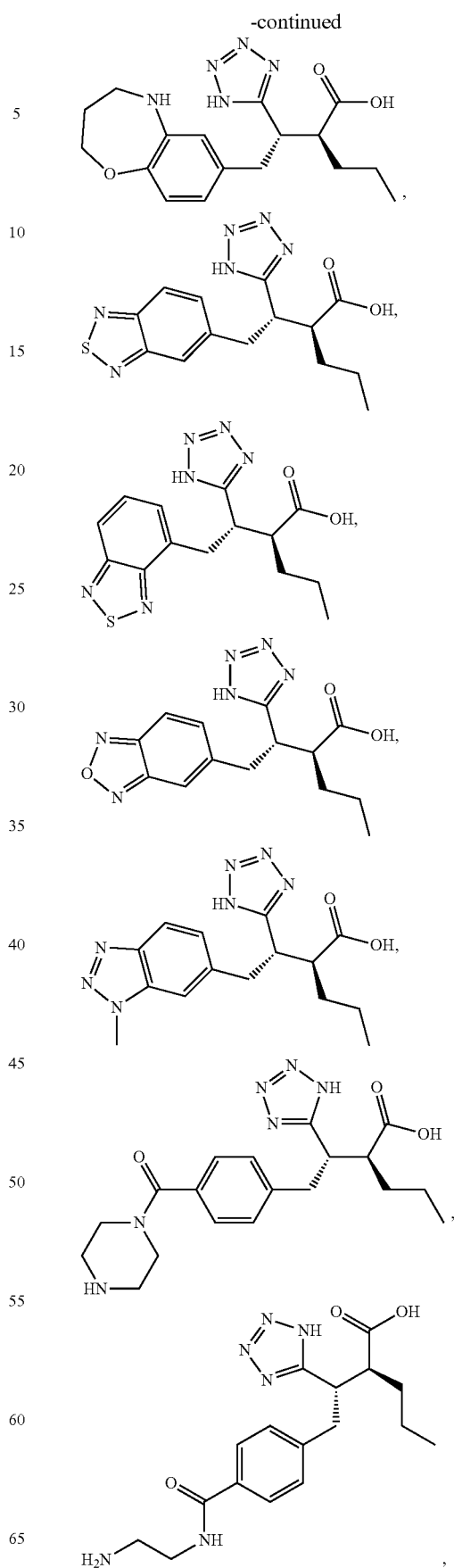

381
-continued
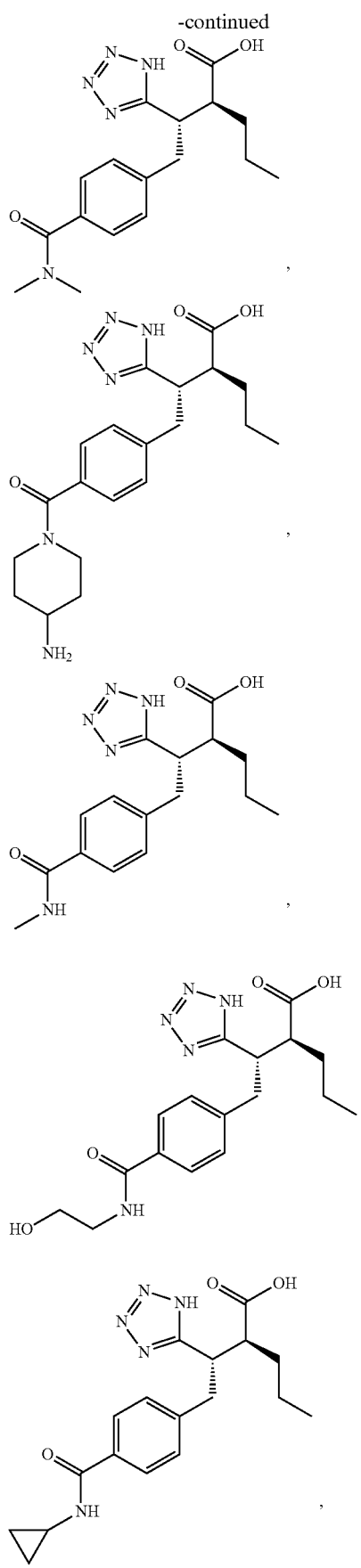
382
-continued
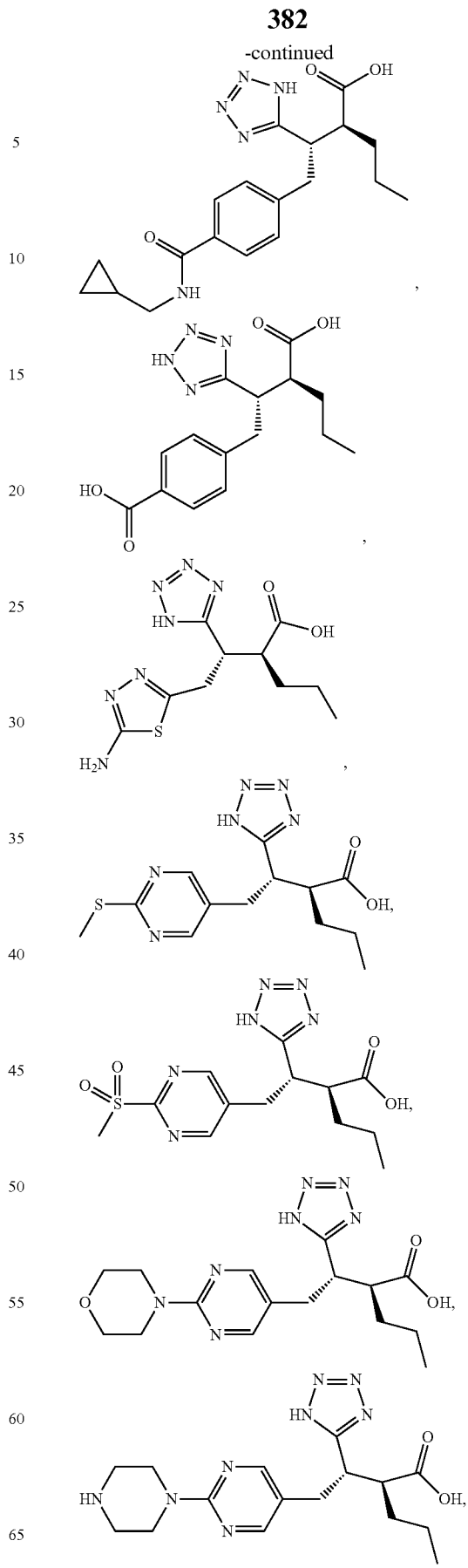

383
-continued
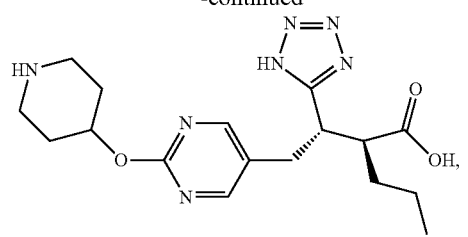
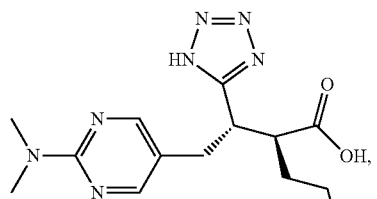
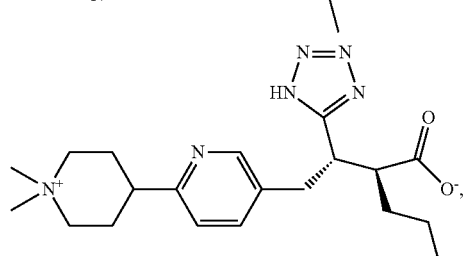
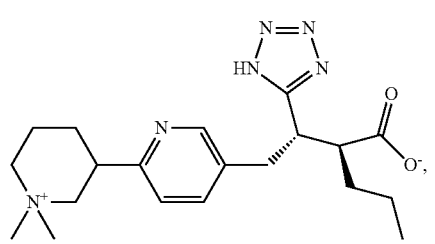
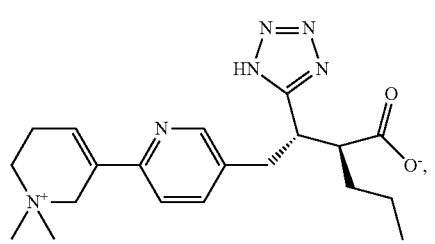
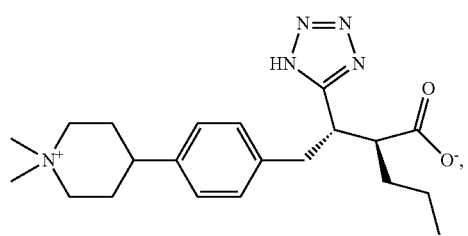
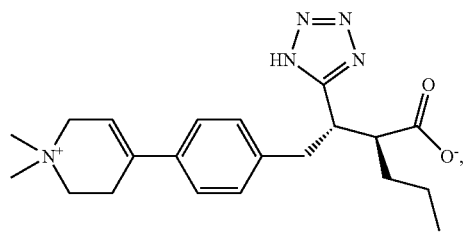
384
-continued
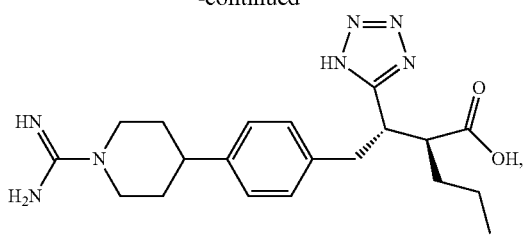
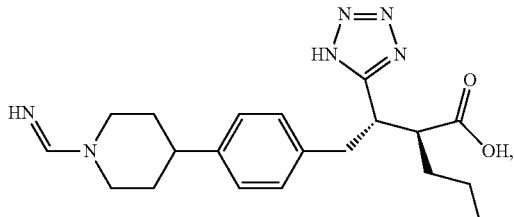
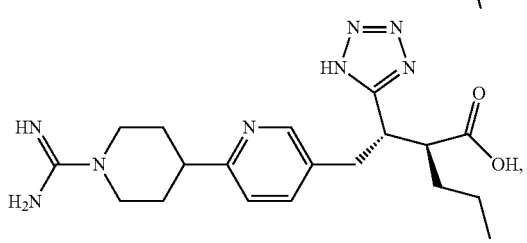
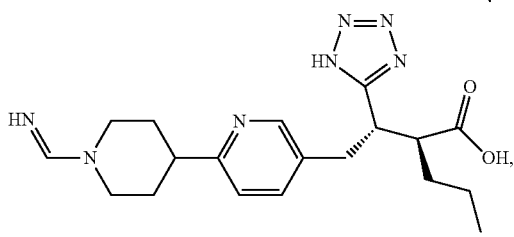
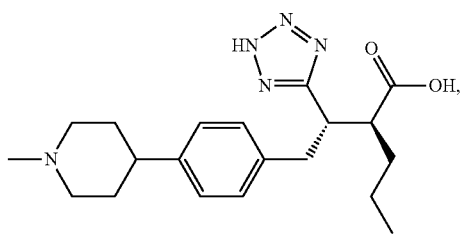
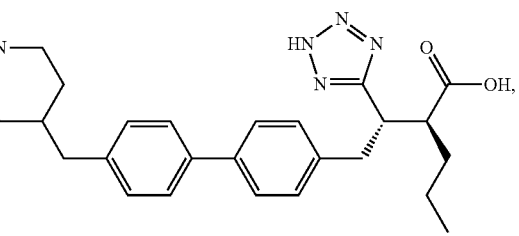
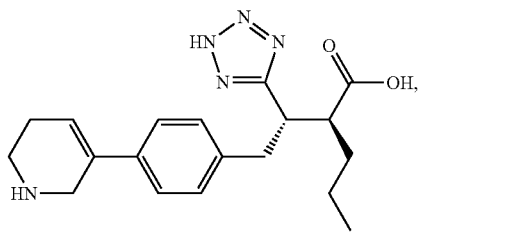

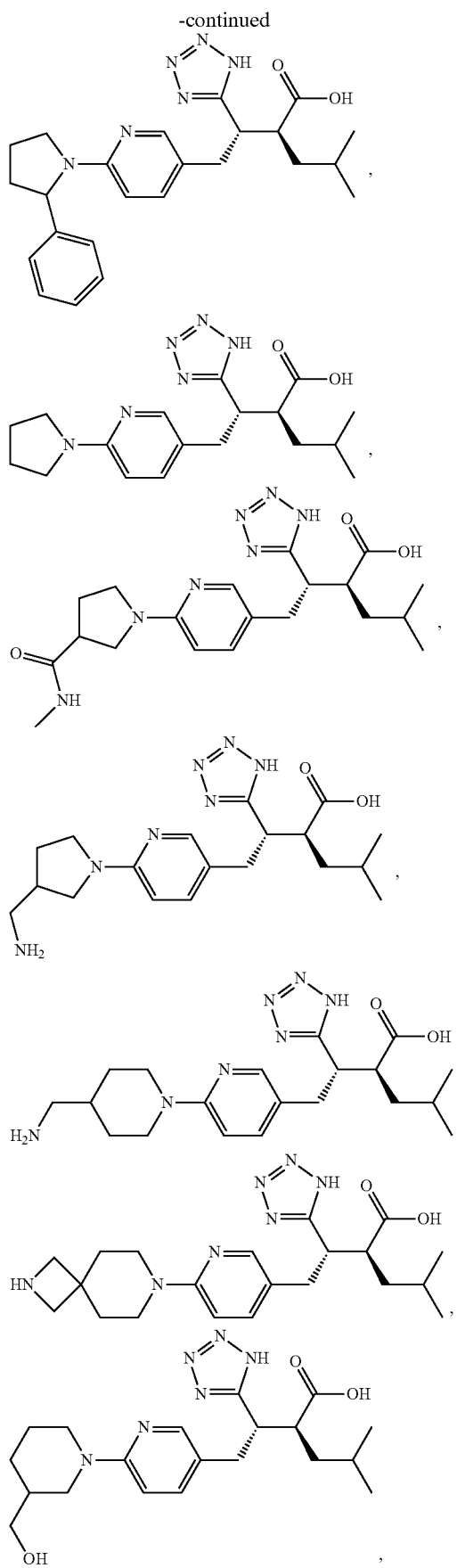
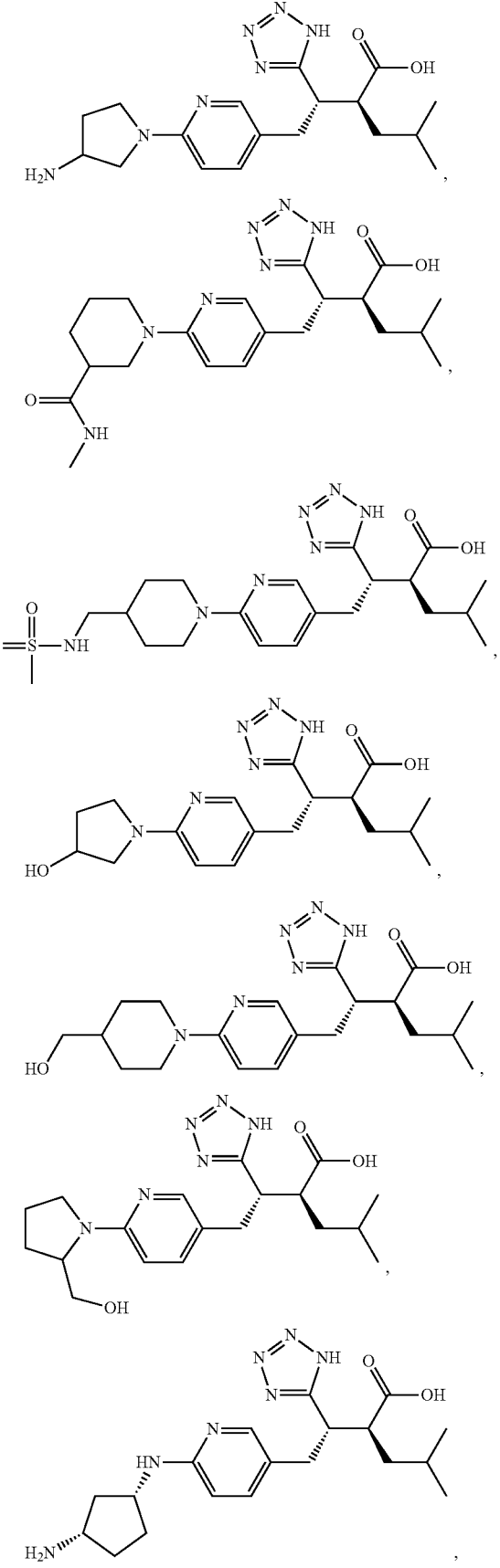

-continued
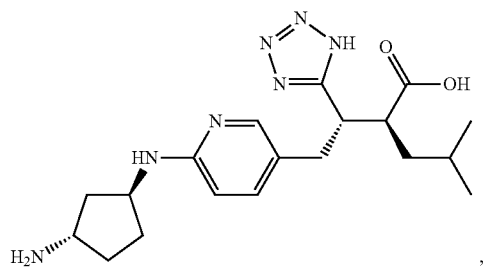
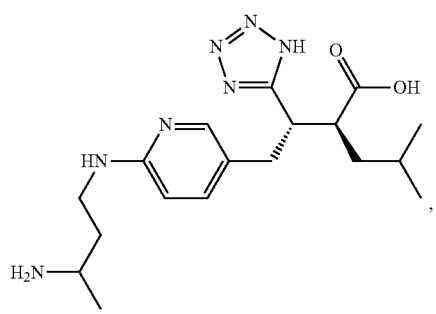
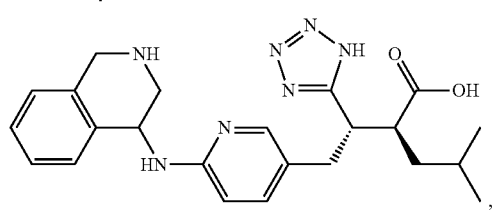
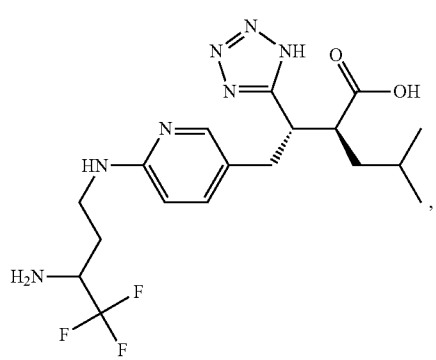
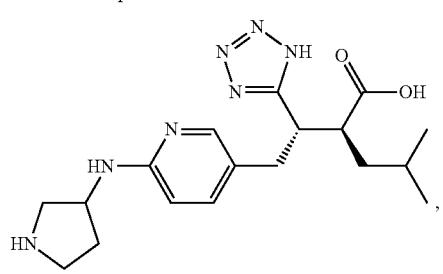
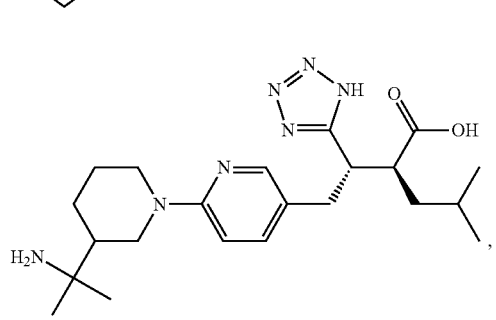
-continued
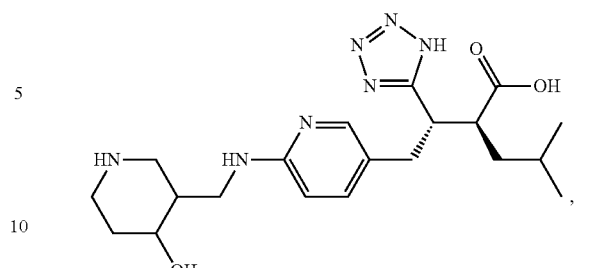
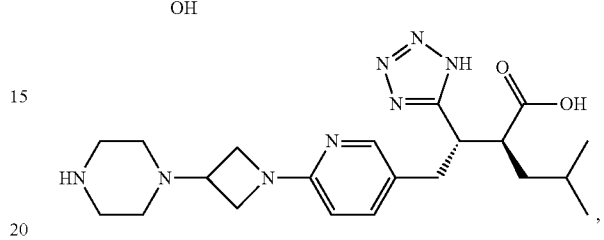
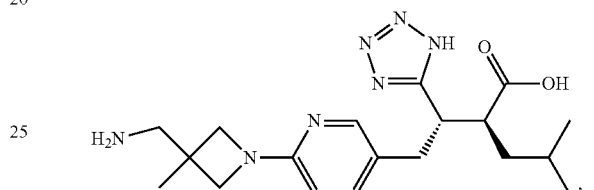
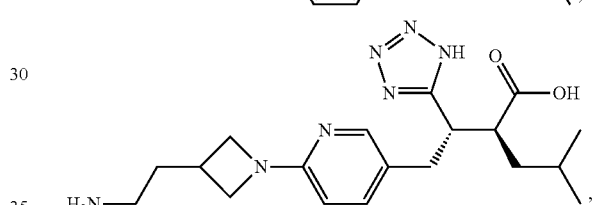
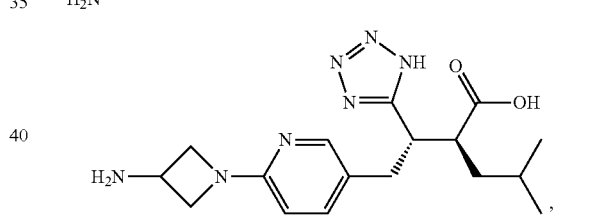
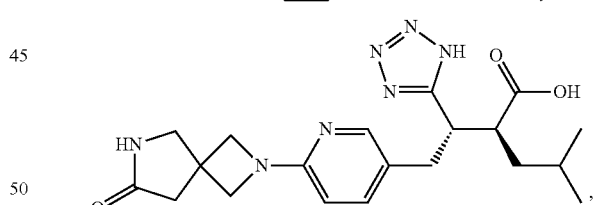
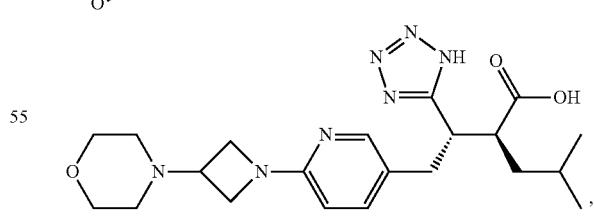
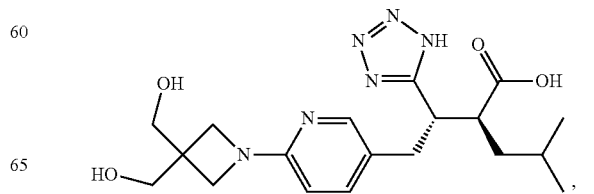

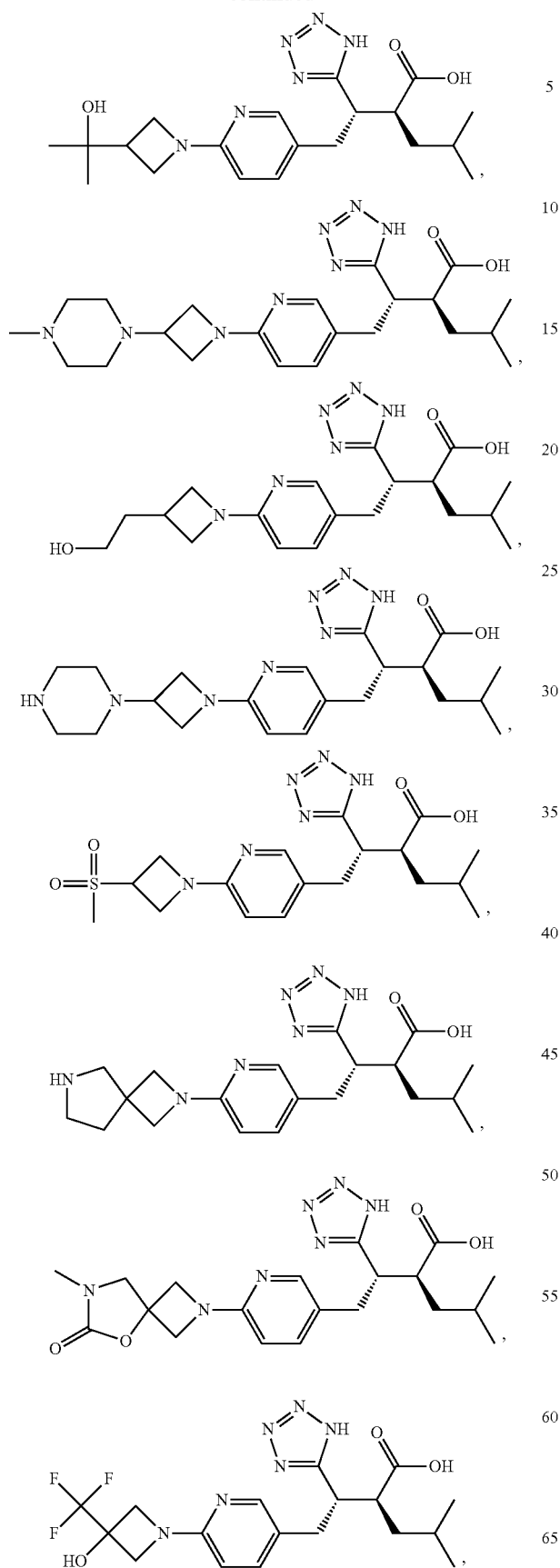
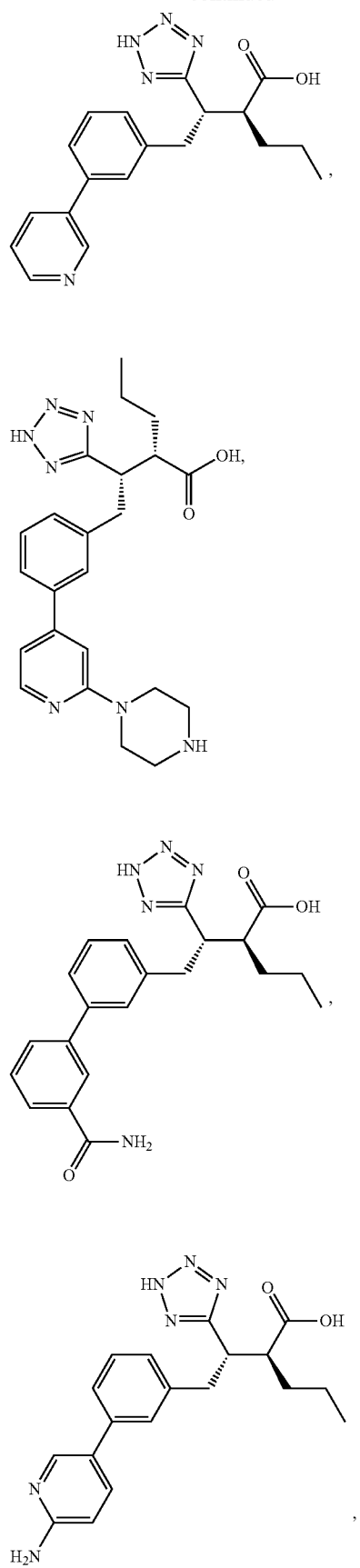

-continued
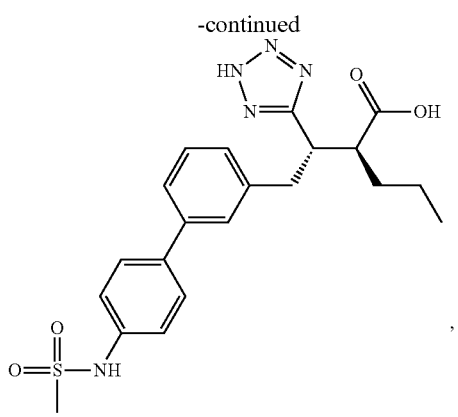
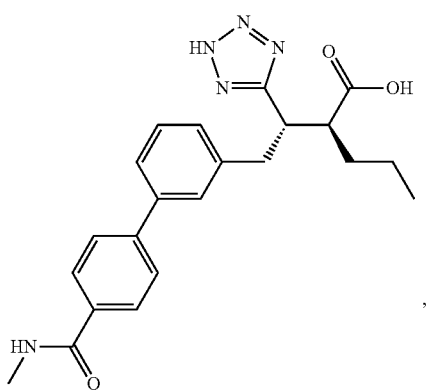
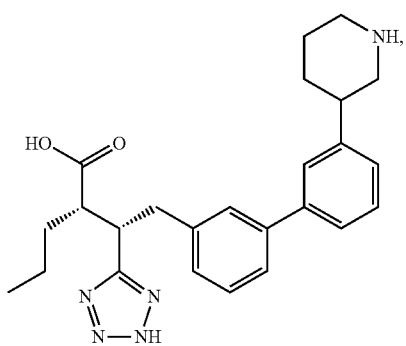
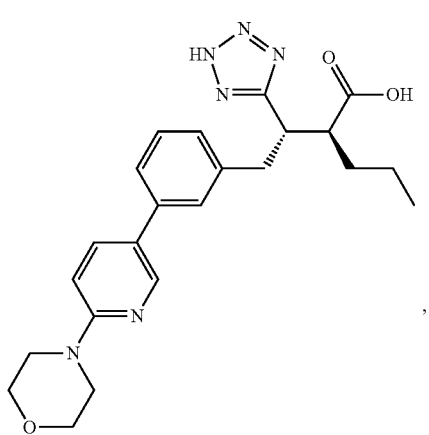
-continued
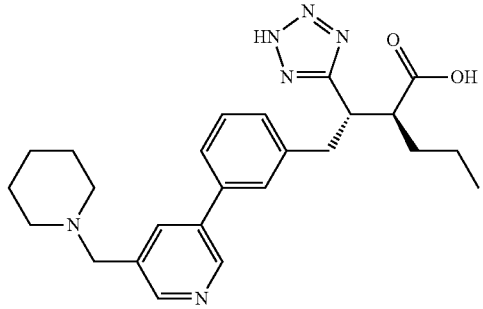
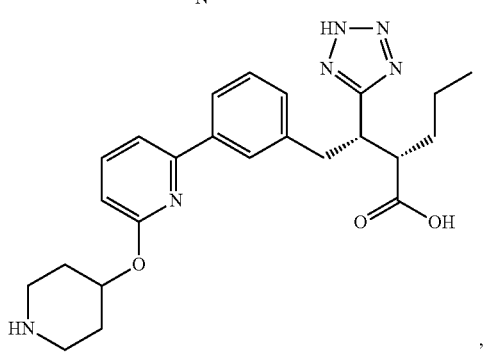
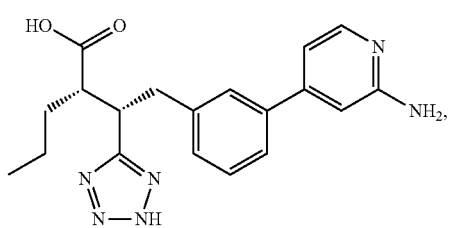
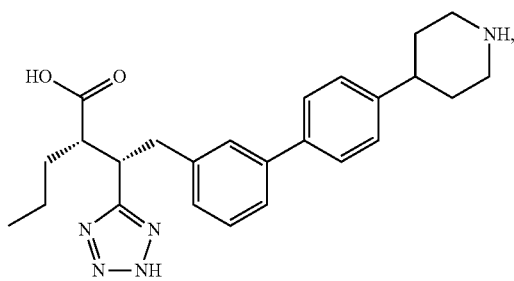
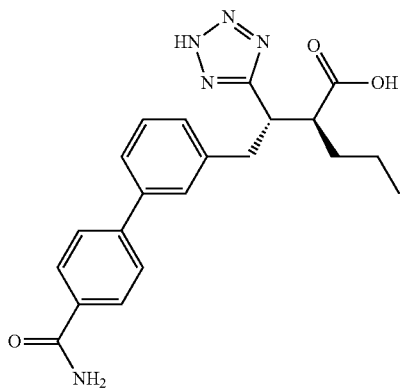

393
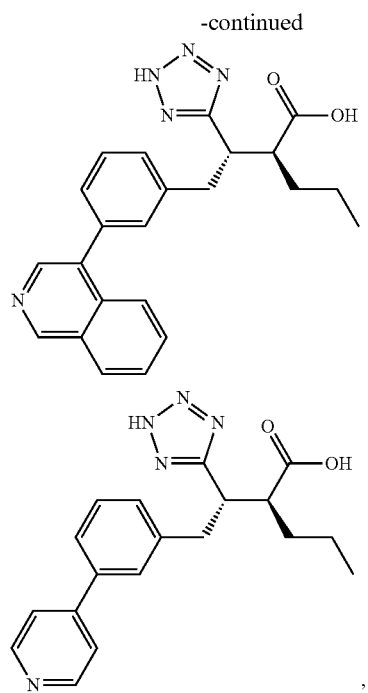
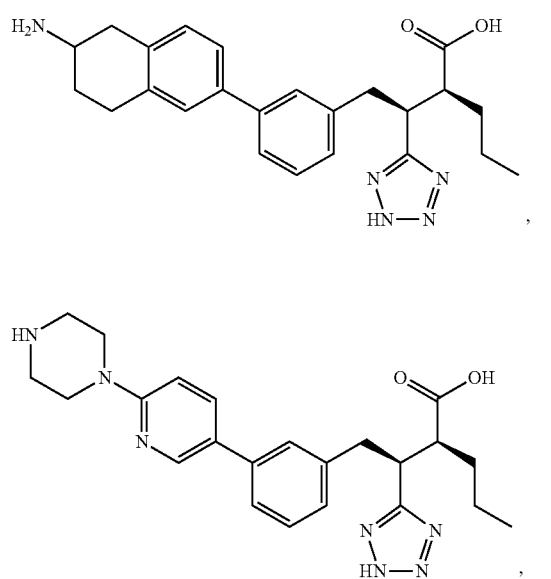
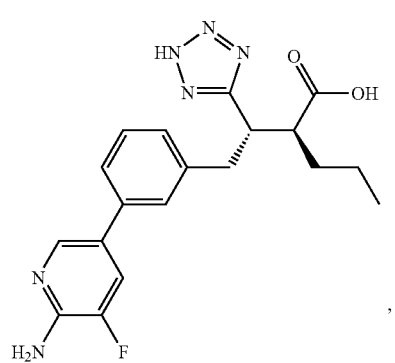
394
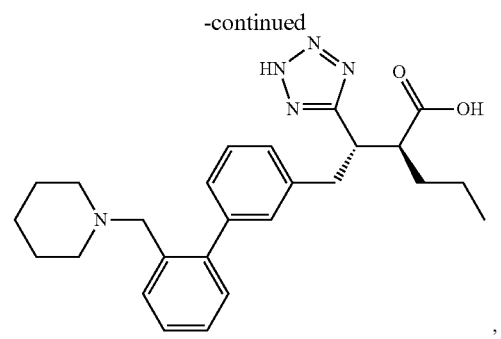
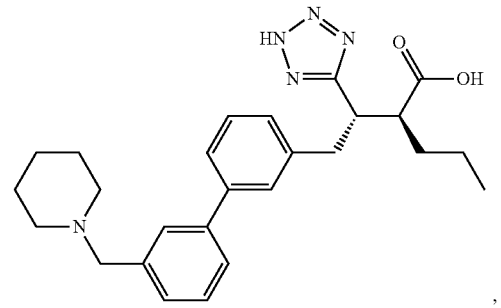
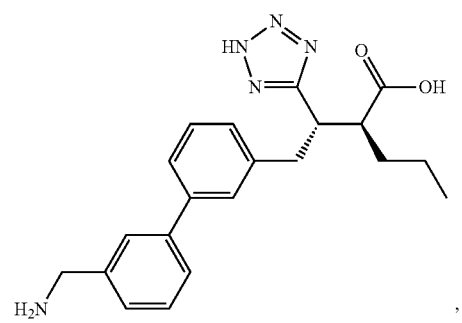
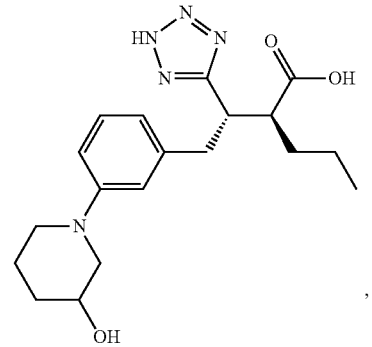
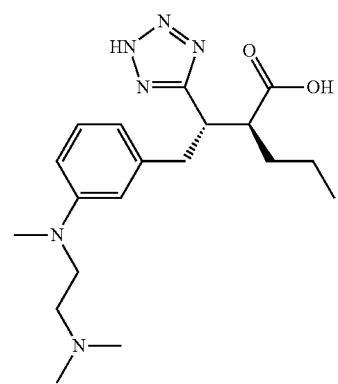

395
-continued
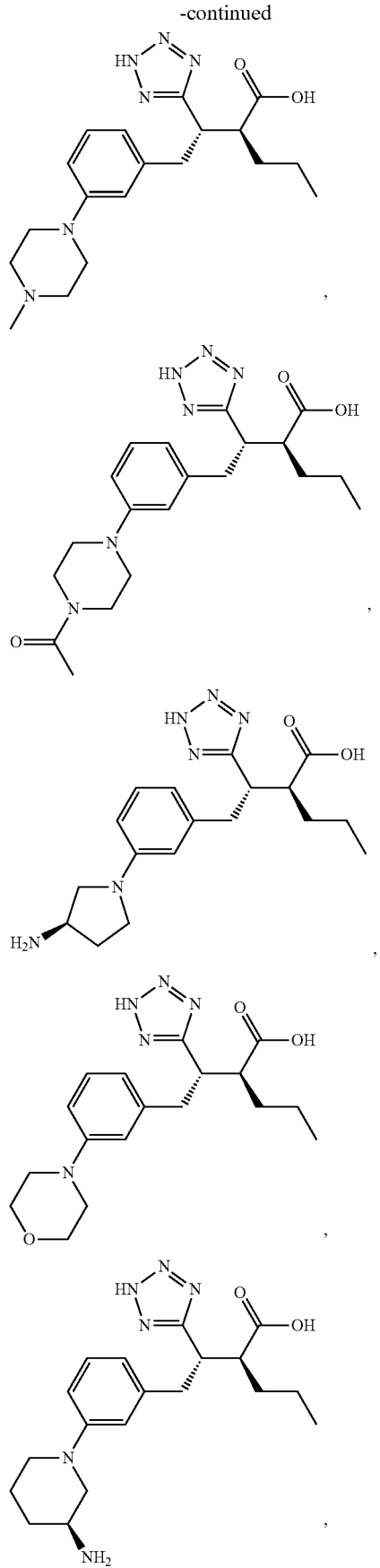
396
-continued
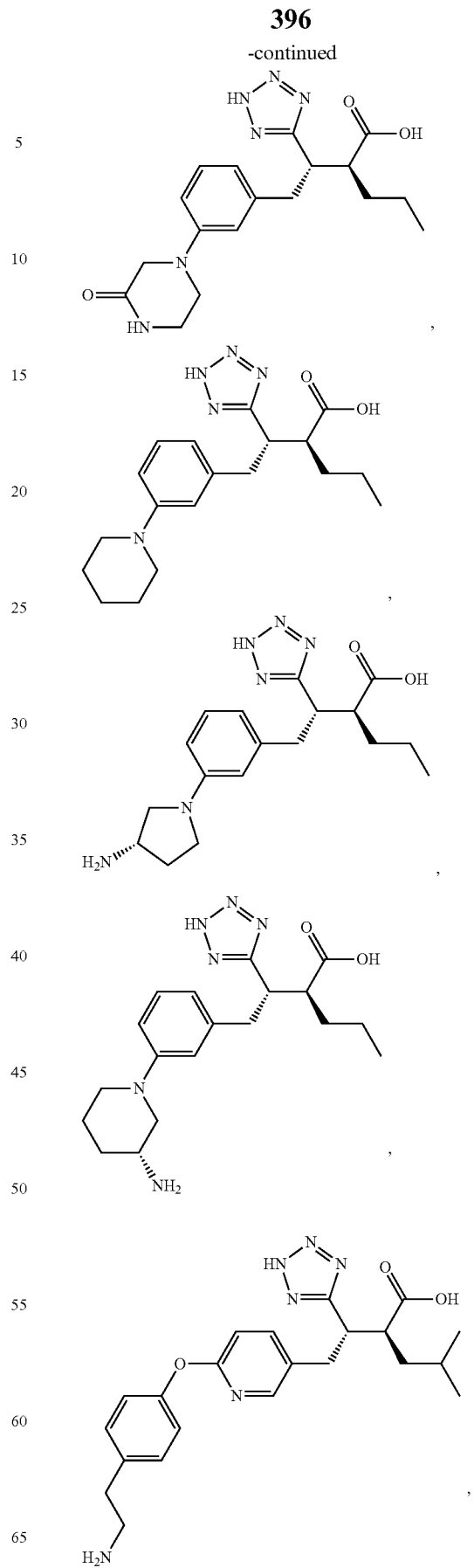

397
-continued
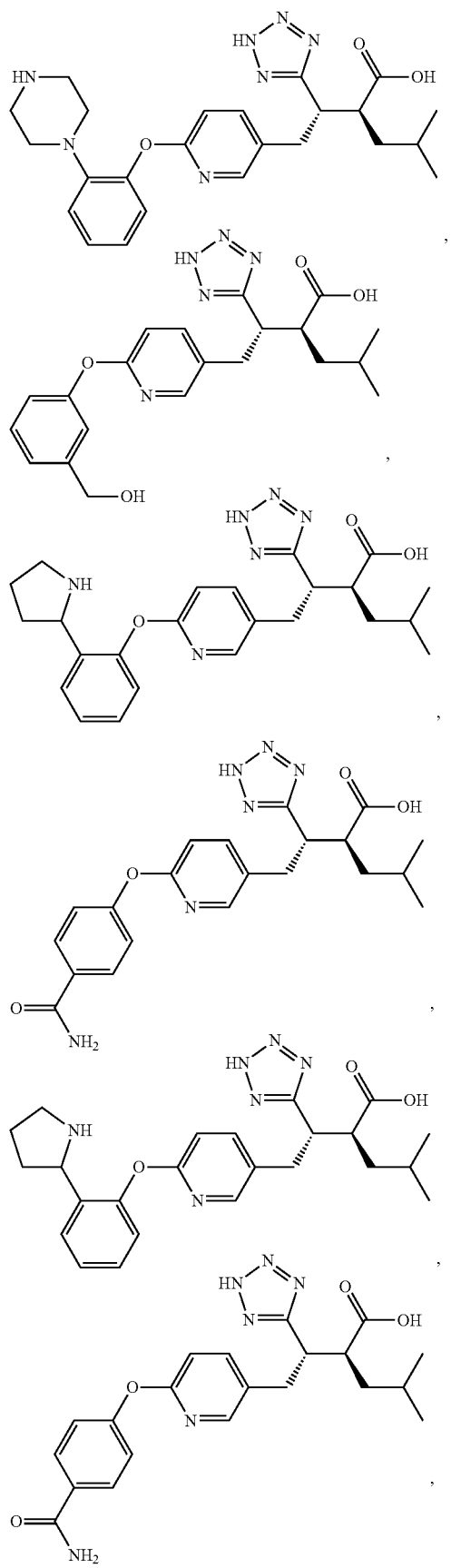
398
-continued
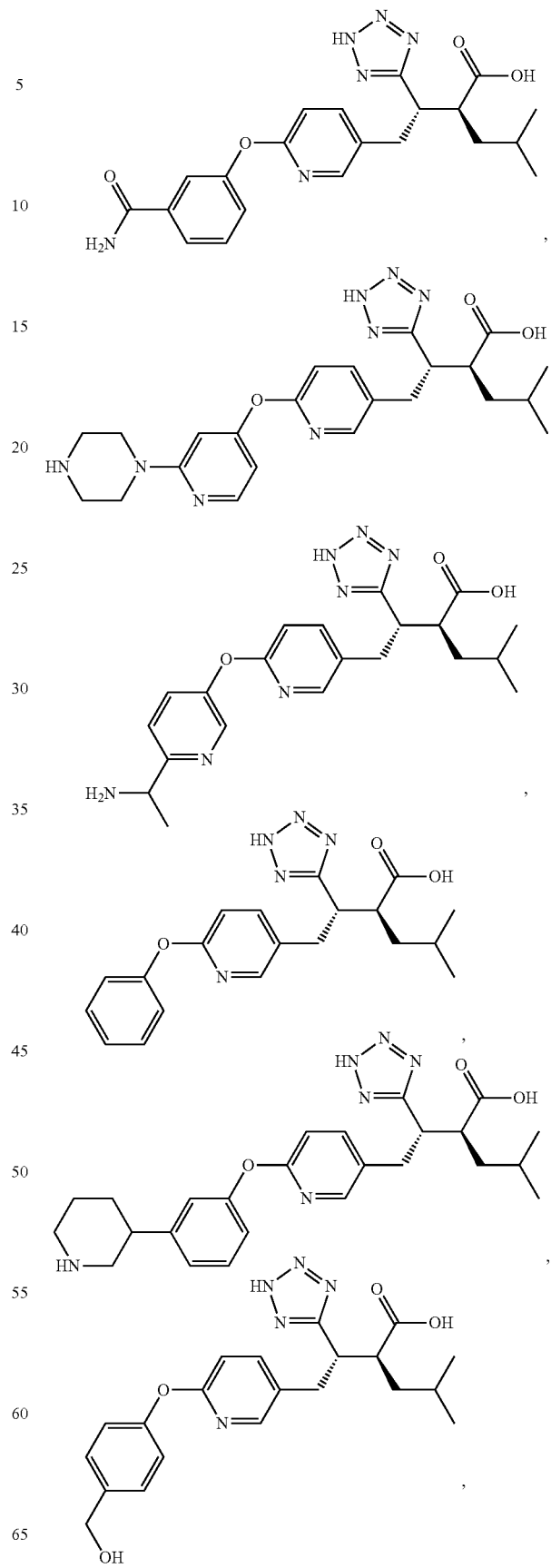

399
-continued
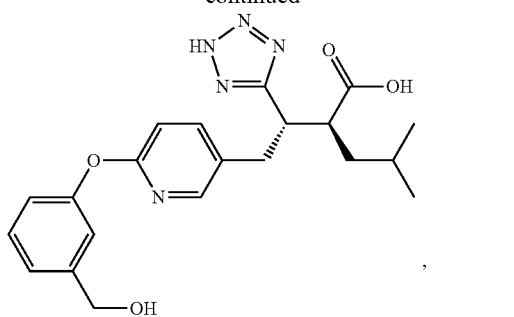
,
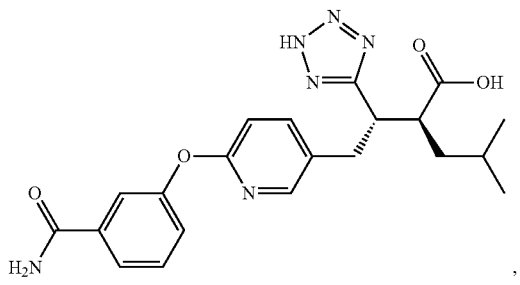
,
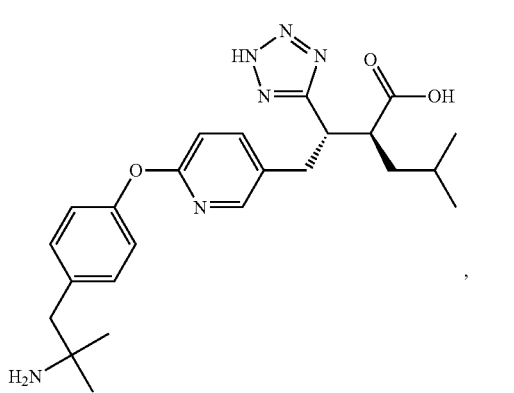
,
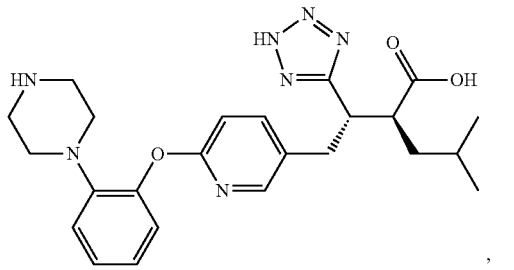
,
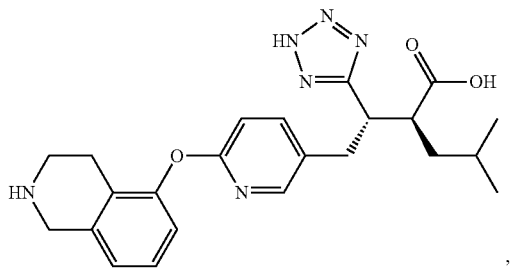
,
400
-continued
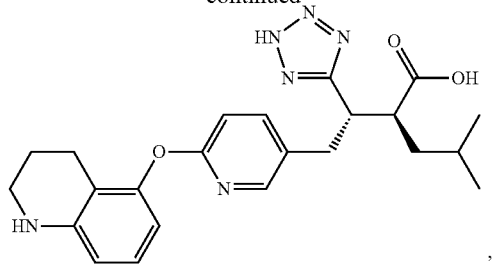
,
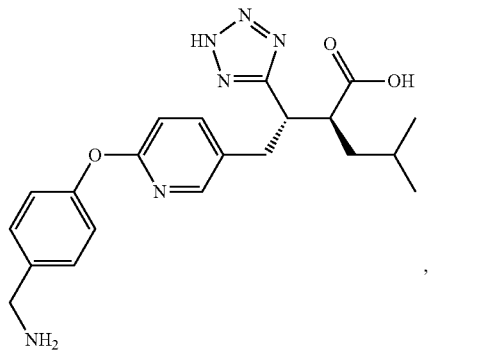
,
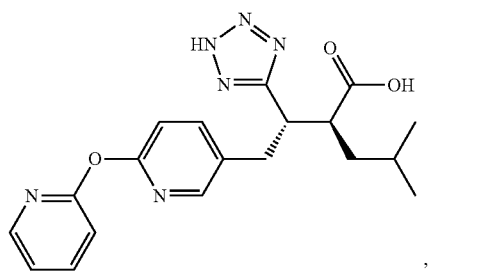
,
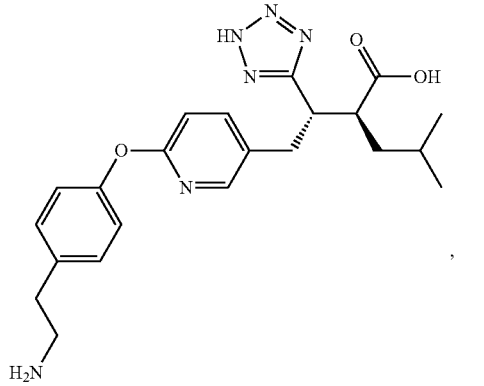
,
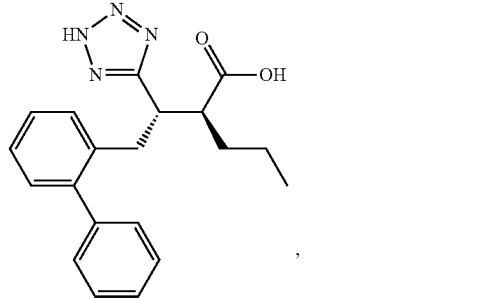
,

401
-continued
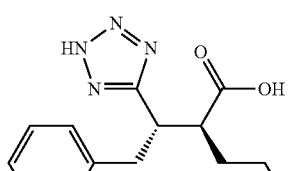
,
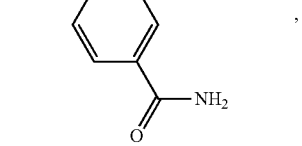
,
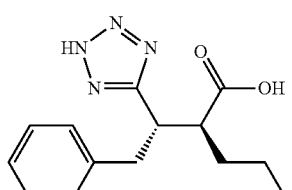
,
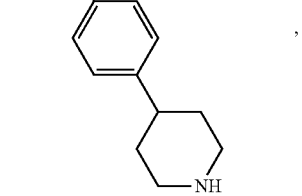
,
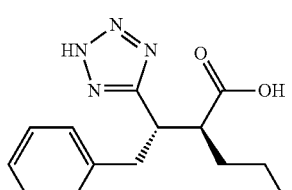
,
402
-continued
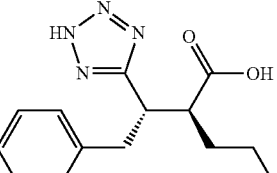
,
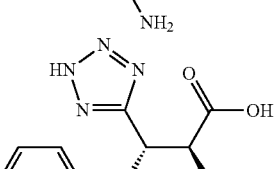
,
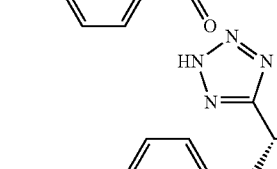
,
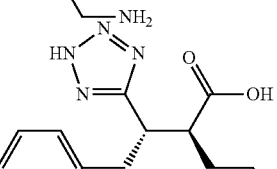
,
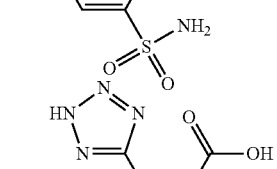
,
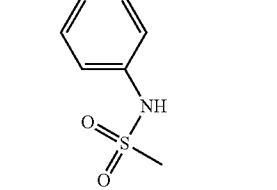
, 403
-continued
404
-continued
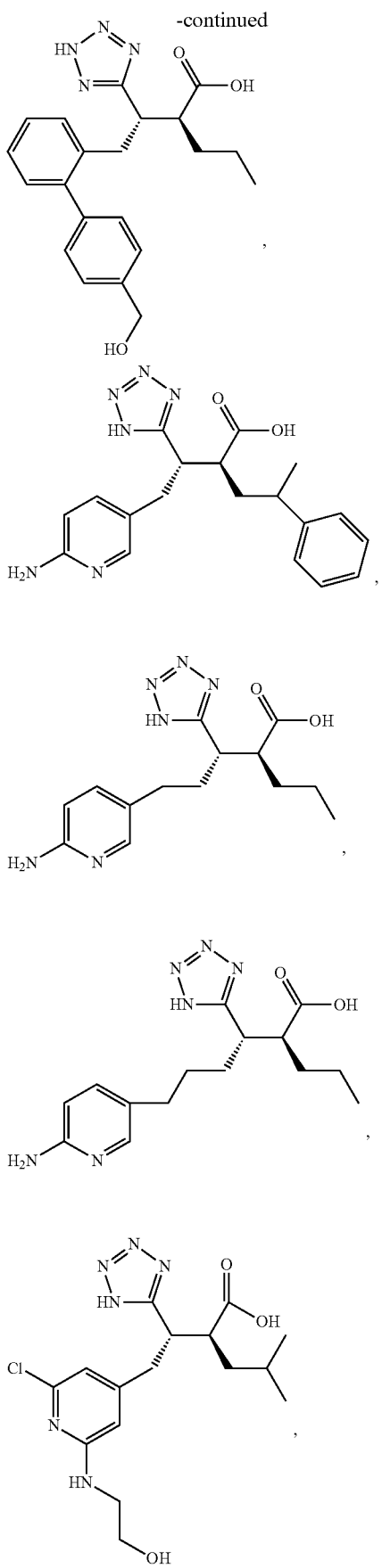
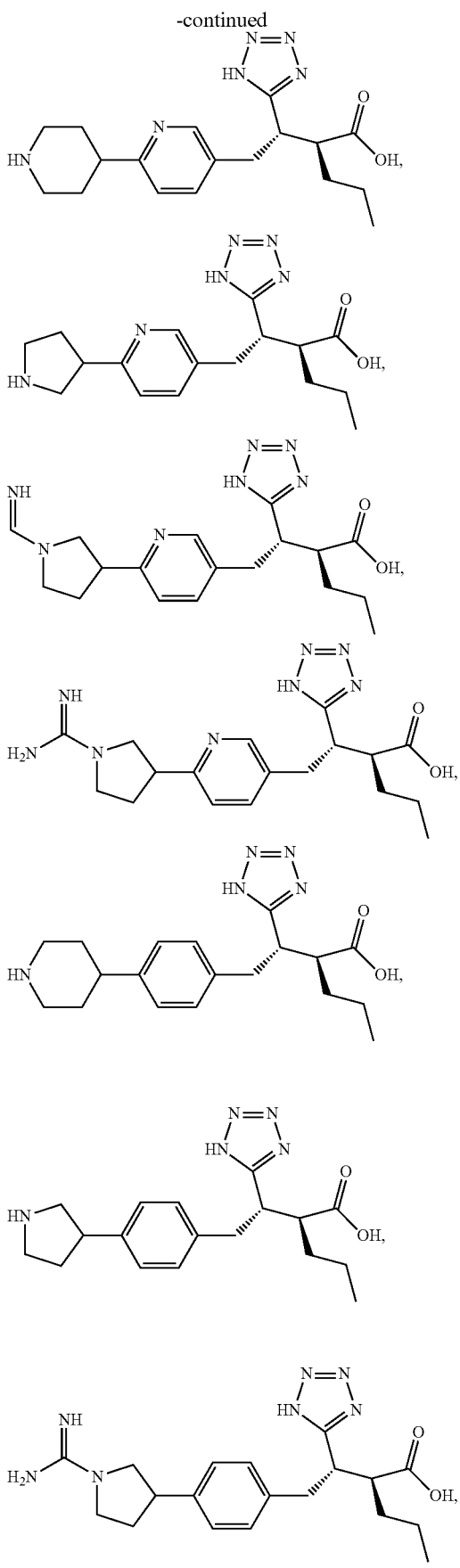

405
-continued
406
-continued
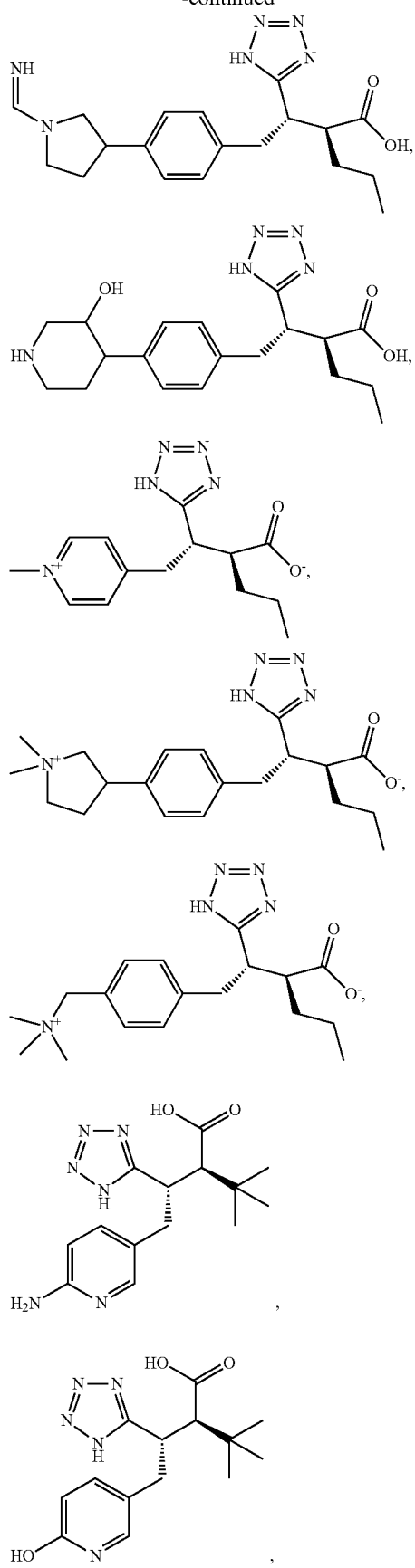
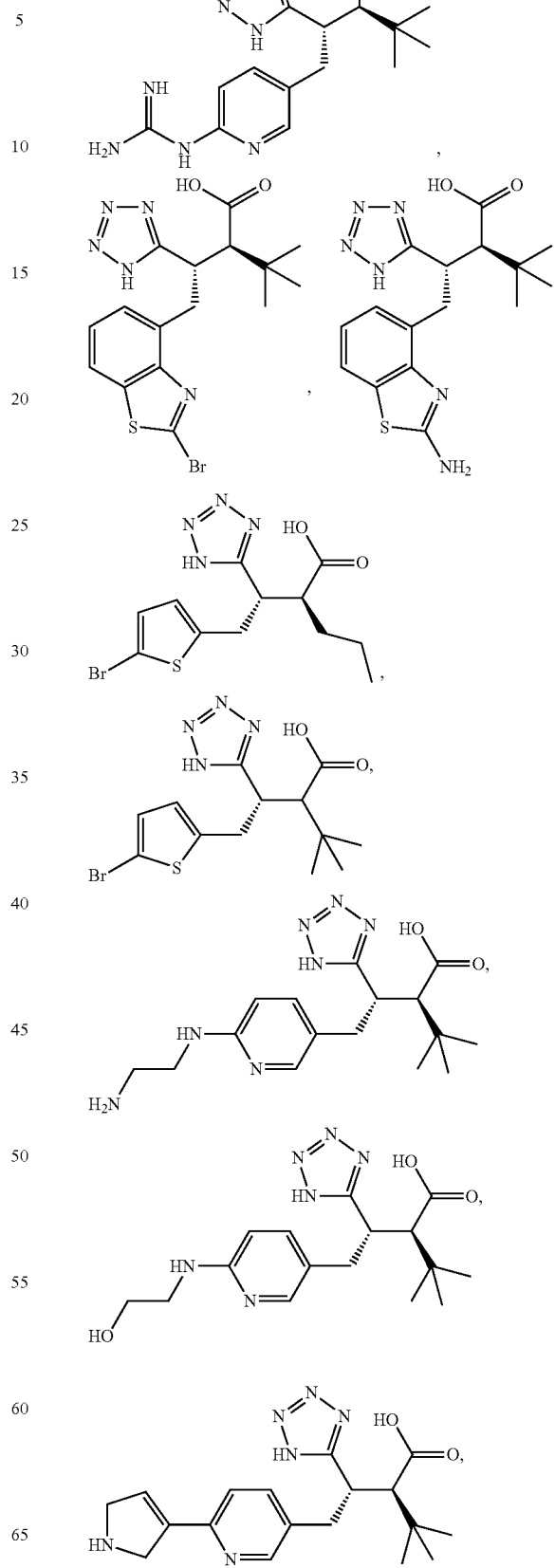

407
-continued
408
-continued
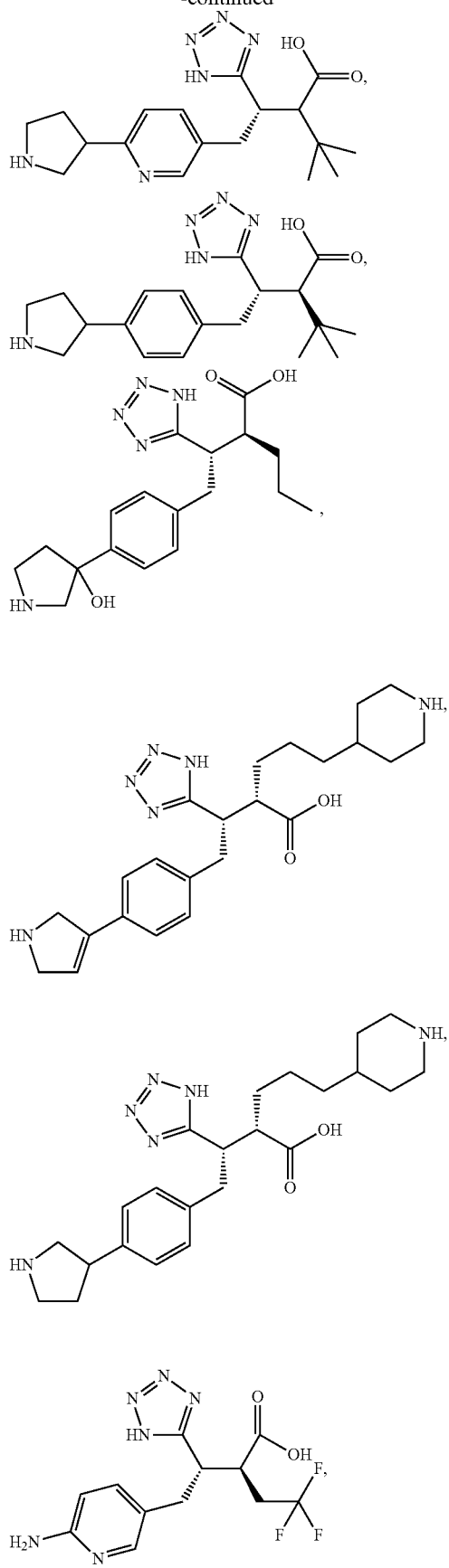
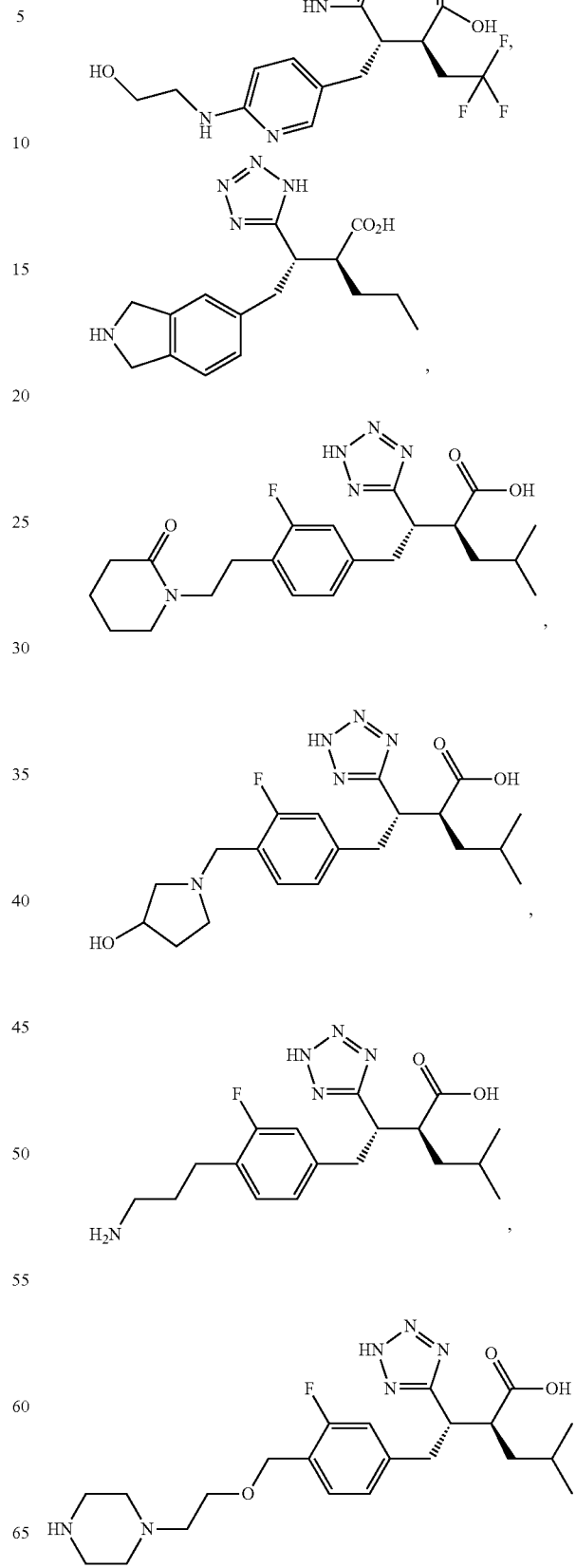

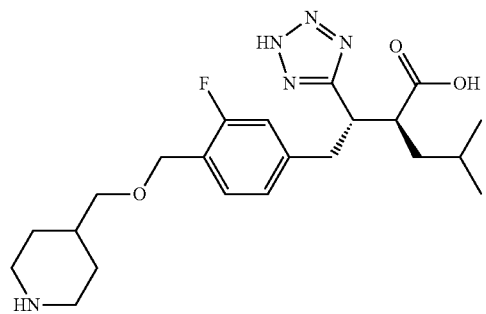
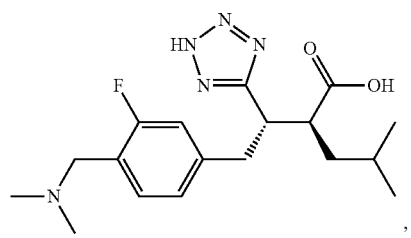
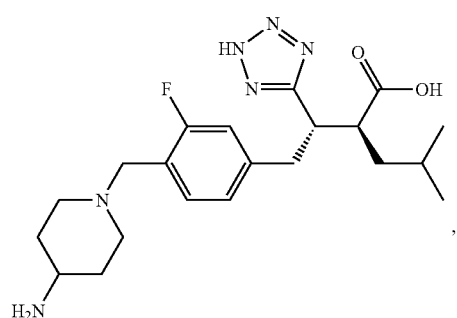
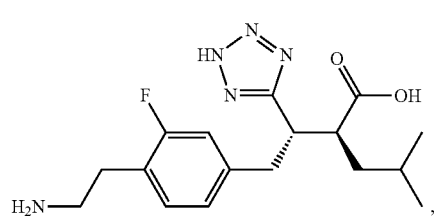
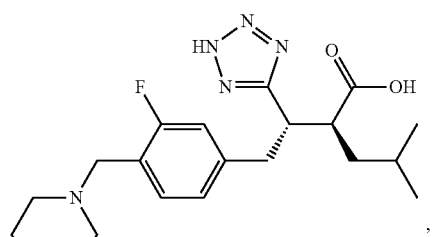
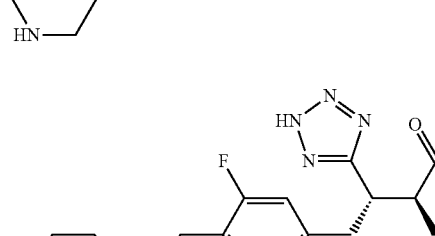
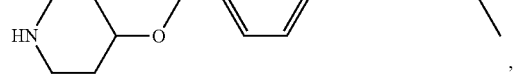
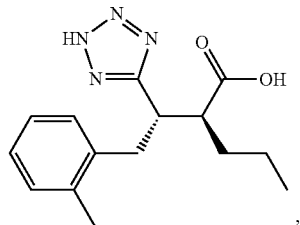
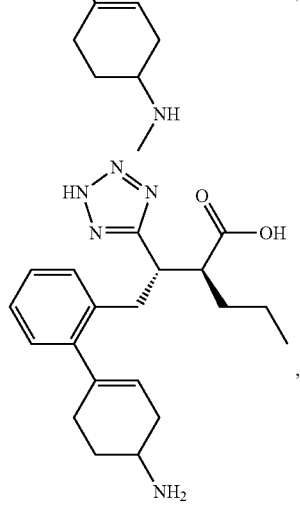
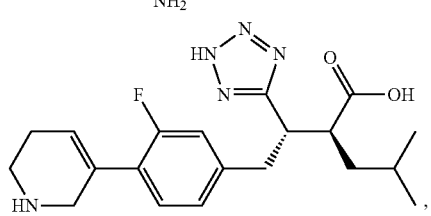
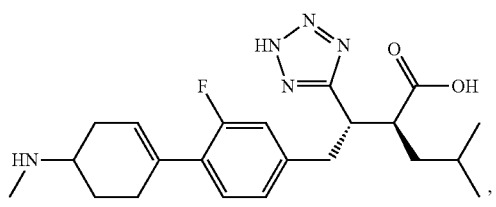
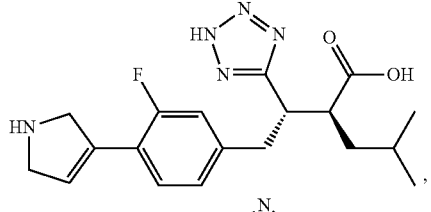
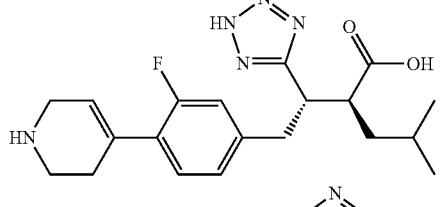
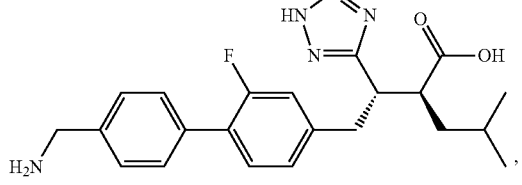

-continued
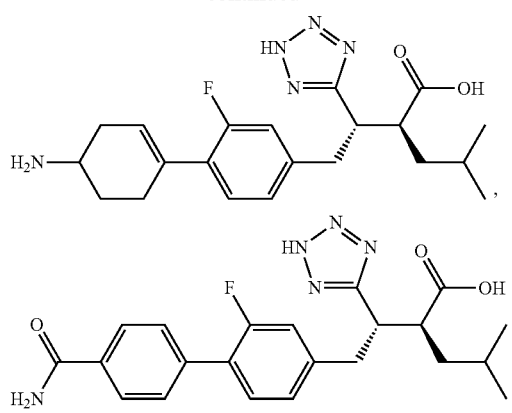
or a pharmaceutically acceptable salt thereof.
10. The compound of claim 6 having the structure:
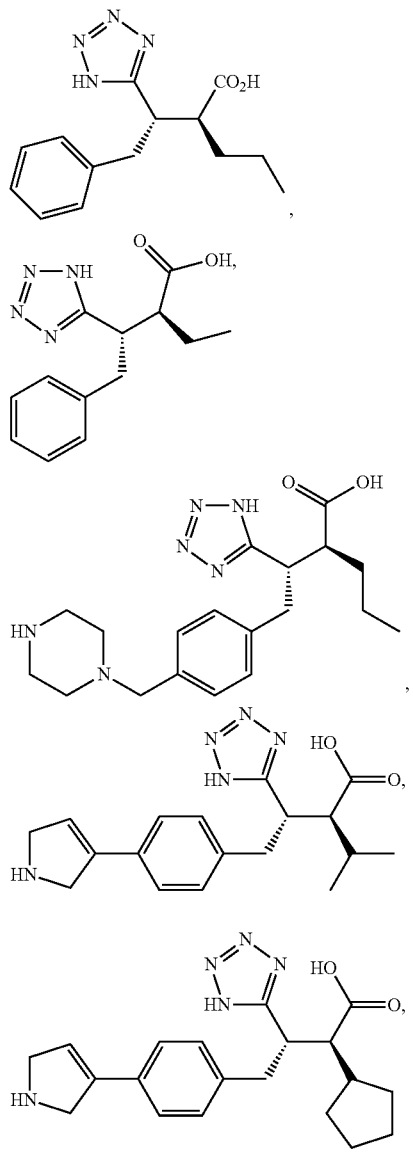
-continued
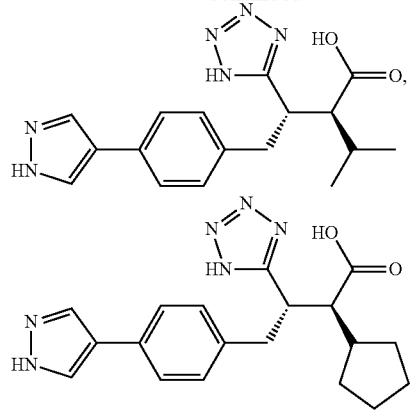
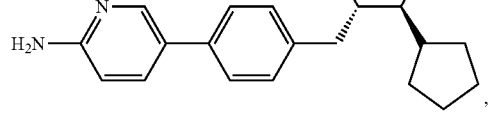
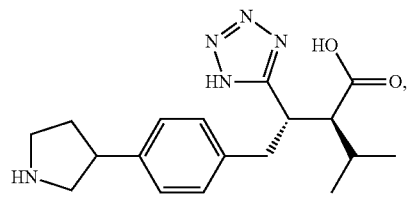
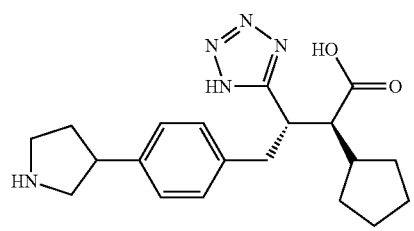
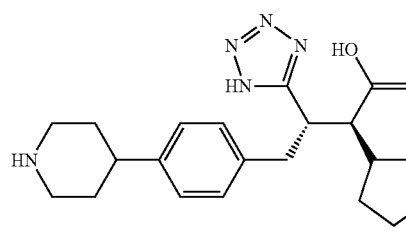
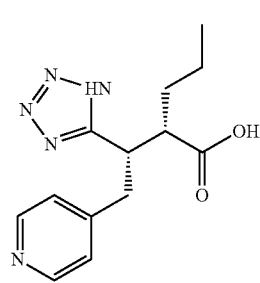

413
-continued
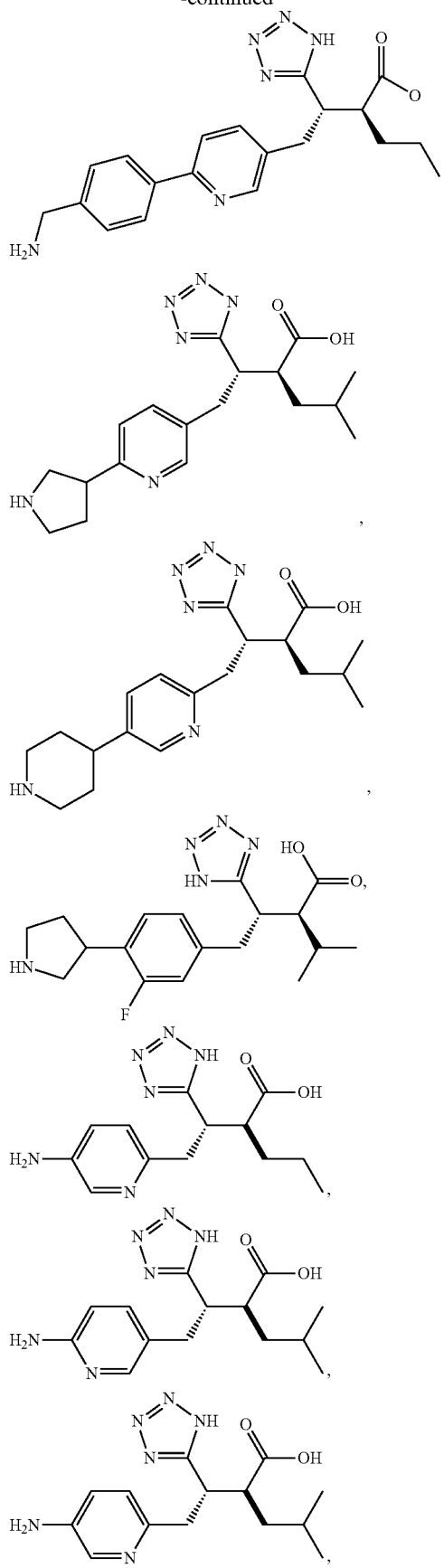
414
-continued
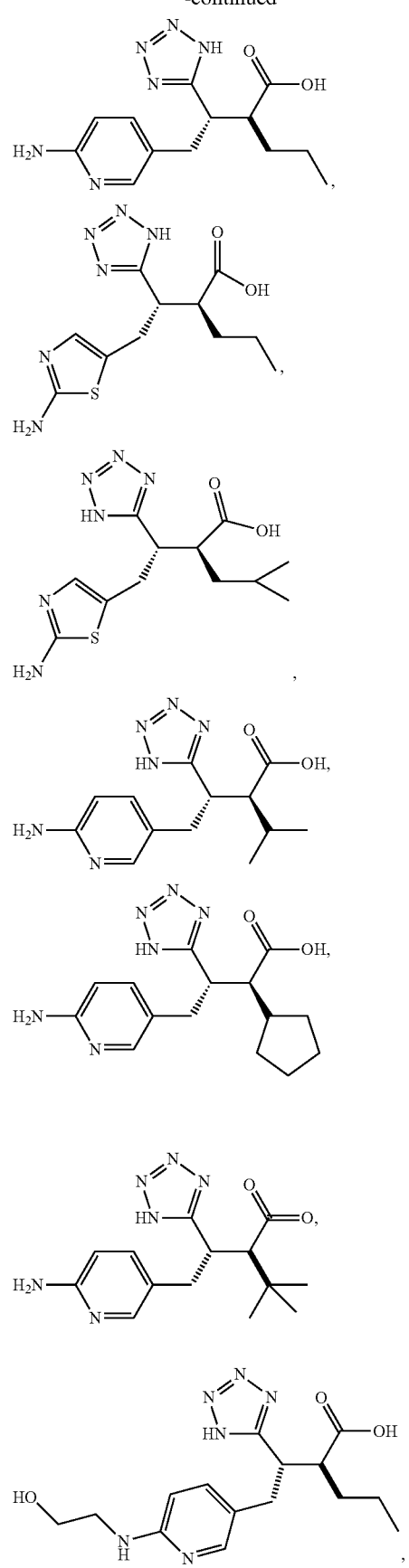

415
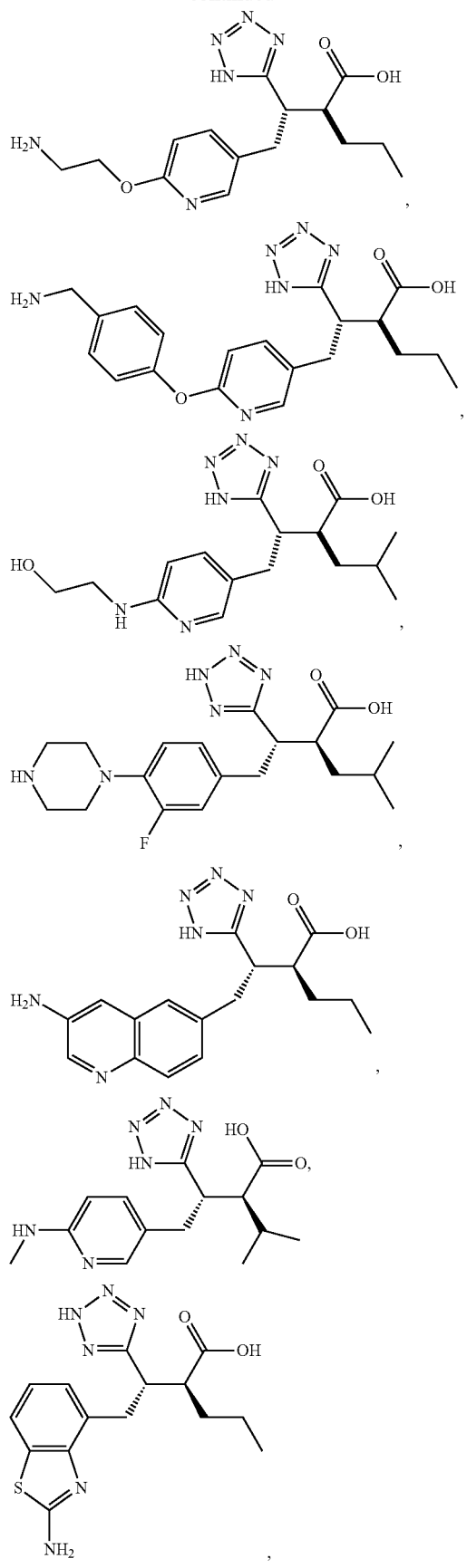
416
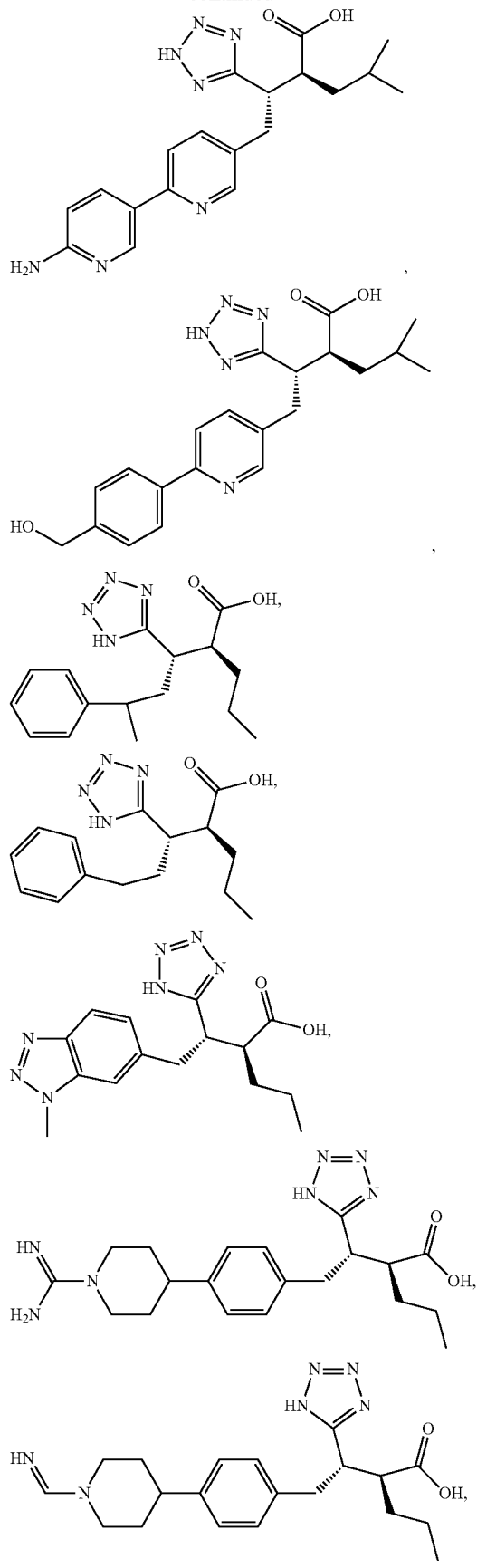

417
-continued
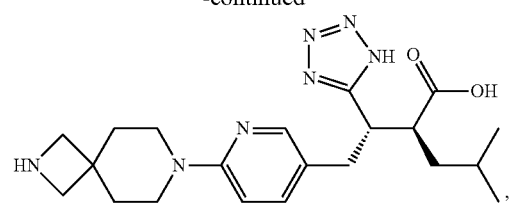
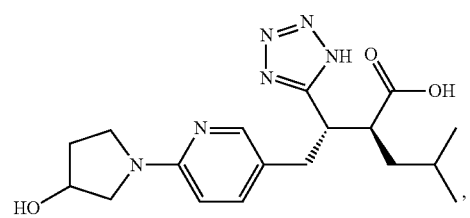
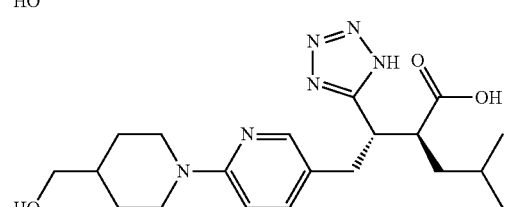
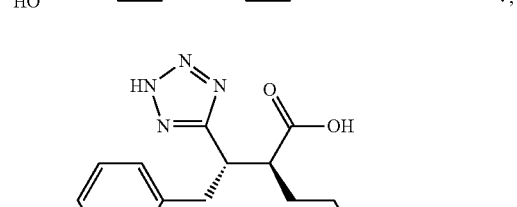
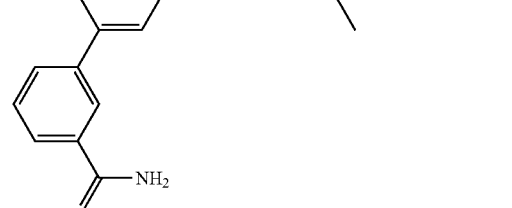
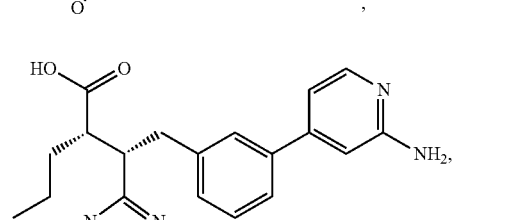
418
-continued
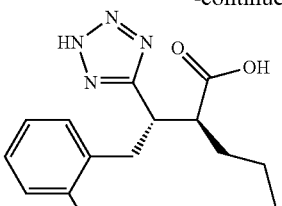
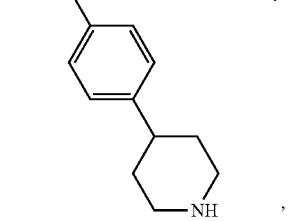
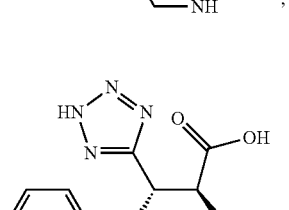
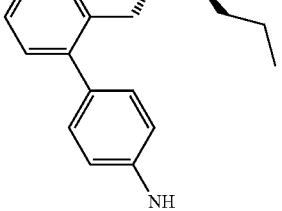
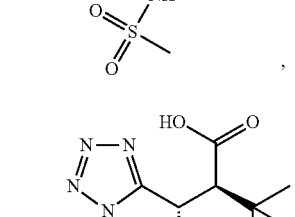
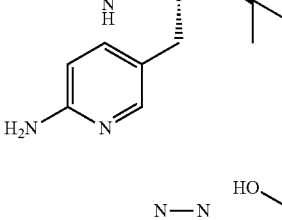

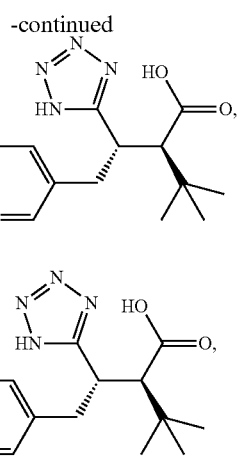

or a pharmaceutically acceptable salt thereof.

11. A pharmaceutical composition which comprises a compound acccording to claim 1, or a pharmaceutically acceptable salt thereof, and a pharmaceutically acceptable carrier.

12. A pharmaceutical composition according to claim 11, which further comprises an effective amount of a beta-lactam antibiotic.

13. The pharmaceutical composition according to claim 12, wherein the beta-lactam antibiotic is selected from the group consisting of imipenem, ertapenem, meropenem, doripenem, biapenem, panipenem, ticarcillin, ampicillin, amoxicillin, carbenicillin, piperacillin, azlocillin, mezlocillin, ticarcillin, cefoperazone, cefotaxime, ceftriaxone, and ceftazidime.

14. The pharmaceutical composition according to claim 12, wherein the beta-lactam antibiotic is imipenem.

15. The pharmaceutical composition according to claim 14, further comprising cilastatin or a pharmaceutically acceptable salt thereof.

16. A method for inhibiting beta-lactamase in a subject which comprises administering to the subject an effective amount of a compound according to claim 1, or a pharmaceutically acceptable salt thereof, optionally in combination with a beta-lactam antibiotic.

17. A method for treating a bacterial infection which comprises administering to a subject in need of such treatment a therapeutically effective amount of a compound according to claim 1, or a pharmaceutically acceptable salt thereof, in combination with a beta-lactam antibiotic.

18. The method of claim 17, wherein the beta-lactam antibiotic is selected from the group consisting of imipenem, ertapenem, meropenem, doripenem, biapenem, panipenem, ticarcillin, ampicillin, amoxicillin, carbenicillin, piperacillin, azlocillin, mezlocillin, ticarcillin, cefoperazone, cefotaxime, ceftriaxone, and ceftazidimem.

19. The method of claim 17, wherein the beta-lactam antibiotic is imipenem.

* * * * *